US009452210B2

(12) United States Patent
D'Aoust et al.

(10) Patent No.: US 9,452,210 B2
(45) Date of Patent: *Sep. 27, 2016

(54) INFLUENZA VIRUS-LIKE PARTICLES (VLPS) COMPRISING HEMAGGLUTININ PRODUCED WITHIN A PLANT

(71) Applicant: MEDICAGO INC., Quebec (CA)

(72) Inventors: Marc-Andre D'Aoust, Quebec (CA); Manon Couture, St-Augustin-de-Desmaures (CA); Frederic Ors, Quebec (CA); Sonia Trépanier, St-Nicolas (CA); Pierre-Olivier Lavoie, Quebec (CA); Michele Dargis, Quebec (CA); Louis-Philippe Vézina, Neuville (CA); Nathalie Landry, St-Romuald (CA)

(73) Assignee: MEDICAGO INC. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/734,886

(22) Filed: Jan. 4, 2013

(65) Prior Publication Data

US 2013/0183341 A1     Jul. 18, 2013

Related U.S. Application Data

(62) Division of application No. 12/669,033, filed as application No. PCT/CA2008/001281 on Jul. 11, 2008, now abandoned.

(60) Provisional application No. 60/959,414, filed on Jul. 13, 2007, provisional application No. 60/990,603, filed on Nov. 27, 2007, provisional application No. 61/013,272, filed on Dec. 12, 2007, provisional application No. 61/022,775, filed on Jan. 22, 2008.

(30) Foreign Application Priority Data

Jan. 21, 2008    (CA) ..................................... 2615372

(51) Int. Cl.
| | |
|---|---|
| *A61K 39/00* | (2006.01) |
| *A61K 48/00* | (2006.01) |
| *A61K 39/145* | (2006.01) |
| *C07K 14/005* | (2006.01) |
| *C12N 7/00* | (2006.01) |
| *C12N 15/82* | (2006.01) |
| *A61K 39/12* | (2006.01) |

(52) U.S. Cl.
CPC ............ *A61K 39/145* (2013.01); *A61K 39/12* (2013.01); *C07K 14/005* (2013.01); *C12N 7/00* (2013.01); *C12N 15/8257* (2013.01); *C12N 15/8258* (2013.01); *A61K 2039/517* (2013.01); *A61K 2039/5258* (2013.01); *A61K 2039/543* (2013.01); *A61K 2039/55505* (2013.01); *A61K 2039/55583* (2013.01); *A61K 2039/58* (2013.01); *C12N 2760/16122* (2013.01); *C12N 2760/16123* (2013.01); *C12N 2760/16134* (2013.01)

(58) Field of Classification Search
None
See application file for complete search history.

(56) References Cited

U.S. PATENT DOCUMENTS

| | | |
|---|---|---|
| 5,232,833 A | 8/1993 | Sanders et al. |
| 5,486,510 A | 1/1996 | Bouic et al. |
| 5,762,939 A | 6/1998 | Smith et al. |
| 5,858,368 A | 1/1999 | Smith et al. |
| 5,958,422 A | 9/1999 | Lomonossoff |
| 6,020,169 A | 2/2000 | Lee et al. |
| 6,042,832 A * | 3/2000 | Koprowski et al. ........ 424/192.1 |
| 6,287,570 B1 | 9/2001 | Foley |
| 6,326,470 B1 | 12/2001 | Cosgrove |
| 6,489,537 B1 | 12/2002 | Rea et al. |
| 6,867,293 B2 | 3/2005 | Andrews et al. |
| 7,125,978 B1 | 10/2006 | Vezina et al. |
| 7,132,291 B2 | 11/2006 | Cardineau et al. |
| 7,763,450 B2 * | 7/2010 | Robinson et al. ......... 435/235.1 |
| 7,897,842 B2 | 3/2011 | Bakker et al. |
| 8,771,703 B2 | 7/2014 | Couture et al. |
| 2001/0006950 A1 | 7/2001 | Punnonen et al. |
| 2003/0079248 A1 | 4/2003 | Mason et al. |
| 2004/0002061 A1 | 1/2004 | Kawaoka |
| 2006/0252132 A1 | 11/2006 | Yang et al. |
| 2007/0207526 A1 | 9/2007 | Coit et al. |

(Continued)

FOREIGN PATENT DOCUMENTS

| | | |
|---|---|---|
| CA | 2615372 | 1/2009 |
| CA | 2693956 A1 | 1/2009 |

(Continued)

OTHER PUBLICATIONS

Huang et al. Virus-like particle expression and assembly in plants: hepatitis B and Norwalk viruses. Vaccine, vol. 23, Issue 15, Mar. 7, 2005, pp. 1851-1858.*

(Continued)

*Primary Examiner* — Michelle S Horning
(74) *Attorney, Agent, or Firm* — Dawn C. Russell; Culhane Meadows PLLC

(57) ABSTRACT

A method for synthesizing influenza virus-like particles (VLPs) within a plant or a portion of a plant is provided. The method involves expression of influenza HA in plants and the purification by size exclusion chromatography. The invention is also directed towards a VLP comprising influenza HA protein and plant lipids. The invention is also directed to a nucleic acid encoding influenza HA as well as vectors. The VLPs may be used to formulate influenza vaccines, or may be used to enrich existing vaccines.

19 Claims, 89 Drawing Sheets

(56) References Cited

U.S. PATENT DOCUMENTS

| | | | |
|---|---|---|---|
| 2007/0286873 A1 | 12/2007 | Williams et al. | |
| 2008/0008725 A1 | 1/2008 | Weeks-Levy et al. | |
| 2009/0191309 A1 | 7/2009 | Rastogi et al. | |
| 2009/0311669 A1 | 12/2009 | Kawaoka | |
| 2010/0239610 A1* | 9/2010 | D'Aoust et al. | 424/210.1 |
| 2010/0310604 A1* | 12/2010 | D'Aoust et al. | 424/210.1 |
| 2011/0191915 A1 | 8/2011 | Couture et al. | |
| 2011/0293650 A1* | 12/2011 | D'Aoust et al. | 424/186.1 |
| 2012/0189658 A1* | 7/2012 | Couture et al. | 424/210.1 |
| 2013/0142826 A1* | 6/2013 | D'Aoust et al. | 424/210.1 |
| 2013/0295609 A1 | 11/2013 | D'Aoust et al. | |

FOREIGN PATENT DOCUMENTS

| | | | |
|---|---|---|---|
| CA | 2707235 A1 | 6/2009 | |
| CN | 1861793 A | 11/2006 | |
| JP | 2005-535288 A | 11/2005 | |
| SG | 158301 | 4/2012 | |
| WO | 86/03224 A | 6/1986 | |
| WO | 00/09725 A2 | 2/2000 | |
| WO | 00/56906 A1 | 9/2000 | |
| WO | 02/074795 A2 | 9/2002 | |
| WO | 03/068163 A2 | 8/2003 | |
| WO | 03/068923 A2 | 8/2003 | |
| WO | 03/068993 A1 | 8/2003 | |
| WO | WO-2004/003207 A1 | 1/2004 | |
| WO | 2004/098530 A2 | 11/2004 | |
| WO | 2004/098533 A2 | 11/2004 | |
| WO | 2005/020889 A2 | 3/2005 | |
| WO | 2006/016380 A2 | 2/2006 | |
| WO | 2006/119516 A2 | 11/2006 | |
| WO | 2007/011904 A2 | 1/2007 | |
| WO | 2007/019094 A2 | 2/2007 | |
| WO | 2007/047831 A2 | 4/2007 | |
| WO | 2007/095318 A2 | 8/2007 | |
| WO | 2007/130327 A2 | 11/2007 | |
| WO | 2008/054540 A2 | 5/2008 | |
| WO | 2008/060669 A2 | 5/2008 | |
| WO | 2008/087391 A1 | 7/2008 | |
| WO | 2008/151440 A1 | 12/2008 | |
| WO | 2009/008573 A1 | 1/2009 | |
| WO | 2009/009876 A1 | 1/2009 | |
| WO | 2009/026397 A2 | 2/2009 | |
| WO | 2009/076778 A1 | 6/2009 | |
| WO | 2010/003225 A1 | 1/2010 | |
| WO | 2010/006452 A1 | 1/2010 | |
| WO | WO-2010/003225 A1 | 1/2010 | |
| WO | 2010/025235 A1 | 3/2010 | |
| WO | 2010/077712 A1 | 7/2010 | |
| WO | 2011/011390 A1 | 1/2011 | |
| WO | 2011/035423 A1 | 1/2011 | |
| WO | WO-2011/011390 A1 | 1/2011 | |
| WO | 2011/035422 A1 | 3/2011 | |
| WO | 2011/102900 A1 | 8/2011 | |
| WO | 2012/061815 A2 | 5/2012 | |
| WO | 2012/083445 A1 | 6/2012 | |

OTHER PUBLICATIONS

Klopfleisch et al. Neurotropism of highly pathogenic avian influenza virus A/chicken/Indonesia/2003 (H5N1) in experimentally infected pigeons (*Columbia livia* f. domestica). Vet Pathol. Jul. 2006;43(4):463-70.*

Denis et al. Immunogenicity of papaya mosaic virus-like particles fused to a hepatitis C virus epitope: evidence for the critical function of multimerization. Virology. Jun. 20, 2007;363(1):59-68.*

Sainsbury et al., "Expression of multiple proteins using full-lengh and deleted versions of cowpea mosaic virus RNA-2", Plant Biotechnology Journal, vol. 6, 2008, pp. 82-92.

Sainsbury et al., "Extremely High-Level and Rapid Transient Protein Production in Plants without the Use of Viral Replication", Plant Physiology, vol. 148, 2008, pp. 1212-1218.

Saint-Jore-Dupas et al., "From planta to pharma with glycosylation in the toolbox", Trends in Biotechnology, vol. 25, No. 7, 2007, pp. 317-323.

Salzberg et al., "Genome Analysis Linking Recent European and African Influenza (H5N1) Viruses", Emerging Infectious Diseases, vol. 13, No. 5 2007, pp. 713-718.

Santi et al., "An Efficient Plant Viral Expression System Generating Orally Immunogenic Norwalk Virus-Like Particles", Vaccine, vol. 26, 2008, pp. 1846-1854.

Scheid et al., "Reversible Inactivation of a Transgene in Arabidopsis Thaliana", Mol Gen Genet, vol. 228, 1991, pp. 104-112.

Schillberg et al., "Apoplastic and cytosolic expression of full-size antibodies and antibody fragments in Nicotiana taincum", Transgenic Research, vol. 8, 1999, pp. 255-263.

Schillberg et al., "Molecular farming of recombinant antibodies in plants", Cellular and Molecular Life Sciences, vol. 60, 2003, pp. 433-445.

Shoji et al., "Plant-expressed HA as a seasonal influenza vaccine candidate", Vaccine, vol. 26, 2008, pp. 2930-2934.

Shorrosh et al., "Molecular Cloning of a Putative Plant Endomembrane Protein Resembling Vertebrate Protein Disulfide-Isomerase and a Phosphatidylinositol-Specific Phospholipase C", Proceedings of the National Academy of Sciences, vol. 88, Dec. 1991, pp. 10941-10945.

Skehel et al., "Receptor Binding and Membrane Fusion in Virus Entry: The Influenza Hemagglutinin", Annual Review of Biochemistry, vol. 69, 2000, pp. 531-569.

Smith et al., "Structural Charaterization of Plant-Derived Hepatitits B Surface Antigen Employed in Oral Immunization Studies", Vaccine, vol. 21, 2003, pp. 4011-4021.

Sriraman et al., "recombinant Anti-hCG Antibodies Retained in the Endoplasmic Reticulum of Transformed Plants Lack Core-Xylose and Core-α(1,3)-Fucose Residues", Plant Biotechnology Journal, vol. 2, 2004, pp. 279-287.

Staehelin, L. Andrew, "The plant ER: a dynamic organelle composed of a large number of discrete functional domains", The Plant Journal, vol. 11, No. 6, 1997, pp. 1151-1165.

Suzuki, Yasuo., "Sialobiology of Influenza. Molecular Mechanism of Host Range Variation of Influenza Viruses", Biological and Pharmaceutical Bulletin, vol. 28, No. 3, Mar. 2005, pp. 399-408.

Szyperski et al., "Structure Comparison of Human Glioma Pathogenesis-Related Protein GIIPR and the Plant Pathogenesis-Related Protein P14a Indicates a Functional link Between the Human Immune System and a Plant Defense System", Proc. Natl. Acad. Sci. USA, vol. 95, Mar. 1998, pp. 2262-2262.

Tacket et al., "Human Immune Responses to a Novel Norwalk Virus Vaccine Delivered in Transgenic Potatoes", The Journal of Infectious Diseases, vol. 182, 2000, pp. 302-305.

Toukach et al., "Sharing of Worldwide Distributed Carbohydrate-Related Digital Resources: Online Connection of the Bacterial Carbohydrate Structure DataBase and GLYCOSCIENCES.de", Nucleic Acids Research, vol. 35, Database Issue, 2007, pp. D280-D286.

Treanor et al., "Safety and Immunogenicity of a Baculovirus-Expressed Hemagglutinin Influenza Vaccine: A Randomized Control Trial", Journal of the American Medical Association, vol. 297, No. 14, 2007, pp. 1577-1582.

Vaccaro et al., "Plasticity of Influenza Haemagglutinin Fusion Peptides and Their Interaction with Lipid Bilayers", Biophysical Journal, vol. 88, 2005, pp. 25-36.

van Ree et al., "β (1,2)-Xylose and α (1,3)-Fucose Residues have a Strong Contribution in IgE binding to Plant *Glycoallergens*", The Journal of Biological Chemistry, vol. 275, No. 15, Apr. 14, 2000, pp. 11451-11458.

Varsani et al., Expression of Human Papillomavirus Type 16 Major Capsid Protein in Transgenic Nicotiana Tabacum cv. Xanthi, Archives of Virology, vol. 148, 2003, pp. 1771-1786.

Verch et al., "Expression and Assembly of a Full-Length Monoclonal Antibody in Plants using a Plant Virus Vector", Journal of Immunological Methods, vol. 220, 1998, pp. 69-75.

Vézina et al., "Transient Co-Expression for Fast and High-Yield Production of Antibodies with Human-like N-Glycans in Plants", Plant Biotechnology Journal, vol. 7, 2009, pp. 442-455.

(56) References Cited

OTHER PUBLICATIONS

Vigerust et al, "N-Linked Glycosylation Attenuates H3N2 Influenza Viruses", Journal of Virology, vol. 81, No. 16, Aug. 2007, pp. 8593-8600.
Wagner et al., "Interdependence of Hemagglutinin Glycosylation and Neuraminidase as Regulators of Influenza Virus Growth: A Study by Reverse Genetics", Journal of Virology, vol. 74, No. 14, Jul. 2000, pp. 6316-6323.
Wakefield et al., "RNA-binding properties of influenza A virus matrix protein M1", Nucleic Acids Research, vol. 17, No. 21, 1989, pp. 8569-8580.
Wang et al., "Expression and purification of an influenza hemagglutinin—one step closer to a recombinant protein-based influenza vaccine", Vaccine, vol. 24, 2006, pp. 2176-2185.
Wang, Weili, "Isolation, Identification and Molecular analysis of the Main of Genes Avian Influenza virus Isolates Different Hosts", China Doctoral Dissertations Full-text Database, Agricultural Science and Technology, 2006, 125 pages (English Abstract Submitted).
Wei et al., "Comparative Efficacy of Neutralizing Antibodies Elicited by Recombinant Hemagglutinin Proteins from Avian H5N1 Influenza Virus", Journal of Virology, vol. 82, No. 13, Jul. 2008, pp. 6200-6208.
Weldon et al., "Enhanced Immunogenicity of Stabilized Trimeric Soluble Influenza Hemagglutinin", PLOS One, vol. 5, No. 9. e12466, Sep. 2010, pp. 1-8.
Wilson et al., "Core α1,3-Fucose is a Key Part of the Epitope Recognized by Antibodies Reacting Against Plant N-Linked Oligosaccharides and is Present in a Wide Variety of Plant Extracts", Glycobiology, vol. 8 No. 7, 1998, pp. 651-661.
Wydro et al., "Optimization of Transient Agrobacterium-Mediated Gene Expression System in Leaves of Nicotiana benethamiana", Acta Biochimica Polonica, vol. 53, No. 2, 2006, pp. 289-298.
"Protoplast Isolation,Macerozyme,PlantMaterials,Cellulase,Enzymes,Micro," Retrieved from Internet on Aug. 30, 2012, 1 page, Available at: <http://www.molecular-plant-biotechnology.info/plant-tissue-culture/protoplast-isolation.html>.
Decision to Grant received for European Patent Application No. 09700061.6, mailed on Aug. 17, 2012, 1 page.
Examination Report received for New Zealand Patent Application No. 587108, mailed on Jun. 27, 2012, 2 pages.
Examination Report received for New Zealand Patent Application No. 587108, mailed on Mar. 21, 2011, 2 pages.
Examination Report received for New Zealand Patent Application No. 590144, mailed on Apr. 15, 2011, 3 pages.
Examination Report received for New Zealand Patent Application No. 597401, mailed on Jul. 9, 2012, 1 page.
Extended European Search Report and European Search Opinion received for European Patent Application No. 09700061.6 , mailed on Mar. 7, 2011, 10 pages.
Extended European Search Report and European Search Opinion received for European Patent Application No. 09793741.1, mailed on Aug. 9, 2011, 9 pages.
Extended European Search Report and European Search Opinion received for European Patent Application No. 09797336.6, mailed on Dec. 29, 2011, 7 pages.
Extended European Search Report received for European Patent Application No. 08783201.0, mailed on Sep. 13, 2010, 8 pages.
Extended European Search Report received for European Patent Application No. 09793751.0, mailed on Sep. 28, 2011, 10 Pages.
Non Final Office Action received for U.S. Appl. No. 12/669,033, mailed on Oct. 4, 2012, 34 pages.
Notice of Allowance received for Canadian Patent Application No. 2,762,042, mailed on Jun. 29, 2012, 1 page.
Office Action received for Canadian Patent Application No. 2,615,372 mailed on Sep. 6, 2012, 5 pages.
Office Action received for Canadian Patent Application No. 2,693,956, mailed on Jan. 20, 2012, 2 pages.
Office Action received for Canadian Patent Application No. 2,693,956, mailed on Jan. 26, 2011, 3 pages.
Office Action received for Canadian Patent Application No. 2,693,956, mailed on Sep. 22, 2011, 3 pages.
Howell et al., "Cloned Cauliflower Mosaic Virus DNA, Infects Turnips (Brassica rapa)", Science, vol. 208, Jun. 13, 1980, pp. 1265-1267.
Huang et al, A DNA Replicon System for Rapid High-Level Production of Virus-Like Particles in Plants, Biotechnology and Bioengineering, vol. 103, No. 4, Jul. 1, 2009, pp. 706-714.
Huang et al., "Plant-Derived Measles Virus Hemagglutinin Protein Induces Neutralizing Antibodies in Mice", Vaccine, vol. 19, 2001, pp. 2163-2171.
Huang et al., "Virus-like particle expression and assembly in plants: hepatiits B and Norwalk viruses", Vaccine, vol. 23, 2005, pp. 1851-1858.
Huang et al., "High-Level Rapid Production of Full-Size Monoclonal Antibodies in Plants by a Single-Vector DNA Replicon System", Biotechnology and Bioengineering, vol. 106, No. 1, May 1, 2010, pp. 9-17.
Hull et al. "Human-Derived, Plant-Produced Monoclonal Antibody for the Treatment of Anthrax", Vaccine, vol. 23, 2005, pp. 2082-2086.
Influenza A virus (A/California/04/2009(H1N1)) segment 4 hemagglutinin (HA) gene, Genbank Accession No. FJ966082.1, NCBI Entrez Nucleotide, 2 pages.
Ito et al. "Receptor Specificity of Influenza A Viruses Correlates with the Agglutination of Erythrocytes from Different Animal Species", Virology 227, 1997, pp. 493-499.
Johansen et al. "Silencing on the Spot, Induction and Suppression of RNA Silencing in the Agrobacterium-Mediated Transient Expession System", Plant Physiology, vol. 126, No. 3, Jul. 2001, pp. 930-938.
Johansson, Bert E., "Immunization with influenza A virus hemagglutinin and neuraminidase produced in recombinant baculovirus results in a balanced and broadened immune response superior to conventional vaccine", Vaccine, vol. 17, 1999, pp. 2073-2080.
Kang et al., "Influenza Vaccines Based on Virus-Like Particles", Virus Res., vol. 143, No. 2, Aug. 2009, 14 pages.
Klein et al., "High-Velocity Microprojectiles for Delivering Nucleic Acids into Living Cells", Nature, vol. 327, May 7, 1987, pp. 70-73.
Knossow et al., "Variation and infectivity neutralization in influenza", Immunology, vol. 119, 2006, pp. 1-7.
Latham et al., "Formation of Wild-Type and Chimeric Influenza Virus-Like Particles following Simultaneous Expression of Only Four Structural Proteins", Journal of Virology, vol. 75, No. 13, 2001, pp. 6154-6165.
Lefebvre et al., "Characterization of Lipid Rafts from Medicago truncatula Root Plasma Membranes: A Proteomic Study Reveals the Presence of a Raft-Associated Redox System", Plant Physiology, vol. 144, 2007, pp. 402-418.
Lin et al., "Genomic analysis of the Hsp70 superfamily in Arabidopsis thaliana", Cell Stress & Chaperones, vol. 6, No. 3, 2001, pp. 201-208.
Liu et al., "Agroinfection as a rapid method of propagating Cowpea mosaic virus-based constructs", Journal of Virological Methods, vol. 105, No. 2, 2002, pp. 343-348.
Low et al., "Future of antibody purification", Journal of Chromatography B, vol. 848, 2007, pp. 48-63.
Macala et al., "Analysis of brain lipids by high performance thin-layer chromatography and densitometry", Journal of Lipid Research, vol. 24, 1983, pp. 1243-1250.
Macario et al., Heat-shock proteins and molecular chaperones: implications for pathogenesis, diagnostics, and therapeutics, Int. J. Clin. Lab. Res.,vol. 25, 1995, pp. 59-70.
Mansour et al., "Plasma membrane lipid alterations induced by NaCl in winter wheat roots", Physiologia Plantarum, vol. 92, 1994, pp. 473-478.
Marozin et al., "Antigenic and Genetic Diversity among Swine Influenza A H1N1 and H1N2 viruses in Europe" Journal of General Virology, vol. 83, 2002, pp. 735-745.
Mason et al., "Expression of hepatitis B surface antigen in transgenic plants", Proc. Natl. Acad. Sci. USA, vol. 89, Dec. 1992, pp. 11745-11749.

(56) References Cited

OTHER PUBLICATIONS

Mason et al., "Expression of Norwalk virus capsid protein in transgenic tobacco and potato and its oral immunogenicity in mice", Proceedings of the National Academy of Sciences USA, vol. 93, 1996, pp. 5335-5340.
McCauley et al., "Structure and function of the influenza virus genome", Biochemical Journal, vol. 211, 1983, pp. 281-294.
McCormick et al., "Rapid Production Specific Vaccines for Lymphoma by Expression of the Tumor-Derived Single-Chain Fv Epitopes in Tobacco Plants" Proc. Natl. Acad. Sci. USA, vol. 96, Jan. 1999, pp. 703-708.
Medeiros et al., "Hemagglutinin Residues of Recent Human A(H3N2) Influenza Viruses That Contribute to the Inability to Agglutinate Chicken Erythrocytes", Virology, vol. 289, 2001, pp. 74-85.
Mena et al., "Rescue of Synthetic Chloramphenicol Acetyltransferase RNA into Influenza Virus-Like Patricles Obtained from Recombinant Plasmids", Journal of Virology, vol. 70, No. 8, 1996, pp. 5016-5024.
Meshcheryakova, et al., "Cowpea Mosaic Virus Chimeric Particles Bearing the Ectodomain of Matrix Protein 2 (M2E) of the Influenza A Virus: Production and Characterization", Molecular Biology, vol. 43, No. 4, 2009, pp. 685-694.
Mett et al., "A Plant-Produced Influenza Subunit Vaccine Protects Ferrets Against Virus Challenge", Influenza and Other Respiratory Viruses, vol. 2, 2008, pp. 33-40.
Moehnke et al., "The Expression of a Mountain Cedar Altergen Comparing Plant-Viral Apoplastic and Yeast Expression Systems", Biotechnol Lett, vol. 30, 2008, pp. 1259-1264.
Mongrand et al., "Lipid Rafts in Higher Plant Cells", The Journal of Biological Chemistry, vol. 279, No. 35, 2004, pp. 36277-36286.
Musiychuk et al., "A launch vector for the production of vaccine antigens in plants", Influenza and Other Respiratory Viruses, vol. 1, 2007, pp. 19-25.
Nakahara et al., "Glycoconjugate Data Bank:Structures—An Annotated Glycan Structure Database and N-Glycan Primary Structure Verification Service," Nucleic Acids Research, vol. 36, Database Issue, Nov. 4, 2007, pp. D368-D371.
Nemchinov et al., "Transient Expression of the Ectodomain of Matrix Protein 2 (M2e) of Avian Influenza A Virus in Plants", Protein Expression and Purification, vol. 56, 2007, pp. 153-159.
Neuhaus et al. "Transgenic Rapeseed Plants Obtained by the Microinjection of DNA into Microspore-Derived Embryoids", Theoretical and Applied Genetics, vol. 75, 1987, pp. 30-36.
Neumann et al., "Plasmid-Driven Formation of Influenza Virus-Like Particles", Journal of Virology, vol. 74, No. 1, 2000, pp. 547-551.
Newell et al., "Vacuole Development in Cultured Evacuolated Oat Mesophyll Protoplasts", Journal of Experimental Botany, vol. 49, No. 322, May 1998, pp. 817-827.
Nishimura et al., "Isolation of Intact Plastids Protoplasts Castor Bean Endosperm" Plant Physiol., vol. 62, 1978, pp. 40-43.
Nuttall et al., "ER-resident chaperone interactions with recombinant antibodies in transgenic plants", Eur. J. Biochem, vol. 269, 2002, pp. 6042-6051.
Olsen et al., "Immunogenicity and efficacy of baculovirus-expressed and DNA-based equine influenza virus hemagglutinin vaccines in mice", Vaccine, vol. 15, No. 10, 1997, pp. 1149-1156.
Parsell et al. "The Function of Heat-Shock Proteins in Stress Tolerance: Degradation and Reactivation of Damaged Proteins", Annu. Rev. Genet., vol. 27, 1993, pp. 437-496.
Plotkin et al., "Hemagglutinin sequence clusters and the antigenic evolution of influenza A virus", PNAS, vol. 99, No. 9, 2002, pp. 6263-6268.
Pushko et al., "Influenza virus-like particles comprised of the HA, NA, and M1 proteins of H9N2 influenza virus induce protective immune responses in BALB/c mice", Vaccine, vol. 23, 2005, pp. 5751-5759.
Pwee et al., "The pea plastocyanin promoter directs cell-specific but not full light-regulated expression in transgenic tobacco plants", The Plant Journal, vol. 3, No. 3, 1993, pp. 437-449.
Quan et al., "Virus-Like Particle Vaccine Induces Protective Immunity against Homologous and Heterologous Strains of Influenza Virus", Journal of Virology, vol. 81, No. 7, 2007, pp. 3514-3524.
Regnard et al., "High Level Protein Expression in Plants through the use of a Novel Autonomously Replicating Geminivirus Shuttle Vector", Plant Biotechnology Journal, vol. 8, 2010, pp. 38-46.
Rowe et al., "Detection of Antibody in Avian Influenza A (H5N1) Virus in Human Serum by Using a Combination of Serologic Assays", Journal of Clinical Microbiology, vol. 37, No. 4, 1999, pp. 937-943.
Roy et al., "Virus-like particles as a vaccine delivery system: Myths and facts", Human Vaccines, vol. 4, No. 1, 2008, pp. 5-12.
Saelens et al. "Protection of Mice Against a Lethal Influenza Virus Challenge After Immunization with Yeast-Derived Secreted Influenza Virus Hemagglutinin", Eur. J. Biochem, vol. 260,1999, pp. 166-175.
Office Action received for Thai Patent Application No. 1101003761, mailed on Apr. 9, 2013, 2 pages.
Office Action received for Indonesian Patent Application No. W-00201002481, mailed on Oct. 8, 2012, 2 pages.
Office Action received for Eurasian Patent Application No. 201001198/28, mailed on Apr. 28, 2012, 5 pages (2 page of English Translation and 3 pages of Office Action).
Air, Gillian M., "Sequence relationships among the hemagglutinin genes of 12 subtypes of influenza A virus", Proceedings of the National Academy of Sciences USA, vol. 76, No. 12, 1981, pp. 7639-7643.
Arntzen et al., "Plant-Derived Vaccines and Antibodies: Potential and Limitations", Vaccine, vol. 23, 2005, pp. 1753-1756.
Berger et al., "Plant sterols: factors affecting their efficacy and safety as functional food ingredients", Lipids in Health and Disease, vol. 3, No. 5, 2004, pp. 1-19.
Berman et al., "Correspondence: Announcing the Worldwide Protein Data Bank" Nature Structural Biology, vol. 10, No. 12, Dec. 2003, p. 980.
Bilang et al., "The 3'-Terminal Region of the Hygromycin-B-Resistance Gene is Important for its Activity in *Escherichia coli* and Nicotiana Tabacum", Gene, vol. 100, 1991, pp. 247-250.
De Block et al., "Transformation of Brassica Napus and Brassica Oleracea using Agrobacterium Tumefaciens and the Expression of the Bar and Neo Genes in the Transgenic Plants", Plant Physiol, vol. 91, 1989, pp. 694-701.
Borisjuk et al., "Expression of avian flu antigen for bird immunization", Plant Biology & Botany, 2007, Abstract only, 2 pages.
Bouic et al., "Plant Sterols and Sterolins: A Review of Their Immune-Modulating Properties", Alternative Medicine Review, vol. 4, No. 3, 1999, pp. 170-177.
Bouic, Patrick J.D., "Sterols and sterolins: new drugs for the immune system?", Drug Discovery Today, vol. 7, No. 14, 2002, pp. 775-778.
Bouic, Patrick J.D., "The role of phytosterols and phytosterolins in immune modulation: a review of the past 10 years", Current Opinion in Clinical Nutrition and Metabolic Care, vol. 4, 2001, pp. 471-475.
Bright et al., "Impact of Glycosylation on the Immunogenicity of a DNA-Based Influenza H5 HA Vaccine", Virology, vol. 308, 2003, pp. 270-278.
Brigneti et al., "Viral pathogenicity determinants are suppressors of transgene silencing in Nicotiana benthamiana", The EMBO Journal, vol. 17, No. 22, 1998, pp. 6739-6746.
Chandler, Garvin Lee, "Influenza Hemagglutinin Expression in Nicotiana trabacum and Nicotiana benthamiana", Masters in Science Thesis, Baylor University, Waco, Texas, 2007, 70 pages.
Chandrasekaran et al., "Glycan topology determines human adaptation of avian H5N1 virus hemagglutinin", Nature Biotechnology, vol. 26, No. 1, 2008, pp. 107-113.
Charland et al., "An Innovative VLP-based Technology to respond to Global Influenza Vaccine Needs", Poster Abstracts, IDSA Seasonal and Pandemic Influenza Meeting, Arlington, Virginia, USA, 2008, pp. 1-42.

(56) References Cited

OTHER PUBLICATIONS

Chen et al., "Influenza Virus Hemagglutinin and Neuraminidase, but Not the Matrix Protein, Are Required for Assembly and Budding of Plasmid-Derived Virus-Like Particles", Journal of Virology, vol. 81, No. 13, 2007, pp. 7111-7123.
Chen et al., "Stabilizing the glycosylation pattern of influenza B hemagglutinin following adaptation to growth in eggs", Vaccine, vol. 26, 2008, pp. 361-371.
Chiba et al., "Diverse suppressors of RNA silencing enhance agroinfection by a viral replicon", Virology, vol. 346, 2006, pp. 7-14.
Cosgrove, Daniel J., "Loosening of Plant Cell Walls by Expansins" Nature, vol. 407, Sep. 2000, pp. 321-326.
Crawford et al., "Baculovirus-derived hemagglutinin vaccines protect against lethal influenza infections by avian H5 and H7 subtypes", Vaccines, vol. 17, 1999, pp. 2265-2274.
Cross et al., "Studies on influenza haemagglutinin fusion peptide mutants generated by reverse genetics", The EMBO Journal, vol. 20, No. 16, 2001, pp. 4432-4442.
D'Aoust et al., "The Production of Hemagglutinin-Based Virus-Like Particles in Plants: A Rapid, Efficient and Safe Response to Pandemic Influenza", Plant Biotechnology Journal, vol. 8, 2010, pp. 607-619.
D'Aoust et al., "Influenza virus-like particles produced by transient expression in Nicotiana benthamiana induce a protective immune response against a lethal viral challenge in mice", Plant Biotechnolgy Journal, vol. 6, 2008, pp. 930-940.
Davey et al., "Plant protoplasts: Status and Biotechnological Perspectives", Biotechnology Advances, vol. 23, 2005, pp. 131-171.
Diaz-Vivancos et al., "The apoplastic antioxidant system in Prunus: response to long-term plum pox virus infection", Journal of Experimental Botany, vol. 57, No. 14, 2006, pp. 3813-3824.
Fischer et al., "Affinity-purification of a TMV-specific recombinant full-size antibody from a transgenic tobacco suspension culture", Journal of Immunological Methods, vol. 226, 1999, pp. 1-10.
Flandorfer et al., "Chimeric Influenza A Viruses with a Functional Influenza B Virus Neuraminidase or Hemagglutinin", Journal of Virology, vol. 77, No. 17, Sep. 2003, pp. 9116-9123.
Frugis et al., "MsJ1, an alfalfa DnaJ-like gene, is tissue-specific and transcriptionally regulated during cell cycle", Plant Molecular Biology, vol. 40, 1999, pp. 397-408.
Galarza et al., "Virus-Like Particle (VLP) Vaccine Conferred Complete Protection against a Lethal Influenza Virus Challenge", Viral Immunology, vol. 18, No. 1, 2005, pp. 244-251.
Gallagher et al., "Addition of Carbohydrate Side Chains at Novel Sites on Influenza Virus Hemagglutinin Can Modulate the Folding, Transport, and Activity of the Molecule", The Journal of Cell Biology, vol. 107, No. 6, Pt. 1, Dec. 1988, pp. 2059-2073.
Gallagher et al., "Glycosylation Requirements for Intracellular Transport and Function of the Hemagglutinin of Influenza Virus", Journal of Virology, vol. 66, No. 12, Dec. 1992, pp. 7136-7145.
Gamblin et al.. "The Structure and Receptor Binding Properties of the 1918 Influenza Hemagglutinin", Science, vol. 303, 2004, pp. 1838-1842.
Garcea et al., "Virus-like particles as vaccines and vessels for the delivery of small molecules", Current Opinion in Biotechnology, vol. 15, 2004, pp. 513-517.
Gillim-Ross et al., "Emerging Respiratory Viruses: Challenges and Vaccine Strategies", Clinical Microbiology Reviews, vol. 19, No. 4, 2006, pp. 614-636.
Giridhar et al., "Increased Protoplast Yield from oat Leaves and Bean Internodes by Non-Injurious Mechanical Perturbation", Protoplasma, vol. 151, 1989, pp. 151-157.
Giritch et al., "Rapid High-Yield Expression of Full-Size IgG Antibodies in Plants Coinfected with Noncompeting Viral Vectors", PNAS, vol. 103, No. 40, Oct. 3, 2006, pp. 14701-14706.
Gomez-Puertas et al., "Efficient formation of influenza virus-like particles: dependence on the expression levels of viral proteins", Journal of General Virology, vol. 80, 1999, pp. 1635-1645.

Gomez-Puertas et al., "Influenza Virus Matrix Protein is the Major Driving Force in Virus Budding", Journal of Virology, vol. 74, No. 24, 2000, pp. 11538-11547.
Gomord et al., "Biopharmaceutical Production in Plants: Problems, Solutions and Opportunities", Trends in Biotechnology, vol. 23, No. 11, Nov. 2005, pp. 559-565.
Greco, et al., "Production of Recombinant HIV-1/HBV Virus-Like Particles in *Nicotiana tabacum* and *Arabidopsis thaliana* Plants for a Bivalent Plant-Based Vaccine", Science Direct Vaccine, vol. 25, 2007, pp. 8228-8240.
Grgacic et al., "Virus-like particles: Passport to immune recognition", Methods, vol. 40, 2006, pp. 60-65.
Guerche et al., "Direct Gene Transfer by Electroporation in Brassica Napus", Plant Science, vol. 52, 1987, pp. 111-116.
Gupta et al., "O-GLYCBASE version 4.0: a revised database of O-glycosylated proteins", Nucleic Acids Research, vol. 27, No. 1, 1999, pp. 370-372.
Hahn et al., "Expresssion of hemagglutinin-neuraminidase protein of Newcastle disease virus in transgenic tobacco", Plant Biotechnology Reporter, vol. 1, 2007, pp. 85-92.
Hamilton et al., "Two classes of short interfering RNA in RNA silencing", The EMBO Journal, vol. 21, No. 17, 2002, pp. 4671-4679.
Harbury et al., "A Switch Between Two-, Three-, and Four-Stranded Coiled Coils in GCN4 Leucine Zipper Mutants", Science, vol. 262, 1993, pp. 1401-1407.
Hartl, F. Ulrich., "Molecular chaperones in cellular protein folding", Nature, vol. 381, Jun. 13, 1996, pp. 571-580.
Hellwig et al., "Plant Cell Cultures for the Production of Recombinant Proteins", Nature Biotechnology, vol. 22, No. 11, Nov. 2004, pp. 1415-1422.
Horimoto et al., "Generation of Influenza A Viruses with Chimeric (Type A/B) Hemagglutinins", Journal of Virology, vol. 77, No. 14, Jul. 2003, pp. 8031-8038.
Horsch et al. "A Simple and General Method for Transferring Genes into Plants", Science, vol. 227, Mar. 8, 1985, pp. 1229-1231.
Office Action received for European Patent Application No. 08783201.0, mailed on Oct. 26, 2012, 3 pages.
Extended European Search Report received for European Patent Application No. 12181077.4, mailed on Feb. 15, 2013, 7 pages.
Restriction Requirement Received for U.S. Appl. No. 12/669,033, mailed on Aug. 13, 2012, 8 pages.
Restriction Requirement Received for U.S. Appl. No. 12/863,772, mailed on Sep. 27, 2012, 9 pages.
Non Final Office Action received for U.S. Appl. No. 12/863,772, mailed on Dec. 14, 2012, 8 pages.
Non Final Office Action received for U.S. Appl. No. 13/001,111, mailed on Apr. 2, 2013, 10 pages.
Office Action received for Canadian Patent Application No. 2,693,956, mailed on Mar. 1, 2013, 2 pages.
Office Action received for Canadian Patent Application No. 2,693,956, mailed on Oct. 16, 2012, 2 pages.
Office Action received for Canadian Patent Application No. 2,707,235, mailed on Mar. 1, 2013, 2 pages.
Office Action received for Canadian Patent Application No. 2,707,235, mailed on Sep. 28, 2012, 2 pages.
Office Action received for Australian Patent Application No. 2008278222 mailed on issued May 21, 2013, 3 pages.
Office Action received for Chinese Patent Application No. 200880107072.9, issued on Feb. 21, 2013, 10 pages (6 pages of English Translation and 4 pages of Office Action).
Office Action received for Chinese Patent Application No. 200980109781.5 issued on Nov. 27, 2012, 8 pages (5 pages of English Translation and 3 pages of Office Action).
Office Action received for Chinese Patent Application No. 200980126670.5, issued on Mar. 15, 2013, 14 pages (9 pages of English Translation and 5 pages of Office Action).
Office Action received for Chinese Patent Application No. 200980126670.5, issued on Nov. 5, 2012, 18 pages (10 pages of English Translation and 8 pages of Office Action).
Office Action received for Chinese Patent Application No. 200980136376.2 issued on Mar. 8, 2013, 9 pages (6 pages of English Translation and 3 pages of Office Action).

(56) References Cited

OTHER PUBLICATIONS

Office Action received for Chinese Patent Application No. 201080042333.0, issued on Mar. 1, 2013, 20 pages (12 pages of English Translation and 8 pages of Office Action).
Office Action received for Russian Patent Application No. 2011105073/10, mailed on Apr. 5, 2013, 9 pages (4 pages of English Translation and 5 pages of Office Action).
Office Action received for Japanese Patent Application No. 2012-516452, mailed on May 28, 2013, 8 pages (3 pages of English Translation and 5 pages of Office Action).
Office Action received for Israel Patent Application No. 210215, mailed on Oct. 25, 2012, 4 pages (2 pages of English Translation and 2 pages of Office Action.
Examination Report received for New Zealand Patent Application No. 587108, mailed on Jan. 28, 2013, 2 pages.
Examination Report received for New Zealand Patent Application No. 598481, mailed on Nov. 14, 2012, 2 pages.
Examination Report received for New Zealand Patent Application No. 598508, mailed on Nov. 15, 2012, 2 pages.
Asahi-Ozaki et al., "Intranasal Administration of Adjuvant-Combined Recombinant Influenza Virus HA Vaccine Protects Mice from the Lethal H5NI Virus Infection", Microbes and Infection, vol. 8, 2006, pp. 2706-2714.
Bright et al., "Influenza Virus-Like Particles Elicit Broader Immune Responses than Whole Virion Inactivated Influenza Virus or Recombinant Hemagglutinin", Vaccine, vol. 25, 2007, pp. 3871-3878.
Firek et al., "Secretion of a Functional Single-Chain Fv Protein in Transgenic Tobacco Plants and Cell Suspension Cultures", Plant Molecular Biology, vol. 23, 1993, pp. 861-870.
Fischer et al., "Towards Molecular Farming in the Future: Transient Protein Expression in Plants", Biotechnol. Appl. Biochem., vol. 30, 1999, pp. 113-116.
Garten et al., "Antigenic and Genetic Characteristics of.Swine-Origin 2009 A(H1N1) Influenza Viruses Circulating• in Humans", Science, vol. 325, Jul. 10, 2009, pp. 197-201.
Garten et al., "Emergence of a Novel Swine-Origin Influenza A (H1N1) Virus in Humans", The New England Journal of Medicine, vol. 360, No. 25, Jun. 18, 2009, pp. 2605-2615.
Garten et al., "Influenza A Virus (A/California/0412009(H1 N1)) Segment 4 Hemagglutinin (HA) Gene, Complete Cds", retrieved from Internet on Aug. 28, 2010 <http://www.ncbi.nlm.nih.gov/nuccore/227809829>, 2009, 2 pages.
Hatta et al., "Molecular Basis for High Virulence of Hong Kong H5N1 Influenza A Viruses", Science, vol. 293, Sep. 7, 2001, pp. 1840-1842.
Horimoto et al., "The Development and Characterization of H5 Influenza Virus Vaccines Derived from a 2003 Human Isolate", Vaccine, vol. 24, 2006, pp. 3669-3676.
Houston et al., "Phylogenetic Analyses Identify 10 Classes of the Protein Disulfide Isomerase Family in Plants, Including Single-Domain Protein Disulfide Isomerase-Related Proteins", Plant Physiology, vol. 137, Feb. 2005, pp. 762-778.
Li et al., "Influenza A Virus Transfectants with Chimeric Hemagglutinins Containing Epitopes from Different Subtypes", Journal of Virology, vol. 66, No. 1, Jan. 1992, pp. 399-404.
Mori et al., "A Novel Amino Acid Substitution at the Receptor-Binding Site on the Hemagglutinin of H3N2 Influenza A Viruses Isolated from 6 Cases with Acute Encephalopathy during the 1997-1998 Season in Tokyo", Archives of Virology, vol. 144, 1999, pp. 147-155.
Nobusawa, Eri, "Protective Antigen of Influenza Virus", Department of Virology, Nagoya City University, Medical School, vol. 55, No. 10, 1997, pp. 2719-2724 (English Abstract Submitted).
Paul et al., "Mutational Analysis of the Human Immunodeficiency Virus Type 1 Vpu Transmembrane Domain That Promotes the Enhanced Release of Virus-Like Particles from the Plasma Membrane of Mammalian Cells", Journal of Virology, vol. 72, No. 2, Feb. 1998, pp. 1270-1279.

Richter et al., "Production of Hepatitis B Surface Antigen in Transgenic Plants for Oral Immunization", Nature Biotechnology, vol. 18, Nov. 2000, pp. 1167-1171.
Shorrosh et al., "Sequence Analysis and Developmental Expression of an Alfalfa Protein Disulfide Isomerase", Plant Molecular Biology, vol. 19, 1992, pp. 319-321.
Twyman et al., "Molecular Farming in Plants: Host Systems and Expression Technology", Trends in Biotechnology, vol. 21, No. 12, Dec. 2003, pp. 570-578.
Weissenhorn et al., "Assembly of a Rod-Shaped Chimera of a Trimeric GCN4 Zipper and the HIV-1 gp41 Ectodomain Expressed in *Escherichia coli*", Proc. Natl. Acad. Sci. USA, vol. 94, Jun. 1997, pp. 6065-6069.
Yang et al., "Immunization by Avian H5 Influenza Hemagglutinin Mutants with Altered Receptor Binding Specificity", Science, vol. 317, Aug. 10, 2007, pp. 825-828.
International Search Report received for PCT Patent Application No. PCT/CA2012/050681, mailed on Feb. 18, 2013, 7 pages.
Office Action received for Eurasian Patent Application No. 201001198/28, mailed on Apr. 24, 2013, 3 pages (1 page of English Translation and 2 pages of Office Action).
Office Action received for Israel Patent Application No. 210451, mailed on Nov. 25, 2012, 2 pages.
Office Action received for Mexican Patent Application No. MX/a/2010/000525, mailed on Mar. 20, 2013, 4 pages.
Office Action received for Mexican Patent Application No. MX/a/2010/007962, mailed on Mar. 27, 2013, 4 pages.
Office Action received for Mexican Patent Application No. MX/a/2011/000459, mailed on Mar. 25, 2013, 3 pages.
Office Action received for Mexican Patent Application No. MX/a/2011/000657, mailed on May 13, 2013, 2 pages.
Office Action received for Mexican Patent Application No. MX/a/2011/000657, mailed on Oct. 5, 2012, 3 pages.
Anonymous: Protoplast preparation (from plant tissue), Dec. 1, 2006 (URL: http://www.ivaan.com/protocols/128.html).
Bertoli, D J., et al. Transgenic plants and insect cells expressing the coat protein of arabis mosaic virus produce empty virus-like particles. J. Gen Virol. 1991. vol. 72:8, pp. 1801-1809.
Biemelt, Sophia, et al. Production of Human Papillomavirus Type 16 Virus-Like particles in Transgenic Plants. J. of Virology, Sep. 2003, pp. 9211-9220.
Copeland, K.M., et al. Functional Chimeras of Human Immunodeficiency Virus Type 1 gp 120 and Influenza A Virus (H3) Hemagglutinin. J of Virol 2005, pp. 6459-6471.
Doyle, C., et al. Analysis of Progressive Deletions of the Transmembrane and Cytoplasmic Domains of Influenza Hemagglutinin. Journal of Cell Biology, 103, pp. 1193-1204, 1986.
Eckert, D., et al. Crystal Structure of GCN4-pIQI, a Trimeric Coiled Coil with Buried Polar Residues. Journal of Molecular Biology, 1998, vol. 284, pp. 859-865.
Ellis, R.J. The molecular chaperone concept. Seminars in Cell Biology, 1990 (1):1-9 (abstract only).
Genbank Accession AFU70328 Influenza A/Vietnam/1203/04 (H5N1) virus HA protein VN1203-ha-spc-opt.
Giddings, G., et al. Transgenic plants as factories for biopharmaceuticals. Nature Biotech. 18, pp. 1151-1155, 2000.
Influenza A virus (A/Caledonia/20/99(H1N1)) hemagglutinin (HA) gene. Genbank Accession No. AY289929, 2003.
Haynes, J. Influenza virus-like particle vaccines. Expert Reviews Vaccines 8(4), 435-445 (2009).
Kaverin, N., et al. Structural Differences among Hemagglutinins of Influenza A Virus Subtypes are Reflected in Their Antigenic Architecture: Analysis of H9 Escape Mutants. J. of Virol. 78:1, pp. 240-249, 2004.
Klopfleisch, R., et al. Neurotropism of Highly Pathogenic Avian Influenza Virus A/Chicken/Indonesia/2003 (H5N1) in Experimentally Infected Pigeons (*Columbia livia* f. domestica). Vet Pathol. vol. 43, pp. 463-470, 2006.
Kobayashi, Y. et al. Chaperones Hsp70 and Hsp40 Suppress Aggregate Formation and Apoptosis in cultured Neuronal Cells Expressing Truncated Androgen Receptor Protein with Expanded Polyglutamine Tract. (The Journal of Biological Chemistry, 275(12), pp. 8772-8778, 2000).

(56) References Cited

OTHER PUBLICATIONS

Lelivelt, C., et al. Stable Plastic Transformation in Lettuce (*Lactuca sativa* L.). Plant Molecular Biology vol. 58, pp. 763-774, 2005.
Liu, L., et al. Cowpea mosaic virus-based systems for the production of antigens and antibodies in plants. Vaccine 23 (2005) pp. 1788-1792.
Ma, Julian K-C., et al. The Production of Recor,nbinant Pharmaceutical Proteins in Plants. Nature 2003, vol. 4, pp. 794-805.
Mishin, V. et al. Effect of Hemagglutinin Glycosylation on Influenza Virus Susceptibility to Neuraminidase Inhibitors. Journal of Virology 2005, pp. 12416-12424.
Rivard, D., et al. An in-built proteinase inhibitor system for the protection of recombinant proteins recovered from transgenic plants. Plant Biotechnology Journal, 4, pp. 359-368, 2006.
Smith, C. Accession EF541394 Influenza A virus (A/Indonesia/5/2005(H5N1)).
Spitsin, S. et al. Immunological assessment of plant-derived avian flu H5/HA1 variants. Vaccine 27 (2009) 1289-1292.
Tatulian, S., et al. Secondary Structure, Orientation, Oligomerization, and Lipid Interactions of the Transmembrane domain of Influenza Hemagglutinin. Biochemistry, 2000, v. 39, pp. 496-507.
Warzecha, H. Biopharmaceuticals from Plants: A multitude of Options for Posttranslational Modifications. Biotechnology and Genetic Engineering Reviews, vol. 25, pp. 315-330, 2008.
Webby, G.N., et al. Purification of the NY-RMV and NY-SGV Isolates of Varley Yellow Dwarf Virus and the Production and Properties of their Antibodies. Plant Disease, Nov. 1992 pp. 1125-1132.
Whitelam, G. The Production of Recombinant Proteins in Plants. (J Sci Food Agric, 68, pp. 1-9, 1995).
Wickramasinghe, S.R., et al. Tangential Flow Microfiltration and Ultrafiltration for HumanInfluenza A Virus Concentration and Purification. Biotechnology and Bioengineering, vol. 92:2, Oct. 20, 2005, pp. 199-208.
Wiley, D.C., et al. The Structure and Function of the Hemagglutinin Membrane Glycoprotein of Influenza Virus. Annual Review of Biochemistry, vol. 56(1), pp. 365-394, 1987.
Yigzaw, Y., et al. Exploitation of the Adsorptive Properties of Depth Filters for Host Cell Protein Removal during Monoclonal Antibody Purification. Biotechnol. Prog. 2006, vol. 22, pp. 288-296.
Office Action dated Jun. 13, 2013 re Australian application AU 2009202819.
Office Action dated Mar. 26, 2014 re AU app 2009267769.
Office Action dated Dec. 18, 2013 re AU application 2010265766.
Exam Report dated Nov. 6, 2013 re Australian application AU 2010300034.
CA 2,707,235 Notice of Allowance dated Aug. 14, 2013.
Office Action dated Jun. 2, 2014 re CA 2,730,185.
CA 2,815,887 Notice of Allowance Aug. 7, 2013.
Office Action dated Jul. 23, 2013 re Chinese application CN 200980126670.5 (Chinese version with English-language translation).
Office Action dated Jan. 15, 2013 re Chinese application CN 200980134868.8 O.A. Jan. 15/13 (Chinese and English-language translation in one document).
Office Action dated May 30, 2013 re Chinese application CN 200980134868.8 (Chinese version with English-language translation).
Decision on Rejection dated Feb. 20, 2014 re CN application CN 200980134868.8 (Chinese and English-language translation in one document).
Office Action dated Mar. 4, 2014 re CN application 011800641274 (Chinese and English-language translation in one document).
Office Action dated Oct. 10, 2013 re Chinese application CN 200980136376.2 (Chinese version with English-language translation).
Office Action Jul. 1, 2014 re CN application 200980136376.2 (Chinese version with English-language translation).
Office Action dated Jun. 28, 2013 re Chinese application CN 201080035066.4 (Chinese version with English-language translation).
Office Action dated Feb. 19, 2014 re Chinese Application CN 201080035066.4 (Chinese and English-language translation in one document).
Notice of Allowance Aug. 20, 2014 re CN 201080035066.4 (Chinese and English-language translation in one document).
Office Action dated Nov. 19, 2013 re Chinese application CN 201080042333.0 (Chinese version with English-language translation).
Decision on Rejection May 28, 2014 re CN 201080042333.0 (Chinese version with English-language translation).
CN 201080042336.4 Office Action dated Jul. 29, 2013 (Chinese version with English-language translation).
Office Action dated Apr. 24, 2014 re CN 201080042336.4 (Chinese and English-language translation in one document).
Office Action dated Sep. 23, 2014 re CN application 201310021693.8 (Chinese and English-language translation in one document).
Office Action dated Dec. 26, 2013 re Eurasian application EA 201001198 (English and Russian versions).
Office Action dated Sep. 3, 2014 re Eurasian App EA 201001198 (Russian and English versions).
Office Action dated Aug. 27, 2013 re Egyptian application EG PCT 61/2010 (English and Arabic versions).
Office Action Sep. 3, 2014 re EG application PCT 61/2010 (English and Arabic in one document).
Office Action dated Oct. 8, 2013 re European application EP 10791119.0.
Exam Report dated Aug. 1, 2013 re European application EP 09793751.0.
Supp. Search Report Apr. 10, 2014 EP 11 83 7364.
Office Action Feb. 6, 2014 re European application 09797336.6.
European Office Action re EP 10791119.0 dated Jul. 4, 2014.
EP 10818191.8 ESR Jan. 3, 2013.
EP 10818191.8 Exam Rpt Oct. 23, 2013.
EP 10818191.8 Office Action Aug. 18, 2014.
EP 10818190.0 ESR Jan. 28, 2013.
EP 10818190.0 Exam Report Oct. 23, 2013.
EP 10818190.0 Office Action Oct. 6, 2014.
Office Action dated May 10, 2013 re Indonesian application ID W-0020102481 (English and Indonesian versions in one document).
Office Action dated Sep. 22, 2014 re ID W-0020102481(English and Indonesian versions in one document).
Office Action dated Aug. 18, 2013 re Israeli application IL 203018 (English only).
Office Action Mar. 30, 2014 re Israeli app 216937 (English only).
Office Action dated Jan. 15, 2014 re JP application 2011-516934 (English only).
IPRP PCT/CA2009/000032 Jul. 27, 2010.
IPRP PCT/CA2009/000941 Jan. 11, 2011.
IPRP PCT/CA2011/001228 Dec. 4, 2012.
Office Action dated Jul. 17, 2013 re Japanese application JP 2010-516334 (English and Japanese versions).
Office Action dated Jan. 15, 2013 re JP application 2010-516334 (English and Japanese versions).
Office Action dated Aug. 30, 2013 re Japanese application JP 2010-542486 (English and Japanese versions).
Office Action dated Jan. 6, 2014 re JP application 2011-516935 (English and Japanese versions).
Office Action dated Feb. 13, 2014 re JP application 2011-517725 (English and Japanese versions).
Final Rejection re Japanese application JP 2012-516452 of Dec. 3, 2013 (English and Japanese versions).
Reconsideration Report re JP 2012-516452 Jul. 18, 2014 (English and Japanese versions).
JP 2012-530059 OA Jun. 11, 2013 (English only).
JP 2012-530059 OA Oct. 22, 2013 (English and Japanese versions).
Japanese application JP 2012-530060 Office Action dated Oct. 29, 2013 (English and Japanese versions).
JP granted patent 5551780 (application 2012-530060) May 30, 2014 (Japanese only).

(56) References Cited

OTHER PUBLICATIONS

Office Action dated Aug. 7, 2013 re Korean application KR 10-2012-7001798 (English and Korean versions).
Office Action dated Sep. 15, 2014 re Malaysian app PI2010000142.
Office Action dated Dec. 5, 2013 re Mexican application MX/a/2010/007962 (English and Spanish versions).
Office Action dated May 20, 2013 re Mexican application MX/a/2011/000657 (English and Spanish in one document).
Office Action dated Oct. 29, 2013 re Mexican application MX/a/2011/000657 (English and Spanish versions).
Office Action dated Jul. 9, 2014 re MX/a/2011/000657 (English and Spanish versions).
Office Action dated Feb. 11, 2014 re MX application MX/a/2012/003372 (Letter from foreign associate—English only).
Office Action dated Aug. 27, 2014 re MX/a/2012/003372 (English and Spanish versions).
Office Action Jul. 14, 2014 re MX/a/2012/003373 (English and Spanish versions).
NZ Letters Patent 598508.
Office Action dated Oct. 21, 2013 re Russian application 2011105073/10 (English and Russian versions).
RU 2011105885/10 Office Action dated Aug. 1, 2013 (English and Russian versions).
Office Action Feb. 27, 2014 re Russian app. 2011105885/10 (English and Russian versions).
Office Action Sep. 29, 2014 re RU 2012115661(English and Russian on one document).
Office Action Jun. 19, 2014 re Russian App. 2012115996 (English and Russian versions).
Office Action Jun. 26, 2014 re Russian app. 2012101946 (English and Russian versions).
Cert. of Grant re SG 187500 Aug. 26, 2014.
Search Report and Written Opinion Apr. 16, 2014 re SG 2012014718.
South Africa Letters Patent 2010/05917.
Office Action Sep. 18, 2014 re Thailand app TH 1101003761 (English and Thai versions in one document).
Notice of Allowance dated Oct. 28, 2013 re U.S. Appl. No. 13/001,111.
U.S. Appl. No. 13/054,452, OA Jul. 12, 2013.
U.S. Appl. No. 13/054,452 final OA May 8, 2014.
U.S. Appl. No. 13/748,531 OA Sep. 12, 2013.
U.S. Appl. No. 13/748,531 OA Jun. 18, 2014.
U.S. Appl. No. 13/497,767 OA Sep. 4, 2014.
U.S. Appl. No. 13/003,570 OA Jul. 17, 2013.
U.S. Appl. No. 13/003,570 final OA May 8, 2014.
Office Action dated Jan. 3, 2014 re U.S. Appl. No. 13/380,346.
Office Action May 21, 2014 re U.S. Appl. No. 13/380,346.
Office Action Aug. 28, 2014 re U.S. Appl. No. 13/497,757.
Canizares, M., et al. A bipartite system for the constitutive an inducible expression of high levels of foreign proteins in plants. Plant Biotechnology Journal (2006), vol. 4, pp. 183-193.
Gomord, V., et al. Plant-specific glycosylation patterns in the context of therapeutic protein productions. Plant Biotech Journal (2010) vol. 8, pp. 564-587.
Helenius, A., et al. Roles of N-Linked Glycans in the Endoplasmic Reticulum. Annu. Rev. Biochem. 2004, 73: pp. 1019-1049.
Novel Swine-Origin Influenza A (H1N1) Virus Investigation Team. Emergence of a Novel Swine-Origin Influenza A (H1N1) Virus in Humans. The New England Journal of Medicine, 2009, vol. 360:25. pp. 2605-2615.
Sorensen, Hans Peter. Advanced genetic strategies for recombinant protein expression in *Escherichia coli*. Journal of Biotechnology 115 (2005) pp. 113-128.
Wang, Wangxia, et al. Role of plant heat-shock proteins and molecular chaperones in the abiotic stress response. TRENDS in Plant Science, vol. 9:5, 2004, pp. 244-252.
Yokoyama, Naoaki, et al. Co-expression of human chaperone Hsp70 and Hsdj or Hsp40 co-factor increases solubility of overexpressed target proteins in insect cells. Biochimica et Biophysica Acta 1493 (2000) pp. 119-124.
Exam Report Dec. 16, 2014 re AU 2009270404.
Exam Report May 7, 2015 re AU 2009270404.
Notice of Acceptance re AU 2010300033 Dec. 17, 2014.
Exam Report dated Dec. 24, 2014 re AU 2010300034.
CA 2,730,171 Office Action May 4, 2015.
Office Action dated Apr. 14, 2015 re CA 2,730,668.
Office Action Nov. 26, 2014 re CN 201180064127.4.
Office Action Mar. 25, 2015 re CN 200980136376.2.
Office Action Nov. 15, 2014 re CN 201080042336.4.
Office Action dated Jan. 13, 2014 re Chinese application 201310021693.8.
Decision to Grant EP 09793751.0 dated Apr. 23, 2015.
Office Action Mar. 27, 2015 re EP 11837364.6.
Intent to Grant EP 09793751.0 Dec. 10, 2014.
Office Action Jan. 9, 2015 re ID W-00201002481.
Office Action Jan. 13, 2015 re JP app. 2011-516934.
Office Action Sep. 28, 2014 re Israeli app IL 218393.
Office Action Oct. 21, 2014 re IL 218422.
Final Office Action Dec. 24, 2014 re JP 2011-516935 (with translation).
Office Action Jan. 26, 2015 re JP 2011-517725.
Office Action Dec. 22, 2014 re KR 10-2010-7002538.
Office Action Feb. 16, 2015 re MX/a/2012/003373.
NZ Letters Patent 598481.
Exam Report Jan. 30, 2015 re NZ app 622731.
Decision of Grant Jan. 23, 2015 re RU 2011105885/10.
Office Action Nov. 12, 2014 re RU 2012115996/10.
Office Action Jan. 22, 2015 re RU app. 2012101946.
U.S. Appl. No. 13/054,452 OA Feb. 9, 2015.
U.S. Appl. No. 13/748,531 OA Jan. 5, 2015.
U.S. Appl. No. 13/003,570 OA Feb. 11, 2015.
Office Action Feb. 9, 2015 re U.S. Appl. No. 13/380,346.
Certificate of Grant dated May 27, 2015 issued in Israeli app. IL 203018.
Decision on Rejection dated May 28, 2015 issued in Chinese Patent Application No. CN 201080042336.4.
Decision to Grant dated Aug. 11, 2015 issued in Japanese Patent Application No. JP 2011-516935.
Decision to Grant dated Aug. 12, 2015 issued in Japanese Patent Application No. JP 2011-517725.
Decision to Grant dated Jul. 20, 2015 issued in Korean Patent Application No. KR 10-2010-7002538.
Exam Report dated Aug. 6, 2015 issued in Indian Patent Application No. 212/DELNP/2010.
Extended European Search Report dated May 12, 2015 issued in European Patent Application No. EP 12836545.9.
Final Office Action dated Jun. 23, 2015 in U.S. Appl. No. 13/748,531.
Notice of Acceptance issued in Australian Patent Application No. AU 2009267769 dated Jul. 2, 2015.
Notice of Allowance dated Jun. 1, 2015 issued in Canadian Patent Application CA 2,730,185.
Notice of Allowance dated May 5, 2015 issued in Russian Patent Application No. RU 012115996.
Notice of Re-Exam dated May 26, 2015 issued in Chinese Patent Application No. CN 200980126670.5 (Eng. Translation).
Office Action dated Aug. 12, 2015 issued in European Patent Application No. 09797336.6.
Office Action dated Aug. 19, 2015 issued in Korean Patent Application No. KR 10-2011-7002827.
Office Action dated Jun. 24, 2015 issued in Chinese Patent Application No. CN 201280047819.2 (associate's translation).
Office Action dated Jun. 24, 2015 issued in Russian Patent Application No. RU 2012115661 (associate's translation).
Office Action dated Jun. 24, 2015 issued in U.S. Appl. No. 13/497,767.

(56) References Cited

OTHER PUBLICATIONS

Office Action dated Jun. 25, 2015 issued in U.S. Appl. No. 13/497,757.
Office Action dated May 21, 2015 issued in Korean Patent Application No. KR 10-2010-7018343.
Office Action dated May 26, 2015 issued in Chinese Patent Application No. CN 201310021693.8.
Office Action dated May 27, 2015 issued in Japanese Patent Application No. JP 2014-039035 (translation by foreign associate).
Office Action dated Sep. 25, 2015 issued in European Patent Application No. EP 10818190.0.
Office Action dated Sep. 7, 2015 issued in Chinese Patent Application No. CN 201180064127.4.
Power, J.B., et al., "A Simple Method for the Isolation of Very Large Numebrs of Leaf Protoplasts by using Mixtures of Cellulase and Pectinase." Biochem J., 111(5), 1969, 33P.
Search Report and Written Opinion dated Aug. 14, 2015 issued in Singapore Patent Application No. SG 2013053467.
Takahashi, Y., et al., "A high-throughput screen of cell-death-inducing factors in Nicotiana benthamiana identifies a novel MAPKK that mediates INF1-induced cell death signaling and non-host resistance to Pseudomonas cichorii." The Plant Journal (2007) 49, pp. 1030-1040.
Wang, K., et al., "Viral proteins function as ion channels", Biochimica et Biophysica Acta. vol. 1808:2, Feb. 2011, pp. 510-515.

\* cited by examiner

AGAGGTACCCCGGGCTGGTATATTTATATGTTGTCAAATAACTCAAAAACCATA
AAAGTTTAAGTTAGCAAGTGTGTACATTTTACTTGAACAAAAATATTCACCTAC
TACTGTTATAAATCATTATTAAACATTAGAGTAAAGAAATATGGATGATAAGAAC
AAGAGTAGTGATATTTTGACAACAATTTTGTTGCAACATTTGAGAAAATTTTGTT
GTTCTCTCTTTTCATTGGTCAAAAACAATAGAGAGAGAAAAAGGAAGAGGGAG
AATAAAAACATAATGTGAGTATGAGAGAGAAAGTTGTACAAAAGTTGTACCAAA
ATAGTTGTACAAATATCATTGAGGAATTTGACAAAAGCTACACAAATAAGGGTT
AATTGCTGTAAATAAATAAGGATGACGCATTAGAGAGATGTACCATTAGAGAAT
TTTTGGCAAGTCATTAAAAAGAAAGAATAAATTATTTTTAAAATTAAAAGTTGAG
TCATTTGATTAAACATGTGATTATTTAATGAATTGATGAAAGAGTTGGATTAAAG
TTGTATTAGTAATTAGAATTTGGTGTCAAATTTAATTTGACATTTGATCTTTTCCT
ATATATTGCCCCATAGAGTCAGTTAACTCATTTTTATATTTCATAGATCAAATAA
GAGAAATAACGGTATATTAATCCCTCCAAAAAAAAAAAACGGTATATTTACTAAA
AAATCTAAGCCACGTAGGAGGATAACAGGATCCCCGTAGGAGGATAACATCCA
ATCCAACCAATCACAACAATCCTGATGAGATAACCCACTTTAAGCCCACGCATC
TGTGGCACATCTACATTATCTAAATCACACATTCTTCCACACATCTGAGCCACA
CAAAAACCAATCCACATCTTTATCACCCATTCTATAAAAATCACACTTTGTGAG
TCTACACTTTGATTCCCTTCAAACACATACAAAGAGAAGAGACTAATTAATTAAT
TAATCATCTTGAGAGAAA<ins>ATGGCGAAAACGTTGCGATTTTCGGCTTATTGTTT
TCTCTTCTTGTGTTGGTTCCTTCT</ins>AGATCT

GAGCTCTAAGTTAAAATGCTTCTTCGTCTCCTATTTATAATATGGTTTGTTATTG
TTAATTTTGTTCTTGTAGAAGAGCTTAATTAATCGTTGTTGTTATGAAATACTATT
TGTATGAGATGAACTGGTGTAATGTAATTCATTTACATAAGTGGAGTCAGAATC
AGAATGTTTCCTCCATAACTAACTAGACATGAAGACCTGCCGCGTACAATTGTC
TTATATTTGAACAACTAAAATTGAACATCTTTTGCCACAACTTTATAAGTGGTTA
ATATAGCTCAAATATATGGTCAAGTTCAATAGATTAATAATGGAAATATCAGTTA
TCGAAATTCATTAACAATCAACTTAACGTTATTAACTACTAATTTTATATCATCCC
CTTTGATAAATGATAGTACA

SEQ ID NO.1

AGATCTTCGCTGACACAATATGTATAGGCTACCATGCCAACAACTCAACCGACACTGTTGACACAGTAC
TTGAGAAGAATGTGACAGTGACACACTCTGTCAACCTACTTGAGGACAGTCACAATGGAAAACTATGTCT
ACTAAAAGGAATAGCCCCACTACAATTGGGTAATTGCAGCGTTGCCGGATGGATCTTAGGAAACCCAGA
ATGCGAATTACTGATTTCCAAGGAATCATGGTCCTACATTGTAGAAACACCAAATCCTGAGAATGGAACA
TGTTACCCAGGGTATTTCGCCGACTATGAGGAACTGAGGGAGCAATTGAGTTCAGTATCTTCATTTGAG
AGATTCGAAATATTCCCCAAAGAAAGCTCATGGCCCAACCACACCGTAACCGGAGTATCAGCATCATGC
TCCCATAATGGGAAAAGCAGTTTTTACAGAAATTTGCTATGGCTGACGGGGAAGAATGGTTTGTACCCA
AACCTGAGCAAGTCCTATGTAAACAACAAAGAGAAAGAAGTCCTTGTACTATGGGGTGTTCATCACCCG
CCTAACATAGGGAACCAAAGGGCACTCTATCATACAGAAAATGCTTATGTCTCTGTAGTGTCTTCACATT
ATAGCAGAAGATTCACCCCAGAAATAGCCAAAAGACCCAAAGTAAGAGATCAGGAAGGAAGAATCAACT
ACTACTGGACTCTGCTGGAACCTGGGGATACAATAATATTTGAGGCAAATGGAAATCTAATAGCGCCAT
GGTATGCTTTTGCACTGAGTAGAGGCTTTGGATCAGGAATCATCACCTCAAATGCACCAATGGATGAAT
GTGATGCGAAGTGTCAAACACCTCAGGGAGCTATAAACAGCAGTCTTCCTTTCCAGAATGTACACCCAG
TCACAATAGGAGAGTGTCCAAAGTATGTCAGGAGTGCAAAATTAAGGATGGTTACAGGACTAAGGAACA
TCCCCATCCATTCAATCCAGAGGTTTGTTTGGAGCCATTGCCGGTTTCATTGAAGGGGGGTGGACTGGAA
TGGTAGATGGGTGGTATGGTTATCATCATCAGAATGAGCAAGGATCTGGCTATGCTGCAGATCAAAAAA
GTACACAAAATGCCATTAACGGGATTACAAACAAGGTCAATTCTGTAATTGAGAAAATGAACACTCAATT
CACAGCTGTGGGCAAAGAGTTCAACAAATTGGAAAGAAGGATGGAAAACTTAAATAAAAAAGTTGATGAT
GGGTTTCTAGACATTTGGACATATAATGCAGAATTGTTGGTTCTACTGGAAAATGAAAGGACTTTGGATT
TCCATGACTCCAATGTGAAGAATCTGTATGAGAAAGTAAAAAGCCAATTAAAGAATAATGCCAAAGAAT
AGGAAACGGGTGTTTTGAGTTCTATCACAAGTGTAACAATGAATGCATGGAGAGTGTGAAAAAT<u>GGTAC</u>
<u>C</u>TATGACTATCCAAAATATTCCGAAGAATCAAAGTTAAACAGGGAGAAAATTGATGGAGTGAAATTGGAA
TCAATGGGA<u>GTATACTAA</u><u>GAGCTCAGGCCT</u>

Fig. 5B

SEQ ID NO. 2

<u>GGTACC</u>TATGACTATCCAAAATATTCCGAAGAATCAAAGTTAAACAGGGAGAAAATTGATGGAGTGAAAT
TGGAATCAATGGGA<u>GTATAC</u>CAGATTCTGGCGATCTACTCAACTGTCGCCAGTTCCCTGGTTCTTTTGGT
CTCCCTGGGGGCAATCAGCTTCTGGATGTGTTCCAATGGGTCTTTGCAGTGTAGAATATGCATCTAA<u>GA</u>
<u>GCTCAGGCCT</u>

Fig. 5C

HA0 from H1 (SEQ ID NO:28)

<u>AGATCT</u>TCGCTGACACAATATGTATAGGCTACCATGCCAACAACTCAACCGACACTGTTGACA
CAGTACTTGAGAAGAATGTGACAGTGACACACTCTGTCAACCTACTTGAGGACAGTCACAATG
GAAAACTATGTCTACTAAAAGGAATAGCCCCACTACAATTGGGTAATTGCAGCGTTGCCGGAT
GGATCTTAGGAAACCCAGAATGCGAATTACTGATTTCCAAGGAATCATGGTCCTACATTGTAG
AAACACCAAATCCTGAGAATGGAACATGTTACCCAGGGTATTTCGCCGACTATGAGGAACTGA
GGGAGCAATTGAGTTCAGTATCTTCATTTGAGAGATTCGAAATATTCCCCAAAGAAAGCTCAT
GGCCCAACCACACCGTAACCGGAGTATCAGCATCATGCTCCCATAATGGGAAAAGCAGTTTTT
ACAGAAATTTGCTATGGCTGACGGGGAAGAATGGTTTGTACCCAAACCTGAGCAAGTCCTATG
TAAACAACAAAGAGAAAGAAGTCCTTGTACTATGGGGTGTTCATCACCCGCCTAACATAGGGA
ACCAAAGGGCACTCTATCATACAGAAAATGCTTATGTCTCTGTAGTGTCTTCACATTATAGCAG
AAGATTCACCCCAGAAATAGCCAAAAGACCCAAAGTAAGAGATCAGGAAGGAAGAATCAACTA
CTACTGGACTCTGCTGGAACCTGGGGATACAATAATATTTGAGGCAAATGGAAATCTAATAGC
GCCATGGTATGCTTTTGCACTGAGTAGAGGCTTTGGATCAGGAATCATCACCTCAAATGCACC
AATGGATGAATGTGATGCGAAGTGTCAAACACCTCAGGGAGCTATAAACAGCAGTCTTCCTTT
CCAGAATGTACACCCAGTCACAATAGGAGAGTGTCCAAAGTATGTCAGGAGTGCAAAATTAAG
GATGGTTACAGGACTAAGGAACATCCCATCCATTCAATCCAGAGGTTTGTTTGGAGCCATTGC
CGGTTTCATTGAAGGGGGGTGGACTGGAATGGTAGATGGGTGGTATGGTTATCATCATCAGA
ATGAGCAAGGATCTGGCTATGCTGCAGATCAAAAAAGTACACAAAATGCCATTAACGGGATTA
CAAACAAGGTCAATTCTGTAATTGAGAAAATGAACACTCAATTCACAGCTGTGGGCAAAGAGT
TCAACAAATTGGAAAGAAGGATGGAAAACTTAAATAAAAAAGTTGATGATGGGTTTCTAGACAT
TTGGACATATAATGCAGAATTGTTGGTTCTACTGGAAAATGAAAGGACTTTGGATTTCCATGAC
TCCAATGTGAAGAATCTGTATGAGAAAGTAAAAAGCCAATTAAAGAATAATGCCAAAGAAATAG
GAAACGGGTGTTTTGAGTTCTATCACAAGTGTAACAATGAATGCATGGAGAGTGTGAAAAAT<u>G
GTACC</u>TATGACTATCCAAAATATTCCGAAGAATCAAAGTTAAACAGGGAGAAAATTGATGGAG
TGAAATTGGAATCAATGGGA<u>GTATAC</u>CAGATTCTGGCGATCTACTCAACTGTCGCCAGTTCCC
TGGTTCTTTTGGTCTCCCTGGGGGCAATCAGCTTCTGGATGTGTTCCAATGGGTCTTTGCAGT
GTAGAATATGCATCTAA<u>GAGCTCAGGCCT</u>

Fig. 6

SEQ ID NO. 3

<u>AAGCTT</u>ATGGAGAAAATAGTGCTTCTTCTTGCAATAGTCAGTCTTGTTAAAAGTGATCAGATTTGCATTGG
TTACCATGCAAACAATTCAACAGAGCAGGTTGACACAATCATGGAAAAGAACGTTACTGTTACACATGCC
CAAGACATACTGGAAAAGACACACAACGGGAAGCTCTGCGATCTAGATGGAGTGAAGCCTCTAATTTTA
AGAGATTGTAGTGTAGCTGGATGGCTCCTCGGGAACCCAATGTGTGACGAATTCATCAATGTACCGGAA
TGGTCTTACATAGTGGAGAAGGCCAATCCAACCAATGACCTCTGTTACCCAGGGAGTTTCAACGACTAT
GAAGAACTGAAACACCTATTGAGCAGAATAAACCATTTTGAGAAAATTCAAATCATCCCCAAAAGTTCTTG
GTCCGATCATGAAGCCTCATCAGGAGTTAGCTCAGCATGTCCATACCTGGGAAGTCCCTCCTTTTTTAGA
AATGTGGTATGGCTTATCAAAAAGAACAGTACATACCCAACAATAAAGAAAAGCTACAATAATACCAACCA
AGAGGATCTTTTGGTACTGTGGGGAATTCACCATCCTAATGATGCGGCAGAGCAGACAAGGCTATATCA
AAACCCAACCACCTATATTTCCATTGGGACATCAACACTAAACCAGAGATTGGTACCAAAAATAGCTACT
AGATCCAAAGTAAACGGGCAAAGTGGAAGGATGGAGTTCTTCTGGACAATTTTAAAACCTAATGATGCAA
TCAACTTCGAGAGTAATGGAAATTTCATTGCTCCAGAATATGCATACAAAATTGTCAAGAAAGGGGACTC
AGCAATTATGAAAAGTGAATTGGAATATGGTAACTGCAACACCAAGTGTCAAACTCCAATGGGGGCGATA
AACTCTAGTATGCCATTCCACAACATACACCCTCTCACCATCGGGGAATGCCCCAAATATGTGAAATCAA
ACAGATTAGTCCTTGCAACAGGGCTCAGAAATAGCCCTCAAAGAGAGAGCAGAAGAAAAAAGAGAGGAC
TATTTGGAGCTATAGCAGGTTTTATAGAGGGAGGATGGCAGGGAATGGTAGATGGTTGGTATGGGTACC
ACCATAGCAATGACAGGGGAGTGGGTACGCTGCAGACAAAGAATCCACTCAAAAGGCAATAGATGGA
GTCACCAATAAGGTCAACTCAATCATTGACAAAATGAACACTCAGTTTGAGGCCGTTGGAAGGGAATTTA
ATAACTTAGAAAGGAGAATAGAGAATTTAAACAAGAAGATGGAAGACGGGTTTCTAGATGTCTGGACTTA
TAATGCCGAACTTCTGGTTCTCATGGAAAATGAGAGAACTCTAGACTTTCATGACTCAAATGTTAAGAAC
CTCTACGACAAGGTCCGACTACAGCTTAGGGATAATGCAAAGGAGCTGGGTAACGGTTGTTTCGAGTTC
TATCACAAATGTGATAATGAATGTATGGAAAGTATAAGAAACGGAACGTACAACTATCCGCAGTATTCAG
AAGAAGCAAGATTAAAAAGAGAGGAAATAAGTGGGGTAAAATTGGAATCAATAGGAACTTACCAAATACT
GTCAATTTATTCAACAGTGGCGAGTTCCCTAGCACTGGCAATCATGATGGCTGGTCTATCTTTATGGATG
TGCTCCAATGGATCGTTACAATGCAGAATTTGCATTTAA<u>GAGCTC</u>

Fig. 7A

SEQ ID NO. 4

5'-GTATTAGTAATTAGAATTTGGTGTC-3'

Fig. 7B

SEQ ID NO. 5

5'-GCAAGAAGAAGCACTATTTTCTCCA<u>TTTCTCTCAAGATGATTA</u>-3'

Fig. 7C

SEQ ID NO. 6

5'-<u>TTAATCATCTTGAGAGAAA</u>ATGGAGAAAATAGTGCTTCTTCTTGC-3'

Fig. 7D

SEQ ID NO. 7

5'-ACTTTGAGCTCTTAAATGCAAATTCTGCATTGTAACGA-3'

Fig. 8A

HA1 peptide sequence (SEQ ID NO:9)

MKAKLLVLLCTFTATYADTICIGYHANNSTDTVDTVLEKNVTVTHSVNLLEDSHNGKLCLLKGIAPLQ
LGNCSVAGWILGNPECELLISKESWSYIVETPNPENGTCYPGYFADYEELREQLSSVSSFERFEIFPK
ESSWPNHTVTGVSASCSHNGKSSFYRNLLWLTGKNGLYPNLSKSYVNNKEKEVLVLWGVHHPPNI
GNQRALYHTENAYVSVVSSHYSRRFTPEIAKRPKVRDQEGRINYYWTLLEPGDTIIFEANGNLIAPWY
AFALSRGFGSGIITSNAPMDECDAKCQTPQGAINSSLPFQNVHPVTIGECPKYVRSAKLRMVTGLRNI
PSIQSRGLFGAIAGFIEGGWTGMVDGWYGYHHQNEQGSGYAADQKSTQNAINGITNKVNSVIEKMN
TQFTAVGKEFNKLERRMENLNKKVDDGFLDIWTYNAELLVLLENERTLDFHDSNVKNLYEKVKSQLK
NNAKEIGNGCFEFYHKCNNECMESVKNGTYDYPKYSEESKLNREKIDGVKLESMGVYQILAIYSTVA
SSLVLLVSLGAISFWMCSNGSLQCRICI*

Fig. 8B

HA5 peptide sequence (SEQ ID No: 10)

MEKIVLLLAIVSLVKSDQICIGYHANNSTEQVDTIMEKNVTVTHAQDILEKTHNGKLCDLDGVKPLILR
DCSVAGWLLGNPMCDEFINVPEWSYIVEKANPTNDLCYPGSFNDYEELKHLLSRINHFEKIQIIPKSS
WSDHEASSGVSSACPYLGSPSFFRNVVWLIKKNSTYPTIKKSYNNTNQEDLLVLWGIHHPNDAAEQ
TRLYQNPTTYISIGTSTLNQRLVPKIATRSKVNGQSGRMEFFWTILKPNDAINFESNGNFIAPEYAYKI
VKKGDSAIMKSELEYGNCNTKCQTPMGAINSSMPFHNIHPLTIGECPKYVKSNRLVLATGLRNSPQR
ESRRKKRGLFGAIAGFIEGGWQGMVDGWYGYHHSNEQGSGYAADKESTQKAIDGVTNKVNSIIDK
MNTQFEAVGREFNNLERRIENLNKKMEDGFLDVWTYNAELLVLMENERTLDFHDSNVKNLYDKVRL
QLRDNAKELGNGCFEFYHKCDNECMESIRNGTYNYPQYSEEARLKREEISGVKLESIGTYQILSIYST
VASSLALAIMMAGLSLWMCSNGSLQCRICI*

Fig. 9

Subtype H7 (SEQ ID NO:11)
>BHB940420|gb:AF071776|Symbol:HA|Name:hemagglutinin precursor|Organism:Influenza A Virus A/chicken/New York/1995|Chromosome:4|Subtype:H7|Host:Avian GACAAAATATGTCTTGGGCACCATGCTGTGGCAAATGGAACAAAAGTGAACACATTAACAGAGAGGGGA
TTGAAGTAGTGAACGCCACAGAGACGGTGGAAACTGCGAATATCAAGAAAATATGTATTCAAGGGAAAAG
GCCAACAGATCTGGGACAATGTGGACTTCTAGGAACCCTAATAGGACCTCCCCAATGTGATCAATTCCTG
GAGTTTTACTCTGATTTGATAATTGAGCGAAGAGAAGGAACCGATGTGTGCTATCCCGGTAAATTCACAA
ATGAAGAATCACTGAGGCAGATCCTTCGAGGGTCAGGAGGAATTGATAAGGAGTCAATGGGTTTCACCTA
TAGTGGAATAAGAACCAATGGAGCGACAAGTGCCTGCAAAAGATCAGGTTCTTCTTTCTATGCAGAGATG
AAGTGGTTGCTGTCGAATTCAGACAATGCGGCATTCCCTCAAATGACAAAGTCGTATAGAAATCCCAGAA
ACAAACCAGCTCTGATAATTTGGGGAGTTCATCACTCTGGATCGGTTAGCGAGCAGACCAAACTCTATGG
AAGTGGAAACAAGTTGATAACAGTAGGAAGCTCAAAATACCAGCAATCATTCACCCCAAGTCCGGGAGCA
CGGCCACAAGTGAATGGACAATCAGGGAGAATCGATTTTCACTGGCTACTCCTTGATCCCAATGACACAG
TGACCTTCACTTTCAATGGGGCATTCATAGCCCCTGACAGGGCAAGTTTCTTTAGAGGAGAATCACTAGG
AGTCCAGAGTGATGTTCCTCTGGATTCTAGTTGTGGAGGGGATTGCTTTCACAGTGGGGGTACGATAGTC
AGTTCCCTGCCATTCCAAAACATCAACCCTAGAACTGTGGGGAGATGCCCTCGGTATGTCAAACAGACAA
GCCTCCTTTTGGCTACAGGAATGAGAAATGTTCCAGAGAATCCAAAGCCCAGAGGCCTTTTTGGAGCAAT
TGCTGGATTCATAGAGAATGGATGGGAGGGTCTCATCGATGGATGGTATGGTTTCAGACATCAAAATGCA
CAAGGGGAAGGAACTGCAGCTGACTACAAAAGCACCCAATCTGCAATAGATCAGATCACAGGCAAATTGA
ATCGTCTGATTGACAAAACAAATCAGCAGTTTGAGCTGATAGACAATGAGTTCAATGAGATAGAACAACA
AATAGGAAATGTCATTAATTGGACACGAGACGCAATGACTGAGGTATGGTCGTATAATGCTGAGCTGTTG
GTGGCAATGGAAAATCAGCATACAATAGATCTTGCGGACTCAGAAATGAACAAACTTTATGAGCGTGTCA
GAAAACAACTAAGGGAGAATGCTGAAGAAGATGGAACTGGATGTTTTGAGATATTCCATAAGTGTGATGA
TCAGTGCATGGAGAGCATAAGGAACAACACTTATGACCATACTCAATACAGAACAGAGTCATTGCAGAAT
AGAATACAGATAGACCCAGTGAAATTGAGTAGTGGATACAAAGACATAATCTTATGGTTTAGCTTCGGGG
CATCATGTTTTCTTCTTCTAGCCGTTGTAATGGGATTGGTTTTCATTTGCATAAAGAATGGAAACATGCG
GTGCACCATTTGTATATAA

Fig. 10A

Subtype H2 (SEQ ID NO:12)
>gi|408516|gb|L11132.1|FLADE88HA Influenza A virus (A/herring gull/DE/677/88 (H2N8))
hemagglutinin (HA) gene, complete cds

```
AGCAAAAGCAGGGGTTATACCATAGACAACCAAAGGCAAGACAATGGCCATCATTTATCTAATTCTTCTG
TTCACAGCAGTGAGAGGGGACCAAATATGCATTGGATACCATTCCAACAATTCCACAGAAAAGGTTGACA
CAATCCTAGAGAGAAATGTCACTGTGACTCACGCTGAGGACATTCTTGAGAAGACTCACAATGGGAAGTT
ATGCAAACTAAATGGAATCCCTCCACTTGAATTAAGGGATTGCAGCATTGCCGGATGGCTCCTTGGGAAT
CCAGAATGTGATATACTTCTAACTGTGCCAGAATGGTCATACATAATAGAAAAAGAAAATCCAAGGAACG
GCTTGTGCTACCCAGGCAGTTTCAATGATTATGAAGAATTGAAGCATCTTATCAGCAGCGTGACACATTT
TGAGAAAGTAAAGATTCTGCCCAGAAATGAATGGACACAGCATACAACAACTGGAGGTTCACAGGCTTGC
GCAGACTATGGTGGTCCGTCATTCTTCCGGAACATGGTCTGGTTGACAAAGAAAGGGTCGAATTATCCAA
TTGCCAAAAGATCTTACAACAATACAAGTGGGGAACAAATGCTGATCATTTGGGGGATACATCACCCCAA
TGATGAAAGTGAACAAAGAGCATTGTATCAGAATGTGGGGACCTATGTGTCAGTAGGAACATCAACACTG
AACAAAAGATCATCCCCAGAAATAGCAACAAGACCTAAAGTGAATGGACAAGGAGGCAGAATGGAATTCT
CGTGGACTATCTTAGATATATGGGACACAATAAATTTTGAGAGTACTGGCAATCTAATTGCACCAGAATA
TGGTTTCAAAATATCCAAACGAGGTAGTTCAGGGATCATGAAAACAGAAGGAAAACTTGAAAACTGCGAG
ACCAAGTGCCAAACTCCTTTGGGAGCAATAAATACAACATTACCCTTTCACAATATCCACCCACTGACCA
TTGGTGAGTGCCCCAAATATGTAAAATCGGAAAGATTAGTCTTAGCAACAGGACTAAGAAACGTCCCTCA
GATTGAGTCAAGGGGATTGTTTGGGGCAATAGCTGGTTTTATAGAGGGTGGATGGCAAGGAATGGTTGAT
GGTTGGTATGGGTATCATCACAGCAATGACCAGGGATCTGGGTATGCAGCAGACAAAGAATCCACTCAAA
AGGCAATTGATGGAATCACCAACAAGGTAAATTCTGTGATCGAAAAGATGAACACCCAATTCGGAGCTGT
TGGAAAAGAATTCAGTAACTTGGAGAGAAGACTGGAGAACTTGAATAAAAAGATGGAGGACGGATTTCTA
GATGTGTGGACATACAATGCCGAGCTCCTAGTTCTAATGGAAAATGAGAGGACACTTGACTTTCATGATT
CTAATGTCAAGAATCTATATGATAAAGTCAGAATGCAACTGAGAGACAATGCAAAAGAACTAGGGAATGG
ATGTTTTGAATTTTATCACAAATGTGATGATGAATGCATGAACAGTGTGAAGAATGGGACATATGATTAT
TCCAAGTATGAAGAGGAGTCTAAACTAAACAGGACTGAAATCAAAGGGGTTAAATTGAGCAATATGGGGG
TTTATCAAATCCTTGCCATCTATGCTACAGTAGCAGGTTCCCTGTCACTGGCAATCATGATAGCTGGGAT
TTCTATATGGATGTGCTCCAACGGGTCTCTGCAATGCAGAATCTGCATATGATCATCAGTCATTTTGTAA
TTAAAAACACCCTTGTTTCTACT
```

Fig. 10B

Subtype H3 (SEQ ID NO:13)

>BHB2107299|gb:EF473574|Symbol:HA|Name:hemagglutinin|Organism:Influenza A
Virus A/Texas/32/2003|Segment:4|Subtype:H3|Host:Human CAAAAACTTCCCGGAAATGACAACAGCACGGCAACGCTGTGCCTTGGGCACCATGCAGTACCAAACGGAA
CGATAGTGAAAACAATCACGAATGACCAAATTGAAGTTACTAATGCTACTGAGCTGGTACAGAGTTCCTC
AACAGGTGGAATATGCGACAGTCCTCATCAGATCCTTGATGGAGAAAACTGCACACTAATAGATGCTCTA
TTGGGAGACCCTCAGTGTGATGGCTTCCAAAATAAGAAATGGGACCTTTTTGTTGAACGCAGCAAAGCCT
ACAGCAACTGTTACCCTTATGATGTGCCGGATTATGCCTCCCTTAGGTCACTAGTTGCCTCATCCGGCAC
ACTGGAGTTTAACAATGAAAGCTTCGATTGGACTGGAGTCACTCAGAATGGAACAAGCTCTGCTTGCAAA
AGGAGATCTAATAAAAGTTTCTTTAGTAGATTGAATTGGTTGACCCACTTAAAATACAAATACCCAGCAT
TGAACGTGACTATGCCAAACAATGAAAAATTTGACAAATTGTACATTTGGGGGGTTCACCACCCGGGTAC
GGACAGTGACCAAATCAGCCTATATGCTCAAGCATCAGGAAGAATCACAGTCTCTACCAAAAGAAGCCAA
CAAACTGTAATCCCGAATATCGGATCTAGACCCAGGGTAAGGGATGTCTCCAGCCGAATAAGCATCTATT
GGACAATAGTAAAACCGGGAGACATACTTTTGATTAACAGCACAGGGAATCTAATTGCTCCTCGGGGTTA
CTTCAAAATACGAAGTGGGAAAAGCTCAATAATGAGATCAGATGCACCCATTGGCAAATGCAATTCCGAA
TGCATCACTCCAAATGGAAGCATTCCCAATGACAAACCATTTCAAAATGTAAACAGGATCACATATGGGG
CCTGTCCCAGATATGTTAAGCAAAACACTCTGAAATTGGCAACAGGGATGCGAAATGTACCAGAGAAACA
AACTAGAGGCATATTTGGCGCAATCGCGGGTTTCATAGAAAATGGTTGGGAGGGAATGGTGGACGGTTGG
TACGGTTTCAGGCATCAAAATTCTGAGGGCACAGGA

Fig. 10C

Subtype H4 (SEQ ID NO:14)
>BHB1050162|gb:DQ021859|Symbol:HA|Name:hemagglutinin|Organism:Influenza A Virus
A/mallard/MN/33/00|Segment:4|Subtype:H4|Host:Avian ATGCTATCAATCACGATTCTGTTTCTGCTCATAGCAGAGGGTTCCTCTCAGAATTACACAGGGAATCCCG
TGATATGCCTGGGACATCATGCCGTATCCAATGGGACAATGGTGAAAACCCTGACTGATGACCAAGTAGA
AGTTGTCACTGCCCAAGAATTAGTGGAATCGCAACATCTACCGGAGTTGTGTCCTAGCCCTTTAAGATTA
GTAGATGGACAAACTTGTGACATCGTCAATGGTGCCTTGGGGAGTCCAGGCTGTGATCACTTGAATGGTG
CAGAATGGGATGTCTTCATAGAACGACCCACTGCTGTGGACACTTGTTATCCATTTGATGTGCCGGATTA
CCAGAGCCTACGGAGTATCCTAGCAAACAATGGGAAATTTGAGTTCATTGCTGAGGAATTCCAATGGAAC
ACAGTCAAACAAAATGGGAAATCCGGAGCATGCAAAAGAGCAAATGTGAATGACTTTTTCAACAGATTGA
ACTGGCTGACCAAATCTGATGGGAATGCATACCCACTTCAAAACCTGACAAAGGTTAACAACGGGGACTA
TGCAAGACTTTACATATGGGGAGTTCATCATCCTTCAACTGACACAGAACAAACCAACTTGTATAAGAAC
AACCCTGGGAGAGTAACTGTTTCCACCAAAACCAGTCAAACAAGTGTGGTACCAAACATTGGCAGTAGAC
CATGGGTAAGAGGCCAAAGCGGCAGGATTAGCTTCTATTGGACAATTGTGGAGCCAGGAGACCTCATAGT
CTTCAACACCATAGGGAATTTAATTGCTCCGAGAGGTCATTACAAGCTTAACAGTCAAAAGAAGAGCACA
ATTCTGAATACTGCAATTCCCATAGGATCTTGTGTTAGTAAATGTCACACAGATAGGGGTTCAATCTCTA
CAACCAAACCCTTTCAGAACATCTCAAGAATATCAATTGGGGACTGTCCCAAGTATGTCAAACAGGGATC
CTTGAAACTAGCTACAGGAATGAGGAATATCCCTGAGAAAGCAACCAGAGGCCTGTTTGGTGCAATTG

Fig. 10D

Subtype H5 (SEQ ID NO:15)

>BHB950029|gb:AF501235|Symbol:HA|Name:hemagglutinin|Organism:Influenza A Virus
A/duck/Shanghai/1/2000|Segment:4|Subtype:H5|Host:Avian ATGGAGAAAATAGTGCTTCTTCTTGCAATAGTCAGTCTTGTTAAAAGTGATCAGATTTGCATTGGTTACC
ATGCAAACAACTCGACAGAGCAGGTTGACACAATAATGGAAAAGAACGTTACTGTTACACATGCCCAAGA
CATACTGGAAAAGACACACAACGGGAAACTCTGCGATCTAGATGGAGTGAAGCCTCTAATTTTGAGAGAT
TGTAGTGTAGCTGGATGGCTCCTCGGAAACCCTATGTGTGACGAATTCATCAATGTGCCGGAATGGTCTT
ACATAGTGGAGAAGGCCAGTCCAGCCAATGACCTCTGTTACCCAGGGGATTTCAACGACTATGAAGAACT
GAAACACCTATTGAGCAGAATAAACCACTTTGAGAAAATTCAGATCATCCCCAAAAGTTCTTGGTCCAAT
CATGAAGCCTCATCAGGGGTGAGCGCAGCATGTCCATACCATGGGAAGCCCTCCTTTTTCAGAAATGTGG
TATGGCTTATCAAAAAGAACAGTGCATACCCAACAATAAAGAGGAGCTACAATAATACCAACCAAGAAGA
TCTTTTGGTACTGTGGGGGATTCACCATCCTAATGATGCGGCAGAGCAGACAAAGCTCTATCAAAACCCA
ACCACCTATATTTCCGTTGGAACATCAACACTAAACCAGAGATTGGTCCCAAAAATAGCTACTAGATCCA
AAGTAAACGGGCAAAGTGGAAGAATGGAGTTCTTCTGGACAATTTTAAAGCCGAATGATGCCATAAATTT
CGAGAGTAATGGAAATTTCATTGCTCCAGAATATGCATACAAAATTGTCAAGAAAGGGGACTCAGCAATT
ATGAAAAGTGAATTGGAATATGGTAACTGCAACACCAAGTGTCAAACTCCAATGGGGGCGATAAACTCTA
GTATGCCATTCCACAACATACACCCTCTCACAATCGGGGAATGCCCCAAATATGTGAAATCAAACAGATT
AGTCCTTGCGACTGGACTCAGAAATACCCCTCAAAGAGATAGAAGAAGAAAAAAGAGAGGACTATTTGGA
GCTATAGCAGGTTTTATAGAGGGAGGATGGCAAGGAATGGTAGATGGTTGGTATGGGTACCACCATAGCA
ATGAGCAGGGGAGTGGATACGCTGCAGACAAAGAATCCACTCAAAAGGCAATAGATGGAGTCACCAATAA
GGTCAACTCGATCATTGACAAAATGAACACTCAGTTTGAGGCCGTTGGAAGGGAATTTAATAACTTAGAA
AGGAGGATAGAAAATTTAAACAAGAAGATGGAAGACGGATTCCTAGATGTCTGGACTTATAATGCTGAAC
TTCTGGTTCTCATGGAAAATGAGAGAACTCTAGACTTTCATGATTCAAATGTCAAGAACCTTTACAACAA
GGTCCGACTACAGCTTAGGGATAATGCAAAGGAGCTGGGTAATGGTTGTTTCGAGTTCTATCACAAATGT
GATAATGAATGTATGGAAAGTGTAAAAAACGGGACGTATGACTACCCGCAGTATTCAGAAGAAGCAAGAC
TAAACAGAGAGGAAATAAGTGGAGTAAAATTGGAATCAATGGGAACTTACCAAATACTGTCAATTTATTC
AACAGTGGCGAGTTCCCTAGCACTGGCAATCATGGTAGCTGGTCTATCTTTATGGATGTGCTCCAATGGG
TCGTTACAATGCAGAATTTGCATTTAA

Fig. 10E

Subtype H6 (SEQ ID NO:16)
>BHB1049778|gb:DQ021667|Symbol:HA|Name:hemagglutinin|Organism:Influenza A Virus
A/northern pintail/TX/828189/02|Segment:4|Subtype:H6|Host:Avian ATGATTGCAATCATTGTAATAGCGATACTGGCAGCAGCCGGAAAGTCAGACAAGATCTGCATTGGGTATC
ATGCCAACAATTCAACAACACAGGTGGATACGATACTTGAGAAGAATGTAACCGTCACACACTCAGTTGA
ATTGCTGGAGAATCAGAAGGAAGAAAGATTCTGCAAGATCTTGAACAAGGCCCCTCTCGACCTAAAGGGA
TGCACCATAGAGGGTTGGATCTTGGGGAATCCCCAATGCGATCTGTTGCTTGGTGACCAAAGCTGGTCAT
ATATAGTGGAAAGACCTACTGCCCAAAATGGGATATGCTACCCAGGAGCTTTGAATGAGGTAGAAGAACT
GAAAGCATTTATCGGATCAGGAGAAAGGGTAGAGAGATTTGAGATGTTTCCCAAAAGCACATGGGCAGGG
GTAGACACCAGCAGTGGGGTAACAAAAGCTTGTCCTTATAATAGTGGTTCATCTTTCTACAGAAACCTCC
TATGGATAATAAAGACCAAGTCAGCAGCGTATCCAGTAATTAAGGGAACTTACAGCAACACTGGAAACCA
GCCAATCCTCTATTTCTGGGGTGTGCACCATCCTCCTGACACCAATGAGCAAAATACTCTGTATGGCTCT
GGCGATCGGTATGTTAGGATGGGAACTGAGAGCATGAATTTTGCCAAGAGCCCAGAAATTGCGGCAAGAC
CCGCTGTGAATGGCCAAAGAGGTCGAATTGATTATTACTGGTCTGTTTTAAAACCAGGAGAAACCTTGAA
TGTGGAATCTAATGGAAATCTAATCGCTCCTTGGTATGCATACAAATTTGTCAACACAAATAATAAGGGA
GCCGTCTTCAAGTCAAATTTACCAATCGAGAATTGCGATGCCACATGCCAGACTATTGCAGGAGTCCTAA
GGACCAATAAAACATTTCAGAATGTGAGCCCTCTGTGGATAGGAGAATGCCCCAAGTATGTGAAAAGTGA
AAGTCTAAGGCTTGCTACTGGACTAAGAAATGTTCCACAGATTGAAACCAGAGGGCTTTTCGGAGCTATC

Fig. 10F

Subtype H8 (SEQ ID NO:17)

\>gi|221317|dbj|D90304.1|FLAHAH8N4 Influenza A virus
(A/Turkey/Ontario/6118/68(H8N4)) gene for hemagglutinin precursor, complete
cds ATGGAAAAATTCATCGCAATAGCAACCTTGGCGAGCACAAATGCATACGATAGGATATGCATTGGGTACC
AATCAAACAACTCCACAGACACAGTGAACACTCTCATAGAACAGAATGTACCAGTCACCCAAACAATGGA
GCTCGTGGAAACAGAGAAACATCCCGCTTATTGTAACACTGATTTAGGTGCCCCATTGGAACTGCGAGAC
TGCAAGATTGAGGCAGTAATCTATGGGAACCCCAAGTGTGACATCCATCTGAAGGATCAAGGTTGGTCAT
ACATAGTGGAGAGGCCCAGCGCACCAGAAGGGATGTGTTACCCTGGATCTGTGGAAAATCTAGAAGAACT
GAGGTTTGTCTTCTCCAGTGCTGCATCTTACAAGAGAATAAGACTATTTGACTATTCCAGGTGGAATGTG
ACTAGATCTGGAACGAGTAAAGCATGCAATGCATCAACAGGTGGCCAATCCTTCTATAGGAGCATCAATT
GGTTGACCAAAAAGGAACCAGACACTTATGACTTCAATGAAGGAGCTTATGTTAATAATGAAGATGGAGA
CATCATTTTCTTATGGGGGATCCATCATCCGCCGGACACAAAAGAGCAGACAACACTATATAAAAATGCA
AACACTTTGAGTAGTGTTACTACTAACACTATAAACAGAAGCTTTCAACCAAATATTGGTCCCAGACCAT
TAGTAAGAGGACAGCAAGGGAGGATGGATTACTATTGGGGCATTCTGAAAAGAGGGGAGACTCTGAAGAT
CAGGACCAACGGAAATTTAATCGCACCTGAATTTGGCTATCTGCTCAAAGGTGAAAGCTACGGCAGAATA
ATTCAAAATGAGGATATACCCATCGGGAACTGTAACACAAAATGTCAAACATATGCGGGAGCAATCAATA
GCAGCAAACCCTTTCAGAATGCAAGTAGGCATTACATGGGAGAATGTCCCAAATATGTGAAGAAGGCAAG
CTTGCGACTTGCAGTTGGGCTTAGGAATACGCCTTCTGTTGAACCCAGAGGACTGTTTGGAGCCATTGCT
GGTTTCATTGAAGGAGGATGGTCTGGAATGATTGATGGGTGGTATGGATTTCATCACAGCAATTCAGAGG
GAACAGGAATGGCAGCTGACCAGAAATCAACACAAGAAGCCATCGATAAGATCACCAATAAAGTCAACAA
TATAGTTGACAAGATGAACAGGGAGTTTGAAGTTGTGAATCATGAGTTCTCTGAAGTTGAAAAAAGAATA
AACATGATAAACGATAAAATAGATGACCAAATTGAAGATCTTTGGGCTTACAATGCAGAGCTCCTTGTGC
TCTTAGAGAACCAGAAAACGCTAGACGAACATGATTCCAATGTCAAAAACCTTTTTGATGAAGTGAAAAG
GAGACTGTCAGCCAATGCAATAGATGCTGGGAACGGTTGCTTTGACATACTTCACAAATGCGACAATGAG
TGTATGGAAACTATAAAGAACGGAACTTACGATCATAAGGAATATGAAGAGGAGGCTAAACTAGAAAGGA
GCAAGATAAATGGAGTAAAACTAGAAGAGAACACCACTTACAAAATTCTTAGCATTTACAGTACAGTGGC
GGCCAGTCTTTGCTTGGCAATCCTGATTGCTGGAGGTTTAATCCTGGGCATGCAAAATGGATCTTGTAGA
TGCATGTTCTGTATTTGA

Fig. 10G

Subtype H9 (SEQ ID NO:18)

>BHB954830|gb:AM087218|Symbol:HA|Name:hemagglutinin|Organism:Influenza A Virus
A/shoveler/Iran/G54/03|Segment:4|Subtype:H9|Host:Avian ATGGAAACAGTATCACTAATGACTATACTACTAGTAGCAACAGCAAGCAATGCAGACAAAATCTGCATCG
GCCACCAGTCAACAAACTCCACAGAAACTGTGGACACGCTAACAGAAACCAATGTTCCTGTGACACATGC
CAAAGAATTGCTCCACACAGAGCACAATGGAATGCTGTGTGCAACAAATCTGGGACATCCCCTAATCTTA
GACACGTGCACTATTGAAGGACTGATCTATGGTAACCCTTCTTGTGACTTGCTGTTGGGAGGAAGAGAAT
GGTCCTACATCGTCGAAAGGTCATCAGCTGTAAATGGAACGTGTTACCCTGGGAATGTAGAGAACCTAGA
GGAACTCAGGACACTTTTTAGTTCCGCTAGTTCCTACCGAAGAATCCAAATCTTCCCAGACACAATCTGG
AATGTGACTTACACTGGAACAAGCAAAGCATGTTCAGATTCATTCTACAGGAGTATGAGATGGCTGACTC
AAAAAAGCGGGTCTTACCCTGTTCAAGACGCTCAATACACAAATAATATGGGAAAGAGCATTCTTTTCGT
GTGGGGCATACATCACCCACCCACTGAAGCTGCACAGACAAATTTGTACACAAGAACCGACACAACAACA
AGCGTGACAACAGAAGACTTAAATAGGATCTTCAAACCGATGGTAGGGCCAAGGCCCCTTGTCAATGGTC
TGCAGGGAAGAATTAATTATTATTGGTCGGTACTAAAACCAGGCCAGACACTGCGAGTAAGATCCAATGG
GAATCTAATTGCTCCATGGTATGGACACATTCTTTCGGGAGGGAGCCATGGAAGAATCCTGAAGACTGAT
TTAAAAAGTAGTAATTGCGTAGTGCAATGTCAGACTGAAAAAGGCGGCTTAAACAGTACATTGCCGTTCC
ACAATATCAGTAAATATGCATTTGGAAACTGTCCCAAATATGTTAGAGTTAAAAGTCTCAAACTGGCAGT
AGGGTTGAGGAACGTGCCTGCTAGATCAAGTAGAGGACTATTCGGAGCCATAGCTGGATTCATAGAAGGA
GGTTGGCCAGGACTAGTCGCTGGTTGGTATGGTTTCCAGCATTCAAATGATCAAGGGGTTGGTATTGCGG
CAGATAGGGATTCAACTCAAAAGGCAATTGATAGAATAACAACCAAGGTGAATAATATAGTCGACAAAAT
GAACAAACAATATGAAATAATTGATCATGAATTCAGTGAGGTTGAAACTAGGCTCAACATGATCAATAAT
AAGATTGATGACCAAATACAAGACATATGGGCATATAATGCAGAGTTGCTAGTACTACTTGAAAACCAGA
AAACACTCGATGAGCATGACGCAAATGTGAAGA

Fig. 10H

Subtype H10 (SEQ ID NO:19)

\>gi|324365|gb|M21647.1|FLAMS84HA Influenza A virus
(A/chicken/Germany/N/1949(H10N7)) hemagglutinin precursor, gene,
complete cds

```
AGCAAAAGCAGGGGTCACAATGTACAAAGTAGTAGTAATAATTGCGCTCCTTGGAGCAGTGAAAGGTCTT
GACAGAATCTGCCTAGGACACCATGCGGTTGCCAATGGAACCATTGTGAAGACCCTTACAAATGAACAAG
AGGAAGTGACCAATGCTACTGAGACGGTAGAGAGCACAAATTTGAATAAATTGTGTATGAAAGGAAGAAG
CTACAAGGACTTGGGCAATTGTCACCCGGTAGGAATGTTGATAGGAACACCTGTTTGTGATCCGCACTTG
ACCGGGACCTGGGACACTCTCATTGAGCGAGAGAATGCCATTGCCCACTGTTATCCAGGGGCAACCATAA
ATGAAGAAGCATTGAGGCAGAAAATAATGGAAAGTGGAGGAATCAGCAAGATGAGCACTGGCTTCACTTA
TGGGTCTTCCATCACCTCAGCTGGGACCACTAAGGCATGCATGAGAAATGGAGGAGATAGTTTCTATGCA
GAGCTCAAATGGCTAGTGTCAAAGACAAAGGGACAAAATTTCCCTCAGACAACAAACACCTATCGGAATA
CGGACACAGCAGAACATCTCATAATATGGGGAATTCATCACCCTTCCAGCACACAGGAAAAGAATGACTT
ATACGGAACTCAGTCACTATCTATATCAGTTGAGAGTTCTACATATCAGAACAACTTTGTTCCAGTTGTT
GGGGCAAGACCTCAGGTCAATGGACAAAGTGGGCGAATTGACTTTCACTGGACACTAGTACAGCCGGGTG
ACAACATAACCTTCTCAGACAATGGAGGTCTAATAGCACCAAGTCGAGTTAGCAAATTAACTGGAAGGGA
TTTGGGAATCCAATCAGAAGCGTTGATAGACAACAGTTGTGAATCCAAATGCTTTTGGAGAGGGGGTTCT
ATAAATACAAAGCTCCCTTTTCAAAATCTGTCACCCAGAACAGTAGGTCAATGCCCCAAATACGTAAATC
AGAGGAGTTTACTGCTTGCAACAGGGATGAGGAATGTGCCAGAAGTGGTGCAGGGAAGGGGTCTGTTTGG
TGCAATAGCAGGGTTCATAGAAAACGGATGGAAGGAATGGTAGACGGCTGGTATGGTTTCAGACACCAA
AATGCCCAGGGCACAGGCCAAGCTGCTGATTACAAGAGTACTCAAGCAGCTATTGACCAAATCACAGGGA
AACTGAACAGGTTGATTGAGAAGACCAACACTGAGTTTGAGTCAATAGAATCTGAATTCAGTGAGACTGA
GCATCAAATTGGTAACGTCATTAATTGGACCAAAGATTCAATAACCGACATTTGGACTTACAACGCAGAG
CTATTAGTGGCAATGGAGAATCAGCACACAATTGACATGGCTGATTCAGAGATGCTAAATCTGTATGAAA
GGGTAAGAAAGCAACTCAGACAGAATGCAGAAGAAGACGGAAAGGGATGTTTTGAGATATATCATACTTG
TGATGATTCGTGCATGGAGAGTATAAGGAACAATACTTATGACCATTCACAATACAGAGAGGAGGCTCTT
CTGAATAGACTGAACATCAACCCAGTGAAACTTTCTTCGGGGTACAAAGACATCATACTTTGGTTTAGCT
TCGGGGAATCATGCTTTGTTCTTCTAGCCGTTGTTATGGGTCTTGTTTTCTTCTGCCTGAAAAATGGAAA
CATGCGATGCACAATCTGTATTTAGTTAAAAACACCTTGTTTCTACT
```

Fig. 10I

Subtype H11 (SEQ ID NO:20)

>gi|221307|dbj|D90306.1|FLAHAH11N Influenza A virus (A/duck/England/56(H11N6)) gene for hemagglutinin precursor, complete cds

```
ATGGAGAAAACACTGCTATTTGCAGCTATTTTCCTTTGTGTGAAAGCAGATGAGATCTGTATCGGGTATT
TAAGCAACAACTCGACAGACAAAGTTGACACAATAATTGAGAACAATGTCACGGTCACTAGCTCAGTGGA
ACTGGTTGAGACAGAACACACTGGATCATTCTGTTCAATCAATGGAAAACAACCAATAAGCCTTGGAGAT
TGTTCATTTGCTGGATGGATATTAGGAAACCCTATGTGTGATGAACTAATTGGAAAGACTTCATGGTCTT
ACATTGTGGAAAAACCCAATCCAACAAATGGAATCTGTTACCCAGGAACTTTAGAGAGTGAAGAAGAACT
AAGACTGAAATTCAGTGGAGTTTTAGAATTTAACAAATTCGAAGTATTCACATCAAATGGATGGGGTGCT
GTAAATTCAGGAGTAGGAGTAACCGCTGCATGCAAATTCGGGGGTTCTAATTCTTTCTTTCGAAACATGG
TATGGCTGATACACCAATCAGGAACATATCCTGTAATAAAGAGAACCTTTAACAACACCAAAGGGAGAGA
TGTACTGATTGTTTGGGGAATTCATCATCCTGCTACACTGACAGAACATCAAGATCTGTATAAAAAGGAC
AGCTCCTATGTAGCAGTGGGTTCAGAGACCTACAACAGAAGATTCACTCCAGAAATCAACACTAGGCCCA
GAGTCAATGGACAGGCCGGACGGATGACATTCTACTGGAAGATAGTCAAACCAGGAGAATCAATAACATT
CGAATCTAATGGGGCGTTCCTAGCTCCTAGATATGCTTTTGAGATTGTCTCTGTTGGAAATGGGAAACTG
TTCAGGAGCGAACTGAACATTGAATCATGCTCTACCAAATGTCAAACAGAAATAGGAGGAATTAATACGA
ACAAAAGCTTCCACAATGTTCACAGAAACACTATCGGGGATTGCCCCAAGTATGTGAATGTCAAATCCTT
AAAGCTTGCAACAGGACCTAGAAATGTCCCAGCAATAGCATCGAGAGGCTTGTTTGGAGCAATAGCTGGA
TTCATAGAAGGGGATGGCCTGGACTGATCAATGGATGGTATGGGTTCCAACACAGGGACGAAGAAGGAA
CAGGCATTGCAGCAGACAAGGAGTCAACTCAAAAGGCAATAGACCAGATAACATCCAAGGTAAATAACAT
CGTTGACAGGATGAATACAAACTTTGAGTCTGTGCAACACGAATTCAGTGAAATAGAGGAAAGAATAAAT
CAATTATCAAAACACGTAGATGATTCTGTGGTTGACATCGGTCATATAATGCACAGCTTCTCGTTTTAC
TTGAAAATGAGAAGACACTGGACCTCCATGACTCAAATGTCAGGAACCTCCATGAGAAAGTCAGAAGAAT
GCTAAAGGACAATGCCAAAGATGAGGGGAACGGATGCTTCACCTTTTACCATAAGTGTGACAATAAATGC
ATTGAACGAGTTAGAAACGGAACATATGATCATAAAGAATTCGAGGAGGAATCAAAAATCAATCGCCAGG
AGATTGAAGGGGTGAAACTAGATTCTAGTGGGAATGTGTATAAAATACTGTCAATTTACAGCTGCATTGC
AAGCAGTCTTGTATTGGCAGCACTCATCATGGGGTTCATGTTTTGGGCATGCAGTAATGGATCATGTAGA
TGTACCATTTGCATTTAG
```

Fig. 10J

Subtype H12 (SEQ ID NO:21)
>gi|221309|dbj|D90307.1|FLAHAH12N Influenza A virus (A/duck/Alberta/60/76(H12N5)) gene for hemagglutinin precursor, complete cds ATGGAAAAATTCATCATTTTGAGTACTGTCTTGGCAGCAAGCTTTGCATATGACAAAATTTGCATTGGAT
ACCAAACAAACAACTCGACTGAAACGGTAAACACACTAAGTGAACAAAACGTTCCGGTGACGCAGGTGGA
AGAACTTGTACATCGTGGGATTGATCCGATCCTGTGTGGAACGGAACTAGGATCACCACTAGTGCTTGAT
GACTGTTCATTAGAGGGTCTAATCCTAGGCAATCCCAAATGTGATCTTTATTTGAATGGCAGGGAATGGT
CATACATAGTAGAGAGGCCCAAAGAGATGGAAGGAGTTTGCTATCCAGGGTCAATTGAAAACCAGGAAGA
GCTAAGATCTCTGTTTTCTTCCATCAAAAAATATGAAAGAGTGAAGATGTTTGATTTCACCAAATGGAAT
GTCACATACACTGGGACCAGCAAGGCCTGCAATAATACATCAAACCAAGGCTCATTCTATAGGAGCATGA
GATGGTTGACCTTAAAATCAGGACAATTTCCAGTCCAAACAGATGAGTACAAGAACACCAGAGATTCAGA
CATTGTATTCACCTGGGCCATTCACCACCCACCAACATCTGATGAACAAGTAAAATTATACAAAAATCCT
GATACTCTCTCTTCAGTCACCACCGTAGAAATCAATAGGAGCTTCAAGCCTAATATAGGGCCAAGACCAC
TCGTGAGAGGACAACAAGGGAGAATGGATTACTACTGGGCTGTTCTTAAACCTGGACAAACAGTCAAAAT
ACAAACCAATGGTAATCTTATTGCACCTGAATATGGTCACTTAATCACAGGGAAATCACATGGCAGGATA
CTCAAGAATAATTTGCCCATGGGACAGTGTGTGACTGAATGTCAATTGAACGAGGGTGTAATGAACACAA
GCAAACCTTTCCAGAACACTAGTAAGCACTATATTGGGAAATGCCCCAAATACATACCATCAGGGAGTTT
AAAATTGGCAATAGGGCTCAGGAATGTCCCACAAGTTCAAGATCGGGGCTCTTTGGAGCAATTGCAGGT
TTCATAGAAGGCGGATGGCCAGGGCTAGTGGCTGGTTGGTACGGATTTCAGCATCAAAATGCGGAGGGGA
CAGGCATAGCTGCAGACAGAGACAGCACCCAAAGGGCAATAGACAATATGCAAAACAAACTCAACAATGT
CATCGACAAAATGAATAAACAATTTGAAGTGGTGAATCATGAGTTTTCAGAAGTGGAAAGCAGAATAAAC
ATGATTAATTCCAAAATTGATGATCAGATAACTGACATATGGGCATACAATGCTGAATTGCTTGTCCTAT
TGGAAAATCAGAAGACATTAGATGAGCATGACGCTAATGTAAGGAATCTACATGATCGGGTCAGAAGAGT
CCTGAGGGAAAATGCAATTGACACAGGAGACGGCTGCTTTGAGATTTTACATAAATGTGACAACAATTGT
ATGGACACGATTAGAAACGGGACATACAATCACAAAGAGTATGAGGAAGAAAGCAAAATCGAACGACAGA
AAGTCAATGGTGTGAAACTTGAGGAGAATTCTACATATAAAATTCTGAGCATCTACAGCAGTGTTGCCTC
AAGCTTAGTTCTACTGCTCATGATTATTGGGGGTTTCATTTTCGGGTGTCAAAATGGAAATGTTCGTTGT
ACTTTCTGTATTTAA

Fig. 10K

Subtype H13 (SEQ ID NO:22)

>gi|221311|dbj|D90308.1|FLAHAH13N Influenza A virus
(A/Gull/Maryland/704/77(H13N6)) gene for hemagglutinin precursor, complete cds ATGGCTCTAAATGTCATTGCAACTTTGACACTTATAAGTGTATGTGTACATGCAGACAGAATATGCGTGG
GGTATCTGAGCACCAATTCATCAGAAAGGGTCGACACGCTCCTTGAAAATGGGGTCCCAGTCACCAGCTC
CATTGATCTGATTGAGACAAACCACACAGGAACATACTGTTCTCTAAATGGAGTCAGTCCAGTGCATTTG
GGAGATTGCAGCTTTGAAGGATGGATTGTAGGAAACCCAGCCTGCACCAGCAACTTTGGGATCAGAGAGT
GGTCATACCTGATTGAGGACCCCGCGGCCCCTCATGGGCTTTGCTACCCTGGAGAATTAAACAACAATGG
TGAACTCAGACACTTGTTCAGTGGAATCAGGTCATTCAGTAGAACGGAATTGATCCCACCTACCTCCTGG
GGGGAAGTACTTGACGGTACAACATCTGCTTGCAGAGATAACACGGGAACCAACAGCTTCTATCGAAATT
TAGTTTGGTTTATAAAGAAGAATACTAGATATCCAGTTATCAGTAAGACCTACAACAATACAACGGGAAG
GGATGTTTTAGTTTTATGGGGAATACATCACCCAGTGTCTGTGGATGAGACAAAGACTCTGTATGTCAAT
AGTGATCCATACACACTGGTTTCCACCAAGTCTTGGAGCGAGAAATATAAACTAGAAACGGGAGTCCGAC
CTGGCTATAATGGACAGAGGAGCTGGATGAAAATTTATTGGTCTTTGATACATCCAGGGGAGATGATTAC
TTTCGAGAGTAATGGTGGATTTTTAGCCCCAAGATATGGGTACATAATTGAAGAATATGGAAAAGGAAGG
ATTTTCCAGAGTCGCATCAGAATGTCTAGGTGCAACACCAAGTGCCAGACTTCGGTTGGAGGGATAAACA
CAAACAGAACGTTCCAAAACATCGATAAGAATGCTCTTGGTGACTGTCCCAAATACATAAAGTCTGGCCA
ACTCAAGCTAGCCACTGGACTCAGAAATGTGCCAGCTATATCGAATAGAGGATTGTTCGGAGCAATTGCA
GGGTTCATAGAAGGAGGCTGGCCAGGTTTAATCAATGGTTGGTACGGTTTTCAGCATCAAAATGAACAGG
GAACAGGAATAGCTGCAGACAAAGAATCAACACAGAAAGCTATAGACCAGATAACAACCAAAATAAATAA
CATTATTGATAAAATGAATGGGAACTATGATTCAATTAGGGGTGAATTCAATCAAGTTGAGAAGCGTATA
AACATGCTTGCAGACAGAATAGATGATGCCGTGACGGACATTTGGTCATACAATGCCAAACTTCTTGTAT
TGCTGGAAAATGATAAAACTTTAGATATGCATGATGCTAATGTAAAGAATTTACATGAGCAAGTACGAAG
AGAATTGAAGGACAATGCAATTGACGAAGGAAATGGCTGTTTTGAACTCCTTCATAAATGCAATGACTCC
TGCATGGAAACTATAAGAAATGGAACGTATGACCACACTGAGTATGCAGAGGAGTCAAAGTTAAAGAGGC
AAGAAATCGATGGGATCAAACTCAAATCAGAAGACAACGTTTACAAAGCATTATCAATATACAGTTGCAT
TGCAAGTAGTGTTGTACTAGTAGGACTCATACTCTCTTTCATCATGTGGGCCTGTAGTAGTGGGAATTGC
CGATTCAATGTTTGTATATAA

Fig. 10L

Subtype H14 (SEQ ID NO:23)

\>gi|324045|gb|M35997.1|FLAH1424 Influenza A/Mallard/Gurjev/263/82
hemagglutinin subtype H14 gene AGCAAAAGCAGGGGAAAATGATTGCACTCATATTGGTTGCACTGGCTCTGAGCCACACTGCTTATTCTCA
GATCACAAATGGGACAACAGGAAACCCCATTATATGCTTGGGGCATCATGCAGTGGAAAACGGCACATCT
GTTAAAACACTAACAGACAATCACGTAGAAGTTGTGTCAGCTAAAGAATTAGTTGAGACGAACCACACTG
ATGAACTGTGCCCAAGCCCCTTGAAGCTTGTCGACGGGCAAGACTGCCACCTCATCAATGGTGCATTGGG
GAGTCCAGGCTGTGACCGTTTGCAGGACACCACTTGGGATGTCTTCATTGAAAGGCCCACTGCAGTAGAC
ACATGTTATCCATTCGACGTCCCAGATTACCAGAGTCTCAGAAGCATCCTAGCAAGCAGTGGGAGTTTGG
AGTTCATCGCCGAACAATTCACCTGGAATGGTGTCAAAGTTGACGGATCAAGCAGTGCTTGTTTGAGGGG
CGGTCGCAACAGCTTCTTCTCCCGACTAAACTGGCTAACCAAAGCAACAAATGGAAACTATGGACCTATT
AACGTCACTAAAGAAAATACGGGCTCTTATGTCAGGCTCTATCTCTGGGGAGTGCATCACCCATCAAGCG
ATAATGAGCAAACGGATCTCTACAAGGTGGCAACAGGGAGAGTAACAGTATCTACCCGCTCGGACCAAAT
CAGTATTGTTCCCAATATAGGAAGTAGACCGAGGGTAAGGAATCAGAGCGGCAGGATAAGCATCTACTGG
ACCCTAGTAAACCCAGGGGACTCCATCATTTTCAACAGTATTGGGAATTTGATTGCACCAAGAGGCCACT
ACAAAATAAGCAAATCTACTAAGAGCACAGTGCTTAAAAGTGACAAAAGGATTGGGTCATGCACAAGCCC
TTGCTTAACTGATAAAGGTTCGATCCAAAGTGACAAACCTTTTCAGAATGTATCAAGGATTGCTATAGGA
AACTGCCCGAAATATGTAAAGCAAGGGTCCCTGATGTTAGCAACTGGAATGCGCAACATCCCTGGCAAAC
AGGCAAAGGGCTTATTTGGGGCAATTGCTGGATTCATTGAAAATGGTTGGCAAGGCCTGATTGATGGGTG
GTATGGATTCAGGCACCAAAATGCTGAAGGAACAGGAACTGCTGCAGACCTGAAGTCAACTCAGGCAGCC
ATTGATCAGATAAATGGCAAGCTGAACAGATTGATAGAGAAGACAAATGAAAAATATCACCAAATAGAAA
AGGAATTCGAACAGGTGGAAGGAAGAATACAAGACCTTGAGAAGTACGTTGAGGACACTAAGATTGATTT
GTGGTCATACAATGCTGAATTGCTAGTAGCACTAGAGAATCAGCACACAATAGATGTCACAGACTCCGAA
ATGAACAAGCTTTTTGAAAGAGTAAGAAGGCAATTAAGAGAGAATGCAGAAGATCAAGGCAACGGTTGTT
TCGAGATATTCCATCAGTGTGACAACAATTGTATAGAAAGCATTAGAAACGGAACTTATGACCACAACAT
CTACAGGGATGAAGCCATCAACAATCGAATCAAAATAAATCCTGTCACTTTGACGATGGGGTACAAGGAC
ATAATCCTGTGGATTTCTTTCTCCATGTCATGCTTTGTCTTCGTGGCACTGATTCTGGGATTTGTTCTAT
GGGCTTGTCAAAACGGGAATATCCGATGCCAAATCTGTATATAAAGAAAAAACACCCTTGTTTCTACTC

Fig. 10M

Subtype H15 (SEQ ID NO:24)

>gi|1226068|gb|L43916.1|FLAHEMAC Influenza A/duck/Australia/341/83 (H15N8) hemagglutinin mRNA, complete cds

```
AGCAAAAGCAGGGGATACAAAATGAACACTCAAATCATCGTCATTCTAGTCCTCGGACTGTCGATGGTGA
GATCTGACAAGATTTGTCTCGGGCACCATGCCGTAGCAAATGGGACAAAAGTCAACACACTAACTGAGAA
AGGAGTGGAAGTGGTCAATGCCACGGAGACAGTGGAGATTACAGGAATAAATAAAGTGTGCACAAAAGGG
AAGAAAGCGGTGGACTTGGGATCTTGTGGAATACTGGGAACTATCATTGGGCCTCCACAATGTGACTCTC
ATCTTAAATTCAAAGCTGATCTGATAATAGAAAGAAGAAATTCAAGTGACATCTGTTACCCAGGGAAATT
CACTAATGAGGAAGCACTGAGACAAATAATCAGAGAATCTGGTGGAATTGACAAAGAGCCAATGGGATTT
AGATATTCAGGAATAAAAACAGACGGGGCAACCAGTGCGTGTAAGAGAACAGTGTCCTCTTTCTACTCAG
AAATGAAATGGCTTTTATCCAGCAAGGCTAACCAGGTGTTCCCACAACTGAATCAGACATACAGGAACAA
CAGAAAAGAACCAGCCCTAATTGTTTGGGGAGTACATCATTCAAGTTCCTTGGATGAGCAAAATAAGCTA
TATGGAGCTGGGAACAAGCTGATAACAGTAGGAAGCTCAAAATACCAACAATCGTTTTCACCAAGTCCAG
GGGACAGGCCCAAAGTGAATGGTCAGGCCGGGAGGATCGACTTTCATTGGATGCTATTGGACCCAGGGGA
TACAGTCACTTTTACCTTCAATGGTGCATTCATAGCCCCAGATAGAGCCACCTTTCTCCGCTCTAATGCC
CCATCGGGAGTTGAGTACAATGGGAAGTCACTGGGAATACAGAGTGATGCACAAATTGATGAATCATGTG
AAGGGGAATGCTTCTACAGTGGAGGGACAATAAACAGCCCTTTGCCATTTCAAAACATCGATAGTTGGGC
TGTCGGAAGGTGCCCCAGATATGTAAAGCAATCAAGCCTGCCGCTGGCCTTAGGAATGAAAAATGTACCA
GAGAAAATACATACTAGGGGACTGTTCGGTGCAATTGCAGGATTCATCGAGAATGGATGGGAAGGACTCA
TTGATGGATGGTATGGATTTAGGCATCAAAATGCACAGGGGCAGGGAACAGCTGCTGACTACAAGAGTAC
TCAGGCTGCAATTGACCAGATAACAGGGAAACTTAATAGATTAATTGAAAAAACCAACACACAGTTTGAA
CTCATAGACAATGAGTTCACTGAAGTGGAGCAGCAGATAGGCAATGTAATAAACTGGACAAGGGACTCCT
TGACTGAGATCTGGTCATACAATGCTGAACTTCTAGTAGCAATGGAAAATCAGCATACAATTGACCTTGC
AGATTCTGAAATGAACAAACTCTATGAGAGAGTGAGAAGACAGCTAAGGGAGAATGCCGAGGAGGATGGA
ACTGGATGTTTTGAGATTTTCCACCGATGTGACGATCAATGTATGGAGAGCATACGAAATAATACTTACA
ATCACACTGAATATCGACAGGAAGCCTTACAGAATAGGATAATGATCAATCCGGTAAAGCTTAGTGGTGG
GTACAAAGATGTGATACTATGGTTTAGCTTCGGGGCATCATGTGTAATGCTTCTAGCCATTGCTATGGGT
CTTATTTTCATGTGTGTGAAAAACGGGAATCTGCGGTGCACTATCTGTATATAATTATTTGAAAAACACC
CTTGTTTCTACT
```

Fig. 10N

Subtype H16 (SEQ ID NO:25)

>gi|56425020|gb|AY684891.1| Influenza A virus (A/black-headed gull/Sweden/5/99(H16N3)) hemagglutinin (HA) gene, complete cds AGCAAAAGCAGGGGATATTGTCAAAACAACAGAATGGTGATCAAAGTGCTCTACTTTCTCATCGTATTGT
TAAGTAGGTATTCGAAAGCAGACAAAATATGCATAGGATATCTAAGCAACAACGCCACAGACACAGTAGA
CACACTGACAGAGAACGGAGTTCCAGTGACCAGCTCAGTTGATCTCGTTGAAACAAACCACACAGGAACA
TACTGCTCACTGAATGGAATCAGCCCAATTCATCTTGGTGACTGCAGCTTTGAGGGATGGATCGTAGGAA
ACCCTTCCTGTGCCACCAACATCAACATCAGAGAGTGGTCGTATCTAATTGAGGACCCCAATGCCCCCAA
CAAACTCTGCTTCCCAGGAGAGTTAGATAATAATGGAGAATTACGACATCTCTTCAGCGGAGTGAACTCT
TTTAGCAGAACAGAATTAATAAGTCCCAACAAATGGGAGACATTCTGGATGGAGTCACCGCTTCTTGCC
GCGATAATGGGGCAAGCAGTTTTTACAGAAATTTGGTCTGGATAGTGAAGAATAAAAATGGAAAATACCC
TGTCATAAAGGGGGATTACAATAACACAACAGGCAGAGATGTTCTAGTACTCTGGGGCATTCACCATCCG
GATACAGAAACAACAGCCATAAACTTGTACGCAAGCAAAAACCCCTACACATTAGTATCAACAAAGGAAT
GGAGCAAAAGATATGAACTAGAAATTGGCACCAGAATAGGTGATGGACAGAGAAGTTGGATGAAACTATA
TTGGCACCTCATGCGCCCTGGAGAGAGGATAATGTTTGAAAGCAACGGGGGCCTTATAGCGCCCAGATAC
GGATACATCATTGAGAAGTACGGTACAGGACGAATTTTCCAAAGTGGAGTGAGAATGGCCAAATGCAACA
CAAAGTGTCAAACATCATTAGGTGGGATAAACACCAACAAAACTTTCCAAAACATAGAGAGAAATGCTCT
TGGAGATTGCCCAAAGTACATAAAGTCTGGACAGCTGAAGCTTGCAACTGGGCTGAGAAATGTCCCATCC
GTTGGTGAAAGAGGTTTGTTTGGTGCAATTGCAGGCTTCATAGAAGGAGGGTGGCCTGGGCTAATTAATG
GATGGTATGGTTTCCAGCATCAGAATGAACAGGGGACTGGCATTGCTGCAGACAAAGCCTCCACTCAGAA
AGCGATAGATGAAATAACAACAAAAATTAACAATATAATAGAGAAGATGAACGGAAACTATGATTCAATA
AGAGGGGAATTCAATCAAGTAGAAAAGAGGATCAACATGCTCGCTGATCGAGTTGATGATGCAGTAACTG
ACATATGGTCGTACAATGCTAAACTTCTTGTACTGCTTGAAAATGGGAGAACATTGGACTTACACGACGC
AAATGTCAGGAACTTACACGATCAGGTCAAGAGAATATTGAAAAGTAATGCTATTGATGAAGGAGATGGT
TGCTTCAATCTTCTTCACAAATGTAATGACTCATGCATGGAAACTATTAGAAATGGGACCTACAATCATG
AAGATTACAGGGAAGAATCACAACTGAAAAGGCAGGAAATTGAGGGAATAAAATTGAAGTCTGAAGACAA
TGTGTATAAAGTACTGTCGATTTATAGCTGCATTGCAAGCAGTATTGTGCTGGTAGGTCTCATACTTGCG
TTCATAATGTGGGCATGCAGCAATGGAAATTGCCGGTTTAATGTTTGTATATAGTCGGAAAAAATACCCT
TGTTTCTACT

Fig. 10O

Influenza B (SEQ ID NO:26)

>gi|325175|gb|K00423.1|FLBHAZO Influenza B/Lee/40, hemagglutinin (seg 4), complete segment AGCAGAAGCGTTGCATTTTCTAATATCCACAAAATGAAGGCAATAATTGTACTACTCATGGTAGTAACAT
CCAATGCAGATCGAATCTGCACTGGGATAACATCGTCAAACTCACCTCATGTGGTTAAAACTGCCACTCA
AGGGGAAGTCAATGTGACTGGTGTGATACCACTAACAACAACACCTACCAAATCTCATTTTGCAAATCTC
AAAGGAACACAGACCAGAGGAAAACTATGCCCAAACTGTTTTAACTGCACAGATCTGGACGTGGCCCTAG
GCAGACCAAAATGCATGGGGAACACACCCTCCGCAAAAGTCTCAATACTCCATGAAGTCAAACCTGCTAC
ATCTGGATGCTTTCCTATAATGCACGACAGAACAAAAATCAGACAACTACCTAATCTTCTCAGAGGATAT
GAAAACATCAGGTTATCAACCAGTAATGTTATCAATACAGAGACGGCACCAGGAGGACCCTACAAGGTGG
GGACCTCAGGATCTTGCCCTAACGTTGCTAATGGGAACGGCTTCTTCAACACAATGGCTTGGGTTATCCC
AAAAGACAACAACAAGACAGCAATAAATCCAGTAACAGTAGAAGTACCATACATTTGTTCAGAAGGGGAA
GACCAAATTACTGTTTGGGGGTTCCACTCTGATGACAAAACCCAAATGGAAAGACTCTATGGAGACTCAA
ATCCTCAAAAGTTCACCTCATCTGCCAATGGAGTAACCACACATTATGTTTCTCAGATTGGTGGCTTCCC
AAATCAAACAGAAGACGAAGGGCTAAAACAAAGCGGCAGAATTGTTGTTGATTACATGGTACAAAAACCT
GGAAAAACAGGAACAATTGTTTATCAAAGAGGCATTTTATTGCCTCAAAAAGTGTGGTGCGCAAGTGGCA
GGAGCAAGGTAATAAAAGGGTCCTTGCCTTTAATTGGTGAAGCAGATTGCCTCCACGAAAAGTACGGTGG
ATTAAATAAAAGCAAGCCTTACTACACAGGAGAGCATGCAAAGGCCATAGGAAATTGCCCAATATGGGTG
AAAACACCCTTGAAGCTGGCCAATGGAACCAAATATAGACCGCCTGCAAAACTATTAAAGGAAAGAGGTT
TCTTCGGAGCTATTGCTGGTTTCTTGGAAGGAGGATGGGAAGGAATGATTGCAGGTTGGCACGGATACAC
ATCTCATGGAGCACATGGAGTGGCAGTGGCAGCAGACCTTAAGAGTACACAAGAAGCTATAAACAAGATA
ACAAAAAATCTCAACTATTTAAGTGAGCTAGAAGTAAAAAACCTTCAAAGACTAAGCGGAGCAATGAATG
AGCTTCACGACGAAATACTCGAGCTAGACGAAAAAGTGGATGATCTAAGAGCTGATACAATAAGCTCACA
AATAGAGCTTGCAGTCTTGCTTTCCAACGAAGGGATAATAAACAGTGAAGATGAGCATCTCTTGGCACTT
GAAAGAAAACTGAAGAAAATGCTTGGCCCCTCTGCTGTAGAAATAGGGAATGGGTGCTTTGAAACCAAAC
ACAAATGCAACCAGACTTGCCTAGACAGGATAGCTGCTGGCACCTTTAATGCAGGAGATTTTTCTCTTCC
CACTTTTGATTCATTAAACATTACTGCTGCATCTTTAAATGATGATGGCTTGGATAATCATACTATACTG
CTCTACTACTCAACTGCTGCTTCTAGCTTGGCTGTAACATTAATGATAGCTATCTTCATTGTCTACATGG
TCTCCAGAGACAATGTTTCTTGTTCCATCTGTCTGTGAGGGAGATTAAGCCCTGTGTTTTCCTTTACTGT
AGTGCTCATTTGCTTGTCACCATTACAAAGAAACGTTATTGAAAAATGCTCTTGTTACTACT

Fig. 10P

Influenza C (SEQ ID NO:27)

>gi|325317|gb|M17868.1|FLCHAJO Influenza C/Johannesburg/66
hemagglutinin esterase RNA (seg 4), complete cds
AGCAGAAGCAGGGGGTTAATAATGTTTTTCTCATTACTCTTGGTGTTGGGCCTCACAGAGGCTGAAAAAA
TAAAGATATGCCTTCAAAAGCAAGTGAACAGTAGCTTCAGCCTACACAATGGCTTCGGAGGAAATTTGTA
TGCCACAGAAGAAAAAAGAATGTTTGAGCTTGTTAAGCCCAAAGCTGGAGCCTCTGTCTTGAATCAAAGT
ACATGGATTGGCTTTGGAGATTCAAGGACTGACAAAAGCAATTCAGCTTTTCCTAGGTCTGCTGATGTTT
CAGCAAAAACTGCTGATAAGTTTCGTTTTTTGTCTGGTGGATCCTTAATGTTGAGTATGTTTGGCCCACC
TGGGAAGGTAGACTACCTTTACCAAGGATGTGGAAAACATAAAGTTTTTTATGAAGGAGTTAACTGGAGT
CCACATGCTGCTATAAATTGTTACAGAAAAAATTGGACTGATATCAAACTGAATTTCCAGAAAAACATTT
ATGAATTGGCTTCACAATCACATTGCATGAGCTTGGTGAATGCCTTGGACAAAACTATTCCTTTACAAGT
GACTGCTGGGACTGCAGGAAATTGCAACAACAGCTTCTTAAAAAATCCAGCATTGTACACACAAGAAGTC
AAGCCTTCAGAAAACAAATGTGGGAAAGAAAATCTTGCTTTCTTCACACTTCCAACCCAATTTGGAACCT
ATGAGTGCAAACTGCATCTTGTGGCTTCTTGCTATTTCATCTATGATAGTAAAGAAGTGTACAATAAAAG
AGGATGTGACAACTACTTTCAAGTGATCTATGATTCATTTGGAAAAGTCGTTGGAGGACTAGATAACAGG
GTATCACCTTACACAGGGAATTCTGGAGACACCCCAACAATGCAATGTGACATGCTCCAGCTGAAACCTG
GAAGATATTCAGTAAGAAGCTCTCCAAGATTCCTTTTAATGCCTGAAAGAAGTTATTGCTTTGACATGAA
AGAAAAAGGACCAGTCACTGCTGTCCAATCCATTTGGGGAAAAGGCAGAGAATCTGACTATGCAGTGGAT
CAAGCTTGCTTGAGCACTCCAGGGTGCATGTTGATCCAAAAGCAAAAGCCATACATTGGAGAAGCTGATG
ATCACCATGGAGATCAAGAAATGAGGGAGTTGCTGTCAGGACTGGACTATGAAGCTAGATGCATATCACA
ATCAGGGTGGGTGAATGAAACCAGTCCTTTTACGGAGAAATACCTCCTTCCTCCCAAATTTGGAAGATGC
CCTTTGGCTGCAAAGGAAGAATCCATTCCAAAAATCCCAGATGGCCTTCTAATTCCCACCAGTGGAACCG
ATACCACTGTAACCAAACCTAAGAGCAGAATTTTTGGAATCGATGACCTCATTATTGGTGTGCTCTTTGT
TGCAATCGTTGAAACAGGAATTGGAGGCTATCTGCTTGGAAGTAGAAAAGAATCAGGAGGAGGTGTGACA
AAAGAATCAGCTGAAAAAGGGTTTGAGAAAATTGGAAATGACATACAAATTTTAAAATCTTCTATAAATA
TCGCAATAGAAAAACTAAATGACAGAATTTCTCATGATGAGCAAGCCATCAGAGATCTAACTTTAGAAAT
TGAAAATGCAAGATCTGAAGCTTTATTGGGAGAATTGGAATAATAAGAGCCTTATTGGTAGGAAATATA
AGCATAGGATTACAGGAATCTTTATGGGAACTAGCTTCAGAAATAACAAATAGAGCAGGAGATCTAGCAG
TTGAAGTCTCCCCAGGTTGCTGGATAATTGACAATAACATTTGTGATCAAAGCTGTCAAAATTTTATTTT
CAAGTTCAACGAAACTGCACCTGTTCCAACCATTCCCCCTCTTGACACAAAAATTGATCTGCAATCAGAT
CCTTTTTACTGGGGAAGCAGCTTGGGCTTAGCAATAACTGCTACTATTTCATTGGCAGCTTTGGTGATCT
CTGGGATCGCCATCTGCAGAACTAAATGATTGAGACAATTTTGAAAAATGGATAATGTGTTGGTCAATAT
TTTGTACAGTTTTATAAAAAACAAAAATCCCCTTGCTACTGCT

Fig. 10Q

SEQ ID NO: 29

5'-AGTTCCCCGGGCTGGTATATTTATATGTTGTC-3'

Fig. 10 R

SEQ ID NO: 30

5'-AATAGAGCTCCATTTTCTCTCAAGATGATTAATTAATTAGTC-3

Fig. 10S

SEQ ID NO: 31

5'-AATAGAGCTCGTTAAAATGCTTCTTCGTCTCCTATTTATAATATGG-3'

Fig. 10T

SEQ ID NO: 32

5'-TTACGAATTCTCCTTCCTAATTGGTGTACTATCATTTATCAAAGGGGA-3'

Fig. 12

1 - Commercial H5 (A/Vietnam/1203/2004) (750 ng)
2 - Leaf protein extract from mock (37.5 µg)
3 - Leaf protein extract from R660-infiltrated plant (37.5 µg)

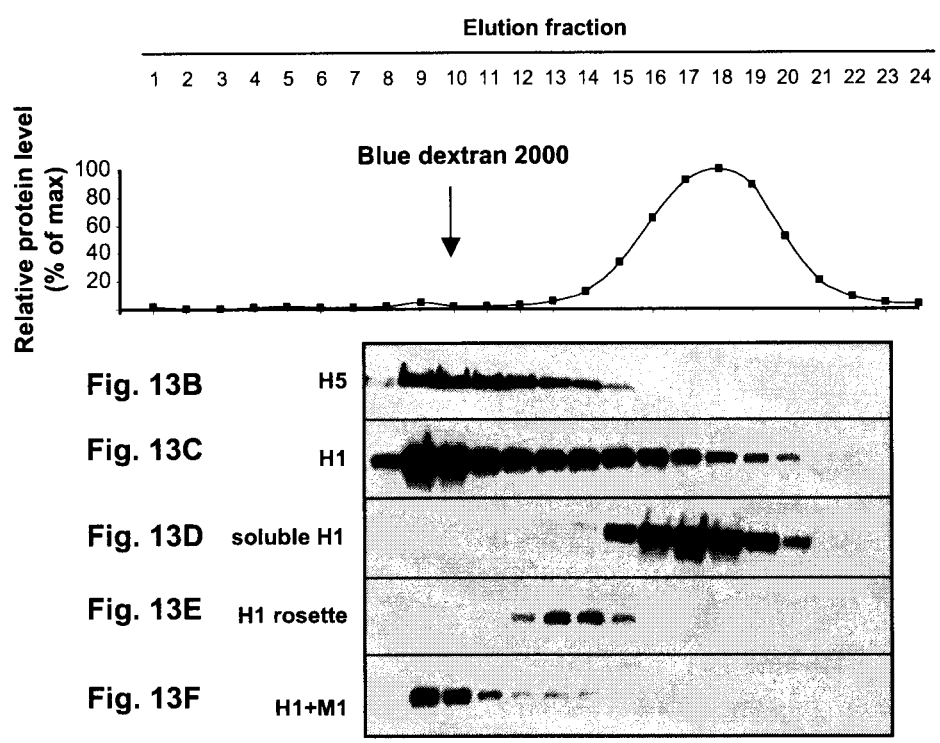

Fig. 16

SEQ ID NO: 33
ATGAAAGCAAAACTACTGGTCCTGTTATGTACATTTACAGCTACATATGCAGA
CACAATATGTATAGGCTACCATGCCAACAACTCAACCGACACTGTTGACACAG
TACTTGAGAAGAATGTGACAGTGACACACTCTGTCAACCTACTTGAGGACAGT
CACAATGGAAAACTATGTCTACTAAAAGGAATAGCCCCACTACAATTGGGTAA
TTGCAGCGTTGCCGGATGGATCTTAGGAAACCCAGAATGCGAATTACTGATTT
CCAAGGAATCATGGTCCTACATTGTAGAAACACCAAATCCTGAGAATGGAACA
TGTTACCCAGGGTATTTCGCCGACTATGAGGAACTGAGGGAGCAATTGAGTTC
AGTATCTTCATTTGAGAGATTCGAAATATTCCCCAAAGAAAGCTCATGGCCCA
ACCACACCGTAACCGGAGTATCAGCATCATGCTCCCATAATGGGAAAAGCAGT
TTTTACAGAAATTTGCTATGGCTGACGGGGAAGAATGGTTTGTACCCAAACCT
GAGCAAGTCCTATGTAAACAACAAAGAGAAAGAAGTCCTTGTACTATGGGGTG
TTCATCACCCGCCTAACATAGGGAACCAAAGGGCCCTCTATCATACAGAAAAT
GCTTATGTCTCTGTAGTGTCTTCACATTATAGCAGAAGATTCACCCCAGAAAT
AGCCAAAAGACCCAAAGTAAGAGATCAGGAAGGAAGAATCAACTACTACTGGA
CTCTGCTGGAACCTGGGGATACAATAATATTTGAGGCAAATGGAAATCTAATA
GCGCCATGGTATGCTTTTGCACTGAGTAGAGGCTTTGGATCAGGAATCATCAC
CTCAAATGCACCAATGGATGAATGTGATGCGAAGTGTCAAACACCTCAGGGAG
CTATAAACAGCAGTCTTCCTTTCCAGAATGTACACCCAGTCACAATAGGAGAG
TGTCCAAAGTATGTCAGGAGTGCAAAATTAAGGATGGTTACAGGACTAAGGAA
CATCCCATCCATTCAATCCAGAGGTTTGTTTGGAGCCATTGCCGGTTTCATTG
AAGGGGGGTGGACTGGAATGGTAGATGGGTGGTATGGTTATCATCATCAGAAT
GAGCAAGGATCTGGCTATGCTGCAGATCAAAAAGTACACAAATGCCATTAA
CGGGATTACAAACAAGGTGAATTCTGTAATTGAGAAATGAACACTCAATTCA
CAGCTGTGGGCAAAGAATTCAACAAATTGGAAAGAAGGATGGAAAACTTAAAT
AAAAAGTTGATGATGGGTTCTAGACATTTGGACATATAATGCAGAATTGTT
GGTTCTACTGGAAAATGAAGGACTTTGGATTTCCATGACTCCAATGTGAAGA
ATCTGTATGAGAAAGTAAAAGCCAATTAAAGAATAATGCCAAAGAAATAGGA
AACGGGTGTTTTGAATTCTATCACAAGTGTAACAATGAATGCATGGAGAGTGT
GAAAATGGAACTTATGACTATCCAAAATATTCCGAAGAATCAAAGTTAAACA
GGGAGAAAATTGATGGAGTGAAATTGGAATCAATGGGAGTCTATCAGATTCTG
GCGATCTACTCAACTGTCGCCAGTTCCCTGGTTCTTTTGGTCTCCCTGGGGGC
AATCAGCTTCTGGATGTGTTCCAATGGGTCTTTGCAGTGTAGAATATGCATCT
GAGACCAGAATTTCA

Fig. 17

SEQ ID NO: 34
CCAAATCCTTAACATTCTTTCAACACCAACAATGGCGAAAAACGTTGCGATT
TTCGGTTTATTGTTTTCTCTTCTTCTGTTGGTTCCTTCTCAGATCTTCGCTG
AGGAATCATCAACTGACGCTAAGGAATTTGTTCTTACATTGGATAACACTAA
TTTCCATGACACTGTTAAGAAGCACGATTTCATCGTCGTTGAATTCTACGCA
CCTTGGTGTGGACACTGTAAGAAGCTAGCCCCAGAGTATGAGAAGGCTGCTT
CTATCTTGAGCACTCACGAGCCACCAGTTGTTTTGGCTAAAGTTGATGCCAA
TGAGGAGCACAACAAAGACCTCGCATCGGAAATGATGTTAAGGGATTCCCA
ACCATTAAGATTTTTAGGAATGGTGGAAAGAACATTCAAGAATACAAAGGTC
CCCGTGAAGCTGAAGGTATTGTTGAGTATTTGAAAAAACAAAGTGGCCCTGC
ATCCACAGAAATTAAATCTGCTGATGATGCGACCGCTTTTGTTGGTGACAAC
AAAGTTGTTATTGTCGGAGTTTTCCCTAAATTTTCTGGTGAGGAGTACGATA
ACTTCATTGCATTAGCAGAGAAGTTGCGTTCTGACTATGACTTTGCTCACAC
TTTGAATGCCAAACACCTTCCAAAGGGAGACTCATCAGTGTCTGGGCCTGTG
GTTAGGTTATTTAAGCCATTTGACGAGCTCTTTGTTGACTCAAAGGATTTCA
ATGTAGAAGCTCTAGAGAAATTCATTGAAGAATCCAGTACCCCAATTGTGAC
TGTCTTCAACAATGAGCCTAGCAATCACCCTTTTGTTGTCAAATTCTTTAAC
TCTCCCAACGCAAAGGCTATGTTGTTCATCAACTTTACTACCGAAGGTGCTG
AATCTTTCAAAACAAAATACCATGAAGTGGCTGAGCAATACAAACAACAGGG
AGTTAGCTTTCTTGTTGGAGATGTTGAGTCTAGTCAAGGTGCCTTCCAGTAT
TTTGGACTGAAGGAAGAACAAGTACCTCTAATTATTATTCAGCATAATGATG
GCAAGAAGTTTTTCAAACCCAATTTGGAACTTGATCAACTCCCAACTTGGTT
GAAGGCATACAAGGATGGCAAGGTTGAACCATTTGTCAAGTCTGAACCTATT
CCTGAAACTAACAACGAGCCTGTTAAAGTGGTGGTTGGGCAAACTCTTGAGG
ACGTTGTTTTCAAGTCTGGGAAGAATGTTTTGATAGAGTTTTATGCTCCTTG
GTGTGGTCACTGCAAGCAGTTGGCTCCAATCTTGGATGAAGTTGCTGTCTCA
TTCCAAAGCGATGCTGATGTTGTTATTGCAAAACTGGATGCAACTGCCAACG
ATATCCCAACCGACACCTTTGATGTCCAAGGCTATCCAACCTTGTACTTCAG
GTCAGCAAGTGGAAAACTATCACAATACGACGGTGGTAGGACAAAGGAAGAC
ATCATAGAATTCATTGAAAAGAACAAGGATAAAACTGGTGCTGCTCATCAAG
AAGTAGAACAACCAAAAGCTGCTGCTCAGCCAGAAGCAGAACAACCAAAAGA
TGAGCTTTGAAAAGTTCCGCTTGGAGGATATCGGCACACAGTCATCTGCGGG
CTTTACAACTCTTTTGTATCTCAGAATCAGAAGTTAGGAAATCTTAGTGCCA
ATCTATCTATTTTTGCGTTTCATTTTATCTTTTTGGTTTACTCTAATGTATT
ACTGAATAATGTGAGTTTTGGCGGAGTTTAGTACTGGAACTTTTGTTTCTGT
AAAAAAAAAAAA

Fig. 18

SEQ ID NO: 35

AGCGAAAGCAGGTAGATATTGAAAGATGAGTCTTCTAACCGAGGTCGAAACGTAC
GTTCTCTCTATCATCCCGTCAGGCCCCCTCAAAGCCGAGATCGCACAGAGACTTG
AAGATGTCTTTGCAGGGAAGAACACCGATCTTGAGGTTCTCATGGAATGGCTAAA
GACAAGACCAATCCTGTCACCTCTGACTAAGGGGATTTTAGGATTTGTGTTCACG
CTCACCGTGCCCAGTGAGCGAGGACTGCAGCGTAGACGCTTTGTCCAAAATGCCC
TTAATGGGAACGGGGATCCAAATAACATGGACAAAGCAGTTAAACTGTATAGGAA
GCTCAAGAGGGAGATAACATTCCATGGGGCCAAAGAAATCTCACTCAGTTATTCT
GCTGGTGCACTTGCCAGTTGTATGGGCCTCATATACAACAGGATGGGGGCTGTGA
CCACTGAAGTGGCATTTGGCCTGGTATGTGCAACCTGTGAACAGATTGCTGACTC
CCAGCATCGGTCTCATAGGCAAATGGTGACAACAACCAACCCACTAATCAGACAT
GAGAACAGAATGGTTTTAGCCAGCACTACAGCTAAGGCTATGGAGCAAATGGCTG
GATCGAGTGAGCAAGCAGCAGAGGCCATGGAGGTTGCTAGTCAGGCTAGGCAAAT
GGTGCAAGCGATGAGAACCATTGGGACTCATCCTAGCTCCAGTGCTGGTCTGAAA
AATGATCTTCTTGAAAATTTGCAGGCCTATCAGAAACGAATGGGGGTGCAGATGC
AACGGTTCAAGTGATCCTCTCGCTATTGCCGCAAATATCATTGGGATCTTGCACT
TGATATTGTGGATTCTTGATCGTCTTTTTTTCAAATGCATTTACCGTCGCTTTAA
ATACGGACTGAAAGGAGGGCCTTCTACGGAAGGAGTGCCAAAGTCTATGAGGGAA
GAATATCGAAAGGAACAGCAGAGTGCTGTGGATGCTGACGATGGTCATTTTGTCA
GCATAGAGCTGGAGTAAAAAACTACCTTGTTTCTACT

FIGURE 27
(A) (B)
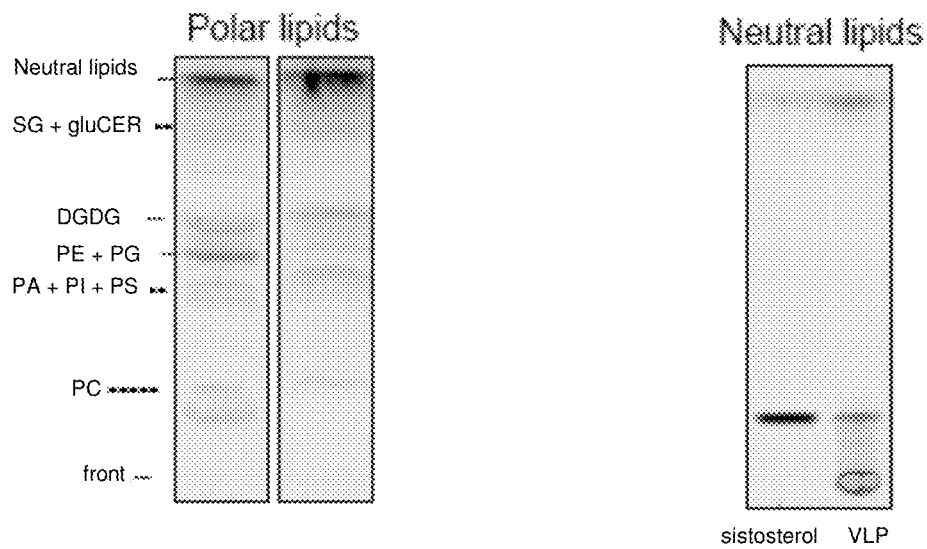
(C)
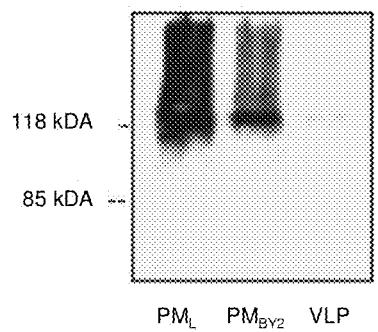

Fig. 28

SEQ ID NO: 36

<u>CACTTTGT</u>GAGTCTACACTTTGATTCCCTTCAAACACATACAAAGAGAAGAGA
CTAATTAATTAATTAATCATCTTGAGAGAAAATGAAAGTAAAACTACTGGTCC
TGTTATGCACATTTACAGCTACATATGCAGACACAATATGTATAGGCTACCAT
GCTAACAACTCGACCGACACTGTTGACACAGTACTTGAAAAGAATGTGACAG
TGACACACTCTGTCAACCTGCTTGAGAACAGTCACAATGGAAAACTATGTCT
ATTAAAAGGAATAGCCCCACTACAATTGGGTAATTGCAGCGTTGCCGGGTG
GATCTTAGGAAACCCAGAATGCGAATTACTGATTTCCAAGGAGTCATGGTCC
TACATTGTAGAAAAACCAAATCCTGAGAATGGAACATGTTACCCAGGGCATT
TCGCTGACTATGAGGAACTGAGGGAGCAATTGAGTTCAGTATCTTCATTTGA
GAGGTTCGAAATATTCCCCAAAGAAAGCTCATGGCCCAACCACACCGTAACC
GGAGTGTCAGCATCATGCTCCCATAATGGGGAAAGCAGTTTTTACAGAAATT
TGCTATGGCTGACGGGGAAGAATGGTTTGTACCCAAACCTGAGCAAGTCCT
ATGCAAACAACAAAGAAAAGAAGTCCTTGTACTATGGGGTGTTCATCACCC
GCCAAACATAGGTGACCAAAAGGCCCTCTATCATACAGAAATGCTTATGTC
TCTGTAGTGTCTTCACATTATAGCAGAAAATTCACCCCAGAAATAGCCAAAAG
ACCCAAAGTAAGAGATCAAGAAGGAAGAATCAATTACTACTGGACTCTGCTT
GAACCCGGGGATACAATAATATTTGAGGCAAATGGAAATCTAATAGCGCCAA
GATATGCTTTCGCACTGAGTAGAGGCTTTGGATCAGGAATCATCAACTCAAA
TGCACCAATGGATAAATGTGATGCGAAGTGCCAAACACCTCAGGGAGCTATA
AACAGCAGTCTTCCTTTCCAGAACGTACACCCAGTCACAATAGGAGAGTGTC
CAAAGTATGTCAGGAGTGCAAAATTAAGGATGGTTACAGGACTAAGGAACAT
CCCATCCATTCAATCCAGAGGTTTGTTTGGAGCCATTGCCGGTTTCATTGAA
GGGGGGTGGACTGGAATGGTAGATGGTTGGTATGGTTATCATCATCAGAAT
GAGCAAGGATCTGGCTATGCTGCAGATCAAAAAGCACACAAAATGCCATTA
ATGGGATTACAAACAAGGTCAATTCTGTAATTGAGAAAATGAACACTCAATTC
ACAGCAGTGGGCAAAGAGTTCAACAAATTGGAAAGAAGGATGGAAAACTTG
AATAAAAAAGTTGATGATGGGTTTATAGACATTTGGACATATAATGCAGAACT
GTTGGTTCTACTGGAAAATGAAAGGACTTTGGATTTCCATGACTCCAATGTG
AAGAATCTGTATGAGAAAGTAAAAAGCCAGTTAAAGAATAATGCTAAAGAAAT
AGGAAATGGGTGTTTTGAGTTCTATCACAAGTGTAACGATGAATGCATGGAG
AGTGTAAAGAATGGAACTTATGACTATCCAAAATATTCCGAAGAATCAAAGTT
AAACAGGGAGAAATTGATGGAGTGAAATTGGAATCAATGGGAGTCTATCAG
ATTCTGGCGATCTACTCAACAGTCGCCAGTTCTCTGGTTCTTTTGGTCTCCC
TGGGGGCAATCAGCTTCTGGATGTGTTCCAATGGGTCTTTACAGTGTAGAAT
ATGCATCTAA<u>GAGCTC</u>

Fig. 29

SEQ ID NO: 37

CACTTTGTGAGTCTACACTTTGATTCCCTTCAAACACATACAAAGAGAAGAGACT
AATTAATTAATTAATCATCTTGAGAGAAAATGAAAGTAAAACTACTGGTCCTGTTA
TGCACATTTACAGCTACATATGCAGACACAATATGTATAGGCTACCATGCCAACA
ACTCAACCGACACTGTTGACACAGTACTTGAGAAGAATGTGACAGTGACACACT
CTGTCAACCTGCTTGAGGACAGTCACAATGGAAAATTATGTCTATTAAAAGGAAT
AGCCCCACTACAATTGGGTAATTGCAGCGTTGCCGGATGGATCTTAGGAAACCC
AGAATGCGAATTACTGATTTCCAGGGAATCATGGTCCTACATTGTAGAAAAACCA
AATCCTGAGAATGGAACATGTTACCCAGGGCATTTCGCCGACTATGAGGAACTG
AGGGAGCAATTGAGTTCAGTATCTTCATTTGAGAGATTCGAAATATTCCCCAAAG
AAAGCTCATGGCCCAACCACACCACAACCGGAGTATCAGCATCATGCTCCCATA
ATGGGGAAAGCAGTTTTTACAAAAATTTGCTATGGCTGACGGGGAAGAATGGTTT
GTACCCAAACCTGAGCAAGTCCTATGCAAACAACAAAGAGAAAGAAGTCCTTGTA
CTATGGGGTGTTCATCACCCGCCTAACATAGGTGACCAAAGGGCTCTCTATCAT
AAAGAAAATGCTTATGTCTCTGTAGTGTCTTCACATTATAGCAGAAAATTCACCCC
AGAAATAGCCAAAAGACCCAAAGTAAGAGATCAAGAAGGAAGAATCAACTACTAC
TGGACTCTACTTGAACCCGGGGATACAATAATATTTGAGGCAAATGGAAATCTAA
TAGCGCCAAGATATGCTTTCGCACTGAGTAGAGGCTTTGGATCAGGAATCATCA
ACTCAAATGCACCAATGGATGAATGTGATGCGAAGTGCCAAACACCTCAGGGAG
CTATAAACAGCAGTCTTCCTTTCCAGAATGTACACCCTGTCACAATAGGAGAGTG
TCCAAAGTATGTCAGGAGTGCAAAATTAAGGATGGTTACAGGACTAAGGAACAT
CCCATCCATTCAATCCAGAGGTTTGTTTGGAGCCATTGCCGGTTTCATTGAAGG
GGGGTGGACTGGAATGGTAGATGGTTGGTATGGTTATCATCATCAGAATGAGCA
AGGATCTGGCTATGCTGCAGATCAAAAAAGCACACAAAATGCCATTAATGGGATT
ACAAACAAGGTCAATTCTGTAATTGAGAAAATGAACACTCAATTCACAGCTGTGG
GCAAAGAGTTCAACAAATTGGAAAGAAGGATGGAAAACTTAAATAAAAAAGTTGA
TGATGGGTTTATAGACATTTGGACATATAATGCAGAATTGTTGGTTCTACTGGAA
AATGAAAGGACTTTGGATTTCCATGACTCCAATGTGAAGAATCTGTATGAGAAAG
TAAAAAGCCAATTAAAGAATAATGCCAAAGAAATAGGAAATGGGTGTTTTGAGTT
CTATCATAAGTGTAACGATGAATGCATGGAGAGTGTAAAAAATGGAACTTATGAC
TATCCAAAATATTCCGAAGAATCAAAGTTAAACAGGGAGAAAATTGATGGAGTGA
AATTGGAATCAATGGGAGTCTATCAGATTCTGGCGATCTACTCAACAGTCGCCAG
TTCTCTGGTTCTTTTGGTCTCCCTGGGGGCAATCAGCTTCTGGATGTGTTCCAAT
GGGTCTTTGCAGTGTAGAATATGCATCTGAGAGCTC

Fig. 30

SEQ ID NO: 38

<u>CACTTTGTG</u>AGTCTACACTTTGATTCCCTTCAAACACATACAAAGAGAAGAGA
CTAATTAATTAATTAATCATCTTGAGAGAAAATGAAGACTATCATTGCTTTGAG
CTACATTCTATGTCTGGTTTTCACTCAAAAACTTCCCGGAAATGACAACAGCA
CGGCAACGCTGTGCCTTGGGCACCATGCAGTACCAAACGGAACGATAGTGA
AAACAATCACGAATGACCAAATTGAAGTTACTAATGCTACTGAGCTGGTTCAG
AGTTCCTCAACAGGTGAAATATGCGACAGTCCTCATCAGATCCTTGATGGAG
AAAACTGCACACTAATAGATGCTCTATTGGGAGACCCTCAGTGTGATGGCTT
CCAAAATAAGAAATGGGACCTTTTTGTTGAACGCAGCAAAGCCTACAGCAACT
GTTACCCTTATGATGTGCCGGATTATGCCTCCCTTAGGTCACTAGTTGCCTCA
TCCGGCACACTGGAGTTTAACAATGAAAGTTTCAATTGGACTGGAGTCACTCA
AAACGGAACAAGCTCTGCTTGCATAAGGAGATCTAATAACAGTTTCTTTAGTA
GATTGAATTGGTTGACCCACTTAAAATTCAAATACCCAGCATTGAACGTGACT
ATGCCAAACAATGAAAAATTTGACAAATTGTACATTTGGGGGGTTCACCACCC
GGGTACGGACAATGACCAAATCTTCCTGTATGCTCAAGCATCAGGAAGAATC
ACAGTCTCTACCAAAAGAAGCCAACAAACTGTAATCCCGAATATCGGATCTAG
ACCCAGAGTAAGGAATATCCCCAGCAGAATAAGCATCTATTGGACAATAGTAA
AACCGGGAGACATACTTTTGATTAACAGCACAGGGAATCTAATTGCTCCTAG
GGGTTACTTCAAAATACGAAGTGGGAAAAGCTCAATAATGAGATCAGATGCA
CCCATTGGCAAATGCAATTCTGAATGCATCACTCCAAACGGAAGCATTCCCAA
TGACAAACCATTCCAAAATGTAAACAGGATCACATACGGGGCCTGTCCCAGA
TATGTTAAGCAAAACACTCTGAAATTGGCAACAGGGATGCGAAATGTACCAG
AGAAACAAACTAGAGGCATATTTGGCGCAATCGCGGGTTTCATAGAAAATGG
TTGGGAGGGAATGGTGGATGGTTGGTATGGTTTCAGGCATCAAAATTCTGAG
GGAATAGGACAAGCAGCAGATCTCAAAAGCACTCAAGCAGCAATCGATCAAA
TCAATGGGAAGCTGAATAGGTTGATCGGGAAAACCAACGAGAAATTCCATCA
GATTGAAAAGAGTTCTCAGAAGTCGAAGGGAGAATCCAGGACCTTGAGAAA
TATGTTGAGGACACCAAAATAGATCTCTGGTCATACAACGCGGAGCTTCTTGT
TGCCCTGGAGAACCAACATACAATTGATCTAACTGACTCAGAAATGAACAAAC
TGTTTGAAAAAACAAAGAAGCAACTGAGGGAAAATGCTGAGGATATGGGCAA
TGGTTGTTTCAAAATATACCACAAATGTGACAATGCCTGCATAGGATCAATCA
GAAATGGAACTTATGACCACGATGTATACAGAGATGAAGCATTAAACAACCG
GTTCCAGATCAAGGGCGTTGAGCTGAAGTCAGGATACAAAGATTGGATACTA
TGGATTTCCTTTGCCATATCATGTTTTTTGCTTTGTGTTGCTTTGTTGGGGTTC
ATCATGTGGGCCTGCCAAAAAGGCAACATTAGGTGCAACATTTGCATTTGA<u>G
AGCTC</u>

Fig. 31

SEQ ID NO: 39

<u>CACTTTGT</u>GAGTCTACACTTTGATTCCCTTCAAACACATACAAAGAGAAGAG
ACTAATTAATTAATTAATCATCTTGAGAGAAA<u>ATG</u>AAGACTATCATTGCTTTG
AGCTACATTCTATGTCTGGTTTTCACTCAAAAACTTCCCGGAAATGACAACA
GCACGGCAACGCTGTGCCTTGGGCACCATGCAGTACCAAACGGAACGATA
GTGAAAACAATCACGAATGACCAAATTGAAGTTACTAATGCTACTGAGCTG
GTTCAGAGTTCCTCAACAGGTGGAATATGCGACAGTCCTCATCAGATCCTT
GATGGAGAAAACTGCACACTAATAGATGCTCTATTGGGAGACCCTCAGTGT
GATGGCTTCCAAAATAAGAAATGGGACCTTTTTGTTGAACGCAGCAAAGCC
TACAGCAACTGTTACCCTTATGATGTGCCGGATTATGCCTCCCTTAGGTCA
CTAGTTGCCTCATCCGGCACACTGGAGTTTAACGATGAAAGTTTCAATTGG
ACTGGAGTCACTCAAAATGGAACAAGCTCTGCTTGCAAAAGGAGATCTAAT
AACAGTTTCTTTAGTAGATTGAATTGGTTGACCCACTTAAAATTCAAATACC
CAGCATTGAACGTGACTATGCCAAACAATGAAAAATTTGACAAATTGTACAT
TTGGGGGGTTCACCACCCGGGTACGGACAATGACCAAATCTTCCTGCATG
CTCAAGCATCAGGAAGAATCACAGTCTCTACCAAAAGAAGCCAACAAACTG
TAATCCCGAATATCGGATCTAGACCCAGAATAAGGAATATCCCCAGCAGAA
TAAGCATCTATTGGACAATAGTAAAACCGGGAGACATACTTTTGATTAACAG
CACAGGGAATCTAATTGCTCCTAGGGGTTACTTCAAAATACGAAGTGGGAA
AAGCTCAATAATGAGATCAGATGCACCCATTGGCAAATGCAATTCTGAATG
CATCACTCCAAATGGAAGCATTCCCAATGACAAACCATTTCAAAATGTAAAC
AGGATCACATATGGGGCCTGTCCCAGATATGTTAAGCAAAACACTCTGAAA
TTGGCAACAGGGATGCGAAATGTACCAGAGAAACAAACTAGAGGCATATTT
GGCGCAATCGCGGGTTTCATAGAAATGGTTGGGAGGGAATGGTGGATGG
TTGGTACGGTTTCAGGCATCAAAATTCTGAGGGAATAGGACAAGCAGCAGA
TCTCAAAAGCACTCAAGCAGCAATCAATCAAATCAATGGGAAGCTGAATAG
GTTGATCGGGAAAACCAACGAGAAATTCCATCAGATTGAAAAAGAGTTCTC
AGAAGTAGAAGGGAGAATCCAGGACCTCGAGAAATATGTTGAGGACACTAA
AATAGATCTCTGGTCATACAACGCGGAGCTTCTTGTTGCCCTGGAGAACCA
ACATACAATTGATCTAACTGACTCAGAAATGAACAAACTGTTTGAAAGAACA
AAGAAGCAACTGAGGGAAAATGCTGAGGATATGGGCAATGGTTGTTTCAAA
ATATACCACAAATGTGACAATGCCTGCATAGGATCAATCAGAAATGGAACTT
ATGACCATGATGTATACAGAGATGAAGCATTAAACAACCGGTTCCAGATCA
AAGGCGTTGAGCTGAAGTCAGGATACAAAGATTGGATACTATGGATTTCCT
TTGCCATATCATGTTTTTTGCTTTGTGTTGCTTTGTTGGGGTTCATCATGTG
GGCCTGCCAAAAAGGCAACATTAGGTGCAACATTTGCATTTGA<u>GAGCTC</u>

Fig. 32

SEQ ID NO: 40

CACTTTGTGAGTCTACACTTTGATTCCCTTCAAACACATACAAAGAGAAGA
GACTAATTAATTAATTAATCATCTTGAGAGAAAATGAAGGCAATAATTGTAC
TACTCATGGTAGTAACATCCAATGCAGATCGAATCTGCACTGGGATAACAT
CGTCAAACTCACCACATGTTGTCAAAACTGCTACTCAAGGGGAGGTCAAT
GTGACTGGTGTAATACCACTGACAACAACACCCACCAAATCTCATTTTGCA
AATCTCAAAGGAACAGAAACCAGAGGGAAACTATGCCCAAAATGCCTCAA
CTGCACAGATCTGGACGTGGCCTTGGGCAGACCAAAATGCACGGGGAAC
ATACCCTCGGCAAGAGTTTCAATACTCCATGAAGTCAGACCTGTTACATCT
GGGTGCTTTCCTATAATGCACGACAGAACAAAAATTAGACAGCTGCCTAAA
CTTCTCAGAGGATACGAACATATCAGGTTATCAACTCATAACGTTATCAAT
GCAGAAAATGCACCAGGAGGACCCTACAAAATTGGAACCTCAGGGTCTTG
CCCTAACGTTACCAATGGAAACGGATTTTTCGCAACAATGGCTTGGGCCG
TCCCAAAAAACGACAACAACAAAACAGCAACAAATTCATTAACAATAGAAG
TACCATACATTTGTACAGAAGGAGAAGACCAAATTACCGTTTGGGGGTTC
CACTCTGATAACGAAACCCAAATGGCAAAGCTCTATGGGGACTCAAAGCC
CCAGAAGTTCACCTCATCTGCCAACGGAGTGACCACACATTACGTTTCAC
AGATTGGTGGCTTCCCAAATCAAACAGAAGACGGAGGACTACCACAAAGC
GGTAGAATTGTTGTTGATTACATGGTGCAAAAATCTGGGAAAACAGGAAC
AATTACCTATCAAAGAGGTATTTTATTGCCTCAAAAAGTGTGGTGCGCAAG
TGGCAGGAGCAAGGTAATAAAAGGATCGTTGCCTTTAATTGGAGAAGCAG
ATTGCCTCCACGAAAAATACGGTGGATTAAACAAAAGCAAGCCTTACTACA
CAGGGGAACATGCAAAGGCCATAGGAAATTGCCCAATATGGGTGAAAACA
CCCTTGAAGCTGGCCAATGGAACCAAATATAGACCTCCTGCAAAACTATTA
AAGGAAAGGGGTTTCTTCGGAGCTATTGCTGGTTTCTTAGAAGGAGGATG
GGAAGGAATGATTGCAGGTTGGCACGGATACACATCCCATGGGGCACAT
GGAGTAGCGGTGGCAGCAGACCTTAAGAGCACTCAAGAGGCCATAAACA
AGATAACAAAAATCTCAACTCTTTGAGTGAGCTGGAAGTAAAGAATCTTC
AAAGACTAAGCGGTGCCATGGATGAACTCCACAACGAAATACTAGAACTA
GACGAGAAAGTGGATGATCTCAGAGCTGATACAATAAGCTCACAAATAGA
ACTCGCAGTCCTGCTTTCCAATGAAGGAATAATAAACAGTGAAGATGAGC
ATCTCTTGGCGCTTGAAAGAAAGCTGAAGAAATGCTGGGCCCTCTGCT
GTAGAGATAGGGAATGGATGCTTTGAAACCAAACACAAGTGCAACCAGAC
CTGTCTCGACAGAATAGCTGCTGGTACCTTTGATGCAGGAGAATTTTCTCT
CCCCACTTTTGATTCACTGAATATTACTGCTGCATCTTTAAATGACGATGG
ATTGGATAATCATACTATACTGCTTTACTACTCAACTGCTGCCTCCAGTTT
GGCTGTAACATTGATGATAGCTATCTTTGTTGTTTATATGGTCTCCAGAGA
CAATGTTTCTTGCTCCATCTGTCTATAAGAGCTC

Fig. 33

SEQ ID NO: 41

CAC<u>TTTGTG</u>AGTCTACACTTTGATTCCCTTCAAACACATACAAAGAGAA
GAGACTAATTAATTAATTAATCATCTTGAGAGAAAATGAAGGCAATAATT
GTACTACTCATGGTAGTAACATCCAATGCAGATCGAATCTGCACTGGAA
TAACATCTTCAAACTCACCTCATGTGGTCAAAACAGCCACTCAAGGGGA
GGTCAATGTGACTGGTGTGATACCACTAACAACAACACCAACAAAATCT
TATTTTGCAAATCTCAAAGGAACAAGGACCAGAGGGAAACTATGCCCA
GACTGTCTCAACTGCACAGATCGGATGTGGCTTTGGGCAGACCAATG
TGTGTGGGGACCACACCTTCGGCGAAGGCTTCAATACTCCACGAAGTC
AAACCTGTTACATCCGGGTGCTTTCCTATAATGCACGACAGAACAAAAA
TCAGGCAACTACCCAATCTTCTCAGAGGATATGAAAATATCAGGCTATC
AACCCAAAACGTCATCGATGCGGAAAAGGCACCAGGAGGACCCTACA
GACTTGGAACCTCAGGATCTTGCCCTAACGCTACCAGTAAGAGCGGAT
TTTTCGCAACAATGGCTTGGGCTGTCCCAAAGGACAACAACAAAAATG
CAACGAACCCACTAACAGTAGAAGTACCATACATTTGTACAGAAGGGG
AAGACCAAATCACTGTTTGGGGGTTCCATTCAGATAACAAAACCCAAAT
GAAGAACCTCTATGGAGACTCAAATCCTCAAAAGTTCACCTCATCTGCT
AATGGAGTAACCACACACTATGTTTCTCAGATTGGCAGCTTCCCAGATC
AAACAGAAGACGGAGGACTACCACAAAGCGGCAGGATTGTTGTTGATT
ACATGATGCAAAAACCTGGGAAAACAGGAACAATTGTCTACCAAAGAG
GTGTTTTGTTGCCTCAAAAGGTGTGGTGCGCGAGTGGCAGGAGCAAA
GTAATAAAAGGGTCCTTGCCTTTAATTGGTGAAGCAGATTGCCTTCATG
AAAAATACGGTGGATTAAACAAAAGCAAGCCTTACTACACAGGAGAACA
TGCAAAAGCCATAGGAAATTGCCCAATATGGGTGAAAACACCTTTGAA
GCTCGCCAATGGAACCAAATATAGACCTCCTGCAAAACTATTAAAGGAA
AGGGGTTTCTTCGGAGCTATTGCTGGTTTCCTAGAAGGAGGATGGGAA
GGAATGATTGCAGGCTGGCACGGATACACATCTCACGGAGCACATGG
AGTGGCAGTGGCGGCGGACCTTAAGAGTACGCAAGAAGCTATAAACAA
GATAACAAAAAATCTCAATTCTTTGAGTGAGCTAGAAGTAAAGAATCTT
CAAAGACTAAGTGGTGCCATGGATGAACTCCACAACGAAATACTCGAG
CTGGATGAGAAAGTGGATGATCTCAGAGCTGACACTATAAGCTCGCAA
ATAGAACTTGCAGTCTTGCTTTCCAACGAAGGAATAATAAACAGTGAAG
ATGAGCATCTATTGGCACTTGAGAGAAAACTAAAGAAAATGCTGGGTC
CCTCTGCTGTAGAGATAGGAAATGGATGCTTCGAAACCAAACACAAGT
GCAACCAGACCTGCTTAGACAGGATAGCTGCTGGCACCTTTAATGCAG
GAGAATTTTCTCTCCCCACTTTTGATTCACTGAACATTACTGCTGCATCT
TTAAATGATGATGGATTGGATAACCATACTATACTGCTCTATTACTCAAC
TGCTGCTTCTAGTTTGGCTGTAACATTGATGCTAGCTA<u>TTTTTATT</u>GTTT
ATATGGTCTCCAGAGACAACGTTTCATGCTCCATCTGTCTATAA<u>GAGCT
C</u>

Fig. 34

SEQ ID NO: 42

<u>CACTTTGTG</u>AGTCTACACTTTGATTCCCTTCAAACACATACAAAGAGAA
GAGACTAATTAATTAATTAATCATCTTGAGAGAAA<u>ATG</u>GCCATCATTTA
TCTAATTCTCCTGTTCACAGCAGTGAGAGGGGACCAAATATGCATTGG
ATACCATGCCAATAATTCCACAGAGAAGGTCGACACAATTCTAGAGCG
GAACGTCACTGTGACTCATGCCAAGGACATTCTTGAGAAGACCCATAA
CGGAAAGTTATGCAAACTAAACGGAATCCCTCCACTTGAACTAGGGGA
CTGTAGCATTGCCGGATGGCTCCTTGGAAATCCAGAATGTGATAGGCT
TCTAAGTGTGCCAGAATGGTCCTATATAATGGAGAAAGAAAACCCGAG
AGACGGTTTGTGTTATCCAGGCAGCTTCAATGATTATGAAGAATTGAAA
CATCTCCTCAGCAGCGTGAAACATTTCGAGAAAGTAAAGATTCTGCCC
AAAGATAGATGGACACAGCATACAACAACTGGAGGTTCACGGGCCTG
CGCGGTGTCTGGTAATCCATCATTCTTCAGGAACATGGTCTGGCTGAC
AAAGAAAGAATCAAATTATCCGGTTGCCAAAGGATCGTACAACAATAC
AAGCGGAGAACAAATGCTAATAATTTGGGGGGTGCACCATCCCAATGA
TGAGACAGAACAAAGAACATTGTACCAGAATGTGGGAACCTATGTTTC
CGTAGGCACATCAACATTGAACAAAAGGTCAACCCCAGACATAGCAAC
AAGGCCTAAAGTGAATGGACTAGGAAGTAGAATGGAGTTCTCTTGGAC
CCTATTGGATATGTGGGACACCATAAATTTTGAGAGTACTGGTAATCTA
ATTGCACCAGAGTATGGATTCAAAATATCGAAAAGAGGTAGTTCAGGG
ATCATGAAAACAGAAGGAACACTTGAGAACTGTGAGACCAAATGCCAA
ACTCCTTTGGGAGCAATAAATACAACATTGCCTTTTCACAATGTCCACC
CACTGACAATAGGTGAGTGCCCCAAATATGTAAAATCGGAGAAGTTGG
TCTTAGCAACAGGACTAAGGAATGTTCCCCAGATTGAATCAAGAGGAT
TGTTTGGGGCAATAGCTGGTTTTATAGAAGGAGGATGGCAAGGAATG
GTTGATGGTTGGTATGGATACCATCACAGCAATGACCAGGGATCAGG
GTATGCAGCAGACAAAGAATCCACTCAAAAGGCATTTGATGGAATCAC
CAACAAGGTAAATTCTGTGATTGAAAAGATGAACACCCAATTTGAAGCT
GTTGGGAAAGAGTTCAGTAACTTAGAGAGAAGACTGGAGAACTTGAAC
AAAAAGATGGAAGACGGGTTCTAGATGTGTGGACATACAATGCTGAG
CTTCTAGTTCTGATGGAAAATGAGAGGACACTTGACTTTCATGATTCTA
ATGTCAAGAATCTGTATGATAAAGTCAGAATGCAGCTGAGAGACAACG
TCAAAGAACTAGGAAATGGATGTTTTGAATTTTATCACAAATGTGATGA
TGAATGCATGAATAGTGTGAAAAACGGGACGTATGATTATCCCAAGTA
TGAAGAAGAGTCTAAACTAAATAGAAATGAAATCAAAGGGGTAAAATTG
AGCAGCATGGGGGTTTATCAAATCCTTGCCATTTATGCTACAGTAGCA
GGTTCTCTGTCACTGGCAATCATGATGGCTGGGATCTCTTTCTGGATG
TGCTCCAACGGGTCTCTGCAGTGCAGGATCTGCATATGA<u>GAGCTC</u>

Fig. 35

SEQ ID NO: 43

<u>CACTTTGT</u>GAGTCTACACTTTGATTCCCTTCAAACACATACAAAGAGAAG
AGACTAATTAATTAATTAATCATCTTGAGAGAAAATGGAGAAAATAGTGCT
TCTTCTTGCAATAGTCAGCCTTGTTAAAAGTGATCAGATTTGCATTGGTTA
CCATGCAAACAACTCGACAGAGCAGGTTGACACAATAATGGAAAAGAAC
GTTACTGTTACACATGCCCAAGACATACTGGAAAAGACACACAACGGGA
AGCTCTGCGATCTAGATGGAGTGAAGCCTCTGATTTTAAGAGATTGTAGT
GTAGCTGGATGGCTCCTCGGAAACCCAATGTGTGACGAGTTCATCAATG
TGCCGGAATGGTCTTACATAGTGGAGAAGGCCAACCCAGCCAATGACCT
CTGTTACCCAGGGAATTTCAACGACTATGAAGAACTGAAACACCTATTGA
GCAGAATAAACCATTTTGAGAAAATTCAGATCATCCCCAAAAGTTCTTGG
TCCGATCATGAAGCCTCATCAGGGGTCAGCTCAGCATGTCCATACCAGG
GAACGCCCTCCTTTTTCAGAAATGTGGTATGGCTTATCAAAAGAACAAT
ACATACCCAACAATAAAGAGAAGCTACAATAATACCAACCAGGAAGATCT
TTTGATACTGTGGGGATTCATCATTCTAATGATGCGGCAGAGCAGACAA
AGCTCTATCAAAACCCAACCACCTATATTTCCGTTGGGACATCAACACTA
AACCAGAGATTGGTACCAAAAATAGCTACTAGATCCAAAGTAAACGGGCA
AAGTGGAAGGATGGATTTCTTCTGGACAATTTTAAAACCGAATGATGCAA
TCAACTTCGAGAGTAATGGAAATTTCATTGCTCCAGAATATGCATACAAA
ATTGTCAAGAAAGGGGACTCAGCAATTGTTAAAAGTGAAGTGGAATATGG
TAACTGCAATACAAAGTGTCAAACTCCAATAGGGGCGATAAACTCAGTA
TGCCATTCCACAACATACACCCTCTCACCATCGGGGAATGCCCCAAATAT
GTGAAATCAAACAAATTAGTCCTTGCGACTGGGCTCAGAAATAGTCCTCT
AAGAGAAAGAAGAAGAAAAGAGGACTATTTGGAGCTATAGCAGGGTTT
ATAGAGGGAGGATGGCAGGGAATGGTAGATGGTTGGTATGGGTACCAC
CATAGCAATGAGCAGGGGAGTGGGTACGCTGCAGACAAAGAATCCACTC
AAAAGGCAATAGATGGAGTCACCAATAAGGTCAACTCGATCATTGACAAA
ATGAACACTCAGTTTGAGGCCGTTGGAAGGGAATTTAATAACTTAGAAAG
GAGAATAGAGAATTTAAACAAGAAATGGAAGACGGATTCCTAGATGTCT
GGACTTATAATGCTGAACTTCTGGTTCTCATGGAAAATGAGAGAACTCTA
GACTTCCATGATTCAAATGTCAAGAACCTTTACGACAAGGTCCGACTACA
GCTTAGGGATAATGCAAAGGAGCTGGGTAACGGTTGTTTCGAGTTCTAT
CACAAATGTGATAATGAATGTATGGAAAGTGTAAGAAACGGAACGTATGA
CTACCCGCAGTATTCAGAAGAAGCAAGATTAAAAAGAGAGGAAATAAGT
GGAGTAAAATTGGAATCAATAGGAACTTACCAAATACTGTCAATTTATTCA
ACAGTTGCGAGTTCTCTAGCACTGGCAATCATGGTGGCTGGTCTATCTTT
GTGGATGTGCTCCAATGGGTCGTTACAATGCAGAATTTGCATTTAA<u>GAGC
TC</u>

Fig. 36

SEQ ID NO: 44

CACTTTGTGAGTCTACACTTTGATTCCCTTCAAACACATACAAAGAGAAGA
GACTAATTAATTAATTAATCATCTTGAGAGAAAATGGAGAAAATAGTGCTTC
TTTTTGCAATAGTCAGTCTTGTTAAAAGTGATCAGATTTGCATTGGTTACCA
TGCAAACAACTCGACAGAGCAGGTTGACACAATAATGGAAAAGAACGTTA
CTGTTACACATGCCCAAGACATACTGGAAAAGACACACAATGGGAAGCTC
TGCGATCTAGATGGAGTGAAGCCTCTAATTTTGAGAGATTGTAGTGTAGCT
GGATGGCTCCTCGGAAACCCAATGTGTGACGAGTTCATCAATGTGCCGGA
ATGGTCTTACATAGTGGAGAAGGCCAATCCAGTCAATGACCTCTGTTACC
CAGGGGATTTCAATGACTATGAAGAATTGAAACACCTATTGAGCAGAATAA
ACCATTTTGAGAAAATTCAGATCATCCCCAAAAGTTCTTGGTCCAGTCATG
AAGCCTCATTGGGGGTCAGCTCAGCATGTCCATACCAGGGAAAGTCCTCC
TTTTTCAGAAATGTGGTATGGCTTATCAAAAGAACAGTACATACCCAACA
ATAAAGAGGAGCTACAATAATACCAACCAAGAAGATCTTTTGGTACTGTGG
GGGATTCACCATCCTAATGATGCGGCAGAGCAGACAAAGCTCTATCAAAA
CCCAACCACCTATATTTCCGTTGGGACATCTACACTAAACCAGAGATTGGT
ACCAAGAATAGCTACTAGATCCAAAGTAAACGGGCAAAGTGGAAGGATGG
AGTTCTTCTGGACAATTTTAAAACCGAATGATGCAATCAACTTCGAGAGTA
ATGGAAATTTCATTGCTCCAGAATATGCATACAAAATTGTCAAGAAAGGGG
ACTCAACAATTATGAAAAGTGAATTGGAATATGGTAACTGCAATACCAAGT
GTCAAACTCCAATGGGGGCGATAAACTCTAGCATGCCATTCCACAATATAC
ACCCTCTCACCATCGGGGAATGCCCCAAATATGTGAAATCAAACAGATTA
GTCCTTGCGACTGGGCTCAGAAATAGCCCTCAAAGAGAGAGAAGAAGAAA
AAAGAGAGGATTATTTGGAGCTATAGCAGGTTTTATAGAGGGAGGATGGC
AGGGAATGGTAGATGGTTGGTATGGGTACCACCATAGCAACGAGCAGGG
GAGTGGGTACGCTGCAGACAAAGAATCCACTCAAAAGGCAATAGATGGAG
TCACCAATAAGGTCAACTCGATTATTGACAAAATGAACACTCAGTTTGAGG
CCGTTGGAAGGGAATTTAACAACTTAGAAAGGAGAATAGAGAATTTAAACA
AGAAGATGGAAGACGGGTTCCTAGATGTCTGGACTTATAATGCTGAACTT
CTAGTTCTCATGGAAAACGAGAGAACTCTAGACTTTCATGACTCAAATGTC
AAGAACCTTTACGACAAGGTCCGACTACAGCTTAGGGATAATGCAAAGGA
GCTGGGTAACGGTTGTTTCGAGTTCTATCATAAATGTGATAATGAATGTAT
GGAAAGTGTAAGAAACGGAACGTATGACTACCCGCAGTATTCAGAAGAAG
CAAGACTAAAAAGAGAGGAAATAAGTGGAGTAAAATTGGAATCAATAGGA
ATTTACCAAATATTGTCAATTTATTCTACAGTGGCCAGCTCCCTAGCACTG
GCAATCATGGTAGCTGGTCTATCCTTATGGATGTGCTCCAATGGGTCGTT
ACAATGCAGAATTTGCATTTAAGAGCTC

Fig. 37

SEQ ID NO: 45

<u>CACTTTGT</u>GAGTCTACACTTTGATTCCCTTCAAACACATACAAAGAGAAGA
GACTAATTAATTAATTAATCATCTTGAGAGAAAATGATTGCAATCATTGTAA
TAGCAATACTGGCAGCAGCCGGAAAGTCAGACAAGATCTGCATTGGGTAT
CATGCCAACAATTCAACAACACAGGTAGATACGATACTTGAGAAGAATGT
GACTGTCACACACTCAATTGAATTGCTGGAAAATCAGAAGGAAGAAAGAT
TCTGCAAGATATTGAACAAGGCCCCTCTCGACTTAAGGGAATGTACCATA
GAGGGTTGGATCTTGGGGAATCCCCAATGCGACCTATTGCTTGGTGATCA
AAGCTGGTCATACATTGTGGAAGACCTACTGCTCAAAACGGGATCTGCT
ACCCAGGAACCTTAAATGAGGTAGAAGAACTGAGGGCACTTATTGGATCA
GGAGAAAGGGTAGAGAGATTTGAGATGTTTCCCCAAAGCACCTGGCAAG
GAGTTGACACCAACAGTGGAACAACAAGATCCTGCCCTTATTCTACTGGT
GCGTCTTTCTACAGAAACCTCCTATGGATAATAAAAACCAAGACAGCAGA
ATATCCAGTAATTAAGGGAATTTACAACAACACTGGAACCCAGCCAATCCT
CTATTTCTGGGGTGTGCATCATCCTCCTAACACCGACGAGCAAGATACTC
TGTATGGCTCTGGTGATCGATACGTTAGAATGGGAACTGAAAGCATGAAT
TTTGCCAAGAGTCCGGAAATTGCGGCAAGGCCTGCTGTGAATGGACAAA
GAGGCAGAATTGATTATTATTGGTCGGTTTTAAAACCAGGGGAAACCTTG
AATGTGGAATCTAATGGAAATCTAATCGCCCCTTGGTATGCATACAAATTT
GTCAACACAAATAGTAAAGGAGCCGTCTTCAGGTCAGATTTACCAATCGA
GAACTGCGATGCCACATGCCAGACTATTGCAGGGGTTCTAAGGACCAATA
AAACATTTCAGAATGTGAGTCCCCTGTGGATAGGAGAATGTCCCAAATAC
GTGAAAAGTGAAAGTCTGAGGCTTGCAACTGGACTAAGAAATGTTCCACA
GATTGAAACTAGAGGACTCTTCGGAGCTATTGCAGGGTTTATTGAAGGAG
GATGGACTGGGATGATAGATGGGTGGTATGGCTATCACCATGAAAATTCT
CAAGGGTCAGGATATGCAGCAGACAGAGAAAGCACTCAAAAGGCTGTAA
ACAGAATTACAAATAAGGTCAATTCCATCATCAACAAAATGAACACACAAT
TTGAAGCTGTCGATCACGAATTTTCAAATCTGGAGAGGAGAATTGACAAT
CTGAACAAAAGAATGCAAGATGGATTTCTGGATGTTTGGACATACAATGC
TGAACTGTTGGTTCTTCTTGAAAACGAAAGAACACTAGACATGCATGACG
CAAATGTGAAGAACCTACATGAAAAGGTCAAATCACAACTAAGGGACAAT
GCTACGATCTTAGGGAATGGTTGCTTTGAATTTTGGCATAAGTGTGACAAT
GAATGCATAGAGTCTGTCAAAAATGGTACATATGACTATCCCAAATACCAG
ACTGAAAGCAAATTAAACAGGCTAAAAATAGAATCAGTAAAGCTAGAGAAC
CTTGGTGTGTATCAAATTCTTGCCATTTATAGTACGGTATCGAGCAGCCTA
GTGTTGGTAGGGCTGATCATGGCAATGGGTCTTTGGATGTGTTCAAATGG
TTCAATGCAGTGCAGGATATGTATATAA<u>GAGCTC</u>

Fig. 38

SEQ ID NO: 46

<u>CACTTTGT</u>GAGTCTACACTTTGATTCCCTTCAAACACATACAAAGAGAAGA
GACTAATTAATTAATTAATCATCTTGAGAGAAA<u>ATG</u>AACACTCAAATTCTAA
TATTAGCCACTTCGGCATTCTTCTATGTACGTGCAGATAAAATCTGCCTAG
GACATCATGCTGTGTCTAATGGAACCAAAGTAGACACCCTTACTGAAAAA
GGAATAGAAGTTGTCAATGCAACAGAAACAGTTGAACAAACAAACATCCC
TAAGATCTGCTCAAAAGGAAAACAGACTGTTGACCTTGGTCAATGTGGAT
TACTAGGGACCGTTATTGGTCCTCCCCAATGTGACCAATTTCTTGAGTTCT
CTGCTAATTTAATAGTTGAAAGAAGGGAAGGTAATGACATTTGTTATCCAG
GCAAATTTGACAATGAAGAAACATTGAGAAAAATACTCAGAAAATCCGGA
GGAATTAAAAAGGAGAATATGGGATTCACATATACCGGAGTGAGAACCAA
TGGAGAGACTAGCGCATGTAGAAGGTCAAGATCTTCCTTTTATGCAGAGA
TGAAATGGCTTCTATCCAGCACAGACAATGGGACATTTCCACAAATGACA
AAGTCCTACAAGAACACTAAGAAGGTACCAGCTCTGATAATCTGGGGAAT
CCACCACTCAGGATCAACTACTGAACAGACTAGATTATATGGAAGTGGGA
ATAAATTGATAACAGTTTGGAGTTCCAAATACCAACAATCTTTTGTCCCAA
ATCCTGGACCAAGACCGCAAATGAATGGTCAATCAGGAAGAATTGACTTT
CACTGGCTGATGCTAGATCCCAATGATACTGTCACTTTCAGTTTTAATGGG
GCCTTTATAGCACCTGACCGCGCCAGTTTTCTAAGAGGTAAATCTCTAGG
AATCCAAAGTGATGCACAACTTGACAATAATTGTGAAGGTGAATGCTATCA
TATTGGAGGTACTATAATTAGCAACTTGCCCTTTCAAAACATTAATAGTAG
GGCAATCGGAAAATGCCCCAGATACGTGAAGCAGAAGAGCTTAATGCTA
GCAACAGGAATGAAAAATGTTCCTGAAGCTCCTGCACATAAACAACTAAC
TCATCACATGCGCAAAAAAGAGGTTTATTTGGTGCAATAGCAGGATTCAT
TGAAAATGGGTGGGAAGGATTAATAGACGGATGGTATGGATATAAGCATC
AGAATGCACAAGGAGAAGGGACTGCTGCAGACTACAAAAGTACACAATCT
GCTATCAACCAAATAACCGGAAAATTGAACAGACTAATAGAAAAACCAAC
CAGCAATTCGAACTAATAGATAATGAGTTCAATGAAATAGAAAACAAATT
GGCAATGTTATTAACTGGACTAGAGATTCTATCATCGAAGTATGGTCATAT
AATGCAGAGTTCCTCGTAGCAGTGGAGAATCAACACACTATTGATTTAACT
GACTCAGAAATGAACAAACTATATGAAAAGGTAAGAAGACAACTGAGAGA
AAATGCTGAGGAAGATGGTAATGGCTGTTTTGAAATATTCCACCAATGTG
ACAATGATTGCATGGCCAGCATTAGAAACAACACATATGACCATAAAAAT
ACAGAAAAGAGGCAATACAAAACAGAATCCAGATTGACGCAGTAAAGTTG
AGCAGTGGTTACAAAGATATAATACTTTGGTTTAGCTTCGGGGCATCATG
TTTCTTATTTCTTGCCATTGCAATGGGTCTTGTTTTCATATGTATAAAAAAT
GGAAACATGCGGTGCACTATTTGTATATAA<u>GAGCTC</u>

Fig. 39

SEQ ID NO: 47

<u>CACTTTGTG</u>AGTCTACACTTTGATTCCCTTCAAACACATACAAAGAGAAGA
GACTAATTAATTAATTAATCATCTTGAGAGAAA<u>ATG</u>GAAACAATATCACTAA
TAACTATACTACTAGTAGTAACAGCAAGCAATGCAGATAAAATCTGCATCG
GCCACCAGTCAACAAACTCCACAGAAACTGTGGACACGCTAACAGAAACC
AATGTTCCTGTGACACATGCCAAAGAATTGCTCCACACAGAGCATAATGGA
ATGCTGTGTGCAACAAGCCTGGGACATCCCCTCATTCTAGACACATGCAC
TATTGAAGGACTAGTCTATGGCAACCCTTCTTGTGACCTGCTGTTGGGAG
GAAGAGAATGGTCCTACATCGTCGAAAGATCATCAGCTGTAAATGGAACG
TGTTACCCTGGGAATGTAGAAAACCTAGAGGAACTCAGGACACTTTTTAGT
TCCGCTAGTTCCTACCAAAGAATCCAAATCTTCCCAGACACAACCTGGAAT
GTGACTTACACTGGAACAAGCAGAGCATGTTCAGGTTCATTCTACAGGAG
TATGAGATGGCTGACTCAAAAGAGCGGTTTTACCCTGTTCAAGACGCCC
AATACACAAATAACAGGGGAAAGAGCATTCTTTTCGTGTGGGGCATACAT
CACCCACCCACCTATACCGAGCAAACAAATTTGTACATAAGAAACGACACA
ACAACAAGCGTGACAACAGAAGATTTGAATAGGACCTTCAAACCAGTGATA
GGGCCAAGGCCCCTTGTCAATGGTCTGCAGGGAAGAATTGATTATTATTG
GTCGGTACTAAAACCAGGCCAAACATTGCGAGTACGATCCAATGGGAATC
TAATTGCTCCATGGTATGGACACGTTCTTTCAGGAGGGAGCCATGGAAGA
ATCCTGAAGACTGATTTAAAAGGTGGTAATTGTGTAGTGCAATGTCAGACT
GAAAAAGGTGGCTTAAACAGTACATTGCCATTCCACAATATCAGTAAATAT
GCATTTGGAACCTGCCCCAAATATGTAAGAGTTAATAGTCTCAAACTGGCA
GTCGGTCTGAGGAACGTGCCTGCTAGATCAAGTAGAGGACTATTTGGAGC
CATAGCTGGATTCATAGAAGGAGGTTGGCCAGGACTAGTCGCTGGCTGG
TATGGTTTCCAGCATTCAAATGATCAAGGGGTTGGTATGGCTGCAGATAG
GGATTCAACTCAAAAGGCAATTGATAAAATAACATCCAAGGTGAATAATAT
AGTCGACAAGATGAACAAGCAATATGAAATAATTGATCATGAATTTAGTGA
GGTTGAAACTAGACTCAATATGATCAATAATAAGATTGATGACCAAATACA
AGACGTATGGGCATATAATGCAGAATTGCTAGTACTACTTGAAAATCAAAA
AACACTCGATGAGCATGATGCGAACGTGAACAATCTATATAACAAGGTGA
AGAGGGCACTGGGCTCCAATGCTATGGAAGATGGGAAAGGCTGTTTCGA
GCTATACCATAAATGTGATGATCAGTGCATGGAAACAATTCGGAACGGGA
CCTATAATAGGAGAAAGTATAGAGAGGAATCAAGACTAGAAAGGCAGAAA
ATAGAGGGGGTTAAGCTGGAATCTGAGGGAACTTACAAAATCCTCACCAT
TTATTCGACTGTCGCCTCATCTCTTGTGCTTGCAATGGGGTTTGCTGCCTT
CCTGTTCTGGGCCATGTCCAATGGATCTTGCAGATGCAACATTTGTATATA
A<u>GAGCTC</u>

Fig. 40A

SEQ ID NO: 48

MKVKLLVLLCTFTATYADTICIGYHANNSTDTVDTVLEKNVTVTHSVNLLENSH
NGKLCLLKGIAPLQLGNCSVAGWILGNPECELLISKESWSYIVEKPNPENGTCY
PGHFADYEELREQLSSVSSFERFEIFPKESSWPNHTVTGVSASCSHNGESSF
YRNLLWLTGKNGLYPNLSKSYANNKEKEVLVLWGVHHPPNIGDQKALYHTEN
AYVSVVSSHYSRKFTPEIAKRPKVRDQEGRINYYWTLLEPGDTIIFEANGNLIAP
RYAFALSRGFGSGIINSNAPMDKCDAKCQTPQGAINSSLPFQNVHPVTIGECP
KYVRSAKLRMVTGLRNIPSIQSRGLFGAIAGFIEGGWTGMVDGWYGYHHQNE
QGSGYAADQKSTQNAINGITNKVNSVIEKMNTQFTAVGKEFNKLERRMENLNK
KVDDGFIDIWTYNAELLVLLENERTLDFHDSNVKNLYEKVKSQLKNNAKEIGNG
CFEFYHKCNDECMESVKNGTYDYPKYSEESKLNREKIDGVKLESMGVYQILAI
YSTVASSLVLLVSLGAISFWMCSNGSLQCRICI

Fig. 40B

SEQ ID NO: 49

MKVKLLVLLCTFTATYADTICIGYHANNSTDTVDTVLEKNVTVTHSVNLLEDSH
NGKLCLLKGIAPLQLGNCSVAGWILGNPECELLISRESWSYIVEKPNPENGTCY
PGHFADYEELREQLSSVSSFERFEIFPKESSWPNHTTTGVSASCSHNGESSFY
KNLLWLTGKNGLYPNLSKSYANNKEKEVLVLWGVHHPPNIGDQRALYHKENA
YVSVVSSHYSRKFTPEIAKRPKVRDQEGRINYYWTLLEPGDTIIFEANGNLIAPR
YAFALSRGFGSGIINSNAPMDECDAKCQTPQGAINSSLPFQNVHPVTIGECPK
YVRSAKLRMVTGLRNIPSIQSRGLFGAIAGFIEGGWTGMVDGWYGYHHQNEQ
GSGYAADQKSTQNAINGITNKVNSVIEKMNTQFTAVGKEFNKLERRMENLNKK
VDDGFIDIWTYNAELLVLLENERTLDFHDSNVKNLYEKVKSQLKNNAKEIGNGC
FEFYHKCNDECMESVKNGTYDYPKYSEESKLNREKIDGVKLESMGVYQILAIY
STVASSLVLLVSLGAISFWMCSNGSLQCRICI

Fig. 41A

SEQ ID NO: 50

MKTIIALSYILCLVFTQKLPGNDNSTATLCLGHHAVPNGTIVKTITNDQIEVTN
ATELVQSSSTGEICDSPHQILDGENCTLIDALLGDPQCDGFQNKKWDLFVE
RSKAYSNCYPYDVPDYASLRSLVASSGTLEFNNESFNWTGVTQNGTSSA
CIRRSNNSFFSRLNWLTHLKFKYPALNVTMPNNEKFDKLYIWGVHHPGTD
NDQIFLYAQASGRITVSTKRSQQTVIPNIGSRPRVRNIPSRISIYWTIVKPGDI
LLINSTGNLIAPRGYFKIRSGKSSIMRSDAPIGKCNSECITPNGSIPNDKPFQ
NVNRITYGACPRYVKQNTLKLATGMRNVPEKQTRGIFGAIAGFIENGWEG
MVDGWYGFRHQNSEGIGQAADLKSTQAAIDQINGKLNRLIGKTNEKFHQIE
KEFSEVEGRIQDLEKYVEDTKIDLWSYNAELLVALENQHTIDLTDSEMNKLF
EKTKKQLRENAEDMGNGCFKIYHKCDNACIGSIRNGTYDHDVYRDEALNN
RFQIKGVELKSGYKDWILWISFAISCFLLCVALLGFIMWACQKGNIRCNICI

Fig. 41B

SEQ ID NO: 51

MKTIIALSYILCLVFTQKLPGNDNSTATLCLGHHAVPNGTIVKTITNDQIEVTN
ATELVQSSSTGGICDSPHQILDGENCTLIDALLGDPQCDGFQNKKWDLFVE
RSKAYSNCYPYDVPDYASLRSLVASSGTLEFNDESFNWTGVTQNGTSSA
CKRRSNNSFFSRLNWLTHLKFKYPALNVTMPNNEKFDKLYIWGVHHPGTD
NDQIFLHAQASGRITVSTKRSQQTVIPNIGSRPRIRNIPSRISIYWTIVKPGDI
LLINSTGNLIAPRGYFKIRSGKSSIMRSDAPIGKCNSECITPNGSIPNDKPFQ
NVNRITYGACPRYVKQNTLKLATGMRNVPEKQTRGIFGAIAGFIENGWEG
MVDGWYGFRHQNSEGIGQAADLKSTQAAINQINGKLNRLIGKTNEKFHQIE
KEFSEVEGRIQDLEKYVEDTKIDLWSYNAELLVALENQHTIDLTDSEMNKLF
ERTKKQLRENAEDMGNGCFKIYHKCDNACIGSIRNGTYDHDVYRDEALNN
RFQIKGVELKSGYKDWILWISFAISCFLLCVALLGFIMWACQKGNIRCNICI

Fig. 42A

SEQ ID NO: 52

MKAIIVLLMVVTSNADRICTGITSSNSPHVVKTATQGEVNVTGVIPLTTTPTKS
HFANLKGTETRGKLCPKCLNCTDLDVALGRPKCTGNIPSARVSILHEVRPVT
SGCFPIMHDRTKIRQLPKLLRGYEHIRLSTHNVINAENAPGGPYKIGTSGSCP
NVTNGNGFFATMAWAVPKNDNNKTATNSLTIEVPYICTEGEDQITVWGFHS
DNETQMAKLYGDSKPQKFTSSANGVTTHYVSQIGGFPNQTEDGGLPQSGRI
VVDYMVQKSGKTGTITYQRGILLPQKVWCASGRSKVIKGSLPLIGEADCLHE
KYGGLNKSKPYYTGEHAKAIGNCPIWVKTPLKLANGTKYRPPAKLLKERGFF
GAIAGFLEGGWEGMIAGWHGYTSHGAHGVAVAADLKSTQEAINKITKNLNS
LSELEVKNLQRLSGAMDELHNEILELDEKVDDLRADTISSQIELAVLLSNEGIIN
SEDEHLLALERKLKKMLGPSAVEIGNGCFETKHKCNQTCLDRIAAGTFDAGE
FSLPTFDSLNITAASLNDDGLDNHTILLYYSTAASSLAVTLMIAIFVVYMVSRD
NVSCSICL

Fig. 42B

SEQ ID NO: 53

MKAIIVLLMVVTSNADRICTGITSSNSPHVVKTATQGEVNVTGVIPLTTTPTKS
YFANLKGTRTRGKLCPDCLNCTDLDVALGRPMCVGTTPSAKASILHEVKPVT
SGCFPIMHDRTKIRQLPNLLRGYENIRLSTQNVIDAEKAPGGPYRLGTSGSC
PNATSKSGFFATMAWAVPKDNNKNATNPLTVEVPYICTEGEDQITVWGFHS
DNKTQMKNLYGDSNPQKFTSSANGVTTHYVSQIGSFPDQTEDGGLPQSGRI
VVDYMMQKPGKTGTIVYQRGVLLPQKVWCASGRSKVIKGSLPLIGEADCLH
EKYGGLNKSKPYYTGEHAKAIGNCPIWVKTPLKLANGTKYRPPAKLLKERGF
FGAIAGFLEGGWEGMIAGWHGYTSHGAHGVAVAADLKSTQEAINKITKNLN
SLSELEVKNLQRLSGAMDELHNEILELDEKVDDLRADTISSQIELAVLLSNEGII
NSEDEHLLALERKLKKMLGPSAVEIGNGCFETKHKCNQTCLDRIAAGTFNAG
EFSLPTFDSLNITAASLNDDGLDNHTILLYYSTAASSLAVTLMLAIFIVYMVSRD
NVSCSICL

Fig. 43A

SEQ ID NO: 54

MAIIYLILLFTAVRGDQICIGYHANNSTEKVDTILERNVTVTHAKDILEKTHNGKLC
KLNGIPPLELGDCSIAGWLLGNPECDRLLSVPEWSYIMEKENPRDGLCYPGSF
NDYEELKHLLSSVKHFEKVKILPKDRWTQHTTTGGSRACAVSGNPSFFRNMV
WLTKKESNYPVAKGSYNNTSGEQMLIIWGVHHPNDETEQRTLYQNVGTYVSV
GTSTLNKRSTPDIATRPKVNGLGSRMEFSWTLLDMWDTINFESTGNLIAPEYGF
KISKRGSSGIMKTEGTLENCETKCQTPLGAINTTLPFHNVHPLTIGECPKYVKSE
KLVLATGLRNVPQIESRGLFGAIAGFIEGGWQGMVDGWYGYHHSNDQGSGYA
ADKESTQKAFDGITNKVNSVIEKMNTQFEAVGKEFSNLERRLENLNKKMEDGFL
DVWTYNAELLVLMENERTLDFHDSNVKNLYDKVRMQLRDNVKELGNGCFEFY
HKCDDECMNSVKNGTYDYPKYEEESKLNRNEIKGVKLSSMGVYQILAIYATVAG
SLSLAIMMAGISFWMCSNGSLQCRICI

Fig. 43B

SEQ ID NO: 55

MEKIVLLLAIVSLVKSDQICIGYHANNSTEQVDTIMEKNVTVTHAQDILEKTHNGK
LCDLDGVKPLILRDCSVAGWLLGNPMCDEFINVPEWSYIVEKANPANDLCYPG
NFNDYEELKHLLSRINHFEKIQIIPKSSWSDHEASSGVSSACPYQGTPSFFRNVV
WLIKKNNTYPTIKRSYNNTQEDLLILWGIHHSNDAAEQTKLYQNPTTYISVGTS
TLNQRLVPKIATRSKVNGQSGRMDFFWTILKPNDAINFESNGNFIAPEYAYKIVK
KGDSAIVKSEVEYGNCNTKCQTPIGAINSSMPFHNIHPLTIGECPKYVKSNKLVL
ATGLRNSPLRERRRKRGLFGAIAGFIEGGWQGMVDGWYGYHHSNEQGSGYA
ADKESTQKAIDGVTNKVNSIIDKMNTQFEAVGREFNNLERRIENLNKKMEDGFL
DVWTYNAELLVLMENERTLDFHDSNVKNLYDKVRLQLRDNAKELGNGCFEFYH
KCDNECMESVRNGTYDYPQYSEEARLKREEISGVKLESIGTYQILSIYSTVASSL
ALAIMVAGLSLWMCSNGSLQCRICI

Fig. 44A

SEQ ID NO: 56

MEKIVLLFAIVSLVKSDQICIGYHANNSTEQVDTIMEKNVTVTHAQDILEKTHNGKL
CDLDGVKPLILRDCSVAGWLLGNPMCDEFINVPEWSYIVEKANPVNDLCYPGDF
NDYEELKHLLSRINHFEKIQIIPKSSWSSHEASLGVSSACPYQGKSSFFRNVVWLI
KKNSTYPTIKRSYNNTNQEDLLVLWGIHHPNDAAEQTKLYQNPTTYISVGTSTLN
QRLVPRIATRSKVNGQSGRMEFFWTILKPNDAINFESNGNFIAPEYAYKIVKKGD
STIMKSELEYGNCNTKCQTPMGAINSSMPFHNIHPLTIGECPKYVKSNRLVLATG
LRNSPQRERRRKKRGLFGAIAGFIEGGWQGMVDGWYGYHHSNEQGSGYAAD
KESTQKAIDGVTNKVNSIIDKMNTQFEAVGREFNNLERRIENLNKKMEDGFLDV
WTYNAELLVLMENERTLDFHDSNVKNLYDKVRLQLRDNAKELGNGCFEFYHKC
DNECMESVRNGTYDYPQYSEEARLKREEISGVKLESIGIYQILSIYSTVASSLALAI
MVAGLSLWMCSNGSLQCRICI

Fig. 44B

SEQ ID NO: 57

MIAIIVIAILAAAGKSDKICIGYHANNSTTQVDTILEKNVTVTHSIELLENQKEERFCK
ILNKAPLDLRECTIEGWILGNPQCDLLLGDQSWSYIVERPTAQNGICYPGTLNEV
EELRALIGSGERVERFEMFPQSTWQGVDTNSGTTRSCPYSTGASFYRNLLWIIK
TKTAEYPVIKGIYNNTGTQPILYFWGVHHPPNTDEQDTLYGSGDRYVRMGTESM
NFAKSPEIAARPAVNGQRGRIDYYWSVLKPGETLNVESNGNLIAPWYAYKFVNT
NSKGAVFRSDLPIENCDATCQTIAGVLRTNKTFQNVSPLWIGECPKYVKSESLRL
ATGLRNVPQIETRGLFGAIAGFIEGGWTGMIDGWYGYHHENSQGSGYAADRES
TQKAVNRITNKVNSIINKMNTQFEAVDHEFSNLERRIDNLNKRMQDGFLDVWTY
NAELLVLLENERTLDMHDANVKNLHEKVKSQLRDNATILGNGCFEFWHKCDNEC
IESVKNGTYDYPKYQTESKLNRLKIESVKLENLGVYQILAIYSTVSSSLVLVGLIMA
MGLWMCSNGSMQCRICI

Fig. 45A

SEQ ID NO: 58

MNTQILILATSAFFYVRADKICLGHHAVSNGTKVDTLTEKGIEVVNATETVEQT
NIPKICSKGKQTVDLGQCGLLGTVIGPPQCDQFLEFSANLIVERREGNDICYPG
KFDNEETLRKILRKSGGIKKENMGFTYTGVRTNGETSACRRSRSSFYAEMKW
LLSSTDNGTFPQMTKSYKNTKKVPALIIWGIHHSGSTTEQTRLYGSGNKLITV
WSSKYQQSFVPNPGPRPQMNGQSGRIDFHWLMLDPNDTVTFSFNGAFIAPD
RASFLRGKSLGIQSDAQLDNNCEGECYHIGGTIISNLPFQNINSRAIGKCPRYV
KQKSLMLATGMKNVPEAPAHKQLTHHMRKKRGLFGAIAGFIENGWEGLIDG
WYGYKHQNAQGEGTAADYKSTQSAINQITGKLNRLIEKTNQQFELIDNEFNEI
EKQIGNVINWTRDSIIEVWSYNAEFLVAVENQHTIDLTDSEMNKLYEKVRRQL
RENAEEDGNGCFEIFHQCDNDCMASIRNNTYDHKKYRKEAIQNRIQIDAVKLS
SGYKDIILWFSFGASCFLFLAIAMGLVFICIKNGNMRCTICI

Fig. 45B

SEQ ID NO: 59

METISLITILLVVTASNADKICIGHQSTNSTETVDTLTETNVPVTHAKELLHTEHN
GMLCATSLGHPLILDTCTIEGLVYGNPSCDLLLGGREWSYIVERSSAVNGTCY
PGNVENLEELRTLFSSASSYQRIQIFPDTTWNVTYTGTSRACSGSFYRSMRW
LTQKSGFYPVQDAQYTNNRGKSILFVWGIHHPPTYTEQTNLYIRNDTTTSVTT
EDLNRTFKPVIGPRPLVNGLQGRIDYYWSVLKPGQTLRVRSNGNLIAPWYGH
VLSGGSHGRILKTDLKGGNCVVQCQTEKGGLNSTLPFHNISKYAFGTCPKYV
RVNSLKLAVGLRNVPARSSRGLFGAIAGFIEGGWPGLVAGWYGFQHSNDQG
VGMAADRDSTQKAIDKITSKVNNIVDKMNKQYEIIDHEFSEVETRLNMINNKID
DQIQDVWAYNAELLVLLENQKTLDEHDANVNNLYNKVKRALGSNAMEDGKG
CFELYHKCDDQCMETIRNGTYNRRKYREESRLERQKIEGVKLESEGTYKILTI
YSTVASSLVLAMGFAAFLFWAMSNGSCRCNICI

Fig. 51

SEQ ID NO: 60
H5 from A/Indonesia/5/2005 (Construct # 660)
AGAGGTACCCCGGGCTGGTATATTTATATGTTGTCAAATAACTCAAAAACCATAAAAGTTTAAGTT
AGCAAGTGTGTACATTTTTACTTGAACAAAAATATTCACCTACTACTGTTATAAATCATTATTAAAC
ATTAGAGTAAAGAAATATGGATGATAAGAACAAGAGTAGTGATATTTTGACAACAATTTTGTTGCA
ACATTTGAGAAAATTTTGTTGTTCTCTCTTTTCATTGGTCAAAAACAATAGAGAGAGAAAAAGGAA
GAGGGAGAATAAAAACATAATGTGAGTATGAGAGAGAAAGTTGTACAAAAGTTGTACCAAAATAG
TTGTACAAATATCATTGAGGAATTTGACAAAAGCTACACAAATAAGGGTTAATTGCTGTAAATAAA
TAAGGATGACGCATTAGAGAGATGTACCATTAGAGAATTTTTGGCAAGTCATTAAAAAGAAAGAAT
AAATTATTTTTAAAATTAAAAGTTGAGTCATTTGATTAAACATGTGATTATTTAATGAATTGATGAAA
GAGTTGGATTAAAGTTGTATTAGTAATTAGAATTTGGTGTCAAATTTAATTTGACATTTGATCTTTT
CCTATATATTGCCCCATAGAGTCAGTTAACTCATTTTTATATTTCATAGATCAAATAAGAGAAATAA
CGGTATATTAATCCCTCCAAAAAAAAAAAACGGTATATTTACTAAAAAATCTAAGCCACGTAGGAG
GATAACAGGATCCCCGTAGGAGGATAACATCCAATCCAACCAATCACAACAATCCTGATGAGATA
ACCCACTTTAAGCCCACGCATCTGTGGCACATCTACATTATCTAAATCACACATTCTTCCACACAT
CTGAGCCACACAAAAACCAATCCACATCTTTATCACCCATTCTATAAAAAATCACACTTTGTGAGT
CTACACTTTGATTCCCTTCAAACACATACAAAGAGAAGAGACTAATTAATTAATTAATCATCTTGA
GAGAAAATGGAGAAAATAGTGCTTCTTCTTGCAATAGTCAGTCTTGTTAAAAGTGATCAGATTTGC
ATTGGTTACCATGCAAACAATTCAACAGAGCAGGTTGACACAATCATGGAAAAGAACGTTACTGT
TACACATGCCCAAGACATACTGGAAAAGACACACAACGGGAAGCTCTGCGATCTAGATGGAGTG
AAGCCTCTAATTTTAAGAGATTGTAGTGTAGCTGGATGGCTCCTCGGGAACCCAATGTGTGACGA
ATTCATCAATGTACCGGAATGGTCTTACATAGTGGAGAAGGCCAATCCAACCAATGACCTCTGTT
ACCCAGGGAGTTTCAACGACTATGAAGAACTGAAACACCTATTGAGCAGAATAAACCATTTTGAG
AAAATTCAAATCATCCCCAAAAGTTCTTGGTCCGATCATGAAGCCTCATCAGGAGTTAGCTCAGC
ATGTCCATACCTGGGAAGTCCCTCCTTTTTTAGAAATGTGGTATGGCTTATCAAAAAGAACAGTA
CATACCCAACAATAAAGAAAAGCTACAATAATACCAACCAAGAGGATCTTTTGGTACTGTGGGGA
ATTCACCATCCTAATGATGCGGCAGAGCAGACAAGGCTATATCAAAACCCAACCACCTATATTTC
CATTGGGACATCAACACTAAACCAGAGATTGGTACCAAAAATAGCTACTAGATCCAAAGTAAACG
GGCAAAGTGGAAGGATGGAGTTCTTCTGGACAATTTTAAAACCTAATGATGCAATCAACTTCGAG
AGTAATGGAAATTTCATTGCTCCAGAATATGCATACAAAATTGTCAAGAAAGGGGACTCAGCAATT
ATGAAAAGTGAATTGGAATATGGTAACTGCAACACCAAGTGTCAAACTCCAATGGGGGCGATAAA
CTCTAGTATGCCATTCCACAACATACACCCTCTCACCATCGGGGAATGCCCCAAATATGTGAAAT
CAAACAGATTAGTCCTTGCAACAGGGCTCAGAAATAGCCCTCAAAGAGAGAGCAGAAGAAAAAA
GAGAGGACTATTTGGAGCTATAGCAGGTTTTATAGAGGGAGGATGGCAGGGAATGGTAGATGGT
TGGTATGGGTACCACCATAGCAATGAGCAGGGGAGTGGGTACGCTGCAGACAAAGAATCCACTC
AAAAGGCAATAGATGGAGTCACCAATAAGGTCAACTCAATCATTGACAAAATGAACACTCAGTTT
GAGGCCGTTGGAAGGGAATTTAATAACTTAGAAAGGAGAATAGAGAATTTAAACAAGAAGATGGA
AGACGGGTTTCTAGATGTCTGGACTTATAATGCCGAACTTCTGGTTCTCATGGAAAATGAGAGAA
CTCTAGACTTTCATGACTCAAATGTTAAGAACCTCTACGACAAGGTCCGACTACAGCTTAGGGAT
AATGCAAAGGAGCTGGGTAACGGTTGTTTCGAGTTCTATCACAAATGTGATAATGAATGTATGGA
AAGTATAAGAAACGGAACGTACAACTATCCGCAGTATTCAGAAGAAGCAAGATTAAAAAGAGAGG
AAATAAGTGGGGTAAAATTGGAATCAATAGGAACTTACCAAATACTGTCAATTTATTCAACAGTGG
CGAGTTCCCTAGCACTGGCAATCATGATGGCTGGTCTATCTTTATGGATGTGCTCCAATGGATCG
TTACAATGCAGAATTTGCATTTAAGAGCTCTAAGTTAAAATGCTTCTTCGTCTCCTATTTATAATAT
GGTTTGTTATTGTTAATTTTGTTCTTGTAGAAGAGCTTAATTAATCGTTGTTGTTATGAAATACTAT
TTGTATGAGATGAACTGGTGTAATGTAATTCATTTACATAAGTGGAGTCAGAATCAGAATGTTTCC
TCCATAACTAACTAGACATGAAGACCTGCCGCGTACAATTGTCTTATATTTGAACAACTAAAATTG
AACATCTTTTGCCACAACTTTATAAGTGGTTAATATAGCTCAAATATATGGTCAAGTTCAATAGATT
AATAATGGAAATATCAGTTATCGAAATTCATTAACAATCAACTTAACGTTATTAACTACTAATTTTAT
ATCATCCCCTTTGATAAATGATAGTACA

Fig. 52

SEQ ID NO: 61

H1 from A/New Caledonia/20/1999 (Construct # 540)
AGAGGTACCCCGGGCTGGTATATTTATATGTTGTCAAATAACTCAAAAACCATAAAAGTTTAAGTT
AGCAAGTGTGTACATTTTTACTTGAACAAAAATATTCACCTACTACTGTTATAAATCATTATTAAAC
ATTAGAGTAAAGAAATATGGATGATAAGAACAAGAGTAGTGATATTTTGACAACAATTTTGTTGCA
ACATTTGAGAAAATTTTGTTGTTCTCTCTTTTCATTGGTCAAAAACAATAGAGAGAGAAAAAGGAA
GAGGGAGAATAAAAACATAATGTGAGTATGAGAGAGAAAGTTGTACAAAAGTTGTACCAAAATAG
TTGTACAAATATCATTGAGGAATTTGACAAAAGCTACACAAATAAGGGTTAATTGCTGTAAATAAA
TAAGGATGACGCATTAGAGAGATGTACCATTAGAGAATTTTTGGCAAGTCATTAAAAAGAAAGAA
TAAATTATTTTTAAAATTAAAAGTTGAGTCATTTGATTAAACATGTGATTATTTAATGAATTGATGAA
AGAGTTGGATTAAAGTTGTATTAGTAATTAGAATTTGGTGTCAAATTTAATTTGACATTTGATCTTT
TCCTATATATTGCCCCATAGAGTCAGTTAACTCATTTTTATATTTCATAGATCAAATAAGAGAAATA
ACGGTATATTAATCCCTCCAAAAAAAAAAAAACGGTATATTTACTAAAAAATCTAAGCCACGTAGGA
GGATAACAGGATCCCCGTAGGAGGATAACATCCAATCCAACCAATCACAACAATCCTGATGAGA
TAACCCACTTTAAGCCCACGCATCTGTGGCACATCTACATTATCTAAATCACACATTCTTCCACAC
ATCTGAGCCACACAAAAACCAATCCACATCTTTATCACCCATTCTATAAAAAATCACACTTTGTGA
GTCTACACTTTGATTCCCTTCAAACACATACAAAGAGAAGAGACTAATTAATTAATTAATCATCTT
GAGAGAAAATGGCGAAAAACGTTGCGATTTTCGGCTTATTGTTTTCTCTTCTTGTGTTGGTTCCTT
CTCAGATCTTCGCTGACACAATATGTATAGGCTACCATGCCAACAACTCAACCGACACTGTTGAC
ACAGTACTTGAGAAGAATGTGACAGTGACACACTCTGTCAACCTACTTGAGGACAGTCACAATG
GAAAACTATGTCTACTAAAAGGAATAGCCCCACTACAATTGGGTAATTGCAGCGTTGCCGGATG
GATCTTAGGAAACCCAGAATGCGAATTACTGATTTCCAAGGAATCATGGTCCTACATTGTAGAAA
CACCAAATCCTGAGAATGGAACATGTTACCCAGGGTATTTCGCCGACTATGAGGAACTGAGGGA
GCAATTGAGTTCAGTATCTTCATTTGAGAGATTCGAAATATTCCCCAAAGAAAGCTCATGGCCCA
ACCACACCGTAACCGGAGTATCAGCATCATGCTCCCATAATGGGAAAAGCAGTTTTTACAGAAAT
TTGCTATGGCTGACGGGGAAGAATGGTTTGTACCCAAACCTGAGCAAGTCCTATGTAAACAACA
AAGAGAAAGAAGTCCTTGTACTATGGGGTGTTCATCACCCGCCTAACATAGGGAACCAAAGGGC
ACTCTATCATACAGAAAATGCTTATGTCTCTGTAGTGTCTTCACATTATAGCAGAAGATTCACCCC
AGAAATAGCCAAAAGACCCAAAGTAAGAGATCAGGAAGGAAGAATCAACTACTACTGGACTCTG
CTGGAACCTGGGGATACAATAATATTTGAGGCAAATGGAAATCTAATAGCGCCATGGTATGCTTT
TGCACTGAGTAGAGGCTTTGGATCAGGAATCATCACCTCAAATGCACCAATGGATGAATGTGAT
GCGAAGTGTCAAACACCTCAGGGAGCTATAAACAGCAGTCTTCCTTTCCAGAATGTACACCCAG
TCACAATAGGAGAGTGTCCAAAGTATGTCAGGAGTGCAAAATTAAGGATGGTTACAGGACTAAG
GAACATCCCATCCATTCAATCCAGAGGTTTGTTTGGAGCCATTGCCGGTTTCATTGAAGGGGGG
TGGACTGGAATGGTAGATGGGTGGTATGGTTATCATCATCAGAATGAGCAAGGATCTGGCTATG
CTGCAGATCAAAAAAGTACACAAAATGCCATTAACGGGATTACAAACAAGGTCAATTCTGTAATT
GAGAAAATGAACACTCAATTCACAGCTGTGGGCAAAGAGTTCAACAAATTGGAAAGAAGGATGG
AAAACTTAAATAAAAAAGTTGATGATGGGTTTCTAGACATTTGGACATATAATGCAGAATTGTTGG
TTCTACTGGAAAATGAAAGGACTTTGGATTTCCATGACTCCAATGTGAAGAATCTGTATGAGAAA
GTAAAAAGCCAATTAAAGAATAATGCCAAAGAAATAGGAAACGGGTGTTTTGAGTTCTATCACAA
GTGTAACAATGAATGCATGGAGAGTGTGAAAAATGGTACCTATGACTATCCAAAATATTCCGAAG
AATCAAAGTTAAACAGGGAGAAAATTGATGGAGTGAAATTGGAATCAATGGGAGTATACCAGATT
CTGGCGATCTACTCAACTGTCGCCAGTTCCCTGGTTCTTTTGGTCTCCCTGGGGGCAATCAGCT
TCTGGATGTGTTCCAATGGGTCTTTGCAGTGTAGAATATGCATCTAAGAGCTCTAAGTTAAAATG
CTTCTTCGTCTCCTATTTATAATATGGTTTGTTATTGTTAATTTTGTTCTTGTAGAAGAGCTTAATT
AATCGTTGTTGTTATGAAATACTATTTGTATGAGATGAACTGGTGTAATGTAATTCATTTACATAAG
TGGAGTCAGAATCAGAATGTTTCCTCCATAACTAACTAGACATGAAGACCTGCCGCGTACAATTG
TCTTATATTTGAACAACTAAAATTGAACATCTTTTGCCACAACTTTATAAGTGGTTAATATAGCTCA
AATATATGGTCAAGTTCAATAGATTAATAATGGAAATATCAGTTATCGAAATTCATTAACAATCAAC
TTAACGTTATTAACTACTAATTTTATATCATCCCCTTTGATAAATGATAGTACA

Fig. 53

SEQ ID NO: 62
H1 from A/Brisbane/59/2007 (construct #774)
CTGGTATATTTATATGTTGTCAAATAACTCAAAAACCATAAAAGTTTAAGTTAGCAAGTGTGTACAT
TTTTACTTGAACAAAAATATTCACCTACTACTGTTATAAATCATTATTAAACATTAGAGTAAAGAAAT
ATGGATGATAAGAACAAGAGTAGTGATATTTTGACAACAATTTTGTTGCAACATTTGAGAAAATTTT
GTTGTTCTCTCTTTTCATTGGTCAAAAACAATAGAGAGAGAAAAAGGAAGAGGGAGAATAAAAACA
TAATGTGAGTATGAGAGAGAAAGTTGTACAAAAGTTGTACCAAAATAGTTGTACAAATATCATTGA
GGAATTTGACAAAAGCTACACAAATAAGGGTTAATTGCTGTAAATAAATAAGGATGACGCATTAGA
GAGATGTACCATTAGAGAATTTTTGGCAAGTCATTAAAAAGAAAGAATAAATTATTTTTAAAATTAA
AAGTTGAGTCATTTGATTAAACATGTGATTATTTAATGAATTGATGAAAGAGTTGGATTAAAGTTGT
ATTAGTAATTAGAATTTGGTGTCAAATTTAATTTGACATTTGATCTTTTCCTATATATTGCCCCATA
GAGTCAGTTAACTCATTTTTATATTTCATAGATCAAATAAGAGAAATAACGGTATATTAATCCCTCC
AAAAAAAAAAAAACGGTATATTTACTAAAAAATCTAAGCCACGTAGGAGGATAACAGGATCCCCGTA
GGAGGATAACATCCAATCCAACCAATCACAACAATCCTGATGAGATAACCCACTTTAAGCCCACG
CATCTGTGGCACATCTACATTATCTAAATCACACATTCTTCCACACATCTGAGCCACACAAAAACC
AATCCACATCTTTATCACCCATTCTATAAAAAATCACACTTTGTGAGTCTACACTTTGATTCCCTTC
AAACACATACAAAGAGAAGAGACTAATTAATTAATTAATCATCTTGAGAGAAAATGAAAGTAAAACT
ACTGGTCCTGTTATGCACATTTACAGCTACATATGCAGACACAATATGTATAGGCTACCATGCTAA
CAACTCGACCGACACTGTTGACACAGTACTTGAAAAGAATGTGACAGTGACACACTCTGTCAACC
TGCTTGAGAACAGTCACAATGGAAAACTATGTCTATTAAAAGGAATAGCCCCACTACAATTGGGT
AATTGCAGCGTTGCCGGGTGGATCTTAGGAAACCCAGAATGCGAATTACTGATTTCCAAGGAGTC
ATGGTCCTACATTGTAGAAAAACCAAATCCTGAGAATGGAACATGTTACCCAGGGCATTTCGCTG
ACTATGAGGAACTGAGGGAGCAATTGAGTTCAGTATCTTCATTTGAGAGGTTCGAAATATTCCCC
AAAGAAAGCTCATGGCCCAACCACACCGTAACCGGAGTGTCAGCATCATGCTCCCATAATGGGG
AAAGCAGTTTTTACAGAAATTTGCTATGGCTGACGGGGAAGAATGGTTTGTACCCAAACCTGAGC
AAGTCCTATGCAAACAACAAAGAAAAAGAAGTCCTTGTACTATGGGGTGTTCATCACCCGCCAAA
CATAGGTGACCAAAAGGCCCTCTATCATACAGAAAATGCTTATGTCTCTGTAGTGTCTTCACATTA
TAGCAGAAAATTCACCCCAGAAATAGCCAAAAGACCCAAAGTAAGAGATCAAGAAGGAAGAATCA
ATTACTACTGGACTCTGCTTGAACCCGGGGATACAATAATATTTGAGGCAAATGGAAATCTAATAG
CGCCAAGATATGCTTTCGCACTGAGTAGAGGCTTTGGATCAGGAATCATCAACTCAAATGCACCA
ATGGATAAATGTGATGCGAAGTGCCAAACACCTCAGGGAGCTATAAACAGCAGTCTTCCTTTCCA
GAACGTACACCCAGTCACAATAGGAGAGTGTCCAAAGTATGTCAGGAGTGCAAAATTAAGGATG
GTTACAGGACTAAGGAACATCCCATCCATTCAATCCAGAGGTTTGTTTGGAGCCATTGCCGGTTT
CATTGAAGGGGGGTGGACTGGAATGGTAGATGGTTGGTATGGTTATCATCATCAGAATGAGCAA
GGATCTGGCTATGCTGCAGATCAAAAAAGCACACAAAATGCCATTAATGGGATTACAAACAAGGT
CAATTCTGTAATTGAGAAAATGAACACTCAATTCACAGCAGTGGGCAAAGAGTTCAACAAATTGG
AAAGAAGGATGGAAAACTTGAATAAAAAAGTTGATGATGGGTTTATAGACATTTGGACATATAATG
CAGAACTGTTGGTTCTACTGGAAAATGAAAGGACTTTGGATTTCCATGACTCCAATGTGAAGAAT
CTGTATGAGAAAGTAAAAAGCCAGTTAAAGAATAATGCTAAAGAAATAGGAAATGGGTGTTTTGAG
TTCTATCACAAGTGTAACGATGAATGCATGGAGAGTGTAAAGAATGGAACTTATGACTATCCAAAA
TATTCCGAAGAATCAAAGTTAAACAGGGAGAAAATTGATGGAGTGAAATTGGAATCAATGGGAGT
CTATCAGATTCTGGCGATCTACTCAACAGTCGCCAGTTCTCTGGTTCTTTTGGTCTCCCTGGGGG
CAATCAGCTTCTGGATGTGTTCCAATGGGTCTTTACAGTGTAGAATATGCATCTAAGAGCTCTAA
GTTAAAATGCTTCTTCGTCTCCTATTTATAATATGGTTTGTTATTGTTAATTTTGTTCTTGTAGAAGA
GCTTAATTAATCGTTGTTGTTATGAAATACTATTTGTATGAGATGAACTGGTGTAATGTAATTCATT
TACATAAGTGGAGTCAGAATCAGAATGTTTCCTCCATAACTAACTAGACATGAAGACCTGCCGCG
TACAATTGTCTTATATTTGAACAACTAAAATTGAACATCTTTTGCCACAACTTTATAAGTGGTTAAT
ATAGCTCAAATATATGGTCAAGTTCAATAGATTAATAATGGAAATATCAGTTATCGAAATTCATTAA
CAATCAACTTAACGTTATTAACTACTAATTTTATATCATCCCCTTTGATAAATGATAGTACA

Fig. 54

SEQ ID NO: 63

H1 from A/Solomon Islands/3/2006 (H1N1) (Construct # 775)

AGAGGTACCCCGGGCTGGTATATTTATATGTTGTCAAATAACTCAAAAACCATAAAAGTTTA
AGTTAGCAAGTGTGTACATTTTTACTTGAACAAAAATATTCACCTACTACTGTTATAAATCAT
TATTAAACATTAGAGTAAAGAAATATGGATGATAAGAACAAGAGTAGTGATATTTTGACAAC
AATTTTGTTGCAACATTTGAGAAAATTTTGTTGTTCTCTCTTTTCATTGGTCAAAAACAATAG
AGAGAGAAAAAGGAAGAGGGAGAATAAAAACATAATGTGAGTATGAGAGAGAAAGTTGTAC
AAAAGTTGTACCAAAATAGTTGTACAAATATCATTGAGGAATTTGACAAAAGCTACACAAATA
AGGGTTAATTGCTGTAAATAAATAAGGATGACGCATTAGAGAGATGTACCATTAGAGAATTT
TTGGCAAGTCATTAAAAAGAAAGAATAAATTATTTTTAAAATTAAAAGTTGAGTCATTTGATTA
AACATGTGATTATTTAATGAATTGATGAAAGAGTTGGATTAAAGTTGTATTAGTAATTAGAAT
TTGGTGTCAAATTTAATTTGACATTTGATCTTTTCCTATATATTGCCCCATAGAGTCAGTTAA
CTCATTTTTATATTTCATAGATCAAATAAGAGAAATAACGGTATATTAATCCCTCCAAAAAAA
AAAAACGGTATATTTACTAAAAAATCTAAGCCACGTAGGAGGATAACAGGATCCCCGTAGG
AGGATAACATCCAATCCAACCAATCACAACAATCCTGATGAGATAACCCACTTTAAGCCCAC
GCATCTGTGGCACATCTACATTATCTAAATCACACATTCTTCCACACATCTGAGCCACACAA
AAACCAATCCACATCTTTATCACCCATTCTATAAAAAATCACACTTTGTGAGTCTACACTTTG
ATTCCCTTCAAACACATACAAAGAGAAGAGACTAATTAATTAATTAATCATCTTGAGAGAAAA
TGAAAGTAAAACTACTGGTCCTGTTATGCACATTTACAGCTACATATGCAGACACAATATGT
ATAGGCTACCATGCCAACAACTCAACCGACACTGTTGACACAGTACTTGAGAAGAATGTGA
CAGTGACACACTCTGTCAACCTGCTTGAGGACAGTCACAATGGAAAATTATGTCTATTAAAA
GGAATAGCCCCACTACAATTGGGTAATTGCAGCGTTGCCGGATGGATCTTAGGAAACCCA
GAATGCGAATTACTGATTTCCAGGGAATCATGGTCCTACATTGTAGAAAAACCAAATCCTGA
GAATGGAACATGTTACCCAGGGCATTTCGCCGACTATGAGGAACTGAGGGAGCAATTGAG
TTCAGTATCTTCATTTGAGAGATTCGAAATATTCCCCAAAGAAAGCTCATGGCCCAACCACA
CCACAACCGGAGTATCAGCATCATGCTCCCATAATGGGGAAAGCAGTTTTTACAAAAATTT
GCTATGGCTGACGGGGAAGAATGGTTTGTACCCAAACCTGAGCAAGTCCTATGCAAACAA
CAAAGAGAAAGAAGTCCTTGTACTATGGGGTGTTCATCACCCGCCTAACATAGGTGACCAA
AGGGCTCTCTATCATAAAGAAAATGCTTATGTCTCTGTAGTGTCTTCACATTATAGCAGAAA
ATTCACCCCAGAAATAGCCAAAAGACCCAAAGTAAGAGATCAAGAAGGAAGAATCAACTAC
TACTGGACTCTACTTGAACCCGGGGATACAATAATATTTGAGGCAAATGGAAATCTAATAGC
GCCAAGATATGCTTTCGCACTGAGTAGAGGCTTTGGATCAGGAATCATCAACTCAAATGCA
CCAATGGATGAATGTGATGCGAAGTGCCAAACACCTCAGGGAGCTATAAACAGCAGTCTTC
CTTTCCAGAATGTACACCCTGTCACAATAGGAGAGTGTCCAAAGTATGTCAGGAGTGCAAA
ATTAAGGATGGTTACAGGACTAAGGAACATCCCATCCATTCAATCCAGAGGTTTGTTTGGA
GCCATTGCCGGTTTCATTGAAGGGGGGTGGACTGGAATGGTAGATGGTTGGTATGGTTAT
CATCATCAGAATGAGCAAGGATCTGGCTATGCTGCAGATCAAAAAAGCACACAAAATGCCA
TTAATGGGATTACAAACAAGGTCAATTCTGTAATTGAGAAAATGAACACTCAATTCACAGCT
GTGGGCAAAGAGTTCAACAAATTGGAAAGAAGGATGGAAAACTTAAATAAAAAAGTTGATG
ATGGGTTTATAGACATTTGGACATATAATGCAGAATTGTTGGTTCTACTGGAAAATGAAAGG
ACTTTGGATTTCCATGACTCCAATGTGAAGAATCTGTATGAGAAAGTAAAAAGCCAATTAAA
GAATAATGCCAAAGAAATAGGAAATGGGTGTTTTGAGTTCTATCATAAGTGTAACGATGAAT
GCATGGAGAGTGTAAAAAATGGAACTTATGACTATCCAAAATATTCCGAAGAATCAAAGTTA
AACAGGGAGAAAATTGATGGAGTGAAATTGGAATCAATGGGAGTCTATCAGATTCTGGCGA
TCTACTCAACAGTCGCCAGTTCTCTGGTTCTTTTGGTCTCCCTGGGGGCAATCAGCTTCTG
GATGTGTTCCAATGGGTCTTTGCAGTGTAGAATATGCATCTGAGAGCTCTAAGTTAAAATGC
TTCTTCGTCTCCTATTTATAATATGGTTTGTTATTGTTAATTTTGTTCTTGTAGAAGAGCTTAA
TTAATCGTTGTTGTTATGAAATACTATTTGTATGAGATGAACTGGTGTAATGTAATTCATTTA
CATAAGTGGAGTCAGAATCAGAATGTTTCCTCCATAACTAACTAGACATGAAGACCTGCCG
CGTACAATTGTCTTATATTTGAACAACTAAAATTGAACATCTTTTGCCACAACTTTATAAGTG
GTTAATATAGCTCAAATATATGGTCAAGTTCAATAGATTAATAATGGAAATATCAGTTATCGA
AATTCATTAACAATCAACTTAACGTTATTAACTACTAATTTTATATCATCCCCTTTGATAAATG
ATAGTACA

Fig. 55

SEQ ID NO: 64
H2 from A/Singapore/1/57 (H2N2) (construct # 780)
AGAGGTACCCCGGGCTGGTATATTTATATGTTGTCAAATAACTCAAAAACCATAAAAGTTTAA
GTTAGCAAGTGTGTACATTTTTACTTGAACAAAAATATTCACCTACTACTGTTATAAATCATTAT
TAAACATTAGAGTAAAGAAATATGGATGATAAGAACAAGAGTAGTGATATTTTGACAACAATTT
TGTTGCAACATTTGAGAAAATTTTGTTGTTCTCTCTTTTCATTGGTCAAAAACAATAGAGAGAG
AAAAAGGAAGAGGGAGAATAAAAACATAATGTGAGTATGAGAGAGAAAGTTGTACAAAAGTTG
TACCAAAATAGTTGTACAAATATCATTGAGGAATTTGACAAAAGCTACACAAATAAGGGTTAAT
TGCTGTAAATAAATAAGGATGACGCATTAGAGAGATGTACCATTAGAGAATTTTTGGCAAGTC
ATTAAAAAGAAAGAATAAATTATTTTTAAAATTAAAAGTTGAGTCATTTGATTAAACATGTGATT
ATTTAATGAATTGATGAAAGAGTTGGATTAAAGTTGTATTAGTAATTAGAATTTGGTGTCAAAT
TTAATTTGACATTTGATCTTTTCCTATATATTGCCCCATAGAGTCAGTTAACTCATTTTTATATT
TCATAGATCAAATAAGAGAAATAACGGTATATTAATCCCTCCAAAAAAAAAAAACGGTATATTT
ACTAAAAAATCTAAGCCACGTAGGAGGATAACAGGATCCCCGTAGGAGGATAACATCCAATC
CAACCAATCACAACAATCCTGATGAGATAACCCACTTTAAGCCCACGCATCTGTGGCACATCT
ACATTATCTAAATCACACATTCTTCCACACATCTGAGCCACACAAAAACCAATCCACATCTTTA
TCACCCATTCTATAAAAAATCACACTTTGTGAGTCTACACTTTGATTCCCTTCAAACACATACA
AAGAGAAGAGACTAATTAATTAATTAATCATCTTGAGAGAAAATGGCCATCATTTATCTAATTC
TCCTGTTCACAGCAGTGAGAGGGGACCAAATATGCATTGGATACCATGCCAATAATTCCACA
GAGAAGGTCGACACAATTCTAGAGCGGAACGTCACTGTGACTCATGCCAAGGACATTCTTGA
GAAGACCCATAACGGAAAGTTATGCAAACTAAACGGAATCCCTCCACTTGAACTAGGGGACT
GTAGCATTGCCGGATGGCTCCTTGGAAATCCAGAATGTGATAGGCTTCTAAGTGTGCCAGAA
TGGTCCTATATAATGGAGAAAGAAAACCCGAGAGACGGTTTGTGTTATCCAGGCAGCTTCAA
TGATTATGAAGAATTGAAACATCTCCTCAGCAGCGTGAAACATTTCGAGAAAGTAAAGATTCT
GCCCAAAGATAGATGGACACAGCATACAACAACTGGAGGTTCACGGGCCTGCGCGGTGTCT
GGTAATCCATCATTCTTCAGGAACATGGTCTGGCTGACAAAGAAAGAATCAAATTATCCGGTT
GCCAAAGGATCGTACAACAATACAAGCGGAGAACAAATGCTAATAATTTGGGGGGTGCACCA
TCCCAATGATGAGACAGAACAAAGAACATTGTACCAGAATGTGGGAACCTATGTTTCCGTAG
GCACATCAACATTGAACAAAAGGTCAACCCCAGACATAGCAACAAGGCCTAAAGTGAATGGA
CTAGGAAGTAGAATGGAGTTCTCTTGGACCCTATTGGATATGTGGGACACCATAAATTTTGAG
AGTACTGGTAATCTAATTGCACCAGAGTATGGATTCAAAATATCGAAAAGAGGTAGTTCAGGG
ATCATGAAAACAGAAGGAACACTTGAGAACTGTGAGACCAAATGCCAAACTCCTTTGGGAGC
AATAAATACAACATTGCCTTTTCACAATGTCCACCCACTGACAATAGGTGAGTGCCCCAAATA
TGTAAAATCGGAGAAGTTGGTCTTAGCAACAGGACTAAGGAATGTTCCCCAGATTGAATCAA
GAGGATTGTTTGGGGCAATAGCTGGTTTTATAGAAGGAGGATGGCAAGGAATGGTTGATGGT
TGGTATGGATACCATCACAGCAATGACCAGGGATCAGGGTATGCAGCAGACAAAGAATCCAC
TCAAAAGGCATTTGATGGAATCACCAACAAGGTAAATTCTGTGATTGAAAAGATGAACACCCA
ATTTGAAGCTGTTGGGAAAGAGTTCAGTAACTTAGAGAGAAGACTGGAGAACTTGAACAAAAA
GATGGAAGACGGGTTTCTAGATGTGTGGACATACAATGCTGAGCTTCTAGTTCTGATGGAAA
ATGAGAGGACACTTGACTTTCATGATTCTAATGTCAAGAATCTGTATGATAAAGTCAGAATGC
AGCTGAGAGACAACGTCAAAGAACTAGGAAATGGATGTTTTGAATTTTATCACAAATGTGATG
ATGAATGCATGAATAGTGTGAAAAACGGGACGTATGATTATCCCAAGTATGAAGAAGAGTCTA
AACTAAATAGAAATGAAATCAAAGGGGTAAAATTGAGCAGCATGGGGGTTTATCAAATCCTTG
CCATTTATGCTACAGTAGCAGGTTCTCTGTCACTGGCAATCATGATGGCTGGGATCTCTTTCT
GGATGTGCTCCAACGGGTCTCTGCAGTGCAGGATCTGCATATGAGAGCTCTAAGTTAAAATG
CTTCTTCGTCTCCTATTTATAATATGGTTTGTTATTGTTAATTTTGTTCTTGTAGAAGAGCTTAA
TTAATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCGTA
CAATTGTCTTATATTTGAACAACTAAAATTGAACATCTTTTGCCACAACTTTATAAGTGGTTAAT
ATAGCTCAAATATATGGTCAAGTTCAATAGATTAATAATGGAAATATCAGTTATCGAAATTCAT
TAACAATCAACTTAACGTTATTAACTACTAATTTTATATCATCCCCTTTGATAAATGATAGTACA

Fig. 56

SEQ ID NO: 65
H5 from A/Anhui/1/2005 (H5N1) (Construct# 781)
AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTT
GTTGCAACATTTGAGAAAATTTTGTTGTTCTCTCTTTTCATTGGTCAAAAACAATAGAGAGAGA
AAAAGGAAGAGGGAGAATAAAAACATAATGTGAGTATGAGAGAGAAAGTTGTACAAAAGTTGT
ACCAAAATAGTTGTACAAATATCATTGAGGAATTTGACAAAAGCTACACAAATAAGGGTTAATT
GCTGTAAATAAATAAGGATGACGCATTAGAGAGATGTACCATTAGAGAATTTTTGGCAAGTCA
TTAAAAAGAAAGAATAAATTATTTTTAAAATTAAAAGTTGAGTCATTTGATTAAACATGTGATTAT
TTAATGAATTGATGAAAGAGTTGGATTAAAGTTGTATTAGTAATTAGAATTTGGTGTCAAATTTA
ATTTGACATTTGATCTTTTCCTATATATTGCCCCATAGAGTCAGTTAACTCATTTTTATATTTCAT
AGATCAAATAAGAGAAATAACGGTATATTAATCCCTCCAAAAAAAAAAAACGGTATATTTACTA
AAAAATCTAAGCCACGTAGGAGGATAACAGGATCCCCGTAGGAGGATAACATCCAATCCAAC
CAATCACAACAATCCTGATGAGATAACCCACTTTAAGCCCACGCATCTGTGGCACATCTACAT
TATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGA
GAAGAGACTAATTAATTAATTAATCATCTTGAGAGAAAATGGAGAAAATAGTGCTTCTTCTTGC
AATAGTCAGCCTTGTTAAAAGTGATCAGATTTGCATTGGTTACCATGCAAACAACTCGACAGA
GCAGGTTGACACAATAATGGAAAAGAACGTTACTGTTACACATGCCCAAGACATACTGGAAAA
GACACACAACGGGAAGCTCTGCGATCTAGATGGAGTGAAGCCTCTGATTTTAAGAGATTGTA
GTGTAGCTGGATGGCTCCTCGGAAACCCAATGTGTGACGAGTTCATCAATGTGCCGGAATGG
TCTTACATAGTGGAGAAGGCCAACCCAGCCAATGACCTCTGTTACCCAGGGAATTTCAACGA
CTATGAAGAACTGAAACACCTATTGAGCAGAATAAACCATTTTGAGAAAATTCAGATCATCCCC
AAAAGTTCTTGGTCCGATCATGAAGCCTCATCAGGGGTCAGCTCAGCATGTCCATACCAGGG
AACGCCCTCCTTTTTCAGAAATGTGGTATGGCTTATCAAAAAGAACAATACATACCCAACAATA
AAGAGAAGCTACAATAATACCAACCAGGAAGATCTTTTGATACTGTGGGGGATTCATCATTCT
AATGATGCGGCAGAGCAGACAAAGCTCTATCAAAACCCAACCACCTATATTTCCGTTGGGACA
TCAACACTAAACCAGAGATTGGTACCAAAAATAGCTACTAGATCCAAAGTAAACGGGCAAAGT
GGAAGGATGGATTTCTTCTGGACAATTTTAAAACCGAATGATGCAATCAACTTCGAGAGTAAT
GGAAATTTCATTGCTCCAGAATATGCATACAAAATTGTCAAGAAAGGGGACTCAGCAATTGTT
AAAAGTGAAGTGGAATATGGTAACTGCAATACAAAGTGTCAAACTCCAATAGGGGCGATAAAC
TCTAGTATGCCATTCCACAACATACACCCTCTCACCATCGGGGAATGCCCCAAATATGTGAAA
TCAAACAAATTAGTCCTTGCGACTGGGCTCAGAAATAGTCCTCTAAGAGAAAGAAGAAGAAAA
AGAGGACTATTTGGAGCTATAGCAGGGTTTATAGAGGGAGGATGGCAGGGAATGGTAGATGG
TTGGTATGGGTACCACCATAGCAATGAGCAGGGGAGTGGGTACGCTGCAGACAAAGAATCCA
CTCAAAAGGCAATAGATGGAGTCACCAATAAGGTCAACTCGATCATTGACAAAATGAACACTC
AGTTTGAGGCCGTTGGAAGGGAATTTAATAACTTAGAAAGGAGAATAGAGAATTTAAACAAGA
AAATGGAAGACGGATTCCTAGATGTCTGGACTTATAATGCTGAACTTCTGGTTCTCATGGAAA
ATGAGAGAACTCTAGACTTCCATGATTCAAATGTCAAGAACCTTTACGACAAGGTCCGACTAC
AGCTTAGGGATAATGCAAAGGAGCTGGGTAACGGTTGTTTCGAGTTCTATCACAAATGTGATA
ATGAATGTATGGAAAGTGTAAGAAACGGAACGTATGACTACCCGCAGTATTCAGAAGAAGCAA
GATTAAAAAGAGAGGAAATAAGTGGAGTAAAATTGGAATCAATAGGAACTTACCAAATACTGT
CAATTTATTCAACAGTTGCGAGTTCTCTAGCACTGGCAATCATGGTGGCTGGTCTATCTTTGT
GGATGTGCTCCAATGGGTCGTTACAATGCAGAATTTGCATTTAAGAGCTCTAAGTTAAAATGC
TTCTTCGTCTCCTATTTATAATATGGTTTGTTATTGTTAATTTTGTTCTTGTAGAAGAGCTTAATT
AATCGTTGTTGTTATGAAATACTATTTGTATGAGATGAACTGGTGTAATGTAATTCATTTACATA
AGTGGAGTCAGAATCAGAATGTTTCCTCCATAACTAACTAGACATGAAGACCTGCCGCGTACA
ATTGTCTTATATTTGAACAACTAAAATTGAACATCTTTTGCCACAACTTTATAAGTGGTTAATAT
AGCTCAAATATATGGTCAAGTTCAATAGATTAATAATGGAAATATCAGTTATCGAAATTCATTAA
CAATCAACTTAACGTTATTAACTACTAATTTTATATCATCCCCTTTGATAAATGATAGTACA

Fig. 57

SEQ ID NO: 66
H5 from A/Vietnam/1194/2004 (H5N1) (Construct # 782)
AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTT
GTTGCAACATTTGAGAAAATTTTGTTGTTCTCTCTTTTCATTGGTCAAAAACAATAGAGAGAGA
AAAAGGAAGAGGGAGAATAAAAACATAATGTGAGTATGAGAGAGAAAGTTGTACAAAAGTTGT
ACCAAAATAGTTGTACAAATATCATTGAGGAATTTGACAAAAGCTACACAAATAAGGGTTAATT
GCTGTAAATAAATAAGGATGACGCATTAGAGAGATGTACCATTAGAGAATTTTTGGCAAGTCA
TTAAAAAGAAAGAATAAATTATTTTTAAAATTAAAAGTTGAGTCATTTGATTAAACATGTGATTAT
TTAATGAATTGATGAAAGAGTTGGATTAAAGTTGTATTAGTAATTAGAATTTGGTGTCAAATTTA
ATTTGACATTTGATCTTTTCCTATATATTGCCCCATAGAGTCAGTTAACTCATTTTTATATTTCAT
AGATCAAATAAGAGAAATAACGGTATATTAATCCCTCCAAAAAAAAAAAACGGTATATTTACTA
AAAAATCTAAGCCACGTAGGAGGATAACAGGATCCCCGTAGGAGGATAACATCCAATCCAAC
CAATCACAACAATCCTGATGAGATAACCCACTTTAAGCCCACGCATCTGTGGCACATCTACAT
TATCTAAATCACACATTCTTCCACACATCTGAGCCACACAAAAACCAATCCACATCTTTATCAC
CCATTCTATAAAAAATCACACTTTGTGAGTCTACACTTTGATTCCCTTCAAACACATACAAAGA
GAAGAGACTAATTAATTAATTAATCATCTTGAGAGAAAATGGAGAAAATAGTGCTTCTTTTTGC
AATAGTCAGTCTTGTTAAAAGTGATCAGATTTGCATTGGTTACCATGCAAACAACTCGACAGA
GCAGGTTGACACAATAATGGAAAAGAACGTTACTGTTACACATGCCCAAGACATACTGGAAAA
GACACACAATGGGAAGCTCTGCGATCTAGATGGAGTGAAGCCTCTAATTTTGAGAGATTGTAG
TGTAGCTGGATGGCTCCTCGGAAACCCAATGTGTGACGAGTTCATCAATGTGCCGGAATGGT
CTTACATAGTGGAGAAGGCCAATCCAGTCAATGACCTCTGTTACCCAGGGGATTTCAATGACT
ATGAAGAATTGAAACACCTATTGAGCAGAATAAACCATTTTGAGAAAATTCAGATCATCCCCAA
AAGTTCTTGGTCCAGTCATGAAGCCTCATTGGGGGTCAGCTCAGCATGTCCATACCAGGGAA
AGTCCTCCTTTTTCAGAAATGTGGTATGGCTTATCAAAAAGAACAGTACATACCCAACAATAAA
GAGGAGCTACAATAATACCAACCAAGAAGATCTTTTGGTACTGTGGGGGATTCACCATCCTAA
TGATGCGGCAGAGCAGACAAAGCTCTATCAAAACCCAACCACCTATATTTCCGTTGGGACATC
TACACTAAACCAGAGATTGGTACCAAGAATAGCTACTAGATCCAAAGTAAACGGGCAAAGTGG
AAGGATGGAGTTCTTCTGGACAATTTTTAAAACCGAATGATGCAATCAACTTCGAGAGTAATGG
AAATTTCATTGCTCCAGAATATGCATACAAAATTGTCAAGAAAGGGGACTCAACAATTATGAAA
AGTGAATTGGAATATGGTAACTGCAATACCAAGTGTCAAACTCCAATGGGGGCGATAAACTCT
AGCATGCCATTCCACAATATACACCCTCTCACCATCGGGGAATGCCCCAAATATGTGAAATCA
AACAGATTAGTCCTTGCGACTGGGCTCAGAAATAGCCCTCAAAGAGAGAGAAGAAGAAAAAA
GAGAGGATTATTTGGAGCTATAGCAGGTTTTATAGAGGGAGGATGGCAGGGAATGGTAGATG
GTTGGTATGGGTACCACCATAGCAACGAGCAGGGGAGTGGGTACGCTGCAGACAAAGAATC
CACTCAAAAGGCAATAGATGGAGTCACCAATAAGGTCAACTCGATTATTGACAAAATGAACAC
TCAGTTTGAGGCCGTTGGAAGGGAATTTAACAACTTAGAAAGGAGAATAGAGAATTTAAACAA
GAAGATGGAAGACGGGTTCCTAGATGTCTGGACTTATAATGCTGAACTTCTAGTTCTCATGGA
AAACGAGAGAACTCTAGACTTTCATGACTCAAATGTCAAGAACCTTTACGACAAGGTCCGACT
ACAGCTTAGGGATAATGCAAAGGAGCTGGGTAACGGTTGTTTCGAGTTCTATCATAAATGTGA
TAATGAATGTATGGAAAGTGTAAGAAACGGAACGTATGACTACCCGCAGTATTCAGAAGAAGC
AAGACTAAAAAGAGAGGAAATAAGTGGAGTAAAATTGGAATCAATAGGAATTTACCAAATATTG
TCAATTTATTCTACAGTGGCCAGCTCCCTAGCACTGGCAATCATGGTAGCTGGTCTATCCTTA
TGGATGTGCTCCAATGGGTCGTTACAATGCAGAATTTGCATTTAAGAGCTCTAAGTTAAAATG
CTTCTTCGTCTCCTATTTATAATATGGTTTGTTATTGTTAATTTTGTTCTTGTAGAAGAGCTTAA
TTAATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCGTA
CAATTGTCTTATATTTGAACAACTAAAATTGAACATCTTTTGCCACAACTTTATAAGTGGTTAAT
ATAGCTCAAATATATGGTCAAGTTCAATAGATTAATAATGGAAATATCAGTTATCGAAATTCATT
AACAATCAACTTAACGTTATTAACTACTAATTTTATATCATCCCCTTTGATAAATGATAGTACA

Fig. 58

SEQ ID NO: 67

H6 from A/Teal/Hong Kong/W312/97 (H6N1) (Construct # 783)

AGAGGTACCCCGGGCTGGTATATTTATATGTTGTCAAATAACTCAAAAACCATAAAAGTTTA
AGTTAGCAAGTGTGTACATTTTTACTTGAACAAAAATATTCACCTACTACTGTTATAAATCAT
TATTAAACATTAGAGTAAAGAAATATGGATGATAAGAACAAGAGTAGTGATATTTTGACAACA
ATTTTGTTGCAACATTTGAGAAAATTTTGTTGTTCTCTCTTTTCATTGGTCAAAAACAATAGA
GAGAGAAAAAGGAAGAGGGAGAATAAAAACATAATGTGAGTATGAGAGAGAAAGTTGTACA
AAAGTTGTACCAAAATAGTTGTACAAATATCATTGAGGAATTTGACAAAAGCTACACAAATAA
GGGTTAATTGCTGTAAATAAATAAGGATGACGCATTAGAGAGATGTACCATTAGAGAATTTT
TGGCAAGTCATTAAAAAGAAAGAATAAATTATTTTTAAAATTAAAAGTTGAGTCATTTGATTAA
ACATGTGATTATTTAATGAATTGATGAAAGAGTTGGATTAAAGTTGTATTAGTAATTAGAATT
TGGTGTCAAATTTAATTTGACATTTGATCTTTTCCTATATATTGCCCCATAGAGTCAGTTAAC
TCATTTTTATATTTCATAGATCAAATAAGAGAAATAACGGTATATTAATCCCTCCAAAAAAAAA
AAACGGTATATTTACTAAAAAATCTAAGCCACGTAGGAGGATAACAGGATCCCCGTAGGAG
GATAACATCCAATCCAACCAATCACAACAATCCTGATGAGATAACCCACTTTAAGCCCACGC
ATCTGTGGCACATCTACATTATCTAAATCACACATTCTTCCACACATCTGAGCCACACAAAA
ACCAATCCACATCTTTATCACCCATTCTATAAAAAATCACACTTTGTGAGTCTACACTTTGAT
TCCCTTCAAACACATACAAAGAGAAGAGACTAATTAATTAATTAATCATCTTGAGAGAAAATG
ATTGCAATCATTGTAATAGCAATACTGGCAGCAGCCGGAAAGTCAGACAAGATCTGCATTG
GGTATCATGCCAACAATTCAACAACACAGGTAGATACGATACTTGAGAAGAATGTGACTGT
CACACACTCAATTGAATTGCTGGAAAATCAGAAGGAAGAAAGATTCTGCAAGATATTGAACA
AGGCCCCTCTCGACTTAAGGGAATGTACCATAGAGGGTTGGATCTTGGGGAATCCCCAAT
GCGACCTATTGCTTGGTGATCAAAGCTGGTCATACATTGTGGAAAGACCTACTGCTCAAAA
CGGGATCTGCTACCCAGGAACCTTAAATGAGGTAGAAGAACTGAGGGCACTTATTGGATCA
GGAGAAAGGGTAGAGAGATTTGAGATGTTTCCCCAAAGCACCTGGCAAGGAGTTGACACC
AACAGTGGAACAACAAGATCCTGCCCTTATTCTACTGGTGCGTCTTTCTACAGAAACCTCCT
ATGGATAATAAAAACCAAGACAGCAGAATATCCAGTAATTAAGGGAATTTACAACAACACTG
GAACCCAGCCAATCCTCTATTTCTGGGGTGTGCATCATCCTCCTAACACCGACGAGCAAGA
TACTCTGTATGGCTCTGGTGATCGATACGTTAGAATGGGAACTGAAAGCATGAATTTTGCCA
AGAGTCCGGAAATTGCGGCAAGGCCTGCTGTGAATGGACAAAGAGGCAGAATTGATTATTA
TTGGTCGGTTTTAAAACCAGGGGAAACCTTGAATGTGGAATCTAATGGAAATCTAATCGCC
CCTTGGTATGCATACAAATTTGTCAACACAAATAGTAAAGGAGCCGTCTTCAGGTCAGATTT
ACCAATCGAGAACTGCGATGCCACATGCCAGACTATTGCAGGGGTTCTAAGGACCAATAAA
ACATTTCAGAATGTGAGTCCCCTGTGGATAGGAGAATGTCCCAAATACGTGAAAAGTGAAA
GTCTGAGGCTTGCAACTGGACTAAGAAATGTTCCACAGATTGAAACTAGAGGACTCTTCGG
AGCTATTGCAGGGTTTATTGAAGGAGGATGGACTGGGATGATAGATGGGTGGTATGGCTAT
CACCATGAAAATTCTCAAGGGTCAGGATATGCAGCAGACAGAGAAAGCACTCAAAAGGCTG
TAAACAGAATTACAAATAAGGTCAATTCCATCATCAACAAAATGAACACACAATTTGAAGCTG
TCGATCACGAATTTTCAAATCTGGAGAGGAGAATTGACAATCTGAACAAAAGAATGCAAGAT
GGATTTCTGGATGTTTGGACATACAATGCTGAACTGTTGGTTCTTCTTGAAAACGAAAGAAC
ACTAGACATGCATGACGCAAATGTGAAGAACCTACATGAAAAGGTCAAATCACAACTAAGG
GACAATGCTACGATCTTAGGGAATGGTTGCTTTGAATTTTGGCATAAGTGTGACAATGAATG
CATAGAGTCTGTCAAAAATGGTACATATGACTATCCCAAATACCAGACTGAAAGCAAATTAA
ACAGGCTAAAAATAGAATCAGTAAAGCTAGAGAACCTTGGTGTGTATCAAATTCTTGCCATT
TATAGTACGGTATCGAGCAGCCTAGTGTTGGTAGGGCTGATCATGGCAATGGGTCTTTGGA
TGTGTTCAAATGGTTCAATGCAGTGCAGGATATGTATATAAGAGCTCTAAGTTAAAATGCTT
CTTCGTCTCCTATTTATAATATGGTTTGTTATTGTTAATTTTGTTCTTGTAGAAGAGCTTAATT
AATCGTTGTTGTTATGAAATACTATTTGTATGAGATGAACTGGTGTAATGTAATTCATTTACA
TAAGTGGAGTCAGAATCAGAATGTTTCCTCCATAACTAACTAGACATGAAGACCTGCCGCG
TACAATTGTCTTATATTTGAACAACTAAAATTGAACATCTTTTGCCACAACTTTATAAGTGGTT
AATATAGCTCAAATATATGGTCAAGTTCAATAGATTAATAATGGAAATATCAGTTATCGAAAT
TCATTAACAATCAACTTAACGTTATTAACTACTAATTTTATATCATCCCCTTTGATAAATGATA
GTACA

Fig. 59

SEQ ID NO: 68
H9 from A/Hong Kong/1073/99 (H9N2) (Construct # 785)
AGAGGTACCCCGGGCTGGTATATTTATATGTTGTCAAATAACTCAAAAACCATAAAAGTTTAA
GTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAAT
TTTGTTGCAACATTTGAGAAAATTTTGTTGTTCTCTCTTTTCATTGGTCAAAAACAATAGAGAG
AGAAAAAGGAAGAGGGAGAATAAAAACATAATGTGAGTATGAGAGAGAAAGTTGTACAAAAG
TTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCA
AGTCATTAAAAAGAAAGAATAAATTATTTTTAAAATTAAAAGTTGAGTCATTTGATTAAACATG
TGATTATTTAATGAATTGATGAAAGAGTTGGATTAAAGTTGTATTAGTAATTAGAATTTGGTGT
CAAATTTAATTTGACATTTGATCTTTTCCTATATATTGCCCCATAGAGTCAGTTAACTCATTTT
TATATTTCATAGATCAAATAAGAGAAATAACGGTATATTAATCCCTCCAAAAAAAAAAAACGG
TATATTTACTAAAAAATCTAAGCCACGTAGGAGGATAACAGGATCCCCGTAGGAGGATAACA
TCCAATCCAACCAATCACAACAATCCTGATGAGATAACCCACTTTAAGCCCACGCATCTGTG
GCACATCTACATTATCTAAATCACACATTCTTCCACACATCTGAGCCACACAAAAACCAATCC
ACATCTTTATCACCCATTCTATAAAAAATCACACTTTGTGAGTCTACACTTTGATTCCCTTCAA
ACACATACAAAGAGAAGAGACTAATTAATTAATTAATCATCTTGAGAGAAAATGGAAACAATA
TCACTAATAACTATACTACTAGTAGTAACAGCAAGCAATGCAGATAAAATCTGCATCGGCCA
CCAGTCAACAAACTCCACAGAAACTGTGGACACGCTAACAGAAACCAATGTTCCTGTGACAC
ATGCCAAAGAATTGCTCCACACAGAGCATAATGGAATGCTGTGTGCAACAAGCCTGGGACA
TCCCCTCATTCTAGACACATGCACTATTGAAGGACTAGTCTATGGCAACCCTTCTTGTGACC
TGCTGTTGGGAGGAAGAGAATGGTCCTACATCGTCGAAAGATCATCAGCTGTAAATGGAAC
GTGTTACCCTGGGAATGTAGAAAACCTAGAGGAACTCAGGACACTTTTTAGTTCCGCTAGTT
CCTACCAAAGAATCCAAATCTTCCCAGACACAACCTGGAATGTGACTTACACTGGAACAAGC
AGAGCATGTTCAGGTTCATTCTACAGGAGTATGAGATGGCTGACTCAAAAGAGCGGTTTTTA
CCCTGTTCAAGACGCCCAATACACAAATAACAGGGGAAAGAGCATTCTTTTCGTGTGGGGC
ATACATCACCCACCCACCTATACCGAGCAAACAAATTTGTACATAAGAAACGACACAACAAC
AAGCGTGACAACAGAAGATTTGAATAGGACCTTCAAACCAGTGATAGGGCCAAGGCCCCTT
GTCAATGGTCTGCAGGGAAGAATTGATTATTATTGGTCGGTACTAAAACCAGGCCAAACATT
GCGAGTACGATCCAATGGGAATCTAATTGCTCCATGGTATGGACACGTTCTTTCAGGAGGG
AGCCATGGAAGAATCCTGAAGACTGATTTAAAAGGTGGTAATTGTGTAGTGCAATGTCAGAC
TGAAAAAGGTGGCTTAAACAGTACATTGCCATTCCACAATATCAGTAAATATGCATTTGGAAC
CTGCCCCAAATATGTAAGAGTTAATAGTCTCAAACTGGCAGTCGGTCTGAGGAACGTGCCT
GCTAGATCAAGTAGAGGACTATTTGGAGCCATAGCTGGATTCATAGAAGGAGGTTGGCCAG
GACTAGTCGCTGGCTGGTATGGTTTCCAGCATTCAAATGATCAAGGGGTTGGTATGGCTGC
AGATAGGGATTCAACTCAAAAGGCAATTGATAAAATAACATCCAAGGTGAATAATATAGTCGA
CAAGATGAACAAGCAATATGAAATAATTGATCATGAATTTAGTGAGGTTGAAACTAGACTCAA
TATGATCAATAATAAGATTGATGACCAAATACAAGACGTATGGGCATATAATGCAGAATTGCT
AGTACTACTTGAAAATCAAAAAACACTCGATGAGCATGATGCGAACGTGAACAATCTATATAA
CAAGGTGAAGAGGGCACTGGGCTCCAATGCTATGGAAGATGGGAAAGGCTGTTTCGAGCTA
TACCATAAATGTGATGATCAGTGCATGGAAACAATTCGGAACGGGACCTATAATAGGAGAAA
GTATAGAGAGGAATCAAGACTAGAAAGGCAGAAAATAGAGGGGGTTAAGCTGGAATCTGAG
GGAACTTACAAAATCCTCACCATTTATTCGACTGTCGCCTCATCTCTTGTGCTTGCAATGGG
GTTTGCTGCCTTCCTGTTCTGGGCCATGTCCAATGGATCTTGCAGATGCAACATTTGTATAT
AAGAGCTCTAAGTTAAAATGCTTCTTCGTCTCCTATTTATAATATGGTTTGTTATTGTTAATTT
TGTTCTTGTAGAAGAGCTTAATTAATCGTTGTTGTTATGAAATACTATTTGTATGAGATGAACT
GGTGTAATGTAATTCATTTACATAAGTGGAGTCAGAATCAGAATGTTTCCTCCATAACTAACT
AGACATGAAGACCTGCCGCGTACAATTGTCTTATATTTGAACAACTAAAATTGAACATCTTTT
GCCACAACTTTATAAGTGGTTAATATAGCTCAAATATATGGTCAAGTTCAATAGATTAATAAT
GGAAATATCAGTTATCGAAATTCATTAACAATCAACTTAACGTTATTAACTACTAATTTTATAT
CATCCCCTTTGATAAATGATAGTACA

Fig. 60

SEQ ID NO: 69
H3 from A/Brisbane/10/2007 (H3N2)
AGAGGTACCCCGGGCTGGTATATTTATATGTTGTCAAATAACTCAAAAACCATAAAAGTTTAAGT
TAGCAAGTGTGTACATTTTTACTTGAACAAAAATATTCACCTACTACTGTTATAAATCATTATTAA
ACATTAGAGTAAAGAAATATGGATGATAAGAACAAGAGTAGTGATATTTTGACAACAATTTTGTT
GCAACATTTGAGAAAATTTTGTTGTTCTCTCTTTTCATTGGTCAAAAACAATAGAGAGAGAAAAA
GGAAGAGGGAGAATAAAAACATAATGTGAGTATGAGAGAGAAAGTTGTACAAAAGTTGTACCAA
AATAGTTGTACAAATATCATTGAGGAATTTGACAAAAGCTACACAAATAAGGGTTAATTGCTGTA
AATAAATAAGGATGACGCATTAGAGAGATGTACCATTAGAGAATTTTTGGCAAGTCATTAAAAAG
AAAGAATAAATTATTTTTAAAATTAAAAGTTGAGTCATTTGATTAAACATGTGATTATTTAATGAAT
TGATGAAAGAGTTGGATTAAAGTTGTATTAGTAATTAGAATTTGGTGTCAAATTTAATTTGACATT
TGATCTTTTCCTATATATTGCCCCATAGAGTCAGTTAACTCATTTTTATATTTCATAGATCAAATA
AGAGAAATAACGGTATATTAATCCCTCCAAAAAAAAAAAACGGTATATTTACTAAAAAATCTAAG
CCACGTAGGAGGATAACAGGATCCCCGTAGGAGGATAACATCCAATCCAACCAATCACAACAA
TCCTGATGAGATAACCCACTTTAAGCCCACGCATCTGTGGCACATCTACATTATCTAAATCACA
CATTCTTCCACACATCTGAGCCACACAAAAACCAATCCACATCTTTATCACCCATTCTATAAAAA
ATCACACTTTGTGAGTCTACACTTTGATTCCCTTCAAACACATACAAAGAGAAGAGACTAATTAA
TTAATTAATCATCTTGAGAGAAAATGAAGACTATCATTGCTTTGAGCTACATTCTATGTCTGGTT
TTCACTCAAAAACTTCCCGGAAATGACAACAGCACGGCAACGCTGTGCCTTGGGCACCATGCA
GTACCAAACGGAACGATAGTGAAAACAATCACGAATGACCAAATTGAAGTTACTAATGCTACTG
AGCTGGTTCAGAGTTCCTCAACAGGTGAAATATGCGACAGTCCTCATCAGATCCTTGATGGAG
AAAACTGCACACTAATAGATGCTCTATTGGGAGACCCTCAGTGTGATGGCTTCCAAAATAAGAA
ATGGGACCTTTTTGTTGAACGCAGCAAAGCCTACAGCAACTGTTACCCTTATGATGTGCCGGAT
TATGCCTCCCTTAGGTCACTAGTTGCCTCATCCGGCACACTGGAGTTTAACAATGAAAGTTTCA
ATTGGACTGGAGTCACTCAAAACGGAACAAGCTCTGCTTGCATAAGGAGATCTAATAACAGTTT
CTTTAGTAGATTGAATTGGTTGACCCACTTAAAATTCAAATACCCAGCATTGAACGTGACTATGC
CAAACAATGAAAAATTTGACAAATTGTACATTTGGGGGGTTCACCACCCGGGTACGGACAATGA
CCAAATCTTCCTGTATGCTCAAGCATCAGGAAGAATCACAGTCTCTACCAAAAGAAGCCAACAA
ACTGTAATCCCGAATATCGGATCTAGACCCAGAGTAAGGAATATCCCCAGCAGAATAAGCATCT
ATTGGACAATAGTAAAACCGGGAGACATACTTTTGATTAACAGCACAGGGAATCTAATTGCTCC
TAGGGGTTACTTCAAAATACGAAGTGGGAAAAGCTCAATAATGAGATCAGATGCACCCATTGG
CAAATGCAATTCTGAATGCATCACTCCAAACGGAAGCATTCCCAATGACAAACCATTCCAAAAT
GTAAACAGGATCACATACGGGGCCTGTCCCAGATATGTTAAGCAAAACACTCTGAAATTGGCA
ACAGGGATGCGAAATGTACCAGAGAAACAAACTAGAGGCATATTTGGCGCAATCGCGGGTTTC
ATAGAAAATGGTTGGGAGGGAATGGTGGATGGTTGGTATGGTTTCAGGCATCAAAATTCTGAG
GGAATAGGACAAGCAGCAGATCTCAAAAGCACTCAAGCAGCAATCGATCAAATCAATGGGAAG
CTGAATAGGTTGATCGGGAAAACCAACGAGAAATTCCATCAGATTGAAAAAGAGTTCTCAGAAG
TCGAAGGGAGAATCCAGGACCTTGAGAAATATGTTGAGGACACCAAAATAGATCTCTGGTCAT
ACAACGCGGAGCTTCTTGTTGCCCTGGAGAACCAACATACAATTGATCTAACTGACTCAGAAAT
GAACAAACTGTTTGAAAAAACAAAGAAGCAACTGAGGGAAAATGCTGAGGATATGGGCAATGG
TTGTTTCAAAATATACCACAAATGTGACAATGCCTGCATAGGATCAATCAGAAATGGAACTTATG
ACCACGATGTATACAGAGATGAAGCATTAAACAACCGGTTCCAGATCAAGGGCGTTGAGCTGA
AGTCAGGATACAAAGATTGGATACTATGGATTTCCTTTGCCATATCATGTTTTTTGCTTTGTGTT
GCTTTGTTGGGGTTCATCATGTGGGCCTGCCAAAAAGGCAACATTAGGTGCAACATTTGCATTT
GAGAGCTCTAAGTTAAAATGCTTCTTCGTCTCCTATTTATAATATGGTTTGTTATTGTTAATTTTG
TTCTTGTAGAAGAGCTTAATTAATCGTTGTTGTTATGAAATACTATTTGTATGAGATGAACTGGT
GTAATGTAATTCATTTACATAAGTGGAGTCAGAATCAGAATGTTTCCTCCATAACTAACTAGACA
TGAAGACCTGCCGCGTACAATTGTCTTATATTTGAACAACTAAAATTGAACATCTTTTGCCACAA
CTTTATAAGTGGTTAATATAGCTCAAATATATGGTCAAGTTCAATAGATTAATAATGGAAATATCA
GTTATCGAAATTCATTAACAATCAACTTAACGTTATTAACTACTAATTTTATATCATCCCCTTTGA
TAAATGATAGTACA

Fig. 61

SEQ ID NO: 70
H3 from A/Wisconsin/67/2005 (H3N2)
AGAGGTACCCCGGGCTGGTATATTTATATGTTGTCAAATAACTCAAAAACCATAAAAGTTTAA
GTTAGCAAGTGTGTACATTTTTACTTGAACAAAAATATTCACCTACTACTGTTATAAATCATTA
TTAAACATTAGAGTAAAGAAATATGGATGATAAGAACAAGAGTAGTGATATTTTGACAACAAT
TTTGTTGCAACATTTGAGAAAATTTTGTTGTTCTCTCTTTTCATTGGTCAAAAACAATAGAGAG
AGAAAAAGGAAGAGGGAGAATAAAAACATAATGTGAGTATGAGAGAGAAAGTTGTACAAAAG
TTGTACCAAAATAGTTGTACAAATATCATTGAGGAATTTGACAAAAGCTACACAAATAAGGGT
TAATTGCTGTAAATAAATAAGGATGACGCATTAGAGAGATGTACCATTAGAGAATTTTTGGCA
AGTCATTAAAAAGAAAGAATAAATTATTTTTAAAATTAAAAGTTGAGTCATTTGATTAAACATGT
GATTATTTAATGAATTGATGAAAGAGTTGGATTAAAGTTGTATTAGTAATTAGAATTTGGTGTC
AAATTTAATTTGACATTTGATCTTTTCCTATATATTGCCCCATAGAGTCAGTTAACTCATTTTTA
TATTTCATAGATCAAATAAGAGAAATAACGGTATATTAATCCCTCCAAAAAAAAAAAACGGTAT
ATTTACTAAAAAATCTAAGCCACGTAGGAGGATAACAGGATCCCCGTAGGAGGATAACATCC
AATCCAACCAATCACAACAATCCTGATGAGATAACCCACTTTAAGCCCACGCATCTGTGGCA
CATCTACATTATCTAAATCACACATTCTTCCACACATCTGAGCCACACAAAAACCAATCCACA
TCTTTATCACCCATTCTATAAAAAATCACACTTTGTGAGTCTACACTTTGATTCCCTTCAAACA
CATACAAAGAGAAGAGACTAATTAATTAATTAATCATCTTGAGAGAAAATGAAGACTATCATT
GCTTTGAGCTACATTCTATGTCTGGTTTTCACTCAAAAACTTCCCGGAAATGACAACAGCAC
GGCAACGCTGTGCCTTGGGCACCATGCAGTACCAAACGGAACGATAGTGAAAACAATCACG
AATGACCAAATTGAAGTTACTAATGCTACTGAGCTGGTTCAGAGTTCCTCAACAGGTGGAAT
ATGCGACAGTCCTCATCAGATCCTTGATGGAGAAAACTGCACACTAATAGATGCTCTATTGG
GAGACCCTCAGTGTGATGGCTTCCAAAATAAGAAATGGGACCTTTTTGTTAACGCAGCAAA
GCCTACAGCAACTGTTACCCTTATGATGTGCCGGATTATGCCTCCCTTAGGTCACTAGTTGC
CTCATCCGGCACACTGGAGTTTAACGATGAAAGTTTCAATTGGACTGGAGTCACTCAAAATG
GAACAAGCTCTGCTTGCAAAAGGAGATCTAATAACAGTTTCTTTAGTAGATTGAATTGGTTGA
CCCACTTAAAATTCAAATACCCAGCATTGAACGTGACTATGCCAAACAATGAAAAATTTGACA
AATTGTACATTTGGGGGGTTCACCACCCGGGTACGGACAATGACCAAATCTTCCTGCATGCT
CAAGCATCAGGAAGAATCACAGTCTCTACCAAAAGAAGCCAACAAACTGTAATCCCGAATAT
CGGATCTAGACCCAGAATAAGGAATATCCCCAGCAGAATAAGCATCTATTGGACAATAGTAA
AACCGGGAGACATACTTTTGATTAACAGCACAGGGAATCTAATTGCTCCTAGGGGTTACTTC
AAAATACGAAGTGGGAAAAGCTCAATAATGAGATCAGATGCACCCATTGGCAAATGCAATTC
TGAATGCATCACTCCAAATGGAAGCATTCCCAATGACAAACCATTTCAAAATGTAAACAGGAT
CACATATGGGGCCTGTCCCAGATATGTTAAGCAAAACACTCTGAAATTGGCAACAGGGATGC
GAAATGTACCAGAGAAACAAACTAGAGGCATATTTGGCGCAATCGCGGGTTTCATAGAAAAT
GGTTGGGAGGGAATGGTGGATGGTTGGTACGGTTTCAGGCATCAAAATTCTGAGGGAATAG
GACAAGCAGCAGATCTCAAAAGCACTCAAGCAGCAATCAATCAAATCAATGGGAAGCTGAAT
AGGTTGATCGGGAAAACCAACGAGAAATTCCATCAGATTGAAAAAGAGTTCTCAGAAGTAGA
AGGGAGAATCCAGGACCTCGAGAAATATGTTGAGGACACTAAAATAGATCTCTGGTCATACA
ACGCGGAGCTTCTTGTTGCCCTGGAGAACCAACATACAATTGATCTAACTGACTCAGAAATG
AACAAACTGTTTGAAAAGAACAAAGAAGCAACTGAGGGAAAATGCTGAGGATATGGGCAATGG
TTGTTTCAAAATATACCACAAATGTGACAATGCCTGCATAGGATCAATCAGAAATGGAACTTA
TGACCATGATGTATACAGAGATGAAGCATTAAACAACCGGTTCCAGATCAAAGGCGTTGAGC
TGAAGTCAGGATACAAAGATTGGATACTATGGATTTCCTTTGCCATATCATGTTTTTTGCTTT
GTGTTGCTTTGTTGGGGTTCATCATGTGGGCCTGCCAAAAAGGCAACATTAGGTGCAACATT
TGCATTTGAGAGCTCTAAGTTAAAATGCTTCTTCGTCTCCTATTTATAATATGGTTTGTTATTG
TTAATTTTGTTCTTGTAGAAGAGCTTAATTAATCGTTGTTGTTATGAAATACTATTTGTATGAG
ATGAACTGGTGTAATGTAATTCATTTACATAAGTGGAGTCAGAATCAGAATGTTTCCTCCATA
ACTAACTAGACATGAAGACCTGCCGCGTACAATTGTCTTATATTTGAACAACTAAAATTGAAC
ATCTTTTGCCACAACTTTATAAGTGGTTAATATAGCTCAAATATATGGTCAAGTTCAATAGATT
AATAATGGAAATATCAGTTATCGAAATTCATTAACAATCAACTTAACGTTATTAACTACTAATTT
TATATCATCCCCTTTGATAAATGATAGTACA

Fig. 62

SEQ ID NO: 71
H7 from A/Equine/Prague/56 (H7N7)
AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATT
AAACATTAGAGTAAAGAAATATGGATGATAAGAACAAGAGTAGTGATATTTTGACAACAATTTT
GTTGCAACATTTGAGAAAATTTTGTTGTTCTCTCTTTTCATTGGTCAAAAACAATAGAGAGAGA
AAAAGGAAGAGGGAGAATAAAAACATAATGTGAGTATGAGAGAGAAAGTTGTACAAAAGTTGT
ACCAAAATAGTTGTACAAATATCATTGAGGAATTTGACAAAAGCTACACAAATAAGGGTTAATT
GCTGTAAATAAATAAGGATGACGCATTAGAGAGATGTACCATTAGAGAATTTTTGGCAAGTCA
TTAAAAAGAAAGAATAAATTATTTTTAAAATTAAAAGTTGAGTCATTTGATTAAACATGTGATTAT
TTAATGAATTGATGAAAGAGTTGGATTAAAGTTGTATTAGTAATTAGAATTTGGTGTCAAATTTA
ATTTGACATTTGATCTTTTCCTATATATTGCCCCATAGAGTCAGTTAACTCATTTTTATATTTCA
TAGATCAAATAAGAGAAATAACGGTATATTAATCCCTCCAAAAAAAAAAAACGGTATATTTACT
AAAAAATCTAAGCCACGTAGGAGGATAACAGGATCCCCGTAGGAGGATAACATCCAATCCAA
CCAATCACAACAATCCTGATGAGATAACCCACTTTAAGCCCACGCATCTGTGGCACATCTACA
TTATCTAAATCACACATTCTTCCACACATCTGAGCCACACAAAAACCAATCCACATCTTTATCA
CCCATTCTATAAAAAATCACACTTTGTGAGTCTACACTTTGATTCCCTTCAAACACATACAAAG
AGAAGAGACTAATTAATTAATTAATCATCTTGAGAGAAAATGAACACTCAAATTCTAATATTAG
CCACTTCGGCATTCTTCTATGTACGTGCAGATAAAATCTGCCTAGGACATCATGCTGTGTCTA
ATGGAACCAAAGTAGACACCCTTACTGAAAAAGGAATAGAAGTTGTCAATGCAACAGAAACAG
TTGAACAAACAAACATCCCTAAGATCTGCTCAAAAGGAAAACAGACTGTTGACCTTGGTCAAT
GTGGATTACTAGGGACCGTTATTGGTCCTCCCAATGTGACCAATTTCTTGAGTTCTCTGCTA
ATTTAATAGTTGAAAGAAGGGAAGGTAATGACATTTGTTATCCAGGCAAATTTGACAATGAAGA
AACATTGAGAAAAATACTCAGAAAATCCGGAGGAATTAAAAAGGAGAATATGGGATTCACATA
TACCGGAGTGAGAACCAATGGAGAGACTAGCGCATGTAGAAGGTCAAGATCTTCCTTTTATG
CAGAGATGAAATGGCTTCTATCCAGCACAGACAATGGGACATTTCCACAAATGACAAAGTCCT
ACAAGAACACTAAGAAGGTACCAGCTCTGATAATCTGGGGAATCCACCACTCAGGATCAACT
ACTGAACAGACTAGATTATATGGAAGTGGGAATAAATTGATAACAGTTTGGAGTTCCAAATAC
CAACAATCTTTTGTCCCAAATCCTGGACCAAGACCGCAAATGAATGGTCAATCAGGAAGAATT
GACTTTCACTGGCTGATGCTAGATCCCAATGATACTGTCACTTTCAGTTTTAATGGGGCCTTT
ATAGCACCTGACCGCGCCAGTTTTCTAAGAGGTAAATCTCTAGGAATCCAAAGTGATGCACAA
CTTGACAATAATTGTGAAGGTGAATGCTATCATATTGGAGGTACTATAATTAGCAACTTGCCCT
TTCAAAACATTAATAGTAGGGCAATCGGAAAATGCCCCAGATACGTGAAGCAGAAGAGCTTAA
TGCTAGCAACAGGAATGAAAAATGTTCCTGAAGCTCCTGCACATAAACAACTAACTCATCACA
TGCGCAAAAAAGAGGTTTATTTGGTGCAATAGCAGGATTCATTGAAAATGGGTGGGAAGGAT
TAATAGACGGATGGTATGGATATAAGCATCAGAATGCACAAGGAGAAGGGACTGCTGCAGAC
TACAAAAGTACACAATCTGCTATCAACCAAATAACCGGAAAATTGAACAGACTAATAGAAAAAA
CCAACCAGCAATTCGAACTAATAGATAATGAGTTCAATGAAATAGAAAAACAAATTGGCAATGT
TATTAACTGGACTAGAGATTCTATCATCGAAGTATGGTCATATAATGCAGAGTTCCTCGTAGC
AGTGGAGAATCAACACACTATTGATTTAACTGACTCAGAAATGAACAAACTATATGAAAAGGTA
AGAAGACAACTGAGAGAAAATGCTGAGGAAGATGGTAATGGCTGTTTTGAAATATTCCACCAA
TGTGACAATGATTGCATGGCCAGCATTAGAAACAACACATATGACCATAAAAAATACAGAAAA
GAGGCAATACAAAACAGAATCCAGATTGACGCAGTAAAGTTGAGCAGTGGTTACAAAGATATA
ATACTTTGGTTTAGCTTCGGGGCATCATGTTTCTTATTTCTTGCCATTGCAATGGGTCTTGTTT
TCATATGTATAAAAAATGGAAACATGCGGTGCACTATTTGTATATAAGAGCTCTAAGTTAAAAT
GCTTCTTCGTCTCCTATTTATAATATGGTTTGTTATTGTTAATTTTGTTCTTGTAGAAGAGCTTA
ATTAATCGTTGTTGTTATGAAATACTATTTGTATGAGATGAACTGGTGTAATGTAATTCATTTAC
ATAAGTGGAGTCAGAATCAGAATGTTTCCTCCATAACTAACTAGACATGAAGACCTGCCGCGT
ACAATTGTCTTATATTTGAACAACTAAAATTGAACATCTTTTGCCACAACTTTATAAGTGGTTAA
TATAGCTCAAATATATGGTCAAGTTCAATAGATTAATAATGGAAATATCAGTTATCGAAATTCAT
TAACAATCAACTTAACGTTATTAACTACTAATTTTATATCATCCCCTTTGATAAATGATAGTACA

Fig. 63

SEQ ID NO: 72
HA from B/Malaysia/2506/2004
AGAGGTACCCCGGGCTGGTATATTTATATGTTGTCAAATAACTCAAAAACCATAAAAGTTTAAG
TTAGCAAGTGTGTACATTTTTACTTGAACAAAAATATTCACCTACTACTGTTATAAATCATTATTA
AACATTAGAGTAAAGAAATATGGATGATAAGAACAAGAGTAGTGATATTTTGACAACAATTTTGT
TGCAACATTTGAGAAAATTTTGTTGTTCTCTCTTTTCATTGGTCAAAAACAATAGAGAGAGAAAA
AGGAAGAGGGAGAATAAAAACATAATGTGAGTATGAGAGAGAAAGTTGTACAAAAGTTGTACC
AAAATAGTTGTACAAATATCATTGAGGAATTTGACAAAAGCTACACAAATAAGGGTTAATTGCTG
TAAATAAATAAGGATGACGCATTAGAGAGATGTACCATTAGAGAATTTTTGGCAAGTCATTAAA
AAGAAAGAATAAATTATTTTTAAAATTAAAAGTTGAGTCATTTGATTAAACATGTGATTATTTAAT
GAATTGATGAAAGAGTTGGATTAAAGTTGTATTAGTAATTAGAATTTGGTGTCAAATTTAATTTG
ACATTTGATCTTTTCCTATATATTGCCCCATAGAGTCAGTTAACTCATTTTTATATTTCATAGATC
AAATAAGAGAAATAACGGTATATTAATCCCTCCAAAAAAAAAAAAACGGTATATTTACTAAAAAAT
CTAAGCCACGTAGGAGGATAACAGGATCCCCGTAGGAGGATAACATCCAATCCAACCAATCAC
AACAATCCTGATGAGATAACCCACTTTAAGCCCACGCATCTGTGGCACATCTACATTATCTAAA
TCACACATTCTTCCACACATCTGAGCCACACAAAAACCAATCCACATCTTTATCACCCATTCTAT
AAAAAATCACACTTTGTGAGTCTACACTTTGATTCCCTTCAAACACATACAAAGAGAAGAGACT
AATTAATTAATTAATCATCTTGAGAGAAAATGAAGGCAATAATTGTACTACTCATGGTAGTAACA
TCCAATGCAGATCGAATCTGCACTGGGATAACATCGTCAAACTCACCACATGTTGTCAAAACTG
CTACTCAAGGGGAGGTCAATGTGACTGGTGTAATACCACTGACAACAACACCCACCAAATCTC
ATTTTGCAAATCTCAAAGGAACAGAAACCAGAGGGAAACTATGCCCAAAATGCCTCAACTGCA
CAGATCTGGACGTGGCCTTGGGCAGACCAAAATGCACGGGGAACATACCCTCGGCAAGAGTT
TCAATACTCCATGAAGTCAGACCTGTTACATCTGGGTGCTTTCCTATAATGCACGACAGAACAA
AAATTAGACAGCTGCCTAAACTTCTCAGAGGATACGAACATATCAGGTTATCAACTCATAACGT
TATCAATGCAGAAAATGCACCAGGAGGACCCTACAAAATTGGAACCTCAGGGTCTTGCCCTAA
CGTTACCAATGGAAACGGATTTTTCGCAACAATGGCTTGGGCCGTCCCAAAAAACGACAACAA
CAAAACAGCAACAAATTCATTAACAATAGAAGTACCATACATTTGTACAGAAGGAGAAGACCAA
ATTACCGTTTGGGGGTTCCACTCTGATAACGAAACCCAAATGGCAAAGCTCTATGGGGACTCA
AAGCCCCAGAAGTTCACCTCATCTGCCAACGGAGTGACCACACATTACGTTTCACAGATTGGT
GGCTTCCCAAATCAAACAGAAGACGGAGGACTACCACAAAGCGGTAGAATTGTTGTTGATTAC
ATGGTGCAAAAATCTGGGAAAACAGGAACAATTACCTATCAAAGAGGTATTTTATTGCCTCAAA
AAGTGTGGTGCGCAAGTGGCAGGAGCAAGGTAATAAAAGGATCGTTGCCTTTAATTGGAGAAG
CAGATTGCCTCCACGAAAAATACGGTGGATTAAACAAAAGCAAGCCTTACTACACAGGGGAAC
ATGCAAAGGCCATAGGAAATTGCCCAATATGGGTGAAAACACCCTTGAAGCTGGCCAATGGAA
CCAAATATAGACCTCCTGCAAAACTATTAAAGGAAAGGGGTTTCTTCGGAGCTATTGCTGGTTT
CTTAGAAGGAGGATGGGAAGGAATGATTGCAGGTTGGCACGGATACACATCCCATGGGGCAC
ATGGAGTAGCGGTGGCAGCAGACCTTAAGAGCACTCAAGAGGCCATAAACAAGATAACAAAAA
ATCTCAACTCTTTGAGTGAGCTGGAAGTAAAGAATCTTCAAAGACTAAGCGGTGCCATGGATG
AACTCCACAACGAAATACTAGAACTAGACGAGAAAGTGGATGATCTCAGAGCTGATACAATAA
GCTCACAAATAGAACTCGCAGTCCTGCTTTCCAATGAAGGAATAATAAACAGTGAAGATGAGC
ATCTCTTGGCGCTTGAAAGAAAGCTGAAGAAAATGCTGGGCCCCTCTGCTGTAGAGATAGGGA
ATGGATGCTTTGAAACCAAACACAAGTGCAACCAGACCTGTCTCGACAGAATAGCTGCTGGTA
CCTTTGATGCAGGAGAATTTTCTCTCCCCACTTTTGATTCACTGAATATTACTGCTGCATCTTTA
AATGACGATGGATTGGATAATCATACTATACTGCTTTACTACTCAACTGCTGCCTCCAGTTTGG
CTGTAACATTGATGATAGCTATCTTTGTTGTTTATATGGTCTCCAGAGACAATGTTTCTTGCTCC
ATCTGTCTATAAGAGCTCTAAGTTAAAATGCTTCTTCGTCTCCTATTTATAATATGGTTTGTTATT
GTTAATTTTGTTCTTGTAGAAGAGCTTAATTAATCGTTGTTGTTATGAAATACTATTTGTATGAGA
TGAACTGGTGTAATGTAATTCATTTACATAAGTGGAGTCAGAATCAGAATGTTTCCTCCATAACT
AACTAGACATGAAGACCTGCCGCGTACAATTGTCTTATATTTGAACAACTAAAATTGAACATCTT
TTGCCACAACTTTATAAGTGGTTAATATAGCTCAAATATATGGTCAAGTTCAATAGATTAATAAT
GGAAATATCAGTTATCGAAATTCATTAACAATCAACTTAACGTTATTAACTACTAATTTTATATCA
TCCCCTTTGATAAATGATAGTACA

Fig. 64

SEQ ID NO: 73
HA from B/Florida/4/2006
AGAGGTACCCCGGGCTGGTATATTTATATGTTGTCAAATAACTCAAAAACCATAAAAGTTTAAGT
TAGCAAGTGTGTACATTTTTACTTGAACAAAAATATTCACCTACTACTGTTATAAATCATTATTAA
ACATTAGAGTAAAGAAATATGGATGATAAGAACAAGAGTAGTGATATTTTGACAACAATTTTGTT
GCAACATTTGAGAAAATTTTGTTGTTCTCTCTTTTCATTGGTCAAAAACAATAGAGAGAGAAAAA
GGAAGAGGGAGAATAAAAACATAATGTGAGTATGAGAGAGAAAGTTGTACAAAAGTTGTACCAA
AATAGTTGTACAAATATCATTGAGGAATTTGACAAAAGCTACACAAATAAGGGTTAATTGCTGTA
AATAAATAAGGATGACGCATTAGAGAGATGTACCATTAGAGAATTTTTGGCAAGTCATTAAAAAG
AAAGAATAAATTATTTTTAAAATTAAAAGTTGAGTCATTTGATTAAACATGTGATTATTTAATGAAT
TGATGAAAGAGTTGGATTAAAGTTGTATTAGTAATTAGAATTTGGTGTCAAATTTAATTTGACATT
TGATCTTTTCCTATATATTGCCCCATAGAGTCAGTTAACTCATTTTTATATTTCATAGATCAAATA
AGAGAAATAACGGTATATTAATCCCTCCAAAAAAAAAAAACGGTATATTTACTAAAAAATCTAAG
CCACGTAGGAGGATAACAGGATCCCCGTAGGAGGATAACATCCAATCCAACCAATCACAACAA
TCCTGATGAGATAACCCACTTTAAGCCCACGCATCTGTGGCACATCTACATTATCTAAATCACA
CATTCTTCCACACATCTGAGCCACACAAAAACCAATCCACATCTTTATCACCCATTCTATAAAAA
ATCACACTTTGTGAGTCTACACTTTGATTCCCTTCAAACACATACAAAGAGAAGAGACTAATTAA
TTAATTAATCATCTTGAGAGAAAATGAAGGCAATAATTGTACTACTCATGGTAGTAACATCCAAT
GCAGATCGAATCTGCACTGGAATAACATCTTCAAACTCACCTCATGTGGTCAAAACAGCCACTC
AAGGGGAGGTCAATGTGACTGGTGTGATACCACTAACAACAACACCAACAAAATCTTATTTTGC
AAATCTCAAAGGAACAAGGACCAGAGGGAAACTATGCCCAGACTGTCTCAACTGCACAGATCT
GGATGTGGCTTTGGGCAGACCAATGTGTGTGGGACCACACCTTCGGCGAAGGCTTCAATAC
TCCACGAAGTCAAACCTGTTACATCCGGGTGCTTTCCTATAATGCACGACAGAACAAAAATCAG
GCAACTACCCAATCTTCTCAGAGGATATGAAAATATCAGGCTATCAACCCAAAACGTCATCGAT
GCGGAAAAGGCACCAGGAGGACCCTACAGACTTGGAACCTCAGGATCTTGCCCTAACGCTAC
CAGTAAGAGCGGATTTTTCGCAACAATGGCTTGGGCTGTCCCAAAGGACAACAACAAAAATGC
AACGAACCCACTAACAGTAGAAGTACCATACATTTGTACAGAAGGGGAAGACCAAATCACTGTT
TGGGGGTTCCATTCAGATAACAAAACCCAAATGAAGAACCTCTATGGAGACTCAAATCCTCAAA
AGTTCACCTCATCTGCTAATGGAGTAACCACACACTATGTTTCTCAGATTGGCAGCTTCCCAGA
TCAAACAGAAGACGGAGGACTACCACAAAGCGGCAGGATTGTTGTTGATTACATGATGCAAAA
ACCTGGGAAAACAGGAACAATTGTCTACCAAAGAGGTGTTTTGTTGCCTCAAAAGGTGTGGTG
CGCGAGTGGCAGGAGCAAAGTAATAAAAGGGTCCTTGCCTTTAATTGGTGAAGCAGATTGCCT
TCATGAAAAATACGGTGGATTAAACAAAAGCAAGCCTTACTACACAGGAGAACATGCAAAAGCC
ATAGGAAATTGCCCAATATGGGTGAAAACACCTTTGAAGCTCGCCAATGGAACCAAATATAGAC
CTCCTGCAAAACTATTAAAGGAAAGGGGTTTCTTCGGAGCTATTGCTGGTTTCCTAGAAGGAG
GATGGGAAGGAATGATTGCAGGCTGGCACGGATACACATCTCACGGAGCACATGGAGTGGCA
GTGGCGGCGGACCTTAAGAGTACGCAAGAAGCTATAAACAAGATAACAAAAAATCTCAATTCTT
TGAGTGAGCTAGAAGTAAAGAATCTTCAAAGACTAAGTGGTGCCATGGATGAACTCCACAACG
AAATACTCGAGCTGGATGAGAAAGTGGATGATCTCAGAGCTGACACTATAAGCTCGCAAATAG
AACTTGCAGTCTTGCTTTCCAACGAAGGAATAATAAACAGTGAAGATGAGCATCTATTGGCACT
TGAGAGAAAACTAAAGAAAATGCTGGGTCCCTCTGCTGTAGAGATAGGAAATGGATGCTTCGA
AACCAAACACAAGTGCAACCAGACCTGCTTAGACAGGATAGCTGCTGGCACCTTTAATGCAGG
AGAATTTTCTCTCCCCACTTTTGATTCACTGAACATTACTGCTGCATCTTTAAATGATGATGGAT
TGGATAACCATACTATACTGCTCTATTACTCAACTGCTGCTTCTAGTTTGGCTGTAACATTGATG
CTAGCTATTTTTATTGTTTATATGGTCTCCAGAGACAACGTTTCATGCTCCATCTGTCTATAAGA
GCTCTAAGTTAAAATGCTTCTTCGTCTCCTATTTATAATATGGTTTGTTATTGTTAATTTTGTTCT
TGTAGAAGAGCTTAATTAATCGTTGTTGTTATGAAATACTATTTGTATGAGATGAACTGGTGTAA
TGTAATTCATTTACATAAGTGGAGTCAGAATCAGAATGTTTCCTCCATAACTAACTAGACATGAA
GACCTGCCGCGTACAATTGTCTTATATTTGAACAACTAAAATTGAACATCTTTTGCCACAACTTT
ATAAGTGGTTAATATAGCTCAAATATATGGTCAAGTTCAATAGATTAATAATGGAAATATCAGTTA
TCGAAATTCATTAACAATCAACTTAACGTTATTAACTACTAATTTTATATCATCCCCTTTGATAAA
TGATAGTACA

Fig. 65

Consensus of SEQ ID NO: 49, 48, 33 and 9

SEQ ID NO: 74
MK($X_1$)KLLVLLCTFTATYADTICIGYHANNSTDTVDTVLEKNVTVTHSVNLL
E($X_2$)SHNGKLCLLKGIAPLQLGNCSVAGWILGNPECELLIS($X_3$)ESWSYIVE($X_4$)P
NPENGTCYPG($X_5$)FADYEELREQLSSVSSFERFEIFPKESSWPNHT($X_6$)TGVSA
SCSHNG($X_7$)SSFY($X_8$)NLLWLTGKNGLYPNLSKSY($X_9$)NNKEKEVLVLWGVHHPPN
IG($X_{10}$)Q ($X_{11}$)ALYH($X_{12}$)ENAYVSVVSSHYSR($X_{13}$)FTPEIAKRPKVRDQEGRINYYWTLL
EPGDTIIFEANGNLIAP($X_{14}$)YAFALSRGFGSGII($X_{15}$)SNAPMD($X_{16}$)CDAKCQTPQG
AINSSLPFQNVHPVTIGECPKYVRSAKLRMVTGLRNIPSIQSRGLFGAIA
GFIEGGWTGMVDGWYGYHHQNEQGSGYAADQKSTQNAINGITNKVNSVIE
KMNTQFTAVGKEFNKLERRMENLNKKVDDGF($X_{17}$)DIWTYNAELLVLLENERT
LDFHDSNVKNLYEKVKSQLKNNAKEIGNGCFEFYHKCN($X_{18}$)ECMESVKNGTY
DYPKYSEESKLNREKIDGVKLESMGVYQILAIYSTVASSLVLLVSLGAIS
FWMCSNGSLQCRICI

Fig. 66

SEQ ID NO: 75

MKAKLLVLLCTFTATYADTICIGYHANNSTDTVDTVLEKNVTVTHSVNLLEDSHNGKLCLLKGIA
PLQLGNCSVAGWILGNPECELLISKESWSYIVETPNPENGTCYPGYFADYEELREQLSSVSSFERFEIF
PKESSWPNHTVTGVSASCSHNGKSSFYRNLLWLTGKNGLYPNLSKSYVNNKEKEVLVLWGVHHPPNI
GNQRALYHTENAYVSVVSSHYSRRFTPEIAKRPKVRDQEGRINYYWTLLEPGDTIIFEANGNLIAPWYAFALS
RGFGSGIITSNAPMDECDAKCQTPQGAINSSLPFQNVHPVTIGECPKYVRSAKLRMVTGLRNIPSIQSRG
LFGAIAGFIEGGWTGMVDGWYGYHHQNEQGSGYAADQKSTQNAINGITNKVNSVIEKMNTQFTAVGK
EFNKLERRMENLNKKVDDGFLDIWTYNAELLVLLENERTLDFHDSNVKNLYEKVKSQLKNNAKEIGNGCFEF
YHKCNNECMESVKNGTYDYPKYSEESKLNREKIDGVKLESMGVYQILAIYSTVASSLVLLVSLGAISFWMC
SNGSLQCRICI

Fig. 67

SEQ ID NO: 76

MSLLTEVETYVLSIIPSGPLKAEIAQRLEDVFAGKNTDLEVLMEWLKTRPILSPLTKGILGFVFTLTVPS
ERGLQRRRFVQNALNGNGDPNNMDKAVKLYRKLKREITFHGAKEISLSYSAGALASCMGLIYNRMGAV
TTEVAFGLVCATCEQIADSQHRSHRQMVTTTNPLIRHENRMVLASTTAKAMEQMAGSSEQAAEAMEVAS
QARQMVQAMRTIGTHPSSSAGLKNDLLENLQAYQKRMGVQMQRFK

INFLUENZA VIRUS-LIKE PARTICLES (VLPS) COMPRISING HEMAGGLUTININ PRODUCED WITHIN A PLANT

CROSS REFERENCE TO RELATED APPLICATIONS

This is a divisional application of U.S. application Ser. No. 12/669,033, filed Jun. 11, 2010, which was a national phase application of PCT/CA2008/001281, filed Jul. 11, 2008, which claims priority to U.S. Provisional Application No. 60/959,414, filed Jul. 13, 2007, U.S. Provisional Application No. 60/990,603, filed Nov. 27, 2007, U.S. Provisional Application No. 61/013,272, filed Dec. 12, 2007, U.S. Provisional Application No. 61/022,775, filed Jan. 22, 2008 and Canadian Application No. 2,615,372, filed Jan. 21, 2008, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 267342000910SeqList.txt, date recorded: Jan. 3, 2013, size: 216 KB).

FIELD OF INVENTION

The present invention relates to the production of virus-like particles. More specifically, the present invention is directed to the production of virus-like particles comprising influenza antigens.

BACKGROUND OF THE INVENTION

Influenza is the leading cause of death in humans due to a respiratory virus. Common symptoms include fever, sore throat, shortness of breath, and muscle soreness, among others. During flu season, influenza viruses infect 10-20% of the population worldwide, leading to 250-500,000 deaths annually Influenza viruses are enveloped virus that bud from the plasma membrane of infected mammalian cells. They are classified into types A, B, or C, based on the nucleoproteins and matrix protein antigens present. Influenza type A viruses may be further divided into subtypes according to the combination of hemagglutinin (HA) and neuraminidase (NA) surface glycoproteins presented. HA governs the ability of the virus to bind to and penetrate the host cell. NA removes terminal sialic acid residues from glycan chains on host cell and viral surface proteins, which prevents viral aggregation and facilitates virus mobility. Currently, 16 HA (H1-H16) and 9 NA (N1-N9) subtypes are recognized. Each type A influenza virus presents one type of HA and one type of NA glycoprotein. Generally, each subtype exhibits species specificity; for example, all HA and NA subtypes are known to infect birds, while only subtypes H1, H2, H3, H5, H7, H9, H10, N1, N2, N3 and N7 have been shown to infect humans (Horimoto 2006; Suzuki 2005). Influenza viruses comprising H5, H7 and H9 are considered the most highly pathogenic forms of influenza A viruses, and are most likely to cause future pandemics.

Influenza pandemics are usually caused by highly transmittable and virulent influenza viruses, and can lead to elevated levels of illness and death globally. The emergence of new influenza A subtypes resulted in 4 major pandemics in the 20$^{th}$ century. The Spanish flu, caused by an H1N1 virus, in 1918-1919 led to the deaths of over 50 million people worldwide between 1917 and 1920. Presently, the risk of the emergence of a new subtype, or of the transmission to humans of a subtype endemic in animals, is always present. Of particular concern is a highly virulent form of avian influenza (also called "bird flu"), outbreaks of which have been reported in several countries around the world. In many cases, this bird flu can result in mortality rates approaching 100% within 48 hours. The spread of the avian influenza virus (H5N1), first identified in Hong Kong in 1997, to other Asian countries and Europe has been postulated to be linked to the migratory patterns of wild birds.

The current method of combating influenza in humans is by annual vaccination. The vaccine is usually a combination of several strains that are predicted to be the dominant strains for the coming "flu-season". The prediction is coordinated by the World Health Organization. Generally, the number of vaccine doses produced each year is not sufficient to vaccinate the world's population. For example, Canada and the United-States obtain enough vaccines doses to immunize about one third of their population, while only 17% of the population of the European Union can be vaccinated. It is evident that current worldwide production of influenza vaccine would be insufficient in the face of a worldwide flu pandemic. Even if the necessary annual production could somehow be met in a given year, the dominant strains change from year to year, thus stockpiling at low-need times in the year is not practical. Economical, large scale production of an effective influenza vaccine is of significant interest to government and private industry alike.

The viral stocks for use in vaccines are produced in fertilized eggs. The virus particles are harvested, and for an inactivated viral vaccine, disrupted by detergent to inactivate. Live attenuated vaccines are made of influenza viruses that were adapted for growth at low temperature which means that at normal body temperature, the vaccine is attenuated. Such a vaccine is licensed in USA for use in individuals from 5 to 49 years of age. Inactivated whole virus vaccines are rendered harmless by inactivation with chemical agents and they have been produced in embryonic eggs or mammalian cell culture. All these types of vaccine show some specific advantages and disadvantages. One advantage of vaccines derived from whole viruses is the type of immunity induced by such vaccines. In general, split vaccines induce a strong antibody response while vaccines made of whole viruses induce both an antibody (humoral) and cellular response. Even though a functional antibody response is a criterion for licensure that correlates with protection induced by a vaccine, there is increasing evidence that a T-cell response is also important in influenza immunity—this may also provide better protection in the elderly.

In order to induce a cellular immune response, vaccines made of whole viruses were developed. Due to the high pathogenicity of the influenza strain (e.g. H5N1), these vaccines are produced in BL3+ facility. For highly pathogenic influenza strains such as H5N1, some manufacturers have modified the hemagglutinin gene sequence in order to reduce the pathogenicity of the influenza strain and to make it avirulent and more easily produced in embryonic eggs or mammalian cell culture. Others also use reassortant influenza strains in which the genetic sequences for the hemagglutinin and neuraminidase proteins are cloned in a high-yielding low pathogenic influenza donor strain (A/PR/8/34; Quan F-S et al, 2007). While these methods may produce useful vaccines, they do not provide a solution to the need for high-volume, low cost and fast production of vaccines in the scale necessary to meet the global need in a normal year, and would almost certainly be insufficient in the face of a pandemic.

Using this reverse genetic technology, one might also need to mutate the genetic sequence of the HA protein to make it avirulent. For highly pathogenic influenza strains, the production of whole virus vaccines either requires confinement procedures or the resulting vaccines do not exactly match the genetic sequence of the circulating virus. In the case of live-attenuated vaccines, there is still a risk that the administered vaccine can recombine with an influenza virus from the host, leading to a new influenza virus.

While this method maintains the antigenic epitope and post-translational modifications, there are a number of drawbacks to this method, including the risk of contamination due to the use of whole virus and variable yields depending on virus strain. Sub-optimal levels of protection may result from genetic heterogeneity in the virus due to its introduction into eggs. Other disadvantages includes extensive planning for obtaining eggs, contamination risks due to chemicals used in purification, and long production times. Also, persons hypersensitive to egg proteins may not be eligible candidates for receiving the vaccine.

In the case of a pandemic, split vaccine production is limited by the need to adapt the strain for growth in eggs and the variable production yields achieved. Although this technology has been used for years for the production of seasonal vaccines, it can hardly respond in a reasonable timeframe to a pandemic and worldwide manufacturing capacity is limited.

To avoid the use of eggs, influenza viruses have also been produced in mammalian cell culture, for example in MDCK or PERC.6 cells, or the like. Another approach is reverse genetics, in which viruses are produced by cell transformation with viral genes. These methods, however, also requires the use of whole virus as well as elaborate methods and specific culture environments.

Several recombinant products have been developed as recombinant influenza vaccine candidates. These approaches have focused on the expression, production, and purification of influenza type A HA and NA proteins, including expression of these proteins using baculovirus infected insect cells (Crawford et al, 1999; Johansson, 1999), viral vectors, and DNA vaccine constructs (Olsen et al., 1997).

Specifics of an influenza virus infection are well known. Briefly, the infectious cycle is initiated by the attachment of the virion surface HA protein to a sialic acid-containing cellular receptor (glycoproteins and glycolipids). The NA protein mediates processing of the sialic acid receptor, and virus penetration into the cell depends on HA-dependent receptor-mediated endocytosis. In the acidic confines of internalized endosomes containing an influenza virion, the HA protein undergoes conformational changes that lead to fusion of viral and cell membranes and virus uncoating and M2-mediated release of MI proteins from nucleocapsid-associated ribonucleoproteins (RNPs), which migrate into the cell nucleus for viral RNA synthesis. Antibodies to HA proteins prevent virus infection by neutralizing virus infectivity, whereas antibodies to NA proteins mediate their effect on the early steps of viral replication.

Crawford et al. (1999) disclose expression of influenza HA in baculovirus infected insect cells. The expressed proteins are described as being capable of preventing lethal influenza disease caused by avian H5 and H7 influenza subtypes. Johansson et al. (1999) teach that baculovirus-expressed influenza HA and NA proteins induce immune responses in animals superior to those induced by a conventional vaccine. Immunogenicity and efficacy of baculovirus-expressed hemagglutinin of equine influenza virus was compared to a homologous DNA vaccine candidate (Olsen et al., 1997). Collectively, these data demonstrate that a high degree of protection against influenza virus challenge can be induced with recombinant HA or NA proteins, using various experimental approaches and in different animal models.

Since previous research has shown that the surface influenza glycoproteins, HA and NA, are the primary targets for elicitation of protective immunity against influenza virus and that M1 provides a conserved target for cellular immunity to influenza, a new vaccine candidate may include these viral antigens as a protein macromolecular particle, such as virus-like particles (VLPs). As vaccine products, VLPs offer the advantage of being more immunogenic than subunit or recombinant antigens and are able to stimulate both humoral and cellular immune response (Grgacic and Anderson, 2006). Further, the particle with these influenza antigens may display conformational epitopes that elicit neutralizing antibodies to multiple strains of influenza viruses.

Production of a non-infectious influenza virus strain for vaccine purposes is one way to avoid inadvertent infection. Alternatively, virus-like particles (VLPs) as substitutes for the cultured virus have been investigated. VLPs mimic the structure of the viral capsid, but lack a genome, and thus cannot replicate or provide a means for a secondary infection.

Several studies have demonstrated that recombinant influenza proteins self-assemble into VLPs in cell culture using mammalian expression plasmids or baculovirus vectors (Gomez-Puertas et al., 1999; Neumann et al., 2000; Latham and Galarza, 2001). Gomez-Puertas et al. (1999) discloses that efficient formation of influenza VLP depends on the expression levels of several viral proteins. Neumann et al. (2000) established a mammalian expression plasmid-based system for generating infectious influenza virus-like particles entirely from cloned cDNAs. Latham and Galarza (2001) reported the formation of influenza VLPs in insect cells infected with recombinant baculovirus co-expressing HA, NA, M1, and M2 genes. These studies demonstrated that influenza virion proteins may self-assemble upon co-expression in eukaryotic cells.

Gomez-Puertas et al. (2000) teach that, in addition to the hemagglutinin (HA), the matrix protein (M1) of the influenza virus is essential for VLP budding from insect cells. However, Chen et al. (2007) teach that M1 might not be required for VLP formation, and observed that efficient release of M1 and VLPs required the presence of HA and sialidase activity provided by NA. The NA cleaves the sialic acids of the glycoproteins at the surface of the cells producing the VLPs, and releasing the VLPs in the medium.

Quan et al 2007 teaches that a VLP vaccine produced in a baculovirus expression system (insect cell) induces a protective immunity against some strains of influenza virus (A/PR8/34 (H1N1)). The VLPs studied by Quan were observed to bud from the plasma membrane, and were considered to be of the correct size and morphology, similar to those obtained in a mammalian system (MDCK cells).

Enveloped viruses may obtain their lipid envelope when 'budding' out of the infected cell and obtain the membrane from the plasma membrane, or from that of an internal organelle. Influenza virus particles and VLPs bud from the plasma membrane of the host cell. In mammalian or baculovirus cell systems, for example, influenza buds from the plasma membrane (Quan et al 2007). Only a few enveloped viruses are known to infect plants (for example, members of the Topoviruses and Rhabdoviruses). Of the known plant enveloped viruses, they are characterized by budding from internal membranes of the host cell, and not from the plasma membrane. Although a small number of recombinant VLPs have been produced in plant hosts, none were derived from the plasma membrane, raising the question whether plasma membrane-derived VLPs, including influenza VLPs can be produced in plants.

Current influenza VLP production technologies rely on the co-expression of multiple viral proteins, and this dependence represents a drawback of these technologies since in case of a pandemic and of yearly epidemics, response time is crucial for vaccination. A simpler VLP production system, relying on the expression of only one viral protein is desirable to accelerate the development of vaccine.

In order to protect the world population from influenza and to stave off future pandemics, vaccine manufacturers will need to develop effective, rapid methods producing vaccine doses. The current use of fertilized eggs to produce vaccines is insufficient and involves a lengthy process.

SUMMARY OF THE INVENTION

It is an object of the invention to provide improved influenza virus like particles (VLPs).

According to the present invention there is provided a nucleic acid comprising a nucleotide sequence encoding an encoding an antigen from an enveloped virus operatively linked to a regulatory region active in a plant. The antigen may be an influenza hemagglutinin (HA).

The present invention also provides a method of producing influenza virus like particles (VLPs) in a plant comprising:
  a) introducing a nucleic acid encoding an antigen from an enveloped virus, for example an influenza hemagglutinin (HA), operatively linked to a regulatory region active in the plant, into the plant, or portion thereof, and
  b) incubating the plant or a portion therefore under conditions that permit the expression of the nucleic acid, thereby producing the VLPs.

The method may further comprise the steps of harvesting the plant and purifying or separating the VLPs from the plant tissue.

The present invention includes the above method wherein, in the step of introducing (step a), the nucleic acid may be either transiently expressed in the plant, or stably expressed in the plant. Furthermore, the VLPs may be purified using size exclusion chromatography.

The present invention also provides a virus like particle (VLP) comprising an influenza virus HA protein and one or more than one plant lipid.

Also included in the present invention is a composition comprising an effective dose of a VLP comprising an influenza virus HA protein, one or more than one plant lipid, and a pharmaceutically acceptable carrier.

The present invention also contemplates fragments or portions of HA proteins that form VLPs in a plant.

The VLP may comprise an HA protein of one, or more than one subtype, including H1, H2, H3, H4, H5, H6, H7, H8, H9, H10, H11, H12, H13, H14, H15 or H16 or fragment or portion thereof. Examples of subtypes comprising such HA proteins include A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949 (H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

In an aspect of the invention, the HA protein may be an H1, H2, H3, H5, H6, H7 or H9 subtype. In another aspect, the H1 protein may be from the A/New Caledonia/20/99 (H1N1), A/PuertoRico/8/34 (H1N1), A/Brisbane/59/2007 (H1N1), or A/Solomon Islands 3/2006 (H1N1) strain. The H3 protein may also be from the A/Brisbane 10/2007 (H3N2) or A/Wisconsin/67/2005 (H3N2) strain. In a further aspect of the invention, the H2 protein may be from the A/Singapore/1/57 (H2N2) strain. The H5 protein may be from the A/Anhui/1/2005 (H5N1), A/Vietnam/1194/2004 (H5N1), or A/Indonesia/5/2005 strain. In an aspect of the invention, the H6 protein may be from the A/Teal/HongKong/W312/97 (H6N1) strain. The H7 protein may be from the A/Equine/Prague/56 (H7N7) strain. In an aspect of the invention, the H9 protein is from the A/HongKong/1073/99 (H9N2) strain. In a further aspect of the invention, the HA protein may be from an influenza virus may be a type B virus, including B/Malaysia/2506/2004 or B/Florida/4/2006. Examples of amino acid sequences of the HA proteins from H1, H2, H3, H5, H6, H7 or H9 subtypes include SEQ ID NOs: 48-59.

The influenza virus HA protein may be H5 Indonesia.

The present invention also provides nucleic acid molecules comprising sequences encoding an HA protein. The nucleic acid molecules may further comprise one or more regulatory regions operatively linked to the sequence encoding an HA protein. The nucleic acid molecules may comprise a sequence encoding an H1, H2, H3, H4, H5, H6, H7, H8, H9, H10, H11, H12, H13, H14, H15 or H16. In an aspect of the invention, the HA protein encoded by the nucleic acid molecule may be an H1, H2, H3, H5, H6, H7 or H9 subtype. The H1 protein encoded by the nucleic acid molecule is from the A/New Caledonia/20/99 (H1N1), A/.PuertoRico/8/34 (H1N1), A/Brisbane/59/2007 (H1N1), or A/Solomon Islands 3/2006 (H1N1) strain. In an aspect of the invention, the H3 protein encoded by the nucleic acid molecule may be from the A/Brisbane 10/2007 (H3N2), or A/Wisconsin/67/2005 (H3N2) strain. In a further aspect of the invention, the H2 protein encoded by the nucleic acid molecule may be from the A/Singapore/1/57 (H2N2) strain. The H5 protein encoded by the nucleic acid molecule may also be from the A/Anhui/1/2005 (H5N1), A/Vietnam/1194/2004 (H5N1), or A/Indonesia/5/2005 strain. In an aspect of the invention, the H6 protein encoded by the nucleic acid molecule may be from the A/Teal/HongKong/W312/97 (H6N1) strain. The H7 protein encoded by the nucleic acid molecule may also be from the A/Equine/Prague/56 (H7N7) strain. Additionally, the H9 protein encoded by the nucleic acid molecule may be from the A/HongKong/1073/99 (H9N2) strain. Examples of sequences of nucleic acid molecules encoding such HA proteins from H1, H2, H3, H5, H6, H7 or H9 subtypes include SEQ ID NOs: 36-47 and 60-73.

The nucleic acid sequence may encode the influenza virus HA protein H5 Indonesia.

Regulatory regions that may be operatively linked to a sequence encoding an HA protein include those that are operative in a plant cell, an insect cell or a yeast cell. Such regulatory regions may include a plastocyanin regulatory region, a regulatory region of Ribulose 1,5-bisphosphate carboxylase/oxygenase (RuBisCO), chlorophyll a/b binding protein (CAB), ST-LS1, a polyhedrin regulatory region, or a gp64 regulatory region. Other regulatory regions include a 5' UTR, 3' UTR or terminator sequences. The plastocyanin regulatory region may be an alfalfa plastocyanin regulatory region; the 5' UTR, 3'UTR or terminator sequences may also be alfalfa sequences.

A method of inducing immunity to an influenza virus infection in a subject, is also provided, the method comprising administering the virus like particle comprising an influenza virus HA protein, one or more than one plant lipid, and a pharmaceutically acceptable carrier. The virus like particle may be administered to a subject orally, intradermally, intranasally, intramuscularly, intraperitoneally, intravenously, or subcutaneously.

The present invention also pertains to a virus like particle (VLP) comprising one or more than one protein derived from a virus selected from the group consisting of Influenza, Measles, Ebola, Marburg, and HIV, and one or more than one lipid derived from a non-sialylating host production cell. The HIV protein may be p24, gp120 or gp41; the Ebolavirus protein may be VP30 or VP35; the Marburg virus protein may be Gp/SGP; the Measles virus protein may be H-protein or F-protein.

Additionally the present invention relates to a virus like particle (VLP) comprising an influenza virus HA protein and one or more than one host lipid. For example if the host is insect, then the virus like particle (VLP) may comprise an influenza virus HA protein and one or more than one insect lipid, or if the host is a yeast, then the virus like particle (VLP) may comprise an influenza virus HA protein and one or more than one yeast lipid.

The present invention also relates to compositions comprising VLPs of two or more strains or subtypes of influenza. The two or more subtypes or strains may be selected from the group comprising: A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949 (H10N7), A/duck/England/56(H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99(H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7) or A/HongKong/1073/99 (H9N2)). The two or more subtypes or strains of VLPs may be present in about equivalent quantities; alternately one or more of the subtypes or strains may be the majority of the strains or subtypes represented.

The present invention pertains to a method for inducing immunity to influenza virus infection in an animal or target organism comprising administering an effective dose of a vaccine comprising one or more than one VLP, the VLP produced using a non-sialyating host, for example a plant host, an insect host, or a yeast host. The vaccine may be administered orally, intradermally, intranasally, intramusclarly, intraperitoneally, intravenously, or subcutaneously. The target organism may be selected from the group comprising humans, primates, horses, pigs, birds (avian) water fowl, migratory birds, quail, duck, geese, poultry, chicken, camel, canine, dogs, feline, cats, tiger, leopard, civet, mink, stone marten, ferrets, house pets, livestock, mice, rats, seal, whales and the like.

The present invention provides a method for producing VLPs containing hemagglutinin (HA) from different influenza strains in a suitable host capable of producing a VLP, for example, a plant, insect, or yeast. VLPs that are produced in plants contain lipids of plant origin, VLPs produced in insect cells comprise lipids from the plasma membrane of insect cells (generally referred to as "insect lipids"), and VLPs produced in yeast comprise lipids from the plasma membrane of yeast cells (generally referred to as "yeast lipids").

The production of VLPs in plants presents several advantages over the production of these particles in insect cell culture. Plant lipids can stimulate specific immune cells and enhance the immune response induced. Plant membranes are made of lipids, phosphatidylcholine (PC) and phosphatidylethanolamine (PE), and also contain glycosphingolipids that are unique to plants and some bacteria and protozoa. Sphingolipids are unusual in that they are not esters of glycerol like PC or PE but rather consist of a long chain amino alcohol that forms an amide linkage to a fatty acid chain containing more than 18 carbons. PC and PE as well as glycosphingolipids can bind to CD1 molecules expressed by mammalian immune cells such as antigen-presenting cells (APCs) like dentritic cells and macrophages and other cells including B and T lymphocytes in the thymus and liver (Tsuji M., 2006). Furthermore, in addition to the potential adjuvant effect of the presence of plant lipids, the ability of plant N-glycans to facilitate the capture of glycoprotein antigens by antigen presenting cells (Saint-Jore-Dupas, 2007), may be advantageous of the production of VLPs in plants.

Without wishing to be bound by theory, it is anticipated that plant-made VLPs will induce a stronger immune reaction than VLPs made in other manufacturing systems and that the immune reaction induced by these plant-made VLPs will be stronger when compared to the immune reaction induced by live or attenuated whole virus vaccines.

Contrary to vaccines made of whole viruses, VLPs provide the advantage as they are non-infectious, thus restrictive biological containment is not as significant an issue as it would be working with a whole, infectious virus, and is not required for production. Plant-made VLPs provide a further advantage again by allowing the expression system to be grown in a greenhouse or field, thus being significantly more economical and suitable for scale-up.

Additionally, plants do not comprise the enzymes involved in synthesizing and adding sialic acid residues to proteins. VLPs may be produced in the absence of neuraminidase (NA), and there is no need to co-express NA, or to treat the producing cells or extract with sialidase (neuraminidase), to ensure VLP production in plants.

The VLPs produced in accordance with the present invention do not comprise M1 protein which is known to bind RNA. RNA is a contaminant of the VLP preparation and is undesired when obtaining regulatory approval for the VLP product.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1A shows a sequence of an alfalfa plastocyanin-based expression cassette used for the expression of H1 in accordance with an embodiment of the present invention (SEQ ID NO:8). Protein disulfide isomerase (PDI) signal peptide is underlined. BglII (AGATCT) and SacI (GAGCTC) restriction sites used for cloning are shown in bold.

FIG. 5A shows the sequence of the N terminal fragment of H1 (SEQ ID NO:1). FIG. 5B shows the C terminal fragment of H1 (SEQ ID NO:2). FIG. 5C shows the complete sequence encoding HA0 of H1 (SEQ ID NO:28).

FIG. 6 shows the sequence encoding H5 flanked by a HindIII site immediately upstream of the initial ATG, and a SacI site immediately downstream of the stop (TAA) codon (SEQ ID NO:3).

FIG. 7A shows the sequence of the primer Plasto-443c (SEQ ID NO:4). FIG. 7B shows the sequence of primer SpHA(Ind)-Plasto.r (SEQ ID NO:5). FIG. 7C shows the sequence of primer Plasto-SpHA(Ind).c (SEQ ID NO:6). FIG. 7D shows the sequence of primer HA(Ind)-Sac.r (SEQ ID NO:7).

FIG. 8A shows the amino acid sequence of the HA1 peptide sequence (SEQ ID NO:9). FIG. 8B shows the amino acid sequence of HA5 peptide sequence (SEQ ID NO:10). Native signal peptide is indicated in bold.

FIG. 9 shows the sequence of HA of influenza A subtype H7 (SEQ ID No: 11).

FIG. 10A shows the sequence of Influenza A HA, subtype H2 (SEQ ID NO:12). FIG. 10B shows the sequence of Influenza A HA subtype H3 (SEQ ID NO:13). FIG. 10C shows the sequence of Influenza A HA subtype H4 (SEQ ID NO:14). FIG. 10D shows the sequence of Influenza A HA subtype H5 (SEQ ID NO:15). FIG. 10E shows the sequence of Influenza A HA subtype H6 (SEQ ID NO:16). FIG. 10F shows the sequence of Influenza A HA subtype H8 (SEQ ID NO:17). FIG. 10G shows the sequence of Influenza A HA subtype H9 (SEQ ID NO:18). FIG. 10H shows the sequence of Influenza A HA subtype H10 (SEQ ID NO:19). FIG. 10I shows the sequence of Influenza A HA subtype H11 (SEQ ID NO:20). FIG. 10J shows the sequence of Influenza A HA subtype H12 (SEQ ID NO:21). FIG. 10K shows the sequence of Influenza A HA subtype H13 (SEQ ID NO:22). FIG. 10L shows the sequence of Influenza A HA subtype H14 (SEQ ID NO:23). FIG. 10M shows the sequence of Influenza A HA subtype H15 (SEQ ID NO:24). FIG. 10N shows the sequence of Influenza A HA subtype H16 (SEQ ID NO:25). FIG. 10O shows the sequence of Influenza B HA (SEQ ID NO:26). FIG. 10P shows the sequence of Influenza C HA (SEQ ID NO:27). FIG. 10Q shows the sequence of primer XmaI-pPlas.c (SEQ ID NO: 29). FIG. 10R shows the sequence of primer SacI-ATG-pPlas.r (SEQ ID NO: 30). FIG. 10S shows the sequence of primer SacI-PlasTer.c (SEQ ID NO: 31). FIG. 10T shows the sequence of primer EcoRI-PlasTer.r (SEQ ID NO: 32).

FIG. 12 shows immunodetection of H5, using anti-H5 (Vietnam) antibodies, in protein extracts from N. benthamiana leaves transformed with construct 660 (lane 3). Commercial H5 from influenza A/Vietnam/1203/2004 was used as positive control of detection (lane 1), and a protein extract from leaves transformed with an empty vector were used as negative control (lane 2).

FIG. 13A shows characterization of hemagglutinin structures by size exclusion chromatography. Protein extract from separate biomasses producing H5, H1, soluble H1, or H1 and M1 were separated by gel filtration on S-500 HR. Commercial H1 in the form of rosettes was also fractionated (H1 rosette). Elution fractions were analyzed for relative protein content (Relative Protein Level—a standard protein elution profile of a biomass fractionation is shown). Blue Dextran 2000 (2 MDa reference standard) elution peak is indicated. FIG. 13B shows elution fractions analyzed for the presence of hemagglutinin by immunoblotting with anti-H5 (Vietnam) antibodies (for H5). FIG. 13C shows elution fractions analyzed for anti-influenza A antibodies for H1. FIG. 13D shows elution fractions analyzed for anti-influenza A antibodies for soluble H1. FIG. 13E shows elution fractions analyzed for anti-influenza A antibodies for H1 rosette. FIG. 13F shows elution fractions analyzed for anti-influenza A antibodies for H1+M1.

FIG. 16 shows a nucleotide sequence for Influenza A virus (A/New Caledonia/20/99(H1N1)) hemagglutinin (HA) gene, complete cds. GenBank Accession No. AY289929 (SEQ ID NO: 33).

FIG. 17 shows a nucleotide sequence for *Medicago sativa* mRNA for protein disulfide isomerase. GenBank Accession No. Z11499 (SEQ ID NO: 34).

FIG. 18 shows a nucleotide sequence for Influenza A virus (A/Puerto Rico/8/34(H1N1)) segment 7, complete sequence. GenBank Accession No. NC_002016.1 (SEQ ID NO: 35).

FIG. 27 (A) Polar lipid composition of purified influenza VLPs. Lipids contained in an equivalent of 40 µg of proteins, were extracted from VLP as described, separated by HP-TLC, and compared to the migration profile of lipids isolated from highly purified tobacco plasma membrane (PM). Lipid abbreviations are as following: DGDG, Digalactosyldiacylglycerol; gluCER, glucosyl-ceramide; PA, phosphatic acid; PC, phosphatidylcholine; PE, phosphatidylethanolamine; PG, phosphatidylglycerol; PI, phosphatidylinositol; PS, phosphatidylserine; SG, Steryl-glycoside. FIG. 27(B) Neutral lipid composition of purified influenza VLPs. Lipids contained in an equivalent of 20 µg of proteins were extracted from VLP as described, separated by HP-TLC and compared to the migration of sitosterol. FIG. 27(C) Immunodetection of the plasma membrane marker proton pump ATPase (PMA) in purified VLPs and highly-purified PM from tobacco leaves (PML) and BY2 tobacco cells (PMBY2). Eighteen micrograms of protein were loaded in each lane.

FIG. 28 shows the sequence spanning from DraIII to SacI sites of clone 774-nucleotide sequence of A/Brisbane/59/2007 (H1N1) (SEQ ID NO: 36). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 29 shows the sequence spanning from DraIII to SacI sites of clone 775-nucleotide sequence of A/Solomon Islands 3/2006 (H1N1) (SEQ ID NO: 37). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 30 shows the sequence spanning from DraIII to SacI sites of clone 776-nucleotide sequence of A/Brisbane 10/2007 (H1N1) (SEQ ID NO: 38). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 31 shows the sequence spanning from DraIII to SacI sites of clone 777-nucleotide sequence of A/Wisconsin/67/2005 (H3N2) (SEQ ID NO: 39). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 32 shows the sequence spanning from DraIII to SacI sites of clone 778-nucleotide sequence of B/Malaysia/2506/2004 (SEQ ID NO: 40). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 33 shows the sequence spanning from DraIII to SacI sites of clone 779-nucleotide sequence of B/Florida/4/2006 (SEQ ID NO: 41). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 34 shows the sequence spanning from DraIII to SacI sites of clone 780-nucleotide sequence of A/Singapore/1/57 (H2N2) (SEQ ID NO: 42). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 35 shows the sequence spanning from DraIII to SacI sites of clone 781-nucleotide sequence of A/Anhui/1/2005 (H5N1) (SEQ ID NO: 43). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 36 shows the sequence spanning from DraIII to SacI sites of clone 782-nucleotide sequence of A/Vietnam/1194/2004 (H5N1) (SEQ ID NO: 44). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 37 shows the sequence spanning from DraIII to SacI sites of clone 783-nucleotide sequence of A/Teal/HongKong/W312/97 (H6N1) (SEQ ID NO: 45). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 38 shows the sequence spanning from DraIII to SacI sites of clone 784-nucleotide sequence of A/Equine/Prague/56 (H7N7) (SEQ ID NO: 46). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 39 shows the sequence spanning from DraIII to SacI sites of clone 785-nucleotide sequence of A/HongKong/1073/99 (H9N2) (SEQ ID NO: 47). The coding sequence is flanked by a plastocyanin regulatory region, starting with a DraIII restriction site at the 5' end and by a stop codon and a SacI site at the 3' end. Restriction sites are underlined; ATG is in bold and underlined.

FIG. 40A shows the amino acid sequence (SEQ ID NO: 48) of the polypeptide translated from clone 774 (A/Brisbane/59/2007 (H1N1)). The open reading frame of clone 774 starts with the ATG indicated in FIG. 28. FIG. 40B shows the amino acid sequence (SEQ ID NO: 49) of the polypeptide translated from clone 775 (A/Solomon Islands 3/2006 (H1N1)). The open reading frame of clone 775 starts with the ATG indicated in FIG. 29.

FIG. 41A shows the amino acid sequence (SEQ ID NO: 50) of the polypeptide translated from clone 776 (A/Brisbane/10/2007 (H3N2)). The open reading frame of clone 776 starts with the ATG indicated in FIG. 30. FIG. 41B shows the amino acid sequence (SEQ ID NO: 51) of the polypeptide translated from clone 777 (A/Wisconsin/67/2005 (H3N2)). The open reading frame of clone 777 starts with the ATG indicated in FIG. 31.

FIG. 42A shows the amino acid sequence (SEQ ID NO: 52) of the polypeptide translated from clone 778 (B/Malaysia/2506/2004). The open reading frame of clone 778 starts with the ATG indicated in FIG. 32. FIG. 42B shows the amino acid sequence (SEQ ID NO: 53) of the polypeptide translated from clone 779 (B/Florida/4/2006). The open reading frame of clone 779 starts with the ATG indicated in FIG. 33.

FIG. 43A shows the amino acid sequence (SEQ ID NO: 54) of the polypeptide translated from clone 780 (A/Singapore/1/57 (H2N2)). The open reading frame of clone 780 starts with the ATG indicated in FIG. 34. FIG. 43B shows the amino acid sequence (SEQ ID NO: 55) of the polypeptide translated from clone 781 (A/Anhui/1/2005 (H5N1)). The open reading frame of clone 781 starts with the ATG indicated in FIG. 35.

FIG. 44A shows the amino acid sequence (SEQ ID NO: 56) of the polypeptide translated from clone 782 (A/Vietnam/1194/2004 (H5N1)). The open reading frame of clone 782 starts with the ATG indicated in FIG. 36. FIG. 44B shows the amino acid sequence (SEQ ID NO: 57) of the polypeptide translated from clone 783 (A/Teal/HongKong/W312/97 (H6N1)). The open reading frame of clone 783 starts with the ATG indicated in FIG. 37.

FIG. 45A shows the amino acid sequence (SEQ ID NO: 58) of the polypeptide translated from clone 784 (A/Equine/Prague/56 (H7N7)). The open reading frame of clone 784 starts with the ATG indicated in FIG. 38. FIG. 45B shows the amino acid sequence (SEQ ID NO: 59) of the polypeptide translated from clone 785 (A/HongKong/1073/99 (H9N2)). The open reading frame of clone 785 starts with the ATG indicated in FIG. 39.

FIG. 51 shows the nucleic acid sequence of an HA expression cassette comprising alfalfa plastocyanin promoter and 5' UTR, hemagglutinin coding sequence of H5 from A/Indonesia/5/2005 (Construct #660), alfalfa plastocyanin 3' UTR and terminator sequences.

FIG. 52 shows the nucleic acid sequence of an HA expression cassette comprising alfalfa plastocyanin promoter and 5' UTR, hemagglutinin coding sequence of H1 from A/New Caledonia/20/1999 (Construct #540), alfalfa plastocyanin 3' UTR and terminator sequences.

FIG. 53 shows the nucleic acid sequence of an HA expression cassette comprising alfalfa plastocyanin promoter and 5' UTR, hemagglutinin coding sequence of H1 from A/Brisbane/59/2007 (construct #774), alfalfa plastocyanin 3' UTR and terminator sequences.

FIG. 54 shows the nucleic acid sequence of an HA expression cassette comprising alfalfa plastocyanin promoter and 5' UTR, hemagglutinin coding sequence of H1 from A/Solomon Islands/3/2006 (H1N1) (construct #775), alfalfa plastocyanin 3' UTR and terminator sequences.

FIG. 55 shows the nucleic acid sequence of an HA expression cassette comprising alfalfa plastocyanin promoter and 5' UTR, hemagglutinin coding sequence of H2 from A/Singapore/1/57 (H2N2) (construct #780), alfalfa plastocyanin 3' UTR and terminator sequences.

FIG. 56 shows the nucleic acid sequence of an HA expression cassette comprising alfalfa plastocyanin promoter and 5' UTR, hemagglutinin coding sequence of H5 from A/Anhui/1/2005 (H5N1) (Construct #781), alfalfa plastocyanin 3' UTR and terminator sequences.

FIG. 57 shows the nucleic acid sequence of an HA expression cassette comprising alfalfa plastocyanin promoter and 5' UTR, hemagglutinin coding sequence of H5 from A/Vietnam/1194/2004 (H5N1) (Construct #782), alfalfa plastocyanin 3' UTR and terminator sequences.

FIG. 58 shows the nucleic acid sequence of an HA expression cassette comprising alfalfa plastocyanin promoter and 5' UTR, hemagglutinin coding sequence of H6 from A/Teal/Hong Kong/W312/97 (H6N1) (Construct #783), alfalfa plastocyanin 3' UTR and terminator sequences.

FIG. 59 shows the nucleic acid sequence of an HA expression cassette comprising alfalfa plastocyanin promoter and 5' UTR, hemagglutinin coding sequence of H9 from A/Hong Kong/1073/99 (H9N2) (Construct #785), alfalfa plastocyanin 3' UTR and terminator sequences.

FIG. 60 shows the nucleic acid sequence of an HA expression cassette comprising alfalfa plastocyanin promoter and 5' UTR, hemagglutinin coding sequence of H3 from A/Brisbane/10/2007 (H3N2), alfalfa plastocyanin 3' UTR and terminator sequences.

FIG. 61 shows the nucleic acid sequence of an HA expression cassette comprising alfalfa plastocyanin promoter and 5' UTR, hemagglutinin coding sequence of H3 from A/Wisconsin/67/2005 (H3N2), alfalfa plastocyanin 3' UTR and terminator sequences.

FIG. 62 shows the nucleic acid sequence of an HA expression cassette comprising alfalfa plastocyanin promoter and 5' UTR, hemagglutinin coding sequence of H7 from A/Equine/Prague/56 (H7N7), alfalfa plastocyanin 3' UTR and terminator sequences.

FIG. 63 shows the nucleic acid sequence of an HA expression cassette comprising alfalfa plastocyanin promoter and 5' UTR, hemagglutinin coding sequence of HA from B/Malaysia/2506/2004, alfalfa plastocyanin 3' UTR and terminator sequences.

FIG. 64 shows the nucleic acid sequence of an HA expression cassette comprising alfalfa plastocyanin promoter and 5' UTR, hemagglutinin coding sequence of HA from B/Florida/4/2006, alfalfa plastocyanin 3' UTR and terminator sequences.

FIG. 65 shows a consensus amino acid sequence (SEQ ID NO: 74) for HA of A/New Caledonia/20/99 (H1N1) (encoded by SEQ ID NO: 33), A/Brisbane/59/2007 (H1N1) (SEQ ID NO: 48), A/Solomon Islands/3/2006 (H1N1) (SEQ ID NO: 49) and SEQ ID NO: 9. X1 (position 3) is A or V; X2 (position 52) is D or N; X3 (position 90) is K or R; X4 (position 99) is K or T; X5 (position 111) is Y or H; X6 (position 145) is V or T; X7 (position 154) is E or K; X8 (position 161) is R or K; X9 (position 181) is V or A; X10 (position 203) is D or N; X11 (position 2o5) is R or K; X12 (position 210) is T or K; X13 (position 225) is R or K; X14 (position 268) is W or R; X15 (position 283) is T or N; X16 (position 290) is E or K; X17 (position 432) is I or L; X18 (position 489) is N or D.

FIG. 66 shows Amino acid sequence of H1 New Caledonia (AAP34324.1) encoded by SEQ ID NO: 33.

FIG. 67 shows the Amino acid sequence of H1 Puerto Rico (NC_0409878.1) encoded by SEQ ID NO: 35.

DETAILED DESCRIPTION

Figure 1B:
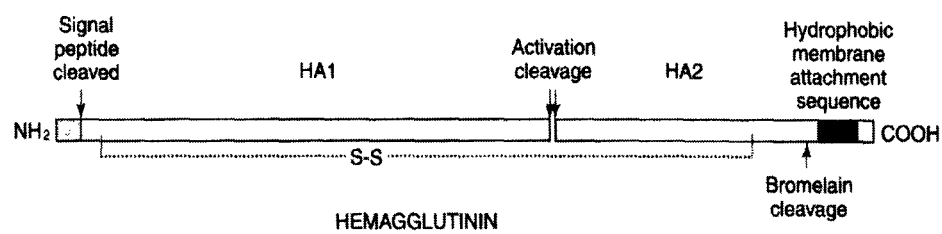
FIG. 1B shows a schematic diagram of functional domains of influenza hemagglutinin. After cleavage of HA0, HA1 and HA2 fragments remain bound together by a disulfide bridge.

The present invention relates to the production of virus-like particles. More specifically, the present invention is directed to the production of virus-like particles comprising influenza antigens. The following description is of a preferred embodiment.

The present invention provides a nucleic acid comprising a nucleotide sequence encoding an antigen from an enveloped virus, for example, the influenza hemagglutinin (HA), operatively linked to a regulatory region active in a plant.

Furthermore, the present invention provides a method of producing virus like particles (VLPs) in a plant. The method involves introducing a nucleic acid encoding an antigen operatively linked to a regulatory region active in the plant, into the plant, or portion of the plant, and incubating the plant or a portion of the plant under conditions that permit the expression of the nucleic acid, thereby producing the VLPs.

VLPs may be produced from influenza virus, however, VLPs may also be produced from other plasma membrane derived virus including but not limited to Measles, Ebola, Marburg, and HIV.

The invention includes VLPs of all types of influenza virus which may infect humans, including for example, but not limited to the very prevalent A (H1N1) sub-type (e.g. A/New Caledonia/20/99 (H1N1)), the A/Indonesia/5/05 sub-type (H5N1) (SEQ ID NO: 60) and the less common B type (for example SEQ ID NO:26, FIG. 10O), and C type (SEQ ID NO:27, FIG. 10P), and to HAs obtained from other influenza subtypes. VLPs of other influenza subtypes are also included in the present invention, for example, A/Brisbane/59/2007 (H1N1; SEQ ID NO:48), A/Solomon Islands/3/2006 (H1N1; SEQ ID NO:49), A/Singapore/1/57 (H2N2; SEQ ID NO:54), A/Anhui/1/2005 (H5N1; SEQ ID NO:55), A/Vietnam/1194/2004 (H5N1; SEQ ID NO:56), A/Teal/Hong Kong/W312/97 (H6N1; SEQ ID NO:57), A/Hong Kong/1073/99 (H9N2; SEQ ID NO:59), A/Brisbane/10/2007 (H3N2; SEQ ID NO:50), A/Wisconsin/67/2005 (H3N2; SEQ ID NO:51), A/Equine/Prague/56 (H7N7; SEQ ID NO:58), B/Malaysia/2506/2004 (SEQ ID NO:52), or B/Florida/4/2006 (SEQ ID NO:53).

The present invention also pertains to influenza viruses which infect other mammals or host animals, for example humans, primates, horses, pigs, birds, avian water fowl, migratory birds, quail, duck, geese, poultry, chicken, camel, canine, dogs, feline, cats, tiger, leopard, civet, mink, stone marten, ferrets, house pets, livestock, mice, rats, seal, whale and the like.

Non limiting examples of other antigens that may be expressed in plasma membrane derived viruses include, the Capsid protein of HIV-p24; gp120, gp41-envelope proteins, the structural proteins VP30 and VP35; Gp/SGP (a glycosylated integral membrane protein) of Filoviruses, for example Ebola or Marburg, or the H protein, and F protein of Paramyxoviruses, for example, Measles.

The invention also includes, but is not limited to, influenza derived VLPs that obtain a lipid envelope from the plasma membrane of the cell in which the VLP proteins are expressed. For example, if the VLP is expressed in a plant-based system, the VLP may obtain a lipid envelope from the plasma membrane of the cell.

Generally, the term "lipid" refers to a fat-soluble (lipophilic), naturally-occurring molecules. The term is also used more specifically to refer to fatty-acids and their derivatives (including tri-, di-, and monoglycerides and phospholipids), as well as other fat-soluble sterol-containing metabolites or sterols. Phospholipids are a major component of all biological membranes, along with glycolipids, sterols and proteins. Examples of phospholipids include phosphatidylethanolamine, phosphatidylcholine, phosphatidylinositol, phosphatidylserine, and the like. Examples of sterols include zoosterols (e.g., cholesterol) and phytosterols. Over 200 phytosterols have been identified in various plant species, the most common being campesterol, stigmasterol, ergosterol, brassicasterol, delta-7-stigmasterol, delta-7-avenasterol, daunosterol, sitosterol, 24-methylcholesterol, cholesterol or beta-sitosterol. As one of skill in the art would understand, the lipid composition of the plasma membrane of a cell may vary with the culture or growth conditions of the cell or organism from which the cell is obtained.

Cell membranes generally comprise lipid bilayers, as well as proteins for various functions. Localized concentrations of particular lipids may be found in the lipid bilayer, referred to as 'lipid rafts'. Without wishing to be bound by theory, lipid rafts may have significant roles in endo and exocytosis, entry or egress of viruses or other infectious agents, intercell signal transduction, interaction with other structural components of the cell or organism, such as intracellular and extracellular matrices.

With reference to influenza virus, the term "hemagglutinin" or "HA" as used herein refers to a glycoprotein found on the outside of influenza viral particles. HA is a homotrimeric membrane type I glycoprotein, generally comprising a signal peptide, an HA1 domain, and an HA2 domain comprising a membrane-spanning anchor site at the C-terminus and a small cytoplasmic tail (FIG. 1B). Nucleotide sequences encoding HA are well known and are available—see, for example, the BioDefence Public Health base or National Center for Biotechnology Information, both of which are incorporated herein by reference.

The term "homotrimer" or "homotrimeric" indicates that an oligomer is formed by three HA protein molecules. Without wishing to be bound by theory, HA protein is synthesized as monomeric precursor protein (HA0) of about 75 kDa, which assembles at the surface into an elongated trimeric protein. Before trimerization occurs, the precursor protein is cleaved at a conserved activation cleavage site (also referred to as fusion peptide) into 2 polypeptide chains, HA1 and HA2 (comprising the transmembrane region), linked by a disulfide bond. The HA1 segment may be 328 amino acids in length, and the HA2 segment may be 221 amino acids in length. Although this cleavage may be important for virus infectivity, it may not be essential for the trimerization of the protein. Insertion of HA within the endoplasmic reticulum (ER) membrane of the host cell, signal peptide cleavage and protein glycosylation are co-translational events. Correct refolding of HA requires glycosylation of the protein and formation of 6 intra-chain disulfide bonds. The HA trimer assembles within the cis- and trans-Golgi complex, the transmembrane domain playing a role in the trimerization process. The crystal structures of bromelain-treated HA proteins, which lack the transmembrane domain, have shown a highly conserved structure amongst influenza strains. It has also been established that HA undergoes major conformational changes during the infection process, which requires the precursor HA0 to be cleaved into the 2 polypeptide chains HA1 and HA2. The HA protein may be processed (i.e., comprise HA1 and HA2 domains), or may be unprocessed (i.e. comprise the HA0 domain).

The present invention pertains to the use of an HA protein comprising the transmembrane domain and includes HA1 and HA2 domains, for example the HA protein may be HA0, or processed HA comprising HA1 and HA2. The HA protein may be used in the production or formation of VLPs using a plant, or plant cell, expression system.

The HA of the present invention may be obtained from any subtype. For example, the HA may be of subtype H1, H2, H3, H4, H5, H6, H7, H8, H9, H10, H11, H12, H13, H14, H15, or H16. The recombinant HA of the present invention may also comprise an amino acid sequence based on the sequence any hemagglutinin known in the art—see, for example, the BioDefence Public Health base or National Center for Biotechnology Information. Furthermore, the HA may be based on the sequence of a hemagglutinin that is isolated from one or more emerging or newly-identified influenza viruses.

The present invention also includes VLPs that comprise HAs obtained from one or more than one influenza subtype. For example, VLPs may comprise one or more than one HA from the subtype H1 (encoded by SEQ ID NO:28), H2 (encoded by SEQ ID NO:12), H3 (encoded by SEQ ID NO:13), H4 (encoded by SEQ ID NO:14), H5 (encoded by SEQ ID NO:15), H6 (encoded by SEQ ID NO:16), H7 (encoded by SEQ ID NO:11), H8 (encoded by SEQ ID NO:17), H9 (encoded by SEQ ID NO:18), H10 (encoded by SEQ ID NO:19), H11 (encoded by SEQ ID NO:20), H12 (encoded by SEQ ID NO:21), H13 (encoded by SEQ ID NO:27), H14 (encoded by SEQ ID NO:23), H15 (encoded by SEQ ID NO:24), H16 (encoded by SEQ ID NO:25), or a combination thereof. One or more that one HA from the one or more than one influenza subtypes may be co-expressed within a plant or insect cell to ensure that the synthesis of the one or more than one HA results in the formation of VLPs comprising a combination of HAs obtained from one or more than one influenza subtype. Selection of the combination of HAs may be determined by the intended use of the vaccine prepared from the VLP. For example a vaccine for use in inoculating birds may comprise any combination of HA subtypes, while VLPs useful for inoculating humans may comprise subtypes one or more than one of subtypes H1, H2, H3, H5, H7, H9, H10, N1, N2, N3 and N7. However, other HA subtype combinations may be prepared depending upon the use of the inoculum.

Therefore, the present invention is directed to a VLP comprising one or more than one HA subtype.

The present invention also provides for nucleic acids encoding hemagglutinins that form VLPs when expressed in plants Influenza HA proteins exhibit a range of similarities and differences with respect to molecular weight, isoelectric point, size, glycan complement and the like. The physico-chemical properties of the various hemagglutinins may be useful to allow for differentiation between the HAs expressed in a plant, insect cell or yeast system, and may be of particular use when more than one HA is co-expressed in a single system. Examples of such physico-chemical properties are provided in Table 1.

Hybridization under stringent hybridization conditions is known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, $3^{rd}$ edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence encoding HA from H1 (SEQ ID NO:28), H5 (SEQ ID NO:3) or H7 (SEQ ID

TABLE 1

Physico-chemical properties of influenza hemagglutinins

| Clone | | | AA | | | Glycans | | | Molecular Weight (kDA) | | | | | | Isoelectric point | | |
|---|---|---|---|---|---|---|---|---|---|---|---|---|---|---|---|---|---|
| No | Type | Influenza strains | HA0 | HA1 | HA2 | HA0 | HA1 | HA2 | HA0 | HA0[1] | HA1 | HA1[1] | HA2 | HA2[1] | HA0 | HA1 | HA2 |
| 774 | H1 | A/Brisbane/59/2007 | 548 | 326 | 222 | 9 | 7 | 2 | 61 | 75 | 36 | 47 | 25 | 28 | 6.4 | 7.5 | 5.3 |
| 775 | H1 | A/Solomon Islands/3/2006 | 548 | 326 | 222 | 9 | 7 | 2 | 61 | 75 | 36 | 47 | 25 | 28 | 6.1 | 6.7 | 5.3 |
| 776 | H3 | A/Brisbane/10/2007 | 550 | 329 | 221 | 12 | 11 | 1 | 62 | 80 | 37 | 54 | 25 | 27 | 8.5 | 9.6 | 5.2 |
| 777 | H3 | A/Wisconsin/67/2005 | 550 | 329 | 221 | 11 | 10 | 1 | 62 | 79 | 37 | 52 | 25 | 27 | 8.8 | 9.6 | 5.3 |
| 778 | B | B/Malaysia/2506/2004 | 570 | 347 | 223 | 12 | 8 | 4 | 62 | 80 | 38 | 50 | 24 | 30 | 8.0 | 9.7 | 4.5 |
| 779 | B | B/Florida/4/2006 | 569 | 346 | 223 | 10 | 7 | 3 | 62 | 77 | 38 | 48 | 24 | 29 | 8.0 | 9.7 | 4.5 |
| 780 | H2 | A/Singapore/1/57 | 547 | 325 | 222 | 6 | 4 | 2 | 62 | 71 | 36 | 42 | 25 | 28 | 6.0 | 7.5 | 4.9 |
| 781 | H5 | A/Anhui/1/2005 | 551 | 329 | 222 | 7 | 5 | 2 | 62 | 73 | 37 | 45 | 25 | 28 | 6.2 | 8.9 | 4.7 |
| 782 | H5 | A/Vietnam/1194/2004 | 552 | 330 | 222 | 7 | 5 | 2 | 63 | 74 | 38 | 45 | 25 | 28 | 6.4 | 9.1 | 4.8 |
| 783 | H6 | A/Teal/Hong Kong/W312/97 | 550 | 328 | 222 | 8 | 5 | 3 | 62 | 75 | 37 | 45 | 25 | 30 | 5.7 | 5.9 | 5.6 |
| 784 | H7 | A/Equine/Prague/56 | 552 | 331 | 221 | 6 | 4 | 2 | 62 | 71 | 37 | 43 | 25 | 28 | 8.9 | 9.7 | 4.9 |
| 785 | H9 | A/Hong Kong/1073/99 | 542 | 320 | 199 | 9 | 7 | 2 | 61 | 75 | 36 | 46 | 23 | 26 | 8.4 | 9.5 | 5.3 |

The present invention also includes nucleotide sequences SEQ ID NO:28; SEQ ID NO:3; SEQ ID NO:11, encoding HA from H1, H5 or H7, respectively, a nucleotide sequence that hybridizes under stringent hybridisation conditions to SEQ ID NO:28; SEQ ID NO:3; SEQ ID NO:11, or a nucleotide sequence that hybridizes under stringent hybridisation conditions to a compliment of SEQ ID NO:28; SEQ ID NO:3; SEQ ID NO:1, wherein the nucleotide sequence encodes a hemagglutinin protein that when expressed forms a VLP, and that the VLP induces the production of an antibody when administered to a subject. For example, expression of the nucleotide sequence within a plant cell forms a VLP, and the VLP may be used to produce an antibody that is capable of binding HA, including mature HA, HA0, HA1, or HA2 of one or more influenza types or subtypes. The VLP, when administered to a subject, induces an immune response.

NO:11), wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1, or HA2. The VLP, when administered to a subject, induces an immune response.

Similarly, the present invention includes HAs associated with the following subtypes H1 (encoded by SEQ ID NO:28), H2 (encoded by SEQ ID NO:12), H3 (encoded by SEQ ID NO:13), H4 (encoded by SEQ ID NO:14), H5 (encoded by SEQ ID NO:15), H6 (encoded by SEQ ID NO:16), H7 (encoded by SEQ ID NO:11), H8 (encoded by SEQ ID NO:17), H9 (encoded by SEQ ID NO:18), H10 (encoded by SEQ ID NO:19), H11 (encoded by SEQ ID NO:20), H12 (encoded by SEQ ID NO:21), H13 (encoded by SEQ ID NO:27), H14 (encoded by SEQ ID NO:23), H15 (encoded by SEQ ID NO:24), H16 (encoded by SEQ ID NO:25); see FIGS. 10A to 10P), and nucleotide sequences that are characterized as having from about 70 to 100% or any amount therebetween, 80 to 100% or any amount there between, 90-100% or any amount therebetween, or 95-100% or any amount therebetween, sequence identity with H1 (SEQ ID NO:28), H2 (SEQ ID NO:12), H3 (SEQ ID NO:13), H4 (SEQ ID NO:14), H5 (SEQ ID NO:15), H6 (SEQ ID NO:16), H7 (SEQ ID NO:11), H8 (SEQ ID NO:17), H9 (SEQ ID NO:18), H10 (SEQ ID NO:19), H11 (SEQ ID NO:20), H12 (SEQ ID NO:21), H13 (SEQ ID NO:27), H14 (SEQ ID NO:23), H15 (SEQ ID NO:24), H16 (SEQ ID NO:25), wherein the nucleotide sequence encodes a hemagglutinin protein that when expressed forms a VLP, and that the VLP induces the production of an antibody. For example, expression of the nucleotide sequence within a plant cell forms a VLP, and the VLP may be used to produce an antibody that is capable of binding HA, including mature HA, HA0, HA1, or HA2. The VLP, when administered to a subject, induces an immune response.

An "immune response" generally refers to a response of the adaptive immune system. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity is of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

A hemagglutination inhibition (HI, or HAI) assay may also be used to demonstrate the efficacy of antibodies induced by a vaccine, or vaccine composition can inhibit the agglutination of red blood cells (RBC) by recombinant HA. Hemagglutination inhibitory antibody titers of serum samples may be evaluated by microtiter HAI (Aymard et al 1973). Erythrocytes from any of several species may be used—e.g. horse, turkey, chicken or the like. This assay gives indirect information on assembly of the HA trimer on the surface of VLP, confirming the proper presentation of antigenic sites on HAs.

Cross-reactivity HAI titres may also be used to demonstrate the efficacy of an immune response to other strains of virus related to the vaccine subtype. For example, serum from a subject immunized with a vaccine composition of a first strain (e.g. VLPs of A/Indonesia 5/05) may be used in an HAI assay with a second strain of whole virus or virus particles (e.g. A/Vietnam/1194/2004), and the HAI titer determined.

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be obtained several ways, including: 1) enumeration of lysis plaques (plaque assay) following crystal violet fixation/coloration of cells; 2) microscopic observation of cell lysis in culture; 3) ELISA and spectrophotometric detection of NP virus protein (correlate with virus infection of host cells)

Sequence identity or sequence similarity may be determined using a nucleotide sequence comparison program, such as that provided within DNASIS (for example, using, but not limited to, the following parameters: GAP penalty 5, # of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST)., or by manual alignment and visual inspection.

The term "hemagglutinin domain" refers to a peptide comprising either the HA0 domain, or the HA1 and HA2 domains. The hemagglutinin domain does not include the signal peptide, transmembrane domain, or the cytoplasmic tail found in the naturally occurring protein.

The term "virus like particle" (VLP), or "virus-like particles" or "VLPs" refers to structures that self-assemble and comprise structural proteins such as influenza HA protein. VLPs are generally morphologically and antigenically similar to virions produced in an infection, but lack genetic information sufficient to replicate and thus are non-infectious. In some examples, VLPs may comprise a single protein species, or more than one protein species. For VLPs comprising more than one protein species, the protein species may be from the same species of virus, or may comprise a protein from a different species, genus, subfamily or family of virus (as designated by the ICTV nomenclature). In other examples, one or more of the protein species comprising a VLP may be modified from the naturally occurring sequence. VLPs may be produced in suitable host cells including plant and insect host cells. Following extraction from the host cell and upon isolation and further purification under suitable conditions, VLPs may be purified as intact structures.

The VLPs produced from influenza derived proteins, in accordance with the present invention do not comprise M1 protein. The M1 protein is known to bind RNA (Wakefield and Brownlee, 1989) which is a contaminant of the VLP preparation. The presence of RNA is undesired when obtaining regulatory approval for the VLP product, therefore a VLP preparation lacking RNA may be advantageous.

The VLPs of the present invention may be produced in a host cell that is characterized by lacking the ability to sialylate proteins, for example lacking sialidase, such as a plant cell, an insect cell, fungi, and other organisms including sponge, coelenterara, annelida, arthoropoda, mollusca, nemathelminthea, trochelmintes, plathelminthes, chaetognatha, tentaculate, *chlamydia*, spirochetes, gram-positive bacteria, cyanobacteria, archaebacteria, as identified in glyco-forum. The VLPs produced as described herein do not typically comprise neuramindase (NA). However, NA may be co-expressed with HA should VLPs comprising HA and NA be desired.

A VLP produced in a plant according to some aspects of the invention may be complexed with plant-derived lipids. The VLP may comprise an HA0, HA1 or HA2 peptide. The plant-derived lipids may be in the form of a lipid bilayer, and may further comprise an envelope surrounding the VLP. The plant derived lipids may comprise lipid components of the plasma membrane of the plant where the VLP is produced, including, but not limited to, phosphatidylcholine (PC), phosphatidylethanolamine (PE), glycosphingolipids, phytosterols or a combination thereof. A plant-derived lipid may alternately be referred to as a ‘plant lipid’. Examples of phytosterols are known in the art, and include, for example, stigmasterol, sitosterol, 24-methylcholesterol and cholesterol—see, for example, Mongrand et al., 2004.

VLPs may be assessed for structure and size by, for example, hemagglutination assay, electron microscopy, or by size exclusion chromatography.

For size exclusion chromatography, total soluble proteins may be extracted from plant tissue by homogenizing (Polytron) sample of frozen-crushed plant material in extraction buffer, and insoluble material removed by centrifugation. Precipitation with PEG may also be of benefit. The soluble protein is quantified, and the extract passed through a Sephacryl™ column. Blue Dextran 2000 may be used as a calibration standard. Following chromatography, fractions may be further analyzed by immunoblot to determine the protein complement of the fraction.

Without wishing to be bound by theory, the capacity of HA to bind to RBC from different animals is driven by the affinity of HA for sialic acids α2,3 or α2,3 and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guina pigs, humans and sheep (see also Ito T. et al, 1997, Virology, vol 227, p493-499; and Medeiros R et al, 2001, Virology, vol 289 p. 74-85). Examples of the species reactivity of HAs of different influenza strains is shown in Tables 2A and 2B.

TABLE 2A

Species of RBC bound by HAs of selected seasonal influenza strains.

| Seasonal | Strain | No | Origin | Horse | Turkey |
|---|---|---|---|---|---|
| H1 | A/Brisbane/59/2007 (H1N1) | 774 | Human | + | ++ |
| | A/Solomon Islands/3/2006 (H1N1) | 775 | Human | + | ++ |
| H3 | A/Brisbane/10/2007 (H3N2) | 776 | Human | + | ++ |
| | A/Wisconsin/67/2005 (H3N2) | 777 | Human | + | ++ |
| B | B/Malaysia/2506/2004 | 778 | Human | + | ++ |
| | B/Florida/4/2006 | 779 | Human | + | ++ |

TABLE 2B

Species of RBC bound by HAs of selected pandemic influenza strains

| Pandemic | Strain | No | Orignie | Horse | Turkey |
|---|---|---|---|---|---|
| H2 | A/Singapore/1/57 (H2N2) | 780 | Human | + | ++ |
| H5 | A/Anhui/1/2005 (H5N1) | 781 | Hu-Av | ++ | + |
| | A/Vietnam/1194/2004 (H5N1) | 782 | Hu-Av | ++ | + |
| H6 | A/Teal/Hong Kong/W312/97 (H6N1) | 783 | Avian | ++ | + |
| H7 | A/Equine/Prague/56 (H7N7) | 784 | Equine | ++ | ++ |
| H9 | A/Hong Kong/1073/99 (H9N2) | 785 | Human | ++ | + |

As used herein, a “protein” refers generally to a string of amino acids connected by a peptide bond, which may be folded into secondary, tertiary or quaternary structure to achieve a particular morphology. Alternately, the terms polypeptide, peptide or peptide fragments may be used in a similar context.

A fragment or portion of a protein, fusion protein or polypeptide includes a peptide or polypeptide comprising a subset of the amino acid complement of a particular protein or polypeptide, provided that the fragment can form a VLP when expressed. The fragment may, for example, comprise an antigenic region, a stress-response-inducing region, or a region comprising a functional domain of the protein or polypeptide. The fragment may also comprise a region or domain common to proteins of the same general family, or the fragment may include sufficient amino acid sequence to specifically identify the full-length protein from which it is derived.

For example, a fragment or portion may comprise from about 60% to about 100%, of the length of the full length of the protein, or any amount therebetween, provided that the fragment can form a VLP when expressed. For example, from about 60% to about 100%, from about 70% to about 100%, from about 80% to about 100%, from about 90% to about 100%, from about 95% to about 100%, of the length of the full length of the protein, or any amount therebetween. Alternately, a fragment or portion may be from about 150 to about 500 amino acids, or any amount therebetween, depending upon the HA, and provided that the fragment can form a VLP when expressed. For example, a fragment may be from 150 to about 500 amino acids, or any amount therebetween, from about 200 to about 500 amino acids, or any amount therebetween, from about 250 to about 500 amino acids, or any amount therebetween, from about 300 to about 500 or any amount therebetween, from about 350 to about 500 amino acids, or any amount therebetween, from about 400 to about 500 or any amount therebetween, from about 450 to about 500 or any amount therebetween, depending upon the HA, and provided that the fragment can form a VLP when expressed. For example, about 5, 10, 20, 30, 40 or 50 amino acids, or any amount therebetween may be removed from the C terminus, the N terminus or both the N and C terminus of an HA protein, provided that the fragment can form a VLP when expressed.

Numbering of amino acids in any given sequence are relative to the particular sequence, however one of skill can readily determine the 'equivalency' of a particular amino acid in a sequence based on structure and/or sequence. For example, if 6 N terminal amino acids were removed when constructing a clone for crystallography, this would change the specific numerical identity of the amino acid (e.g. relative to the full length of the protein), but would not alter the relative position of the amino acid in the structure.

Comparisons of a sequence or sequences may be done using a BLAST algorithm (Altschul et al., 1990. J. Mol Biol 215:403-410). A BLAST search allows for comparison of a query sequence with a specific sequence or group of sequences, or with a larger library or database (e.g. GenBank or GenPept) of sequences, and identify not only sequences that exhibit 100% identity, but also those with lesser degrees of identity. Nucleic acid or amino acid sequences may be compared using a BLAST algorithm. Furthermore the identity between two or more sequences may be determined by aligning the sequences together and determining the % identity between the sequences. Alignment may be carried out using the BLAST Algorithm (for example as available through GenBank; using default parameters: Program: blastn; Database: nr; Expect 10; filter: default; Alignment: pairwise; Query genetic Codes: Standard(1)), or BLAST2 through EMBL using default parameters: Matrix BLOSUM62; Filter: default, echofilter: on, Expect:10, cutoff: default; Strand: both; Descriptions: 50, Alignments: 50; or FASTA, using default parameters), or by manually comparing the sequences and calculating the % identity.

The present invention describes, but is not limited to, the cloning of a nucleic acid encoding HA into a plant expression vector, and the production of influenza VLPs from the plant, suitable for vaccine production. Examples of such nucleic acids include, for example, but not limited to, an influenza A/New Caledonia/20/99 (H1N1) virus HA (e.g. SEQ ID NO: 61), an HA from A/Indonesia/5/05 sub-type (H5N1) (e.g. SEQ ID NO: 60), A/Brisbane/59/2007 (H1N1) (e.g. SEQ ID NO: 36, 48, 62), A/Solomon Islands/3/2006 (H1N1) (e.g. SEQ ID NO: 37, 49, 63), A/Singapore/1/57 (H2N2) (e.g. SEQ ID NO: 42, 54, 64), A/Anhui/1/2005 (H5N1) (e.g. SEQ ID NO: 43, 55, 65), A/Vietnam/1194/2004 (H5N1) (e.g. SEQ ID NO: 44, 56, 66), A/Teal/Hong Kong/W312/97 (H6N1) (e.g. SEQ ID NO: 45, 57, 67), A/Hong Kong/1073/99 (H9N2) (e.g. SEQ ID NO: 47, 59, 68), A/Brisbane/10/2007 (H3N2) (e.g. SEQ ID NO: 38, 50, 69), A/Wisconsin/67/2005 (H3N2) (e.g. SEQ ID NO: 39, 51, 70), A/Equine/Prague/56 (H7N7) (e.g. SEQ ID NO: 46, 58, 71), B/Malaysia/2506/2004 (e.g. SEQ ID NO: 40, 52, 72), B/Florida/4/2006 (e.g. SEQ ID NO: 41, 53, 73). The corresponding clone or construct numbers for these strains is provided in Table 1. Nucleic acid sequences corresponding to SEQ ID NOs: 36-47 comprise a plastocyanin upstream and operatively linked to the coding sequence of the HA for each of the types or subtypes, as illustrated in FIGS. 28-39. Nucleic acid sequences corresponding to SEQ ID NO: 60-73 comprise an HA expression cassette comprising alfalfa plastocyanin promoter and 5' UTR, hemagglutinin coding sequence of an HA, alfalfa plastocyanin 3' UTR and terminator sequences, as illustrated in FIGS. 51-64.

The VLPs may also be used to produce reagents comprised of recombinant influenza structural proteins that self-assemble into functional and immunogenic homotypic macromolecular protein structures, including subviral influenza particles and influenza VLP, in transformed hosts cells, for example plant cells or insect cells.

Therefore, the invention provides for VLPs, and a method for producing viral VLPs in a plant expression system, from the expression of a single envelope protein. The VLPs may be influenza VLPs, or VLPs produced from other plasma membrane-derived virus including, but not limited to, Measles, Ebola, Marburg, and HIV.

Proteins from other enveloped viruses, for example but not limited to Filoviridae (e.g. Ebola virus, Marburg virus, or the like), Paramyxoviridae (e.g. Measles virus, Mumps virus, Respiratory syncytial virus, pneumoviruses, or the like), Retroviridae (e.g. Human Immunodeficiency Virus-1, Human Immunodeficiency Virus-2, Human T-Cell Leukemia Virus-1, or the like), Flaviviridae (e.g. West Nile Encephalitis, Dengue virus, Hepatitis C virus, yellow fever virus, or the like), Bunyaviridae (e.g. Hantavirus or the like), Coronaviridae (e.g. coronavirus, SARS, or the like), as would be known to those of skill in the art, may also be used. Non limiting examples of antigens that may be expressed in plasma membrane derived viruses include, the capsid protein of HIV-p24; HIV glycoproteins gp120 or gp41, Filovirus proteins including VP30 or VP35 of Ebolavirus or Gp/SGP of Marburg virus or the H protein or F protein of the Measles paramyxovirus. For example, P24 of HIV (e.g. GenBank reference gi:19172948) is the protein obtained by translation and cleavage of the gag sequence of the HIV virus genome (e.g. GenBank reference gi:9629357); gp120 and gp41 of HIV are glycoproteins obtained by translation and cleavage of the gp160 protein (e.g. GenBank reference gi:9629363), encoded by env of the HIV virus genome. VP30 of Ebolavirus (GenPept Reference gi: 55770813) is the protein obtained by translation of the vp30 sequence of the Ebolavirus genome (e.g. GenBank Reference gi:55770807); VP35 of Ebolavirus (GenPept Reference gi:55770809) is the protein obtained by translation of the vp35 sequence of the Ebolavirus genome. Gp/SGP of Marburg virus (GenPept Reference gi:296965) is the protein obtained by translation of the (sequence) of the Marburg virus genome (GenBank Reference gi:158539108). H protein (GenPept Reference gi: 9626951) is the protein of the H sequence of the Measles virus genome (GenBank Reference gi: 9626945); F protein (GenPept reference gi: 9626950) is the protein of the F sequence of the Measles virus genome.

However, other coat proteins may be used within the methods of the present invention as would be know to one of skill in the art.

The invention, therefore, provides for a nucleic acid molecule comprising a sequence encoding HIV-p24, HIV-gp120, HIV-gp41, Ebolavirus-VP30, Ebolavirus-VP35, Marburg virus Gp/SGP, Measles virus-H protein or -F protein. The nucleic acid molecule may be operatively linked to a regulatory region active in an insect, yeast or plant cell, or in a particular plant tissue.

The present invention further provides the cloning of a nucleic acid encoding an HA, for example but not limited to, human influenza A/Indonesia/5/05 virus HA (H5N1) into a plant or insect expression vector (e.g. baculovirus expression vector) and production of influenza vaccine candidates or reagents comprised of recombinant influenza structural proteins that self-assemble into functional and immunogenic homotypic macromolecular protein structures, including subviral influenza particles and influenza VLP, in transformed plant cells or transformed insect cells.

The nucleic acid encoding the HA of influenza subtypes, for example but not limited to, A/New Caledonia/20/99 (H1N1), A/Indonesia/5/05 sub-type (H5N1), A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006 may be expressed, for example, using a Baculovirus Expression System in an appropriate cell line, for example, *Spodoptera frugiperda* cells (e.g. Sf-9 cell line; ATCC PTA-4047). Other insect cell lines may also be used.

The nucleic acid encoding the HA may, alternately, be expressed in a plant cell, or in a plant. The nucleic acid encoding HA may be synthesized by reverse transcription and polymerase chain reaction (PCR) using HA RNA. As an example, the RNA may be isolated from human influenza A/New Caledonia/20/99 (H1N1) virus or human influenza A/Indonesia/5/05 (H5N1) virus, or other influenza viruses e.g. A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006, or from cells infected with an influenza virus. For reverse transcription and PCR, oligonucleotide primers specific for HA RNA, for example but not limited to, human influenza A/New Caledonia/20/99 (H1N1) virus HA sequences or human influenza A/Indonesia/5/05 (H5N1) virus HA0 sequences, or HA sequences from influenza subtypes A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006 may be used. Additionally, a nucleic acid encoding HA may be chemically synthesized using methods as would known to one of skill in the art.

The resulting cDNA copies of these genes may be cloned in a suitable expression vector as required by the host expression system. Examples of appropriate expression vectors for plants are described below, alternatively, baculovirus expression vector, for example, pFastBacl (InVitrogen), resulting in pFastBacl-based plasmids, using known methods, and information provided by the manufacturer's instructions may be used.

The present invention is further directed to a gene construct comprising a nucleic acid encoding HA, as described above, operatively linked to a regulatory element that is operative in a plant. Examples of regulatory elements operative in a plant cell and that may be used in accordance with the present invention include but are not limited to a plastocyanin regulatory region (U.S. Pat. No. 7,125,978; which is incorporated herein by reference), or a regulatory region of Ribulose 1,5-bisphosphate carboxylase/oxygenase (RuBisCO; U.S. Pat. No. 4,962,028; which is incorporated herein by reference), chlorophyll a/b binding protein (CAB; Leutwiler et al; 1986; which is incorporated herein by reference), ST-LS1 (associated with the oxygen-evolving complex of photosystem II and described by Stockhaus et al. 1987, 1989; which is incorporated herein by reference). An example of a plastocyanin regulatory region is a sequence comprising nucleotides 10-85 of SEQ ID NO: 36, or a similar region of any one of SEQ ID NOS: 37-47.

If the construct is expressed in an insect cell, examples of regulatory elements operative in an insect cell include but are not limited to the polyhedrin promoter (Possee and Howard 1987. Nucleic Acids Research 15:10233-10248), the gp64 promoter (Kogan et al, 1995. J Virology 69:1452-1461) and the like.

Therefore, an aspect of the invention provides for a nucleic acid comprising a regulatory region and a sequence encoding an influenza HA. The regulatory region may be a plastocyanin regulatory element, and the influenza HA may be selected from a group of influenza strains or subtypes, comprising A/New Caledonia/20/99 (H1N1), A/Indonesia/5/05 sub-type (H5N1), A/Brisbane/59/2007 (H1N1), A/Solomon Islands/3/2006 (H1N1), A/Singapore/1/57 (H2N2), A/Anhui/1/2005 (H5N1), A/Vietnam/1194/2004 (H5N1), A/Teal/Hong Kong/W312/97 (H6N1), A/Hong Kong/1073/99 (H9N2), A/Brisbane/10/2007 (H3N2), A/Wisconsin/67/2005 (H3N2), A/Equine/Prague/56 (H7N7), B/Malaysia/2506/2004, B/Florida/4/2006. Nucleic acid sequences comprising a plastocyanin regulatory element and an influenza HA are exemplified herein by SEQ ID NOs: 36-47.

It is known that there may be sequence differences in the sequence of influenza hemagglutinin amino acids sequences, or the nucleic acids encoding them, when influenza virus is cultured in eggs, or mammalian cells, (e.g. MDCK cells) or when isolated from an infected subject. Non-limiting examples of such differences are illustrated herein, including Example 18. Furthermore, as one of skill in the art would realize, additional variation may be observed within influenza hemagglutinins obtained from new strains as additional mutations continue to occur. Due to the known sequence variability between different influenza hemagglutinins, the present invention includes VLPs that may be made using any influenza hemagglutin provided that when expressed in a host as described herein, the influenza hemagglutin forms a VLP.

Sequence alignments and consensus sequences may be determined using any of several software packages known in the art, for example MULTALIN (F. CORPET, 1988, Nucl. Acids Res., 16 (22), 10881-10890), or sequences may be aligned manually and similarities and differences between the sequences determined.

The structure of hemagglutinins is well-studied and the structures are known to be highly conserved. When hemagglutinin structures are superimposed, a high degree of structural conservation is observed (rmsd<2A). This structural conservation is observed even though the amino acid sequence may vary in some positions (see, for example, Skehel and Wiley, 2000 Ann Rev Biochem 69:531-69; Vaccaro et al 2005). Regions of hemagglutinins are also well-conserved, for example:

Structural domains: The HA0 polyprotein is cleaved to provide mature HA. HA is a homotrimer with each monomer comprising a receptor binding domain (HA1) and a membrane-anchoring domain (HA2) linked by a single disulphide bond; the N-terminal 20 residues of the HA2 subunit may also be referred to as the HA fusion domain or sequence. A 'tail' region (internal to the membrane envelope) is also present. Each hemagglutinin comprises these regions or domains. Individual regions or domains are typically conserved in length.

All hemagglutinins contain the same number and position of intra- and inter-molecular disulfide bridges. The quantity and position on the amino acid sequence of the cysteines that participate in disulfide bridge network is conserved among the HAs. Examples of structures illustrating the characteristic intra- and intermolecular disulfide bridges and other conserved amino acids and their relative positions are described in, for example, Gamblin et al 2004 (Science 303:1838-1842). Exemplary structures and sequences include 1RVZ, 1RVX, 1RVT, 1RV0, 1RUY, 1RU7, available from the Protein Data Bank.

Cytoplasmic tail—the majority of hemagglutinins comprise 3 cysteines at conserved positions. One or more of these cysteines may be palmitoylated as a post-translational modification.

Amino acid variation is tolerated in hemagglutinins of influenza viruses. This variation provides for new strains that are continually identified. Infectivity between the new strains may vary. However, formation of hemagglutinin trimers, which subsequently form VLPs is maintained. The present invention, therefore, provides for a hemagglutinin amino acid sequence, or a nucleic acid encoding a hemagglutinin amino acid sequence, that forms VLPs in a plant, and includes known sequences and variant sequences that may develop.

FIG. 65 illustrates an example of such known variation. This figure shows a consensus amino acid sequence (SEQ ID NO: 74) for HA of the following H1N1 strains:

A/New Caledonia/20/99 (H1N1) (encoded by SEQ ID NO: 33),

A/Brisbane/59/2007 (H1N1) (SEQ ID NO: 48),

A/Solomon Islands/3/2006 (H1N1) (SEQ ID NO: 49) and SEQ ID NO: 9. X1 (position 3) is A or V; X2 (position 52) is D or N; X3 (position 90) is K or R; X4 (position 99) is K or T; X5 (position 111) is Y or H; X6 (position 145) is V or T; X7 (position 154) is E or K; X8 (position 161) is R or K; X9 (position 181) is V or A; X10 (position 203) is D or N; X11 (position 2o5) is R or K; X12 (position 210) is T or K; X13 (position 225) is R or K; X14 (position 268) is W or R; X15 (position 283) is T or N; X16 (position 290) is E or K; X17 (position 432) is I or L; X18 (position 489) is N or D.

As another example of such variation, a sequence alignment and consensus sequence for HA of A/New Caledonia/20/99 (H1N1) (encoded by SEQ ID NO: 33), A/Brisbane/59/2007 (H1N1) (SEQ ID NO: 48), A/Solomon Islands/3/2006 (H1N1) (SEQ ID NO: 49), A/PuertoRico/8/34 (H1N1) and SEQ ID NO: 9 is shown below in Table 3.

TABLE 3

Sequence alignment and consensus sequence for HA of selected H1N1 strains

```
SEQ ID NO. Sequence 1                                                  50
         75  MKAKLLVLLC  TFTATYADTI  CIGYHANNST  DTVDTVLEKN  VTVTHSVNLL
          9  MKAKLLVLLC  TFTATYADTI  CIGYHANNST  DTVDTVLEKN  VTVTHSVNLL
         48  MKVKLLVLLC  TFTATYADTI  CIGYHANNST  DTVDTVLEKN  VTVTHSVNLL
         49  MKVKLLVLLC  TFTATYADTI  CIGYHANNST  DTVDTVLEKN  VTVTHSVNLL
         76  ..........  ..........  ..........  ..........  ..........
  Consensus  mkxkllvllc  tgtatyadti  cigyhannst  dtvdtvlekn  vtvthsvnll 51                                                 100
         75  EDSHNGKLCL  LKGIAPLQLG  NCSVAGWILG  NPECELLISK  ESWSYIVETP
          9  EDSHNGKLCL  LKGIAPLQLG  NCSVAGWILG  NPECELLISK  ESWSYIVETP
         48  ENSHNGKLCL  LKGIAPLQLG  NCSVAGWILG  NPECELLISK  ESWSYIVEKP
         49  EDSHNGKLCL  LKGIAPLQLG  NCSVAGWILG  NPECELLISR  ESWSYIVEKP
         76  ..........  ..........  ..........  ..........  ..........
  Consensus  exshngklcl  lkgiaplqlg  ncsvagwilg  npecellis.  eswsyive.p 101                                                 150
         75  NPENGTCYPG  YFADYEELRE  QLSSVSSFER  FEIFPKESSW  PNHTVTGVSA
          9  NPENGTCYPG  YFADYEELRE  QLSSVSSFER  FEIFPKESSW  PNHTVTGVSA
         48  NPENGTCYPG  HFADYEELRE  QLSSVSSFER  FEIFPKESSW  PNHTVTGVSA
         49  NPENGTCYPG  HFADYEELRE  QLSSVSSFER  FEIFPKESSW  PNHTTTGVSA
         76  ..........  ..........  ..........  ..........  ..........
  Consensus  npengtcypg  xfadyeelre  qlssvssfer  feifpkessw  pnhtxtgvsa 151                                                 200
         75  SCSHNGKSSF  YRNLLWLTGK  NGLYPNLSKS  YVNNKEKEVL  VLWGVHHPPN
          9  SCSHNGKSSF  YRNLLWLTGK  NGLYPNLSKS  YVNNKEKEVL  VLWGVHHPPN
         48  SCSHNGESSF  YRNLLWLTGK  NGLYPNLSKS  YANNKEKEVL  VLWGVHHPPN
         49  SCSHNGESSF  YKNLLWLTGK  NGLYPNLSKS  YANNKEKEVL  VLWGVHHPPN
         76  ..........  ..........  ..........  ..........  ..........
  Consensus  scshngxssf  yxnllwltgk  nglypnlsks  yxnnkekevl  vlwgvhhppn 201                                                 250
         75  IGNQRALYHT  ENAYVSVVSS  HYSRRFTPEI  AKRPKVRDQE  GRINYYWTLL
          9  IGNQRALYHT  ENAYVSVVSS  HYSRRFTPEI  AKRPKVRDQE  GRINYYWTLL
         48  IGDQKALYHT  ENAYVSVVSS  HYSRKFTPEI  AKRPKVRDQE  GRINYYWTLL
         49  IGDQRALYHK  ENAYVSVVSS  HYSRKFTPEI  AKRPKVRDQE  GRINYYWTLL
         76  ..........  .....MSLLT  EVETYVLSII  PSGPLKAEIA  QRLEDVFAGK
  Consensus  igxqxalyhx  enayvsvvss  hysrxftpei  akrPkvr#qe  gRi#yywtll
```

TABLE 3-continued

Sequence alignment and consensus sequence for HA
of selected H1N1 strains

SEQ ID NO.Sequence

```
              251                                             300
        75 EPGDTIIFEA NGNLIAPWYA FALSRGFGSG IITSNAPMDE CDAKCQTPQG
         9 EPGDTIIFEA NGNLIAPWYA FALSRGFGSG IITSNAPMDE CDAKCQTPQG
        48 EPGDTIIFEA NGNLIAPRYA FALSRGFGSG IINSNAPMDK CDAKCQTPQG
        49 EPGDTIIFEA NGNLIAPRYA FALSRGFGSG IINSNAPMDK CDAKCQTPQG
        76 NTDLEVLMEW ...LKTRPIL SPLTKGILGF VFTLTVPSER GLQRRRFVQN
 Consensus #pgdt!ifEa ngnLiapxya faLsrGfgsg !itsnaPm#x cdakcqtpQg 301                                             350
        75 AINSSLPFQN VHPVTIGECP KYVRSAKLRM VT.GLRNIPS IQSRGLFGAI
         9 AINSSLPFQN VHPVTIGECP KYVRSAKLRM VT.GLRNIPS IQSRGLFGAI
        48 AINSSLPFQN VHPVTIGECP KYVRSAKLRM VT.GLRNIPS IQSRGLFGAI
        49 AINSSLPFQN VHPVTIGECP KYVRSAKLRM VT.GLRNIPS IQSRGLFGAI
        76 ALNG.....N GDPNNMDKAV KLYRKLKREI TFHGAKEISL SYSAGALASC
 Consensus AiNsslpfqN vhPvtigecp KyvRsaKlrm vtxGlr#Ips iqSrGlfgai 351                                             400
        75 AGFIEGGWTG MVDGWYGYHH QNEQGSGYAA DQKSTQNAIN GITNKVNSVI
         9 AGFIEGGWTG MVDGWYGYHH QNEQGSGYAA DQKSTQNAIN GITNKVNSVI
        48 AGFIEGGWTG MVDGWYGYHH QNEQGSGYAA DQKSTQNAIN GITNKVNSVI
        49 AGFIEGGWTG MVDGWYGYHH QNEQGSGYAA DQKSTQNAIN GITNKVNSVI
        76 MGLIYNRM.G AVTTEVAFGL VCATCEQIAD SQHRSHRQMV TTTNPLIRHE
 Consensus aGfIeggwtG mVdgwyg%hh qneqgsgyAa dQkstqnain giTNkvnsvi 401                                             450
        75 EKMNTQFTAV GKEFNKLERR MENLNKKVDD GFLDIWTYNA ELLVLLENER
         9 EKMNTQFTAV GKEFNKLERR MENLNKKVDD GFLDIWTYNA ELLVLLENER
        48 EKMNTQFTAV GKEFNKLERR MENLNKKVDD GFIDIWTYNA ELLVLLENER
        49 EKMNTQFTAV GKEFNKLERR MENLNKKVDD GFIDIWTYNA ELLVLLENER
        76 NRMVLASTTA .KAMEQMAGS SEQAAEAMEV A........S QARQMVQAMR
 Consensus #kMntqfTav gKef#k$err mE#lnkkv#d gfxdiwtyna #llv$l#neR 451                                             500
        75 TLDFHDSNVK NLYEKVKSQL KNNAKEIGNG CFEFYHKCNN ECMESVKNGT
         9 TLDFHDSNVK NLYEKVKSQL KNNAKEIGNG CFEFYHKCNN ECMESVKNGT
        48 TLDFHDSNVK NLYEKVKSQL KNNAKEIGNG CFEFYHKCND ECMESVKNGT
        49 TLDFHDSNVK NLYEKVKSQL KNNAKEIGNG CFEFYHKCND ECMESVKNGT
        76 TIGTHPSSSA GLKNDLLENL QAYQKRMGVQ MQRFK..... ..........
 Consensus TldfHdSnvk nLy#kvks#L knnaKeiGng cfeFyhkcnx ecmesvkngt 501                                             550
        75 YDYPKYSEES KLNREKIDGV KLESMGVYQI LAIYSTVASS LVLLVSLGAI
         9 YDYPKYSEES KLNREKIDGV KLESMGVYQI LAIYSTVASS LVLLVSLGAI
        48 YDYPKYSEES KLNREKIDGV KLESMGVYQI LAIYSTVASS LVLLVSLGAI
        49 YDYPKYSEES KLNREKIDGV KLESMGVYQI LAIYSTVASS LVLLVSLGAI
        76 .......... .......... .......... .......... ..........
 Consensus ydypkysees lknrekidgv klesmgvyqi laiystvass lvllvslgai 551        566
        75 SFWMCSNGSL QCRICI
         9 SFWMCSNGSL QCRICI
        48 SFWMCSNGSL QCRICI
        49 SFWMCSNGSL QCRICI
        76 .......... ......
 Consensus sfwmcsngsl qcrici
```

The consensus sequence indicates in upper case letters amino acids common to all sequences at a designated position; lower case letters indicate amino acids common to at least half, or a majority of the sequences; the symbol ! is any one of I or V; the symbol $ is any one of L or M; the symbol % is any one of F or Y; the symbol # is any one of N, D, Q, E, B or Z; the symbol "." is no amino acid (e.g. a deletion); X at position 3 is any one of A or V; X at position 52 is any one of E or N; X at position 90 is K or R; X at position 99 is T or K; X at position 111 is any one of Y or H; X at position 145 is any one of V or T; X at position 157 is K or E; X at position 162 is R or K; X at position 182 is V or A; X at position 203 is N or D; X at position 205 is R or K; X at position 210 is T or K; X at position 225 is K or Y; X at position 333 is H or a deletion; X at position 433 is I or L; X at position 49) is N or D.

As another example of such variation, a sequence alignment and consensus sequence for HA of A/Anhui/1/2005 (H5N1) (SEQ ID NO: 55), A/Vietnam/1194/2004 (H5N1) and A/Indonesia/5/2006 (H5N1) (SEQ ID NO: 10) is shown below in Table 4.

TABLE 4

Sequence alignment and consensus sequence for
HA of selected H1N1 strains

SEQ ID NO. Sequence

```
                  1                                                              50
             10   MEKIVLLLAI  VSLVKSDQIC  IGYHANNSTE  QVDTIMEKNV  TVTHAQDILE
             56   MEKIVLLFAI  VSLVKSDQIC  IGYHANNSTE  QVDTIMEKNV  TVTHAQDILE
             55   MEKIVLLLAI  VSLVKSDQIC  IGYHANNSTE  QVDTIMEKNV  TVTHAQDILE
      Consensus   MEKIVLLlAI  VSLVKSDQIC  IGYHANNSTE  QVDTIMEKNV  TVTHAQDILE 51                                                             100
             10   KTHNGKLCDL  DGVKPLILRD  CSVAGWLLGN  PMCDEFINVP  EWSYIVEKAN
             56   KTHNGKLCDL  DGVKPLILRD  CSVAGWLLGN  PMCDEFINVP  EWSYIVEKAN
             55   KTHNGKLCDL  DGVKPLILRD  CSVAGWLLGN  PMCDEFINVP  EWSYIVEKAN
      Consensus   KTHNGKLCDL  DGVKPLILRD  CSVAGWLLGN  PMCDEFINVP  EWSYIVEKAN 101                                                             150
             10   PTNDLCYPGS  FNDYEELKHL  LSRINHFEKI  QIIPKSSWSD  HEASSGVSSA
             56   PVNDLCYPGD  FNDYEELKHL  LSRINHFEKI  QIIPSKKWSS  HEASLGVSSA
             55   PANDLCYPGN  FNDYEELKHL  LSRINHFEKI  QIIPKSSWSD  HEASSGVSSA
      Consensus   PxNDLCYPGx  FNDYEELKHL  LSRINHFEKI  QIIPSKKWSd  HEASSGVSSA 151                                                             200
             10   CPYLGSPSFF  RNVVWLIKKN  STYPTIKKSY  NNTNQEDLLV  LWGIHHPNDA
             56   CPYQGKSSFF  RNVVWLIKKN  STYPTIKRSY  NNTNQEDLLV  LWGIHHPNDA
             55   CPYQGTPSFF  RNVVWLIKKN  NTYPTIKRSY  NNTNQEDLLI  LWGIHHSNDA
      Consensus   CPYqGxpSFF  RNVVWLIKKN  sTYPTIKrSY  NNTNQEDLL!  LWGIHHpNDA 201                                                             250
             10   AEQTRLYQNP  TTYISIGTST  LNQRLVPKIA  TRSKVNGQSG  RMEFFWTILK
             56   AEQTKLYQNP  TTYISVGTST  LNQRLVPRIA  TRSKVNGQSG  RMEFFWTILK
             55   AEQTKLYQNP  TTYISVGTST  LNQRLVPKIA  TRSKVNGQSG  RMDFFWTILK
      Consensus   AEQTkLYQNP  TTYIS!GTST  LNQRLVPkIA  TRSKVNGQSG  RM#FFWTILK 251                                                             300
             10   PNDAINFESN  GNFIAPEYAY  KIVKKGDSAI  MKSELEYGNC  NTKCQTPMGA
             56   PNDAINFESN  GNFIAPEYAY  KIVKKGDSTI  MKSELEYGNC  NTKCQTPMGA
             55   PNDAINFESN  GNFIAPEYAY  KIVKKGDSAI  VKSEVEYGNC  NTKCQTPIGA
      Consensus   PNDAINFESN  GNFIAPEYAY  KIVKKGDSaI  mKSE1EYGNC  NTKCQTPmGA 301                                                             350
             10   INSSMPFHNI  HPLTIGECPK  YVKSNRLVLA  TGLRNSPQRE  SRKKKRGLFG
             56   INSSMPFHNI  HPLTIGECPK  YVKSNRLVLA  TGLRNSPQRE  RRRKKRGLFG
             55   INSSMPFHNI  HPLTIGECPK  YVKSNKLVLA  TGLRNSPLRE  RRRK.RGLFG
      Consensus   INSSMPFHNI  HPLTIGECPK  YVKSNrLVLA  TGLRNSPqRE  rRRKkRGLFG 351                                                             400
             10   AIAGFIEGGW  QGMVDGWYGY  HHSNEQGSGY  AADKESTQKA  IDGVTNKVNS
             56   AIAGFIEGGW  QGMVDGWYGY  HHSNEQGSGY  AADKESTQKA  IDGVTNKVNS
             55   AIAGFIEGGW  QGMVDGWYGY  HHSNEQGSGY  AADKESTQKA  IDGVTNKVNS
      Consensus   AIAGFIEGGW  QGMVDGWYGY  HHSNEQGSGY  AADKESTQKA  IDGVTNKVNS 401                                                             450
             10   IIDKMNTQFE  AVGREFNNLE  RRIENLNKKM  EDGFLDVWTY  NAELLVLMEN
             56   IIDKMNTQFE  AVGREFNNLE  RRIENLNKKM  EDGFLDVWTY  NAELLVLMEN
             55   IIDKMNTQFE  AVGREFNNLE  RRIENLNKKM  EDGFLDVWTY  NAELLVLMEN
      Consensus   IIDKMNTQFE  AVGREFNNLE  RRIENLNKKM  EDGFLDVWTY  NAELLVLMEN 451                                                             500
             10   ERTLDFHDSN  VKNLYDKVRL  QLRDNAKELG  NGCFEFYHKC  DNECMESIRN
             56   ERTLDFHDSN  VKNLYDKVRL  QLRDNAKELG  NGCFEFYHKC  DNECMESVRN
             55   ERTLDFHDSN  VKNLYDKVRL  QLRDNAKELG  NGCFEFYHKC  DNECMESVRN
      Consensus   ERTLDFHDSN  VKNLYDKVRL  QLRDNAKELG  NGCFEFYHKC  DNECMES!RN 501                                                             550
             10   GTYNYPQYSE  EARLKREEIS  GVKLESIGTY  QILSIYSTVA  SSLALAIMMA
             56   GTYDYPQYSE  EARLKREEIS  GVKLESIGIY  QILSIYSTVA  SSLALAIMVA
             55   GTYDYPQYSE  EARLKREEIS  GVKLESIGTY  QILSIYSTVA  SSLALAIMVA
      Consensus   GTY#YPQYSE  EARLKREEIS  GVKLESIGtY  QILSIYSTVA  SSLALAIMvA 551         568
             10   GLSLWMCSNG  SLQCRICI
             56   GLSLWMCSNG  SLQCRICI
             55   GLSLWMCSNG  SLQCRICI
      Consensus   GLSLWMCSNG  SLQCRICI
```

The consensus sequence indicates in upper case letters amino acids common to all sequences at a designated position; lower case letters indicate amino acids common to at least half, or a majority of the sequences; the symbol ! is any one of I or V; the symbol $ is any one of L or M; the symbol % is any one of F or Y; the symbol # is any one of N, D, Q, E, B or Z; X at position 102 is any of T, V or A; X t position 110 is any of S, D or N; X at position 156 is any of S, K or T.

The above-illustrated and described alignments and consensus sequences are non-limiting examples of variants in hemagglutinin amino acid sequences that may be used in various embodiments of the invention for the production of VLPs in a plant.

A nucleic acid encoding an amino acid sequence may be easily determined, as the codons for each amino acid are known in the art. Provision of an amino acid sequence, therefore, teaches the degenerate nucleic acid sequences that encode it. The present invention, therefore, provides for a nucleic acid sequence encoding the hemagglutinin of those influenza strains and subtypes disclosed herein (e.g. A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56 (H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)), as well as the degenerate sequences that encode the above hemagglutinins.

Further, an amino acid sequence encoded by a nucleic acid may be easily determined, as the codon or codons for each amino acid are known. Provision of a nucleic acid, therefore, teaches an amino acid sequence encoded by it. The invention, therefore, provides for amino acid sequences of the hemagglutinin of those influenza strains and subtypes disclosed herein those disclosed herein (e.g. A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56 (H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

In plants, influenza VLPs bud from the plasma membrane (see Example 5, and FIG. 19) therefore the lipid composition of the VLPs reflects their origin. The VLPs produced according to the present invention comprise HA of one or more than one type or subtype of influenza, complexed with plant derived lipids. Plant lipids can stimulate specific immune cells and enhance the immune response induced. Plant membranes are made of lipids, phosphatidylcholine (PC) and phosphatidylethanolamine (PE), and also contain glycosphingolipids, saponins, and phytosterols. Additionally, lipid rafts are also found in plant plasma membranes—these microdomains are enriched in sphingolipids and sterols. In plants, a variety of phytosterols are known to occur, including stigmasterol, sitosterol, 24-methylcholesterol and cholesterol (Mongrand et al., 2004).

PC and PE, as well as glycosphingolipids can bind to CD1 molecules expressed by mammalian immune cells such as antigen-presenting cells (APCs) like dendritic cells and macrophages and other cells including B and T lymphocytes in the thymus and liver (Tsuji M., 2006). CD1 molecules are structurally similar to major histocompatibility complex (MHC) molecules of class I and their role is to present glycolipid antigens to NKT cells (Natural Killer T cells). Upon activation, NKT cells activate innate immune cells such as NK cells and dendritic cells and also activate adaptive immune cells like the antibody-producing B cells and T-cells.

A variety of phytosterols may be found in a plasma membrane—the specific complement may vary depending on the species, growth conditions, nutrient resources or pathogen state, to name a few factors. Generally, beta-sitosterol is the most abundant phytosterol.

The phytosterols present in an influenza VLP complexed with a lipid bilayer, such as an plasma-membrane derived envelope may provide for an advantageous vaccine composition. Without wishing to be bound by theory, plant-made VLPs complexed with a lipid bilayer, such as a plasma-membrane derived envelope, may induce a stronger immune reaction than VLPs made in other expression systems, and may be similar to the immune reaction induced by live or attenuated whole virus vaccines.

Therefore, in some embodiments, the invention provides for a VLP complexed with a plant-derived lipid bilayer. In some embodiments the plant-derived lipid bilayer may comprise the envelope of the VLP.

The VLP produced within a plant may induce an HA comprising plant-specific N-glycans. Therefore, this invention also provides for a VLP comprising HA having plant specific N-glycans.

Furthermore, modification of N-glycan in plants is known (see for example U.S. 60/944,344; which is incorporated herein by reference) and HA having modified N-glycans may be produced. HA comprising a modified glycosylation pattern, for example with reduced fucosylated, xylosylated, or both, fucosylated and xylosylated, N-glycans may be obtained, or HA having a modified glycosylation pattern may be obtained, wherein the protein lacks fucosylation, xylosylation, or both, and comprises increased galatosylation. Furthermore, modulation of post-translational modifications, for example, the addition of terminal galactose may result in a reduction of fucosylation and xylosylation of the expressed HA when compared to a wild-type plant expressing HA.

For example, which is not to be considered limiting, the synthesis of HA having a modified glycosylation pattern may be achieved by co-expressing the protein of interest along with a nucleotide sequence encoding beta-1.4galactosyltransferase (GalT), for example, but not limited to mammalian GalT, or human GalT however GalT from another sources may also be used. The catalytic domain of GalT may also be fused to a CTS domain (i.e. the cytoplasmic tail, transmembrane domain, stem region) of N-acetylglucosaminyl transferase (GNT1), to produce a GNT1-GalT hybrid enzyme, and the hybrid enzyme may be co-expressed with HA. The HA may also be co-expressed along with a nucleotide sequence encoding N-acetylglucosaminyltrasnferase III (GnT-III), for example but not limited to mammalian GnT-III or human GnT-III, GnT-III from other sources may also be used. Additionally, a GNT1-GnT-III hybrid enzyme, comprising the CTS of GNT1 fused to GnT-III may also be used.

Therefore the present invention also includes VLP's comprising HA having modified N-glycans.

Without wishing to be bound by theory, the presence of plant N-glycans on HA may stimulate the immune response by promoting the binding of HA by antigen presenting cells. Stimulation of the immune response using plant N glycan has been proposed by Saint-jore-Dupas et al. (2007). Furthermore, the conformation of the VLP may be advantageous for the presentation of the antigen, and enhance the adjuvant effect of VLP when complexed with a plant derived lipid layer.

By "regulatory region" "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (FIG. 1*b* or SEQ ID NO:23); U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165), actin 2 (An et al., 1996*, Plant J.,* 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed.

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The one or more than one nucleotide sequence of the present invention may be expressed in any suitable plant host that is transformed by the nucleotide sequence, or constructs, or vectors of the present invention. Examples of suitable hosts include, but are not limited to, agricultural crops including alfalfa, canola, *Brassica* spp., maize, *Nicotiana* spp., alfalfa, potato, ginseng, pea, oat, rice, soybean, wheat, barley, sunflower, cotton and the like.

The one or more chimeric genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon. One or more of the chimeric genetic constructs of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence.

Non-limiting examples of suitable 3' regions are the 3' transcribed non-translated regions containing a polyadenylation signal of *Agrobacterium* tumor inducing (Ti) plasmid genes, such as the nopaline synthase (Nos gene) and plant genes such as the soybean storage protein genes, the small subunit of the ribulose-1, 5-bisphosphate carboxylase (ssRUBISCO; U.S. Pat. No. 4,962,028; which is incorporated herein by reference) gene, the promoter used in regulating plastocyanin expression (Pwee and Gray 1993; which is incorporated herein by reference). An example of a plastocyanin promoter is described in U.S. Pat. No. 7,125,978 (which is incorporated herein by reference)

As described herein, promoters comprising enhancer sequences with demonstrated efficiency in leaf expression, have been found to be effective in transient expression. Without wishing to be bound by theory, attachment of upstream regulatory elements of a photosynthetic gene by attachment to the nuclear matrix may mediate strong expression. For example up to −784 from the translation start site of the pea plastocyanin gene may be used mediate strong reporter gene expression.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

Also considered part of this invention are transgenic plants, plant cells or seeds containing the chimeric gene construct of the present invention. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

Also considered part of this invention are transgenic plants, trees, yeast, bacteria, fungi, insect and animal cells containing the chimeric gene construct comprising a nucleic acid encoding recombinant HA0 for VLP production, in accordance with the present invention.

The regulatory elements of the present invention may also be combined with coding region of interest for expression within a range of host organisms that are amenable to transformation, or transient expression. Such organisms include, but are not limited to plants, both monocots and dicots, for example but not limited to corn, cereal plants, wheat, barley, oat, *Nicotiana* spp, *Brassica* spp, soybean, bean, pea, alfalfa, potato, tomato, ginseng, and *Arabidopsis*.

Methods for stable transformation, and regeneration of these organisms are established in the art and known to one of skill in the art. The method of obtaining transformed and regenerated plants is not critical to the present invention.

By "transformation" it is meant the stable interspecific transfer of genetic information (nucleotide sequence) that is manifested genotypically, phenotypically or both. The interspecific transfer of genetic information from a chimeric construct to a host may be heritable and the transfer of genetic information considered stable, or the transfer may be transient and the transfer of genetic information is not inheritable.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. However, it is also contemplated that the plant material may be subjected to minimal processing steps as defined below, or more rigorous processing, including partial or substantial protein purification using techniques commonly known within the art including, but not limited to chromatography, electrophoresis and the like.

By the term "minimal processing" it is meant plant matter, for example, a plant or portion thereof comprising a protein of interest which is partially purified to yield a plant extract, homogenate, fraction of plant homogenate or the like (i.e. minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

Examples of a subject or target organism that the VLPs of the present invention may be administered to include, but are not limited to, humans, primates, birds, water fowl, migratory birds, quail, duck, geese, poultry, chicken, swine, sheep, equine, horse, camel, canine, dogs, feline, cats, tiger, leopard, civet, mink, stone marten, ferrets, house pets, livestock, rabbits, mice, rats, guinea pigs or other rodents, seal, whale and the like. Such target organisms are exemplary, and are not to be considered limiting to the applications and uses of the present invention.

It is contemplated that a plant comprising the protein of interest, or expressing the VLP comprising the protein of interest may be administered to a subject or target organism, in a variety of ways depending upon the need and the situation. For example, the protein of interest obtained from the plant may be extracted prior to its use in either a crude, partially purified, or purified form. If the protein is to be purified, then it may be produced in either edible or non-edible plants. Furthermore, if the protein is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to an animal with little or not further processing it is preferred that the plant tissue being administered is edible.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristexa virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

Furthermore, VLPs may be produced that comprise a combination of HA subtypes. For example, VLPs may comprise one or more than one HA from the subtype H1, H2, H3, H4, H5, H6, H7, H8, H9, H10, H11, H12, H13, H14, H15, H16, or a combination thereof. Selection of the combination of HAs may be determined by the intended use of the vaccine prepared from the VLP. For example a vaccine for use in inoculating birds may comprise any combination of HA subtypes, while VLPs useful for inoculating humans may comprise subtypes one or more than one of subtypes H1, H2, H3, H5. However, other HA subtype combinations may be prepared depending upon the use of the VLP. In order to produce VLPs comprising combinations of HA subtypes, the desired HA subtype may be co-expressed within the same cell, for example a plant cell.

Furthermore, VLPs produced as described herein do not comprise neuraminidase (NA). However, NA may be co-expressed with HA should VLPs comprising HA and NA be desired.

Therefore, the present invention further includes a suitable vector comprising the chimeric construct suitable for use with either stable or transient expression systems. The genetic information may be also provided within one or more than one construct. For example, a nucleotide sequence encoding a protein of interest may be introduced in one construct, and a second nucleotide sequence encoding a protein that modifies glycosylation of the protein of interest may be introduced using a separate construct. These nucleotide sequences may then be co-expressed within a plant. However, a construct comprising a nucleotide sequence encoding both the protein of interest and the protein that modifies glycosylation profile of the protein of interest may also be used. In this case the nucleotide sequence would comprise a first sequence comprising a first nucleic acid sequence encoding the protein of interest operatively linked to a promoter or regulatory region, and a second sequence comprising a second nucleic acid sequence encoding the protein that modifies the glycosylation profile of the protein of interest, the second sequence operatively linked to a promoter or regulatory region.

By "co-expressed" it is meant that two, or more than two, nucleotide sequences are expressed at about the same time within the plant, and within the same tissue of the plant. However, the nucleotide sequences need not be expressed at exactly the same time. Rather, the two or more nucleotide sequences are expressed in a manner such that the encoded products have a chance to interact. For example, the protein that modifies glycosylation of the protein of interest may be expressed either before or during the period when the protein of interest is expressed so that modification of the glycosylation of the protein of interest takes place. The two or more than two nucleotide sequences can be co-expressed using a transient expression system, where the two or more sequences are introduced within the plant at about the same time under conditions that both sequences are expressed. Alternatively, a platform plant comprising one of the nucleotide sequences, for example the sequence encoding the protein that modifies the glycosylation profile of the protein of interest, may be transformed, either transiently or in a stable manner, with an additional sequence encoding the protein of interest. In this case, the sequence encoding the protein that modifies the glycosylation profile of the protein of interest may be expressed within a desired tissue, during a desired stage of development, or its expression may be induced using an inducible promoter, and the additional sequence encoding the protein of interest may be expressed under similar conditions and in the same tissue, to ensure that the nucleotide sequences are co-expressed.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach, *Methods for Plant Molecular Biology*, Academy Press, New York VIII, pp. 421-463 (1988); Geierson and Corey, *Plant Molecular Biology*, 2d Ed. (1988); and Miki and Iyer, *Fundamentals of Gene Transfer in Plants*. In *Plant Metabolism*, 2d Ed. D T. Dennis, D H Turpin, D D Lefebrve, D B Layzell (eds), Addison Wesly, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Methods for Plant Molecular Biology (Weissbach and Weissbach, eds., Academic Press Inc., 1988), Methods in Plant Molecular Biology (Schuler and Zielinski, eds., Academic Press Inc., 1989), Liu and Lomonossoff (J. Virol Meth, 105:343-348, 2002,), U.S. Pat. Nos. 4,945,050; 5,036, 006; and 5,100,792, U.S. patent application Ser. No. 08/438, 666, filed May 10, 1995, and Ser. No. 07/951,715, filed Sep. 25, 1992, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al. 1997 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage of t-DNA inside the nucleus is transient.

If the nucleotide sequence of interest encodes a product that is directly or indirectly toxic to the plant, then by using the method of the present invention, such toxicity may be reduced throughout the plant by selectively expressing the nucleotide sequence of interest within a desired tissue or at a desired stage of plant development. In addition, the limited period of expression resulting from transient expression may reduce the effect when producing a toxic product in the plant. An inducible promoter, a tissue-specific promoter, or a cell specific promoter, may be used to selectively direct expression of the sequence of interest.

The recombinant HA VLPs of the present invention can be used in conjunction with existing influenza vaccines, to supplement the vaccines, render them more efficacious, and to reduce the administration dosages necessary. As would be known to a person of skill in the art, the vaccine may be directed against one or more than one influenza virus. Examples of suitable vaccines include, but are not limited to those commercially available from Sanofi-Pasteur, ID Biomedical, Merial, Sinovac, Chiron, Roche, MedImmune, GlaxoSmithKline, Novartis, Sanofi-Aventis, Serono, Shire Pharmaceuticals and the like.

If desired, the VLPs of the present invention may be admixed with a suitable adjuvant as would be known to one of skill in the art. Furthermore, the VLP may be used in a vaccine composition comprising an effective dose of the VLP for the treatment of a target organism, as defined above. Furthermore, the VLP produced according to the present invention may be combined with VLPs obtained using different influenza proteins, for example, neuraminidase (NA).

Therefore, the present invention provides a method for inducing immunity to influenza virus infection in an animal or target organism comprising administering an effective dose of a vaccine comprising one or more than one VLP. The vaccine may be administered orally, intradermally, intranasally, intramuscularly, intraperitoneally, intravenously, or subcutaneously.

Administration of VLPs produced according to the present invention is described in Example 6. Administration of plant-made H5 VLP resulted in a significantly higher response when compared to administration of soluble HA (see FIGS. 21A and 21B).

Figure 26A:
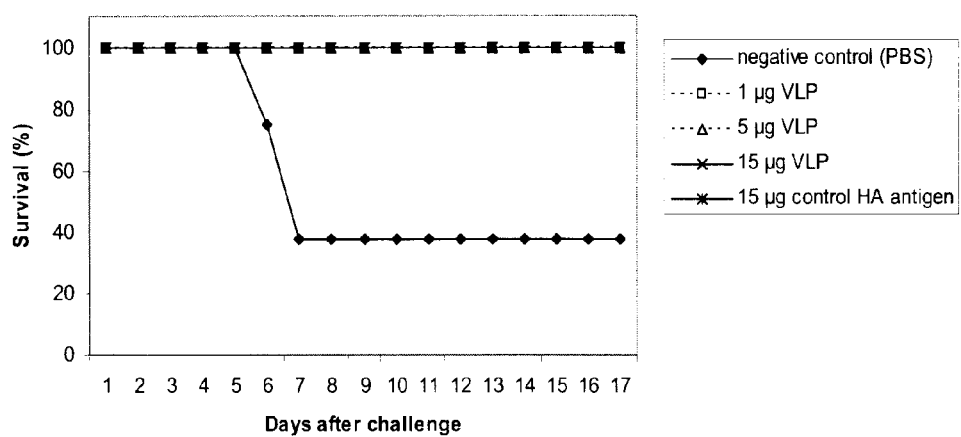
FIG. 26(A) Survival rate of mice after challenge with 10 $LD_{50}$ ($4.09\times10^5$ $CCID_{50}$) of plant made VLP H5, influenza strain A/Turkey/582/06 (H5N1).

As shown in FIGS. 26A and 26 B a subject administered A/Indonesia/5/05 H5 VLPs provided cross-protection to a challenge with influenza A/Turkey/582/06 (H5N1; "Turkey H5N1"). Administration of Indonesia H5 VLPs before challenge did not result in any loss of body mass. However in subject not administered H5VLPs, but challenged with Turkey H5N1, exhibited significant loss of body mass, and several subject died.

These data, therefore, demonstrate that plant-made influenza VLPs comprising the H5 hemagglutinin viral protein induce an immune response specific for pathogenic influenza strains, and that virus-like particles may bud from a plant plasma membrane.

Therefore, the present invention provides a composition comprising an effective dose of a VLP comprising an influenza virus HA protein, one or more than one plant lipid, and a pharmaceutically acceptable carrier. The influenza virus HA protein may be H5 Indonesia/5/2006. Also provided is a method of inducing immunity to an influenza virus infection in a subject. The method comprising administering the virus like particle comprising an influenza virus HA protein, one or more than one plant lipid, and a pharmaceutically acceptable carrier. The virus like particle may be administered to a subject orally, intradermally, intranasally, intramusclarly, intraperitoneally, intravenously, or subcutaneously.

Compositions according to various embodiments of the invention may comprise VLPs of two or more influenza strains or subtypes. "Two or more" refers to two, three, four, five, six, seven, eight, nine, 10 or more strains or subtypes. The strains or subtypes represented may be of a single subtype (e.g. all H1N1, or all H5N1), or may be a combination of subtypes. Exemplary subtype and strains include, but are not limited to, those disclosed herein (e.g. A/New Caledonia/20/99 (H1N1)A/Indonesia/5/2006 (H5N1), A/chicken/New York/1995, A/herring gull/DE/677/88 (H2N8), A/Texas/32/2003, A/mallard/MN/33/00, A/duck/Shanghai/1/2000, A/northern pintail/TX/828189/02, A/Turkey/Ontario/6118/68(H8N4), A/shoveler/Iran/G54/03, A/chicken/Germany/N/1949(H10N7), A/duck/England/56 (H11N6), A/duck/Alberta/60/76(H12N5), A/Gull/Maryland/704/77(H13N6), A/Mallard/Gurjev/263/82, A/duck/Australia/341/83 (H15N8), A/black-headed gull/Sweden/5/99 (H16N3), B/Lee/40, C/Johannesburg/66, A/PuertoRico/8/34 (H1N1), A/Brisbane/59/2007 (H1N1), A/Solomon Islands 3/2006 (H1N1), A/Brisbane 10/2007 (H3N2), A/Wisconsin/67/2005 (H3N2), B/Malaysia/2506/2004, B/Florida/4/2006, A/Singapore/1/57 (H2N2), A/Anhui/1/2005 (H5N1), A/Vietnam/1194/2004 (H5N1), A/Teal/HongKong/W312/97 (H6N1), A/Equine/Prague/56 (H7N7), A/HongKong/1073/99 (H9N2)).

The choice of combination of strains and subtypes may depend on the geographical area of the subjects likely to be exposed to influenza, proximity of animal species to a human population to be immunized (e.g. species of waterfowl, agricultural animals such as swine, etc) and the strains they carry, are exposed to or are likely to be exposed to, predictions of antigenic drift within subtypes or strains, or combinations of these factors. Examples of combinations used in past years are available. Some or all of these strains may be employed in the combinations shown, or in other combinations, in the production of a vaccine composition.

More particularly, exemplary combinations may include VLPs from two or more strains or subtypes selected from the group comprising: A/Brisbane/59/2007 (H1N1), an A/Brisbane/59/2007 (H1N1)-like virus, A/Brisbane/10/2007 (H3N2), an A/Brisbane/10/2007 (H3N2)-like virus, B/Florida/4/2006 or an B/Florida/4/2006-like virus.

Another exemplary combination may include VLPs from two or more strains or subtypes selected from the group comprising A/Indonesia/5/2005, an A/Indonesia/5/2005-like virus, A/Vietnam/1194/2004, an A/Vietnam/1194/2004-like virus, A/Anhui/1/05, an A/Anhui/1/05-like virus, A/goose/Guiyang/337/2006, A/goose/Guiyang/337/2006-like virus, A/chicken/Shanxi/2/2006, or A/chicken/Shanxi/2/2006-like virus.

Another exemplary combination may include VLPs of A/Chicken/Italy/13474/99 (H7 type) or A/Chicken/British Columbia/04 (H7N3) strains of influenza.

Another exemplary combination may include VLPs of A/Chicken/HongKong/G9/97 or A/HongKong/1073/99. Another exemplary combination may comprise VLPs of A/Solomon Islands/3/2006. Another exemplary combination may comprise VLPs of A/Brisbane/10/2007. Another exemplary combination may comprise VLPs of A/Wisconsin/67/2005. Another exemplary combination may comprise VLPs of the B/Malaysia/2506/2004, B/Florida/4/2006 or B/Brisbane/3/2007 strains or subtypes.

The two or more VLPs may be expressed individually, and the purified or semi-purified VLPs subsequently combined. Alternately, the VLPs may be co-expressed in the same host, for example a plant. The VLPs may be combined or produced in a desired ratio, for example about equivalent ratios, or may be combined in such a manner that one subtype or strain comprises the majority of the VLPs in the composition.

Therefore, the invention provides for compositions comprising VLPs of two or more strains or subtypes.

Figure 22A:
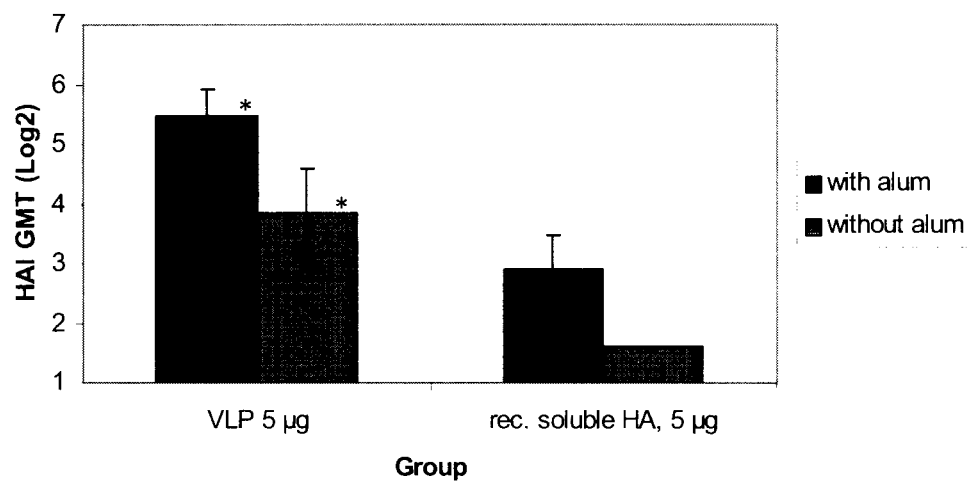
FIG. 22(A) Effect of alum on immunogenicity of the VLPs in mice immunized through intramuscular injection.
Figure 22B:
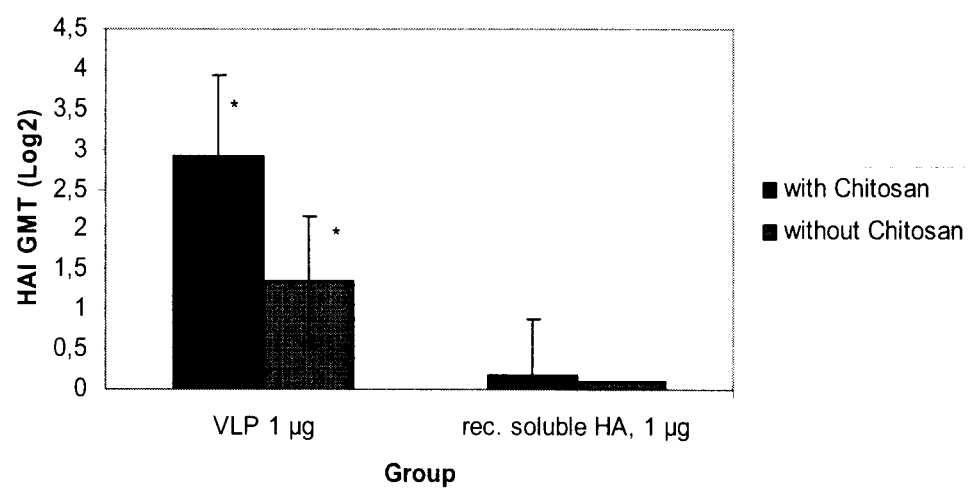
FIG. 22(B) Effect of Chitosan on immunogenicity of the VLPs in mice immunized through intranasal administration. HAI antibody responses were measured using inactivated whole H5N1 viruses (A/Indonesia/5/05). GMT: geometric mean titer. Values are the GMT (log 2) of reciprocal end-point titers of five mice per group. Bars represent mean deviation. * $p<0.05$ compared to the corresponding recombinant soluble HA.
Figure 23A:
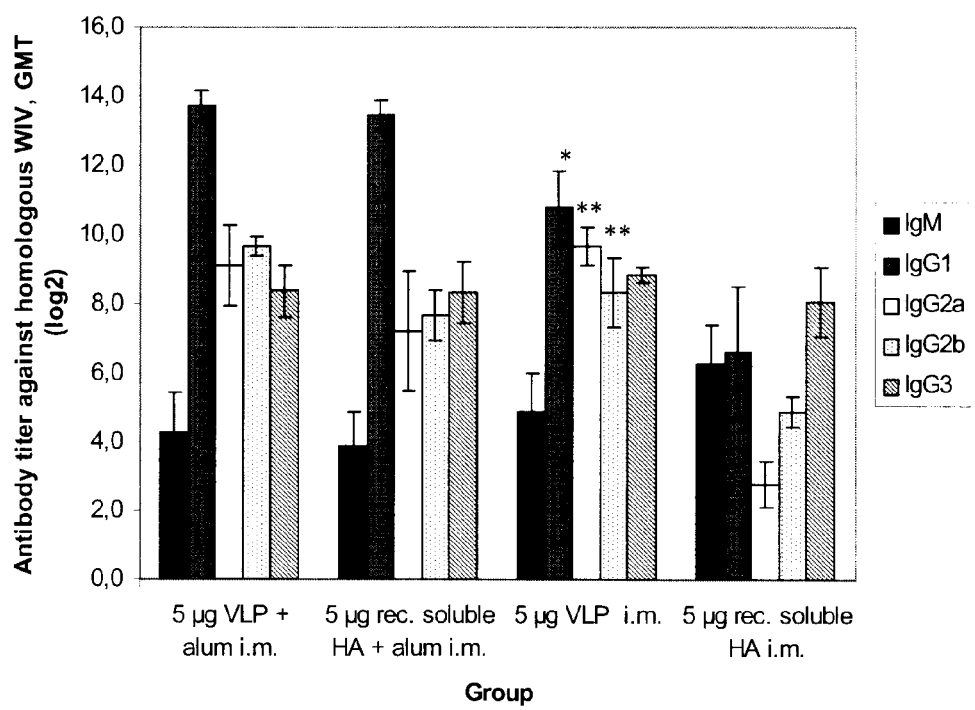
FIG. 23(A) Antibody response to VLP administration using Anti-Indonesia/5/05 immunoglobulin isotype in mice vaccinated with intramuscular injection, 30 days after boost. Values are the GMT (log 2) of reciprocal end-point titers of five mice per group. ELISA performed using whole inactivated viruses as the coating agent. Bars represent mean deviation. * $p<0.05$, ** $p<0.001$ compared to the corresponding recombinant soluble HA.

VLPs of enveloped viruses generally acquire their envelope from the membrane they bud through. Plant plasma membranes have a phytosterol complement that may have immunostimulatory effects. To investigate this possibility, plant-made H5 VLPs were administered to animals in the presence or absence of an adjuvant, and the HAI (hemagglutination inhibition antibody response) determined (FIGS. 22A, 22B). In the absence of an added adjuvant plant-made H5 VLPs demonstrate a significant HAI, indicative of a systemic immune response to administration of the antigen. Furthermore, the antibody isotype profiles of VLPs administered in the present or absence of adjuvant are similar (FIG. 23A).

Table 5 lists sequences provided in various embodiments of the invention.

TABLE 5

Sequence description for sequence identifiers.

| SEQ ID No | Sequence Description | In Disclosure |
|---|---|---|
| 1 | N terminal H1 fragment | FIG. 5a |
| 2 | C terminal H1 fragment | FIG. 5b |
| 3 | H5 coding sequence | FIG. 6 |
| 4 | primer Plato-443c | FIG. 7a |
| 5 | primer SpHA(Ind)-Plasto.r | FIG. 7b |
| 6 | primer Plasto-SpHA(Ind).c | FIG. 7c |
| 7 | primer HA(Ind)-Sac.r | FIG. 7d |
| 8 | Sequence of the alfalfa plastocyanin-based expression cassette used for the expression of H1 | FIG. 1 |
| 9 | HA1 peptide sequence (A/New Caledonia/20/99) | FIG. 8a |
| 10 | HA5 peptide sequence (A/Indonesia/5/2006) | FIG. 8b |
| 11 | Influenza A Subtype H7 coding sequence (A/chicken/New York/1995) | FIG. 9 |
| 12 | Influenza A Subtype H2 coding sequence (A/herring gull/DE/677/88 (H2N8)) | FIG. 10a |
| 13 | Influenza A Subtype H3 coding sequence (A/Texas/32/2003) | FIG. 10b |
| 14 | Influenza A Subtype H4 coding sequence (A/mallard/MN/33/00) | FIG. 10c |
| 15 | Influenza A Subtype H5 coding sequence (A/duck/Shanghai/1/2000) | FIG. 10d |
| 16 | Influenza A Subtype H6 coding sequence (A/northern pintail/TX/828189/02) | FIG. 10e |
| 17 | Influenza A Subtype H8 coding sequence (A/Turkey/Ontario/6118/68(H8N4)) | FIG. 10f |
| 18 | Influenza A Subtype H9 coding sequence (A/shoveler/Iran/G54/03) | FIG. 10g |
| 19 | Influenza A Subtype H10 coding sequence (A/chicken/Germany/N/1949 (H10N7)) | FIG. 10h |
| 20 | Influenza A Subtype H11 coding sequence (A/duck/England/56(H11N6)) | FIG. 10i |
| 21 | Influenza A Subtype H12 coding sequence (A/duck/Alberta/60/76(H12N5)) | FIG. 10j |
| 22 | Influenza A Subtype H13 coding sequence (A/Gull/Maryland/704/77 (H13N6)) | FIG. 10k |
| 23 | Influenza A Subtype H14 coding sequence (A/Mallard/Gurjev/263/82) | FIG. 10l |
| 24 | Influenza A Subtype H15 coding sequence (A/duck/Australia/341/83 (H15N8)) | FIG. 10m |
| 25 | Influenza A Subtype H16 coding sequence (A/black-headed gull/Sweden/5/99(H16N3)) | FIG. 10n |
| 26 | Influenza B HA coding sequence (B/Lee/40) | FIG. 10o |
| 27 | Influenza C HA coding sequence (C/Johannesburg/66) | FIG. 10p |
| 28 | Complete HA0 H1 sequence | FIG. 5c |
| 29 | Primer XmaI-pPlas.c | FIG. 10q |
| 30 | Primer SacI-ATG-pPlas.r | FIG. 10r |
| 31 | Primer SacI-PlasTer.c | FIG. 10s |
| 32 | Primer EcoRI-PlasTer.r | FIG. 10t |

TABLE 5-continued

Sequence description for sequence identifiers.

| SEQ ID No | Sequence Description | In Disclosure |
|---|---|---|
| 33 | A/New Caledonia/20/99 (H1N1) GenBank Accession No. AY289929 | FIG. 16 |
| 34 | M. Sativa protein disulfide isomerase GenBank Accession No. Z11499 | FIG. 17 |
| 35 | A/.PuertoRico/8/34 (H1N1) GenBank Accession No. NC_002016.1 | FIG. 18 |
| 36 | Clone 774: DNA from DraIII to Sac1 comprising plastocyanin regulatory region operatively linked to sequence encoding HA of A/Brisbane/59/2007 (H1N1) | FIG. 28 |
| 37 | Clone 775: DNA from DraIII to Sac1comprising plastocyanin regulatory region operatively linked to sequence encoding HA of A/Solomon Islands 3/2006 (H1N1) | FIG. 29 |
| 38 | Clone 776: DNA from DraIII to Sac1comprising plastocyanin regulatory region operatively linked to sequence encoding HA of A/Brisbane 10/2007 (H3N2) | FIG. 30 |
| 39 | Clone 777: DNA from DraIII to Sac1comprising plastocyanin regulatory region operatively linked to sequence encoding HA of A/Wisconsin/67/2005 (H3N2) | FIG. 31 |
| 40 | Clone 778: DNA from DraIII to Sac1comprising plastocyanin regulatory region operatively linked to sequence encoding HA of B/Malaysia/2506/2004 | FIG. 32 |
| 41 | Clone 779: DNA from DraIII to Sac1comprising plastocyanin regulatory region operatively linked to sequence encoding HA of B/Florida/4/2006 | FIG. 33 |
| 42 | Clone 780: DNA from DraIII to Sac1comprising plastocyanin regulatory region operatively linked to sequence encoding HA of A/Singapore/1/57 (H2N2) | FIG. 34 |
| 43 | Clone 781: DNA from DraIII to Sac1comprising plastocyanin regulatory region operatively linked to sequence encoding HA of A/Anhui/1/2005 (H5N1) | FIG. 35 |
| 44 | Clone 782: DNA from DraIII to Sac1comprising plastocyanin regulatory region operatively linked to sequence encoding HA of A/Vietnam/1194/2004 (H5N1) | FIG. 36 |
| 45 | Clone 783: DNA from DraIII to Sac1comprising plastocyanin regulatory region operatively linked to sequence encoding HA of A/Teal/HongKong/W312/97 (H6N1) | FIG. 37 |
| 46 | Clone 784: DNA from DraIII to Sac1comprising plastocyanin regulatory region operatively linked to sequence encoding HA of A/Equine/Prague/56 (H7N7) | FIG. 38 |
| 47 | Clone 785: DNA from DraIII to Sac1comprising plastocyanin regulatory region operatively linked to sequence encoding HA of A/HongKong/1073/99 (H9N2) | FIG. 39 |
| 48 | Clone 774 HA amino acid sequence A/Brisbane/59/2007 (H1N1) | FIG. 40A |
| 49 | Clone 775 HA amino acid sequence A/Solomon Islands 3/2006 (H1N1) | FIG. 40B |
| 50 | Clone 776 HA amino acid sequence A/Brisbane 10/2007 (H3N2) | FIG. 41A |
| 51 | Clone 777 HA amino acid sequence A/Wisconsin/67/2005 (H3N2) | FIG. 41B |
| 52 | Clone 778 HA amino acid sequence B/Malaysia/2506/2004 | FIG. 42A |
| 53 | Clone 779 HA amino acid sequence B/Florida/4/2006 | FIG. 42B |
| 54 | Clone 780 HA amino acid sequence A/Singapore/1/57 (H2N2) | FIG. 43A |
| 55 | Clone 781 HA amino acid sequence A/Anhui/1/2005 (H5N1) | FIG. 43B |
| 56 | Clone 782 HA amino acid sequence A/Vietnam/1194/2004 (H5N1) | FIG. 44A |
| 57 | Clone 783 HA amino acid sequence A/Teal/HongKong/W312/97 (H6N1) | FIG. 44B |
| 58 | Clone 784 HA amino acid sequence A/Equine/Prague/56 (H7N7) | FIG. 45A |
| 59 | Clone 785 HA amino acid sequence A/HongKong/1073/99 (H9N2) | FIG. 45B |
| 60 | HA expression cassette comprising alfalfa plastocyanin promoter and 5' UTR, hemagglutinin coding sequence of H5 from A/Indonesia/5/2005 (Construct # 660), alfalfa plastocyanin 3' UTR and terminator sequences | FIG. 51 |
| 61 | HA expression cassette comprising alfalfa plastocyanin promoter and 5' UTR, hemagglutinin coding sequence of H1 from A/New Caledonia/20/1999 (Construct # 540), alfalfa plastocyanin 3' UTR and terminator sequences | FIG. 52 |
| 62 | HA expression cassette comprising alfalfa plastocyanin promoter and 5' UTR, hemagglutinin coding sequence of H1 from A/Brisbane/59/2007 (construct #774), alfalfa plastocyanin 3' UTR and terminator sequences | FIG. 53 |
| 63 | HA expression cassette comprising alfalfa plastocyanin promoter and 5' UTR, hemagglutinin coding sequence of H1 from A/Solomon Islands/3/2006 (H1N1) (construct #775), alfalfa plastocyanin 3' UTR and terminator sequences | FIG. 54 |
| 64 | HA expression cassette comprising alfalfa plastocyanin promoter and 5' UTR, hemagglutinin coding sequence of H2 from A/Singapore/1/57 (H2N2) (construct # 780), alfalfa plastocyanin 3' UTR and terminator sequences | FIG. 55 |
| 65 | HA expression cassette comprising alfalfa plastocyanin promoter and 5' UTR, hemagglutinin coding sequence of H5 from A/Anhui/1/2005 (H5N1) (Construct # 781), alfalfa plastocyanin 3' UTR and terminator sequences | FIG. 56 |
| 66 | HA expression cassette comprising alfalfa plastocyanin promoter and 5' UTR, hemagglutinin coding sequence of H5 from A/Vietnam/1194/2004 (H5N1) (Construct # 782), alfalfa plastocyanin 3' UTR and terminator sequences | FIG. 57 |
| 67 | HA expression cassette comprising alfalfa plastocyanin promoter and 5' UTR, hemagglutinin coding sequence of H6 from A/Teal/Hong Kong/W312/97 (H6N1) (Construct # 783), alfalfa plastocyanin 3' UTR and terminator sequences | FIG. 58 |
| 68 | HA expression cassette comprising alfalfa plastocyanin promoter and 5' UTR, hemagglutinin coding sequence of H9 from A/Hong Kong/1073/99 (H9N2) (Construct # 785), alfalfa plastocyanin 3' UTR and terminator sequences | FIG. 59 |
| 69 | HA expression cassette comprising alfalfa plastocyanin promoter and 5' UTR, hemagglutinin coding sequence of H3 from A/Brisbane/10/2007 (H3N2), alfalfa plastocyanin 3' UTR and terminator sequences | FIG. 60 |
| 70 | HA expression cassette comprising alfalfa plastocyanin promoter and 5' UTR, hemagglutinin coding sequence of H3 from A/Wisconsin/67/2005 (H3N2), alfalfa | FIG. 61 |

TABLE 5-continued

Sequence description for sequence identifiers.

| SEQ ID No | Sequence Description | In Disclosure |
|---|---|---|
| | plastocyanin 3' UTR and terminator sequences | |
| 71 | HA expression cassette comprising alfalfa plastocyanin promoter and 5' UTR, hemagglutinin coding sequence of H7 from A/Equine/Prague/56 (H7N7), alfalfa plastocyanin 3' UTR and terminator sequences | FIG. 62 |
| 72 | HA expression cassette comprising alfalfa plastocyanin promoter and 5' UTR, hemagglutinin coding sequence of HA from B/Malaysia/2506/2004, alfalfa plastocyanin 3' UTR and terminator sequences | prophetic FIG. 63 |
| 73 | HA expression cassette comprising alfalfa plastocyanin promoter and 5' UTR, hemagglutinin coding sequence of HA from B/Florida/4/2006, alfalfa plastocyanin 3' UTR and terminator sequences | FIG. 64 |
| 74 | Consensus of SEQ ID NO: 49, 48, 33 and 9 | FIG. 65 |
| 75 | Amino acid sequence of H1 New Caledonia (AAP34324.1) encoded by SEQ ID NO: 33 | FIG. 67 |
| 76 | Amino acid sequence of H1 Puerto Rico (NC_0409878.1) encoded by SEQ ID NO: 35 | FIG. 68 |

The invention will now be described in detail by way of reference only to the following non-limiting examples.

Methods and Materials

1. Assembly of Expression Cassettes

All manipulations were done using the general molecular biology protocols of Sambrook and Russell (2001; which is incorporated herein by reference). The first cloning step consisted in assembling a receptor plasmid containing upstream and downstream regulatory elements of the alfalfa plastocyanin gene. The plastocyanin promoter and 5'UTR sequences were amplified from alfalfa genomic DNA using oligonucleotide primers XmaI-pPlas.c (SEQ ID NO: 29; FIG. 10Q) and SacI-ATG-pPlas.r (SEQ ID NO: 30; FIG. 10R). The resulting amplification product was digested with XmaI and SacI and ligated into pCAMBIA2300 (Cambia, Canberra, Australia), previously digested with the same enzymes, to create pCAMBIApromo Plasto. Similarly, the 3'UTR sequences and terminator of the plastocyanin gene was amplified from alfalfa genomic DNA using the following primers: SacI-PlasTer.c (SEQ ID NO: 31; FIG. 10S) and EcoRI-PlasTer.r (SEQ ID NO: 32; FIG. 10T), and the product was digested with SacI and EcoRI before being inserted into the same sites of pCAMBIApromoPlasto to create pCAMBIAPlasto.

The open reading frame from the H1 gene of influenza strain A/New Caledonia/20/99 (H1N1) was synthesized in two fragments (Plant Biotechnology Institute, National Research Council, Saskatoon, Canada). A first fragment synthesized corresponds to the wild-type H1 coding sequence (GenBank acc. No. AY289929; SEQ ID NO: 33; FIG. 16) lacking the signal peptide coding sequence at the 5' end and the transmembrane domain coding sequence at the 3' end. A BglII restriction site was added at the 5' end of the coding sequence and a dual SacI/StuI site was added immediately downstream of the stop codon at the 3' terminal end of the fragment, to yield SEQ ID NO: 1 (FIG. 5A). A second fragment encoding the C-terminal end of the H1 protein (comprising a transmembrane domain and cytoplasmic tail) from the KpnI site to the stop codon, and flanked in 3' by SacI and StuI restriction sites was also synthesized (SEQ ID NO. 2; FIG. 5B).

Figure 2A:
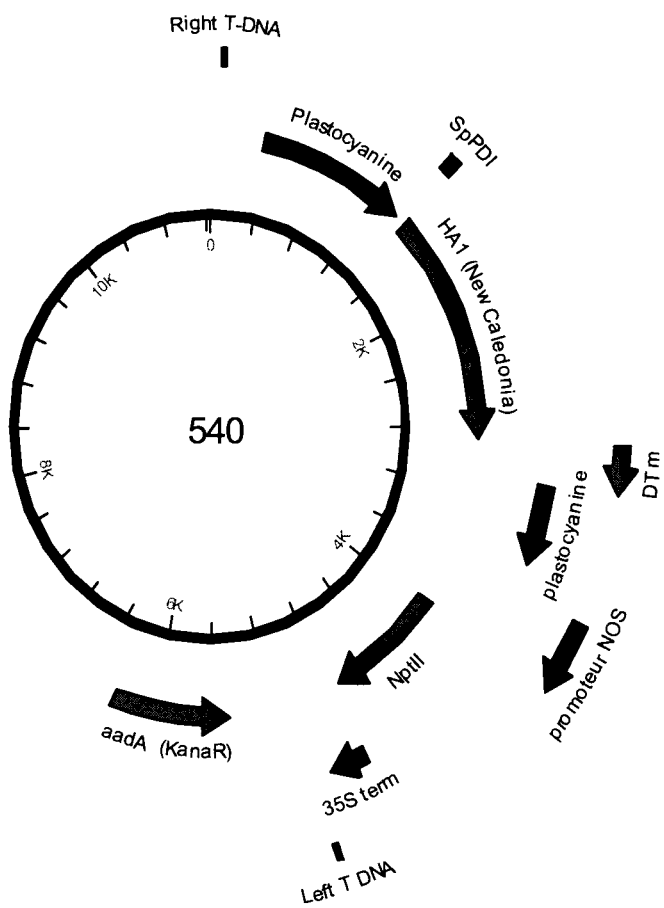
FIG. 2A shows a representation of plasmid 540 assembled for the expression of HA subtype H1.

The first H1 fragment was digested with BglII and SacI and cloned into the same sites of a binary vector (pCAMBIAPlasto) containing the plastocyanin promoter and 5'UTR fused to the signal peptide of alfalfa protein disulfide isomerase (PDI) gene (nucleotides 32-103; Accession No. Z11499; SEQ ID NO: 34; FIG. 17) resulting in a PDI-H1 chimeric gene downstream of the plastocyanin regulatory elements. The sequence of the plastocyanin-based cassette containing the PDI signal peptide is presented in FIG. 1 (SEQ ID NO:8). The resulting plasmid contained H1 coding region fused to the PDI signal peptide and flanked by plastocyanin regulatory elements. The addition of the C-terminal end coding region (encoding the transmembrane domain and the cytoplasmic tail) was obtained by inserting the synthesized fragment (SEQ ID NO: 2; FIG. 5B) previously digested with KpnI and SacI, into the H1 expression plasmid. The resulting plasmid, named 540, is presented in FIG. 11 (also see FIG. 2A).

2. Assembly of H5 Expression Cassette

Figure 2B:
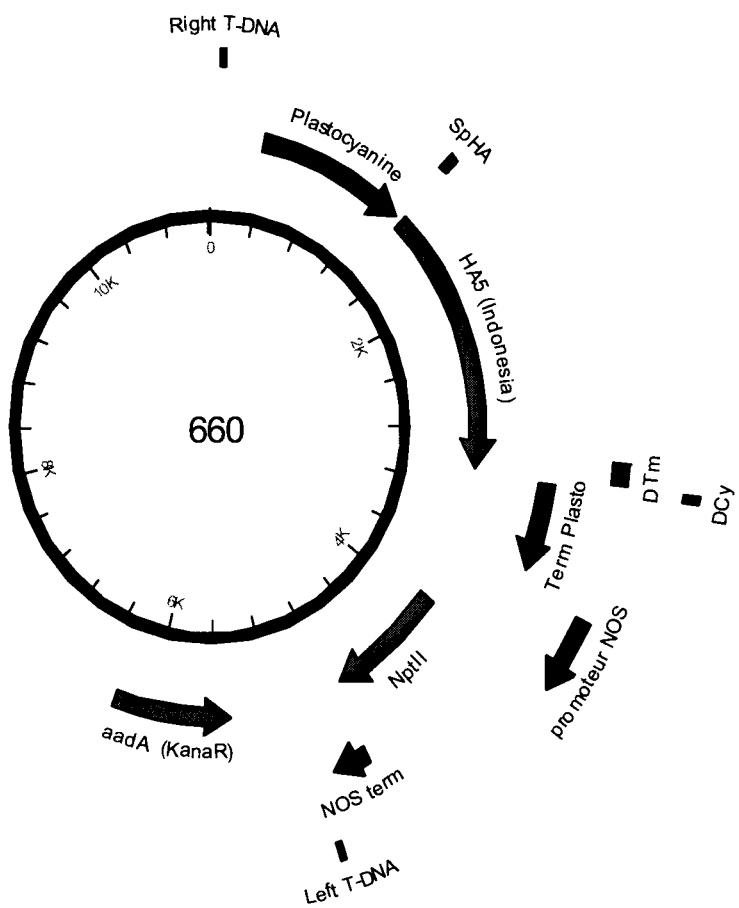
FIG. 2B shows a representation of plasmid 660 assembled for the expression of HA subtype H5.
Figure 3A:
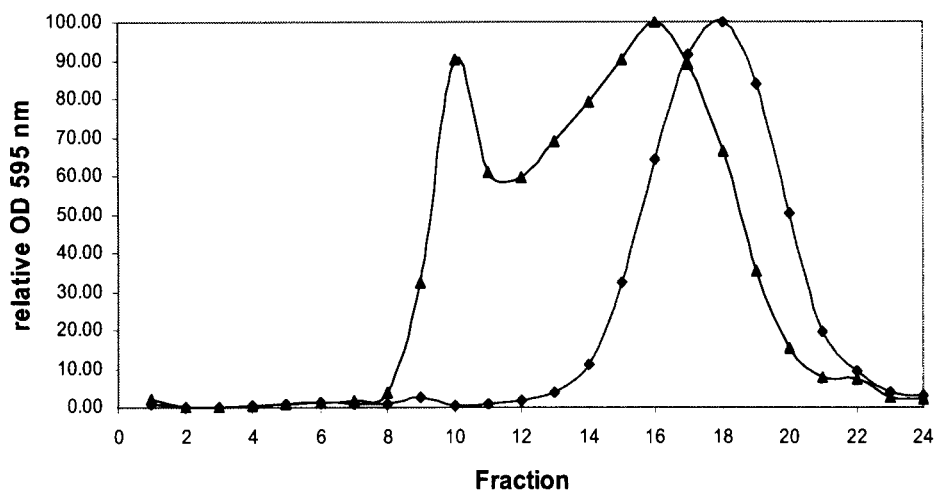
FIG. 3A shows the elution profile from a size exclusion chromatography of protein extracts from leaves producing hemagglutinin H1; Blue Dextran 2000 (triangles) and proteins (diamonds).
Figure 3B:
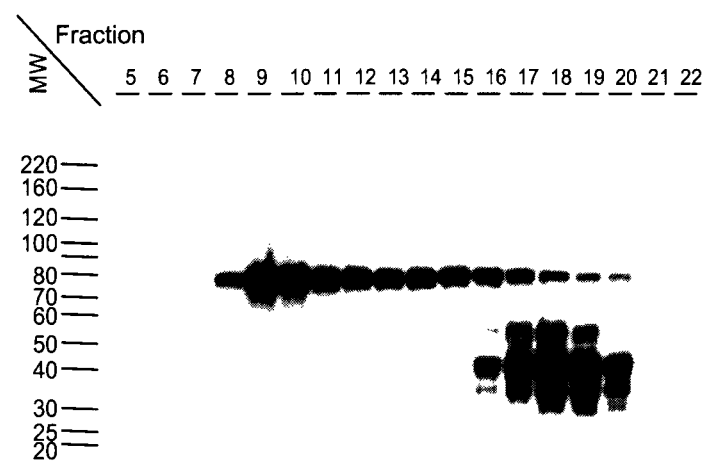
FIG. 3B shows immunodetection (western blot; anti H1) of H1 elution fractions following size exclusion chromatography (S500HR beads).
Figure 3C:
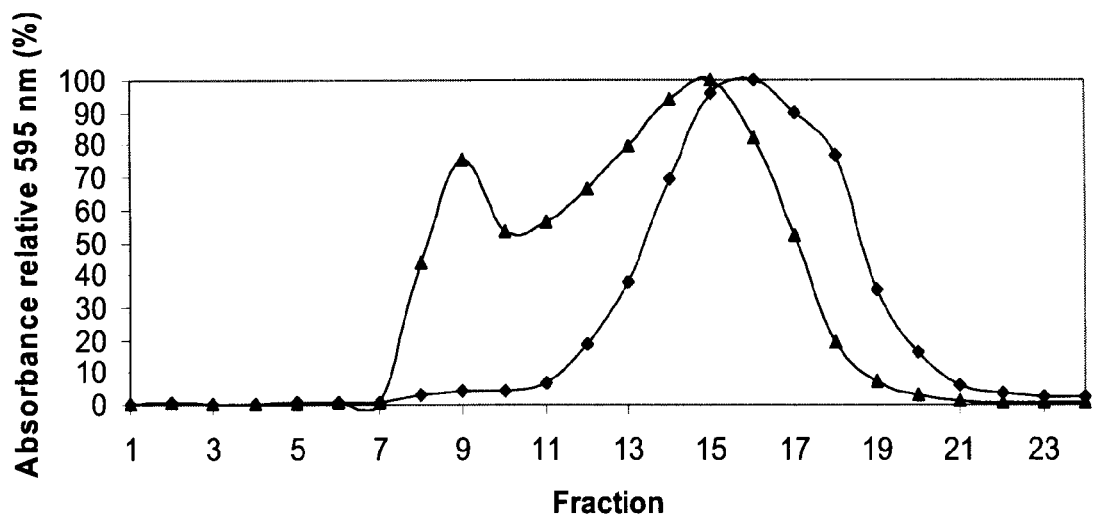
FIG. 3C show the elution profile of H5; Blue Dextran 2000 (triangles) and proteins (diamonds).
Figure 3D:
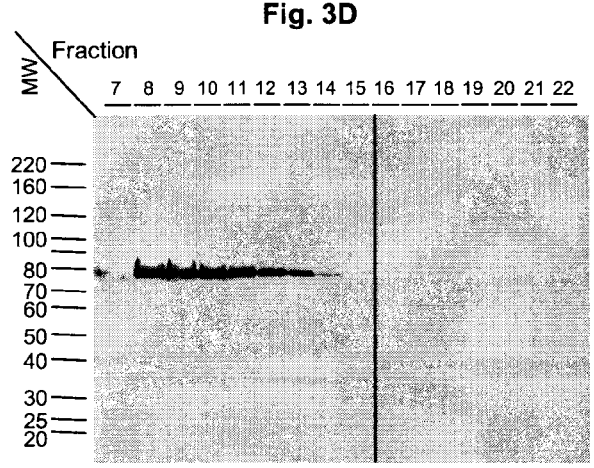
FIG. 3D shows immunodetection (western blot; anti H5) of H5 elution fractions following size exclusion chromatography (S500HR beads).

A fragment encoding hemagglutinin from influenza strain A/Indonesia/5/05 (H5N1; Acc. No. LANL ISDN125873) was synthesized by Epoch Biolabs (Sugar Land, Tex., USA). The fragment produced, containing the complete H5 coding region including the native signal peptide flanked by a HindIII site immediately upstream of the initial ATG, and a SacI site immediately downstream of the stop (TAA) codon, is presented in SEQ ID NO: 3 (FIG. 6). The H5 coding region was cloned into a plastocyanin-based expression cassette by the PCR-based ligation method presented in Darveau et al. (1995). Briefly, a first PCR amplification was obtained using primers Plato-443c (SEQ ID NO: 4; FIG. 7A) and SpHA(Ind)-Plasto.r (SEQ ID NO:5; FIG. 7B) and pCAMBIA promoPlasto as template. In parallel, a second amplification was performed with primers Plasto-SpHA(Ind).c (SEQ ID NO: 6; FIG. 7C) and HA(Ind)-Sac.r (SEQ ID NO:7; FIG. 7D) with H5 coding fragment as template. The amplification obtained from both reactions were mixed together and the mixture served as template for a third reaction (assembling reaction) using Plato-443c (SEQ ID NO: 4; FIG. 7A) and HA(Ind)-Sac.r (SEQ ID NO: 7; FIG. 7D) as primers. The resulting fragment was digested with BamHI (in the plastocyanin promoter) and SacI (at the 3' end of the fragment) and cloned into pCAMBIAPlasto previously digested with the same enzymes. The resulting plasmid, named 660, is presented in FIG. 2B (also see FIG. 11).

Figure 11:
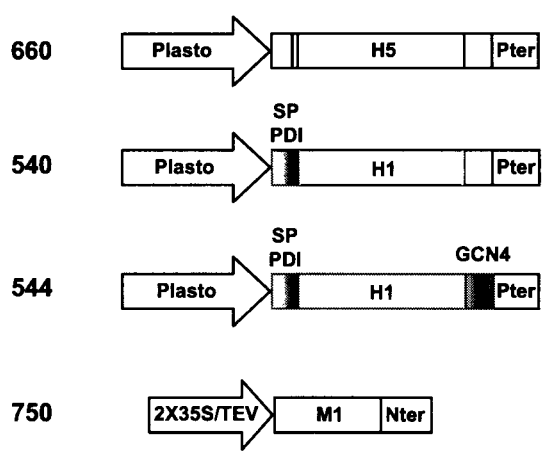
FIG. 11 shows a schematic representation of several constructs as used herein. Construct 660 comprises the nucleotide sequence to encode the HA subtype H5 under operatively linked to the plastocyanin promoter (plasto) and terminator (Pter); construct 540 comprises the nucleotide sequence to encode the HA subtype H1 in combination with an alfalfa protein disulfide isomerase signal peptide (SP PDI), and is operatively linked to a plastocyanin promoter (Plasto) and terminator (Pter); construct 544 assembled for the expression of HA subtype H1, the nucleotide sequence encoding H1 is combined with an alfalfa protein disulfide isomerase signal peptide (SP PDI) and an GCN4pII leucine zipper (in place of the transmembrane domain and cytoplasmic tail of HI) and operatively linked to the plastocyanin promoter (Plasto) and terminator (Pter); and construct 750 for the expression of M1 coding region from influenza A/PR/8/34 is combined to the tobacco etch virus (TEV) 5'UTR, and operatively linked with the double 35S promoter and Nos terminator.

The cassette encoding the soluble form of H1 was prepared by replacing the region coding for the transmembrane domain and the cytoplasmic tail in 540 by a fragment encoding the leucine zipper GCN4 pII variant (Harbury et al, 1993, Science 1993; 262: 1401-1407). This fragment was synthesized with flanking KpnI and SacI sites to facilitate cloning. The plasmid resulting from this replacement was named 544 and the expression cassette is illustrated in FIG. 11.

A fusion between the tobacco etch virus (TEV) 5'UTR and the open reading frame of the influenza A/PR/8/34 M1 gene (Acc. # NC_002016) was synthesized with a flanking SacI site added downstream of the stop codon. The fragment was digested with SwaI (in the TEV 5'UTR) and SacI, and cloned into a 2X35S/TEV based expression cassette in a pCAMBIA binary plasmid. The resulting plasmid bore the M1 coding region under the control of a 2X35S/TEV promoter and 5'UTR and the NOS terminator (construct 750; FIG. 11).

An HcPro construct (35HcPro) was prepared as described in Hamilton et al. (2002). All clones were sequenced to confirm the integrity of the constructs. The plasmids were used to transform *Agrobacteium tumefaciens* (AGL1; ATCC, Manassas, Va. 20108, USA) by electroporation (Mattanovich et al., 1989). The integrity of all *A. tumefaciens* strains were confirmed by restriction mapping.

3. Preparation of Plant Biomass, Inoculum, Agroinfiltration, and Harvesting

*Nicotiana benthamiana* or *Nicotiana tabacum* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions. Prior to transformation, apical and axillary buds were removed at various times as indicated below, either by pinching the buds from the plant, or by chemically treating the plant

*Agrobacteria* transfected with constructs 660, 540, 544, 750 or 35SHcPro were grown in a YEB medium supplemented with 10 mM 2-[N-morpholino]ethanesulfonic acid (MES), 20 µM acetosyringone, 50 µg/ml kanamycin and 25 µg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6). Syringe-infiltration was performed as described by Liu and Lomonossoff (2002, *Journal of Virological Methods*, 105:343-348). For vacuum-infiltration, *A. tumefaciens* suspensions were centrifuged, resuspended in the infiltration medium and stored overnight at 4° C. On the day of infiltration, culture batches were diluted in 2.5 culture volumes and allowed to warm before use. Whole plants of *N. benthamiana* or *N. tabacum* were placed upside down in the bacterial suspension in an air-tight stainless steel tank under a vacuum of 20-40 Torr for 2-min. Following syringe or vacuum infiltration, plants were returned to the greenhouse for a 4-5 day incubation period until harvest.

4. Leaf Sampling and Total Protein Extraction

Following incubation, the aerial part of plants was harvested, frozen at −80° C., crushed into pieces. Total soluble proteins were extracted by homogenizing (Polytron) each sample of frozen-crushed plant material in 3 volumes of cold 50 mM Tris pH 7.4, 0.15 M NaCl, and 1 mM phenylmethanesulfonyl fluoride. After homogenization, the slurries were centrifuged at 20,000 g for 20 min at 4° C. and these clarified crude extracts (supernatant) kept for analyses. The total protein content of clarified crude extracts was determined by the Bradford assay (Bio-Rad, Hercules, Calif.) using bovine serum albumin as the reference standard.

5. Size Exclusion Chromatography of Protein Extract

Size exclusion chromatography (SEC) columns of 32 ml Sephacryl™ S-500 high resolution beads (S-500 HR: GE Healthcare, Uppsala, Sweden, Cat. No. 17-0613-10) were packed and equilibrated with equilibration/elution buffer (50 mM Tris pH8, 150 mM NaCl). One and a half milliliter of crude protein extract was loaded onto the column followed by an elution step with 45 mL of equilibration/elution buffer. The elution was collected in fractions of 1.5 mL relative protein content of eluted fractions was monitored by mixing 10 µL of the fraction with 200 µL of diluted Bio-Rad protein dye reagent (Bio-Rad, Hercules, Calif. The column was washed with 2 column volumes of 0.2N NaOH followed by 10 column volumes of 50 mM Tris pH8, 150 mM NaCl, 20% ethanol. Each separation was followed by a calibration of the column with Blue Dextran 2000 (GE Healthcare Bio-Science Corp., Piscataway, N.J., USA). Elution profiles of Blue Dextran 2000 and host soluble proteins were compared between each separation to ensure uniformity of the elution profiles between the columns used.

6. Protein Analysis and Immunoblotting

Protein concentrations were determined by the BCA protein assay (Pierce Biochemicals, Rockport Ill.). Proteins were separated by SDS-PAGE under reducing conditions and stained with Coomassie Blue. Stained gels were scanned and densitometry analysis performed using ImageJ Software (NIH).

Proteins from elution fraction from SEC were precipitated with acetone (Bollag et al., 1996), resuspended in 1/5 volume in equilibration/elution buffer and separated by SDS-PAGE under reducing conditions and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% TWEEN-20 non-ionic detergent (Sigma-Aldrich Corporation, St. Louis, Mo.) in Tris-buffered saline (TBS-T) for 16-18 h at 4° C.

Immunoblotting was performed by incubation with a suitable antibody (Table 6), in 2 µg/ml in 2% skim milk in TBS-TWEEN-20 non-ionic detergent (Sigma-Aldrich Corporation, St. Louis, Mo.) 0.1%. Secondary antibodies used for chemiluminescence detection were as indicated in Table 4, diluted as indicated in 2% skim milk in TBS-TWEEN-20 non-ionic detergent (Sigma-Aldrich Corporation, St. Louis, Mo.) 0.1%. Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.).

TABLE 6

Electrophoresis conditions, antibodies, and dilutions for immunoblotting of expressed proteins.

| HA | Influenza strain | Electrophoresis condition | Primary antibody | Dilution | Secondary antibody | Dilution |
|---|---|---|---|---|---|---|
| H1 | A/Brisbane/59/2007 (H1N1) | Reducing | FII 10-I50 | 4 µg/ml | Goat anti-mouse (JIR 115-035-146) | 1:10000 |
| H1 | A/Solomon Islands/3/2006 (H1N1) | Reducing | NIBSC 07/104 | 1:2000 | Rabbit anti-sheep (JIR 313-035-045) | 1:10000 |

TABLE 6-continued

Electrophoresis conditions, antibodies, and dilutions for immunoblotting of expressed proteins.

| HA | Influenza strain | Electrophoresis condition | Primary antibody | Dilution | Secondary antibody | Dilution |
|---|---|---|---|---|---|---|
| H1 | A/New Caledonia/20/99 (H1N1) | Reducing | FII 10-I50 | 4 µg/ml | Goat anti-mouse (JIR 115-035-146) | 1:10000 |
| H2 | A/Singapore/1/57 (H2N2) | Non-reducing | NIBSC 00/440 | 1:1000 | Rabbit anti-sheep (JIR 313-035-045) | 1:10000 |
| H5 | A/Indonesia/5/2005 (H5N1) | Reducing | ITC IT-003-005V | 1:4000 | Goat anti-rabbit (JIR 111-035-144) | 1:10000 |
| H5 | A/Anhui/1/2005 (H5N1) | Reducing | NIBSC 07/338 | 1:750 | Rabbit anti-sheep (JIR 313-035-045) | 1:10000 |
| H5 | A/Vietnam/1194/2004 (H5N1) | Non-reducing | ITC IT-003-005 | 1:2000 | Goat anti-rabbit (JIR 111-035-144) | 1:10000 |
| H6 | A/Teal/Hong Kong/W312/97 (H6N1) | Non-reducing | BEI NR 663 | 1:500 | Rabbit anti-sheep (JIR 313-035-045) | 1:10000 |
| H9 | A/Hong Kong/1073/99 (H9N2) | Reducing | NIBSC 07/146 | 1:1000 | Rabbit anti-sheep (JIR 313-035-045) | 1:10000 |

HA: HA subtype;
FII: Fitzgerald Industries International, Concord, MA, USA;
NISBIC: National Institute for Biological Standards and Control;
JIR: Jackson ImmunoResearch, West Grove, PA, USA;
BEI NR: Biodefense and emerging infections research resources repository;
ITC: Immune Technology Corporation, Woodside, NY, USA;

Hemagglutination assay for H5 was based on a method described by Nayak and Reichl (2004). Briefly, serial double dilutions of the test samples (100 µL) were made in V-bottomed 96-well microtiter plates containing 100 µL PBS, leaving 100 µL of diluted sample per well. One hundred microliters of a 0.25% turkey red blood cells suspension (Bio Link Inc., Syracuse, N.Y.) were added to each well, and plates were incubated for 2 h at room temperature. The reciprocal of the highest dilution showing complete hemagglutination was recorded as HA activity. In parallel, a recombinant HA standard (A/Vietnam/1203/2004 H5N1) (Protein Science Corporation, Meriden, Conn.) was diluted in PBS and run as a control on each plate.

7. Sucrose Gradient Ultracentrifugation

One milliliter of fractions 9, 10 and 11 eluted from the gel filtration chromatography on H5-containing biomass were pooled, loaded onto a 20-60% (w/v) discontinuous sucrose density gradient, and centrifuged 17.5 h at 125 000 g (4° C.). The gradient was fractionated in 19 3-mL fractions starting from the top, and dialyzed to remove sucrose prior to immunological analysis and hemagglutination assays.

8. Electron Microscopy

Elution fractions from SEC to be observed by electron microscopy (EM) were first concentrated using 30 MWCO ultrafiltration units (Millipore, Billerica, Mass., USA). The concentrated fractions were fixed in PBS pH 7.4 containing 2% glutaraldehyde for 24 h at 4° C. Once fixed the samples were adsorbed onto Formvar-coated 200-mesh nickel grids (Canemco, Lakefield, Canada) for 2 min, and the grids were washed twice with deionized water before being stained in 1% phosphotungstic acid. Observation was performed under transmission electron microscopy at magnifications ranging from 10,000× to 150,000× (for images in FIGS. 4A and 4B).

Alternately, one hundred microliters of the samples to be examined were placed in an Airfuge ultracentrifugation tube (Beckman Instruments, Palo Alto, Calif., USA). A grid was placed at the bottom of the tube which was then centrifuged 5 min at 120 000 g. The grid was removed, gently dried, and placed on a drop of 3% phosphotungstic acid at pH 6 for staining Grids were examined on a Hitachi 7100 transmission electron microscope (TEM) (for images in FIGS. 14B, 15B and 15C).

For images in FIG. 19, Leaf blocks of approximately 1 $mm^3$ were fixed in PBS containing 2.5% glutaraldehyde and washed in PBS containing 3% sucrose before a post-fixation step in 1.33% osmium tetroxide. Fixed samples were imbedded in Spurr resin and ultrathin layers were laid on a grid. Samples were positively stained with 5% uranyl acetate and 0.2% lead citrate before observation. Grids were examined on a Hitachi 7100 transmission electron microscope (TEM).

9. Plasma Membrane Lipid Analysis

Plasma membranes (PM) were obtained from tobacco leaves and cultured BY2 cells after cell fractionation according to Mongrand et al. by partitioning in an aqueous polymer two-phase system with polyethylene glycol 3350/dextran T-500 (6.6% each). All steps were performed at 4° C.

Lipids were extracted and purified from the different fractions according to Bligh and Dyer. Polar and neutral lipids were separated by mono-dimensional HP-TLC using the solvent systems described in Lefebvre et al. Lipids of PM fractions were detected after staining with copper acetate as described by Macala et al. Lipids were identified by comparison of their migration time with those of standards (all standards were obtained from Sigma-Aldrich, St-Louis, Mo., USA, except for SG which was obtained from Matreya, Pleasant Gap, Pa., USA).

10. H5 VLP Purification

Frozen 660-infiltrated leaves of *N. benthamiana* were homogenized in 1.5 volumes of 50 mM Tris pH 8, NaCl 150 mM and 0.04% sodium meta-bisulfite using a commercial blender. The resulting extract was supplemented with 1 mM PMSF and adjusted to pH 6 with 1 M acetic acid before being heated at 42° C. for 5 min. Diatomaceous earth (DE) was added to the heat-treated extract to adsorb the contaminants precipitated by the pH shift and heat treatment, and the slurry was filtered through a Whatman paper filter. The resulting clarified extract was centrifuged at 10,000×g for 10 minutes at RT to remove residual DE, passed through 0.8/0.2 μm Acropack 20 filters and loaded onto a fetuin-agarose affinity column (Sigma-Aldrich, St-Louis, Mo., USA). Following a wash step in 400 mM NaCl, 25 mM Tris pH 6, bound proteins were eluted with 1.5 M NaCl, 50 mM MES pH 6. Eluted VLP were supplemented with TWEEN-80 non-ionic detergent (Sigma-Aldrich Corporation, St. Louis, Mo.) to a final concentration of 0.0005% (v/v). VLP were concentrated on a 100 kDa MWCO Amicon membrane, centrifuged at 10,000×g for 30 minutes at 4° C. and resuspended in PBS pH 7.4 with 0.01% TWEEN-80 non-ionic detergent (Sigma-Aldrich Corporation, St. Louis, Mo.) and 0.01% thimerosal. Suspended VLPs were filter-sterilized before use.

11. Animal Studies

Mice

Studies on the immune response to influenza VLP administration were performed with 6-8 week old female BALB/c mice (Charles River Laboratories). Seventy mice were randomly divided into fourteen groups of five animals. Eight groups were used for intramuscular immunization and six groups were used to test intranasal route of administration. All groups were immunized in a two-dose regiment, the boost immunization being done 3 weeks following the first immunization.

For intramuscular administration in hind legs, unanaesthetized mice were immunized with either the plant-made VLP H5 vaccine (0.1, 1, 5 or 12 μg), or a control hemagglutinin (HA) antigen. The control HA comprised recombinant soluble hemagglutinin produced based on strain A/Indonesia/5/05 H5N1 and purified from 293 cell culture (Immune Technology Corp., New York, USA) (used at 5 μg per injection unless otherwise indicated). Buffer control was PBS. This antigen consists of amino acids 18-530 of the HA protein, and has a His-tag and a modified cleavage site. Electron microscopy confirmed that this commercial product is not in the form of VLPs.

To measure the effect of adjuvant, two groups of animals were immunized with 5 μg plant-made VLP H5 vaccine plus one volume Alhydrogel 2% (alum, Accurate Chemical & Scientific Corporation, Westbury, N.Y., US) or with 5 μg recombinant hemagglutinin purified from 293 cell culture plus 1 volume alum. Seventy mice were randomly divided into fourteen groups of five animals. Eight groups were used for intramuscular immunization and six groups were used to test intranasal route of administration. All groups were immunized according to a prime-boost regimen, the boost immunization performed 3 weeks following the first immunization.

For intramuscular administration in hind legs, unanaesthetized mice were immunized with the plant-made H5 VLP (0.1, 1, 5 or 12 μg), or the control hemagglutinin (HA) antigen (5 μg) or PBS. All antigen preparations were mixed with Alhydrogel 1% (alum, Accurate Chemical & Scientific Corporation, Westbury, N.Y., US) in a 1:1 volume ratio prior to immunizations. To measure the effect of adjuvant, two groups of animals were immunized with either 5 μg plant-made VLP H5 vaccine or with 5 μg of control HA antigen without any adjuvant.

For intranasal administration, mice were briefly anaesthetized by inhalation of isoflurane using an automated induction chamber. They were then immunized by addition of 4 μl drop/nostril with the plant-made VLP vaccine (0.1 or 1 μg), or with control HA antigen (1 μg) or with PBS. All antigen preparations were mixed with chitosan glutamate 1% (Protosan, Novamatrix/FMC BioPolymer, Norway) prior to immunizations. The mice then breathed in the solutions. To verify the effect of adjuvant with the intranasal route of administration, two groups of animals were immunized with 1 μg plant-made VLP H5 vaccine or with 1 μg control HA antigen.

Ferrets

Ten groups of 5 ferrets (male, 18-24 weeks old, mass of approx 1 kg) were used. Treatment for each group is as described in Table 7. The adjuvant used was Alhydrogel (alum) (Superfos Biosector, Denmark) 2% (final=1%). Vaccine composition was membrane-associated A/Indonesia/5/05 (H5N1) VLPs produced as described. The vaccine control (positive control) was a fully glycosylated membrane-bound recombinant H5 from Indonesia strain produced using adenovirus in 293 cell culture by Immune Technology Corporation (ITC).

TABLE 7

Treatment groups

| Group | n | Product injected to animals | Route of administration | Adjuvant |
|---|---|---|---|---|
| 1 | 5 | PBS (negative control) | i.m.* | — |
| 2 | 5 | Vaccine-plant, 1 μg | i.m. | — |
| 3 | 5 | Vaccine-plant, 1 μg | i.m. | Alum |
| 4 | 5 | Vaccine-plant, 5 μg | i.m. | — |
| 5 | 5 | Vaccine-plant, 5 μg | i.m. | Alum |
| 6 | 5 | Vaccine-plant, 7.5 μg | i.m. | — |
| 7 | 5 | Vaccine-plant, 15 μg | i.m. | — |
| 8 | 5 | Vaccine-plant, 15 μg | i.m. | Alum |
| 9 | 5 | Vaccine-plant, 30 μg | i.m. | — |
| 10 | 5 | Vaccine-control, 5 μg | i.m. | — |

* i.m.: intramuscular

Ferrets were assessed for overall health and appearance (body weight, rectal temperature, posture, fur, movement patterns, breathing, excrement) regularly during the study. Animals were immunized by intramuscular injection (0.5-1.0 total volume) in quadriceps at day 0, 14 and 28; for protocols incorporating adjuvant, the vaccine composition was combined with Alhydrogel immediately prior to immunization in a 1:1 volume ratio). Serum samples were obtained on day 0 before immunizing, and on day 21 and 35. Animals were sacrificed (exsanguination/cardiac puncture) on days 40-45, and, spleens were collected and necropsy performed.

Anti-influenza antibody titres may be quantified in ELISA assays using homologous or heterologous inactivated H5N1 viruses.

Hemagglutination inhibitory antibody titers of serum samples (pre-immune, day 21 and day 35) were evaluated by microtiter HAI as described (Aymard et al 1973). Briefly, sera were pretreated with receptor-destroying enzyme, heat-inactivated and mixed with a suspension of erythrocytes (washed red blood cells-RBC). Horse washed RBC (10%) from Lampire are recommended and considering that the assay may vary depending of the source of the RBC (horse-dependant), washed RBCs from 10 horses have been tested to select the most sensitive batch. Alternately, turkey RBC may be used. Antibody titer was expressed as the reciprocal of the highest dilution which completely inhibits hemagglutination.

Cross-reactive HAI titers: HAI titers of ferrets immunized with a vaccine for the A/Indonesia/5/05 (clade 2.1) were measured using inactivated H5N1 influenza strains from another subclade or clade such as the clade 1 Vietnam strains A/Vietnam/1203/2004 and A/Vietnam/1194/2004 or the A/Anhui/01/2005 (subclade 2.3) or the A/turkey/Turkey/1/05 (subclade 2.2). All analyses were performed on individual samples.

Data analysis: Statistical analysis (ANOVA) will be performed on all data to establish if differences between groups are statistically significant.

Experimental Design for Lethal Challenge (Mice)

One hundred twenty eight mice were randomly divided into sixteen groups of eight animals, one group being unimmunized and not challenged (negative control). All groups were immunized via intramuscular administration in a two-dose regimen, the second immunization being done 2 weeks following the first immunization.

For intramuscular administration in hind legs, unanaesthetized mice were immunized with the plant-made H5 VLP (1, 5 or 15 μg), or 15 μg of control HA antigen or PBS. All antigen preparations were mixed with one volume of Alhydrogel 1% prior to immunizations (alum, Accurate Chemical & Scientific Corporation, Westbury, N.Y., US).

During the immunization period, mice were weighted once a week and observation and monitored for local reactions at the injection site.

Twenty two days following the second immunization, anesthetized mice were challenged intranasally (i.n.) into a BL4 containment laboratory (P4-Jean Mérieux-INSERM, Lyon, France) with $4.09 \times 10^6$ 50% cell culture infective dose (CCID50) of influenza A/Turkey/582/06 virus (kindly provided by Dr. Bruno Lina, Lyon University, Lyon, France). Following challenge, mice were observed for ill clinical symptoms and weighed daily, over a fourteen day period. Mice with severe infection symptoms and weight loss of ≥25% were euthanized after anaesthesia.

Blood Collection, Lung and Nasal Washes and Spleen Collection

Lateral saphenous vein blood collection was performed fourteen days after the first immunization and fourteen days after second immunization on unanaesthetized animal Serum was collected by centrifuging at 8000 g for 10 min.

Four weeks after second immunisation, mice were anaesthetized with $CO_2$ gas and immediately upon termination, cardiac puncture was used to collect blood.

After final bleeding, a catheter was inserted into the trachea towards the lungs and one ml of cold PBS-protease inhibitor cocktail solution was put into a 1 cc syringe attached to the catheter and injected into the lungs and then removed for analysis. This wash procedure was performed two times. The lung washes were centrifuged to remove cellular debris. For nasal washes, a catheter was inserted towards the nasal area and 0.5 ml of the PBS-protease inhibitor cocktail solution was pushed through the catheter into the nasal passages and then collected. The nasal washes were centrifuged to remove cellular debris. Spleen collection was performed on mice immunized intramuscularly with 5 μg of adjuvanted plant-made vaccine or 5 μg adjuvanted recombinant H5 antigen as well as on mice immunized intranasaly with 1 μg of adjuvanted plant-made vaccine or 1 μg adjuvanted recombinant H5 antigen. Collected spleens were placed in RPMI supplemented with gentamycin and mashed in a 50 ml conical tube with plunger from a 10 ml syringe. Mashed spleens were rinsed 2 times and centrifuged at 2000 rpm for 5 min and resuspended in ACK lysing buffer for 5 min at room temperature. The splenocytes were washed in PBS-gentamycin, resuspended in 5% RPMI and counted. Splenocytes were used for proliferation assay.

Antibody Titers

Anti-influenza antibody titers of sera were measured at 14 days after the first immunization as well as 14 and 28 days after the second immunisation. The titer were determined by enzyme-linked immunosorbent assay (ELISA) using the inactivated virus A/Indonesia/5/05 as the coating antigen. The end-point titers were expressed as the reciprocal value of the highest dilution that reached an OD value of at least 0.1 higher than that of negative control samples.

For antibody class determination (IgG1, IgG2a, IgG2b, IgG3, IgM), the titers were evaluated by ELISA as previously described.

Hemagglutination Inhibition (HI) Titers

Hemagglutination inhibition (HI) titers of sera were measured at 14 and 28 days after the second immunisation as previously described (WHO 2002; Kendal 1982). Inactivated virus preparations from strains A/Indonesia/5/05 or A/Vietnam/1203/2004 were used to test mouse serum samples for HI activity. Sera were pre-treated with receptor-destroying enzyme II (RDE II) (Denka Seiken Co., Tokyo, Japan) prepared from *Vibrio cholerae* (Kendal 1982). HI assays were performed with 0.5% turkey red blood cells. HI antibody titres were defined as the reciprocal of the highest dilution causing complete inhibition of agglutination.

EXAMPLES

Example 1

Transient Expression of Influenza Virus A/Indonesia/5/05 (H5N1) Hemagglutinin by Agroinfiltration in *N. benthamiana* Plants The ability of the transient expression system to produce influenza hemagglutinin was determined through the expression of the H5 subtype from strain A/Indonesia/5/05 (H5N1). As presented in FIG. 11, the hemagglutinin gene coding sequence (Acc. # EF541394), with its native signal peptide and transmembrane domain, was first assembled in the plastocyanin expression cassette—promoter, 5'UTR, 3'UTR and transcription termination sequences from the alfalfa plastocyanin gene—and the assembled cassette (660) was inserted into to a pCAMBIA binary plasmid. This plasmid was then transfected into *Agrobacterium* (AGL1), creating the recombinant strain AGL1/660, which was used for transient expression.

*N. benthamiana* plants were infiltrated with AGL1/660, and the leaves were harvested after a six-day incubation period. To determine whether H5 accumulated in the agroinfiltrated leaves, protein were first extracted from infiltrated leaf tissue and analyzed by Western blotting using anti-H5 (Vietnam) polyclonal antibodies. A unique band of approximately 72 kDa was detected in extracts (FIG. 12), corresponding in size to the uncleaved HA0 form of influenza hemagglutinin. The commercial H5 used as positive control (A/Vietnam/1203/2004; Protein Science Corp., Meriden, Conn., USA) was detected as two bands of approximately 48 and 28 kDa, corresponding to the molecular weight of HA1 and HA2 fragments, respectively. This demonstrated that expression of H5 in infiltrated leaves results in the accumulation of the uncleaved translation product.

The formation of active HA trimers was demonstrated by the capacity of crude protein extracts from AGL1/660-transformed leaves to agglutinate turkey red blood cells (data not shown).

Example 2

Characterization of Hemagglutinin-Containing Structures in Plant Extracts Using Size Exclusion Chromatography The assembly of plant-produced influenza hemagglutinin into high molecular weight structures was assessed by gel filtration. Crude protein extracts from AGL1/660-infiltrated plants (1.5 mL) were fractionated by size exclusion chromatography (SEC) on Sephacryl™ S-500 HR columns (GE Healthcare Bio-Science Corp., Piscataway, N.J., USA). Elution fractions were assayed for their total protein content and for HA abundance using immunodetection with anti-HA antibodies (FIG. 13A). As shown in FIG. 13A, Blue Dextran (2 MDa) elution peaked early in fraction 10 while the bulk of host proteins was retained in the column and eluted between fractions 14 and 22. When proteins from 200 µL of each SEC elution fraction were concentrated (5-fold) by acetone-precipitation and analyzed by Western blotting (FIG. 15A, H5), hemagglutinin (H5) was primarily found in fractions 9 to 14 (FIG. 13B). Without wishing to be bound by theory, this suggests that the HA protein had either assembled into a large superstructure or that it has attached to a high molecular weight structure.

A second expression cassette was assembled with the H1 nucleic acid sequence from A/New Caledonia/20/99 (H1N1) (SEQ ID NO: 33; FIG. 16; GenBank Accession No. AY289929) to produce construct 540 (FIG. 11). A chimeric gene construct was designed so as to produce a soluble trimeric form of H1 in which the signal peptide originated from a plant protein disulfide isomerase gene, and the transmembrane domain of H1 was replaced by the pII variant of the GCN4 leucine zipper, a peptide shown to self-assemble into trimers (Harbury et al., 1993) (cassette 544, FIG. 11). Although lacking the transmembrane domain, this soluble trimeric form was capable of hemagglutination (data not shown).

Protein extracts from plants infiltrated with AGL1/540 or AGL1/544 were fractionated by SEC and the presence of H1 eluted fractions was examined by Western blotting with anti-influenza A antibodies (Fitzgerald, Concord, Mass., USA). In AGL1/540-infiltrated leaves, H1 accumulated mainly as a very high molecular weight structure, with the peak was skewed toward smaller size structures (H1; FIG. 13C). In AGL1/544-infiltrated leaves, the soluble form of H1 accumulated as isolated trimers as demonstrated by the elution pattern from gel filtration which parallels the host protein elution profile (soluble H1; FIG. 13D). In comparison, H1 rosettes (Protein Science Corp., Meriden, Conn., USA), consisting in micelles of 5-6 trimers of hemagglutinin eluted at fractions 12 to 16 (FIG. 13E), earlier than the soluble form of H1 (FIG. 13D) and later than the native H1 (FIG. 13C).

To evaluate the impact of M1 co-expression on hemagglutinin assembly into structure, a M1 expression cassette was assembled using the nucleic acid corresponding to the coding sequence of the A/PR/8/34 (H1N1) M1 (SEQ ID NO: 35; FIG. 18; GenBank Accession No. NC_002016). The construct was named 750 and is presented in FIG. 11. For the co-expression of M1 and H1, suspensions of AGL1/540 and AGL1/750 were mixed in equal volume before infiltration. Co-infiltration of multiple *Agrobacterium* suspensions permits co-expression of multiple transgenes. The Western blot analysis of SEC elution fractions shows that the co-expression of M1 did not modify the elution profile of the H1 structures, but resulted in a decrease in H1 accumulation in the agroinfiltrated leaves (see FIG. 13F).

Example 3

Figure 14A:
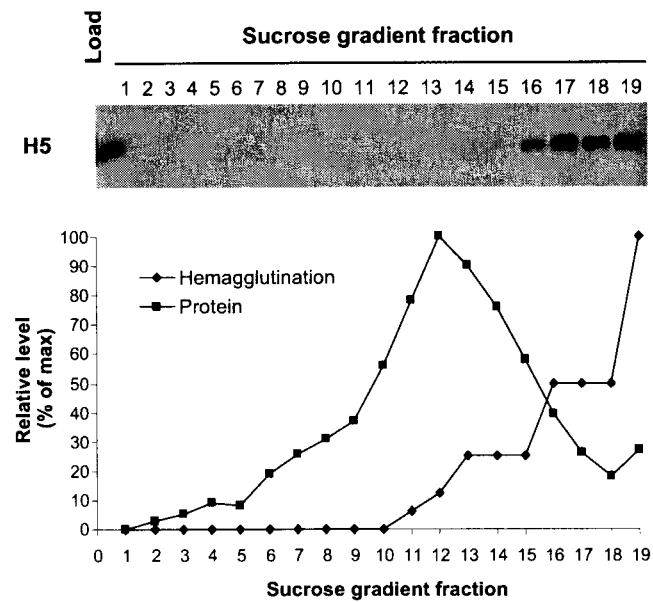
FIG. 14A shows concentration of influenza H5 structures by sucrose gradient centrifugation and electron microscopy examination of hemagglutinin-concentrated fractions and characterization of fractions from sucrose density gradient centrifugation. Each fraction was analyzed for the presence of H5 by immunoblotting using anti-H5 (Vietnam) antibodies (upper panel), and for their relative protein content and hemagglutination capacity (graph).
Figure 14B:
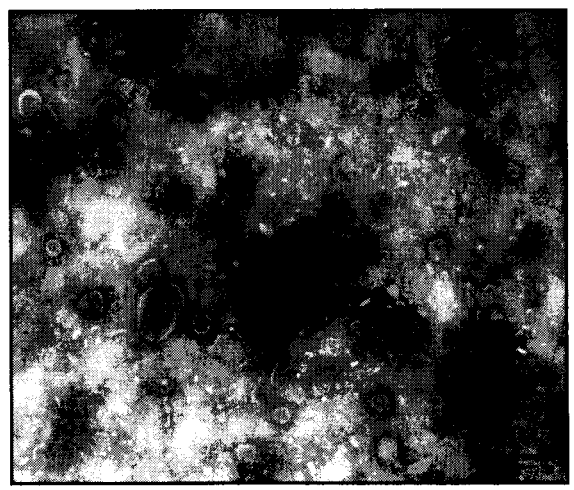
FIG. 14B shows negative staining transmission electron microscopy examination of pooled fractions 17, 18 and 19 from sucrose gradient centrifugation. The bar represents 100 nm.

Isolation of H5 Structures by Centrifugation in Sucrose Gradient and Observation Under Electron Microscopy The observation of hemagglutinin structure under electron microscopy (EM) required a higher concentration and purity level than that obtained from SEC on crude leaf protein extracts. To allow EM observation of H5 structures, a crude leaf protein extract was first concentrated by PEG precipitation (20% PEG) followed by resuspension in 1/10 volumes of extraction buffer. The concentrated protein extract was fractionated by S-500 HR gel filtration and elution fractions 9, 10, and 11 (corresponding to the void volume of the column) were pooled and further isolated from host proteins by ultracentrifugation on a 20-60% sucrose density gradient. The sucrose gradient was fractionated starting from the top and the fractions were dialysed and concentrated on a 100 NMWL centrifugal filter unit prior to analysis. As shown on the Western blots and hemagglutination results (FIG. 14A), H5 accumulated mainly in fractions 16 to 19 which contained ≈60% sucrose, whereas most of the host proteins peaked at fraction 13. Fractions 17, 18, and 19 were pooled, negatively stained, and observed under EM. Examination of the sample clearly demonstrated the presence of spiked spheric structures ranging in size from 80 to 300 nm which matched the morphological characteristics of influenza VLPs (FIG. 14B).

Example 4

Purification of Influenza H5 VLPs from Plant Biomass

Figure 15A:
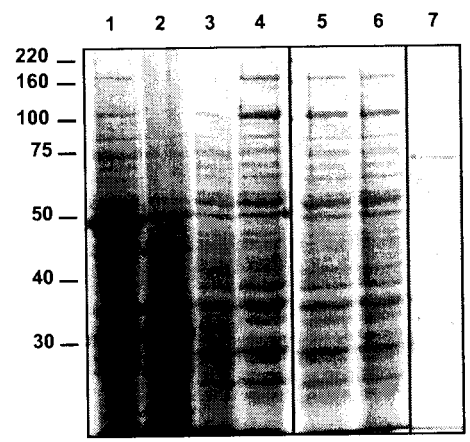
FIG. 15A shows purification of influenza H5 VLPs; Coomassie Blue stained SDS-PAGE analysis of protein content in the clarification steps—lane 1, crude extract; lane 2, pH 6-adjusted extract; lane 3, heat-treated extract; lane 4, DE-filtrated extract; the fetuin affinity purification steps: lane 5, load; lane 6, wash; lane 7, elution (10× concentrated).

In addition to an abundant content of soluble proteins, plant leaf extracts contain a complex mixture of soluble sugars, nucleic acids and lipids. The crude extract was clarified by a pH shift and heat treatment followed by filtration on diatomaceous earth (see Material and method section for a detailed description of the clarification method). FIG. 15A (lanes 1-4) presents a Coomassie Blue stained gel comparing protein content at the various steps of clarification. A comparison of protein content in the crude extract (lane 1) and in the clarified extract (lane 4) reveals the capacity of the clarification steps to reduce the global protein content and remove most of the major contaminant visible at 50 kDa in crude leaf extracts. The 50 kDa band corresponds to the RuBisCO large subunit, representing up to 30% of total leaf proteins.

Influenza H5 VLPs were purified from these clarified extracts by affinity chromatography on a fetuin column. A comparison of the load fraction (FIG. 15A, lane 5) with the flowthrough (FIG. 15A, lane 6) and the eluted VLPs (FIG. 15A, lane 7) demonstrates the specificity of the fetuin affinity column for influenza H5 VLPs in plant clarified extract.

Figure 15B:
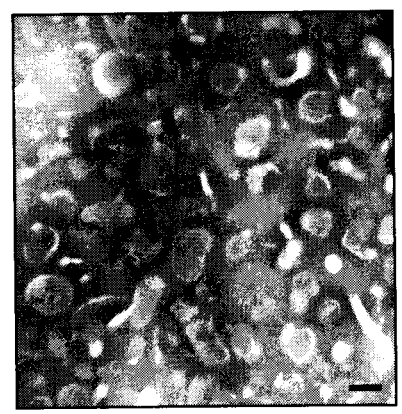
FIG. 15B shows negative staining transmission electron microscopy examination of the purified H5 VLP sample. The bar represents 100 nm.
Figure 15C:
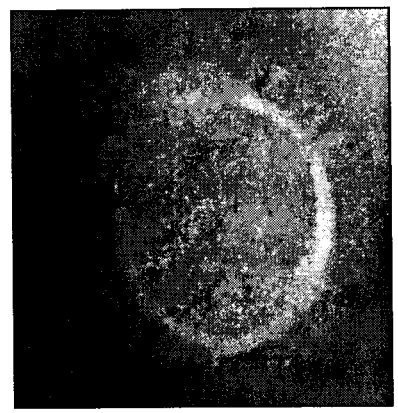
FIG. 15 C shows isolated H5 VLP enlarged to show details of the structure.
FIG. 15D shows the H5 VLP product on a Coomassie-stained reducing SDS-PAGE (lane A) and Western blot (lane B) using rabbit polyclonal antibody raised against HA from strain A/Vietnam/1203/2004 (H5N1).

The purification procedure resulted in over 75% purity in H5, as determined by densitometry on the Coomassie Blue stained SDS-PAGE gel (FIG. 15A, lane 7). In order to assess the structural quality of the purified product, the purified H5 was concentrated on a 100 NMWL (nominal molecular weight limit) centrifugal filter unit and examined under EM after negative staining FIG. 15B shows a representative sector showing the presence of profuse VLPs. A closer examination confirmed the presence of spikes on the VLPs (FIG. 15C).

Figure 15D:
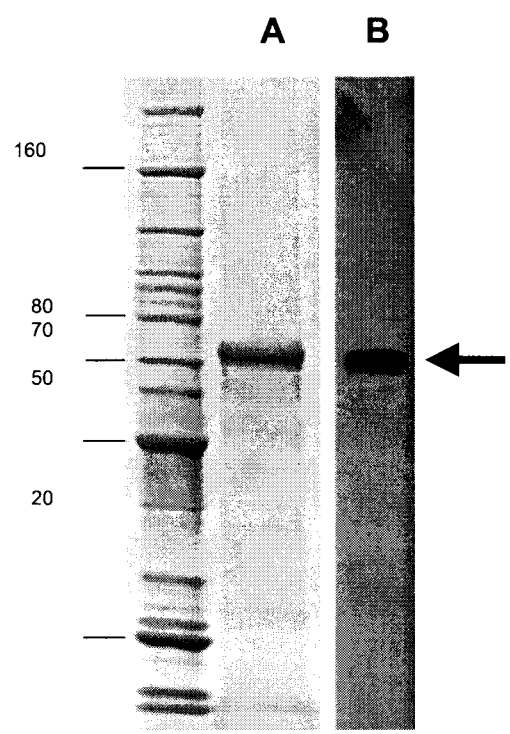

As shown in FIG. 15D, H5 VLPs were purified to approx. 89% purity from clarified leaf extract by affinity chromatography on a fetuin column, based on the density of the Coomassie Blue stained H5 hemagglutinin and on total protein content determination by the BCA method.

The bioactivity of HA VLPs was confirmed by their capacity to agglutinate turkey red blood cells (data not shown).

Figure 20A:
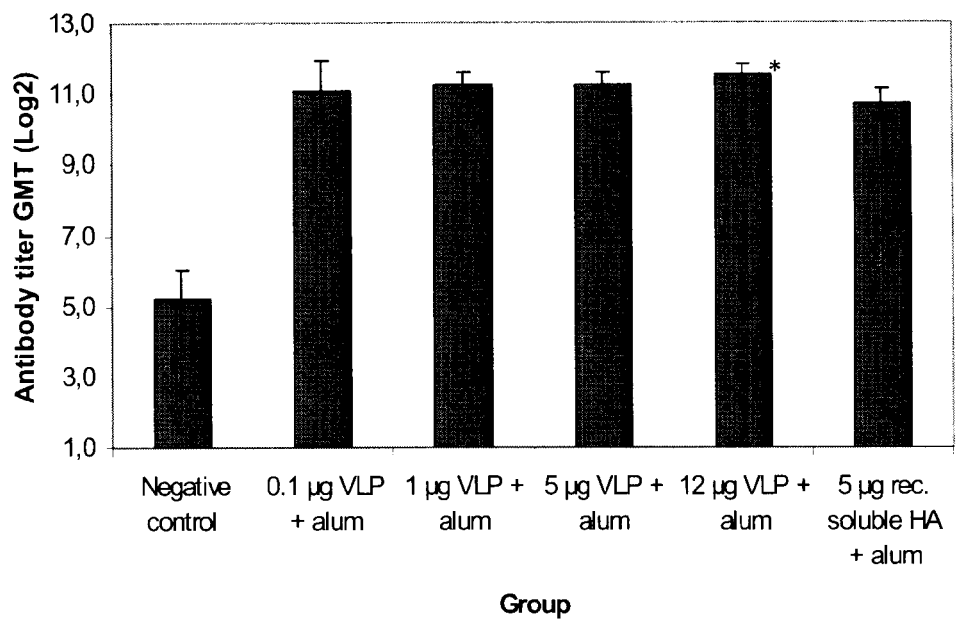
FIG. 20(A) Induction of serum antibody responses 14 days after boost in Balb/c mice vaccinated with plant-made influenza H5 VLP or recombinant soluble HA through intramuscular injection.
Figure 20B:
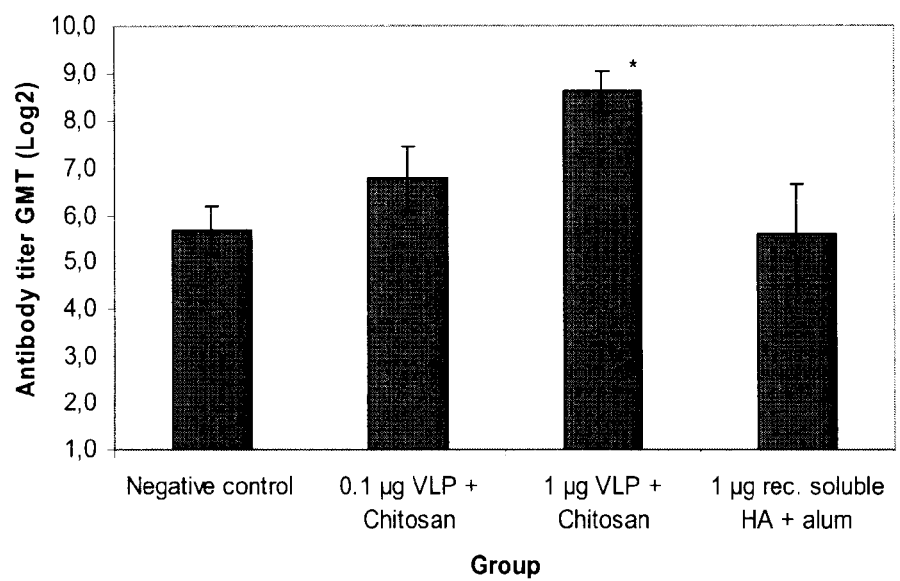
FIG. 20(B) Antibody responses of mice immunized through intranasal administration. Antibody responses were measured against inactivated whole H5N1 viruses (A/Indonesia/5/05). GMT: geometric mean titer. Values are the GMT (log 2) of reciprocal end-point titers of five mice per group. Bars represent mean deviation. * $p<0.05$ compared to recombinant soluble HA.

FIG. 20B also confirms the identity of the purified VLP visualized by Western blotting and immunodetection with an anti-H5 polyclonal serum (A/Vietnam/1203/2004). A unique band of approximately 72 kDa is detected and corresponds in size to the uncleaved HA0 form of influenza hemagglutinin. FIG. 15c shows the VLP structure of the vaccine with the hemagglutinin spikes covering its structure.

VLPs were formulated for immunization of mice by filtering through a 0.22 µm filter; endotoxin content was measured using the endotoxin LAL (*Limulus Amebocyte* Lysate) detection kit (Lonza, Walkserville, Miss., USA). The filtered vaccine contained 105.8±11.6% EU/ml (endotoxin units/ml).

Example 5

Localization of Influenza VLPs in Plants

Figure 19:
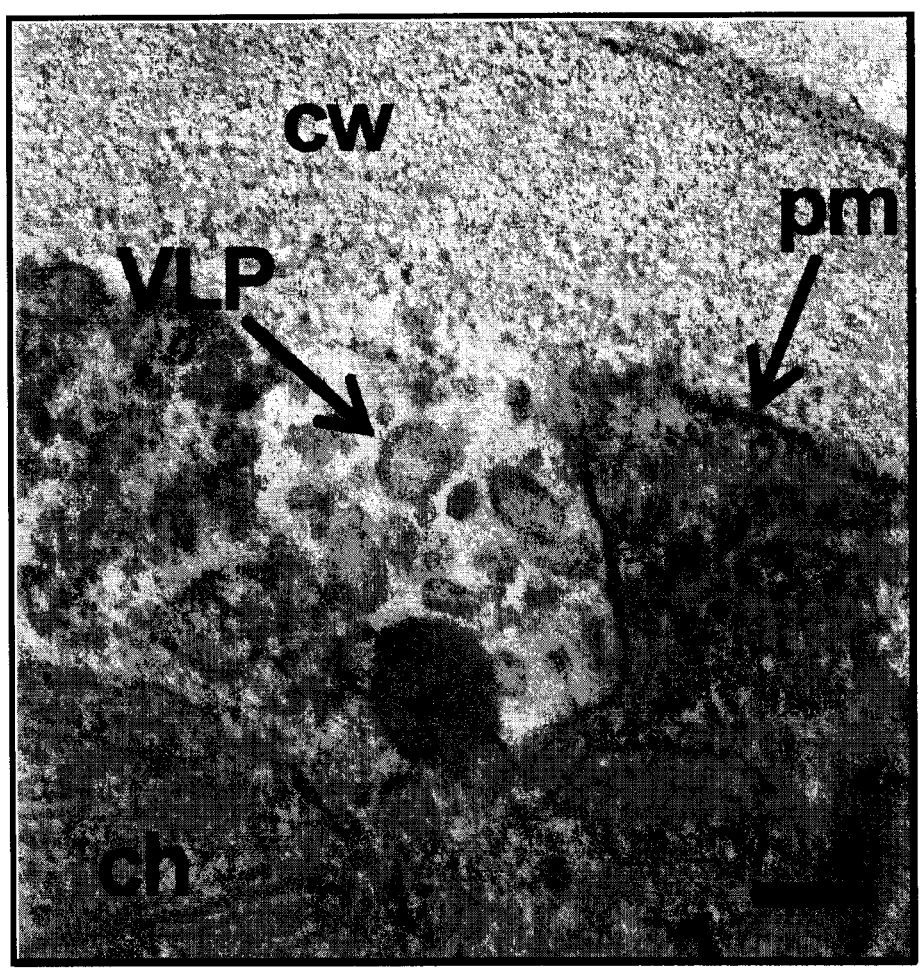
FIG. 19 shows localization of VLP accumulation by positive staining transmission electron microscopy observation of H5 producing tissue. CW: cell wall, ch: chloroplast, pm: plasma membrane, VLP: virus-like particle. The bar represents 100 nm.

To localize the VLPs and confirm their plasma membrane origin, thin leaf sections of H5-producing plants were fixed and examined under TEM after positive staining Observation of leaf cells indicated the presence of VLPs in extracellular cavities formed by the invagination of the plasma membrane (FIG. 19). The shape and position of the VLPs observed demonstrated that despite the apposition of their plasma membranes on the cell wall, plant cells have the plasticity required to produce influenza VLPs derived from their plasma membrane and accumulate them in the apoplastic space.

Example 6

Plasma Membrane Lipid Analysis

Further confirmation of the composition and origin of the plant influenza VLPs was obtained from analyses of the lipid content. Lipids were extracted from purified VLPs and their composition was compared to that of highly purified tobacco plasma membranes by high performance thin layer chromatography (HP-TLC). The migration patterns of polar and neutral lipids from VLPs and control plasma membranes were similar. Purified VLPs contained the major phospholipids (phosphatidylcholine and phosphatidylethanolamine) and sphingolipids (glucosyl-ceramide) found in the plasma membrane (FIG. 27A), and both contained free sterols as the sole neutral lipids (FIG. 27B). However, immunodetection of a plasma membrane protein marker (ATPase) in purified VLP extracts showed that the VLP lipid bilayer does not contain one of the major proteins associated with plant plasma membranes, suggesting that host proteins may have been excluded from the membranes during the process of VLPs budding from the plant cells (FIG. 27C).

Example 7

Immunogenicity of the H5 VLPs and Effect of Route of Administration

Mice were administered plant-made H5 VLPs by intramuscular injection, or intranasal (inhalation). 0.1 to 12 ug of VLPs were injected intramuscularly into mice, with alum as an adjuvant, according to the described methods. Peak antibody titers were observed with the lowest antigen quantity, in a similar magnitude to that of 5 ug recombinant, soluble hemagglutinin (HA) (FIG. 20A).

0.1 to 1 ug plant-made H5 VLPs were administered intranasally with a chitosan adjuvant provided for an antibody response greater than that of the recombinant soluble HA with an alum adjuvant (FIG. 20B).

For both administration routes, and over a range of antigen quantities, seroconversion was observed in all of the mice tested. Recombinant H5 soluble antigen conferred low (<1/40) or negligible (1<1/10 for the non-adjuvanted recombinant H5) HI titres.

Example 8

Hemagglutination-Inhibition Antibody Titer (HAI) H5 VLP

Figure 21A:
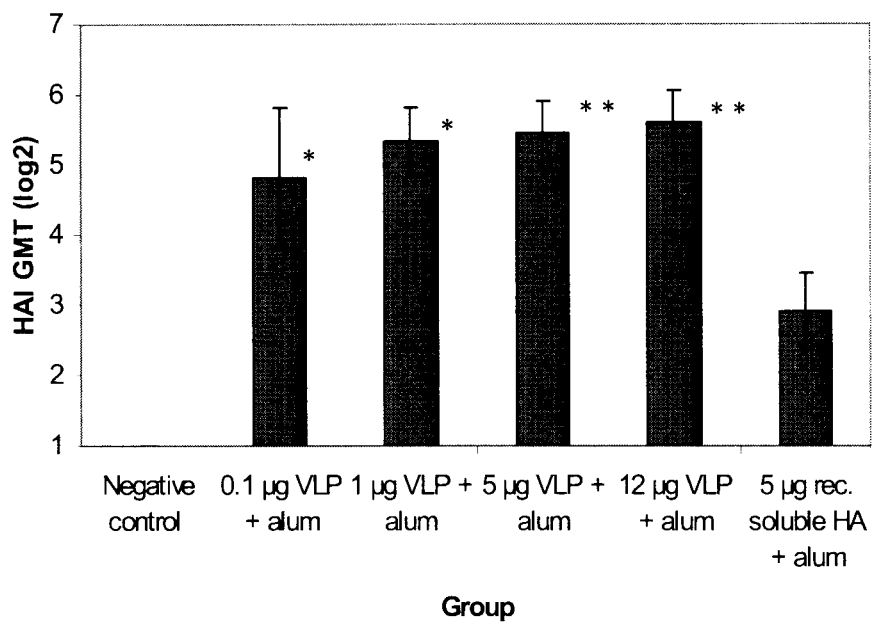
FIG. 21(A) Hemagglutination inhibition antibody response (HAI) 14 days after boost in Balb/c mice vaccinated with plant-made influenza H5 VLP or recombinant soluble HA through intramuscular injection.

FIG. 21A, B illustrates the hemagglutination inhibition (HAI) antibody response 14 days following a "boost" with plant-made H5 VLP, or recombinant soluble HA. The lowest dose of antigen (0.1 ug) when administered intramuscularly produced a superior HAI response to a 10-fold greater administration (5 ug) of recombinant soluble HA. Increasing doses of H5 VLP provided a modest increase in HAI over the lowest dose.

Figure 4A:
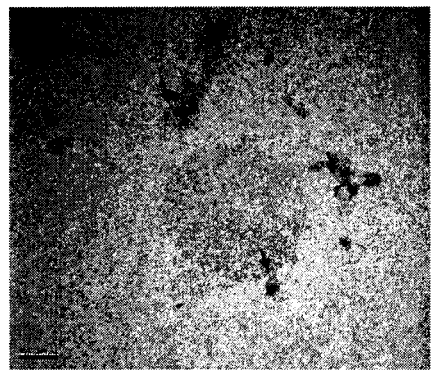
FIG. 4A shows an electron microscopy photomicrograph of large hemagglutinin H1 structures from elution fraction 9 from a size exclusion column showing a 50 000-fold enlargement of a VLP from H1 showing the presence of multiple similar structures (the bar represents 200 nm).
Figure 4B:
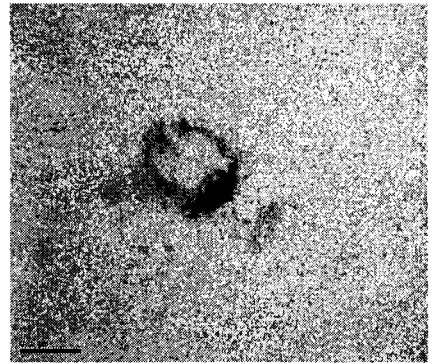
FIG. 4B shows a 150 000-fold enlargement of a VLP from H1 (the bar represents 100 nm).
Figure 4C:
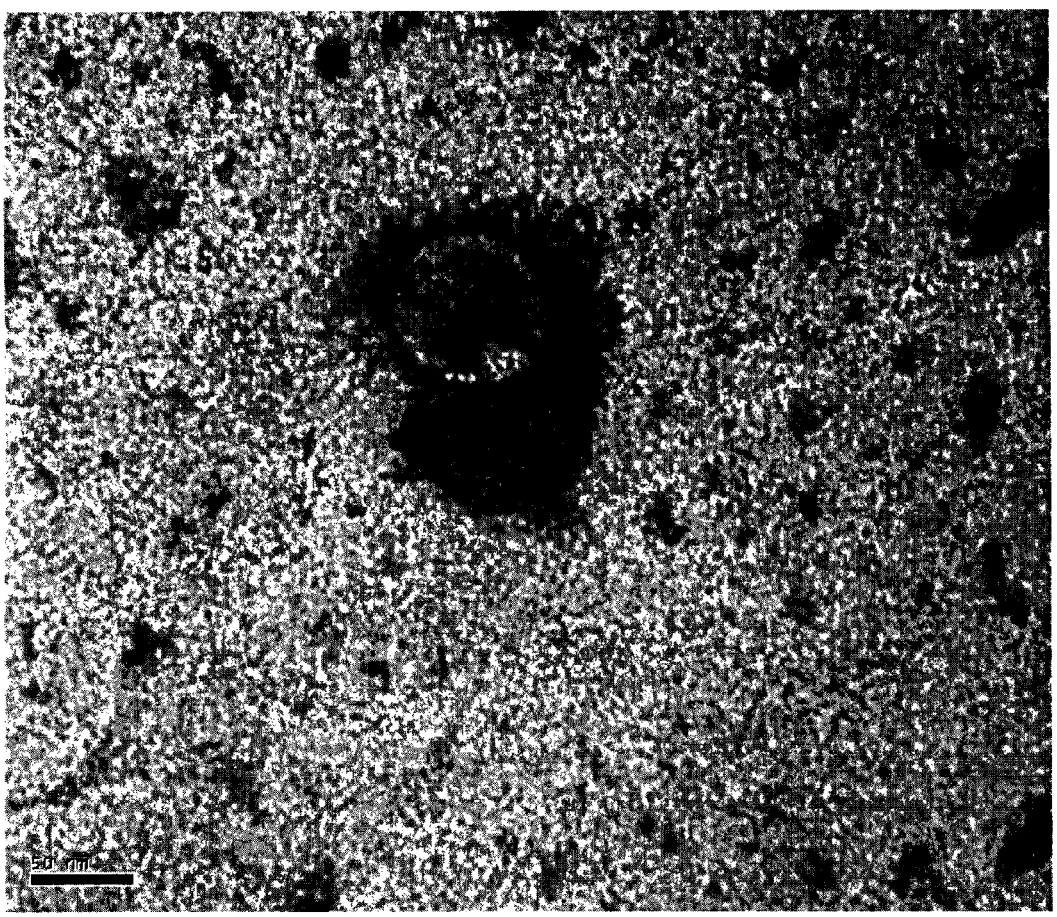
FIG. 4C shows a 50 000-fold enlargement of a VLP from H5 showing the presence of multiple similar structures (the bar represents 50 nm).
Figure 21B:
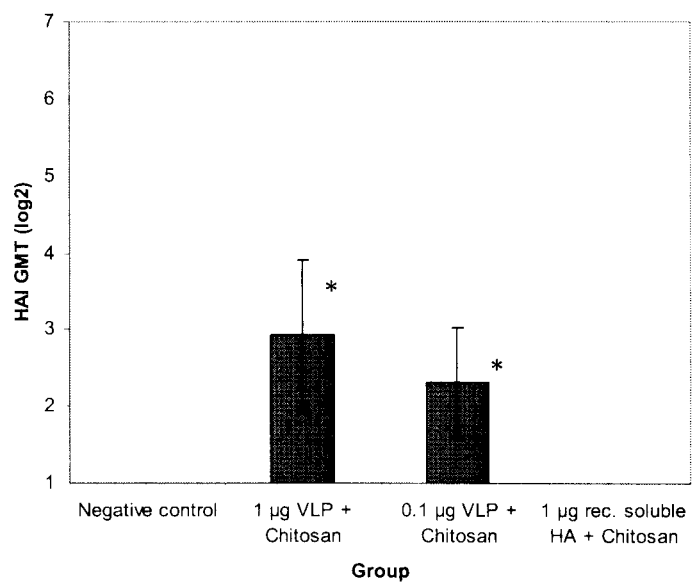
FIG. 21(B) Antibody responses of mice immunized through intranasal administration. HAI antibody responses were measured using inactivated whole H5N1 viruses (A/Indonesia/5/05). GMT: geometric mean titer. Values are the GMT (log 2) of reciprocal end-point titers of five mice per group. Bars represent mean deviation. * $p<0.05$ and ** $p<0.01$ compared to recombinant soluble HA.

HAI response following intranasal administration was significantly increased in mice administered plant-made H5 VLPs (1.0 or 0.1 ug) compared to those administered 1 ug recombinant soluble HA, which was similar to the negative control. All mice immunized by intramuscular injection of H5 VLPs (from 0.1 to 12 µg) had higher HAI titers than mice immunised with the control HA antigen (FIG. 4a—now 21A). For the same dose of 5 µg, VLPs induced HAI titers 20 times higher than the corresponding dose of the control HA antigen. VLPs also induced significantly higher HAI titers than the control HA antigen when delivered through the intranasal route (FIG. 21b). For a given dose of H5 VLP the levels of HAI titers were lower in mice immunised intranasally than for mice immunised intramuscularly; 1 µg VLP induced a mean HAI titer of 210 when administered i.m. while the same dose induced a mean HAI titer of 34 administered i.n.

Figure 24:
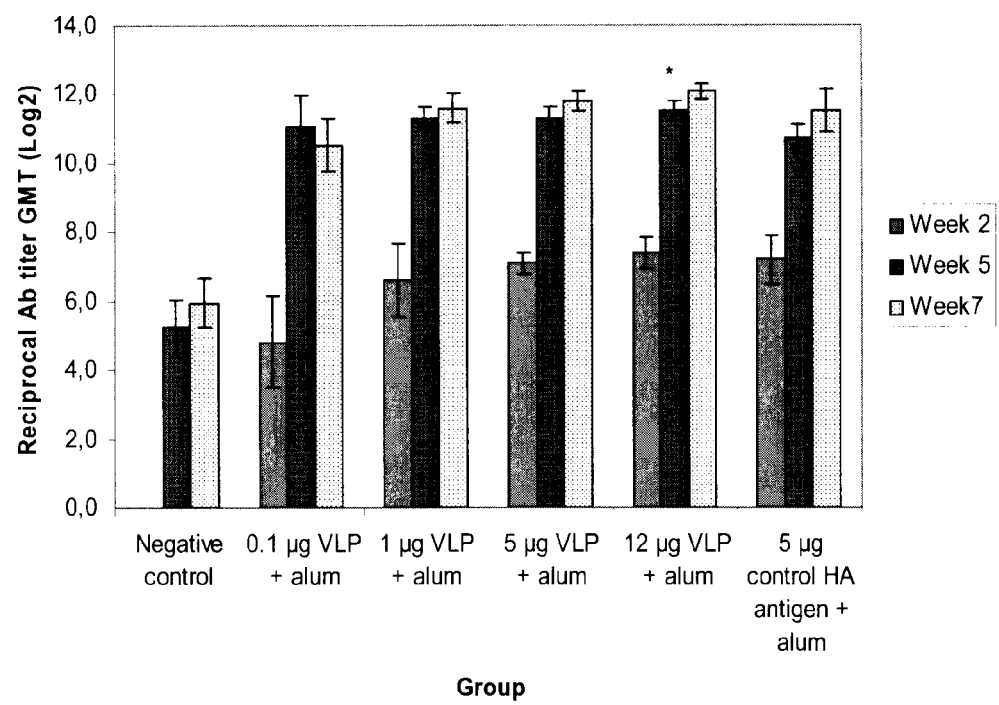
FIG. 24 shows antibody titer against homologous whole inactivated viruses (A/Indonesia/5/05), 2 weeks after first dose (week 2), 14 days after boost (week 5) or 30 days after boost (week 7). GMT: geometric mean titer. Values are the GMT ($\log_2$) of reciprocal end-point titers of five mice per group. * $p<0.05$ compared to recombinant soluble HA.

When administered intramuscularly, all doses of VLPs induced high level of antibodies capable of binding homologous whole inactivated viruses (FIGS. 20b and 24). No significant difference was found between the plant-made VLP vaccine and the control HA antigen (except the 12 µg VLP group 14 days after boost), as both antigen preparations induce high binding antibody titers against the homologous strain. However, when administered intranasally, VLPs induced higher binding antibody titers in than did the control HA antigen (FIG. 20b). When mixed with Chitosan, immunization with one microgram VLP induced a reciprocal mean Ab titer of 5 500, 8.6 times higher than the level found in mice immunized with 1 µg of the control HA antigen (reciprocal mean Ab titer of 920).

The immunogenicity of the plant-derived influenza VLPs was then investigated through a dose-ranging study in mice. Groups of five BALB/c mice were immunized intramuscularly twice at 3-week intervals with 0.1 µg to 12 µg of VLPs containing HA from influenza A/Indonesia/5/05 (H5N1) formulated in alum (1:1 ratio). Hemagglutination-inhibition titers (HI), using whole inactivated virus antigen (A/Indonesia/5/05 (H5N1)), were measured on sera collected 14 days after the second immunization. Immunization with doses of VLP as low as 0.1 µg induced the production of antibodies that inhibited viruses from agglutinating erythrocytes at high dilutions (FIG. 21A). Parallel immunization of mice with 5 µg of non-VLP alum-adjuvanted control H5 antigen (also from A/Indonesia/5/05) induce an HI response that was 2-3 logs lower than that achieved with the lowest VLP dose.

For both administration routes, and over a range of antigen quantities, the HAI response is superior in mice administered VLPs.

Example 9

Effect of Adjuvant on Immunogenicity of H5 VLPs

Plant-made H5 VLPs have a plasma membrane origin (FIG. 19, Example 5). Without wishing to be bound by theory, enveloped viruses or VLPs of enveloped viruses generally acquire their envelope from the membrane they bud through. Plant plasma membranes have a phytosterol complement that is rarely, if ever found in animal cells, and several of these sterols have been demonstrated to exhibit immunostimulatory effects.

Plant-made H5 VLPs were administered intramuscularly (FIG. 22A) or intranasally (FIG. 22B) to mice in the presence or absence of an adjuvant, and the HAI (hemagglutination inhibition antibody response) determined VLPs, in the presence or absence of an added adjuvant (alum or chitosan, as in these examples) in either system of administration demonstrated a significantly greater HAI hemagglutinin inhibition than recombinant soluble HA. Even in the absence of an added adjuvant (i.e. alum or chitosan), plant-made H5 VLPs demonstrate a significant HAI, indicative of a systemic immune response to administration of the antigen.

Alum enhanced the mean level of HAI titers by a factor of 5 for intramuscular administration of VLP (FIG. 22a) and by a factor of 3.7 for the control HA antigen. When administered i.m., 5 µg VLPs induced a mean HAI titer 12 times higher than the corresponding dose of control HA antigen. Chitosan did not boost the mean HAI level of the control HA antigen (FIG. 22b) while it increased the mean HAI level of mice immunised with 1 µg VLP administered i.n. by a factor of 5-fold.

Example 10

Antibody Isotypes

Mice administered plant-made H5 VLPs or recombinant soluble HA in the presence or absence of alum as an added adjuvant demonstrate a variety of immunoglobulin isotypes (FIG. 23A).

In the presence of an added adjuvant, the antibody isotype profiles of VLPs and the HA are similar, with IgG1 being the dominant isotype. When VLPs or HA are administered without an added adjuvant, IgG1 response is reduced, but remains the dominant isotype response to VLPs, with IgM, IgG2a, IgG2B and IgG3 maintaining similar titers as in the presence of an added adjuvant. IgG1, IgG2a, and IgG2b titers are markedly reduced when HA is administered without an added adjuvant.

These data, therefore, demonstrate that plant-made VLPs do not require an added adjuvant to elicit a antibody response in a host.

Figure 23B:
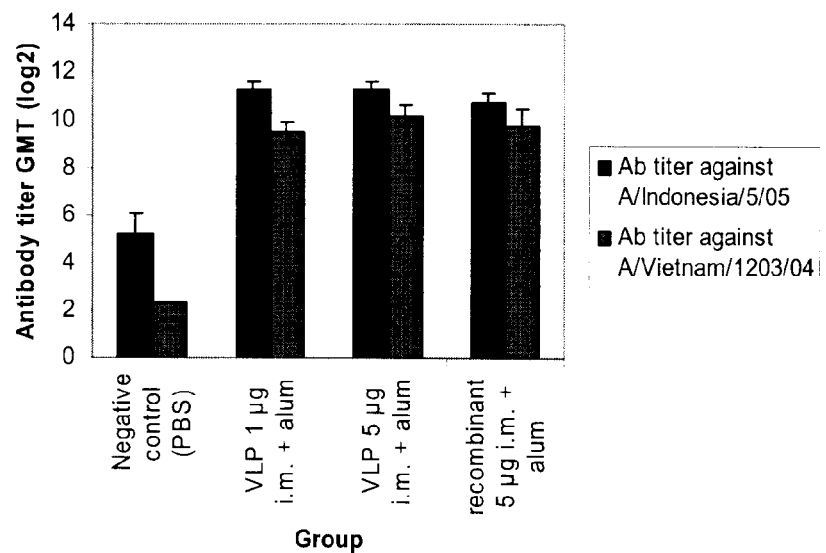
FIG. 23(B) Antibody titers against whole inactivated viruses. All groups are statistically different to negative control.

Antibody titers against whole inactivated influenza virus strains (A/Indonesia/5/05; A/Vietnam/1203/04)I in mice administered plant-made VLPs or soluble recombinant HA intramuscularly in the presence of an added antigen are illustrated in FIG. 23B. No significant difference is observed in the antibody titers for these influenza strains in mice administered 1 ug or 5 ug of VLPs or 5 ug of soluble HA.

Example 11

Cross-Reactivity of Serum Antibodies Induced by the H5 VLP Vaccine

Figure 25A:
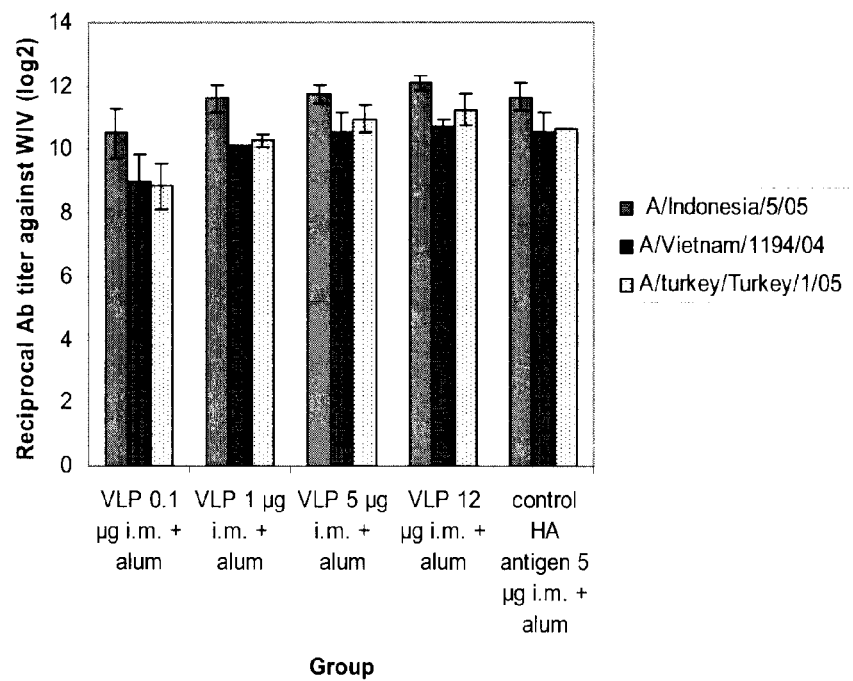
FIG. 25(A) Antibody titers against whole inactivated viruses show in vitro cross-reactivity of serum.

Cross-reactivity of serum antibodies induced by H5 VLP was assessed against whole inactivated influenza viruses of different strains. All VLP doses (from 0.1 to 12 µg) as well as 5 µg of control HA antigen induced high binding antibody titers against a clade 1 strain (A/Vietnam/1194/04), the homologous strain A/Indonesia/5/05 of clade 2.1, and a clade 2.2 strain A/turkey/Turkey/1/05 (FIG. 25A).

Figure 25B:
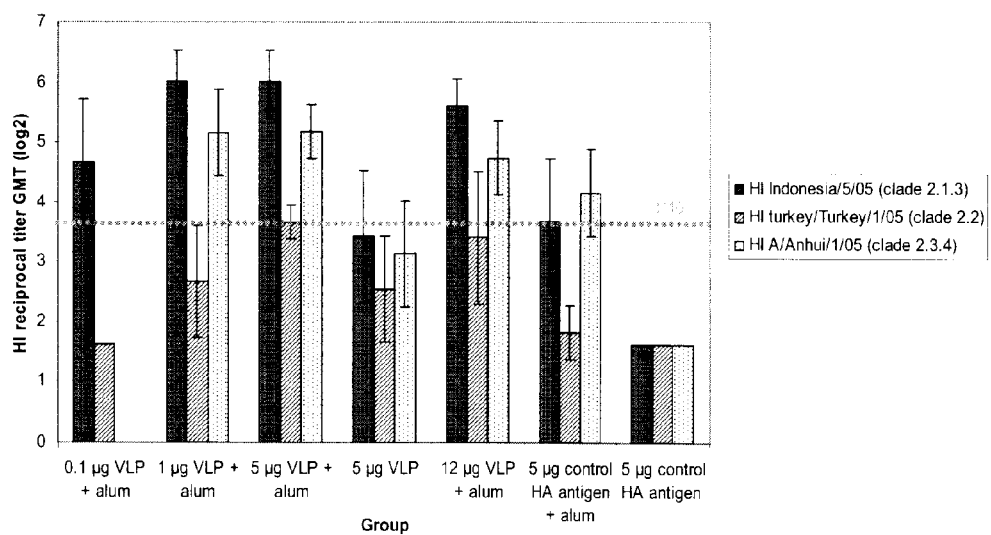
FIG. 25(B) Hemagglutination-inhibition titers against various whole inactivated viruses. Values are the GMT (log 2) of reciprocal end-point titers of five mice per group. Bars represent mean deviation. All groups are statistically different to negative control. * $p<0.05$, ** $p<0.001$ compared to the corresponding recombinant soluble HA.

However, only the plant-made VLP induced HAI titer against the A/turkey/Turkey/1/05 strain (FIG. 25b). HAI titers for the A/Indonesia/5/05 were high for VLPs.

Example 12

Cross-Protection Conferred by Immunization with Plant-Made H5 VLP

Mice that previously had been administered a two-dose regimen of A/Indonesia/5/05 H5 VLPs as described, were subsequently challenged intranasally with influenza A/Turkey/582/06 (H5N1) ("Turkey H5N1") infectious virus, and observed. The dose administered, per animal, was 10 $LD_{50}$ ($4.09 \times 10^5$ $CCID_{50}$).

By 7 days post-challenge, only 37.5% of the mice administered the PBS vaccine control had survived exposure to Turkey H5N1 (FIG. 26A). 100% of animals administered the control antigen (HA) or 1, 5 or 15 ug of Indonesia H5 VLPs survived up to 17 days post-challenge, when the experiment was terminated.

Figure 26B:
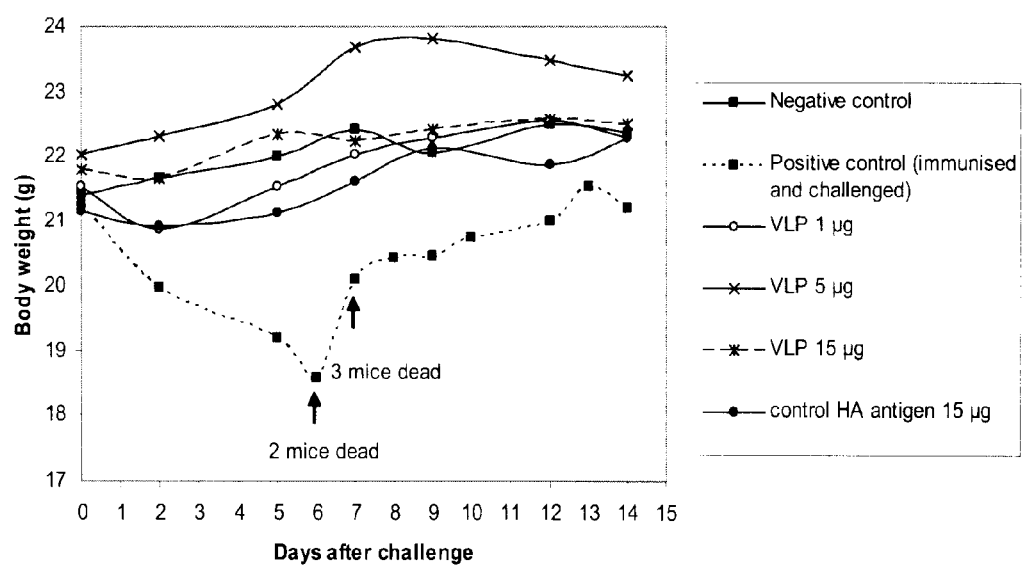
FIG. 26(B) Body weight of immunised mice after challenge. Values are the mean body weight of surviving mice.

Body mass of the mice was also monitored during the experiment, and the average mass of the surviving mice plotted (FIG. 26B). Mice administered 1, 5 or 15 ug of the Indonesia H5 VLPs before challenge did not lose any appreciable mass during the course of the experiment, and in particular mice administered 5 ug of the VLPs appear to have gained significant mass. Negative control mice (no Turkey H5N1 challenge) did not appreciably gain or lose body mass. Positive control mice (not administered VLPs, but challenged with Turkey H5N1) exhibited significant loss of body mass during the course of the experiment, and three of these mice died. As body mass is an average of all mice in the cohort, removal of the 'sickest' mice (the 3 that died) may lead to an apparent overall increase in mass, however note that the average body mass of the positive control cohort is still significantly below that of the negative or the VLP-treated cohorts.

These data, therefore, demonstrate that plant-made influenza VLPs comprising the H5 hemagglutinin viral protein induce an immune response specific for pathogenic influenza strains, and that virus-like particles may bud from a plant plasma membrane.

These data, therefore, demonstrate that plants are capable of producing influenza virus-like particles, and also for the first time, that virus-like particles can bud from a plant plasma membrane.

Further, using the current transient expression technology, a first antigen lot was produced only 16 days after the sequence of the target HA was obtained. Under the current yields for H5 VLPs, and at an exemplary dose of 5 μg per subject, each kg of infiltrated leaf may produce ~20,000 vaccine doses. This unique combination of platform simplicity, surge capacity and powerful immunogenicity provides for, among other embodiments, a new method response in the context of a pandemic.

Example 13

Figure 46:
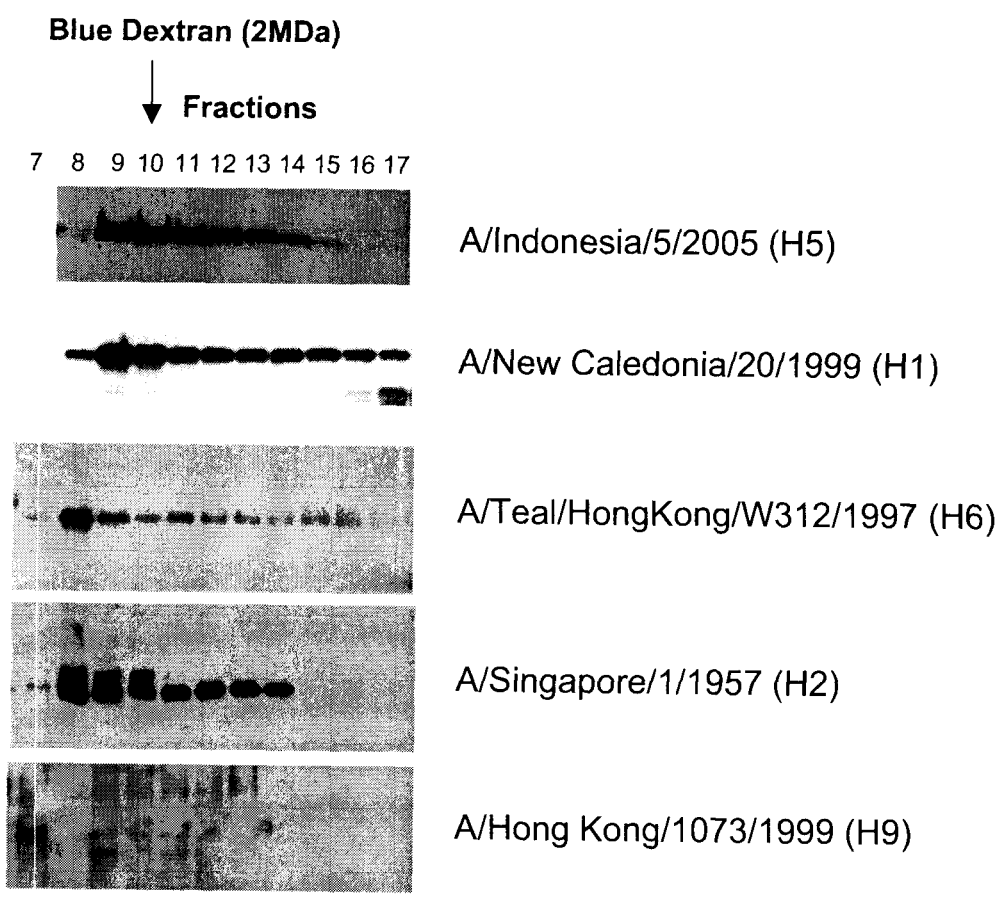
FIG. 46 shows immunodetection (western blot) of elution fractions of plant-produced VLPs, following size exclusion chromatography. Hemagglutinin subtypes H1, H2, H5, H6 and H9 are shown. Hemagglutinin is detected in fractions 7-14, corresponding to the elution of VLPs.

Characterization of Hemagglutinin-Containing Structures in Plant Extracts Using Size Exclusion Chromatography The assembly of plant-produced influenza hemagglutinin of different subtypes into high molecular weight structures was assessed by gel filtration. Crude or concentrated protein extracts from AGL1/660-, AGL1/540-, AGL1/783-, AGL1/780- and AGL1/785-infiltrated plants (1.5 mL) were fractionated by size exclusion chromatography (SEC) on Sephacryl™ S-500 HR columns (GE Healthcare Bio-Science Corp., Piscataway, N.J., USA). As shown in FIG. 46, Blue Dextran (2 MDa) elution peaked early in fraction 10. When proteins from 200 μL of each SEC elution fraction were concentrated (5-fold) by acetone-precipitation and analyzed by Western blotting (FIG. 46), hemagglutinins were primarily found in fractions 7 to 14, and are indicative of the incorporation of HA into VLPs. Without wishing to be bound by theory, this suggests that the HA protein had either assembled into a large superstructure or that it has attached to a high molecular weight structure, irrespectively of the subtype produced.

Example 14

Transient Expression of Seasonal Influenza Virus Hemagglutinin by Agroinfiltration in *N. benthamiana* Plants The ability of the transient expression system to produce seasonal influenza hemagglutinins was determined through the expression of the H1 subtype from strains A/Brisbane/59/2007 (H1N1) (plasmid #774), A/New Caledonia/20/1999 (H1N1) (plasmid #540) and A/Solomon Islands/3/2006 (H1N1) (plasmid #775). The hemagglutinin gene coding sequences were first assembled in the plastocyanin expression cassette—promoter, 5'UTR, 3'UTR and transcription termination sequences from the alfalfa plastocyanin gene—and the assembled cassettes were inserted into to a pCAMBIA binary plasmid. The plasmids were then transfected into *Agrobacterium* (AGL1), producing *Agrobacterium* strains AGL1/774, AGL1/540 and AGL1/775, respectively.

Figure 47:
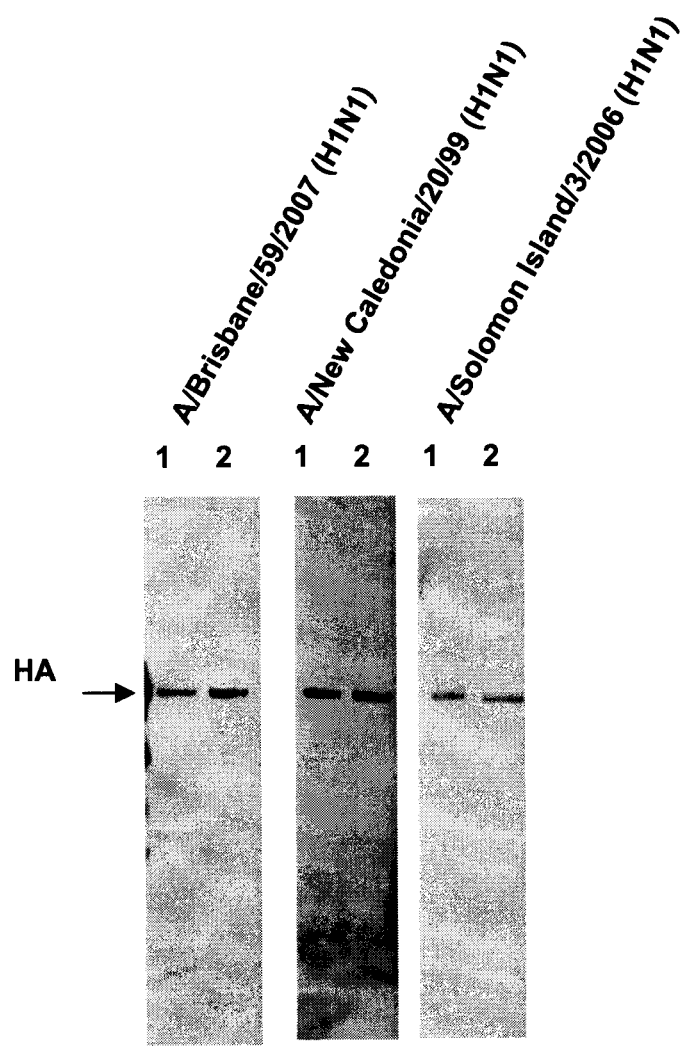
FIG. 47 shows an immunoblot analysis of expression of a series of H1 hemagglutinin from annual epidemic strains. Ten and twenty micrograms of protein extracts were loaded in lanes 1 and 2, respectively.

*N. benthamiana* plants were infiltrated with AGL1/774, AGL1/540 and AGL1/775, and the leaves were harvested after a six-day incubation period. To determine whether H1 accumulated in the agroinfiltrated leaves, protein were first extracted from infiltrated leaf tissue and analyzed by Western blotting using anti-H1 antibodies. A unique band of approximately 72 kDa was detected in extracts (FIG. 47), corresponding in size to the uncleaved HA0 form of influenza hemagglutinin. This demonstrated that expression of different annual epidemic strains of hemagglutinin in infiltrated leaves results in the accumulation of the uncleaved translation product.

Example 15

Transient Expression of Potential Pandemic Influenza Virus Hemagglutinin by Agroinfiltration in *N. benthamiana* Plants The ability of the transient expression system to produce potential influenza hemagglutinins was determined through the expression of the H5 subtype from strains A/Anhui/1/2005 (H5N1) (plasmid #781), A/Indonesia/5/2005 (H5N1) (plasmid #660) and A/Vietnam/1194/2004 (H5N1) (plasmid #782). The hemagglutinin gene coding sequences were first assembled in the plastocyanin expression cassette—promoter, 5'UTR, 3'UTR and transcription termination sequences from the alfalfa plastocyanin gene—and the assembled cassettes were inserted into to a pCAMBIA binary plasmid. The plasmids were then transfected into *Agrobacterium* (AGL1).

Figure 48:
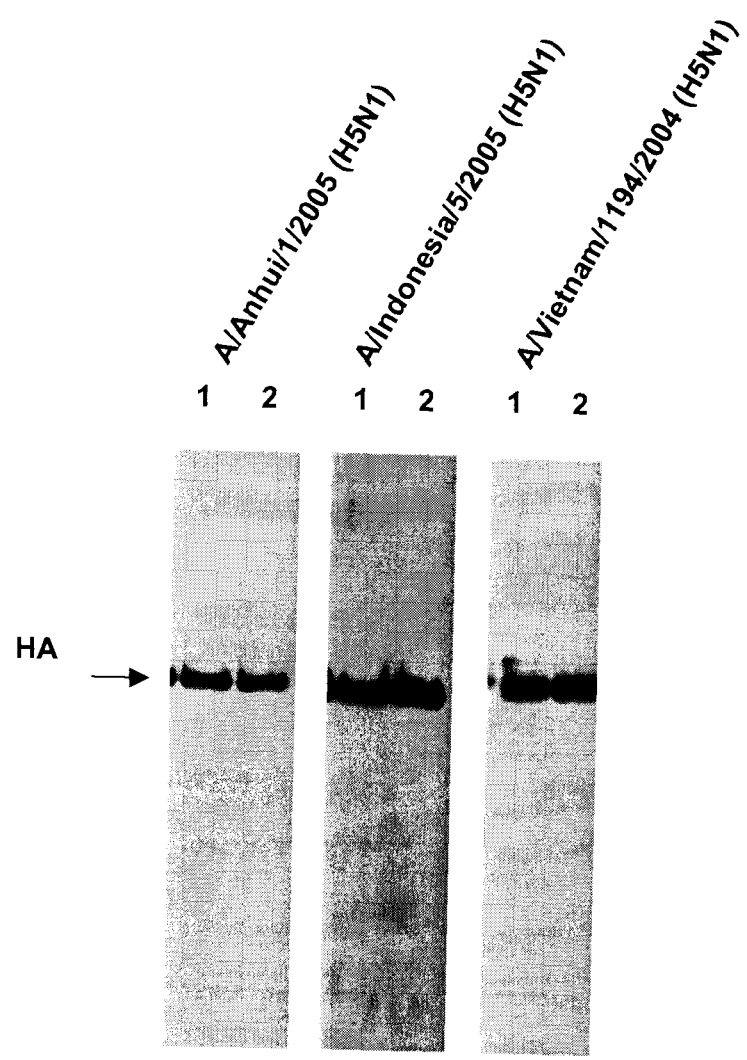
FIG. 48 shows an immunoblot analysis of expression of a series of H5 hemagglutinin from potential pandemic strains. Ten and twenty micrograms of protein extracts were loaded in lanes 1 and 2, respectively.

*N. benthamiana* plants were infiltrated with AGL1/781, AGL1/660 and AGL1/782, and the leaves were harvested after a six-day incubation period. To determine whether H5 accumulated in the agroinfiltrated leaves, protein were first extracted from infiltrated leaf tissue and analyzed by Western blotting using anti-H5 antibodies. A unique band of approximately 72 kDa was detected in extracts (FIG. 48), corresponding in size to the uncleaved HA0 form of influenza hemagglutinin. This demonstrated that expression of different potential pandemic strains of hemagglutinin in infiltrated leaves results in the accumulation of the uncleaved translation product.

Example 16

Transient Expression of H5 by Agroinfiltration in *N. tabacum* Plants

The ability of the transient expression system to produce influenza hemagglutinin in leaves of *Nicotiana tabacum* was analysed through the expression of the H5 subtype from strain A/Indonesia/5/2005 (H5N1) (plasmid #660). The hemagglutinin gene coding sequences were first assembled in the plastocyanin expression cassette—promoter, 5'UTR, 3'UTR and transcription termination sequences from the alfalfa plastocyanin gene—and the assembled cassettes were inserted into to a pCAMBIA binary plasmid. The plasmids were then transfected into *Agrobacterium* (AGL1).

Figure 49:
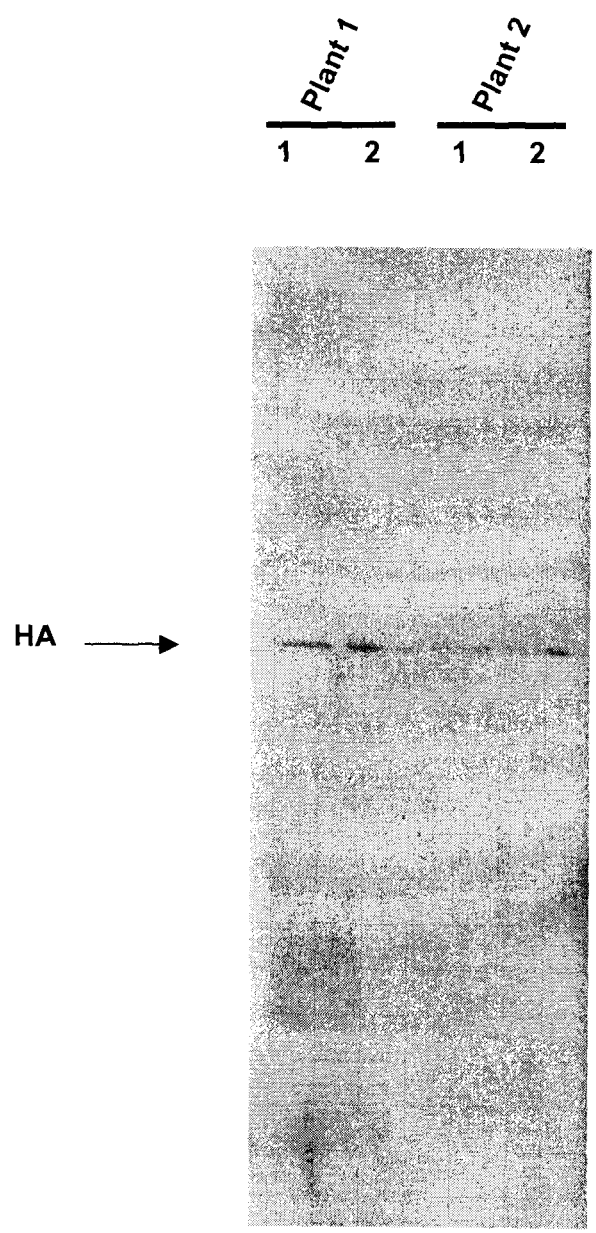
FIG. 49 show an immunoblot of H5 from strain A/Indonesia/5/2005 in protein extracts from *Nicotiana tabacum* leaves, agroinfiltrated with AGL1/660. Two plants were infiltrated and 10 and 20 µg of soluble protein from each plant were loaded in lanes 1 and 2, respectively.

*N. tabacum* plants were infiltrated with AGL1/660 and the leaves were harvested after a six-day incubation period. To determine whether H5 accumulated in the agroinfiltrated leaves, protein were first extracted from infiltrated leaf tissue and analyzed by Western blotting using anti-H5 antibodies. A unique band of approximately 72 kDa was detected in extracts (FIG. 49), corresponding in size to the uncleaved HA0 form of influenza hemagglutinin. This demonstrated that expression of hemagglutinin in infiltrated *N. tabacum* leaves results in the accumulation of the uncleaved translation product.

Example 17

Figure 50A:
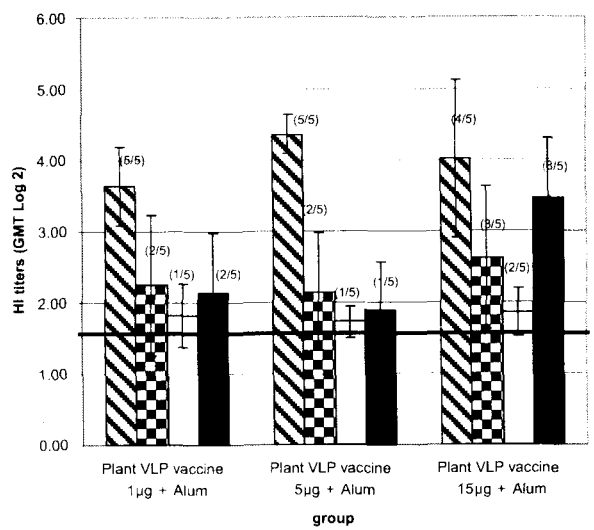
FIG. 50(A) Hemagglutination-inhibition (HI) titers in ferret sera, 14 days after 1st immunization and FIG. 50(B) after 2nd boost with plant-made influenza H5 VLP show the in vitro cross-reactivity of serum antibodies. HAI antibody responses were measured using the following inactivated whole H5N1 viruses: A/turkey/Turkey/1/05, A/Vietnam/1194/04, A/Anhui/5/05 and the homologous strain A/Indonesia/5/05. Values are the GMT (log 2) of reciprocal endpoint titers of five ferrets per group. Diagonal stripe—A/Indonesia/6/06 (clade 2.1.3); checked—A/turkey/Turkey/1/05 (clade 2.2); white bar—A/Vietnam/1194/04 (clade 1); black bar A/Anhui/5/05. Responders are indicated. Bars represent mean deviation.
Figure 50B:
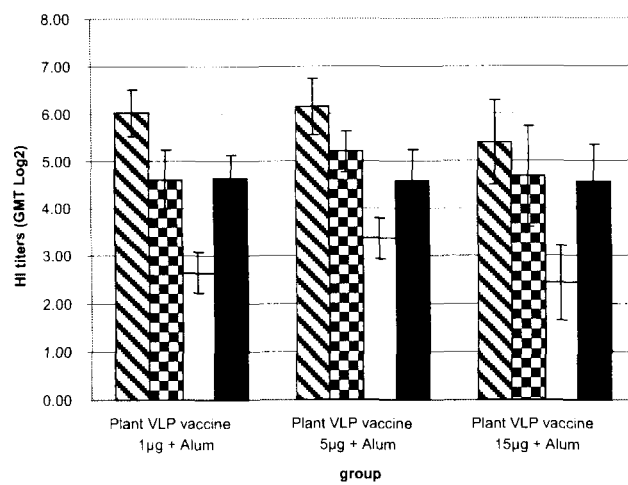

Immunogenicity of Plant-Made H5N1 VLP Vaccine from A/Indonesia/5/05 (H5N1) in Ferrets A dose escalation study in ferrets was performed to evaluate the immunogenicity of plant derived VLPs. In vitro cross-reactivity of serum antibody induced by the H5 VLP vaccine at 3 doses (1, 5 and 15 ug) was assessed by hemagglutination inhibition of three other H5N1 strains—A/turkey/Turkey/1/05 (clade 2.2), A/Vietnam/1194/04 (clade 1) and A/Anhui/5/05 (all whole, inactivated virus), using serum taken 14 days after the first dose of vaccine (FIG. 50A), and 14 days after the $2^{nd}$ dose (FIG. 50 B). For all 3 dose concentrations, cross-reactivity is observed Example 17

Analysis of the Immunogenicity Results According to CHMP Criteria

The EMEA's Committee for Medicinal Products for Human Use (CHMP) (http://www.emea.europa.eu/htms/general/contacts/CHMP/CHMP.html) sets out three criteria (applied following the second dose) for vaccine efficacy: 1—Number of seroconversion or significant increase in HI titers (4-fold)>40%; 2—Mean geometric increase of at least 2.5; 3—proportion of subjects achieving an HI titer of 1/40 should be at least 70%. Analysis of these criteria in the ferret model is shown in Tables 8-11. (*) is indicative of meeting or exceeding the CHMP criteria. A summary of cross-immunogenicity analysis in relation to CHMP criteria for licensure is shown in Table 12.

Animals were assessed daily for body weight, temperature and overall condition. No sign of sickness or discomfort was recorded during the study. Body weight and temperature was within normal ranges during the study. The vaccine was safe and tolerated by the study animals.

TABLE 8

Data for homologous strain (A/Indonesia/5/05)

| Day | Criteria | 1 µg | 1 µg adjuvanted | 5 µg | 5 µg adjuvanted | 7.5 µg | 15 µg | 15 µg adjuvanted | 30 µg | 5 µg ITC |
|---|---|---|---|---|---|---|---|---|---|---|
| 14 (post 1st inj.) | % 4-fold increase in HI titer | 0% | 100% | 0% | 100%* | 20% | 20% | 80%* | 0% | 0% |
| | Mean geometric increase | 0% | 7.6 | 0% | 15.6* | 1.3 | 1.2 | 11.2* | 0% | 0% |
| | % of HI titer of 1/40 | 0% | 60% | 0% | 100%* | 20% | 0% | 80%* | 0% | 0% |
| | Mean HI titer | | 38 | | 78 | | | 56 | | |
| 35 (14 days post boost) | % 4-fold increase in HI titer | 0% | 100%* | 0% | 60%* | 0% | 0% | 40%* | 0% | 0% |
| | Mean geometric increase | 0% | 10.8* | 0% | 5.9* | 0.7 | 0% | 4* | 0% | 0% |
| | % of HI titer of 1/40 | 0% | 100%* | 0% | 100%* | 0% | 0% | 100%* | 0% | 0% |
| | Mean HI titer | | 411 | | 465 | | | 217 | | |

TABLE 9

Data for heterologous strain (A/Vietnam/1194/04)

| Day | Criteria | 1 µg | 1 µg adjuvanted | 5 µg | 5 µg adjuvanted | 7.5 µg | 15 µg | 15 µg adjuvanted | 30 µg | 5 µg ITC |
|---|---|---|---|---|---|---|---|---|---|---|
| 14 (post 1st inj.) | % 4-fold increase in HI titer | | 0% | | 0% | | | 0% | | |
| | Mean geometric increase | | 1.2 | | 1.2 | | | 1.3 | | |
| | % of HI titer of 1/40 | | 0% | | 0% | | | 0% | | |
| 35 (post boost) | % 4-fold increase in HI titer | | 60% | | 80%* | | | 60% | | |
| | Mean geometric increase | | 2.3 | | 5.1* | | | 1.78 | | |
| | % of HI titer of 1/40 | | 0% | | 80%* | | | 20% | | |

TABLE 10

Data for heterologous strain (A/turkey/Turkey/1/05)

| Day | Criteria | 1 µg | 1 µg adjuvanted | 5 µg | 5 µg adjuvanted | 7.5 µg | 15 µg | 15 µg adjuvanted | 30 µg | 5 µg ITC |
|---|---|---|---|---|---|---|---|---|---|---|
| 14 (post 1st inj.) | % 4-fold increase in HI titer | | 40% | | 20% | | | 60% | | |
| | Mean geometric increase | | 1.9 | | 1.7 | | | 2.8 | | |
| | % of HI titer of 1/40 | | 40% | | 20% | | | 40% | | |

TABLE 10-continued

Data for heterologous strain (A/turkey/Turkey/1/05)

| | | Study group | | | | | | |
|---|---|---|---|---|---|---|---|---|
| Day | Criteria | 1 µg | 1 µg adjuvanted | 5 µg | 5 µg adjuvanted | 7.5 µg | 15 µg | 15 µg adjuvanted | 30 µg | 5 µg ITC |

| Day | Criteria | 1 µg adjuvanted | 5 µg adjuvanted | 15 µg adjuvanted |
|---|---|---|---|---|
| 35 (post boost) | % 4-fold increase in HI titer | 80%* | 100%* | 80%* |
| | Mean geometric increase | 10.6* | 20.8* | 7.7* |
| | % of HI titer of 1/40 | 100%* | 100%* | 100%* |

TABLE 11

Data for heterologous strain (A/Anhui/5/05)

| Day | Criteria | 1 µg adjuvanted | 5 µg adjuvanted | 15 µg adjuvanted |
|---|---|---|---|---|
| 14 (post 1st inj.) | % 4-fold increase in HI titer | 40% | 20% | 80%* |
| | Mean geometric increase | 1.8 | 1.3 | 6.4* |
| | % of HI titer of 1/40 | 20% | 20% | 80%* |
| 35 (post boost) | % 4-fold increase in HI titer | 100%* | 100%* | 60%* |
| | Mean geometric increase | 11.8* | 14.4* | 3* |
| | % of HI titer of 1/40 | 100%* | 80%* | 80%* |

TABLE 12

Summary of cross-immunogenicity analysis in relation to CHMP criteria for licensure.

| Strain | Criteria | 1 µg adjuvanted | 5 µg adjuvanted | 15 µg adjuvanted |
|---|---|---|---|---|
| A/turkey/Turkey/1/05 (clade 2.2) | % 4-fold increase in HI titer | 80%* | 100%* | 80%* |
| | Mean geometric increase | 10.6* | 20.8* | 7.7* |
| | % of HI titer of 1/40 | 100

TABLE 13-continued

Variation in Influenza subtypes for selected HA coding sequences

| | Strain | Sequence database reference No. | Origin | SP | HA1 | HA2 | DTm | Divergence |
|---|---|---|---|---|---|---|---|---|
| | A/Solomon Islands/3/2006 | EU100724 | ? | Y | Y | Y | Y | 189: R ou G, 220: K (MDCK) T(Egg), 249: Q (MDCK) R(Egg), 550: L (MDCK) R (Egg) |
| | A/Solomon Islands/3/2006 | ISDN220951 | MDCK | Y | Y | N | N | 189: R ou G, 220: K (MDCK) T(Egg), 249: Q (MDCK) R(Egg), 550: L (MDCK) R (Egg) |
| | A/Solomon Islands/3/2006 | ISDN220953 | Egg | Y | Y | N | N | 189: R ou G, 220: K (MDCK) T(Egg), 249: Q (MDCK) R(Egg), 550: L (MDCK) R (Egg) |
| | A/Solomon Islands/3/2006 | EU124137 | Egg | Y | Y | N | N | 189: R ou G, 220: K (MDCK) T(Egg), 249: Q (MDCK) R(Egg), 550: L (MDCK) R (Egg) |
| | A/Solomon Islands/3/2006 | EU124135 | MDCK | Y | Y | N | N | 189: R ou G, 220: K (MDCK) T(Egg), 249: Q (MDCK) R(Egg), 550: L (MDCK) R (Egg) |
| | A/Solomon Islands/3/2006 | EU124177 | MDCK | Y | Y | Y | Y | 189: R ou G, 220: K (MDCK) T(Egg), 249: Q (MDCK) R(Egg), 550: L (MDCK) R (Egg) |
| H1 | A/Brisbane/ 59/2007 | ISDN282676 | MDCK | Y | Y | Y | | 203: D/I/N D est le plus abondant chez les H1 |
| | A/Brisbane/ 59/2007 | ISDN285101 | Egg | Y | Y | N | N | 203: D/I/N D est le plus abondant chez les H1 |
| | A/Brisbane/ 59/2007 | ISDN285777 | Egg | Y | Y | Y | Y | 203: D/I/N D est le plus abondant chez les H1 |
| | A/Brisbane/ 59/2007 | ISDN282677 | Egg | Y | Y | Y | Y | 203: D/I/N D est le plus abondant chez les H1 |
| H3 | A/Brisbane/ 10/2007 | ISDN274893 | Egg | Y | Y | Y | Y | 202: V/G, 210: L/P, 215: del Ala, 242: S/I |
| | A/Brisbane/ 10/2007 | ISDN257648 | MDCK | N | Y | Y | Y | 202: V/G, 210: L/P, 215: del Ala, 242: S/I |
| | A/Brisbane/ 10/2007 | ISDN256751 | Egg | Y | Y | Y | Y | 202: V/G, 210: L/P, 215: del Ala, 242: S/I |
| | A/Brisbane/ 10/2007 | ISDN273757 | Egg | Y | Y | Y | Y | 202: V/G, 210: L/P, 215: del Ala, 242: S/I |
| | A/Brisbane/ 10/2007 | ISDN273759 | Egg | Y | Y | Y | Y | 202: V/G, 210: L/P, 215: del Ala, 242: S/I |
| | A/Brisbane/ 10/2007 | EU199248 | Egg | N | Y | Y | Y | 202: V/G, 210: L/P, 215: del Ala, 242: S/I |
| | A/Brisbane/ 10/2007 | EU199366 | Egg | Y | Y | Y | Y | 202: V/G, 210: L/P, 215: del Ala, 242: S/I |
| | A/Brisbane/ 10/2007 | ISDN257043 | Egg | N | Y | Y | Y | 202: V/G, 210: L/P, 215: del Ala, 242: S/I |
| | A/Brisbane/ 10/2007 | EU199250 | MDCK | N | Y | Y | Y | 202: V/G, 210: L/P, 215: del Ala, 242: S/I |
| | A/Brisbane/ 10/2007 | ISDN275357 | Egg | N | Y | N | N | 202: V/G, 210: L/P, 215: del Ala, 242: S/I |
| | A/Brisbane/ 10/2007 | ISDN260430 | Egg | N | Y | Y | Y | 202: V/G, 210: L/P, 215: del Ala, 242: S/I |
| H3 | A/Wisconsin/ 67/2005 | ISDN131464 (vaccine rec.) | ? | N | Y | Y | N | 138: A/S 156: H/Q 186: G/V 196: H/Y |
| | A/Wisconsin/ 67/2005 | DQ865947 | ? | N | Y | partiel | N | 138: A/S 156: H/Q 186: G/V 196: H/Y |
| | A/Wisconsin/ 67/2005 | EF473424 | ? | N | Y | Y | N | 138: A/S 156: H/Q 186: G/V 196: H/Y |
| | A/Wisconsin/ 67/2005 | ISDN138723 | Egg | N | Y | Y | Y | 138: A/S 156: H/Q 186: G/V 196: H/Y |

TABLE 13-continued

Variation in Influenza subtypes for selected HA coding sequences

| | Strain | Sequence database reference No. | Origin | SP | HA1 | HA2 | DTm | Divergence |
|---|---|---|---|---|---|---|---|---|
| | A/Wisconsin/ 67/2005 | EF473455 | Egg | N | Y | Y | Y | 138: A/S 156: H/Q 186: G/V 196: H/Y |
| | A/Wisconsin/ 67/2005 | ISDN138724 | ? | N | Y | Y | Y | 138: A/S 156: H/Q 186: G/V 196: H/Y |
| B | B/Malaysia/ 2506/2004 | ISDN126672 (vaccine rec.) | Egg | Y | Y | N | N | 120 K/N 210 T/A |
| | B/Malaysia/ 2506/2004 | EF566433 | Egg | Y | Y | N | N | 120 K/N 210 T/A |
| | B/Malaysia/ 2506/2004 | ISDN231265 | Egg | Y | Y | Y | Y | 120 K/N 210 T/A |
| | B/Malaysia/ 2506/2004 | ISDN231557 | MDCK | Y | Y | Y | Y | 120 K/N 210 T/A |
| | B/Malaysia/ 2506/2004 | EF566394 | MDCK | Y | Y | N | N | 120 K/N 210 T/A |
| | B/Malaysia/ 2506/2004 | EU124274 | Egg | Y | Y | Y | Y | 120 K/N 210 T/A |
| | B/Malaysia/ 2506/2004 | EU124275 | MDCK | Y | Y | Y | Y | 120 K/N 210 T/A |
| | B/Malaysia/ 2506/2004 | ISDN124776 | MDCK | Y | Y | N | N | 120 K/N 210 T/A |
| B | B/Florida/4/ 2006 | ISDN261649 | Egg | Y | Y | Y | N | lacking glycosylation site at position 211; 10 amino acids of DTm/cytoplasmic tail |
| | B/Florida/ 4/2006 | EU100604 | MDCK | N | Y | N | N | |
| | B/Florida/ 4/2006 | ISDN218061 | MDCK | N | Y | N | N | |
| | B/Florida/ 4/2006 | ISDN285778 | Egg | Y | Y | Y | Y | Includes cytoplasmic tail |
| B | B/Brisbane/ 3/2007 | ISDN256628 | Egg | N | Y | N | N | lacking glycosylation site at position 211 |
| | B/Brisbane/ 3/2007 | ISDN263782 | Egg | Y | Y | Y | Y | lacking glycosylation site at position 211 |
| | B/Brisbane/ 3/2007 | ISDN263783 | MDCK | Y | Y | Y | Y | |
| H5 | A/Viet Nam/1194/ 2004 | ISDN38686 (Vaccine rec.) | ? | Y | Y | Y | Y | |
| | A/Viet Nam/1194/ 2004 | AY651333 | ? | Y | Y | Y | Y | |
| | A/Viet Nam/1194/ 2004 | EF541402 | ? | Y | Y | Y | Y | |
| H5 | A/Anhui1/ 1/2005 | DQ37928 (vaccine rec.) | ? | Y | Y | Y | Y | |
| | A/Anhui1/ 1/2005 | ISDN131465 | Egg | Y | Y | Y | Y | |
| H7 | A/Chicken/ Italy/13474/ 1999 | AJ91720 | ARN gen | Y | Y | Y | Y | |
| H7 | A/Equine/Prague/ 56 | AB298277 (Lab reassortant) | ? | Y | Y | Y | Y | 152 (R/G) 169 (T/I) 208 (N/D) (glycosylation site abolished) |
| | A/Equine/ Prague/56 | X62552 | ? | Y | Y | Y | Y | |
| H9 | A/Hong Kong/1073/ 1999 | AJ404626 | ? | Y | Y | Y | Y | |
| | A/Hong Kong/1073/ 1999 | AB080226 | ? | N | Y | N | N | |
| H2 | A/Singapore/ 1/1957 | AB296074 | ? | Y | Y | Y | Y | |
| | A/Singapore/ 1/1957 | L20410 | RNA | Y | Y | Y | Y | |

TABLE 13-continued

Variation in Influenza subtypes for selected HA coding sequences

| | Strain | Sequence database reference No. | Origin | SP | HA1 | HA2 | DTm | Divergence |
|---|---|---|---|---|---|---|---|---|
| | A/Singapore/1/1957 | L11142 | ? | Y | Y | Y | Y | |
| H2 | A/Japan/305/1957 | L20406 | ? | Y | Y | Y | Y | |
| | A/Japan/305/1957 | L20407 | ? | Y | Y | Y | Y | |
| | A/Japan/305/1957 | CY014976 | ? | Y | Y | Y | Y | |
| | A/Japan/305/1957 | AY209953 | ? | Y | Y | N | N | |
| | A/Japan/305/1957 | J02127 | ? | Y | Y | Y | Y | |
| | A/Japan/305/1957 | DQ508841 | ? | Y | Y | Y | Y | |
| | A/Japan/305/1957 | AY643086 | ? | Y | Y | Y | N | |
| | A/Japan/305/1957 | AB289337 | ? | Y | Y | Y | Y | |
| | A/Japan/305/1957 | AY643085 | ? | Y | Y | Y | Y | |
| | A/Japan/305/1957 | AY643087 | Drug resistant | Y | Y | Y | N | |
| H6 | A/Teal/Hong Kong/W312/1997 (H6N1) | AF250479 | Egg | Y | Y | Y | Y | |

Y, N—Yes, No, respectively
SP—presence of signal peptide sequence Y/N
HA1—complete HA1 domain Y/N
HA2—complete HA2 domain Y/N
DTm—complete transmembrane domain Y/N Strain: H1 from A/Solomon Islands/3/2006

Eight amino acid sequences were compared, and variations identified. (Table 14). Position 171 exhibited a variation of glycine (G) or arginine (R) in some sequences.

TABLE 14

A/Solomon Islands/3/2006 amino acid variation

| Amino acid #* | MDCK | Egg |
|---|---|---|
| 212 | K | T |
| 241 | Q | R |
| 542 | L | R |

*Numbering from the starting M

Strain: H1 from A/Brisbane/59/2007

Position 203 exhibited a variation of aspartic acid (D), isoleucine (I) or asparagine (N).

Strain: H3 from A/Brisbane/10/2007

Sequence variations were observed at 5 positions (Table 15). In position 215, a deletion is observed in two sampled sequences.

TABLE 15

H3 from A/Brisbane/10/2007 amino acid variation

| | Origin | 202, | 210, | 215, | 235 | 242* |
|---|---|---|---|---|---|---|
| ISDN274893 | Egg | V | L | — | Y | I |
| ISDN273759 | Egg | G | P | A | S | I |
| EU199248 | Egg | G | P | A | S | I |
| EU199366 | Egg | G | P | A | S | I |
| ISDN273757 | Egg | V | L | — | S | S |
| ISDN257043 | Egg | G | P | A | S | I |
| EU199250 | MDCK | G | L | A | S | I |
| ISDN375357 | Egg | G | P | A | S | I |
| ISDN260430 | Egg | G | P | A | S | I |
| ISDN256751 | Egg | G | P | A | S | I |
| ISDN257648 | MDCK | G | L | A | S | I |

*Numbering from the starting M

Strain: H3 from A/Wisconsin/67/2005

Sequence variations in this strain were observed at 4 positions (Table 16).

TABLE 16

H3 from A/Wisconsin/67/2005 amino acid variation

| | Origin | 138, | 156, | 186, | 196 |
|---|---|---|---|---|---|
| ISDN138724 | Unknown | A | H | G | H |
| DQ865947 | Unknown | S | H | V | Y |
| EF473424 | Unknown | A | H | G | H |
| ISDN138723 | Egg | S | Q | V | Y |
| ISDN131464 | Unknown | A | H | G | H |
| EF473455 | Egg | A | H | G | H |

*Numbering from the mature protein

Strain: B from B/Malaysia/2506/2004

Variation at two positions is observed (Table 17). Position 120 is not a glycosylation site; position 210 is involved in glycosylation; this glycosylation is abolished following culture in eggs.

TABLE 17

Hemagglutinin from B/Malaysia/2506/2004 amino acid variation

| Amino acid #* | MDCK | Egg |
|---|---|---|
| 120 | K | N |
| 210 | T | A |

*Numbering from the middle of SP

Strain: Hemagglutinin from B/Florida/4/2006; ISDN261649

Observed variations include amino acid sequence variation at position 211, depending on the culture system. Asparatine (N) is found in sequences isolated from MDCK cells, while glutamic acid (D) is found in sequence isolated from eggs. Position 211 is a glycosylation site, and is abolished following culture in eggs.

Strain: H2 from A/Singapore/1/1957

Sequence variations were observed in 6 position s (Table 18).

TABLE 18

H2 from A/Singapore/1/1957 amino acid variation

| | | Amino acid No. | | | | | |
|---|---|---|---|---|---|---|---|
| | Origin | 166 | 168 | 199\ | 236 | 238 | 358 |
| L20410 | Viral RNA | K | E | T | L | S | V |
| L11142 | Unknown | E | G | K | L | S | I |
| AB296074 | Unknown | K | G | T | Q | G | V |
| Consensus A/Japan/305/1957 | | K | G | T | Q/L | G | V |

[1]Numbering from the mature protein

Strains: H5 from A/Vietnam/1194/2004 and H5 from A/Anhui/1/2005

There were no variations observed in the amino acid sequence upon aligning the primary sequences of either of these H5 strains.

Strain: H6 from A/Teal/Hong Kong/W312/1997

Only one entry was available for strain (AF250179).

Strain: H7 from A/Equine/Prague/56

A total of 2 sequence entries were found in the databases. The entry AB298877 was excluded as it is a laboratory reassortant.

Strain: H9 from A/Hong Kong/1073/1999; AJ404626

A total of 2 sequence entries were found in the databases. Only one was complete.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Aymard, H. M., M. T. Coleman, W. R. Dowdle, W. G. Layer, G. C. Schild, and R. G. Webster. 1973. Influenza virus neuraminidase-inhibition test procedures. Bull. W.H.O. 48: 199-202

Bollag, D. M., Rozycki, M. D., and Edelstein, S. J. (1996) Protein methods (2$^{nd}$ edition). Wiley-Liss, New York, USA.

Bligh, E. G., & Dyer, W. J. Can. J. Med. Sci. 37, 911-917 (1959).

Chen, B. J., Leser, G. P., Morita, E., and Lamb R. A. (2007) Influenza virus hemagglutinin and neuraminidase, but not the matrix protein, are required for assembly and budding of plasmid-derived virus-like particles. J. Virol. 81, 7111-7123.

Chen Z, Aspelund A, Jin H. 2008 Stabilizing the glycosylation pattern of influenza B hemagglutinin following adaptation to growth in eggs. Vaccine vol 26 p 361-371

Crawford, J., Wilkinson, B., Vosnesensky, A., Smith, G., Garcia, M., Stone, H., and Perdue, M. L. (1999). Baculovirus-derived hemagglutinin vaccines protect against lethal influenza infections by avian H5 and H7 subtypes. Vaccine 17, 2265-2274.

Darveau, A., Pelletier, A. & Perreault, J. PCR-mediated synthesis of chimeric molecules. Methods Neurosc. 26, 77-85 (1995).

Grgacic E V L, Anderson D A. Virus-like particles: passport to immune recognition. Methods 2006; 40: 60-65.

Gillim-Ross, L., and Subbarao, K. (2006) Emerging respiratory viruses: challenges and vaccine strategies. Clin. Microbiol. Rev. 19, 614-636.

Gomez-Puertas, P., Mena, I., Castillo, M., Vivo, A., Perez-Pastrana, E. and Portela, A. (1999) Efficient formation of influenza virus-like particles: dependence on the expression level of viral proteins. J. Gen. Virol. 80, 1635-1645.

Gomez-Puertas, P., Albo, C., Perez-Pastrana, E., Vivo, A., and Portela, A. (2000) Influenza Virus protein is the major driving force in virus budding. J. Virol. 74, 11538-11547.

Hamilton, A., Voinnet, O., Chappell, L. & Baulcombe, D. Two classes of short interfering RNA in RNA silencing. EMBO J. 21, 4671-4679 (2002).

Höfgen, R. & Willmitzer, L. Storage of competent cells for Agrobacterium transformation. Nucleic Acid Res. 16, 9877 (1988).

Harbury P B, Zhang T, Kim P S, Alber T. (1993) A switch between two-, three-, and four-stranded coiled coils in GCN4 leucine zipper mutants. Science; 262: 1401-1407)

Horimoto T., Kawaoka Y. Strategies for developing vaccines against h5N1 influenza a viruses. Trends in Mol. Med. 2006; 12(11):506-514.

Huang Z, Elkin G, Maloney B J, Beuhner N, Arntzen C J, Thanavala Y, Mason H S. Virus-like particle expression and assembly in plants: hepatitis B and Norwalk viruses. Vaccine. 2005 Mar. 7; 23(15):1851-8.

Johansson, B. E. (1999) Immunization with influenza A virus hemagglutinin and neuraminidase produced in recombinant baculovirus results in a balanced and broadened immune response superior to conventional vaccine. Vaccine 17, 2073-2080.

Latham, T., and Galarza, J. M. (2001). Formation of wild-type and chimeric influenza virus-like particles following simultaneous expression of only four structural proteins. J. Virol. 75, 6154-6165.

Lefebvre, B. et al. Plant Physiol. 144, 402-418 (2007).

Leutwiler L S et al 1986. Nucleic Acid Sresearch 14910): 4051-64

Liu, L & Lomonossoff, G. P. Agroinfection as a rapid method for propagating Cowpea mosaic virus-based constructs. J. Virol. Methods 105, 343-348 (2002).

Macala, L. J., Yo, R. K. & Ando, S. J Lipid Res. 24, 1243-1250 (1983)

Mattanovich, D., Rüker, F., da Câmara Machado, A., Laimer, M., Regner, F., Steinkellner, H., Himmler, G., and Katinger, H. (1989) Efficient transformation of *Agrobacterium* spp. By electroporation. Nucl. Ac. Res. 17, 6747.

Mena, I., Vivo, A., Perez, E., and Portela, A. (1996) Rescue of synthetic chloramphenicol acetyltransferase RNA into influenza virus-like particles obtained from recombinant plasmids. J. Virol. 70, 5016-5024.

Mongrand S, Morel J, Laroche J, Clayerol S, Carde J P, Hartmann M A et al. Lipid rafts in higher plant cells. The Journal of Biological Chemistry 2004; 279(35): 36277-36286.

Neumann, G., Watanabe, T., and Kawaoka, Y. (2000) Plasmid-driven formation of virus-like particles. J. Virol. 74, 547-551.

Nayak D P, Reichl U. (2004) Neuraminidase activity assays for monitoring MDCK cell culture derived influenza virus. J Virol Methods 122(1):9-15.

Olsen, C. W., McGregor, M. W., Dybdahl-Sissoko, N., Schram, B. R., Nelson, K. M., Lunn, D., Macklin, M. D., and Swain, W. F. (1997) Immunogenicity and efficacy of baculovirus-expressed and DNA-based equine influenza virus hemagglutinin vaccines in mice. Vaccine 15, 1149-1156.

Quan F S, Huang C, Compans R W, Kang S M. Virus-like particle vaccine induces protective immunity against homologous and heterologous strains of influenza virus. Journal of Virology 2007; 81(7): 3514-3524.

Rowe, T. et al. 1999. Detection of antibody to avian influenza a (h5N1) virus in human serum by using a cmbiation of serologic assays. J. Clin Microbiol 37(4):937-43

Saint-Jore-Dupas C et al. 2007. From planta to pharma with glycosylation in the toolbox. Trends in Biotechnology 25(7):317-23

Sambrook J, and Russell D W. Molecular cloning: a laboratory manual. Cold Spring Harbor, N.Y. Cold Spring Harbor Laboratory Press, 2001.

Stockhaus J et al 1987. Analysis of cis-active sequences involved in the leaf-specific expression of a potato gene in transgenic plants. Proceedings of the National Academy of Sciences U.S.S. 84(22):7943-7947.

Stockhaus J et al 1989. Identification of enhancer elements in the upstream region of the nuclear photosynthetic gene ST-LS1. Plant Cell. 1(8):805-13.

Suzuki, Y. (2005) Sialobiology of influenza. Molecular mechanism of host range variation of influenza viruses. Biol. Pharm. Bull 28, 399-408.

Tsuji M., Cell. Mol. Life Sci., 63 (2006); 1889-1898

Wakefield L., G. G. Brownlee Nuc Acid Res. 17 (1989); 8569-8580.

Kendal, A P, Pereira M S, Skehel J. Concepts and procedures for laboratory-based influenza surveillance. Atlanta: CDC; 1982. p. B17-B35

WHO. Manual on animal influenza diagnosis and surveillance. Department of communicable disease surveillance and response. World Health Organisation Global Influenza Program. 2002.

Skehel J J and Wildy D C Ann Rev Biochem 2000 69:531-69

Vaccaro L et al 2005. Biophysical J. 88:25-36.

Gamblin, S. J., Haire, L. F., Russell, R. J., Stevens, D. J., Xiao, B., Ha, Y., Vasisht, N., Steinhauer, D. A., Daniels, R. S., Elliot, A., Wiley, D. C., Skehel, J. J. (2004) The structure and receptor binding properties of the 1918 influenza hemagglutinin. Science 303: 1838-1842

What is claimed is:

1. A method of producing influenza virus like particles (VLPs) in a plant, the VLPs comprising protein, wherein the protein consists of influenza hemagglutinin (HA), comprising:
   a) introducing a nucleic acid comprising a nucleotide sequence encoding the hemagglutinin (HA) operatively linked to a regulatory region active in the plant into the plant, or portion thereof,
   b) incubating the plant under conditions that permit the expression of the nucleic acid, thereby producing the VLPs comprising protein, wherein the protein consists of influenza hemagglutinin (HA),
   c) harvesting the plant, and
   d) purifying the VLPs, wherein the VLPs range in size from 80-300 nm.

2. The method of claim 1, wherein the HA is selected from the group of H1, H2, H3, H4, H5, H6, H7, H8, H9, H10, H11, H12, H13, H14, H15, and H16.

3. The method of claim 2, wherein in the step of introducing (step a), the nucleic acid is transiently expressed in the plant.

4. The method of claim 2, wherein, in the step of introducing (step a), the nucleic acid is stably expressed in the plant.

5. A virus like particle (VLP) produced by the method of claim 1, wherein the VLP further comprises one or more than one lipid derived from a plant.

6. The VLP of claim 5, wherein the HA is H5 Indonesia.

7. A composition comprising an effective dose of the VLP of claim 5 for inducing an immune response, and a pharmaceutically acceptable carrier.

8. A VLP produced by the method of claim 1, wherein the HA comprises plant-specific N-glycans, or modified N-glycans.

9. The VLP of claim 5, for use in inducing immunity to an influenza virus infection in a subject.

10. The VLP of claim 9, wherein the VLP is suitable for oral, intradermal, intranasal, intramuscular, intraperitoneal, intravenous, or subcutaneous administration.

11. A composition comprising an effective dose of the VLP of claim 8 for inducing an immune response and a pharmaceutically acceptable carrier.

12. The composition of claim 11 for use in inducing immunity to an influenza virus infection in a subject.

13. The composition of claim 12, wherein the composition is suitable for oral, intradermal, intranasal, intramuscular, intraperitoneal, intravenous, or subcutaneous administration.

14. A food supplement comprising the VLP of claim 5.

15. A virus like particle (VLP) produced by the method of claim 2, wherein the VLP further comprises one or more than one lipid derived from a plant.

16. A composition comprising an effective dose of the VLP of claim 15 for inducing an immune response, and a pharmaceutically acceptable carrier.

17. A VLP produced by the method of claim 2, wherein the HA comprises plant-specific N-glycans, or modified N-glycans.

18. The VLP of claim 17, for use in inducing immunity to an influenza virus infection in a subject.

19. The VLP of claim 17, wherein the VLP is suitable for oral, intradermal, intranasal, intramuscular, intraperitoneal, intravenous, or subcutaneous administration.

* * * * *

SEQUENCE LISTING

<160> NUMBER OF SEQ ID NOS: 76

<210> SEQ ID NO 1
<211> LENGTH: 1556
<212> TYPE: DNA
<213> ORGANISM: Influenza Virus

<400> SEQUENCE: 1

```
agatcttcgc tgacacaata tgtataggct accatgccaa caactcaacc gacactgttg      60
acacagtact tgagaagaat gtgacagtga cacactctgt caacctactt gaggacagtc     120
acaatggaaa actatgtcta ctaaaaggaa tagccccact acaattgggt aattgcagcg     180
ttgccggatg gatcttagga aacccagaat gcgaattact gatttccaag gaatcatggt     240
cctacattgt agaaacacca aatcctgaga atggaacatg ttacccaggg tatttcgccg     300
actatgagga actgagggag caattgagtt cagtatcttc atttgagaga ttcgaaatat     360
tccccaaaga aagctcatgg cccaaccaca cgtaaccgg agtatcagca tcatgctccc     420
ataatgggaa aagcagtttt tacagaaatt tgctatggct gacggggaag aatggtttgt     480
acccaaacct gagcaagtcc tatgtaaaca acaaagagaa agaagtcctt gtactatggg     540
gtgttcatca cccgcctaac atagggaacc aaagggcact ctatcataca gaaaatgctt     600
atgtctctgt agtgtcttca cattatagca gaagattcac cccagaaata gccaaaagac     660
ccaaagtaag agatcaggaa ggaagaatca actactactg gactctgctg gaacctgggg     720
atacaataat atttgaggca aatggaaatc taatagcgcc atggtatgct tttgcactga     780
gtagaggctt tggatcagga atcatcacct caaatgcacc aatggatgaa tgtgatgcga     840
```

```
agtgtcaaac acctcaggga gctataaaca gcagtcttcc tttccagaat gtacacccag    900
tcacaatagg agagtgtcca aagtatgtca ggagtgcaaa attaaggatg gttacaggac    960
taaggaacat cccatccatt caatccagag gtttgtttgg agccattgcc ggtttcattg   1020 aagggggtg gactggaatg gtagatgggt ggtatggtta tcatcatcag aatgagcaag   1080
gatctggcta tgctgcagat caaaaaagta cacaaaatgc cattaacggg attacaaaca   1140
aggtcaattc tgtaattgag aaaatgaaca ctcaattcac agctgtgggc aaagagttca   1200
acaaattgga agaaggatg gaaaacttaa ataaaaagt tgatgatggg tttctagaca    1260
tttggacata taatgcagaa ttgttggttc tactggaaaa tgaaaggact ttggatttcc   1320
atgactccaa tgtgaagaat ctgtatgaga agtaaaaag ccaattaaag aataatgcca    1380
aagaaatagg aaacggtgt tttgagttct atcacaagtg taacaatgaa tgcatggaga    1440
gtgtgaaaaa tggtacctat gactatccaa atattccga agaatcaaag ttaaacaggg   1500
agaaaattga tggagtgaaa ttggaatcaa tgggagtata ctaagagctc aggcct      1556

<210> SEQ ID NO 2
<211> LENGTH: 219
<212> TYPE: DNA
<213> ORGANISM: Influenza Virus

<400> SEQUENCE: 2
ggtacctatg actatccaaa atattccgaa gaatcaaagt taaacaggga gaaaattgat     60
ggagtgaaat tggaatcaat gggagtatac cagattctgg cgatctactc aactgtcgcc    120
agttccctgg ttcttttggt ctccctgggg gcaatcagct tctggatgtg ttccaatggg    180
tctttgcagt gtagaatatg catctaagag ctcaggcct                           219

<210> SEQ ID NO 3
<211> LENGTH: 1719
<212> TYPE: DNA
<213> ORGANISM: Influenza Virus

<400> SEQUENCE: 3
aagcttatgg agaaaatagt gcttcttctt gcaatagtca gtcttgttaa aagtgatcag     60
atttgcattg gttaccatgc aaacaattca acagagcagg ttgacacaat catggaaaag    120
aacgttactg ttacacatgc ccaagacata ctggaaaaga cacacaacgg aagctctgc    180 gatctagatg gagtgaagcc tctaatttta agagattgta gtgtagctgg atggctcctc    240
gggaacccaa tgtgtgacga attcatcaat gtaccggaat ggtcttacat agtggagaag    300
gccaatccaa ccaatgacct ctgttaccca gggagtttca cgactatga agaactgaaa    360 cacctattga gcagaataaa ccattttgag aaaattcaaa tcatccccaa agttcttgg    420 tccgatcatg aagcctcatc aggagttagc tcagcatgtc catacctggg aagtccctcc   480
ttttttagaa atgtggtatg gcttatcaaa aagaacagta catacccaac aataaagaaa    540
agctacaata taccaaccaa agaggatctt ttggtactgt ggggaattca ccatcctaat    600
gatgcggcag agcagacaag gctatatcaa aacccaacca cctatatttc cattgggaca    660
tcaacactaa accagagatt ggtaccaaaa atagctacta gatccaaagt aaacgggcaa    720
agtggaagga tggagttctt ctggacaatt ttaaaaccta atgatgcaat caacttcgag    780
agtaatggaa atttcattgc tccagaatat gcatacaaaa ttgtcaagaa aggggactca    840
gcaattatga aaagtgaatt ggaatatggt aactgcaaca ccaagtgtca aactccaatg    900
ggggcgataa actctagtat gccattccac aacatacacc ctctcaccat cggggaatgc    960
```

```
cccaaatatg tgaaatcaaa cagattagtc cttgcaacag ggctcagaaa tagccctcaa    1020
agagagagca gaagaaaaaa gagaggacta tttggagcta tagcaggttt tatagaggga    1080
ggatggcagg gaatggtaga tggttggtat gggtaccacc atagcaatga gcaggggagt    1140
gggtacgctg cagacaaaga atccactcaa aaggcaatag atggagtcac caataaggtc    1200
aactcaatca ttgacaaaat gaacactcag tttgaggccg ttggaaggga atttaataac    1260
ttagaaagga gaatagagaa tttaaacaag aagatggaag acgggtttct agatgtctgg    1320
acttataatg ccgaacttct ggttctcatg gaaaatgaga gaactctaga ctttcatgac    1380
tcaaatgtta agaacctcta cgacaaggtc cgactacagc ttagggataa tgcaaaggag    1440
ctgggtaacg gttgtttcga gttctatcac aaatgtgata atgaatgtat ggaaagtata    1500
agaaacggaa cgtacaacta ccgcagtat tcagaagaag caagattaaa aagagaggaa    1560
ataagtgggg taaaattgga atcaatagga acttaccaaa tactgtcaat ttattcaaca    1620
gtggcgagtt ccctagcact ggcaatcatg atggctggtc tatctttatg gatgtgctcc    1680
aatggatcgt tacaatgcag aatttgcatt taagagctc                          1719
```

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
gtattagtaa ttagaatttg gtgtc                                          25

<210> SEQ ID NO 5
<211> LENGTH: 44
<212> TYPE: DNA
<213> ORGANISM: Artificial Sequence
<220> FEATURE:
<223> OTHER INFORMATION: Primer

<400> SEQUENCE: 5
gcaagaagaa gcactatttt ctccattttc tctcaagatg atta                     44

<210> SEQ ID NO 6
<211> LENGTH: 45
<212> TYPE: DNA
<213> ORGANISM: Artificial Sequence
<220> FEATURE:
<223> OTHER INFORMATION: Primer

<400> SEQUENCE: 6
ttaatcatct tgagagaaaa tggagaaaat agtgcttctt cttgc                    45

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
actttgagct cttaaatgca aattctgcat tgtaacga                            38

<210> SEQ ID NO 8
<211> LENGTH: 1471
<212> TYPE: DNA

<213> ORGANISM: Artificial Sequence
<220> FEATURE:
<223> OTHER INFORMATION: Expression Cassette

<400> SEQUENCE: 8

```
agaggtaccc cgggctggta tatttatatg ttgtcaaata actcaaaaac cataaaagtt      60
taagttagca agtgtgtaca ttttacttg aacaaaaata ttcacctact actgttataa     120
atcattatta aacattagag taaagaaata tggatgataa gaacaagagt agtgatattt     180
tgacaacaat tttgttgcaa catttgagaa aattttgttg ttctctcttt tcattggtca     240
aaaacaatag agagagaaaa aggaagaggg agaataaaaa cataatgtga gtatgagaga     300
gaaagttgta caaaagttgt accaaaatag ttgtacaaat atcattgagg aatttgacaa     360
aagctacaca aataagggtt aattgctgta aataaataag gatgacgcat agagagatg      420
taccattaga gaattttttgg caagtcatta aaaagaaaga ataaattatt tttaaaatta    480
aaagttgagt catttgatta aacatgtgat tatttaatga attgatgaaa gagttggatt     540
aaagttgtat tagtaattag aatttggtgt caaatttaat ttgacatttg atctttttcct   600
atatattgcc ccatagagtc agttaactca tttttatatt tcatagatca aataagagaa     660
ataacggtat attaatccct ccaaaaaaaa aaacggtat atttactaaa aaatctaagc     720
cacgtaggag gataacagga tccccgtagg aggataacat ccaatccaac caatcacaac     780
aatcctgatg agataaccca cttttaagccc acgcatctgt ggcacatcta cattatctaa     840
atcacacatt cttccacaca tctgagccac acaaaaacca atccacatct ttatcaccca     900
ttctataaaa aatcacactt tgtgagtcta cactttgatt cccttcaaac acatacaaag    960
agaagagact aattaattaa ttaatcatct tgagagaaaa tggcgaaaaa cgttgcgatt   1020
ttcggcttat tgtttttctct tcttgtgttg gttccttctc agatctgagc tctaagttaa   1080
aatgcttctt cgtctcctat ttataatatg gtttgttatt gttaattttg ttcttgtaga   1140
agagcttaat taatcgttgt tgttatgaaa tactatttgt atgagatgaa ctggtgtaat   1200
gtaattcatt tacataagtg gagtcagaat cagaatgttt cctccataac taactagaca   1260
tgaagacctg ccgcgtacaa ttgtcttata tttgaacaac taaaattgaa catcttttgc   1320
cacaacttta taagtggtta atatagctca aatatatggt caagttcaat agattaataa   1380
tggaaatatc agttatcgaa attcattaac aatcaactta acgttattaa ctactaattt   1440
tatatcatcc cctttgataa atgatagtac a                                   1471
```

<210> SEQ ID NO 9
<211> LENGTH: 565
<212> TYPE: PRT
<213> ORGANISM: Influenza Virus

<400> SEQUENCE: 9

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80
```

-continued

```
Asn Pro Glu Cys Glu Leu Leu Ile Ser Lys Glu Ser Trp Ser Tyr Ile
                85                  90                  95
Val Glu Thr Pro Asn Pro Glu Asn Gly Thr Cys Tyr Pro Gly Tyr Phe
            100                 105                 110
Ala Asp Tyr Glu Glu Leu Arg Glu Gln Leu Ser Ser Val Ser Ser Phe
        115                 120                 125
Glu Arg Phe Glu Ile Phe Pro Lys Glu Ser Ser Trp Pro Asn His Thr
    130                 135                 140
Val Thr Gly Val Ser Ala Ser Cys Ser His Asn Gly Lys Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Val Asn Asn Lys Glu Lys Glu Val Leu Val Leu
            180                 185                 190
Trp Gly Val His His Pro Pro Asn Ile Gly Asn Gln Arg Ala Leu Tyr
        195                 200                 205
His Thr Glu Asn Ala Tyr Val Ser Val Val Ser Ser His Tyr Ser Arg
    210                 215                 220
Arg Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Trp Tyr Ala Phe Ala
            260                 265                 270
Leu Ser Arg Gly Phe Gly Ser Gly Ile Ile Thr Ser Asn Ala Pro Met
        275                 280                 285
Asp Glu Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
    370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
    450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asn Glu Cys Met Glu Ser Val Lys
                485                 490                 495
Asn Gly Thr Tyr Asp Tyr Pro Lys Tyr Ser Glu Glu Ser Lys Leu Asn
```

```
                  500                 505                 510
Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 10
<211> LENGTH: 568
<212> TYPE: PRT
<213> ORGANISM: Influenza Virus

<400> SEQUENCE: 10

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly Ser Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Leu Gly Ser Pro Ser Phe Phe
145                 150                 155                 160

Arg Asn Val Val Trp Leu Ile Lys Lys Asn Ser Thr Tyr Pro Thr Ile
                165                 170                 175

Lys Lys Ser Tyr Asn Asn Thr Asn Gln Glu Asp Leu Leu Val Leu Trp
            180                 185                 190

Gly Ile His His Pro Asn Asp Ala Ala Glu Gln Thr Arg Leu Tyr Gln
        195                 200                 205

Asn Pro Thr Thr Tyr Ile Ser Ile Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300
```

```
Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565

<210> SEQ ID NO 11
<211> LENGTH: 1629
<212> TYPE: DNA
<213> ORGANISM: Influenza A Virus

<400> SEQUENCE: 11
gacaaaatat gtcttgggca ccatgctgtg gcaaatggaa caaaagtgaa cacattaaca     60
gagaggggga ttgaagtagt gaacgccaca gagacggtgg aaactgcgaa tatcaagaaa    120
atatgtattc aagggaaaag gccaacagat ctgggacaat gtggacttct aggaacccta    180
ataggacctc cccaatgtga tcaattcctg gagttttact ctgatttgat aattgagcga    240
agagaaggaa ccgatgtgtg ctatcccggt aaattcacaa atgaagaatc actgaggcag    300
atccttcgag ggtcaggagg aattgataag gagtcaatgg gtttcaccta tagtggaata    360
agaaccaatg gagcgacaag tgcctgcaaa agatcaggtt cttctttcta tgcagagatg    420
aagtggttgc tgtcgaattc agacaatgcg gcattccctc aaatgacaaa gtcgtataga    480
aatcccagaa acaaaccagc tctgataatt tggggagttc atcactctgg atcggttagc    540
gagcagacca aactctatgg aagtggaaac aagttgataa cagtaggaag ctcaaaatac    600
```

```
cagcaatcat tcaccccaag tccgggagca cggccacaag tgaatggaca atcagggaga      660
atcgattttc actggctact ccttgatccc aatgacacag tgaccttcac tttcaatggg      720
gcattcatag cccctgacag ggcaagtttc tttagaggag aatcactagg agtccagagt      780
gatgttcctc tggattctag ttgtggaggg gattgctttc acagtggggg tacgatagtc      840
agttccctgc cattccaaaa catcaaccct agaactgtgg ggagatgccc tcggtatgtc      900
aaacagacaa gcctcctttt ggctacagga atgagaaatg ttccagagaa tccaaagccc      960
agaggccttt ttggagcaat gctggattca atagagaatg gatgggaggg tctcatcgat     1020
ggatggtatg gtttcagaca tcaaaatgca caggggaag gaactgcagc tgactacaaa     1080
agcacccaat ctgcaataga tcagatcaca ggcaaattga atcgtctgat tgacaaaaca     1140
aatcagcagt ttgagctgat agacaatgag ttcaatgaga tagaacaaca aataggaaat     1200
gtcattaatt ggacacgaga cgcaatgact gaggtatggt cgtataatgc tgagctgttg     1260
gtggcaatgg aaaatcagca tacaatagat cttgcggact cagaaatgaa caaactttat     1320
gagcgtgtca gaaacaact aagggagaat gctgaagaag atggaactgg atgttttgag     1380
atattccata gtgtgatga tcagtgcatg gagagcataa ggaacaacac ttatgaccat     1440
actcaataca gaacagagtc attgcagaat agaatacaga tagacccagt gaaattgagt     1500
agtggataca agacataat cttatggttt agcttcgggg catcatgttt tcttcttcta     1560
gccgttgtaa tgggattggt tttcatttgc ataaagaatg gaaacatgcg gtgcaccatt     1620
tgtatataa                                                             1629
```

<210> SEQ ID NO 12
<211> LENGTH: 1773
<212> TYPE: DNA
<213> ORGANISM: Influenza A Virus

<400> SEQUENCE: 12

```
agcaaaagca ggggttatac catagacaac caaaggcaag acaatggcca tcatttatct       60
aattcttctg ttcacagcag tgagagggga ccaaatatgc attggatacc attccaacaa      120
ttccacagaa aaggttgaca caatcctaga gagaaatgtc actgtgactc acgctgagga      180
cattcttgag aagactcaca atgggaagtt atgcaaacta aatggaatcc ctccacttga      240
attaagggat tgcagcattg ccggatggct ccttgggaat ccagaatgtg atatacttct      300
aactgtgcca gaatggtcat acataataga aaagaaaat ccaaggaacg gcttgtgcta      360
cccaggcagt ttcaatgatt atgaagaatt gaagcatctt atcagcagcg tgacacattt      420
tgagaaagta aagattctgc ccagaaatga atggacacag catacaacaa ctggaggttc      480
acaggcttgc gcagactatg gtggtccgtc attcttccgg aacatggtct ggttgacaaa      540
gaaagggtcg aattatccaa ttgccaaaag atcttacaac aatacaagtg gggaacaaat      600
gctgatcatt ggggatac atcaccccaa tgatgaaagt gaacaaagag cattgtatca      660
gaatgtgggg acctatgtgt cagtaggaac atcaacactg aacaaagat catccccaga      720 aatagcaaca agacctaaag tgaatggaca aggaggcaga atggaattct cgtggactat      780
cttagatata tgggacacaa taaatttga gagtactggc aatctaattg caccagaata      840 tggttctcaaa atatccaaac gaggtagttc agggatcatg aaaacagaag gaaaacttga      900
aaactgcgag accaagtgcc aaactccttt gggagcaata aatacaacat tacccttca      960 caatatccac ccactgacca ttggtgagtg ccccaaatat gtaaaatcgg aaagattagt     1020
cttagcaaca ggactaagaa acgtccctca gattgagtca aggggattgt ttggggcaat     1080
```
agctggtttt atagagggtg gatggcaagg aatggttgat ggttggtatg ggtatcatca 1140
cagcaatgac cagggatctg ggtatgcagc agacaaagaa tccactcaaa aggcaattga 1200
tggaatcacc aacaaggtaa attctgtgat cgaaaagatg aacacccaat tcggagctgt 1260
tggaaaagaa ttcagtaact tggagagaag actggagaac ttgaataaaa agatggagga 1320
cggatttcta gatgtgtgga catacaatgc cgagctccta gttctaatgg aaaatgagag 1380
gacacttgac tttcatgatt ctaatgtcaa gaatctatat gataaagtca gaatgcaact 1440
gagagacaat gcaaaagaac tagggaatgg atgttttgaa ttttatcaca aatgtgatga 1500
tgaatgcatg aacagtgtga agaatgggac atatgattat tccaagtatg aagaggagtc 1560
taaactaaac aggactgaaa tcaaaggggt taaattgagc aatatggggg tttatcaaat 1620
ccttgccatc tatgctacag tagcaggttc cctgtcactg gcaatcatga tagctgggat 1680
ttctatatgg atgtgctcca acgggtctct gcaatgcaga atctgcatat gatcatcagt 1740
cattttgtaa ttaaaaacac ccttgtttct act 1773

<210> SEQ ID NO 13
<211> LENGTH: 1086
<212> TYPE: DNA
<213> ORGANISM: Influenza A Virus

<400> SEQUENCE: 13
caaaaacttc ccggaaatga caacagcacg gcaacgctgt gccttgggca ccatgcagta 60
ccaaacggaa cgatagtgaa aacaatcacg aatgaccaaa ttgaagttac taatgctact 120
gagctggtac agagttcctc aacaggtgga atatgcgaca gtcctcatca gatccttgat 180
ggagaaaact gcacactaat agatgctcta ttgggagacc ctcagtgtga tggcttccaa 240
aataagaaat gggacctttt tgttgaacgc agcaaagcct acagcaactg ttacccttat 300
gatgtgccgg attatgcctc ccttaggtca ctagttgcct catccggcac actggagttt 360
aacaatgaaa gcttcgattg gactggagtc actcagaatg gaacaagctc tgcttgcaaa 420
aggagatcta ataaaagttt ctttagtaga ttgaattggt tgacccactt aaaatacaaa 480
tacccagcat tgaacgtgac tatgccaaac aatgaaaaat ttgacaaatt gtacatttgg 540
ggggttcacc acccgggtac ggacagtgac caaatcagcc tatatgctca agcatcagga 600
agaatcacag tctctaccaa aagaagccaa caaactgtaa tcccgaatat cggatctaga 660
cccagggtaa gggatgtctc cagccgaata agcatctatt ggacaatagt aaaaccggga 720
gacatacttt tgattaacag cacagggaat ctaattgctc ctcggggtta cttcaaaata 780
cgaagtggga aaagctcaat aatgagatca gatgcaccca ttggcaaatg caattccgaa 840
tgcatcactc caaatggaag cattcccaat gacaaaccat ttcaaaatgt aaacaggatc 900
acatatgggg cctgtcccag atatgttaag caaaacactc tgaaattggc aacagggatg 960
cgaaatgtac cagagaaaca aactagaggc atatttggcg caatcgcggg tttcatagaa 1020
aatggttggg agggaatggt ggacggttgg tacggtttca ggcatcaaaa ttctgagggc 1080
acagga 1086

<210> SEQ ID NO 14
<211> LENGTH: 1048
<212> TYPE: DNA
<213> ORGANISM: Influenza A Virus

<400> SEQUENCE: 14

| | |
|---|---|
| atgctatcaa tcacgattct gtttctgctc atagcagagg gttcctctca gaattacaca | 60 |
| gggaatcccg tgatatgcct gggacatcat gccgtatcca atgggacaat ggtgaaaacc | 120 |
| ctgactgatg accaagtaga agttgtcact gcccaagaat tagtggaatc gcaacatcta | 180 |
| ccggagttgt gtcctagccc tttaagatta gtagatggac aaacttgtga catcgtcaat | 240 |
| ggtgccttgg ggagtccagg ctgtgatcac ttgaatggtg cagaatggga tgtcttcata | 300 |
| gaacgaccca ctgctgtgga cacttgttat ccatttgatg tgccggatta ccagagccta | 360 |
| cggagtatcc tagcaaacaa tgggaaattt gagttcattg ctgaggaatt ccaatggaac | 420 |
| acagtcaaac aaaatgggaa atccggagca tgcaaaagag caaatgtgaa tgactttttc | 480 |
| aacagattga actggctgac caaatctgat gggaatgcat acccacttca aaacctgaca | 540 |
| aaggttaaca cgggactat gcaagactt acatatggg agttcatca tccttcaact | 600 |
| gacacagaac aaaccaactt gtataagaac aaccctggga gtaactgt ttccaccaaa | 660 |
| accagtcaaa caagtgtggt accaaacatt ggcagtagac catgggtaag aggccaaagc | 720 |
| ggcaggatta gcttctattg gacaattgtg agccaggag acctcatagt cttcaacacc | 780 |
| atagggaatt taattgctcc gagaggtcat tacaagctta acagtcaaaa gaagagcaca | 840 |
| attctgaata ctgcaattcc cataggatct tgtgttagta atgtcacac agatagggt | 900 |
| tcaatctcta caaccaaacc cttcagaac atctcaagaa tatcaattgg ggactgtccc | 960 |
| aagtatgtca acagggatc cttgaaacta gctacaggaa tgaggaatat ccctgagaaa | 1020 |
| gcaaccagag gcctgtttgg tgcaattg | 1048 |

<210> SEQ ID NO 15
<211> LENGTH: 1707
<212> TYPE: DNA
<213> ORGANISM: Influenza A Virus

<400> SEQUENCE: 15

| | |
|---|---|
| atggagaaaa tagtgcttct tcttgcaata gtcagtcttg ttaaaagtga tcagatttgc | 60 |
| attggttacc atgcaaacaa ctcgacagag caggttgaca caataatgga aaagaacgtt | 120 |
| actgttacac atgcccaaga catactggaa aagacacaca acgggaaact ctgcgatcta | 180 |
| gatggagtga agcctctaat tttgagagat tgtagtgtag ctggatggct cctcggaaac | 240 |
| cctatgtgtg acgaattcat caatgtgccg aatggtctt acatagtgga aaggccagt | 300 |
| ccagccaatg acctctgtta cccagggat ttcaacgact atgaagaact gaaacaccta | 360 |
| ttgagcagaa taaaccactt tgagaaaatt cagatcatcc ccaaaagttc ttggtccaat | 420 |
| catgaagcct catcagggt gagcgcagca tgtccatacc atgggaagcc ctccttttc | 480 |
| agaaatgtgg tatggcttat caaaaagaac agtgcatacc aacaataaa gaggagctac | 540 |
| aataatacca ccaagaaga tctttttggta ctgtggggga ttcaccatcc taatgatgcg | 600 |
| gcagagcaga caaagctcta tcaaaaccca accacctata tttccgttgg aacatcaaca | 660 |
| ctaaaccaga gattggtccc aaaaatagct actagatcca aagtaaacgg caaagtggaa | 720 |
| agaatggagt tcttctggac aattttaaag ccgaatgatg ccataaattt cgagagtaat | 780 |
| ggaaatttca ttgctccaga atatgcatac aaaattgtca agaaggga ctcagcaatt | 840 |
| atgaaaagtg aattggaata tggtaactgc aacaccaagt gtcaaactcc aatggggcg | 900 |
| ataaactcta gtatgccatt ccacaacata caccctctca aatcggga atgcccaaa | 960 |
| tatgtgaaat caaacagatt agtccttgcg actggactca gaaataccccc tcaaagagat | 1020 |
| agaagaagaa aaagagagg actatttgga gctatagcag gttttataga gggaggatgg | 1080 | caaggaatgg tagatggttg gtatgggtac caccatagca atgagcaggg gagtggatac 1140 gctgcagaca aagaatccac tcaaaaggca atagatggag tcaccaataa ggtcaactcg 1200 atcattgaca aaatgaacac tcagtttgag gccgttggaa gggaatttaa taacttagaa 1260 aggaggatag aaaatttaaa caagaagatg gaagacggat tcctagatgt ctggacttat 1320 aatgctgaac ttctggttct catggaaaat gagagaactc tagactttca tgattcaaat 1380 gtcaagaacc tttacaacaa ggtccgacta cagcttaggg ataatgcaaa ggagctgggt 1440 aatggttgtt tcgagttcta tcacaaatgt gataatgaat gtatggaaag tgtaaaaaac 1500 gggacgtatg actacccgca gtattcagaa gaagcaagac taaacagaga ggaaataagt 1560 ggagtaaaat tggaatcaat gggaacttac caaatactgt caatttattc aacagtggcg 1620 agttccctag cactggcaat catggtagct ggtctatctt tatggatgtg ctccaatggg 1680 tcgttacaat gcagaatttg catttaa 1707

<210> SEQ ID NO 16
<211> LENGTH: 1050
<212> TYPE: DNA
<213> ORGANISM: Influenza A Virus

<400> SEQUENCE: 16
atgattgcaa tcattgtaat agcgatactg gcagcagccg gaaagtcaga caagatctgc 60
attgggtatc atgccaacaa ttcaacaaca caggtggata cgatacttga gaagaatgta 120
accgtcacac actcagttga attgctggag aatcagaagg aagaaagatt ctgcaagatc 180
ttgaacaagg cccctctcga cctaaaggga tgcaccatag agggttggat cttggggaat 240
ccccaatgcg atctgttgct tggtgaccaa agctggtcat atatagtgga aagacctact 300
gcccaaaatg ggatatgcta cccaggagct ttgaatgagg tagaagaact gaaagcattt 360
atcggatcag gagaaagggt agagagattt gagatgtttc ccaaaagcac atgggcaggg 420
gtagacacca gcagtggggt aacaaaagct tgtccttata atagtggttc atctttctac 480
agaaacctcc tatggataat aaagaccaag tcagcagcgt atccagtaat taagggaact 540
tacagcaaca ctggaaacca gccaatcctc tatttctggg gtgtgcacca tcctcctgac 600
accaatgagc aaaatactct gtatggctct ggcgatcggt atgttaggat gggaactgag 660
agcatgaatt ttgccaagag cccagaaatt gcggcaagac ccgctgtgaa tggccaaaga 720
ggtcgaattg attattactg gtctgtttta aaaccaggag aaaccttgaa tgtggaatct 780
aatggaaatc taatcgctcc ttggtatgca tacaaatttg tcaacacaaa taataaggga 840
gccgtcttca agtcaaattt accaatcgag aattgcgatg ccacatgcca gactattgca 900
ggagtcctaa ggaccaataa aacatttcag aatgtgagcc ctctgtggat aggagaatgc 960
cccaagtatg tgaaaagtga aagtctaagg cttgctactg gactaagaaa tgttccacag 1020
attgaaacca gagggctttt cggagctatc 1050

<210> SEQ ID NO 17
<211> LENGTH: 1698
<212> TYPE: DNA
<213> ORGANISM: Influenza A Virus

<400> SEQUENCE: 17
atggaaaaat tcatcgcaat agcaaccttg gcgagcacaa atgcatacga taggatatgc 60
attgggtacc aatcaaacaa ctccacagac acagtgaaca ctctcataga acagaatgta 120

-continued

| | |
|---|---|
| ccagtcaccc aaacaatgga gctcgtggaa acagagaaac atcccgctta ttgtaacact | 180 |
| gatttaggtg ccccattgga actgcgagac tgcaagattg aggcagtaat ctatgggaac | 240 |
| cccaagtgtg acatccatct gaaggatcaa ggttggtcat acatagtgga gaggcccagc | 300 |
| gcaccagaag ggatgtgtta ccctggatct gtggaaaatc tagaagaact gaggtttgtc | 360 |
| ttctccagtg ctgcatctta aagagaata agactatttg actattccag gtggaatgtg | 420 |
| actagatctg gaacgagtaa agcatgcaat gcatcaacag gtggccaatc cttctatagg | 480 |
| agcatcaatt ggttgaccaa aaaggaacca gacacttatg acttcaatga aggagcttat | 540 |
| gttaataatg aagatggaga catcattttc ttatggggga tccatcatcc gccggacaca | 600 |
| aaagagcaga caacactata aaaaatgca aacactttga gtagtgttac tactaacact | 660 |
| ataaacagaa gctttcaacc aaatattggt cccagaccat tagtaagagg acagcaaggg | 720 |
| aggatggatt actattgggg cattctgaaa agagggagag ctctgaagat caggaccaac | 780 |
| ggaaatttaa tcgcacctga atttggctat ctgctcaaag gtgaaagcta cggcagaata | 840 |
| attcaaaatg aggatatacc catcgggaac tgtaacacaa aatgtcaaac atatgcggga | 900 |
| gcaatcaata gcagcaaacc cttttcagaat gcaagtaggc attacatggg agaatgtccc | 960 |
| aaatatgtga agaaggcaag cttgcgactt gcagttgggc ttaggaatac gccttctgtt | 1020 |
| gaacccagag gactgtttgg agccattgct ggtttcattg aaggaggatg gtctggaatg | 1080 |
| attgatgggt ggtatggatt tcatcacagc aattcagagg gaacaggaat ggcagctgac | 1140 |
| cagaaatcaa cacaagaagc catcgataag atcaccaata agtcaacaa tatagttgac | 1200 |
| aagatgaaca gggagtttga agttgtgaat catgagttct ctgaagttga aaaaagaata | 1260 |
| aacatgataa acgataaaat agatgaccaa attgaagatc tttgggctta caatgcagag | 1320 |
| ctccttgtgc tcttagagaa ccagaaaacg ctagacgaac atgattccaa tgtcaaaaac | 1380 |
| cttttttgatg aagtgaaaag gagactgtca gccaatgcaa tagatgctgg gaacggttgc | 1440 |
| tttgacatac ttcacaaatg cgacaatgag tgtatgaaa ctataaagaa cggaacttac | 1500 |
| gatcataagg aatatgaaga ggaggctaaa ctagaaagga gcaagataaa tggagtaaaa | 1560 |
| ctagaagaga acaccactta caaaattctt agcatttaca gtacagtggc ggccagtctt | 1620 |
| tgcttggcaa tcctgattgc tggaggttta atcctgggca tgcaaaatgg atcttgtaga | 1680 |
| tgcatgttct gtatttga | 1698 |

<210> SEQ ID NO 18
<211> LENGTH: 1363
<212> TYPE: DNA
<213> ORGANISM: Influenza A Virus

<400> SEQUENCE: 18

| | |
|---|---|
| atggaaacag tatcactaat gactatacta ctagtagcaa cagcaagcaa tgcagacaaa | 60 |
| atctgcatcg gccaccagtc aacaaactcc acagaaactg tggacacgct aacagaaacc | 120 |
| aatgttcctg tgacacatgc caaagaattg ctccacacag agcacaatgg aatgctgtgt | 180 |
| gcaacaaatc tgggacatcc cctaatctta gacacgtgca ctattgaagg actgatctat | 240 |
| ggtaacccct cttgtgactt gctgttggga ggaagagaat ggtcctacat cgtcgaaagg | 300 |
| tcatcagctg taaatggaac gtgttacccc gggaatgtag agaacctaga ggaactcagg | 360 |
| acacttttta gttccgctag ttcctaccga agaatccaaa tcttcccaga cacaatctgg | 420 |
| aatgtgactt acactggaac aagcaaagca tgttcagatt cattctacag gagtatgaga | 480 |
| tggctgactc aaaaagcgg tcttaccct gttcaagacg ctcaatacac aaataatatg | 540 |

```
ggaaagagca ttcttttcgt gtggggcata catcacccac ccactgaagc tgcacagaca      600
aatttgtaca caagaaccga cacaacaaca agcgtgacaa cagaagactt aaataggatc      660
ttcaaaccga tggtagggcc aaggcccctt gtcaatggtc tgcagggaag aattaattat      720
tattggtcgg tactaaaacc aggccagaca ctgcgagtaa gatccaatgg gaatctaatt      780
gctccatggt atggacacat tctttcggga gggagccatg gaagaatcct gaagactgat      840
ttaaaaagta gtaattgcgt agtgcaatgt cagactgaaa aaggcggctt aaacagtaca      900
ttgccgttcc acaatatcag taaatatgca tttggaaact gtcccaaata tgttagagtt      960
aaaagtctca aactggcagt aggggttgagg aacgtgcctg ctagatcaag tagaggacta     1020
ttcggagcca tagctggatt catagaagga ggttggccag gactagtcgc tggttggtat     1080
ggtttccagc attcaaatga tcaaggggtt ggtattgcgg cagataggga ttcaactcaa     1140
aaggcaattg atagaataac aaccaaggtg aataatatag tcgacaaaat gaacaaacaa     1200
tatgaaataa ttgatcatga attcagtgag gttgaaacta ggctcaacat gatcaataat     1260
aagattgatg accaaataca agacatatgg gcatataatg cagagttgct agtactactt     1320
gaaaaccaga aaacactcga tgagcatgac gcaaatgtga aga                        1363

<210> SEQ ID NO 19
<211> LENGTH: 1727
<212> TYPE: DNA
<213> ORGANISM: Influenza A Virus

<400> SEQUENCE: 19
agcaaaagca ggggtcacaa tgtacaaagt agtagtaata attgcgctcc ttggagcagt       60
gaaaggtctt gacagaatct gcctaggaca ccatgcggtt gccaatggaa ccattgtgaa      120
gacccttaca aatgaacaag aggaagtgac caatgctact gagacggtag agagcacaaa      180
tttgaataaa ttgtgtatga aggaagaag ctacaaggac ttgggcaatt gtcacccggt      240
aggaatgttg ataggaacac ctgtttgtga tccgcacttg accgggacct gggacactct      300
cattgagcga gagaatgcca ttgcccactg ttatccaggg gcaaccataa atgaagaagc      360
attgaggcag aaaataatgg aaagtgggag aatcagcaag atgagcactg gcttcactta      420
tgggtcttcc atcacctcag ctgggaccac taaggcatgc atgagaaatg gaggagatag      480
tttctatgca gagctcaaat ggctagtgtc aaagacaaag ggacaaaatt tccctcagac      540
aacaaacacc tatcggaata cggacacagc agaacatctc ataatatggg gaattcatca      600
cccttccagc acacaggaaa agaatgactt atacggaact cagtcactat ctatatcagt      660
tgagagttct acatatcaga acaactttgt tccagttgtt ggggcaagac ctcaggtcaa      720
tggacaaagt gggcgaattg actttcactg gacactagta cagccgggtg acaacataac      780
cttctcagac aatggaggtc taatagcacc aagtcgagtt agcaaattaa ctggaaggga      840
tttgggaatc caatcagaag cgttgataga caacagttgt gaatccaaat gcttttggag      900 aggggggttct ataaatacaa agctcccttt tcaaaatctg tcacccagaa cagtaggtca      960
atgccccaaa tacgtaaatc agaggagttt actgcttgca acagggatga ggaatgtgcc     1020
agaagtggtg cagggaaggg gtctgtttgg tgcaatagca gggttcatag aaaacggatg     1080
ggaaggaatg gtagacggct ggtatggttt cagacaccaa aatgcccagg cacaggcca     1140 agctgctgat tacaagagta tcaagcagc tattgaccaa atcacaggga aactgaacag     1200
gttgattgag aagaccaaca ctgagtttga gtcaatagaa tctgaattca gtgagactga     1260
```

```
gcatcaaatt ggtaacgtca ttaattggac caaagattca ataaccgaca tttggactta    1320
caacgcagag ctattagtgg caatggagaa tcagcacaca attgacatgg ctgattcaga    1380
gatgctaaat ctgtatgaaa gggtaagaaa gcaactcaga cagaatgcag aagaagacgg    1440
aaagggatgt tttgagatat atcatacttg tgatgattcg tgcatggaga gtataaggaa    1500
caatacttat gaccattcac aatacagaga ggaggctctt ctgaatagac tgaacatcaa    1560
cccagtgaaa ctttcttcgg ggtacaaaga catcatactt tggtttagct tcggggaatc    1620
atgctttgtt cttctagccg ttgttatggg tcttgttttc ttctgcctga aaaatggaaa    1680
catgcgatgc acaatctgta tttagttaaa acaccttgt ttctact                  1727
```

<210> SEQ ID NO 20
<211> LENGTH: 1698
<212> TYPE: DNA
<213> ORGANISM: Influenza A Virus

<400> SEQUENCE: 20

```
atggagaaaa cactgctatt tgcagctatt ttcctttgtg tgaaagcaga tgagatctgt      60
atcgggtatt taagcaacaa ctcgacagac aaagttgaca caataattga gaacaatgtc     120
acggtcacta gctcagtgga actggttgag acagaacaca ctggatcatt ctgttcaatc     180
aatggaaaac aaccaataag ccttggagat tgttcatttg ctggatggat attaggaaac     240
cctatgtgtg atgaactaat tggaaagact tcatggtctt acattgtgga aaacccaat      300 ccaacaaatg gaatctgtta cccaggaact ttagagagtg aagaagaact aagactgaaa     360
ttcagtggag ttttagaatt taacaaattc gaagtattca catcaaatgg atggggtgct     420
gtaaattcag gagtaggagt aaccgctgca tgcaaattcg ggggttctaa ttctttcttt     480
cgaaacatgg tatggctgat acaccatca ggaacatatc ctgtaataaa gagaaccttt     540
aacaacacca agggagaga tgtactgatt gtttggggaa ttcatcatcc tgctacactg     600
acagaacatc aagatctgta taaaaaggac agctcctatg tagcagtggg ttcagagacc     660
tacaacagaa gattcactcc agaaatcaac actaggccca gagtcaatgg acaggccgga     720
cggatgacat tctactggaa gatagtcaaa ccaggagaat caataacatt cgaatctaat     780
ggggcgttcc tagctcctag atatgctttt gagattgtct ctgttggaaa tgggaaactg     840
ttcaggagcg aactgaacat tgaatcatgc tctaccaaaa gtcaaacaga ataggagga     900 attaatacga acaaaagctt ccacaatgtt cacagaaaca ctatcgggga ttgccccaag     960
tatgtgaatg tcaaatcctt aaagcttgca acaggaccta gaatgtccc agcaatagca    1020 tcgagaggct gtttggagc aatagctgga ttcatagaag ggggatggcc tggactgatc    1080
aatggatggt atgggttcca acacaggga gaagaaggaa caggcattgc agcagacaag    1140
gagtcaactc aaaaggcaat agaccagata acatccaagg taaataacat cgttgacagg    1200
atgaatacaa actttgagtc tgtgcaacac gaattcagtg aaatagagga agaataaat    1260 caattatcaa aacacgtaga tgattctgtg gttgacatct ggtcatataa tgcacagctt    1320
ctcgttttac ttgaaaatga aagacactg gacctccatg actcaaatgt caggaaccct    1380
catgagaaag tcagaagaat gctaaggac aatgccaaag atgaggggaa cggatgcttc    1440 acctttacc ataagtgtga caataaatgc attgaacgag ttagaaacgg aacatatgat    1500
cataaagaat tcgaggagga atcaaaaaatc aatcgccagg agattgaagg ggtgaaacta    1560
gattctagtg ggaatgtgta taaaatactg tcaatttaca gctgcattgc aagcagtctt    1620
gtattggcag cactcatcat ggggttcatg ttttgggcat gcagtaatgg atcatgtaga    1680
```
tgtaccattt gcatttag 1698

<210> SEQ ID NO 21
<211> LENGTH: 1695
<212> TYPE: DNA
<213> ORGANISM: Influenza A Virus

<400> SEQUENCE: 21
atggaaaaat tcatcatttt gagtactgtc ttggcagcaa gctttgcata tgacaaaatt 60
tgcattggat accaaacaaa caactcgact gaaacggtaa acacactaag tgaacaaaac 120
gttccggtga cgcaggtgga agaacttgta catcgtggga ttgatccgat cctgtgtgga 180
acggaactag gatcaccact agtgcttgat gactgttcat tagagggtct aatcctaggc 240
aatcccaaat gtgatcttta tttgaatggc agggaatggt catacatagt agagaggccc 300
aaagagatgg aaggagtttg ctatccaggg tcaattgaaa accaggaaga gctaagatct 360
ctgttttctt ccatcaaaaa atatgaaaga gtgaagatgt ttgatttcac caaatggaat 420
gtcacataca ctgggaccag caaggcctgc aataatacat caaaccaagg ctcattctat 480
aggagcatga gatggttgac cttaaaatca ggacaatttc cagtccaaac agatgagtac 540
aagaacacca gagattcaga cattgtattc acctgggcca ttcaccaccc accaacatct 600
gatgaacaag taaaattata caaaaatcct gatactctct cttcagtcac caccgtagaa 660
atcaatagga gcttcaagcc taatataggg ccaagaccac tcgtgagagg acaacaaggg 720
agaatggatt actactgggc tgttcttaaa cctggacaaa cagtcaaaat acaaaccaat 780
ggtaatctta ttgcacctga atatggtcac ttaatcacag ggaaatcaca tggcaggata 840
ctcaagaata atttgcccat gggacagtgt gtgactgaat gtcaattgaa cgagggtgta 900
atgaacacaa gcaaaccttt ccagaacact agtaagcact atattgggaa atgccccaaa 960
tacataccat cagggagttt aaaattggca atagggctca ggaatgtccc acaagttcaa 1020
gatcgggggc tctttggagc aattgcaggt ttcatagaag gcggatggcc agggctagtg 1080
gctggttggt acggatttca gcatcaaaat gcggaggga caggcatagc tgcagacaga 1140
gacagcaccc aaagggcaat agacaatatg caaaacaaac tcaacaatgt catcgacaaa 1200
atgaataaac aatttgaagt ggtgaatcat gagttttcag aagtggaaag cagaataaac 1260
atgattaatt ccaaaattga tgatcagata actgacatat gggcatacaa tgctgaattg 1320
cttgtcctat tggaaaatca gaagacatta gatgagcatg acgctaatgt aaggaatcta 1380
catgatcggg tcagaagagt cctgagggaa aatgcaattg acacaggaga cggctgcttt 1440
gagattttac ataaatgtga caacaattgt atggacacga ttagaaacgg gacatacaat 1500
cacaaagagt atgaggaaga aagcaaaatc gaacgacaga aagtcaatgg tgtgaaactt 1560
gaggagaatt ctacatataa aattctgagc atctacagca gtgttgcctc aagcttagtt 1620
ctactgctca tgattattgg gggtttcatt ttcgggtgtc aaaatggaaa tgttcgttgt 1680
actttctgta tttaa 1695

<210> SEQ ID NO 22
<211> LENGTH: 1701
<212> TYPE: DNA
<213> ORGANISM: Influenza A Virus

<400> SEQUENCE: 22
atggctctaa atgtcattgc aactttgaca cttataagtg tatgtgtaca tgcagacaga 60

| | |
|---|---|
| atatgcgtgg ggtatctgag caccaattca tcagaaaggg tcgacacgct ccttgaaaat | 120 |
| ggggtcccag tcaccagctc cattgatctg attgagacaa accacacagg aacatactgt | 180 |
| tctctaaatg gagtcagtcc agtgcatttg ggagattgca gctttgaagg atggattgta | 240 |
| ggaaacccag cctgcaccag caactttggg atcagagagt ggtcatacct gattgaggac | 300 |
| cccgcggccc ctcatgggct tgctaccct ggagaattaa acaacaatgg tgaactcaga | 360 |
| cacttgttca gtggaatcag gtcattcagt agaacggaat tgatcccacc tacctcctgg | 420 |
| ggggaagtac ttgacggtac aacatctgct tgcagagata cacgggaac caacagcttc | 480 |
| tatcgaaatt tagtttggtt tataaagaag aatactagat atccagttat cagtaagacc | 540 |
| tacaacaata caacgggaag ggatgtttta gttttatggg gaatacatca cccagtgtct | 600 |
| gtggatgaga caaagactct gtatgtcaat agtgatccat acacactggt ttccaccaag | 660 |
| tcttggagcg agaaatataa actagaaacg ggagtccgac ctggctataa tggacagagg | 720 |
| agctggatga aaatttattg gtctttgata catccagggg agatgattac tttcgagagt | 780 |
| aatggtggat ttttagcccc aagatatggg tacataattg aagaatatgg aaaggaagg | 840 |
| attttccaga gtcgcatcag aatgtctagg tgcaacacca gtgccagac ttcggttgga | 900 |
| gggataaaca caaacagaac gttccaaaac atcgataaga atgctcttgg tgactgtccc | 960 |
| aaatacataa agtctggcca actcaagcta gccactggac tcagaaatgt gccagctata | 1020 |
| tcgaatagag gattgttcgg agcaattgca ggttcatag aaggaggctg gccaggttta | 1080 |
| atcaatggtt ggtacggttt tcagcatcaa aatgaacagg gaacaggaat agctgcagac | 1140 |
| aaagaatcaa cacagaaagc tatagaccag ataacaacca aataaataa cattattgat | 1200 |
| aaaatgaatg ggaactatga ttcaattagg ggtgaattca atcaagttga aagcgtata | 1260 |
| aacatgcttg cagacagaat agatgatgcc gtgacggaca tttggtcata caatgccaaa | 1320 |
| cttcttgtat tgctggaaaa tgataaaact ttagatatgc atgatgctaa tgtaaagaat | 1380 |
| ttacatgagc aagtacgaag agaattgaag gacaatgcaa ttgacgaagg aaatggctgt | 1440 |
| tttgaactcc ttcataaatg caatgactcc tgcatggaaa ctataagaaa tggaacgtat | 1500 |
| gaccacactg agtatgcaga ggagtcaaag ttaaagaggc aagaaatcga tgggatcaaa | 1560 |
| ctcaaatcag aagacaacgt ttacaaagca ttatcaatat acagttgcat tgcaagtagt | 1620 |
| gttgtactag taggactcat actctctttc atcatgtggg cctgtagtag tgggaattgc | 1680 |
| cgattcaatg tttgtatata a | 1701 |

<210> SEQ ID NO 23
<211> LENGTH: 1749
<212> TYPE: DNA
<213> ORGANISM: Influenza A Virus

<400> SEQUENCE: 23

| | |
|---|---|
| agcaaaagca ggggaaaatg attgcactca tattggttgc actggctctg agccacactg | 60 |
| cttattctca gatcacaaat gggacaacag gaaacccat tatatgcttg ggcatcatg | 120 |
| cagtggaaaa cggcacatct gttaaaacac taacagacaa tcacgtagaa gttgtgtcag | 180 |
| ctaaagaatt agttgagacg aaccacactg atgaactgtg cccaagcccc ttgaagcttg | 240 |
| tcgacgggca agactgccac ctcatcaatg gtgcattggg gagtccaggc tgtgaccgtt | 300 |
| tgcaggacac cacttgggat gtcttcattg aaaggcccac tgcagtagac acatgttatc | 360 |
| cattcgacgt cccagattac cagagtctca gaagcatcct agcaagcagt gggagtttgg | 420 |
| agttcatcgc cgaacaattc acctggaatg gtgtcaaagt tgacggatca agcagtgctt | 480 |

```
gtttgagggg cggtcgcaac agcttcttct cccgactaaa ctggctaacc aaagcaacaa 540
atggaaacta tggacctatt aacgtcacta aagaaaatac gggctcttat gtcaggctct 600
atctctgggg agtgcatcac ccatcaagcg ataatgagca aacggatctc tacaaggtgg 660
caacagggag agtaacagta tctacccgct cggaccaaat cagtattgtt cccaatatag 720
gaagtagacc gagggtaagg aatcagagcg gcaggataag catctactgg accctagtaa 780
acccagggga ctccatcatt ttcaacagta ttgggaattt gattgcacca agaggccact 840
acaaaataag caaatctact aagagcacag tgcttaaaag tgacaaaagg attgggtcat 900
gcacaagccc ttgcttaact gataaaggtt cgatccaaag tgacaaacct tttcagaatg 960
tatcaaggat tgctatagga aactgcccga aatatgtaaa gcaagggtcc ctgatgttag 1020
caactggaat gcgcaacatc cctggcaaac aggcaaaggg cttatttggg gcaattgctg 1080
gattcattga aaatggttgg caaggcctga ttgatgggtg gtatggattc aggcaccaaa 1140
atgctgaagg aacaggaact gctgcagacc tgaagtcaac tcaggcagcc attgatcaga 1200
taaatggcaa gctgaacaga ttgatagaga agacaaatga aaaatatcac caaatagaaa 1260
aggaattcga acaggtggaa ggaagaatac aagaccttga gaagtacgtt gaggacacta 1320
agattgattt gtggtcatac aatgctgaat tgctagtagc actagagaat cagcacacaa 1380
tagatgtcac agactccgaa atgaacaagc tttttgaaag agtaagaagg caattaagag 1440
agaatgcaga agatcaaggc aacggttgtt tcgagatatt ccatcagtgt gacaacaatt 1500
gtatagaaag cattagaaac ggaacttatg accacaacat ctacagggat gaagccatca 1560
acaatcgaat caaaataaat cctgtcactt tgacgatggg gtacaaggac ataatcctgt 1620
ggatttcttt ctccatgtca tgctttgtct tcgtggcact gattctggga tttgttctat 1680
gggcttgtca aaacgggaat atccgatgcc aaatctgtat ataaagaaaa aacacccttg 1740
tttctactc 1749

<210> SEQ ID NO 24
<211> LENGTH: 1762
<212> TYPE: DNA
<213> ORGANISM: Influenza A Virus
<400> SEQUENCE: 24
agcaaaagca ggggatacaa aatgaacact caaatcatcg tcattctagt cctcggactg 60
tcgatggtga gatctgacaa gatttgtctc gggcaccatg ccgtagcaaa tgggacaaaa 120
gtcaacacac taactgagaa aggagtggaa gtggtcaatg ccacggagac agtggagatt 180
acaggaataa ataaagtgtg cacaaaaggg aagaaagcgg tggacttggg atcttgtgga 240
atactgggaa ctatcattgg gcctccacaa tgtgactctc atcttaaatt caaagctgat 300
ctgataatag aaagaagaaa ttcaagtgac atctgttacc cagggaaatt cactaatgag 360
gaagcactga gacaaataat cagagaatct ggtggaattg acaaagagcc aatgggattt 420
agatattcag gaataaaaac agacggggca accagtgcgt gtaagagaac agtgtcctct 480
ttctactcag aaatgaaatg gcttttatcc agcaaggcta accaggtgtt cccacaactg 540
aatcagacat acaggaacaa cagaaaagaa ccagccctaa ttgtttgggg agtacatcat 600
tcaagttcct tggatgagca aaataagcta tatggagctg ggaacaagct gataacagta 660
ggaagctcaa aataccaaca atcgttttca ccaagtccag gggacaggcc caaagtgaat 720
ggtcaggccg ggaggatcga ctttcattgg atgctattgg acccagggga tacagtcact 780
```

-continued

| | |
|---|---|
| tttaccttca atggtgcatt catagcccca gatagagcca cctttctccg ctctaatgcc | 840 |
| ccatcgggag ttgagtacaa tgggaagtca ctgggaatac agagtgatgc acaaattgat | 900 |
| gaatcatgtg aaggggaatg cttctacagt ggagggacaa taaacagccc tttgccattt | 960 |
| caaaacatcg atagttgggc tgtcggaagg tgccccagat atgtaaagca atcaagcctg | 1020 |
| ccgctggcct taggaatgaa aaatgtacca gagaaaatac atactagggg actgttcggt | 1080 |
| gcaattgcag gattcatcga aatggatgg aaggactca ttgatggatg gtatggatt | 1140 |
| aggcatcaaa atgcacaggg gcagggaaca gctgctgact acaagagtac tcaggctgca | 1200 |
| attgaccaga taacagggaa acttaataga ttaattgaaa aaccaacac acagtttgaa | 1260 |
| ctcatagaca atgagttcac tgaagtggag cagcagatag gcaatgtaat aaactggaca | 1320 |
| agggactcct tgactgagat ctggtcatac aatgctgaac ttctagtagc aatggaaaat | 1380 |
| cagcatacaa ttgaccttgc agattctgaa atgaacaaac tctatgagag agtgagaaga | 1440 |
| cagctaaggg agaatgccga ggaggatgga actggatgtt ttgagatttt ccaccgatgt | 1500 |
| gacgatcaat gtatggagag catacgaaat aatacttaca atcacactga atatcgacag | 1560 |
| gaagccttac agaataggat aatgatcaat ccggtaaagc ttagtggtgg gtacaaagat | 1620 |
| gtgatactat ggtttagctt cggggcatca tgtgtaatgc ttctagccat tgctatgggt | 1680 |
| cttatttca tgtgtgtgaa aaacgggaat ctgcggtgca ctatctgtat ataattattt | 1740 |
| gaaaaacacc cttgtttcta ct | 1762 |

<210> SEQ ID NO 25
<211> LENGTH: 1760
<212> TYPE: DNA
<213> ORGANISM: Influenza A Virus

<400> SEQUENCE: 25

| | |
|---|---|
| agcaaaagca ggggatattg tcaaacaac agaatggtga tcaaagtgct ctactttctc | 60 |
| atcgtattgt taagtaggta ttcgaaagca gacaaaatat gcataggata tctaagcaac | 120 |
| aacgccacag acacagtaga cacactgaca gagaacggag ttccagtgac cagctcagtt | 180 |
| gatctcgttg aaacaaacca cacaggaaca tactgctcac tgaatggaat cagcccaatt | 240 |
| catcttggtg actgcagctt tgagggatgg atcgtaggaa acccttcctg tgccaccaac | 300 |
| atcaacatca gagagtggtc gtatctaatt gaggaccca atgccccaa caaactctgc | 360 |
| tttcccaggag agttagataa taatggagaa ttacgacatc tcttcagcgg agtgaactct | 420 |
| tttagcagaa cagaattaat aagtcccaac aaatggggag acattctgga tggagtcacc | 480 |
| gcttcttgcc gcgataatgg ggcaagcagt ttttacagaa atttggtctg atagtgaag | 540 |
| aataaaaatg gaaataccc tgtcataaag ggggattaca ataacacaac aggcagagat | 600 |
| gttctagtac tctggggcat tcaccatccg gatacagaaa caacagccat aaacttgtac | 660 |
| gcaagcaaaa acccctacac attagtatca acaaaggaat ggagcaaaag atatgaacta | 720 |
| gaaattggca ccagaatagg tgatggacag agaagttgga tgaaactata ttggcacctc | 780 |
| atgcgccctg agagaggat aatgtttgaa agcaacgggg ccttatagc gcccagatac | 840 |
| ggatacatca ttgagaagta cggtacagga cgaattttcc aaagtggagt gagaatggcc | 900 |
| aaatgcaaca caaagtgtca acatcatta ggtgggataa acaccaacaa aactttccaa | 960 |
| aacatagaga gaaatgctct tggagattgc ccaaagtaca taaagtctgg acagctgaag | 1020 |
| cttgcaactg ggctgagaaa tgtcccatcc gttggtgaaa gaggttttgt tggtgcaatt | 1080 |
| gcaggcttca tagaaggagg gtggcctggg ctaattaatg gatggtatgg tttccagcat | 1140 |

```
cagaatgaac aggggactgg cattgctgca gacaaagcct ccactcagaa agcgatagat 1200
gaaataacaa caaaaattaa caatataata gagaagatga acggaaacta tgattcaata 1260
agaggggaat tcaatcaagt agaaaagagg atcaacatgc tcgctgatcg agttgatgat 1320
gcagtaactg acatatggtc gtacaatgct aaacttcttg tactgcttga aaatgggaga 1380
acattggact tacacgacgc aaatgtcagg aacttacacg atcaggtcaa gagaatattg 1440
aaaagtaatg ctattgatga aggagatggt tgcttcaatc ttcttcacaa atgtaatgac 1500
tcatgcatgg aaactattag aaatgggacc tacaatcatg aagattacag ggaagaatca 1560
caactgaaaa ggcaggaaat tgagggaata aaattgaagt ctgaagacaa tgtgtataaa 1620
gtactgtcga tttatagctg cattgcaagc agtattgtgc tggtaggtct catacttgcg 1680
ttcataatgt gggcatgcag caatggaaat tgccggttta atgtttgtat atagtcggaa 1740
aaaataccct tgtttctact 1760

<210> SEQ ID NO 26
<211> LENGTH: 1882
<212> TYPE: DNA
<213> ORGANISM: Influenza A Virus
<400> SEQUENCE: 26
agcagaagcg ttgcattttc taatatccac aaaatgaagg caataattgt actactcatg 60
gtagtaacat ccaatgcaga tcgaatctgc actgggataa catcgtcaaa ctcacctcat 120
gtggttaaaa ctgccactca aggggaagtc aatgtgactg gtgtgatacc actaacaaca 180
acacctacca aatctcattt tgcaaatctc aaaggaacac agaccagagg aaaactatgc 240
ccaaactgtt ttaactgcac agatctggac gtggccctag gcagaccaaa atgcatgggg 300
aacacaccct ccgcaaaagt ctcaatactc catgaagtca aacctgctac atctggatgc 360
tttcctataa tgcacgacag aacaaaaatc agacaactac ctaatcttct cagaggatat 420
gaaaacatca ggttatcaac cagtaatgtt atcaatacag agacggcacc aggaggaccc 480
tacaaggtgg ggacctcagg atcttgccct aacgttgcta atgggaacgg cttcttcaac 540
acaatggctt gggttatccc aaaagacaac aacaagacag caataaatcc agtaacagta 600
gaagtaccat acatttgttc agaaggggaa gaccaaatta ctgtttgggg gttccactct 660
gatgacaaaa cccaaatgga aagactctat ggagactcaa atcctcaaaa gttcacctca 720
tctgccaatg gagtaaccac acattatgtt tctcagattg gtggcttccc aaatcaaaca 780
gaagacgaag ggctaaaaca aagcggcaga attgttgttg attacatggt acaaaaacct 840
ggaaaaacag gaacaattgt ttatcaaaga ggcattttat tgcctcaaaa agtgtggtgc 900
gcaagtggca ggagcaaggt aataaaaggg tccttgcctt taattggtga agcagattgc 960
ctccacgaaa agtacggtgg attaaataaa agcaagcctt actacacagg agagcatgca 1020
aaggccatag gaaattgccc aatatgggtg aaaacaccct tgaagctggc caatggaacc 1080
aaatatagac cgcctgcaaa actattaaag gaaagaggtt tcttcggagc tattgctggt 1140
ttcttggaag gaggatggga aggaatgatt gcaggttggc acggatacac atctcatgga 1200
gcacatggag tggcagtggc agcagacctt aagagtacac aagaagctat aaacaagata 1260
acaaaaaatc tcaactattt aagtgagcta gaagtaaaaa accttcaaag actaagcgga 1320
gcaatgaatg agcttcacga cgaaatactc gagctagacg aaaaagtgga tgatctaaga 1380
gctgatacaa taagctcaca aatagagctt gcagtcttgc tttccaacga agggataata 1440
```

| | |
|---|---|
| aacagtgaag atgagcatct cttggcactt gaaagaaaac tgaagaaaat gcttggcccc | 1500 |
| tctgctgtag aaatagggaa tgggtgcttt gaaaccaaac acaaatgcaa ccagacttgc | 1560 |
| ctagacagga tagctgctgg cacctttaat gcaggagatt tttctcttcc cacttttgat | 1620 |
| tcattaaaca ttactgctgc atctttaaat gatgatggct tggataatca tactatactg | 1680 |
| ctctactact caactgctgc ttctagcttg ctgtaacat taatgatagc tatcttcatt | 1740 |
| gtctacatgg tctccagaga caatgttttct tgttccatct gtctgtgagg gagattaagc | 1800 |
| cctgtgtttt cctttactgt agtgctcatt tgcttgtcac cattacaaag aaacgttatt | 1860 |
| gaaaaatgct cttgttacta ct | 1882 |

<210> SEQ ID NO 27
<211> LENGTH: 2073
<212> TYPE: DNA
<213> ORGANISM: Influenza A Virus

<400> SEQUENCE: 27

| | |
|---|---|
| agcagaagca gggggttaat aatgttttc tcattactct tggtgttggg cctcacagag | 60 |
| gctgaaaaaa taaagatatg ccttcaaaag caagtgaaca gtagcttcag cctacacaat | 120 |
| ggcttcggag gaaatttgta tgccacagaa gaaaaaagaa tgtttgagct tgttaagccc | 180 |
| aaagctggag cctctgtctt gaatcaaagt acatggattg ctttggaga ttcaaggact | 240 |
| gacaaaagca attcagcttt tcctaggtct gctgatgttt cagcaaaaac tgctgataag | 300 |
| tttcgttttt tgtctggtgg atccttaatg ttgagtatgt ttggcccacc tgggaaggta | 360 |
| gactaccttt accaaggatg tggaaaacat aaagttttt atgaaggagt taactggagt | 420 |
| ccacatgctg ctataaattg ttacagaaaa aattggactg atatcaaact gaatttccag | 480 |
| aaaaacattt atgaattggc ttcacaatca cattgcatga gcttggtgaa tgccttggac | 540 |
| aaaactattc ctttacaagt gactgctggg actgcaggaa attgcaacaa cagcttctta | 600 |
| aaaaatccag cattgtacac acaagaagtc aagccttcag aaaacaaatg tgggaaagaa | 660 |
| atcttgcttt tcttcacact tccaacccaa tttggaacct atgagtgcaa actgcatctt | 720 |
| gtggcttctt gctatttcat ctatgatagt aaagaagtgt acaataaaag aggatgtgac | 780 |
| aactactttc aagtgatcta tgattcattt ggaaaagtcg ttggaggact agataacagg | 840 |
| gtatcacctt acacagggaa ttctggagac accccaacaa tgcaatgtga catgctccag | 900 |
| ctgaaacctg gaagatattc agtaagaagc tctccaagat tcctttttaat gcctgaaaga | 960 |
| agttattgct ttgacatgaa agaaaaagga ccagtcactg ctgtccaatc catttgggga | 1020 |
| aaaggcagag aatctgacta tgcagtggat caagcttgct gagcactcc agggtgcatg | 1080 |
| ttgatccaaa agcaaaagcc atacattgga gaagctgatg atcaccatgg agatcaagaa | 1140 |
| atgagggagt tgctgtcagg actggactat gaagctagat gcatatcaca atcagggtgg | 1200 |
| gtgaatgaaa ccagtccttt tacggagaaa tacctcctc ctcccaaatt tggaagatgc | 1260 |
| cctttggctg caaggaaga atccattcca aaaatcccag atggccttct aattcccacc | 1320 |
| agtggaaccg ataccactgt aaccaaacct aagagcagaa tttttggaat cgatgacctc | 1380 |
| attattggtg tgctctttgt tgcaatcgtt gaaacaggaa ttggaggcta tctgcttgga | 1440 |
| agtagaaaag aatcaggagg aggtgtgaca aaagaatcag ctgaaaaagg gtttgagaaa | 1500 |
| attggaaatg acatacaaat tttaaaatct tctataaata tcgcaataga aaaactaaat | 1560 |
| gacagaattt ctcatgatga gcaagccatc agagatctaa ctttagaaat tgaaaatgca | 1620 |
| agatctgaag ctttattggg agaattggga ataataagag ccttattggt aggaaatata | 1680 |

| | |
|---|---|
| agcataggat tacaggaatc tttatgggaa ctagcttcag aaataacaaa tagagcagga | 1740 |
| gatctagcag ttgaagtctc cccaggttgc tggataattg acaataacat ttgtgatcaa | 1800 |
| agctgtcaaa attttatttt caagttcaac gaaactgcac ctgttccaac cattcccct | 1860 |
| cttgacacaa aaattgatct gcaatcagat ccttttact ggggaagcag cttgggctta | 1920 |
| gcaataactg ctactatttc attggcagct ttggtgatct ctgggatcgc catctgcaga | 1980 |
| actaaatgat tgagacaatt ttgaaaaatg gataatgtgt tggtcaatat tttgtacagt | 2040 |
| tttataaaaa acaaaaatcc ccttgctact gct | 2073 |

<210> SEQ ID NO 28
<211> LENGTH: 1670
<212> TYPE: DNA
<213> ORGANISM: Influenza Virus

<400> SEQUENCE: 28

| | |
|---|---|
| agatcttcgc tgacacaata tgtataggct accatgccaa caactcaacc gacactgttg | 60 |
| acacagtact tgagaagaat gtgacagtga cacactctgt caacctactt gaggacagtc | 120 |
| acaatggaaa actatgtcta ctaaaaggaa tagccccact acaattgggt aattgcagcg | 180 |
| ttgccggatg gatcttagga aacccagaat gcgaattact gatttccaag gaatcatggt | 240 |
| cctacattgt agaaacacca atcctgaga atggaacatg ttacccaggg tatttcgccg | 300 |
| actatgagga actgagggag caattgagtt cagtatcttc atttgagaga ttcgaaatat | 360 |
| tccccaaaga aagctcatgg cccaaccaca ccgtaaccgg agtatcagca tcatgctccc | 420 |
| ataatgggaa aagcagtttt tacagaaatt tgctatggct gacggggaag aatggtttgt | 480 |
| acccaaacct gagcaagtcc tatgtaaaca caaagagaa agaagtcctt gtactatggg | 540 |
| gtgttcatca cccgcctaac atagggaacc aaagggcact ctatcataca gaaaatgctt | 600 |
| atgtctctgt agtgtcttca cattatagca gaagattcac cccagaaata gccaaaagac | 660 |
| ccaaagtaag agatcaggaa ggaagaatca actactactg gactctgctg gaacctgggg | 720 |
| atacaataat atttgaggca aatggaaatc taatagcgcc atggtatgct tttgcactga | 780 |
| gtagaggctt tggatcagga atcatcacct caaatgcacc aatggatgaa tgtgatgcga | 840 |
| agtgtcaaac acctcaggga gctataaaca gcagtcttcc tttccagaat gtacacccag | 900 |
| tcacaatagg agagtgtcca aagtatgtca ggagtgcaaa attaaggatg gttacaggac | 960 |
| taaggaacat cccatccatt caatccagag gtttgtttgg agccattgcc ggtttcattg | 1020 |
| aagggggtg gactggaatg gtagatgggt ggtatggtta tcatcatcag aatgagcaag | 1080 |
| gatctggcta tgctgcagat caaaaagta cacaaaatgc cattaacggg attacaaaca | 1140 |
| aggtcaattc tgtaattgag aaaatgaaca ctcaattcac agctgtgggc aaagagttca | 1200 |
| acaaattgga agaaggatg gaaaacttaa ataaaaagt tgatgatggg tttctagaca | 1260 |
| tttggacata taatgcagaa ttgttggttc tactggaaaa tgaaaggact ttggatttcc | 1320 |
| atgactccaa tgtgaagaat ctgtatgaga agtaaaaag ccaattaaag aataatgcca | 1380 |
| aagaaatagg aaacggggtgt tttgagttct atcacaagtg taacaatgaa tgcatggaga | 1440 |
| gtgtgaaaaa tggtacctat gactatccaa atattccga agaatcaaag ttaaacaggg | 1500 |
| agaaaattga tggagtgaaa ttggaatcaa tgggagtata ccagattctg gcgatctact | 1560 |
| caactgtcgc cagttccctg gttcttttgg tctccctggg ggcaatcagc ttctggatgt | 1620 |
| gttccaatgg gtcttttgcag tgtagaatat gcatctaaga gctcaggcct | 1670 |

<210> SEQ ID NO 29
<211> LENGTH: 32
<212> TYPE: DNA
<213> ORGANISM: Artificial Sequence
<220> FEATURE:
<223> OTHER INFORMATION: Primer

<400> SEQUENCE: 29
agttccccgg gctggtatat ttatatgttg tc                          32

<210> SEQ ID NO 30
<211> LENGTH: 46
<212> TYPE: DNA
<213> ORGANISM: Artificial Sequence
<220> FEATURE:
<223> OTHER INFORMATION: Primer

<400> SEQUENCE: 30
aatagagctc cattttctct caagatgatt aattaattaa ttagtc           46

<210> SEQ ID NO 31
<211> LENGTH: 46
<212> TYPE: DNA
<213> ORGANISM: Artificial Sequence
<220> FEATURE:
<223> OTHER INFORMATION: Primer

<400> SEQUENCE: 31
aatagagctc gttaaaatgc ttcttcgtct cctatttata atatgg           46

<210> SEQ ID NO 32
<211> LENGTH: 48
<212> TYPE: DNA
<213> ORGANISM: Artificial Sequence
<220> FEATURE:
<223> OTHER INFORMATION: Primer

<400> SEQUENCE: 32
ttacgaattc tccttcctaa ttggtgtact atcatttatc aaagggga         48

<210> SEQ ID NO 33
<211> LENGTH: 1711
<212> TYPE: DNA
<213> ORGANISM: Influenza Virus

<400> SEQUENCE: 33
atgaaagcaa aactactggt cctgttatgt acatttacag ctacatatgc agacacaata    60
tgtataggct accatgccaa caactcaacc gacactgttg acacagtact tgagaagaat   120
gtgacagtga cacactctgt caacctactt gaggacagtc acaatggaaa actatgtcta   180
ctaaaaggaa tagccccact acaattgggt aattgcagcg ttgccggatg gatcttagga   240
aacccagaat gcgaattact gatttccaag gaatcatggt cctacattgt agaaacacca   300
aatcctgaga atggaacatg ttacccaggg tatttcgccg actatgagga actgagggag   360
caattgagtt cagtatcttc atttgagaga ttcgaaatat tccccaaaga aagctcatgg   420
cccaaccaca ccgtaaccgg agtatcagca tcatgctccc ataatgggaa aagcagtttt   480
tacagaaatt tgctatggct gacggggaag aatggtttgt acccaaacct gagcaagtcc   540
tatgtaaaca caaagagaa agaagtcctt gtactatggg gtgttcatca cccgcctaac   600
atagggaacc aaaagggccct ctatcataca gaaaatgctt atgtctctgt agtgtcttca   660
cattatagca gaagattcac cccagaaata gccaaaagac ccaaagtaag agatcaggaa   720

```
ggaagaatca actactactg gactctgctg gaacctgggg atacaataat atttgaggca      780
aatggaaatc taatagcgcc atggtatgct tttgcactga gtagaggctt tggatcagga      840
atcatcacct caaatgcacc aatggatgaa tgtgatgcga agtgtcaaac acctcaggga      900
gctataaaca gcagtcttcc tttccagaat gtacacccag tcacaatagg agagtgtcca      960
aagtatgtca ggagtgcaaa attaaggatg gttacaggac taaggaacat cccatccatt     1020
caatccagag gtttgtttgg agccattgcc ggtttcattg aaggggggtg gactggaatg     1080
gtagatgggt ggtatggtta tcatcatcag aatgagcaag gatctggcta tgctgcagat     1140
caaaaaagta cacaaaatgc cattaacggg attacaaaca aggtgaattc tgtaattgag     1200
aaaatgaaca ctcaattcac agctgtgggc aaagaattca acaaattgga agaaggatg     1260 gaaaacttaa ataaaaaagt tgatgatggg tttctagaca tttggacata taatgcagaa     1320
ttgttggttc tactggaaaa tgaaaggact ttggatttcc atgactccaa tgtgaagaat     1380
ctgtatgaga agtaaaaaag ccaattaaag aataatgcca agaaatagg aaacgggtgt      1440 tttgaattct atcacaagtg taacaatgaa tgcatggaga gtgtgaaaaa tggaacttat     1500
gactatccaa atattccga agaatcaaag ttaaacaggg agaaaattga tggagtgaaa      1560
ttggaatcaa tgggagtcta tcagattctg gcgatctact caactgtcgc cagttccctg     1620
gttcttttgg tctccctggg ggcaatcagc ttctggatgt gttccaatgg gtctttgcag     1680
tgtagaatat gcatctgaga ccagaatttc a                                    1711

<210> SEQ ID NO 34
<211> LENGTH: 1781
<212> TYPE: DNA
<213> ORGANISM: Medicago Sativa

<400> SEQUENCE: 34
ccaaatcctt aacattcttt caacaccaac aatggcgaaa aacgttgcga ttttcggttt       60
attgttttct cttcttctgt tggttccttc tcagatcttc gctgaggaat catcaactga      120
cgctaaggaa tttgttctta cattggataa cactaatttc catgacactg ttaagaagca      180
cgatttcatc gtcgttgaat tctacgcacc ttggtgtgga cactgtaaga agctagcccc      240
agagtatgag aaggctgctt ctatcttgag cactcacgag ccaccagttg ttttggctaa      300
agttgatgcc aatgaggagc acaacaaaga cctcgcatcg gaaaatgatg ttaagggatt      360
cccaaccatt aagattttta ggaatggtgg aaagaacatt caagaataca aggtccccg      420 tgaagctgaa ggtattgttg agtatttgaa aaaacaaagt ggccctgcat ccacagaaat      480
taaatctgct gatgatgcga ccgcttttgt tggtgacaac aaagttgtta ttgtcggagt      540
tttccctaaa ttttctggtg aggagtacga taacttcatt gcattagcag agaagttgcg      600
ttctgactat gactttgctc acactttgaa tgccaaacac cttccaaagg gagactcatc      660
agtgtctggg cctgtggtta ggttatttaa gccatttgac gagctctttg ttgactcaaa      720
ggatttcaat gtagaagctc tagagaaatt cattgaagaa tccagtaccc caattgtgac      780
tgtcttcaac aatgagccta gcaatcaccc ttttgttgtc aaattcttta actctcccaa      840
cgcaaaggct atgttgttca tcaactttac taccgaaggt gctgaatctt tcaaaacaaa      900
ataccatgaa gtggctgagc aatacaaaca acagggagtt agctttcttg ttggagatgt      960
tgagtctagt caaggtgcct tccagtattt tggactgaag gaagaacaag tacctctaat     1020
tattattcag cataatgatg gcaagaagtt tttcaaaccc aatttggaac ttgatcaact     1080
```

```
cccaacttgg ttgaaggcat acaaggatgg caaggttgaa ccatttgtca agtctgaacc      1140
tattcctgaa actaacaacg agcctgttaa agtggtggtt gggcaaactc ttgaggacgt      1200
tgttttcaag tctgggaaga atgttttgat agagttttat gctccttggt gtggtcactg      1260
caagcagttg gctccaatct tggatgaagt tgctgtctca ttccaaagcg atgctgatgt      1320
tgttattgca aaactggatg caactgccaa cgatatccca accgacacct tgatgtcca      1380 aggctatcca accttgtact tcaggtcagc aagtggaaaa ctatcacaat acgacggtgg      1440
taggacaaag gaagacatca tagaattcat tgaaaagaac aaggataaaa ctggtgctgc      1500
tcatcaagaa gtagaacaac caaaagctgc tgctcagcca gaagcagaac aaccaaaaga      1560
tgagctttga aaagttccgc ttggaggata tcggcacaca gtcatctgcg ggctttacaa      1620
ctcttttgta tctcagaatc agaagttagg aaatcttagt gccaatctat ctattttgc       1680 gtttcatttt atcttttggg tttactctaa tgtattactg aataatgtga gttttggcgg      1740
agtttagtac tggaactttt gtttctgtaa aaaaaaaaa a                           1781

<210> SEQ ID NO 35
<211> LENGTH: 1027
<212> TYPE: DNA
<213> ORGANISM: Influenza Virus

<400> SEQUENCE: 35
agcgaaagca ggtagatatt gaaagatgag tcttctaacc gaggtcgaaa cgtacgttct       60
ctctatcatc ccgtcaggcc ccctcaaagc cgagatcgca cagagacttg aagatgtctt      120
tgcagggaag aacaccgatc ttgaggttct catggaatgg ctaaagacaa gaccaatcct      180
gtcacctctg actaagggga ttttaggatt tgtgttcacg ctcaccgtgc ccagtgagcg      240
aggactgcag cgtagacgct ttgtccaaaa tgcccttaat gggaacgggg atccaaataa      300
catggacaaa gcagttaaac tgtataggaa gctcaagagg gagataacat tccatggggc      360
caaagaaatc tcactcagtt attctgctgg tgcacttgcc agttgtatgg cctcatata       420 caacaggatg ggggctgtga ccactgaagt ggcatttggc ctggtatgtg caacctgtga      480
acagattgct gactcccagc atcggtctca taggcaaatg gtgacaacaa ccaacccact      540
aatcagacat gagaacagaa tggttttagc cagcactaca gctaaggcta tggagcaaat      600
ggctggatcg agtgagcaag cagcagaggc catggaggtt gctagtcagg ctaggcaaat      660
ggtgcaagcg atgagaacca ttgggactca tcctagctcc agtgctggtc tgaaaaatga      720
tcttcttgaa aatttgcagg cctatcagaa acgaatgggg gtgcagatgc aacggttcaa      780
gtgatcctct cgctattgcc gcaaatatca ttgggatctt gcacttgata ttgtggattc      840
ttgatcgtct ttttttcaaa tgcatttacc gtcgctttaa atacggactg aaaggagggc      900
cttctacgga aggagtgcca aagtctatga gggaagaata tcgaaggaa cagcagagtg       960 ctgtggatgc tgacgatggt cattttgtca gcatagagct ggagtaaaaa actaccttgt     1020
ttctact                                                               1027

<210> SEQ ID NO 36
<211> LENGTH: 1788
<212> TYPE: DNA
<213> ORGANISM: Artificial Sequence
<220> FEATURE:
<223> OTHER INFORMATION: Clone

<400> SEQUENCE: 36
cactttgtga gtctacactt tgattccctt caaacacata caaagagaag agactaatta       60
```

```
attaattaat catcttgaga gaaaatgaaa gtaaaactac tggtcctgtt atgcacattt    120
acagctacat atgcagacac aatatgtata ggctaccatg ctaacaactc gaccgacact    180
gttgacacag tacttgaaaa gaatgtgaca gtgacacact ctgtcaacct gcttgagaac    240
agtcacaatg gaaaactatg tctattaaaa ggaatagccc cactacaatt gggtaattgc    300
agcgttgccg ggtggatctt aggaaaccca gaatgcgaat tactgatttc caaggagtca    360
tggtcctaca ttgtagaaaa accaaatcct gagaatggaa catgttaccc agggcatttc    420
gctgactatg aggaactgag ggagcaattg agttcagtat cttcatttga gaggttcgaa    480
atattcccca agaaaagctc atggcccaac cacaccgtaa ccggagtgtc agcatcatgc    540
tcccataatg gggaaagcag tttttacaga aatttgctat ggctgacggg gaagaatggt    600
ttgtacccaa acctgagcaa gtcctatgca acaacaaag aaaagaagt ccttgtacta    660 tggggtgttc atcacccgcc aaacataggt gaccaaaagg ccctctatca tacagaaaat    720
gcttatgtct ctgtagtgtc ttcacattat agcagaaaat tcaccccaga aatagccaaa    780
agacccaaag taagagatca agaaggaaga atcaattact actggactct gcttgaaccc    840
ggggatacaa taatatttga ggcaaatgga aatctaatag cgccaagata tgctttcgca    900
ctgagtagag gctttggatc aggaatcatc aactcaaatg caccaatgga taaatgtgat    960
gcgaagtgcc aaacacctca gggagctata acagcagtc ttcctttcca gaacgtacac   1020
ccagtcacaa taggagagtg tccaaagtat gtcaggagtg caaaattaag gatggttaca   1080
ggactaagga acatcccatc cattcaatcc agaggtttgt ttggagccat tgccggtttc   1140
attgaagggg ggtggactgg aatggtagat ggttggtatg gttatcatca tcagaatgag   1200
caaggatctg gctatgctgc agatcaaaaa agcacacaaa atgccattaa tgggattaca   1260
aacaaggtca attctgtaat tgagaaaatg aacactcaat tcacagcagt gggcaaagag   1320
ttcaacaaat tggaaagaag gatggaaaac ttgaataaaa aagttgatga tgggtttata   1380
gacatttgga catataatgc agaactgttg gttctactgg aaaatgaaag gactttggat   1440
ttccatgact ccaatgtgaa gaatctgtat gagaaagtaa aaagccagtt aaagaataat   1500
gctaaagaaa taggaaatgg gtgttttgag ttctatcaca gtgtaacga tgaatgcatg   1560 gagagtgtaa agaatggaac ttatgactat ccaaaatatt ccgaagaatc aaagttaaac   1620
agggagaaaa ttgatggagt gaaattggaa tcaatgggag tctatcagat tctggcgatc   1680
tactcaacag tcgccagttc tctggttctt ttggtctccc tgggggcaat cagcttctgg   1740
atgtgttcca tgggtctttt acagtgtaga atatgcatct aagagctc                1788

<210> SEQ ID NO 37
<211> LENGTH: 1788
<212> TYPE: DNA
<213> ORGANISM: Artificial Sequence
<220> FEATURE:
<223> OTHER INFORMATION: Clone

<400> SEQUENCE: 37
cactttgtga gtctacactt tgattccctt caaacacata caaagagaag agactaatta     60
attaattaat catcttgaga gaaaatgaaa gtaaaactac tggtcctgtt atgcacattt    120
acagctacat atgcagacac aatatgtata ggctaccatg ccaacaactc aaccgacact    180
gttgacacag tacttgagaa gaatgtgaca gtgacacact ctgtcaacct gcttgaggac    240
agtcacaatg gaaaattatg tctattaaaa ggaatagccc cactacaatt gggtaattgc    300
```

```
agcgttgccg atggatcttt aggaaaccca gaatgcgaat tactgatttc cagggaatca      360
tggtcctaca ttgtagaaaa accaaatcct gagaatggaa catgttaccc agggcatttc      420
gccgactatg aggaactgag ggagcaattg agttcagtat cttcatttga gagattcgaa      480
atattcccca agaaagctca tggcccaaca cacaccacaa ccggagtatc agcatcatgc      540
tcccataatg gggaaagcag ttttttacaaa aatttgctat ggctgacggg aagaatggt      600 ttgtacccaa acctgagcaa gtcctatgca acaacaaag agaaagaagt ccttgtacta      660
tggggtgttc atcacccgcc taacataggt gaccaaaggg ctctctatca taagaaaaat      720
gcttatgtct ctgtagtgtc ttcacattat agcagaaaat tcaccccaga aatagccaaa      780
agacccaaag taagagatca agaaggaaga atcaactact actggactct acttgaaccc      840
ggggatacaa taatatttga ggcaaatgga atctaatag cgccaagata tgctttcgca      900
ctgagtagag ctttggatc aggaatcatc aactcaaatg caccaatgga tgaatgtgat      960
gcgaagtgcc aaacacctca gggagctata acagcagtc ttcctttcca gaatgtacac     1020
cctgtcacaa taggagagtg tccaaagtat gtcaggagtg caaaattaag gatggttaca     1080
ggactaagga acatcccatc cattcaatcc agaggtttgt ttggagccat gccggtttc     1140 attgaagggg ggtggactgg aatggtagat ggttggtatg gttatcatca tcagaatgag     1200
caaggatctg gctatgctgc agatcaaaaa agcacacaaa atgccattaa tgggattaca     1260
aacaaggtca attctgtaat tgagaaaatg aacactcaat tcacagctgt gggcaaagag     1320
ttcaacaaat tggaaagaag gatggaaaac ttaaataaaa agtttgatga tgggttata     1380 gacatttgga catataatgc agaattgttg gttctactgg aaaatgaaag gacttttgga     1440
ttccatgact ccaatgtgaa gaatctgtat gagaaagtaa aagccaatt aaagaataat     1500 gccaaagaaa taggaaatgg gtgttttgag ttctatcata gtgtaacga tgaatgcatg     1560 gagagtgtaa aaaatggaac ttatgactat ccaaaatatt ccgaagaatc aaagttaaac     1620
agggagaaaa ttgatggagt gaaattgaa tcaatgggag tctatcagat tctggcgatc     1680
tactcaacag tcgccagttc tctggttctt ttggtctccc tgggggcaat cagcttctgg     1740
atgtgttcca tgggtctttt gcagtgtaga atatgcatct gagagctc              1788
```

<210> SEQ ID NO 38
<211> LENGTH: 1791
<212> TYPE: DNA
<213> ORGANISM: Artificial Sequence
<220> FEATURE:
<223> OTHER INFORMATION: Clone

<400> SEQUENCE: 38

```
cactttgtga gtctacactt tgattcccct caaacacata caagagaag agactaatta       60 attaattaat catcttgaga gaaaatgaag actatcattg ctttgagcta cattctatgt      120
ctggttttca ctcaaaaact tcccggaaat gacaacagca cggcaacgct gtgccttggg      180
caccatgcag taccaaacgg aacgatagtg aaaacaatca cgaatgacca aattgaagtt      240
actaatgcta ctgagctggt tcagagttcc tcaacaggtg aaatatgcga cagtcctcat      300
cagatccttg atggagaaaa ctgcacacta atagatgctc tattgggaga ccctcagtgt      360
gatggcttcc aaaataagaa atgggaccct tttgttgaac gcagcaaagc ctacagcaac      420
tgttaccctt atgatgtgcc ggattatgcc tcccttaggt cactagttgc ctcatccggc      480
acactggagt taacaatga aagtttcaat tggactggag tcactcaaaa cggaacaagc      540
tctgcttgca taaggagatc taataacagt ttctttagta gattgaattg gttgacccac      600
```

```
ttaaaattca ataccccagc attgaacgtg actatgccaa acaatgaaaa atttgacaaa      660
ttgtacattt ggggggttca ccacccgggt acggacaatg accaaatctt cctgtatgct      720
caagcatcag gaagaatcac agtctctacc aaaagaagcc aacaaactgt aatcccgaat      780
atcggatcta gacccagagt aaggaatatc cccagcagaa taagcatcta ttggacaata      840
gtaaaaccgg gagacatact tttgattaac agcacaggga atctaattgc tcctaggggt      900
tacttcaaaa tacgaagtgg gaaaagctca ataatgagat cagatgcacc cattggcaaa      960
tgcaattctg aatgcatcac tccaaacgga agcattccca atgacaaacc attccaaaat     1020
gtaaacagga tcatacggg ggcctgtccc agatatgtta agcaaaacac tctgaaattg     1080
gcaacaggga tgcgaaatgt accagagaaa caaactagag gcatatttgg cgcaatcgcg     1140
ggtttcatag aaaatggttg ggagggaatg gtggatggtt ggtatggttt caggcatcaa     1200
aattctgagg gaataggaca agcagcagat ctcaaaagca ctcaagcagc aatcgatcaa     1260
atcaatggga agctgaatag gttgatcggg aaaaccaacg agaaattcca tcagattgaa     1320
aaagagttct cagaagtcga agggagaatc caggaccttg agaaatatgt tgaggacacc     1380
aaaatagatc tctggtcata caacgcggag cttcttgttg ccctggagaa ccaacataca     1440
attgatctaa ctgactcaga aatgaacaaa ctgtttgaaa aaacaaagaa gcaactgagg     1500
gaaaatgctg aggatatggg caatggttgt ttcaaaatat accacaaatg tgacaatgcc     1560
tgcataggat caatcagaaa tggaacttat gaccacgatg tatacagaga tgaagcatta     1620
aacaaccggt tccagatcaa gggcgttgag ctgaagtcag gatacaaaga ttggatacta     1680
tggatttcct ttgccatatc atgttttttg ctttgtgttg ctttgttggg gttcatcatg     1740
tgggcctgcc aaaaggcaa cattaggtgc aacatttgca tttgagagct c              1791

<210> SEQ ID NO 39
<211> LENGTH: 1791
<212> TYPE: DNA
<213> ORGANISM: Artificial Sequence
<220> FEATURE:
<223> OTHER INFORMATION: Clone

<400> SEQUENCE: 39
cactttgtga gtctacactt tgattccctt caaacacata caaagagaag agactaatta       60
attaattaat catcttgaga gaaaatgaag actatcattg ctttgagcta cattctatgt      120
ctggttttca ctcaaaaact tccccggaaat gacaacagca cggcaacgct gtgccttggg      180
caccatgcag taccaaacgg aacgatagtg aaaacaatca cgaatgacca aattgaagtt      240
actaatgcta ctgagctggt tcagagttcc tcaacaggtg aaatatgcga cagtcctcat      300
cagatccttg atggagaaaa ctgcacacta atagatgctc tattgggaga ccctcagtgt      360
gatggcttcc aaaataagaa atgggaccttt tttgttgaac gcagcaaagc ctacagcaac      420
tgttacccct tatgatgtgcc ggattatgcc tcccttaggt cactagttgc ctcatccggc      480
acactggagt ttaacgatga agtttcaatg tggactggag tcactcaaaa tggaacaagc      540
tctgcttgca aaaggagatc taataacagt ttctttagta gattgaattg gttgacccac      600
ttaaaattca ataccccagc attgaacgtg actatgccaa acaatgaaaa atttgacaaa      660
ttgtacattt ggggggttca ccacccgggt acggacaatg accaaatctt cctgcatgct      720
caagcatcag gaagaatcac agtctctacc aaaagaagcc aacaaactgt aatcccgaat      780
atcggatcta gacccagaat aaggaatatc cccagcagaa taagcatcta ttggacaata      840
```

```
gtaaaaccgg gagacatact tttgattaac agcacaggga atctaattgc tcctaggggt        900
tacttcaaaa tacgaagtgg gaaaagctca ataatgagat cagatgcacc cattggcaaa        960
tgcaattctg aatgcatcac tccaaatgga agcattccca atgacaaacc atttcaaaat       1020
gtaaacagga tcacatatgg ggcctgtccc agatatgtta agcaaaacac tctgaaattg       1080
gcaacaggga tgcgaaatgt accagagaaa caaactagag gcatatttgg cgcaatcgcg       1140
ggtttcatag aaaatggttg ggagggaatg gtggatggtt ggtacggttt caggcatcaa       1200
aattctgagg gaataggaca agcagcagat ctcaaaagca ctcaagcagc aatcaatcaa       1260
atcaatggga agctgaatag gttgatcggg aaaaccaacg agaaattcca tcagattgaa       1320
aaagagttct cagaagtaga agggagaatc caggacctcg agaaatatgt tgaggacact       1380
aaaatagatc tctggtcata caacgcggag cttcttgttg ccctggagaa ccaacataca       1440
attgatctaa ctgactcaga aatgaacaaa ctgtttgaaa gaacaaagaa gcaactgagg       1500
gaaaatgctg aggatatggg caatggttgt tcaaaatat accacaaatg tgacaatgcc       1560
tgcataggat caatcagaaa tggaacttat gaccatgatg tatacagaga tgaagcatta       1620
aacaaccggt tccagatcaa aggcgttgag ctgaagtcag gatacaaaga ttggatacta       1680
tggatttcct ttgccatatc atgttttttg ctttgtgttg ctttgttggg gttcatcatg       1740
tgggcctgcc aaaaaggcaa cattaggtgc aacatttgca tttgagagct c              1791
```

<210> SEQ ID NO 40
<211> LENGTH: 1848
<212> TYPE: DNA
<213> ORGANISM: Artificial Sequence
<220> FEATURE:
<223> OTHER INFORMATION: Clone

<400> SEQUENCE: 40

```
cactttgtga gtctacactt tgattccctt caaacacata caaagagaag agactaatta         60
attaattaat catcttgaga gaaaatgaag gcaataattg tactactcat ggtagtaaca        120
tccaatgcag atcgaatctg cactgggata acatcgtcaa actcaccaca tgttgtcaaa        180
actgctactc aaggggaggt caatgtgact ggtgtaatac cactgacaac aacacccacc        240
aaatctcatt ttgcaaatct caaaggaaca gaaaccagag ggaaactatg cccaaaatgc        300
ctcaactgca cagatctgga cgtggccttg ggcagaccaa atgcacgggg aacatacccc       360
tcggcaagag tttcaatact ccatgaagtc agacctgtta catctgggtg ctttcctata       420
atgcacgaca gaacaaaaat tagacagctg cctaaacttc tcagaggata cgaacatatc       480
aggttatcaa ctcataacgt tatcaatgca gaaaatgcac caggaggacc ctacaaaatt       540
ggaacctcag ggtcttgccc taacgttacc aatggaaacg attttttcgc aacaatggct       600
tgggccgtcc caaaaaacga caacaacaaa acagcaacaa attcattaac aatagaagta       660
ccatacattt gtacagaagg agaagaccaa attaccgttt gggggttcca ctctgataac       720
gaaacccaaa tggcaaagct ctatgggggac tcaaagcccc agaagttcac ctcatctgcc       780
aacggagtga ccacacatta cgtttcacag attggtggct tcccaaatca aacagaagac       840
ggaggactac cacaaagcgg tagaattgtt gttgattaca tggtgcaaaa atctgggaaa       900
acaggaacaa ttacctatca agaggtattt tattgcctca aaaagtgtg gtgcgcaagt       960 ggcaggagca aggtaataaa aggatcgttg cctttaattg agaagcaga ttgcctccac      1020 gaaaaatacg gtggattaaa caaaagcaag ccttactaca cagggggaaca tgcaaaggcc      1080 ataggaaatt gcccaatatg ggtgaaaaca cccttgaagc tggccaatgg aaccaaatat      1140
```

| | |
|---|---|
| agacctcctg caaaactatt aaaggaaagg ggtttcttcg gagctattgc tggtttctta | 1200 |
| gaaggaggat gggaaggaat gattgcaggt tggcacggat acacatccca tggggcacat | 1260 |
| ggagtagcgg tggcagcaga ccttaagagc actcaagagg ccataaacaa gataacaaaa | 1320 |
| aatctcaact ctttgagtga gctggaagta aagaatcttc aaagactaag cggtgccatg | 1380 |
| gatgaactcc acaacgaaat actagaacta gacgagaaag tggatgatct cagagctgat | 1440 |
| acaataagct cacaaataga actcgcagtc ctgctttcca atgaaggaat aataaacagt | 1500 |
| gaagatgagc atctcttggc gcttgaaaga aagctgaaga aaatgctggg ccctctgct | 1560 |
| gtagagatag ggaatggatg ctttgaaacc aaacacaagt gcaaccagac ctgtctcgac | 1620 |
| agaatagctg ctggtacctt tgatgcagga gaattttctc tccccacttt tgattcactg | 1680 |
| aatattactg ctgcatcttt aaatgacgat ggattggata atcatactat actgctttac | 1740 |
| tactcaactg ctgcctccag tttggctgta acattgatga tagctatctt tgttgtttat | 1800 |
| atggtctcca gagacaatgt ttcttgctcc atctgtctat aagagctc | 1848 |

<210> SEQ ID NO 41
<211> LENGTH: 1845
<212> TYPE: DNA
<213> ORGANISM: Artificial Sequence
<220> FEATURE:
<223> OTHER INFORMATION: Clone

<400> SEQUENCE: 41

| | |
|---|---|
| cactttgtga gtctacactt tgattccctt caaacacata caaagagaag agactaatta | 60 |
| attaattaat catcttgaga gaaaatgaag gcaataattg tactactcat ggtagtaaca | 120 |
| tccaatgcag atcgaatctg cactggaata acatcttcaa actcacctca tgtggtcaaa | 180 |
| acagccactc aagggaggt caatgtgact ggtgtgatac cactaacaac aacaccaaca | 240 |
| aaatcttatt ttgcaaatct caaaggaaca aggaccagag ggaaactatg cccagactgt | 300 |
| ctcaactgca cagatctgga tgtggctttg gcagaccaa tgtgtgtggg gaccacacct | 360 |
| tcggcgaagg cttcaatact ccacgaagtc aaacctgtta catccgggtg ctttcctata | 420 |
| atgcacgaca gaacaaaaat caggcaacta cccaatcttc tcagaggata tgaaaatatc | 480 |
| aggctatcaa cccaaaacgt catcgatgcg gaaaaggcac caggaggacc ctacagactt | 540 |
| ggaacctcag gatcttgccc taacgctacc agtaagagcg gattttcgc aacaatggct | 600 |
| tgggctgtcc caaaggacaa caacaaaaat gcaacgaacc cactaacagt agaagtacca | 660 |
| tacatttgta cagaagggga agaccaaatc actgtttggg ggttccattc agataacaaa | 720 |
| acccaaatga gaacctcta tggagactca atcctcaaa agttcaccct atctgctaat | 780 |
| ggagtaacca cacactatgt ttctcagatt ggcagcttcc cagatcaaac agaagacgga | 840 |
| ggactaccac aaagcggcag gattgttgtt gattacatga tgcaaaaacc tgggaaaaca | 900 |
| ggaacaattg tctaccaaag aggtgttttg ttgcctcaaa aggtgtggtg cgcgagtggc | 960 |
| aggagcaaag taataaaagg gtccttgcct ttaattggtg aagcagattg ccttcatgaa | 1020 |
| aaatacggtg gattaaacaa agcaagcct tactacacag agaacatgc aaaagccata | 1080 |
| ggaaattgcc caatatgggt gaaaacacct ttgaagctcg ccaatggaac caaatataga | 1140 |
| cctcctgcaa aactattaaa ggaaggggt tcttcggag ctattgctgg tttcctagaa | 1200 |
| ggaggatggg aaggaatgat tgcaggctgg acggatca catctcacgg agcacatgga | 1260 |
| gtggcagtgg cggcggacct taagagtacg caagaagcta taaacaagat aacaaaaat | 1320 |

```
ctcaattctt tgagtgagct agaagtaaag aatcttcaaa gactaagtgg tgccatggat      1380
gaactccaca cgaaatact cgagctggat gagaaagtgg atgatctcag agctgacact       1440
ataagctcgc aaatagaact tgcagtcttg ctttccaacg aaggaataat aaacagtgaa      1500
gatgagcatc tattggcact tgagagaaaa ctaaagaaaa tgctgggtcc ctctgctgta      1560
gagataggaa atggatgctt cgaaaccaaa cacaagtgca accagacctg cttagacagg      1620
atagctgctg gcacctttaa tgcaggagaa ttttctctcc ccacttttga ttcactgaac      1680
attactgctg catcttaaa tgatgatgga ttggataacc atactatact gctctattac       1740
tcaactgctg cttctagttt ggctgtaaca ttgatgctag ctatttttat tgtttatatg      1800
gtctccagag acaacgtttc atgctccatc tgtctataag agctc                      1845

<210> SEQ ID NO 42
<211> LENGTH: 1779
<212> TYPE: DNA
<213> ORGANISM: Artificial Sequence
<220> FEATURE:
<223> OTHER INFORMATION: Clone

<400> SEQUENCE: 42
cactttgtga gtctacactt tgattcccct caaacacata caaagagaag agactaatta       60
attaattaat catcttgaga gaaaatggcc atcatttatc taattctcct gttcacagca      120
gtgagagggg accaaatatg cattggatac catgccaata attccacaga gaaggtcgac      180
acaattctag agcggaacgt cactgtgact catgccaagg acattcttga agacccccat      240
aacgaaaagt tatgcaaact aaacggaatc cctccacttg aactagggga ctgtagcatt      300
gccggatggc tccttggaaa tccagaatgt gataggcttc taagtgtgcc agaatggtcc      360
tatataatga gaaagaaaa cccgagagac ggtttgtgtt atccaggcag cttcaatgat      420
tatgaagaat gaaacatctc cctcagcagc gtgaaacatt cgagaaagt aaagattctg       480 cccaaagata gatggacaca gcatacaaca actggaggtt cacgggcctg cgcggtgtct      540
ggtaatccat cattcttcag gaacatggtc tggctgacaa agaaagaatc aaattatccg      600
gttgccaaag gatcgtacaa caatacaagc ggagaacaaa tgctaataat ttgggggtg      660 caccatccca atgatgagac agaacaaaga acattgtacc agaatgtggg aacctatgtt      720
tccgtaggca catcaacatt gaacaaaagg tcaaccccag acatagcaac aaggcctaaa      780
gtgaatggac taggaagtag aatggagttc tcttggaccc tattggatat gtgggacacc      840
ataaattttg agagtactgg taatctaatt gcaccagagt atggattcaa atatcgaaaa      900
agaggtagtt cagggatcat gaaaacagaa ggaacacttg agaactgtga gaccaaatgc       960
caaactcctt gggagcaat aaatacaaca ttgccttttc acaatgtcca cccactgaca      1020
ataggtgagt gccccaaata tgtaaaatcg gagaagttgg tcttagcaac aggactaagg      1080
aatgttcccc agattgaatc aagaggattg tttggggcaa tagctggttt tatagaagga      1140
ggatggcaag gaatggttga tggttggtat ggataccatc acagcaatga ccagggatca      1200
gggtatgcag cagacaaaga atccactcaa aaggcatttg atggaatcac caacaaggta      1260
aattctgtga ttgaaaagat gaacacccaa tttgaagctg ttgggaaaga gttcagtaac      1320
ttagagagaa gactggagaa cttgaacaaa aagatggaag acgggtttct agatgtgtgg      1380
acatacaatg ctgagcttct agttctgatg gaaaatgaga ggacacttga ctttcatgat      1440
tctaatgtca gaatctgta tgataaagtc agaatgcagc tgagagacaa cgtcaaagaa      1500
ctaggaaatg gatgttttga attttatcac aaatgtgatg atgaatgcat gaatagtgtg      1560
```

```
aaaaacggga cgtatgatta tcccaagtat gaagaagagt ctaaactaaa tagaaatgaa   1620
atcaaagggg taaaattgag cagcatgggg gtttatcaaa tccttgccat ttatgctaca   1680
gtagcaggtt ctctgtcact ggcaatcatg atggctggga tctctttctg gatgtgctcc   1740
aacgggtctc tgcagtgcag gatctgcata tgagagctc                          1779
```

<210> SEQ ID NO 43
<211> LENGTH: 1794
<212> TYPE: DNA
<213> ORGANISM: Artificial Sequence
<220> FEATURE:
<223> OTHER INFORMATION: Clone

<400> SEQUENCE: 43

```
cactttgtga gtctacactt tgattcccct caaacacata caaagagaag agactaatta     60
attaattaat catcttgaga gaaaatggag aaaatagtgc ttcttcttgc aatagtcagc    120
cttgttaaaa gtgatcagat ttgcattggt taccatgcaa acaactcgac agagcaggtt    180
gacacaataa tggaaaagaa cgttactgtt acacatgccc aagacatact ggaaaagaca    240
cacaacggga agctctgcga tctagatgga gtgaagcctc tgattttaag agattgtagt    300
gtagctggat ggctcctcgg aaacccaatg tgtgacgagt tcatcaatgt gccggaatgg    360
tcttacatag tggagaaggc caacccagcc aatgacctct gttacccagg gaatttcaac    420
gactatgaag aactgaaaca cctattgagc agaataaacc attttgagaa aattcagatc    480
atccccaaaa gttcttggtc cgatcatgaa gcctcatcag ggtcagctc agcatgtcca    540 taccagggaa cgccctcctt tttcagaaat gtggtatggc ttatcaaaaa gaacaataca    600
tacccaacaa taaagagaag ctacaataat accaaccagg aagatctttt gatactgtgg    660
gggattcatc attctaatga tgcggcagag cagacaaagc tctatcaaaa cccaaccacc    720
tatatttccg ttgggacatc aacactaaac cagagattgg taccaaaaat agctactaga    780
tccaaagtaa acgggcaaag tggaaggatg gatttcttct ggacaatttt aaaaccgaat    840
gatgcaatca acttcgagag taatggaaat ttcattgctc cagaatatgc atacaaaatt    900
gtcaagaaag gggactcagc aattgttaaa agtgaagtgg aatatggtaa ctgcaataca    960
aagtgtcaaa ctccaatagg ggcgataaac tctagtatgc cattccacaa catacaccct   1020
ctcaccatcg gggaatgccc caaatatgtg aaatcaaaca attagtcct tgcgactggg   1080 ctcagaaata gtcctctaag agaaagaaga agaaaaagag gactatttgg agctatagca   1140
gggtttatag agggaggatg gcagggaatg gtagatggtt ggtatgggta ccaccatagc   1200
aatgagcagg ggagtgggta cgctgcagac aaagaatcca ctcaaaaggc aatagatgga   1260
gtcaccaata aggtcaactc gatcattgac aaaatgaaca ctcagtttga ggccgttgga   1320
agggaattta ataacttaga aaggagaata gagaatttaa acaagaaaat ggaagacgga   1380
ttcctagatg tctggactta taatgctgaa cttctggttc tcatgaaaaa tgagagaact   1440
ctagacttcc atgattcaaa tgtcaagaac ctttacgaca aggtccgact acagcttagg   1500
gataatgcaa aggagctggg taacggttgt ttcgagttct atcacaaatg tgataatgaa   1560
tgtatggaaa gtgtaagaaa cggaacgtat gactacccgc agtattcaga agaagcaaga   1620
ttaaaaagag aggaaataag tggagtaaaa ttggaatcaa taggaactta ccaaatactg   1680
tcaatttatt caacagttgc gagttctcta gcactggcaa tcatggtggc tggtctatct   1740
ttgtggatgt gctccaatgg gtcgttacaa tgcagaattt gcatttaaga gctc         1794
```

<210> SEQ ID NO 44
<211> LENGTH: 1797
<212> TYPE: DNA
<213> ORGANISM: Artificial Sequence
<220> FEATURE:
<223> OTHER INFORMATION: Clone

<400> SEQUENCE: 44

```
cactttgtga gtctacactt tgattcccct caaacacata caaagagaag agactaatta      60
attaattaat catcttgaga gaaaatggag aaaatagtgc ttcttttttgc aatagtcagt    120
cttgttaaaa gtgatcagat ttgcattggt taccatgcaa acaactcgac agagcaggtt    180
gacacaataa tggaaaagaa cgttactgtt acacatgccc aagacatact ggaaaagaca    240
cacaatggga agctctgcga tctagatgga gtgaagcctc taattttgag agattgtagt    300
gtagctggat ggctcctcgg aaacccaatg tgtgacgagt tcatcaatgt gccggaatgg    360
tcttacatag tggagaaggc caatccagtc aatgacctct gttacccagg ggatttcaat    420
gactatgaag aattgaaaca cctattgagc agaataaacc attttgagaa aattcagatc    480
atccccaaaa gttcttggtc cagtcatgaa gcctcattgg gggtcagctc agcatgtcca    540
taccagggaa agtcctcctt tttcagaaat gtggtatggc ttatcaaaaa gaacagtaca    600
tacccaacaa taaagaggag ctacaataat accaaccaag aagatctttt ggtactgtgg    660
gggattcacc atcctaatga tgcggcagag cagacaaagc tctatcaaaa cccaaccacc    720
tatatttccg ttgggacatc tacactaaac cagagattgg taccaagaat agctactaga    780
tccaaagtaa acgggcaaag tggaaggatg gagttcttct ggacaatttt taaaaccgaat   840
gatgcaatca acttcgagag taatggaaat ttcattgctc cagaatatgc atacaaaatt    900
gtcaagaaag gggactcaac aattatgaaa agtgaattgg aatatggtaa ctgcaatacc    960
aagtgtcaaa ctccaatggg ggcgataaac tctagcatgc cattccacaa tatacaccct   1020
ctcaccatcg ggaatgccc caaatatgtg aaatcaaaca gattagtcct tgcgactggg   1080
ctcagaaata gccctcaaag agagaagaa agaaaaaaga gaggattatt tggagctata   1140
gcaggttta tagagggagg atggcaggga atggtagatg gttggtatgg gtaccaccat   1200
agcaacgagc aggggagtgg gtacgctgca gacaaagaat ccactcaaaa ggcaatagat   1260
ggagtcacca ataaggtcaa ctcgattatt gacaaaatga acactcagtt tgaggccgtt   1320
ggaagggaat ttaacaactt agaaaggaga atagagaatt aaacaagaa gatggaagac   1380
gggttcctag atgtctggac ttataatgct gaacttctag ttctcatgga aaacgagaga   1440
actctagact ttcatgactc aaatgtcaag aacctttacg acaaggtccg actacagctt   1500
agggataatg caaaggagct gggtaacggt tgtttcgagt tctatcataa atgtgataat   1560
gaatgtatgg aaagtgtaag aaacggaacg tatgactacc cgcagtattc agaagaagca   1620
agactaaaaa gagaggaaat aagtggagta aaattggaat caataggaat ttaccaaata   1680
ttgtcaattt attctacagt ggccagctcc ctagcactgg caatcatggt agctggtcta   1740
tccttatgga tgtgctccaa tgggtcgtta caatgcagaa tttgcattta agagctc     1797
```

<210> SEQ ID NO 45
<211> LENGTH: 1791
<212> TYPE: DNA
<213> ORGANISM: Artificial Sequence
<220> FEATURE:
<223> OTHER INFORMATION: Clone

<400> SEQUENCE: 45

```
cactttgtga gtctacactt tgattccctt caaacacata caaagagaag agactaatta      60
attaattaat catcttgaga gaaaatgatt gcaatcattg taatagcaat actggcagca     120
gccggaaagt cagacaagat ctgcattggg tatcatgcca acaattcaac aacacaggta     180
gatacgatac ttgagaagaa tgtgactgtc acacactcaa ttgaattgct ggaaaatcag     240
aaggaagaaa gattctgcaa gatattgaac aaggcccctc tcgacttaag ggaatgtacc     300
atagagggtt ggatcttggg gaatccccaa tgcgacctat tgcttggtga tcaaagctgg     360
tcatacattg tggaaagacc tactgctcaa aacgggatct gctacccagg aaccttaaat     420
gaggtagaag aactgagggc acttattgga tcaggagaaa gggtagagag atttgagatg     480
tttccccaaa gcacctggca aggagttgac accaacagtg gaacaacaag atcctgccct     540
tattctactg gtgcgtcttt ctacagaaac ctcctatgga ataaaaaac caagacagca     600 gaatatccag taattaaggg aatttacaac aacactggaa cccagccaat cctctatttc     660
tggggtgtgc atcatcctcc taacaccgac gagcaagata ctctgtatgg ctctggtgat     720
cgatacgtta aatgggaac tgaaagcatg aattttgcca agagtccgga aattgcggca     780
aggcctgctg tgaatggaca agaggcagaa ttgattatt attggtcggt tttaaaacca     840
ggggaaacct tgaatgtgga atctaatgga aatctaatcg ccccttggta tgcatacaaa     900
tttgtcaaca caaatagtaa aggagccgtc ttcaggtcag atttaccaat cgagaactgc     960
gatgccacat gccagactat tgcaggggtt ctaaggacca ataaaacatt tcagaatgtg    1020
agtcccctgt ggataggaga atgtcccaaa tacgtgaaaa gtgaaagtct gaggcttgca    1080
actggactaa gaaatgttcc acagattgaa actagaggac tcttcggagc tattgcaggg    1140
tttattgaag gaggatggac tgggatgata atgggtggt atggctatca ccatgaaaat    1200
tctcaagggt caggatatgc agcagacaga gaaagcactc aaaaggctgt aaacagaatt    1260
acaaataagg tcaattccat catcaacaaa atgaacacac aatttgaagc tgtcgatcac    1320
gaattttcaa atctggagag gagaattgac aatctgaaca aaagaatgca agatggattt    1380
ctggatgttt ggacatacaa tgctgaactg ttggttcttc ttgaaaacga agaacacta    1440 gacatgcatg acgcaaatgt gaagaaccta catgaaaagg tcaaatcaca actaagggac    1500
aatgctacga tcttagggaa tggttgcttt gaattttggc ataagtgtga caatgaatgc    1560
atagagtctg tcaaaaatgg tacatatgac tatcccaaat accagactga agcaaatta    1620 aacaggctaa aaatagaatc agtaaagcta gagaaccttg tgtgtatca aattcttgcc    1680 atttatagta cggtatcgag cagcctagtg ttggtagggc tgatcatggc aatgggtctt    1740
tggatgtgtt caaatggttc aatgcagtgc aggatatgta tataagagct c             1791
```

<210> SEQ ID NO 46
<211> LENGTH: 1803
<212> TYPE: DNA
<213> ORGANISM: Artificial Sequence
<220> FEATURE:
<223> OTHER INFORMATION: Clone

<400> SEQUENCE: 46

```
cactttgtga gtctacactt tgattccctt caaacacata caaagagaag agactaatta      60
attaattaat catcttgaga gaaaatgaac actcaaattc taatattagc cacttcggca     120
ttcttctatg tacgtgcaga taaaatctgc ctaggacatc atgctgtgtc taatggaacc     180
aaagtagaca cccttactga aaaggaata gaagttgtca atgcaacaga aacagttgaa     240
```

-continued

| | |
|---|---|
| caaacaaaca tccctaagat ctgctcaaaa ggaaaacaga ctgttgacct tggtcaatgt | 300 |
| ggattactag ggaccgttat tggtcctccc caatgtgacc aatttcttga gttctctgct | 360 |
| aatttaatag ttgaaagaag ggaaggtaat gacatttgtt atccaggcaa atttgacaat | 420 |
| gaagaaacat tgagaaaaat actcagaaaa tccggaggaa ttaaaaagga gaatatggga | 480 |
| ttcacatata ccggagtgag aaccaatgga gagactagcg catgtagaag gtcaagatct | 540 |
| tccttttatg cagagatgaa atggcttcta tccagcacag acaatgggac atttccacaa | 600 |
| atgacaaagt cctacaagaa cactaagaag gtaccagctc tgataatctg gggaatccac | 660 |
| cactcaggat caactactga acagactaga ttatatggaa gtgggaataa attgataaca | 720 |
| gtttggagtt ccaaatacca acaatctttt gtcccaaatc ctggaccaag accgcaaatg | 780 |
| aatggtcaat caggaagaat tgactttcac tggctgatgc tagatcccaa tgatactgtc | 840 |
| actttcagtt ttaatggggc ctttatagca cctgaccgcg ccagttttct aagaggtaaa | 900 |
| tctctaggaa tccaaagtga tgcacaactt gacaataatt gtgaaggtga atgctatcat | 960 |
| attggaggta ctataattag caacttgccc tttcaaaaca ttaatagtag ggcaatcgga | 1020 |
| aaatgcccca gatacgtgaa gcagaagagc ttaatgctag caacaggaat gaaaatgtt | 1080 |
| cctgaagctc ctgcacataa acaactaact catcacatgc gcaaaaaag aggtttattt | 1140 |
| ggtgcaatag caggattcat tgaaaatggg tgggaaggat taatagacgg atggtatgga | 1200 |
| tataagcatc agaatgcaca aggagaaggg actgctgcag actacaaaag tacacaatct | 1260 |
| gctatcaacc aaataaccgg aaaattgaac agactaatag aaaaaaccaa ccagcaattc | 1320 |
| gaactaatag ataatgagtt caatgaaata gaaaaacaaa ttggcaatgt tattaactgg | 1380 |
| actagagatt ctatcatcga agtatggtca tataatgcag agttcctcgt agcagtggag | 1440 |
| aatcaacaca ctattgattt aactgactca gaaatgaaca actatatga aaggtaaga | 1500 |
| agacaactga gagaaaatgc tgaggaagat ggtaatggct gttttgaaat attccaccaa | 1560 |
| tgtgacaatg attgcatggc cagcattaga acaacacat atgaccataa aaaatacaga | 1620 |
| aaagaggcaa tacaaaacag aatccagatt gacgcagtaa agttgagcag tggttacaaa | 1680 |
| gatataatac tttggtttag cttcgggca tcatgtttct tatttcttgc cattgcaatg | 1740 |
| ggtcttgttt tcatatgtat aaaaaatgga acatgcggt gcactatttg tatataagag | 1800 |
| ctc | 1803 |

<210> SEQ ID NO 47
<211> LENGTH: 1773
<212> TYPE: DNA
<213> ORGANISM: Artificial Sequence
<220> FEATURE:
<223> OTHER INFORMATION: Clone

<400> SEQUENCE: 47

| | |
|---|---|
| cactttgtga gtctacactt tgattccctt caaacacata caagagaag agactaatta | 60 |
| attaattaat catcttgaga gaaaatggaa acaatatcac taataactat actactagta | 120 |
| gtaacagcaa gcaatgcaga taaaatctgc atcggccacc agtcaacaaa ctccacagaa | 180 |
| actgtggaca cgctaacaga aaccaatgtt cctgtgacac atgccaaaga attgctccac | 240 |
| acagagcata atggaatgct gtgtgcaaca agcctgggac atcccctcat tctagacaca | 300 |
| tgcactattg aaggactagt ctatggcaac ccttcttgtg acctgctgtt gggaggaaga | 360 |
| gaatggtcct acatcgtcga agatcatca gctgtaaatg aacgtgtta ccctgggaat | 420 |
| gtagaaaacc tagaggaact caggacactt tttagttccg ctagttccta ccaaagaatc | 480 |

```
caaatcttcc cagacacaac ctggaatgtg acttacactg gaacaagcag agcatgttca    540
ggttcattct acaggagtat gagatggctg actcaaaaga gcggttttta ccctgttcaa    600
gacgcccaat acacaaataa caggggaaag agcattcttt tcgtgtgggg catacatcac    660
ccacccacct ataccgagca aacaaatttg tacataagaa acgacacaac aacaagcgtg    720
acaacagaag atttgaatag gaccttcaaa ccagtgatag gccaaggcc ccttgtcaat    780 ggtctgcagg gaagaattga ttattattgg tcggtactaa aaccaggcca aacattgcga    840
gtacgatcca atgggaatct aattgctcca tggtatggac acgttctttc aggagggagc    900
catggaagaa tcctgaagac tgatttaaaa ggtggtaatt gtgtagtgca atgtcagact    960
gaaaaaggtg gcttaaacag tacattgcca ttccacaata tcagtaaata tgcatttgga   1020
acctgcccca aatatgtaag agttaatagt ctcaaactgg cagtcggtct gaggaacgtg   1080
cctgctagat caagtagagg actatttgga gccatagctg gattcataga aggaggttgg   1140
ccaggactag tcgctggctg gtatggtttc cagcattcaa atgatcaagg ggttggtatg   1200
gctgcagata gggattcaac tcaaaaggca attgataaaa taacatccaa ggtgaataat   1260
atagtcgaca agatgaacaa gcaatatgaa ataattgatc atgaatttag tgaggttgaa   1320
actagactca atatgatcaa taataagatt gatgaccaaa tacaagacgt atgggcatat   1380
aatgcagaat tgctagtact acttgaaaat caaaaaacac tcgatgagca tgatgcgaac   1440
gtgaacaatc tatataacaa ggtgaagagg gcactgggct ccaatgctat ggaagatggg   1500
aaaggctgtt tcgagctata ccataaatgt gatgatcagt gcatggaaac aattcggaac   1560
gggacctata taggagaaa gtatagagag gaatcaagac tagaaaggca gaaaatagag   1620
ggggttaagc tggaatctga gggaacttac aaaatcctca ccatttattc gactgtcgcc   1680
tcatctcttg tgcttgcaat ggggtttgct gccttcctgt tctgggccat gtccaatgga   1740
tcttgcagat gcaacatttg tatataagag ctc                               1773
```

<210> SEQ ID NO 48
<211> LENGTH: 565
<212> TYPE: PRT
<213> ORGANISM: Artificial Sequence
<220> FEATURE:
<223> OTHER INFORMATION: Clone

<400> SEQUENCE: 48

```
Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125
```

```
Glu Arg Phe Glu Ile Phe Pro Lys Glu Ser Ser Trp Pro Asn His Thr
        130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Ala Leu Tyr
            195                 200                 205

His Thr Glu Asn Ala Tyr Val Ser Val Val Ser Ser His Tyr Ser Arg
210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
            275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
```

-continued

```
                545                 550                 555                 560

Cys Arg Ile Cys Ile
                565

<210> SEQ ID NO 49
<211> LENGTH: 565
<212> TYPE: PRT
<213> ORGANISM: Artificial Sequence
<220> FEATURE:
<223> OTHER INFORMATION: Clone

<400> SEQUENCE: 49

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Lys Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
```

```
                340             345             350
Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 50
<211> LENGTH: 566
<212> TYPE: PRT
<213> ORGANISM: Artificial Sequence
<220> FEATURE:
<223> OTHER INFORMATION: Clone

<400> SEQUENCE: 50

Met Lys Thr Ile Ile Ala Leu Ser Tyr Ile Leu Cys Leu Val Phe Thr
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
```

```
            130                 135                 140
Gly Val Thr Gln Asn Gly Thr Ser Ala Cys Ile Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ile Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
        355                 360                 365

Phe Arg His Gln Asn Ser Glu Gly Ile Gly Gln Ala Ala Asp Leu Lys
    370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
        435                 440                 445

Asn Gln His Thr Ile Asp Leu Thr Asp Ser Glu Met Asn Lys Leu Phe
    450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
            500                 505                 510

Asn Asn Arg Phe Gln Ile Lys Gly Val Glu Leu Lys Ser Gly Tyr Lys
        515                 520                 525

Asp Trp Ile Leu Trp Ile Ser Phe Ala Ile Ser Cys Phe Leu Leu Cys
    530                 535                 540

Val Ala Leu Leu Gly Phe Ile Met Trp Ala Cys Gln Lys Gly Asn Ile
545                 550                 555                 560
```

<210> SEQ ID NO 51
<211> LENGTH: 566
<212> TYPE: PRT
<213> ORGANISM: Artificial Sequence
<220> FEATURE:
<223> OTHER INFORMATION: Clone

<400> SEQUENCE: 51

```
Met Lys Thr Ile Ile Ala Leu Ser Tyr Ile Cys Leu Val Phe Thr
1               5                   10                  15

Gln Lys Leu Pro Gly Asn Asp Asn Ser Thr Ala Thr Leu Cys Leu Gly
                20                  25                  30

His His Ala Val Pro Asn Gly Thr Ile Val Lys Thr Ile Thr Asn Asp
            35                  40                  45

Gln Ile Glu Val Thr Asn Ala Thr Glu Leu Val Gln Ser Ser Ser Thr
        50                  55                  60

Gly Gly Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
                100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asp Glu Ser Phe Asn Trp Thr
        130                 135                 140

Gly Val Thr Gln Asn Gly Thr Ser Ser Ala Cys Lys Arg Arg Ser Asn
145                 150                 155                 160

Asn Ser Phe Phe Ser Arg Leu Asn Trp Leu Thr His Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Gly Thr Asp Asn Asp Gln Ile
        195                 200                 205

Phe Leu His Ala Gln Ala Ser Gly Arg Ile Thr Val Ser Thr Lys Arg
210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350
```

```
Gly Phe Ile Glu Asn Gly Trp Glu Gly Met Val Asp Gly Trp Tyr Gly
            355                 360                 365

Phe Arg His Gln Asn Ser Glu Gly Ile Gly Gln Ala Ala Asp Leu Lys
        370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
            405                 410                 415

Glu Val Glu Gly Arg Ile Gln Asp Leu Glu Lys Tyr Val Glu Asp Thr
        420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
        450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
            485                 490                 495

Ile Arg Asn Gly Thr Tyr Asp His Asp Val Tyr Arg Asp Glu Ala Leu
        500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
            565

<210> SEQ ID NO 52
<211> LENGTH: 585
<212> TYPE: PRT
<213> ORGANISM: Artificial Sequence
<220> FEATURE:
<223> OTHER INFORMATION: Clone

<400> SEQUENCE: 52

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
            85                  90                  95

Ser Ile Leu His Glu Val Arg Pro Val Thr Ser Gly Cys Phe Pro Ile
        100                 105                 110

Met His Asp Arg Thr Lys Ile Arg Gln Leu Pro Lys Leu Leu Arg Gly
    115                 120                 125

Tyr Glu His Ile Arg Leu Ser Thr His Asn Val Ile Asn Ala Glu Asn
            130                 135                 140
```

-continued

```
Ala Pro Gly Gly Pro Tyr Lys Ile Gly Thr Ser Gly Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
            195                 200                 205

His Ser Asp Asn Glu Thr Gln Met Ala Lys Leu Tyr Gly Asp Ser Lys
            210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
                275                 280                 285

Trp Cys Ala Ser Gly Arg Ser Lys Val Ile Lys Gly Ser Leu Pro Leu
290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
                355                 360                 365

Ala Gly Phe Leu Glu Gly Gly Trp Glu Gly Met Ile Ala Gly Trp His
                370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
                420                 425                 430

Asp Glu Leu His Asn Glu Ile Leu Glu Leu Asp Glu Lys Val Asp Asp
                435                 440                 445

Leu Arg Ala Asp Thr Ile Ser Ser Gln Ile Glu Leu Ala Val Leu Leu
                450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
                515                 520                 525

Phe Asp Ser Leu Asn Ile Thr Ala Ala Ser Leu Asn Asp Asp Gly Leu
                530                 535                 540

Asp Asn His Thr Ile Leu Leu Tyr Tyr Ser Thr Ala Ala Ser Ser Leu
545                 550                 555                 560
```

```
Ala Val Thr Leu Met Ile Ala Ile Phe Val Val Tyr Met Val Ser Arg
            565                 570                 575

Asp Asn Val Ser Cys Ser Ile Cys Leu
            580                 585

<210> SEQ ID NO 53
<211> LENGTH: 584
<212> TYPE: PRT
<213> ORGANISM: Artificial Sequence
<220> FEATURE:
<223> OTHER INFORMATION: Clone

<400> SEQUENCE: 53

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Arg Thr
    50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Lys Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Asn Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asn Asn Lys Asn Ala Thr Asn Pro Leu Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Ser Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335
```

```
Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Asp Glu His Leu Leu Ala Leu Glu
465                 470                 475                 480

Arg Lys Leu Lys Lys Met Leu Gly Pro Ser Ala Val Glu Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 54
<211> LENGTH: 562
<212> TYPE: PRT
<213> ORGANISM: Artificial Sequence
<220> FEATURE:
<223> OTHER INFORMATION: Clone

<400> SEQUENCE: 54

Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110
```

```
Tyr Glu Glu Leu Lys His Leu Leu Ser Ser Val Lys His Phe Glu Lys
            115                 120                 125

Val Lys Ile Leu Pro Lys Asp Arg Trp Thr Gln His Thr Thr Thr Gly
130                 135                 140

Gly Ser Arg Ala Cys Ala Val Ser Gly Asn Pro Ser Phe Phe Arg Asn
145                 150                 155                 160

Met Val Trp Leu Thr Lys Lys Glu Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Asn Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
210                 215                 220

Pro Asp Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
        290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
```

```
                  530                 535                 540
Gly Ile Ser Phe Trp Met Cys Ser Asn Gly Ser Leu Gln Cys Arg Ile
545                 550                 555                 560

Cys Ile

<210> SEQ ID NO 55
<211> LENGTH: 567
<212> TYPE: PRT
<213> ORGANISM: Artificial Sequence
<220> FEATURE:
<223> OTHER INFORMATION: Clone

<400> SEQUENCE: 55

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
            100                 105                 110

Asp Tyr Glu Glu Leu Lys His Leu Leu Ser Arg Ile Asn His Phe Glu
        115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Gln Gly Thr Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Ile Leu Trp
            180                 185                 190

Gly Ile His His Ser Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Asp Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Val Lys Ser Glu Val Glu Tyr Gly
        275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Lys Leu Val Leu Ala Thr Gly Leu Arg Asn Ser
                325                 330                 335
```

-continued

```
Pro Leu Arg Glu Arg Arg Lys Arg Gly Leu Phe Gly Ala Ile Ala
            340                 345                 350

Gly Phe Ile Glu Gly Gly Trp Gln Gly Met Val Asp Gly Trp Tyr Gly
            355                 360                 365

Tyr His His Ser Asn Glu Gln Gly Ser Gly Tyr Ala Ala Asp Lys Glu
            370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
            420                 425                 430

Phe Leu Asp Val Trp Thr Tyr Asn Ala Glu Leu Leu Val Leu Met Glu
            435                 440                 445

Asn Glu Arg Thr Leu Asp Phe His Asp Ser Asn Val Lys Asn Leu Tyr
            450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
            500                 505                 510

Leu Lys Arg Glu Glu Ile Ser Gly Val Lys Leu Glu Ser Ile Gly Thr
            515                 520                 525

Tyr Gln Ile Leu Ser Ile Tyr Ser Thr Val Ala Ser Ser Leu Ala Leu
            530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 56
<211> LENGTH: 568
<212> TYPE: PRT
<213> ORGANISM: Artificial Sequence
<220> FEATURE:
<223> OTHER INFORMATION: Clone

<400> SEQUENCE: 56

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
            100                 105                 110

Asp Tyr Glu Glu Leu Lys His Leu Leu Ser Arg Ile Asn His Phe Glu
            115                 120                 125
```

```
Lys Ile Gln Ile Ile Pro Lys Ser Ser Trp Ser His Glu Ala Ser
            130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Thr Ile Met Lys Ser Glu Leu Glu Tyr Gly
            275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
                340                 345                 350

Ala Gly Phe Ile Glu Gly Gly Trp Gln Gly Met Val Asp Gly Trp Tyr
            355                 360                 365

Gly Tyr His His Ser Asn Glu Gln Gly Ser Gly Tyr Ala Ala Asp Lys
            370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
            435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
            515                 520                 525

Ile Tyr Gln Ile Leu Ser Ile Tyr Ser Thr Val Ala Ser Ser Leu Ala
530                 535                 540
```

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 57
<211> LENGTH: 566
<212> TYPE: PRT
<213> ORGANISM: Artificial Sequence
<220> FEATURE:
<223> OTHER INFORMATION: Clone

<400> SEQUENCE: 57

Met Ile Ala Ile Ile Val Ile Ala Ile Leu Ala Ala Gly Lys Ser
1               5                   10                  15

Asp Lys Ile Cys Ile Gly Tyr His Ala Asn Asn Ser Thr Thr Gln Val
                20                  25                  30

Asp Thr Ile Leu Glu Lys Asn Val Thr Val Thr His Ser Ile Glu Leu
            35                  40                  45

Leu Glu Asn Gln Lys Glu Glu Arg Phe Cys Lys Ile Leu Asn Lys Ala
    50                  55                  60

Pro Leu Asp Leu Arg Glu Cys Thr Ile Glu Gly Trp Ile Leu Gly Asn
65                  70                  75                  80

Pro Gln Cys Asp Leu Leu Leu Gly Asp Gln Ser Trp Ser Tyr Ile Val
                85                  90                  95

Glu Arg Pro Thr Ala Gln Asn Gly Ile Cys Tyr Pro Gly Thr Leu Asn
            100                 105                 110

Glu Val Glu Glu Leu Arg Ala Leu Ile Gly Ser Gly Glu Arg Val Glu
        115                 120                 125

Arg Phe Glu Met Phe Pro Gln Ser Thr Trp Gln Gly Val Asp Thr Asn
130                 135                 140

Ser Gly Thr Thr Arg Ser Cys Pro Tyr Ser Thr Gly Ala Ser Phe Tyr
145                 150                 155                 160

Arg Asn Leu Leu Trp Ile Ile Lys Thr Lys Thr Ala Glu Tyr Pro Val
                165                 170                 175

Ile Lys Gly Ile Tyr Asn Asn Thr Gly Thr Gln Pro Ile Leu Tyr Phe
            180                 185                 190

Trp Gly Val His His Pro Pro Asn Thr Asp Glu Gln Asp Thr Leu Tyr
        195                 200                 205

Gly Ser Gly Asp Arg Tyr Val Arg Met Gly Thr Glu Ser Met Asn Phe
210                 215                 220

Ala Lys Ser Pro Glu Ile Ala Ala Arg Pro Ala Val Asn Gly Gln Arg
225                 230                 235                 240

Gly Arg Ile Asp Tyr Tyr Trp Ser Val Leu Lys Pro Gly Glu Thr Leu
                245                 250                 255

Asn Val Glu Ser Asn Gly Asn Leu Ile Ala Pro Trp Tyr Ala Tyr Lys
            260                 265                 270

Phe Val Asn Thr Asn Ser Lys Gly Ala Val Phe Arg Ser Asp Leu Pro
        275                 280                 285

Ile Glu Asn Cys Asp Ala Thr Cys Gln Thr Ile Ala Gly Val Leu Arg
290                 295                 300

Thr Asn Lys Thr Phe Gln Asn Val Ser Pro Leu Trp Ile Gly Glu Cys
305                 310                 315                 320

Pro Lys Tyr Val Lys Ser Glu Ser Leu Arg Leu Ala Thr Gly Leu Arg
                325                 330                 335

```
Asn Val Pro Gln Ile Glu Thr Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Glu Asn Ser Gln Gly Ser Gly Tyr Ala Ala Asp Arg Glu Ser
        370                 375                 380

Thr Gln Lys Ala Val Asn Arg Ile Thr Asn Lys Val Asn Ser Ile Ile
385                 390                 395                 400

Asn Lys Met Asn Thr Gln Phe Glu Ala Val Asp His Glu Phe Ser Asn
                405                 410                 415

Leu Glu Arg Arg Ile Asp Asn Leu Asn Lys Arg Met Gln Asp Gly Phe
            420                 425                 430

Leu Asp Val Trp Thr Tyr Asn Ala Glu Leu Leu Val Leu Leu Glu Asn
        435                 440                 445

Glu Arg Thr Leu Asp Met His Asp Ala Asn Val Lys Asn Leu His Glu
    450                 455                 460

Lys Val Lys Ser Gln Leu Arg Asp Asn Ala Thr Ile Leu Gly Asn Gly
465                 470                 475                 480

Cys Phe Glu Phe Trp His Lys Cys Asp Asn Glu Cys Ile Glu Ser Val
                485                 490                 495

Lys Asn Gly Thr Tyr Asp Tyr Pro Lys Tyr Gln Thr Glu Ser Lys Leu
            500                 505                 510

Asn Arg Leu Lys Ile Glu Ser Val Lys Leu Glu Asn Leu Gly Val Tyr
        515                 520                 525

Gln Ile Leu Ala Ile Tyr Ser Thr Val Ser Ser Ser Leu Val Leu Val
    530                 535                 540

Gly Leu Ile Met Ala Met Gly Leu Trp Met Cys Ser Asn Gly Ser Met
545                 550                 555                 560

Gln Cys Arg Ile Cys Ile
                565

<210> SEQ ID NO 58
<211> LENGTH: 570
<212> TYPE: PRT
<213> ORGANISM: Artificial Sequence
<220> FEATURE:
<223> OTHER INFORMATION: Clone

<400> SEQUENCE: 58

Met Asn Thr Gln Ile Leu Ile Leu Ala Thr Ser Ala Phe Phe Tyr Val
1               5                   10                  15

Arg Ala Asp Lys Ile Cys Leu Gly His His Ala Val Ser Asn Gly Thr
                20                  25                  30

Lys Val Asp Thr Leu Thr Glu Lys Gly Ile Glu Val Val Asn Ala Thr
            35                  40                  45

Glu Thr Val Glu Gln Thr Asn Ile Pro Lys Ile Cys Ser Lys Gly Lys
        50                  55                  60

Gln Thr Val Asp Leu Gly Gln Cys Gly Leu Leu Gly Thr Val Ile Gly
65                  70                  75                  80

Pro Pro Gln Cys Asp Gln Phe Leu Glu Phe Ser Ala Asn Leu Ile Val
                85                  90                  95

Glu Arg Arg Glu Gly Asn Asp Ile Cys Tyr Pro Gly Lys Phe Asp Asn
            100                 105                 110

Glu Glu Thr Leu Arg Lys Ile Leu Arg Lys Ser Gly Gly Ile Lys Lys
        115                 120                 125
```

```
Glu Asn Met Gly Phe Thr Tyr Thr Gly Val Arg Thr Asn Gly Glu Thr
130                 135                 140

Ser Ala Cys Arg Arg Ser Arg Ser Ser Phe Tyr Ala Glu Met Lys Trp
145                 150                 155                 160

Leu Leu Ser Ser Thr Asp Asn Gly Thr Phe Pro Gln Met Thr Lys Ser
                165                 170                 175

Tyr Lys Asn Thr Lys Lys Val Pro Ala Leu Ile Ile Trp Gly Ile His
                180                 185                 190

His Ser Gly Ser Thr Thr Glu Gln Thr Arg Leu Tyr Gly Ser Gly Asn
                195                 200                 205

Lys Leu Ile Thr Val Trp Ser Ser Lys Tyr Gln Gln Ser Phe Val Pro
210                 215                 220

Asn Pro Gly Pro Arg Pro Gln Met Asn Gly Gln Ser Gly Arg Ile Asp
225                 230                 235                 240

Phe His Trp Leu Met Leu Asp Pro Asn Asp Thr Val Thr Phe Ser Phe
                245                 250                 255

Asn Gly Ala Phe Ile Ala Pro Asp Arg Ala Ser Phe Leu Arg Gly Lys
                260                 265                 270

Ser Leu Gly Ile Gln Ser Asp Ala Gln Leu Asp Asn Asn Cys Glu Gly
                275                 280                 285

Glu Cys Tyr His Ile Gly Gly Thr Ile Ile Ser Asn Leu Pro Phe Gln
290                 295                 300

Asn Ile Asn Ser Arg Ala Ile Gly Lys Cys Pro Arg Tyr Val Lys Gln
305                 310                 315                 320

Lys Ser Leu Met Leu Ala Thr Gly Met Lys Asn Val Pro Glu Ala Pro
                325                 330                 335

Ala His Lys Gln Leu Thr His His Met Arg Lys Lys Arg Gly Leu Phe
                340                 345                 350

Gly Ala Ile Ala Gly Phe Ile Glu Asn Gly Trp Glu Gly Leu Ile Asp
                355                 360                 365

Gly Trp Tyr Gly Tyr Lys His Gln Asn Ala Gln Gly Glu Gly Thr Ala
370                 375                 380

Ala Asp Tyr Lys Ser Thr Gln Ser Ala Ile Asn Gln Ile Thr Gly Lys
385                 390                 395                 400

Leu Asn Arg Leu Ile Glu Lys Thr Asn Gln Gln Phe Glu Leu Ile Asp
                405                 410                 415

Asn Glu Phe Asn Glu Ile Glu Lys Gln Ile Gly Asn Val Ile Asn Trp
                420                 425                 430

Thr Arg Asp Ser Ile Ile Glu Val Trp Ser Tyr Asn Ala Glu Phe Leu
                435                 440                 445

Val Ala Val Glu Asn Gln His Thr Ile Asp Leu Thr Asp Ser Glu Met
450                 455                 460

Asn Lys Leu Tyr Glu Lys Val Arg Arg Gln Leu Arg Glu Asn Ala Glu
465                 470                 475                 480

Glu Asp Gly Asn Gly Cys Phe Glu Ile Phe His Gln Cys Asp Asn Asp
                485                 490                 495

Cys Met Ala Ser Ile Arg Asn Asn Thr Tyr Asp His Lys Lys Tyr Arg
                500                 505                 510

Lys Glu Ala Ile Gln Asn Arg Ile Gln Ile Asp Ala Val Lys Leu Ser
                515                 520                 525

Ser Gly Tyr Lys Asp Ile Ile Leu Trp Phe Ser Phe Gly Ala Ser Cys
530                 535                 540

Phe Leu Phe Leu Ala Ile Ala Met Gly Leu Val Phe Ile Cys Ile Lys
```

```
                545                 550                 555                 560
Asn Gly Asn Met Arg Cys Thr Ile Cys Ile
                565                 570

<210> SEQ ID NO 59
<211> LENGTH: 560
<212> TYPE: PRT
<213> ORGANISM: Artificial Sequence
<220> FEATURE:
<223> OTHER INFORMATION: Clone

<400> SEQUENCE: 59

Met Glu Thr Ile Ser Leu Ile Thr Ile Leu Leu Val Val Thr Ala Ser
 1               5                  10                  15

Asn Ala Asp Lys Ile Cys Ile Gly His Gln Ser Thr Asn Ser Thr Glu
             20                  25                  30

Thr Val Asp Thr Leu Thr Glu Thr Asn Val Pro Val Thr His Ala Lys
         35                  40                  45

Glu Leu Leu His Thr Glu His Asn Gly Met Leu Cys Ala Thr Ser Leu
     50                  55                  60

Gly His Pro Leu Ile Leu Asp Thr Cys Thr Ile Glu Gly Leu Val Tyr
 65                  70                  75                  80

Gly Asn Pro Ser Cys Asp Leu Leu Leu Gly Gly Arg Glu Trp Ser Tyr
                 85                  90                  95

Ile Val Glu Arg Ser Ser Ala Val Asn Gly Thr Cys Tyr Pro Gly Asn
            100                 105                 110

Val Glu Asn Leu Glu Glu Leu Arg Thr Leu Phe Ser Ser Ala Ser Ser
        115                 120                 125

Tyr Gln Arg Ile Gln Ile Phe Pro Asp Thr Thr Trp Asn Val Thr Tyr
    130                 135                 140

Thr Gly Thr Ser Arg Ala Cys Ser Gly Ser Phe Tyr Arg Ser Met Arg
145                 150                 155                 160

Trp Leu Thr Gln Lys Ser Gly Phe Tyr Pro Val Gln Asp Ala Gln Tyr
                165                 170                 175

Thr Asn Asn Arg Gly Lys Ser Ile Leu Phe Val Trp Gly Ile His His
            180                 185                 190

Pro Pro Thr Tyr Thr Glu Gln Thr Asn Leu Tyr Ile Arg Asn Asp Thr
        195                 200                 205

Thr Thr Ser Val Thr Thr Glu Asp Leu Asn Arg Thr Phe Lys Pro Val
    210                 215                 220

Ile Gly Pro Arg Pro Leu Val Asn Gly Leu Gln Gly Arg Ile Asp Tyr
225                 230                 235                 240

Tyr Trp Ser Val Leu Lys Pro Gly Gln Thr Leu Arg Val Arg Ser Asn
                245                 250                 255

Gly Asn Leu Ile Ala Pro Trp Tyr Gly His Val Leu Ser Gly Gly Ser
            260                 265                 270

His Gly Arg Ile Leu Lys Thr Asp Leu Lys Gly Gly Asn Cys Val Val
        275                 280                 285

Gln Cys Gln Thr Glu Lys Gly Gly Leu Asn Ser Thr Leu Pro Phe His
    290                 295                 300

Asn Ile Ser Lys Tyr Ala Phe Gly Thr Cys Pro Lys Tyr Val Arg Val
305                 310                 315                 320

Asn Ser Leu Lys Leu Ala Val Gly Leu Arg Asn Val Pro Ala Arg Ser
                325                 330                 335

Ser Arg Gly Leu Phe Gly Ala Ile Ala Gly Phe Ile Glu Gly Gly Trp
```

```
                     340                 345                 350
Pro Gly Leu Val Ala Gly Trp Tyr Gly Phe Gln His Ser Asn Asp Gln
                355                 360                 365
Gly Val Gly Met Ala Ala Asp Arg Asp Ser Thr Gln Lys Ala Ile Asp
            370                 375                 380
Lys Ile Thr Ser Lys Val Asn Asn Ile Val Asp Lys Met Asn Lys Gln
385                 390                 395                 400
Tyr Glu Ile Ile Asp His Glu Phe Ser Glu Val Glu Thr Arg Leu Asn
                405                 410                 415
Met Ile Asn Asn Lys Ile Asp Asp Gln Ile Gln Asp Val Trp Ala Tyr
                420                 425                 430
Asn Ala Glu Leu Leu Val Leu Leu Glu Asn Gln Lys Thr Leu Asp Glu
                435                 440                 445
His Asp Ala Asn Val Asn Asn Leu Tyr Asn Lys Val Lys Arg Ala Leu
            450                 455                 460
Gly Ser Asn Ala Met Glu Asp Gly Lys Gly Cys Phe Glu Leu Tyr His
465                 470                 475                 480
Lys Cys Asp Asp Gln Cys Met Glu Thr Ile Arg Asn Gly Thr Tyr Asn
                485                 490                 495
Arg Arg Lys Tyr Arg Glu Glu Ser Arg Leu Glu Arg Gln Lys Ile Glu
                500                 505                 510
Gly Val Lys Leu Glu Ser Glu Gly Thr Tyr Lys Ile Leu Thr Ile Tyr
                515                 520                 525
Ser Thr Val Ala Ser Ser Leu Val Leu Ala Met Gly Phe Ala Ala Phe
            530                 535                 540
Leu Phe Trp Ala Met Ser Asn Gly Ser Cys Arg Cys Asn Ile Cys Ile
545                 550                 555                 560

<210> SEQ ID NO 60
<211> LENGTH: 3111
<212> TYPE: DNA
<213> ORGANISM: Artificial Sequence
<220> FEATURE:
<223> OTHER INFORMATION: Expression Cassette

<400> SEQUENCE: 60
agaggtaccc cgggctggta tatttatatg ttgtcaaata actcaaaaac cataaaagtt      60
taagttagca agtgtgtaca tttttacttg aacaaaaata ttcacctact actgttataa     120
atcattatta aacattagag taaagaaata tggatgataa gaacaagagt agtgatattt     180
tgacaacaat tttgttgcaa catttgagaa aattttgttg ttctctcttt tcattggtca     240
aaaacaatag agagagaaaa aggaagaggg agaataaaaa cataatgtga gtatgagaga     300
gaaagttgta caaagttgt accaaaatag ttgtacaaat atcattgagg aatttgacaa     360
aagctacaca aataagggtt aattgctgta aataaataag gatgacgcat tagagagatg     420
taccattaga gaattttttgg caagtcatta aaaagaaaga ataaattatt tttaaaatta    480
aaagttgagt catttgatta aacatgtgat tatttaatga attgatgaaa gagttggatt     540
aaagttgtat tagtaattag aatttggtgt caaatttaat ttgacatttg atcttttcct     600
atatattgcc ccatagagtc agttaactca tttttatatt tcatagatca aataagagaa     660
ataacggtat attaatccct ccaaaaaaaa aaaacggtat atttactaaa aaatctaagc     720
cacgtaggag gataacagga tccccgtagg aggataacat ccaatccaac caatcacaac     780
aatcctgatg agataaccca ctttaagccc acgcatctgt ggcacatcta cattatctaa     840
```

```
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggagaaaat agtgcttctt   1020
cttgcaatag tcagtcttgt taaaagtgat cagatttgca ttggttacca tgcaaacaat   1080
tcaacagagc aggttgacac aatcatggaa aagaacgtta ctgttacaca tgcccaagac   1140
atactggaaa agacacacaa cgggaagctc tgcgatctag atggagtgaa gcctctaatt   1200
ttaagagatt gtagtgtagc tggatggctc ctcgggaacc caatgtgtga cgaattcatc   1260
aatgtaccgg aatggtctta catagtggag aaggccaatc caaccaatga cctctgttac   1320
ccagggagtt caacgactat gaagaactga aaacacctat tgagcagaat aaaccatttt   1380
gagaaaattc aaatcatccc caaaagttct tggtccgatc atgaagcctc atcaggagtt   1440
agctcagcat gtccatacct gggaagtccc tcctttttta gaaatgtggt atggcttatc   1500
aaaaagaaca gtacataccc aacaataaag aaaagctaca ataataccaa ccaagaggat   1560
cttttggtac tgtggggaat tcaccatcct aatgatgcgg cagagcagac aaggctatat   1620
caaaacccaa ccacctatat ttccattggg acatcaacac taaaccagag attggtacca   1680
aaaatagcta ctagatccaa agtaaacggg caaagtggaa ggatggagtt cttctggaca   1740
atttttaaaac ctaatgatgc aatcaacttc gagagtaatg gaaatttcat tgctccagaa   1800
tatgcataca aaattgtcaa gaaggggac tcagcaatta tgaaaagtga attggaatat   1860
ggtaactgca acaccaagtg tcaaactcca atgggggcga taaactctag tatgccattc   1920
cacaacatac accctctcac catcggggaa tgccccaaat atgtgaaatc aaacagatta   1980
gtccttgcaa cagggctcag aaatagccct caaagagaga gcagaagaaa aagagagga   2040
ctatttggag ctatagcagg ttttatagag ggaggatggc agggaatggt agatggttgg   2100
tatgggtacc accatagcaa tgagcagggg agtgggtacg ctgcagacaa agaatccact   2160
caaaaggcaa tagatggagt caccaataag gtcaactcaa tcattgacaa aatgaacact   2220
cagtttgagg ccgttggaag ggaatttaat aacttagaaa ggagaataga gaatttaaac   2280
aagaagatgg aagacgggtt tctagatgtc tggacttata tgccgaact tctggttctc   2340
atggaaaatg agagaactct agactttcat gactcaaatg ttaagaacct ctacgacaag   2400
gtccgactac agcttaggga taatgcaaag gagctgggta acggttgttt cgagttctat   2460
cacaaatgtg ataatgaatg tatggaaagt ataagaaacg gaacgtacaa ctatccgcag   2520
tattcagaag aagcaagatt aaaaagagag gaaataagtg gggtaaaatt ggaatcaata   2580
ggaacttacc aaatactgtc aatttattca acagtggcga gttccctagc actggcaatc   2640
atgatggctg gtctatcttt atggatgtgc tccaatggat cgttacaatg cagaatttgc   2700
atttaagagc tctaagttaa aatgcttctt cgtctcctat ttataatatg gtttgttatt   2760
gttaattttg ttcttgtaga agagcttaat taatcgttgt tgttatgaaa tactatttgt   2820
atgagatgaa ctggtgtaat gtaattcatt tacataagtg gagtcagaat cagaatgttt   2880
cctccataac taactagaca tgaagacctg ccgcgtacaa ttgtcttata tttgaacaac   2940
taaaattgaa catcttttgc cacaacttta taagtggtta atatagctca aatatatggt   3000
caagttcaat agattaataa tggaaatatc agttatcgaa attcattaac aatcaactta   3060
acgttattaa ctactaattt tatatcatcc cctttgataa atgatagtac a            3111
```

<210> SEQ ID NO 61
<211> LENGTH: 3123

<212> TYPE: DNA
<213> ORGANISM: Artificial Sequence
<220> FEATURE:
<223> OTHER INFORMATION: Expression Cassette

<400> SEQUENCE: 61

```
agaggtaccc cgggctggta tatttatatg ttgtcaaata actcaaaaac cataaaagtt      60
taagttagca agtgtgtaca tttttacttg aacaaaaata ttcacctact actgttataa     120
atcattatta aacattagag taaagaaata tggatgataa gaacaagagt agtgatattt     180
tgacaacaat tttgttgcaa catttgagaa aattttgttg ttctctcttt tcattggtca     240
aaaacaatag agagagaaaa aggaagaggg agaataaaaa cataatgtga gtatgagaga     300
gaaagttgta caaaagttgt accaaaatag ttgtacaaat atcattgagg aatttgacaa     360
aagctacaca aataagggtt aattgctgta aataaataag gatgacgcat tagagagatg     420
taccattaga gaattttttgg caagtcatta aaaagaaaga ataaattatt tttaaaatta     480
aaagttgagt catttgatta aacatgtgat tatttaatga attgatgaaa gagttggatt     540
aaagttgtat tagtaattag aatttggtgt caaatttaat ttgacatttg atcttttcct     600
atatattgcc ccatagagtc agttaactca tttttatatt tcatagatca aataagagaa     660
ataacggtat attaatccct ccaaaaaaaa aaaacggtat atttactaaa aaatctaagc     720
cacgtaggag gataacagga tccccgtagg aggataacat ccaatccaac caatcacaac     780
aatcctgatg agataaccca cttttaagccc acgcatctgt ggcacatcta cattatctaa     840
atcacacatt cttccacaca tctgagccac acaaaaacca atccacatct ttatcaccca     900
ttctataaaa aatcacactt tgtgagtcta cactttgatt cccttcaaac acatacaaag     960
agaagagact aattaattaa ttaatcatct tgagagaaaa tggcgaaaaa cgttgcgatt    1020
ttcggcttat tgtttttctct tcttgtgttg gttccttctc agatcttcgc tgacacaata    1080
tgtataggct accatgccaa caactcaacc gacactgttg acacagtact tgagaagaat    1140
gtgacagtga cacactctgt caacctactt gaggacagtc acaatggaaa actatgtcta    1200
ctaaaaggaa tagccccact acaattgggt aattgcagcg ttgccggatg gatcttagga    1260
aacccagaat gcgaattact gatttccaag gaatcatggt cctacattgt agaaacacca    1320
aatcctgaga atggaacatg ttacccaggg tatttcgccg actatgagga actgagggag    1380
caattgagtt cagtatcttc atttgagaga ttcgaaatat tccccaaaga aagctcatgg    1440
cccaaccaca ccgtaaccgg agtatcagca tcatgctccc ataatgggaa aagcagtttt    1500
tacagaaatt tgctatggct gacggggaag aatggtttgt acccaaacct gagcaagtcc    1560
tatgtaaaca acaaagagaa agaagtcctt gtactatggg gtgttcatca cccgcctaac    1620
atagggaacc aaagggcact ctatcataca gaaaatgctt atgtctctgt agtgtcttca    1680
cattatagca gaagattcac cccagaaata gccaaaagac ccaaagtaag agatcaggaa    1740
ggaagaatca actactactg gactctgctg gaacctgggg atacaataat atttgaggca    1800
aatggaaatc taatagcgcc atggtatgct tttgcactga gtagaggctt tggatcagga    1860
atcatcacct caaatgcacc aatggatgaa tgtgatgcga agtgtcaaac acctcaggga    1920
gctataaaca gcagtcttcc tttccagaat gtacacccag tcacaatagg agagtgtcca    1980
aagtatgtca ggagtgcaaa attaaggatg gttacaggac taaggaacat cccatccatt    2040
caatccagag gtttgtttgg agccattgcc ggtttcattg aagggggtg gactggaatg    2100
gtagatgggt ggtatggtta tcatcatcag aatgagcaag gatctggcta tgctgcagat    2160
```

```
caaaaaagta cacaaaatgc cattaacggg attacaaaca aggtcaattc tgtaattgag   2220
aaaatgaaca ctcaattcac agctgtgggc aaagagttca acaaattgga agaaggatg    2280 gaaaacttaa ataaaaaagt tgatgatggg tttctagaca tttggacata taatgcagaa   2340
ttgttggttc tactgaaaaa tgaaaggact ttggatttcc atgactccaa tgtgaagaat   2400
ctgtatgaga agtaaaaag ccaattaaag aataatgcca agaaatagg aaacgggtgt     2460 tttgagttct atcacaagtg taacaatgaa tgcatggaga gtgtgaaaaa tggtacctat   2520
gactatccaa atattccga agaatcaaag ttaaacaggg agaaaattga tggagtgaaa   2580
ttggaatcaa tgggagtata ccagattctg gcgatctact caactgtcgc cagttccctg   2640
gttcttttgg tctccctggg ggcaatcagc ttctggatgt gttccaatgg gtctttgcag   2700
tgtagaatat gcatctaaga gctctaagtt aaaatgcttc ttcgtctcct atttataata   2760
tggtttgtta ttgttaattt tgttcttgta gaagagctta attaatcgtt gttgttatga   2820
aatactattt gtatgagatg aactggtgta atgtaattca tttacataag tggagtcaga   2880
atcagaatgt ttcctccata actaactaga catgaagacc tgccgcgtac aattgtctta   2940
tatttgaaca actaaaattg aacatctttt gccacaactt tataagtggt taatatagct   3000
caaatatatg gtcaagttca atagattaat aatgaaata tcagttatcg aaattcatta    3060
acaatcaact taacgttatt aactactaat tttatatcat cccctttgat aaatgatagt   3120
aca                                                                 3123
```

<210> SEQ ID NO 62
<211> LENGTH: 3088
<212> TYPE: DNA
<213> ORGANISM: Artificial Sequence
<220> FEATURE:
<223> OTHER INFORMATION: Expression Cassette

<400> SEQUENCE: 62

```
ctggtatatt tatatgttgt caaataactc aaaaaccata aaagtttaag ttagcaagtg     60
tgtacatttt tacttgaaca aaaatattca cctactactg ttataaatca ttattaaaca    120
ttagagtaaa gaaatatgga tgataagaac aagagtagtg atattttgac aacaattttg    180
ttgcaacatt tgagaaaatt ttgttgttct ctcttttcat tggtcaaaaa caatagagag    240
agaaaaagga agaggagaa taaaaacata atgtgagtat gagagagaaa gttgtacaaa    300
agttgtacca aaatagttgt acaaatatca ttgaggaatt tgacaaaagc tacacaaata    360
agggttaatt gctgtaaata ataaggatg acgcattaga gagatgtacc attagagaat    420
ttttggcaag tcattaaaaa gaaagaataa attattttta aaattaaaag ttgagtcatt   480
tgattaaaca tgtgattatt taatgaattg atgaaagagt tggattaaag ttgtattagt    540
aattagaatt tggtgtcaaa tttaattgga catttgatct tttcctatat attgccccat   600
agagtcagtt aactcatttt tatatttcat agatcaaata agagaaataa cggtatatta   660
atccctccaa aaaaaaaaa cggtatattt actaaaaaat ctaagccacg taggaggata   720
acaggatccc cgtaggagga taacatccaa tccaaccaat cacaacaatc ctgatgagat   780
aacccacttt aagcccacgc atctgtggca catctacatt atctaaatca cacattcttc   840
cacacatctg agccacacaa aaaccaatcc acatctttat cacccattct ataaaaaatc   900
acactttgtg agtctacact ttgattccct tcaaacacat acaaagagaa gagactaatt   960
aattaattaa tcatcttgag agaaaatgaa agtaaaacta ctggtcctgt tatgcacatt  1020
tacagctaca tatgcagaca caatatgtat aggctaccat gctaacaact cgaccgacac  1080
```

| | | |
|---|---|---|
| tgttgacaca gtacttgaaa agaatgtgac agtgacacac tctgtcaacc tgcttgagaa | 1140 |
| cagtcacaat ggaaaactat gtctattaaa aggaatagcc ccactacaat gggtaattg | 1200 |
| cagcgttgcc gggtggatct taggaaaccc agaatgcgaa ttactgattt ccaaggagtc | 1260 |
| atggtcctac attgtagaaa aaccaaatcc tgagaatgga acatgttacc cagggcattt | 1320 |
| cgctgactat gaggaactga gggagcaatt gagttcagta tcttcatttg agaggttcga | 1380 |
| aatattcccc aaagaaagct catggcccaa ccacaccgta accggagtgt cagcatcatg | 1440 |
| ctcccataat ggggaaagca gtttttacag aaatttgcta tggctgacgg ggaagaatgg | 1500 |
| tttgtaccca aacctgagca agtcctatgc aaacaacaaa gaaaaagaag tccttgtact | 1560 |
| atggggtgtt catcacccgc caaacatagg tgaccaaaag gccctctatc atacagaaaa | 1620 |
| tgcttatgtc tctgtagtgt cttcacatta tagcagaaaa ttcacccag aaatagccaa | 1680 |
| aagacccaaa gtaagagatc aagaaggaag aatcaattac tactggactc tgcttgaacc | 1740 |
| cggggataca ataatatttg aggcaaatgg aaatctaata gcgccaagat atgctttcgc | 1800 |
| actgagtaga ggctttggat caggaatcat caactcaaat gcaccaatgg ataaatgtga | 1860 |
| tgcgaagtgc caaacacctc agggagctat aaacagcagt cttcctttcc agaacgtaca | 1920 |
| cccagtcaca ataggagagt gtccaaagta tgtcaggagt gcaaaattaa ggatggttac | 1980 |
| aggactaagg aacatcccat ccattcaatc cagaggtttg tttggagcca ttgccggttt | 2040 |
| cattgaaggg gggtggactg gaatggtaga tggttggtat ggttatcatc atcagaatga | 2100 |
| gcaaggatct ggctatgctg cagatcaaaa aagcacacaa aatgccatta atgggattac | 2160 |
| aaacaaggtc aattctgtaa ttgagaaaat gaacactcaa ttcacagcag tgggcaaaga | 2220 |
| gttcaacaaa ttggaaagaa ggatggaaaa cttgaataaa aaagttgatg atgggtttat | 2280 |
| agacatttgg acatataatg cagaactgtt ggttctactg gaaaatgaaa ggactttgga | 2340 |
| tttccatgac tccaatgtga agaatctgta tgagaaagta aaaagccagt taaagaataa | 2400 |
| tgctaaagaa ataggaaatg ggtgttttga gttctatcac aagtgtaacg atgaatgcat | 2460 |
| ggagagtgta aagaatggaa cttatgacta tccaaaatat tccgaagaat caaagttaaa | 2520 |
| cagggagaaa attgatggag tgaaattgga atcaatggga gtctatcaga ttctggcgat | 2580 |
| ctactcaaca gtcgccagtt ctctggttct tttggtctcc ctgggggcaa tcagcttctg | 2640 |
| gatgtgttcc aatgggtctt tacagtgtag aatatgcatc taagagctct aagttaaaat | 2700 |
| gcttcttcgt ctcctattta taatatggtt tgttattgtt aattttgttc ttgtagaaga | 2760 |
| gcttaattaa tcgttgttgt tatgaaatac tatttgtatg agatgaactg gtgtaatgta | 2820 |
| attcatttac ataagtggag tcagaatcag aatgtttcct ccataactaa ctagacatga | 2880 |
| agacctgccg cgtacaattg tcttatattt gaacaactaa aattgaacat cttttgccac | 2940 |
| aactttataa gtggttaata tagctcaaat atatggtcaa gttcaataga ttaataatgg | 3000 |
| aaatatcagt tatcgaaatt cattaacaat caacttaacg ttattaacta ctaattttat | 3060 |
| atcatcccct ttgataaatg atagtaca | 3088 |

<210> SEQ ID NO 63
<211> LENGTH: 3102
<212> TYPE: DNA
<213> ORGANISM: Artificial Sequence
<220> FEATURE:
<223> OTHER INFORMATION: Expression Cassette

<400> SEQUENCE: 63

```
agaggtaccc cgggctggta tatttatatg ttgtcaaata actcaaaaac cataaaagtt      60
taagttagca agtgtgtaca tttttacttg aacaaaaata ttcacctact actgttataa     120
atcattatta aacattagag taaagaaata tggatgataa gaacaagagt agtgatattt     180
tgacaacaat tttgttgcaa catttgagaa aattttgttg ttctctcttt tcattggtca     240
aaaacaatag agagagaaaa aggaagaggg agaataaaaa cataatgtga gtatgagaga     300
gaaagttgta caaagttgt accaaaatag ttgtacaaat atcattgagg aatttgacaa      360
aagctacaca aataagggtt aattgctgta aataaataag gatgacgcat tagagagatg     420
taccattaga gaattttttgg caagtcatta aaaagaaaga ataaattatt tttaaaatta    480
aaagttgagt catttgatta aacatgtgat tatttaatga attgatgaaa gagttggatt     540
aaagttgtat tagtaattag aatttggtgt caaatttaat ttgacatttg atcttttcct    600
atatattgcc ccatagagtc agttaactca ttttttatatt tcatagatca aataagagaa    660
ataacggtat attaatccct ccaaaaaaaa aaaacggtat atttactaaa aaatctaagc     720
cacgtaggag gataacagga tccccgtagg aggataaact ccaatccaac caatcacaac    780
aatcctgatg agataaccca cttttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tgaaagtaaa actactggtc    1020
ctgttatgca catttacagc tacatatgca gacacaatat gtataggcta ccatgccaac    1080
aactcaaccg acactgttga cacagtactt gagaagaatg tgacagtgac acactctgtc    1140
aacctgcttg aggacagtca caatggaaaa ttatgtctat taaaaggaat agccccacta    1200
caattgggta attgcagcgt tgccggatgg atcttaggaa acccagaatg cgaattactg    1260
atttccaggg aatcatggtc ctacattgta gaaaaaccaa atcctgagaa tggaacatgt    1320
tacccagggc atttcgccga ctatgaggaa ctggggagc aattgagttc agtatcttca    1380
tttgagagat tcgaaatatt ccccaaagaa agctcatggc ccaaccacac cacaaccgga    1440
gtatcagcat catgctccca taatgggaa agcagttttt acaaaaattt gctatggctg    1500
acggggaaga atggtttgta cccaaacctg agcaagtcct atgcaaacaa caaagagaaa    1560
gaagtccttg tactatgggg tgttcatcac ccgcctaaca taggtgacca aagggctctc    1620
tatcataaag aaaatgctta tgtctctgta gtgtcttcac attatagcag aaaattcacc    1680
ccagaaatag ccaaaagacc caaagtaaga gatcaagaag gaagaatcaa ctactactgg    1740
actctacttg aacccgggga tacaataata tttgaggcaa atggaaatct aatagcgcca    1800
agatatgctt tcgcactgag tagaggcttt ggatcaggaa tcatcaactc aaatgcacca    1860
atggatgaat gtgatgcgaa gtgccaaaca cctcagggag ctataaacag cagtcttcct    1920
ttccagaatg tacaccctgt cacaatagga gagtgtccaa agtatgtcag gagtgcaaaa    1980
ttaaggatgg ttacaggact aaggaacatc ccatccattc aatccagagg tttgtttgga    2040
gccattgccg gtttcattga aggggggtgg actggaatgg tagatggttg gtatggttat    2100
catcatcaga atgagcaagg atctggctat gctgcagatc aaaaaagcac acaaaatgcc    2160
attaatggga ttacaaacaa ggtcaattct gtaattgaga aatgaacac tcaattcaca    2220 gctgtgggca aagagttcaa caaattggaa agaaggatgg aaaacttaaa taaaaaagtt    2280
gatgatgggt ttatagacat ttggacatat aatgcagaat tgttggttct actgaaaaat    2340
gaaaggactt tggatttcca tgactccaat gtgaagaatc tgtatgagaa agtaaaaagc    2400
```

```
caattaaaga ataatgccaa agaaatagga aatgggtgtt ttgagttcta tcataagtgt    2460
aacgatgaat gcatggagag tgtaaaaaat ggaacttatg actatccaaa atattccgaa    2520
gaatcaaagt taaacaggga gaaaattgat ggagtgaaat tggaatcaat gggagtctat    2580
cagattctgg cgatctactc aacagtcgcc agttctctgg ttcttttggt ctccctgggg    2640
gcaatcagct tctggatgtg ttccaatggg tctttgcagt gtagaatatg catctgagag    2700
ctctaagtta aaatgcttct tcgtctccta tttataatat ggtttgttat tgttaatttt    2760
gttcttgtag aagagcttaa ttaatcgttg ttgttatgaa atactatttg tatgagatga    2820
actggtgtaa tgtaattcat ttacataagt ggagtcagaa tcagaatgtt tcctccataa    2880
ctaactagac atgaagacct gccgcgtaca attgtcttat atttgaacaa ctaaaattga    2940
acatcttttg ccacaacttt ataagtggtt aatatagctc aaatatatgg tcaagttcaa    3000
tagattaata atggaaatat cagttatcga aattcattaa caatcaactt aacgttatta    3060
actactaatt ttatatcatc ccctttgata aatgatagta ca                      3102

<210> SEQ ID NO 64
<211> LENGTH: 3093
<212> TYPE: DNA
<213> ORGANISM: Artificial Sequence
<220> FEATURE:
<223> OTHER INFORMATION: Expression Cassette

<400> SEQUENCE: 64
agaggtaccc cgggctggta tatttatatg ttgtcaaata actcaaaaac cataaaagtt      60
taagttagca agtgtgtaca tttttacttg aacaaaaata ttcacctact actgttataa     120
atcattatta aacattagag taaagaaata tggatgataa gaacaagagt agtgatattt     180
tgacaacaat tttgttgcaa catttgagaa aattttgttg ttctctcttt tcattggtca     240
aaaacaatag agagagaaaa aggaagaggg agaataaaaa cataatgtga gtatgagaga     300
gaaagttgta caaaagttgt accaaaatag ttgtacaaat atcattgagg aatttgacaa     360 aagctcacaca aataagggtt aattgctgta aataaataag gatgacgcat tagagagatg    420
taccattaga gaattttttgg caagtcatta aaaagaaaga ataaattatt tttaaaatta    480
aaagttgagt catttgatta aacatgtgat tatttaatga attgatgaaa gagttggatt     540
aaagttgtat tagtaattag aatttggtgt caaatttaat ttgacatttg atctttttcct    600 atatattgcc ccatagagtc agttaactca ttttttatatt tcatagatca aataagagaa    660
ataacggtat attaatccct ccaaaaaaaa aaaacgtgat atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggccatcat ttatctaatt    1020
ctcctgttca cagcagtgag aggggaccaa atatgcattg gataccatgc caataattcc    1080
acagagaagg tcgacacaat tctagagcgg aacgtcactg tgactcatgc caaggacatt    1140
cttgagaaga cccataacgg aaagttatgc aaactaaacg gaatccctcc acttgaacta    1200
ggggactgta gcattgccgg atggctcctt ggaaatccag aatgtgatag cttctaagt    1260 gtgccagaat ggtcctatat aatggagaaa gaaaacccga gagacggttt tgtgttatcca   1320
```

```
ggcagcttca atgattatga agaattgaaa catctcctca gcagcgtgaa acatttcgag   1380
aaagtaaaga ttctgcccaa agatagatgg acacagcata caacaactgg aggttcacgg   1440
gcctgcgcgg tgtctggtaa tccatcattc ttcaggaaca tggtctggct gacaaagaaa   1500
gaatcaaatt atccggttgc caaggatcg tacaacaata caagcggaga acaaatgcta   1560
ataatttggg gggtgcacca tcccaatgat gagacagaac aaagaacatt gtaccagaat   1620
gtgggaacct atgtttccgt aggcacatca acattgaaca aaggtcaac cccagacata   1680 gcaacaaggc ctaaagtgaa tggactagga agtagaatgg agttctcttg gacccctattg   1740 gatatgtggg acaccataaa ttttgagagt actggtaatc taattgcacc agagtatgga   1800
ttcaaaatat cgaaaagagg tagttcaggg atcatgaaaa cagaaggaac acttgagaac   1860
tgtgagacca atgccaaac tcctttggga gcaataaata caacattgcc ttttcacaat   1920
gtccacccac tgacaatagg tgagtgcccc aaatatgtaa aatcggagaa gttggtctta   1980
gcaacaggac taaggaatgt tccccagatt gaatcaagag gattgtttgg ggcaatagct   2040
ggttttatag aaggaggatg gcaaggaatg gttgatggtt ggtatggata ccatcacagc   2100
aatgaccagg gatcagggta tgcagcagac aaagaatcca ctcaaaaggc atttgatgga   2160
atcaccaaca aggtaaattc tgtgattgaa aagatgaaca cccatttga gctgttggg    2220 aaagagttca gtaacttaga gagaagactg gagaacttga acaaaagat ggaagacggg   2280 tttctagatg tgtggacata caatgctgag cttctagttc tgatgaaaaa tgagaggaca   2340
cttgactttc atgattctaa tgtcaagaat ctgtatgata agtcagaat gcagctgaga   2400 gacaacgtca aagaactagg aaatggatgt tttgaatttt atcacaaatg tgatgatgaa   2460
tgcatgaata gtgtgaaaaa cgggacgtat gattatccca gtatgaaga agagtctaaa   2520 ctaaatagaa atgaaatcaa aggggtaaaa ttgagcagca tggggggttta tcaaatcctt   2580 gccatttatg ctacagtagc aggttctctg tcactggcaa tcatgatggc tgggatctct   2640
ttctggatgt gctccaacgg gtctctgcag tgcaggatct gcatatgaga gctctaagtt   2700
aaaatgcttc ttcgtctcct atttataata tggtttgtta ttgttaattt tgttcttgta   2760
gaagagctta ttaatcgtt gttgttatga aatactattt gtatgagatg aactggtgta   2820
atgtaattca tttacataag tggagtcaga atcagaatgt ttcctccata actaactaga   2880
catgaagacc tgccgcgtac aattgtctta tatttgaaca actaaaattg aacatctttt   2940
gccacaactt tataagtggt taatatagct caaatatatg gtcaagttca atagattaat   3000
aatggaaata tcagttatcg aaattcatta acaatcaact taacgttatt aactactaat   3060
tttatatcat cccctttgat aaatgatagt aca                                3093
```

<210> SEQ ID NO 65
<211> LENGTH: 3108
<212> TYPE: DNA
<213> ORGANISM: Artificial Sequence
<220> FEATURE:
<223> OTHER INFORMATION: Expression Cassette
<400> SEQUENCE: 65

```
agaggtaccc cgggctggta tatttatatg ttgtcaaata actcaaaaac cataaaagtt     60
taagttagca agtgtgtaca tttttacttg aacaaaaata ttcacctact actgttataa    120
atcattatta aacattagag taaagaaata tggatgataa gaacaagagt agtgatattt    180
tgacaacaat tttgttgcaa catttgagaa aatttgttg ttctctcttt tcattggtca     240 aaacaatag agagagaaaa aggaagaggg agaataaaaa cataatgtga gtatgagaga    300
```

```
gaaagttgta caaaagttgt accaaaatag ttgtacaaat atcattgagg aatttgacaa    360
aagctacaca aataagggtt aattgctgta aataaataag gatgacgcat tagagagatg    420
taccattaga gaattttgg caagtcatta aaaagaaaga ataaattatt tttaaaatta     480
aaagttgagt catttgatta aacatgtgat tatttaatga attgatgaaa gagttggatt    540
aaagttgtat tagtaattag aatttggtgt caaatttaat ttgacatttg atcttttcct    600
atatattgcc ccatagagtc agttaactca tttttatatt tcatagatca aataagagaa    660
ataacggtat attaatccct ccaaaaaaaa aaacggtat atttactaaa aaatctaagc     720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggagaaaat agtgcttctt   1020
cttgcaatag tcagccttgt taaaagtgat cagatttgca ttggttacca tgcaaacaac   1080
tcgacagagc aggttgacac aataatggaa aagaacgtta ctgttacaca tgcccaagac   1140
atactggaaa agacacacaa cgggaagctc tgcgatctag atggagtgaa gcctctgatt   1200
ttaagagatt gtagtgtagc tggatggctc ctcggaaacc caatgtgtga cgagttcatc   1260
aatgtgccgg aatggtctta catagtggag aaggccaacc cagccaatga cctctgttac   1320
ccagggaatt tcaacgacta tgaagaactg aaacacctat tgagcagaat aaaccatttt   1380
gagaaaattc agatcatccc caaaagttct tggtccgatc atgaagcctc tcagggtc     1440
agctcagcat gtccatacca gggaacgccc tccttttca gaaatgtggt atggcttatc    1500
aaaagaaca atacataccc aacaataaag agaagctaca ataataccaa ccaggaagat   1560
cttttgatac tgtgggggat tcatcattct aatgatgcgg cagagcagac aaagctctat   1620
caaaacccaa ccacctatat ttccgttggg acatcaacac taaaccagag attggtacca   1680
aaaatagcta ctagatccaa agtaaacggg caaagtggaa ggatggattt cttctggaca   1740
attttaaaac cgaatgatgc aatcaacttc gagagtaatg gaaatttcat tgctccagaa   1800
tatgcataca aaattgtcaa gaaggggac tcagcaattg ttaaaagtga agtggaatat    1860
ggtaactgca atacaaagtg tcaaactcca ataggggcga taaactctag tatgccattc   1920
cacaacatac accctctcac catcggggaa tgccccaaat atgtgaaatc aaacaaatta   1980
gtccttgcga ctgggctcag aaatagtcct ctaagagaaa aagaagaaa aagaggacta   2040
tttggagcta tagcagggtt tatagaggga ggatggcagg gaatggtaga tggttggtat   2100
gggtaccacc atagcaatga gcaggggagt gggtacgctg cagacaaaga atccactcaa   2160
aaggcaatag atggagtcac caataaggtc aactcgatca ttgacaaaat gaacactcag   2220
tttgaggccg ttggaaggga atttaataac ttagaaagga atagagaa tttaaacaag    2280
aaaatggaag acggattcct agatgtctgg acttataatg ctgaacttct ggttctcatg   2340
gaaaatgaga gaactctaga cttccatgat tcaaatgtca agaaccttta cgacaaggtc   2400
cgactacagc ttagggataa tgcaaggag ctgggtaacg gttgtttcga gttctatcac   2460
aaatgtgata atgaatgtat ggaaagtgta agaaacggaa cgtatgacta cccgcagtat   2520
tcagaagaag caagattaaa aagagaggaa ataagtggga taaaattgga atcaatagga   2580
acttaccaaa tactgtcaat ttattcaaca gttgcgagtt ctctagcact ggcaatcatg   2640
```

```
gtggctggtc tatctttgtg gatgtgctcc aatgggtcgt tacaatgcag aatttgcatt    2700
taagagctct aagttaaaat gcttcttcgt ctcctattta taatatggtt tgttattgtt    2760
aattttgttc ttgtagaaga gcttaattaa tcgttgttgt tatgaaatac tatttgtatg    2820
agatgaactg gtgtaatgta attcatttac ataagtggag tcagaatcag aatgtttcct    2880
ccataactaa ctagacatga agacctgccg cgtacaattg tcttatattt gaacaactaa    2940
aattgaacat cttttgccac aactttataa gtggttaata tagctcaaat atatggtcaa    3000
gttcaataga ttaataatgg aaatatcagt tatcgaaatt cattaacaat caacttaacg    3060
ttattaacta ctaattttat atcatcccct ttgataaatg atagtaca                 3108

<210> SEQ ID NO 66
<211> LENGTH: 3111
<212> TYPE: DNA
<213> ORGANISM: Artificial Sequence
<220> FEATURE:
<223> OTHER INFORMATION: Expression Cassette

<400> SEQUENCE: 66
agaggtaccc cgggctggta tatttatatg ttgtcaaata actcaaaaac cataaaagtt      60
taagttagca agtgtgtaca tttttacttg aacaaaaata ttcacctact actgttataa     120
atcattatta aacattagag taaagaaata tggatgataa gaacaagagt agtgatattt     180
tgacaacaat tttgttgcaa catttgagaa aatttttgttg ttctctcttt tcattggtca    240
aaaacaatag agagagaaaa aggaagaggg agaataaaaa cataatgtga gtatgagaga     300
gaaagttgta caaagttgt accaaaatag ttgtacaaat atcattgagg aatttgacaa      360
aagctacaca aataagggtt aattgctgta aataaataag gatgacgcat tagagagatg     420
taccattaga gaatttttgg caagtcatta aaaagaaaga ataaattatt tttaaaatta    480
aaagttgagt catttgatta aacatgtgat tatttaatga attgatgaaa gagttggatt     540
aaagttgtat tagtaattag aatttggtgt caaatttaat ttgacatttg atctttttcct    600 atatattgcc ccatagagtc agttaactca ttttttatatt tcatagatca aataagagaa    660
ataacggtat attaatccct ccaaaaaaaa aaaacggtat atttactaaa aaatctaagc     720
cacgtaggag gataacagga tccccgtagg aggataacat ccaatccaac caatcacaac     780
aatcctgatg agataaccca cttttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tggagaaaat agtgcttctt    1020
tttgcaatag tcagtcttgt taaaagtgat cagatttgca ttggttacca tgcaaacaac    1080
tcgacagagc aggttgacac aataatggaa aagaacgtta ctgttacaca tgcccaagac    1140
atactggaaa agacacacaa tgggaagctc tgcgatctag atggagtgaa gcctctaatt    1200
ttgagagatt gtagtgtagc tggatggctc ctcggaaacc caatgtgtga cgagttcatc    1260
aatgtgccgg aatggtctta catagtggag aaggccaatc cagtcaatga cctctgttac    1320
ccagggattt caatgactac tgaagaattg aaacacctat tgagcagaat aaaccatttt    1380
gagaaaattc agatcatccc caaaagttct tggtccagtc atgaagcctc attggggtc    1440 agctcagcat gtccatacca gggaaagtcc tcctttttca gaaatgtggt atggcttatc    1500
aaaaagaaca gtacataccc aacaataaag aggagctaca ataataccaa ccaagaagat    1560
cttttggtac tgtgggggat tcaccatcct aatgatgcgg cagagcagac aaagctctat    1620
```

```
caaaacccaa ccacctatat ttccgttggg acatctacac taaaccagag attggtacca    1680
agaatagcta ctagatccaa agtaaacggg caaagtggaa ggatggagtt cttctggaca    1740
attttaaaac cgaatgatgc aatcaacttc gagagtaatg gaaatttcat tgctccagaa    1800
tatgcataca aaattgtcaa gaaggggac tcaacaatta tgaaaagtga attggaatat    1860
ggtaactgca ataccaagtg tcaaactcca atggggcga taaactctag catgccattc    1920
cacaatatac accctctcac catcggggaa tgccccaaat atgtgaaatc aaacagatta    1980
gtccttgcga ctgggctcag aaatagccct caaagagaga gaagaagaaa aagagagga    2040 ttatttggag ctatagcagg ttttatagag ggaggatggc agggaatggt agatggttgg    2100
tatgggtacc accatagcaa cgagcagggg agtgggtacg ctgcagacaa agaatccact    2160
caaaaggcaa tagatggagt caccaataag gtcaactcga ttattgacaa aatgaacact    2220
cagtttgagg ccgttggaag ggaatttaac aacttagaaa ggagaataga gaatttaaac    2280
aagaagatgg aagacgggtt cctagatgtc tggacttata atgctgaact tctagttctc    2340
atggaaaacg agagaactct agactttcat gactcaaatg tcaagaacct ttacgacaag    2400
gtccgactac agcttaggga taatgcaaag gagctgggta acggttgttt cgagttctat    2460
cataaatgtg ataatgaatg tatggaaagt gtaagaaacg gaacgtatga ctacccgcag    2520
tattcagaag aagcaagact aaaaagagag gaaataagtg gagtaaaatt ggaatcaata    2580
ggaatttacc aaatattgtc aatttattct acagtggcca gctccctagc actggcaatc    2640
atggtagctg gtctatcctt atggatgtgc tccaatgggt cgttacaatg cagaatttgc    2700
atttaagagc tctaagttaa aatgcttctt cgtctcctat ttataatatg gtttgttatt    2760
gttaattttg ttcttgtaga agagcttaat taatcgttgt tgttatgaaa actatttgt    2820 atgagatgaa ctggtgtaat gtaattcatt tacataagtg gagtcagaat cagaatgttt    2880
cctccataac taactagaca tgaagacctg ccgcgtacaa ttgtcttata tttgaacaac    2940
taaaattgaa catcttttgc cacaacttta taagtggtta atatagctca aatatatggt    3000
caagttcaat agattaataa tggaaatatc agttatcgaa attcattaac aatcaactta    3060
acgttattaa ctactaattt tatatcatcc cctttgataa atgatagtac a              3111
```

<210> SEQ ID NO 67
<211> LENGTH: 3105
<212> TYPE: DNA
<213> ORGANISM: Artificial Sequence
<220> FEATURE:
<223> OTHER INFORMATION: Expression Cassette

<400> SEQUENCE: 67

```
agaggtaccc cgggctggta tatttatatg ttgtcaaata actcaaaaac cataaaagtt      60
taagttagca agtgtgtaca tttttacttg aacaaaaata ttcacctact actgttataa     120
atcattatta aacattagag taaagaaata tggatgataa gaacaagagt agtgatattt     180
tgacaacaat tttgttgcaa catttgagaa aattttgttg ttctctcttt tcattggtca     240 aaacaatag agagagaaaa aggaagaggg agaataaaaa cataatgtga gtatgagaga     300
gaaagttgta caaagttgt accaaaatag ttgtacaaat atcattgagg aatttgacaa     360
aagctacaca aataagggtt aattgctgta aataaataag gatgacgcat tagagagatg     420
taccattaga gaattttttgg caagtcatta aaaagaaaga ataaattatt tttaaaatta     480
aaagttgagt catttgatta aacatgtgat tatttaatga attgatgaaa gagttggatt     540
```

```
aaagttgtat tagtaattag aatttggtgt caaatttaat ttgacatttg atctttcct      600
atatattgcc ccatagagtc agttaactca tttttatatt tcatagatca aataagagaa     660
ataacggtat attaatccct ccaaaaaaaa aaacggtat atttactaaa aaatctaagc      720
cacgtaggag gataacagga tccccgtagg aggataacat ccaatccaac caatcacaac     780
aatcctgatg agataaccca cttaagccc acgcatctgt ggcacatcta cattatctaa      840
atcacacatt cttccacaca tctgagccac acaaaaacca atccacatct ttatcaccca     900
ttctataaaa aatcacactt tgtgagtcta cactttgatt cccttcaaac acatacaaag    960
agaagagact aattaattaa ttaatcatct tgagagaaaa tgattgcaat cattgtaata   1020
gcaatactgg cagcagccgg aaagtcagac aagatctgca ttgggtatca tgccaacaat    1080
tcaacaacac aggtagatac gatacttgag aagaatgtga ctgtcacaca ctcaattgaa    1140
ttgctggaaa atcagaagga agaaagattc tgcaagatat tgaacaaggc ccctctcgac    1200
ttaagggaat gtaccataga gggttggatc ttggggaatc cccaatgcga cctattgctt    1260
ggtgatcaaa gctggtcata cattgtgaa  agacctactg ctcaaaacgg gatctgctac   1320
ccaggaacct taaatgaggt agaagaactg agggcactta ttggatcagg agaaagggta    1380
gagagatttg agatgtttcc ccaaagcacc tggcaaggag ttgacaccaa cagtggaaca    1440
acaagatcct gcccttattc tactggtgcg tctttctaca gaaacctcct atggataata   1500
aaaaccaaga cagcagaata tccagtaatt aagggaattt acaacaacac tggaacccag    1560
ccaatcctct atttctgggg tgtgcatcat cctcctaaca ccgacgagca agatactctg    1620
tatggctctg gtgatcgata cgttagaatg ggaactgaaa gcatgaattt tgccaagagt    1680
ccggaaattg cggcaaggcc tgctgtgaat ggacaaagag gcagaattga ttattattgg    1740
tcggttttaa aaccagggga aaccttgaat gtggaatcta atggaaatct aatcgcccct    1800
tggtatgcat acaaatttgt caacacaaat agtaaaggag ccgtcttcag gtcagattta    1860
ccaatcgaga actgcgatgc cacatgccag actattgcag gggttctaag gaccaataaa    1920
acatttcaga atgtgagtcc cctgtggata ggagaatgtc ccaaatacgt gaaaagtgaa    1980
agtctgaggc ttgcaactgg actaagaaat gttccacaga ttgaaactag aggactcttc    2040
ggagctattg cagggtttat tgaaggagga tggactggga tgatagatgg gtggtatggc    2100
tatcaccatg aaaattctca agggtcagga tatgcagcag acagagaaag cactcaaaag    2160
gctgtaaaca gaattacaaa taaggtcaat tccatcatca caaaatgaa  cacacaattt   2220
gaagctgtcg atcacgaatt tcaaatctg  gagaggagaa ttgacaatct gaacaaaaga    2280
atgcaagatg gatttctgga tgtttggaca tacaatgctg aactgttggt tcttcttgaa    2340
aacgaaagaa cactagacat gcatgacgca aatgtgaaga acctacatga aaaggtcaaa    2400
tcacaactaa gggacaatgc tacgatctta gggaatggtt gctttgaatt tggcataag    2460
tgtgacaatg aatgcataga gtctgtcaaa aatggtacat atgactatcc caaataccag   2520
actgaaagca aattaaacag gctaaaaata gaatcagtaa agctagagaa cctggtgtg    2580
tatcaaattc ttgccatta  tagtacggta tcgagcagcc tagtgttggt agggctgatc    2640
atggcaatgg gtctttggat gtgttcaaat ggttcaatgc agtgcaggat atgtatataa    2700
gagctctaag ttaaaatgct tcttcgtctc ctatttataa tatggtttgt tattgttaat    2760
tttgttcttg tagaagagct taattaatcg ttgttgttat gaaatactat ttgtatgaga    2820
tgaactggtg taatgtaatt catttacata agtggagtca gaatcagaat gtttcctcca    2880
taactaacta gacatgaaga cctgccgcgt acaattgtct tatatttgaa caactaaaat   2940
```

```
tgaacatctt ttgccacaac tttataagtg gttaatatag ctcaaatata tggtcaagtt    3000
caatagatta ataatggaaa tatcagttat cgaaattcat taacaatcaa cttaacgtta    3060
ttaactacta attttatatc atcccctttg ataaatgata gtaca                   3105

<210> SEQ ID NO 68
<211> LENGTH: 3087
<212> TYPE: DNA
<213> ORGANISM: Artificial Sequence
<220> FEATURE:
<223> OTHER INFORMATION: Expression Cassette

<400> SEQUENCE: 68
agaggtaccc cgggctggta tatttatatg ttgtcaaata actcaaaaac cataaaagtt      60
taagttagca agtgtgtaca tttttacttg aacaaaaata ttcacctact actgttataa     120
atcattatta aacattagag taaagaaata tggatgataa gaacaagagt agtgatattt     180
tgacaacaat tttgttgcaa catttgagaa aattttgttg ttctctcttt tcattggtca     240
aaaacaatag agagagaaaa aggaagaggg agaataaaaa cataatgtga gtatgagaga     300
gaaagttgta caaagttgt accaaaatag ttgtacaaat atcattgagg aatttgacaa     360
aagctacaca ataagggtt aattgctgta aataaataag gatgacgcat tagagagatg     420
taccattaga gaattttttgg caagtcatta aaaagaaaga ataaattatt tttaaaatta     480
aaagttgagt catttgatta aacatgtgat tatttaatga attgatgaaa gagttggatt     540
aaagttgtat tagtaattag aatttggtgt caaatttaat ttgacatttg atcttttcct     600
atatattgcc ccatagagtc agttaactca ttttttatatt tcatagatca aataagagaa     660
ataacggtat attaatccct ccaaaaaaaa aaacggtat atttactaaa aaatctaagc     720
cacgtaggag gataacagga tccccgtagg aggataacat ccaatccaac caatcacaac     780
aatcctgatg agataaccca ctttaagccc acgcatctgt ggcacatcta cattatctaa     840
atcacacatt cttccacaca tctgagccac acaaaaacca atccacatct ttatcaccca     900
ttctataaaa aatcacactt tgtgagtcta cactttgatt cccttcaaac acatacaaag     960
agaagagact aattaattaa ttaatcatct tgagagaaaa tggaaacaat atcactaata    1020
actatactac tagtagtaac agcaagcaat gcagataaaa tctgcatcgg ccaccagtca    1080
acaaactcca cagaaactgt ggacacgcta acagaaacca atgttcctgt gacacatgcc    1140
aaagaattgc tccacacaga gcataatgga atgctgtgtg caacaagcct gggacatccc    1200
ctcattctag acacatgcac tattgaagga ctagtctatg caaccccttc ttgtgacctg    1260
ctgttgggag aagagaatg gtcctacatc gtcgaaagat catcagctgt aaatggaacg    1320
tgttaccctg gaatgtaga aacctagag gaactcagga cacttttag ttccgctagt    1380 tcctaccaaa gaatccaaat cttcccagac acaacctgga atgtgactta cactggaaca    1440
agcagagcat gttcaggttc attctacagg agtatgagat ggctgactca aaagagcggt    1500
ttttaccctg ttcaagacgc ccaatacaca aataacaggg gaaagagcat tcttttcgtg    1560
tggggcatac atcacccacc cacctatacc gagcaaacaa atttgtacat aagaaacgac    1620
acaacaacaa gcgtgacaac agaagatttg aataggacct tcaaaccagt gataggccca    1680 aggcccccttg tcaatggtct gcagggaaga attgattatt attggtcggt actaaaacca    1740
ggccaaacat tgcgagtacg atccaatggg aatctaattg ctccatggta tggacacgtt    1800
cttttcagga ggagccatgg aagaatcctg aagactgatt taaaggtgg taattgtgta    1860
```

| | |
|---|---|
| gtgcaatgtc agactgaaaa aggtggctta aacagtacat tgccattcca caatatcagt | 1920 |
| aaatatgcat ttggaacctg ccccaaatat gtaagagtta atagtctcaa actggcagtc | 1980 |
| ggtctgagga acgtgcctgc tagatcaagt agaggactat ttggagccat agctggattc | 2040 |
| atagaaggag gttggccagg actagtcgct ggctggtatg gtttccagca ttcaaatgat | 2100 |
| caaggggttg gtatggctgc agatagggat tcaactcaaa aggcaattga taaaataaca | 2160 |
| tccaaggtga ataatatagt cgacaagatg aacaagcaat atgaaataat tgatcatgaa | 2220 |
| tttagtgagg ttgaaactag actcaatatg atcaataata agattgatga ccaaatacaa | 2280 |
| gacgtatggg catataatgc agaattgcta gtactacttg aaaatcaaaa aacactcgat | 2340 |
| gagcatgatg cgaacgtgaa caatctatat aacaaggtga gagggcact gggctccaat | 2400 |
| gctatggaag atgggaaagg ctgtttcgag ctataccata aatgtgatga tcagtgcatg | 2460 |
| gaaacaattc ggaacgggac ctataatagg agaaagtata gagaggaatc aagactagaa | 2520 |
| aggcagaaaa tagagggggt taagctggaa tctgagggaa cttacaaaat cctcaccatt | 2580 |
| tattcgactg tcgcctcatc tcttgtgctt gcaatggggt ttgctgcctt cctgttctgg | 2640 |
| gccatgtcca atggatcttg cagatgcaac atttgtatat aagagctcta agttaaaatg | 2700 |
| cttcttcgtc tcctatttat aatatggttt gttattgtta attttgttct tgtagaagag | 2760 |
| cttaattaat cgttgttgtt atgaaatact atttgtatga gatgaactgg tgtaatgtaa | 2820 |
| ttcatttaca taagtggagt cagaatcaga atgtttcctc cataactaac tagacatgaa | 2880 |
| gacctgccgc gtacaattgt cttatatttg aacaactaaa attgaacatc ttttgccaca | 2940 |
| actttataag tggttaatat agctcaaata tatggtcaag ttcaatagat taataatgga | 3000 |
| aatatcagtt atcgaaattc attaacaatc aacttaacgt tattaactac taattttata | 3060 |
| tcatccccctt tgataaatga tagtaca | 3087 |

<210> SEQ ID NO 69
<211> LENGTH: 3105
<212> TYPE: DNA
<213> ORGANISM: Artificial Sequence
<220> FEATURE:
<223> OTHER INFORMATION: Expression Cassette

<400> SEQUENCE: 69

| | |
|---|---|
| agaggtaccc cgggctggta tatttatatg ttgtcaaata actcaaaaac cataaaagtt | 60 |
| taagttagca agtgtgtaca tttttacttg aacaaaaata ttcacctact actgttataa | 120 |
| atcattatta aacattagag taaagaaata tggatgataa gaacaagagt agtgatattt | 180 |
| tgacaacaat tttgttgcaa catttgagaa aattttgttg ttctctcttt tcattggtca | 240 |
| aaaacaatag agagagaaaa aggaagaggg agaataaaaa cataatgtga gtatgagaga | 300 |
| gaaagttgta caaaagttgt accaaaatag ttgtacaaat atcattgagg aatttgacaa | 360 |
| aagctcacaca ataagggtt aattgctgta aataaataag gatgacgcat tagagagatg | 420 |
| taccattaga gaattttttgg caagtcatta aaaagaaaga ataaattatt tttaaaatta | 480 |
| aaagttgagt catttgatta aacatgtgat tatttaatga attgatgaaa gagttggatt | 540 |
| aaagttgtat tagtaattag aatttggtgt caaatttaat ttgacatttg atcttttcct | 600 |
| atatattgcc ccatagagtc agttaactca tttttatatt tcatagatca aataagagaa | 660 |
| ataacggtat attaatccct ccaaaaaaaa aaaacggtat atttactaaa aaatctaagc | 720 |
| cacgtaggag gataacagga tccccgtagg aggataacct ccaatccaac caatcacaac | 780 |
| aatcctgatg agataacccca ctttaagccc acgcatctgt ggcacatcta cattatctaa | 840 |

```
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tgaagactat cattgctttg   1020
agctacattc tatgtctggt tttcactcaa aaacttcccg gaaatgacaa cagcacggca   1080
acgctgtgcc ttgggcacca tgcagtacca acggaacga tagtgaaaac aatcacgaat   1140
gaccaaattg aagttactaa tgctactgag ctggttcaga gttcctcaac aggtgaaata   1200
tgcgacagtc ctcatcagat ccttgatgga gaaaactgca cactaataga tgctctattg   1260
ggagaccctc agtgtgatgg cttccaaaat aagaaatggg acctttttgt tgaacgcagc   1320
aaagcctaca gcaactgtta cccttatgat gtgccggatt atgcctccct taggtcacta   1380
gttgcctcat ccggcacact ggagtttaac aatgaaagtt tcaattggac tggagtcact   1440
caaaacggaa caagctctgc ttgcataagg agatctaata acagtttctt tagtagattg   1500
aattggttga cccacttaaa attcaaatac ccagcattga acgtgactat gccaaacaat   1560
gaaaaatttg acaaattgta catttggggg gttcaccacc cgggtacgga caatgaccaa   1620
atcttcctgt atgctcaagc atcaggaaga atcacagtct ctaccaaaag aagccaacaa   1680
actgtaatcc cgaatatcgg atctagaccc agagtaagga atatccccag cagaataagc   1740
atctattgga caatagtaaa accgggagac atacttttga ttaacagcac agggaatcta   1800
attgctccta ggggttactt caaaatacga agtgggaaaa gctcaataat gagatcagat   1860
gcacccattg gcaaatgcaa ttctgaatgc atcactccaa acggaagcat tcccaatgac   1920
aaaccattcc aaaatgtaaa caggatcaca tacgggcct gtcccagata tgttaagcaa   1980
aacactctga aattggcaac agggatgcga aatgtaccag agaaacaaac tagaggcata   2040
tttggcgcaa tcgcgggttt catagaaaat ggttgggagg gaatggtgga tggttggtat   2100
ggtttcaggc atcaaaattc tgagggaata ggacaagcag cagatctcaa aagcactcaa   2160
gcagcaatcg atcaaatcaa tgggaagctg aataggttga tcgggaaaac caacgagaaa   2220
ttccatcaga ttgaaaaaga gttctcagaa gtcgaaggga aatccagga ccttgagaaa   2280
tatgttgagg acaccaaaat agatctctgg tcatacaacg cggagcttct tgttgccctg   2340
gagaaccaac atacaattga tctaactgac tcagaaatga acaaactgtt tgaaaaaaca   2400
aagaagcaac tgagggaaaa tgctgaggat atgggcaatg gttgttttcaa aatataccac   2460
aaatgtgaca atgcctgcat aggatcaatc agaaatggaa cttatgacca cgatgtatac   2520
agagatgaag cattaaacaa ccggttccag atcaagggcg ttgagctgaa gtcaggatac   2580
aaagattgga tactatggat ttcctttgcc atatcatgtt ttttgctttg tgttgctttg   2640
ttggggttca tcatgtgggc ctgccaaaaa ggcaacatta ggtgcaacat ttgcatttga   2700
gagctctaag ttaaaatgct tcttcgtctc ctatttataa tatggtttgt tattgttaat   2760
tttgttcttg tagaagagct taattaatcg ttgttgttat gaaatactat ttgtatgaga   2820
tgaactggtg taatgtaatt catttacata agtggagtca gaatcagaat gtttcctcca   2880
taactaacta gacatgaaga cctgccgcgt acaattgtct tatatttgaa caactaaaat   2940
tgaacatctt ttgccacaac tttataagtg gttaatatag ctcaaatata tggtcaagtt   3000
caatagatta ataatggaaa tatcagttat cgaaattcat taacaatcaa cttaacgtta   3060
ttaactacta attttatatc atcccctttg ataaatgata gtaca                  3105
```

<210> SEQ ID NO 70

<211> LENGTH: 3105
<212> TYPE: DNA
<213> ORGANISM: Artificial Sequence
<220> FEATURE:
<223> OTHER INFORMATION: Expression Cassette

<400> SEQUENCE: 70

| | | | | | |
|---|---|---|---|---|---|
| agaggtaccc | cgggctggta | tatttatatg | ttgtcaaata | actcaaaaac | cataaaagtt | 60 |
| taagttagca | agtgtgtaca | tttttacttg | aacaaaaata | ttcacctact | actgttataa | 120 |
| atcattatta | aacattagag | taaagaaata | tggatgataa | gaacaagagt | agtgatattt | 180 |
| tgacaacaat | tttgttgcaa | catttgagaa | aattttgttg | ttctctcttt | tcattggtca | 240 |
| aaaacaatag | agagagaaaa | aggaagaggg | agaataaaaa | cataatgtga | gtatgagaga | 300 |
| gaaagttgta | caaagttgt | accaaaatag | ttgtacaaat | atcattgagg | aatttgacaa | 360 |
| aagctacaca | aataagggtt | aattgctgta | aataaataag | gatgacgcat | tagagagatg | 420 |
| taccattaga | gaattttggg | caagtcatta | aaaagaaaga | ataaattatt | tttaaaatta | 480 |
| aaagttgagt | catttgatta | aacatgtgat | tatttaatga | attgatgaaa | gagttggatt | 540 |
| aaagttgtat | tagtaattag | aatttggtgt | caaatttaat | ttgacatttg | atcttttcct | 600 |
| atatattgcc | ccatagagtc | agttaactca | tttttatatt | tcatagatca | aataagagaa | 660 |
| ataacggtat | attaatccct | ccaaaaaaaa | aaaacggtat | atttactaaa | aaatctaagc | 720 |
| cacgtaggag | gataacagga | tccccgtagg | aggataacc | ccaatccaac | caatcacaac | 780 |
| aatcctgatg | agataaccca | ctttaagccc | acgcatctgt | ggcacatcta | cattatctaa | 840 |
| atcacacatt | cttccacaca | tctgagccac | acaaaaacca | atccacatct | ttatcaccca | 900 |
| ttctataaaa | aatcacactt | tgtgagtcta | cactttgatt | cccttcaaac | acatacaaag | 960 |
| agaagagact | aattaattaa | ttaatcatct | tgagagaaaa | tgaagactat | cattgctttg | 1020 |
| agctacattc | tatgtctggt | tttcactcaa | aaacttcccg | gaaatgacaa | cagcacggca | 1080 |
| acgctgtgcc | ttgggcacca | tgcagtacca | acggaacga | tagtgaaaac | aatcacgaat | 1140 |
| gaccaaattg | aagttactaa | tgctactgag | ctggttcaga | gttcctcaac | aggtggaata | 1200 |
| tgcgacagtc | ctcatcagat | ccttgatgga | gaaaactgca | cactaataga | tgctctattg | 1260 |
| ggagaccctc | agtgtgatgg | cttccaaaat | aagaaatggg | accttttgt | tgaacgcagc | 1320 |
| aaagcctaca | gcaactgtta | cccttatgat | gtgccggatt | atgcctccct | taggtcacta | 1380 |
| gttgcctcat | ccggcacact | ggagtttaac | gatgaaagtt | tcaattggac | tggagtcact | 1440 |
| caaaatggaa | caagctctgc | ttgcaaaagg | agatctaata | acagtttctt | tagtagattg | 1500 |
| aattggttga | cccacttaaa | attcaaatac | ccagcattga | acgtgactat | gccaaacaat | 1560 |
| gaaaaatttg | acaaattgta | catttggggg | gttcaccacc | cgggtacgga | caatgaccaa | 1620 |
| atcttcctgc | atgctcaagc | atcaggaaga | atcacagtct | ctaccaaaag | aagccaacaa | 1680 |
| actgtaatcc | cgaatatcgg | atctagaccc | agaataagga | atatccccag | cagaataagc | 1740 |
| atctattgga | caatagtaaa | accggagac | atacttttga | ttaacagcac | agggaatcta | 1800 |
| attgctccta | ggggttactt | caaaatacga | agtgggaaaa | gctcaataat | gagatcagat | 1860 |
| gcacccattg | gcaaatgcaa | ttctgaatgc | atcactccaa | atggaagcat | tcccaatgac | 1920 |
| aaaccatttc | aaaatgtaaa | caggatcaca | tatgggccct | gtcccagata | tgttaagcaa | 1980 |
| aacactctga | aattggcaac | agggatgcga | aatgtaccag | agaaacaaac | tagaggcata | 2040 |
| tttggcgcaa | tcgcgggttt | catagaaaat | ggttgggagg | gaatggtgga | tggttggtac | 2100 |
| ggtttcaggc | atcaaaattc | tgagggaata | ggacaagcag | cagatctcaa | aagcactcaa | 2160 |

```
gcagcaatca atcaaatcaa tgggaagctg aataggttga tcgggaaaac caacgagaaa      2220
ttccatcaga ttgaaaaaga gttctcagaa gtagaaggga gaatccagga cctcgagaaa      2280
tatgttgagg acactaaaat agatctctgg tcatacaacg cggagcttct tgttgccctg      2340
gagaaccaac atacaattga tctaactgac tcagaaatga acaaactgtt tgaaagaaca      2400
aagaagcaac tgagggaaaa tgctgaggat atgggcaatg gttgtttcaa aatataccac      2460
aaatgtgaca atgcctgcat aggatcaatc agaaatggaa cttatgacca tgatgtatac      2520
agagatgaag cattaaacaa ccggttccag atcaaaggcg ttgagctgaa gtcaggatac      2580
aaagattgga tactatggat ttcctttgcc atatcatgtt ttttgctttg tgttgctttg      2640
ttggggttca tcatgtgggc ctgccaaaaa ggcaacatta ggtgcaacat ttgcatttga      2700
gagctctaag ttaaaatgct tcttcgtctc ctatttataa tatggtttgt tattgttaat      2760
tttgttcttg tagaagagct taattaatcg ttgttgttat gaaatactat ttgtatgaga      2820
tgaactggtg taatgtaatt catttacata agtggagtca gaatcagaat gtttcctcca      2880
taactaacta gacatgaaga cctgccgcgt acaattgtct tatatttgaa caactaaaat      2940
tgaacatctt ttgccacaac tttataagtg gttaatatag ctcaaatata tggtcaagtt      3000
caatagatta ataatggaaa tatcagttat cgaaattcat taacaatcaa cttaacgtta      3060
ttaactacta attttatatc atccccttg ataaatgata gtaca                      3105

<210> SEQ ID NO 71
<211> LENGTH: 3117
<212> TYPE: DNA
<213> ORGANISM: Artificial Sequence
<220> FEATURE:
<223> OTHER INFORMATION: Expression Cassette

<400> SEQUENCE: 71
agaggtaccc cgggctggta tatttatatg ttgtcaaata actcaaaaac cataaaagtt        60
taagttagca agtgtgtaca tttttacttg aacaaaaata ttcacctact actgttataa       120
atcattatta aacattagag taaagaaata tggatgataa gaacaagagt agtgatattt       180
tgacaacaat tttgttgcaa catttgagaa aattttgttg ttctctcttt tcattggtca       240
aaaacaatag agagagaaaa aggaagaggg agaataaaaa cataatgtga gtatgagaga       300
gaaagttgta caaaagttgt accaaaatag ttgtacaaat atcattgagg aatttgacaa       360
aagctacaca ataagggtt  aattgctgta aataaataag gatgacgcat tagagagatg       420
taccattaga gaatttttgg caagtcatta aaaagaaaga ataaattatt tttaaaatta       480
aaagttgagt catttgatta aacatgtgat tatttaatga attgatgaaa gagttggatt       540
aaagttgtat tagtaattag aattggtgt  caaatttaat ttgacatttg atcttttcct       600
atatattgcc ccatagagtc agttaactca tttttatatt tcatagatca aataagagaa       660
ataacggtat attaatccct ccaaaaaaaa aaacggtat  atttactaaa aaatctaagc       720
cacgtaggag gataacagga tccccgtagg aggataacat ccaatccaac caatcacaac       780
aatcctgatg agataaccca ctttaagccc acgcatctgt ggcacatcta cattatctaa       840
atcacacatt cttccacaca tctgagccac acaaaaacca atccacatct ttatcaccca       900
ttctataaaa aatcacactt tgtgagtcta cactttgatt ccct tcaaac acatacaaag      960 agaagagact aattaattaa ttaatcatct tgagagaaaa tgaacactca aattctaata      1020
ttagccactt cggcattctt ctatgtacgt gcagataaaa tctgcctagg acatcatgct      1080
```

```
gtgtctaatg gaaccaaagt agacaccctt actgaaaaag gaatagaagt tgtcaatgca    1140
acagaaacag ttgaacaaac aaacatccct aagatctgct caaaaggaaa acagactgtt    1200
gaccttggtc aatgtggatt actagggacc gttattggtc ctccccaatg tgaccaattt    1260
cttgagttct ctgctaattt aatagttgaa agaagggaag gtaatgacat ttgttatcca    1320
ggcaaatttg acaatgaaga acattgaga aaaatactca gaaaatccgg aggaattaaa    1380
aaggagaata tgggattcac atataccgga gtgagaacca atggagagac tagcgcatgt    1440
agaaggtcaa gatcttcctt ttatgcagag atgaaatggc ttctatccag cacagacaat    1500
gggacatttc cacaaatgac aaagtcctac aagaacacta agaaggtacc agctctgata    1560
atctggggaa tccaccactc aggatcaact actgaacaga ctagattata tggaagtggg    1620
aataaattga taacagtttg gagttccaaa taccaacaat cttttgtccc aaatcctgga    1680
ccaagaccgc aaatgaatgg tcaatcagga agaattgact ttcactggct gatgctagat    1740
cccaatgata ctgtcacttt cagtttaat ggggccttta tagcacctga ccgcgccagt    1800
tttctaagag gtaaatctct aggaatccaa agtgatgcac aacttgacaa taattgtgaa    1860
ggtgaatgct atcatattgg aggtactata attagcaact tgcccttca aaacattaat    1920 agtagggcaa tcggaaaatg ccccagatac gtgaagcaga gagcttaat gctagcaaca    1980 ggaatgaaaa atgttcctga agctcctgca cataaacaac taactcatca catgcgcaaa    2040
aaaagaggtt tatttggtgc aatagcagga ttcattgaaa atgggtggga aggattaata    2100
gacggatggt atggatataa gcatcagaat gcacaaggag aagggactgc tgcagactac    2160
aaaagtacac aatctgctat caaccaaata accggaaaat tgaacagact aatagaaaaa    2220
accaaccagc aattcgaact aatagataat gagttcaatg aaatagaaaa acaaattggc    2280
aatgttatta ctggactaga agattctatc atcgaagtat ggtcatataa tgcagagttc    2340
ctcgtagcag tggagaatca acacactatt gatttaactg actcagaaat gaacaaacta    2400
tatgaaaagg taagaagaca actgagagaa atgctgagg aagatggtaa tggctgtttt    2460
gaaatattcc accaatgtga caatgattgc atggccagca ttagaaacaa cacatatgac    2520
cataaaaaat acagaaaaga ggcaatacaa aacagaatcc agattgacgc agtaaagttg    2580
agcagtggtt acaaagatat aatactttgg tttagcttcg gggcatcatg tttcttattt    2640
cttgccattg caatgggtct tgtttttcata tgtataaaaa atggaaacat gcggtgcact    2700
atttgtatat aagagctcta agttaaaatg cttcttcgtc tcctatttat aatatggttt    2760
gttattgtta attttgttct tgtagaagag cttaattaat cgttgttgtt atgaaatact    2820
atttgtatga gatgaactgg tgtaatgtaa ttcatttaca taagtggagt cagaatcaga    2880
atgtttcctc cataactaac tagacatgaa gacctgccgc gtacaattgt cttatatttg    2940
aacaactaaa attgaacatc ttttgccaca actttataag tggttaatat agctcaaata    3000
tatggtcaag ttcaatagat taataatgga aatatcagtt atcgaaattc attaacaatc    3060
aacttaacgt tattaactac taattttata tcatccccctt tgataaatga tagtaca     3117
```

<210> SEQ ID NO 72
<211> LENGTH: 3162
<212> TYPE: DNA
<213> ORGANISM: Artificial Sequence
<220> FEATURE:
<223> OTHER INFORMATION: Expression Cassette

<400> SEQUENCE: 72

```
agaggtaccc cgggctggta tatttatatg ttgtcaaata actcaaaaac cataaaagtt      60
```

```
taagttagca agtgtgtaca tttttacttg aacaaaaata ttcacctact actgttataa    120
atcattatta aacattagag taaagaaata tggatgataa gaacaagagt agtgatattt    180
tgacaacaat tttgttgcaa catttgagaa aattttgttg ttctctcttt tcattggtca    240
aaaacaatag agagagaaaa aggaagaggg agaataaaaa cataatgtga gtatgagaga    300
gaaagttgta caaaagttgt accaaaatag ttgtacaaat atcattgagg aatttgacaa    360
aagctacaca ataagggtt  aattgctgta ataaataag  gatgacgcat tagagagatg    420
taccattaga gaattttgg  caagtcatta aaaagaaaga ataaattatt tttaaaatta    480
aaagttgagt catttgatta aacatgtgat tatttaatga attgatgaaa gagttggatt    540
aaagttgtat tagtaattag aatttggtgt caaatttaat ttgacatttg atcttttcct    600
atatattgcc ccatagagtc agttaactca tttttatatt tcatagatca aataagagaa    660
ataacggtat attaatccct ccaaaaaaaa aaacggtat  atttactaaa aaatctaagc    720
cacgtaggag gataacagga tccccgtagg aggataacat ccaatccaac caatcacaac    780
aatcctgatg agataaccca ctttaagccc acgcatctgt ggcacatcta cattatctaa    840
atcacacatt cttccacaca tctgagccac acaaaaacca atccacatct ttatcaccca    900
ttctataaaa aatcacactt tgtgagtcta cactttgatt cccttcaaac acatacaaag    960
agaagagact aattaattaa ttaatcatct tgagagaaaa tgaaggcaat aattgtacta   1020
ctcatggtag taacatccaa tgcagatcga atctgcactg ggataacatc gtcaaactca   1080
ccacatgttg tcaaaactgc tactcaaggg gaggtcaatg tgactggtgt aataccactg   1140
acaacaacac ccaccaaatc tcattttgca aatctcaaag gaacagaaac cagagggaaa   1200
ctatgcccaa aatgcctcaa ctgcacagat ctggacgtgg ccttgggcag accaaaatgc   1260
acggggaaca taccctcggc aagagtttca atactccatg aagtcagacc tgttacatct   1320
gggtgctttc ctataatgca cgacagaaca aaaattagac agctgcctaa acttctcaga   1380
ggatacgaac atatcaggtt atcaactcat aacgttatca atgcagaaaa tgcaccagga   1440
ggaccctaca aaattggaac ctcagggtct tgccctaacg ttaccaatgg aaacggattt   1500
ttcgcaacaa tggcttgggc cgtcccaaaa aacgacaaca acaaaacagc aacaaattca   1560
ttaacaatag aagtaccata catttgtaca gaaggagaag accaaattac cgtttggggg   1620
ttccactctg ataacgaaac ccaaatggca aagctctatg ggactcaaaa gccccagaag   1680
ttcacctcat ctgccaacgg agtgaccaca cattacgttt cacagattgg tggcttccca   1740
aatcaaacag aagacggagg actaccacaa agcggtagaa ttgttgttga ttacatggtg   1800
caaaaatctg ggaaaacagg aacaattacc tatcaaagag gtattttatt gcctcaaaaa   1860
gtgtggtgcg caagtggcag gagcaaggta ataaaaggat cgttgccttt aattggagaa   1920
gcagattgcc tccacgaaaa atacggtgga ttaaacaaaa gcaagcctta ctacacaggg   1980
gaacatgcaa aggccatagg aaattgccca atatgggtga aaacacccct gaagctggcc   2040
aatggaacca aatatagacc tcctgcaaaa ctattaaagg aaaggggttt cttcggagct   2100
attgctggtt tcttagaagg aggatgggaa ggaatgattg caggttggca cggatacaca   2160
tcccatgggg cacatggagt agcggtggca gcagacctta agagcactca agaggccata   2220
aacaagataa caaaaaatct caactctttg agtgagctgg aagtaaagaa tcttcaaaga   2280
ctaagcggtg ccatggatga actccacaac gaaatactag aactgacga  gaaagtggat   2340 gatctcagag ctgatacaat aagctcacaa atagaactcg cagtcctgct ttccaatgaa   2400
```

-continued

| | |
|---|---|
| ggaataataa acagtgaaga tgagcatctc ttggcgcttg aaagaaagct gaagaaaatg | 2460 |
| ctgggcccct ctgctgtaga gatagggaat ggatgctttg aaaccaaaca caagtgcaac | 2520 |
| cagacctgtc tcgacagaat agctgctggt acctttgatg caggagaatt ttctctcccc | 2580 |
| acttttgatt cactgaatat tactgctgca tctttaaatg acgatggatt ggataatcat | 2640 |
| actatactgc tttactactc aactgctgcc tccagtttgg ctgtaacatt gatgatagct | 2700 |
| atctttgttg tttatatggt ctccagagac aatgtttctt gctccatctg tctataagag | 2760 |
| ctctaagtta aaatgcttct tcgtctccta tttataatat ggtttgttat tgttaatttt | 2820 |
| gttcttgtag aagagcttaa ttaatcgttg ttgttatgaa atactatttg tatgagatga | 2880 |
| actggtgtaa tgtaattcat ttacataagt ggagtcagaa tcagaatgtt tcctccataa | 2940 |
| ctaactagac atgaagacct gccgcgtaca attgtcttat atttgaacaa ctaaaattga | 3000 |
| acatcttttg ccacaacttt ataagtggtt aatatagctc aaatatatgg tcaagttcaa | 3060 |
| tagattaata atggaaatat cagttatcga aattcattaa caatcaactt aacgttatta | 3120 |
| actactaatt ttatatcatc cccttttgata aatgatagta ca | 3162 |

<210> SEQ ID NO 73
<211> LENGTH: 3159
<212> TYPE: DNA
<213> ORGANISM: Artificial Sequence
<220> FEATURE:
<223> OTHER INFORMATION: Expression Cassette

<400> SEQUENCE: 73

| | |
|---|---|
| agaggtaccc cgggctggta tatttatatg ttgtcaaata actcaaaaac cataaaagtt | 60 |
| taagttagca agtgtgtaca ttttttacttg aacaaaaata ttcacctact actgttataa | 120 |
| atcattatta aacattagag taaagaaata tggatgataa gaacaagagt agtgatattt | 180 |
| tgacaacaat tttgttgcaa catttgagaa aattttgttg ttctctcttt tcattggtca | 240 |
| aaaacaatag agagagaaaa aggaagaggg agaataaaaa cataatgtga gtatgagaga | 300 |
| gaaagttgta caaaagttgt accaaaatag ttgtacaaat atcattgagg aatttgacaa | 360 |
| aagctacaca aataagggtt aattgctgta aataaataag gatgacgcat tagagagatg | 420 |
| taccattaga gaattttttgg caagtcatta aaaagaaaga ataaattatt tttaaaatta | 480 |
| aaagttgagt catttgatta aacatgtgat tatttaatga attgatgaaa gagttggatt | 540 |
| aaagttgtat tagtaattag aatttggtgt caaatttaat ttgacatttg atcttttcct | 600 |
| atatattgcc ccatagagtc agttaactca tttttatatt tcatagatca ataagagaa | 660 |
| ataacggtat attaatccct ccaaaaaaaa aaaacggtat atttactaaa aaatctaagc | 720 |
| cacgtaggag gataacagga tccccgtagg aggataacat ccaatccaac caatcacaac | 780 |
| aatcctgatg agataaccca ctttaagccc acgcatctgt ggcacatcta cattatctaa | 840 |
| atcacacatt cttccacaca tctgagccac acaaaaacca atccacatct ttatcaccca | 900 |
| ttctataaaa aatcacactt tgtgagtcta cactttgatt cccttcaaac acatacaaag | 960 |
| agaagagact aattaattaa ttaatcatct tgagagaaaa tgaaggcaat aattgtacta | 1020 |
| ctcatggtag taacatccaa tgcagatcga atctgcactg gaataacatc ttcaaactca | 1080 |
| cctcatgtgg tcaaaacagc cactcaaggg gaggtcaatg tgactggtgt gataccacta | 1140 |
| acaacaacac caacaaaatc ttattttgca aatctcaaag gaacaaggac cagagggaaa | 1200 |
| ctatgcccag actgtctcaa ctgcacagat ctggatgtgg ctttgggcag accaatgtgt | 1260 |
| gtggggacca caccttcggc gaaggcttca atactccacg aagtcaaacc tgttacatcc | 1320 |

```
gggtgctttc ctataatgca cgacagaaca aaaatcaggc aactacccaa tcttctcaga    1380
ggatatgaaa atatcaggct atcaacccaa acgtcatcg atgcggaaaa ggcaccagga    1440
ggaccctaca gacttggaac ctcaggatct tgccctaacg ctaccagtaa gagcggattt    1500
ttcgcaacaa tggcttgggc tgtcccaaag gacaacaaca aaaatgcaac gaacccacta    1560
acagtagaag taccatacat ttgtacagaa ggggaagacc aaatcactgt ttgggggttc    1620
cattcagata acaaaaccca aatgaagaac ctctatggag actcaaatcc tcaaaagttc    1680
acctcatctg ctaatggagt aaccacacac tatgtttctc agattggcag cttcccagat    1740
caaacagaag acgaggact accacaaagc ggcaggattt tgttgatta catgatgcaa    1800 aaacctggga aaacaggaac aattgtctac caaagaggtg ttttgttgcc tcaaaaggtg    1860
tggtgcgcga gtggcaggag caaagtaata aagggtcct tgcctttaat tggtgaagca    1920
gattgccttc atgaaaaata cggtggatta acaaaagca agccttacta cacaggagaa    1980
catgcaaaag ccataggaaa ttgcccaata tgggtgaaaa caccttgaa gctcgccaat    2040 ggaaccaaat atagacctcc tgcaaaacta ttaaaggaaa ggggtttctt cggagctatt    2100 gctggttcc tagaaggag atgggaagga atgattgcag gctggcacgg atacacatct    2160
cacggagcac atggagtggc agtggcggcg gaccttaaga gtacgcaaga agctataaac    2220
aagataacaa aaatctcaa ttctttgagt gagctagaa taagaatct tcaaagacta    2280 agtggtgcca tggatgaact ccacaacgaa atactcgagc tggatgagaa agtggatgat    2340
ctcagagctg acactataag ctcgcaaata gaacttgcag tcttgctttc caacgaagga    2400
ataataaaca gtgaagatga gcatctattg gcacttgaga gaaaactaaa gaaaatgctg    2460
ggtccctctg ctgtagagat aggaaatgga tgcttcgaaa ccaaacacaa gtgcaaccag    2520
acctgcttag acaggatagc tgctggcacc tttaatgcag gagaattttc tctccccact    2580
tttgattcac tgaacattac tgctgcatct ttaaatgatg atggattgga taaccatact    2640
atactgctct attactcaac tgctgcttct agtttggctg taacattgat gctagctatt    2700
tttattgttt atatggtctc cagagacaac gtttcatgct ccatctgtct ataagagctc    2760
taagttaaaa tgcttcttcg tctcctattt ataatatggt ttgttattgt taattttgtt    2820
cttgtagaag agcttaatta atcgttgttg ttatgaaata ctatttgtat gagatgaact    2880
ggtgtaatgt aattcattta cataagtgga gtcagaatca gaatgtttcc tccataacta    2940
actagacatg aagacctgcc gcgtacaatt gtcttatatt tgaacaacta aaattgaaca    3000
tcttttgcca caactttata agtggttaat atagctcaaa tatatggtca agttcaatag    3060
attaataatg gaaatatcag ttatcgaaat tcattaacaa tcaacttaac gttattaact    3120
actaatttta tatcatcccc tttgataaat gatagtaca                          3159
```

<210> SEQ ID NO 74
<211> LENGTH: 565
<212> TYPE: PRT
<213> ORGANISM: Artificial Sequence
<220> FEATURE:
<223> OTHER INFORMATION: Consensus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:

```
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (111)..(111)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (162)..(162)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid
<220> FEATURE:
<221> NAME/KEY: misc_feature
<222> LOCATION: (210)..(210)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (268)..(268)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (432)..(432)
<223> OTHER INFORMATION: Xaa can be any naturally occurring amino acid
<220> FEATURE:
<221> NAME/KEY: misc_feature
<222> LOCATION: (489)..(489)
<223> OTHER INFORMATION: Xaa can be any naturally occurring amino acid

<400> SEQUENCE: 74

Met Lys Xaa Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Xaa Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
```

```
                65                  70                  75                  80
Asn Pro Glu Cys Glu Leu Leu Ile Ser Xaa Glu Ser Trp Ser Tyr Ile
                    85                  90                  95

Val Glu Xaa Pro Asn Pro Glu Asn Gly Thr Cys Tyr Pro Gly Xaa Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
            130                 135                 140

Xaa Thr Gly Val Ser Ala Ser Cys Ser His Asn Gly Xaa Ser Ser Phe
145                 150                 155                 160

Tyr Xaa Asn Leu Leu Trp Leu Thr Gly Lys Asn Gly Leu Tyr Pro Asn
                165                 170                 175

Leu Ser Lys Ser Tyr Xaa Asn Asn Lys Glu Lys Glu Val Leu Val Leu
                180                 185                 190

Trp Gly Val His His Pro Pro Asn Ile Gly Xaa Gln Xaa Ala Leu Tyr
            195                 200                 205

His Xaa Glu Asn Ala Tyr Val Ser Val Val Ser Ser His Tyr Ser Arg
    210                 215                 220

Xaa Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Xaa Tyr Ala Phe Ala
                260                 265                 270

Leu Ser Arg Gly Phe Gly Ser Gly Ile Ile Xaa Ser Asn Ala Pro Met
            275                 280                 285

Asp Xaa Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Xaa
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Xaa Glu Cys Met Glu Ser Val Lys
                485                 490                 495
```

```
Asn Gly Thr Tyr Asp Tyr Pro Lys Tyr Ser Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 75
<211> LENGTH: 565
<212> TYPE: PRT
<213> ORGANISM: Influenza Virus

<400> SEQUENCE: 75

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Glu Cys Asp Ala Lys Cys Gln Thr Pro Gln Gly Ala Ile Asn Ser
```

```
                290             295             300
Ser Leu Pro Phe Gln Asn Val His Pro Val Thr Ile Gly Glu Cys Pro
305                 310             315                 320

Lys Tyr Val Arg Ser Ala Lys Leu Arg Met Val Thr Gly Leu Arg Asn
                325             330                 335

Ile Pro Ser Ile Gln Ser Arg Gly Leu Phe Gly Ala Ile Ala Gly Phe
            340             345                 350

Ile Glu Gly Gly Trp Thr Gly Met Val Asp Gly Trp Tyr Gly Tyr His
        355             360             365

His Gln Asn Glu Gln Gly Ser Gly Tyr Ala Ala Asp Gln Lys Ser Thr
    370             375             380

Gln Asn Ala Ile Asn Gly Ile Thr Asn Lys Val Asn Ser Val Ile Glu
385             390             395                 400

Lys Met Asn Thr Gln Phe Thr Ala Val Gly Lys Glu Phe Asn Lys Leu
                405             410                 415

Glu Arg Arg Met Glu Asn Leu Asn Lys Lys Val Asp Asp Gly Phe Leu
            420             425             430

Asp Ile Trp Thr Tyr Asn Ala Glu Leu Leu Val Leu Leu Glu Asn Glu
        435             440             445

Arg Thr Leu Asp Phe His Asp Ser Asn Val Lys Asn Leu Tyr Glu Lys
    450             455             460

Val Lys Ser Gln Leu Lys Asn Asn Ala Lys Glu Ile Gly Asn Gly Cys
465             470             475                 480

Phe Glu Phe Tyr His Lys Cys Asn Asn Glu Cys Met Glu Ser Val Lys
                485             490                 495

Asn Gly Thr Tyr Asp Tyr Pro Lys Tyr Ser Glu Glu Ser Lys Leu Asn
            500             505             510

Arg Glu Lys Ile Asp Gly Val Lys Leu Glu Ser Met Gly Val Tyr Gln
        515             520             525

Ile Leu Ala Ile Tyr Ser Thr Val Ala Ser Ser Leu Val Leu Leu Val
    530             535             540

Ser Leu Gly Ala Ile Ser Phe Trp Met Cys Ser Asn Gly Ser Leu Gln
545             550             555                 560

Cys Arg Ile Cys Ile
            565

<210> SEQ ID NO 76
<211> LENGTH: 252
<212> TYPE: PRT
<213> ORGANISM: Influenza Virus

<400> SEQUENCE: 76

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95
```

-continued

```
Val Lys Leu Tyr Arg Lys Leu Lys Arg Glu Ile Thr Phe His Gly Ala
            100                 105                 110
Lys Glu Ile Ser Leu Ser Tyr Ser Ala Gly Ala Leu Ala Ser Cys Met
            115                 120                 125
Gly Leu Ile Tyr Asn Arg Met Gly Ala Val Thr Thr Glu Val Ala Phe
            130                 135                 140
Gly Leu Val Cys Ala Thr Cys Glu Gln Ile Ala Asp Ser Gln His Arg
145                     150                 155                 160
Ser His Arg Gln Met Val Thr Thr Asn Pro Leu Ile Arg His Glu
                165                 170                 175
Asn Arg Met Val Leu Ala Ser Thr Thr Ala Lys Ala Met Glu Gln Met
            180                 185                 190
Ala Gly Ser Ser Glu Gln Ala Ala Glu Ala Met Glu Val Ala Ser Gln
            195                 200                 205
Ala Arg Gln Met Val Gln Ala Met Arg Thr Ile Gly Thr His Pro Ser
            210                 215                 220
Ser Ser Ala Gly Leu Lys Asn Asp Leu Leu Glu Asn Leu Gln Ala Tyr
225                     230                 235                 240
Gln Lys Arg Met Gly Val Gln Met Gln Arg Phe Lys
                245                 250
```